US008906873B2

(12) United States Patent
Hung et al.

(10) Patent No.: US 8,906,873 B2
(45) Date of Patent: Dec. 9, 2014

(54) MODULATION OF HUNTINGTIN EXPRESSION

(75) Inventors: Gene Hung, Carlsbad, CA (US); C. Frank Bennett, Carlsbad, CA (US); Susan M. Freier, San Diego, CA (US); Holly Kordasiewicz, San Diego, CA (US); Lisa Stanek, Cambridge, MA (US); Don W. Cleveland, Del Mar, CA (US); Seng H. Cheng, Natick, MA (US); Lamya Shihabuddin, Brighton, MA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 13/395,188

(22) PCT Filed: Sep. 10, 2010

(86) PCT No.: PCT/US2010/048532
§ 371 (c)(1),
(2), (4) Date: May 30, 2012

(87) PCT Pub. No.: WO2011/032045
PCT Pub. Date: Mar. 17, 2011

(65) Prior Publication Data
US 2012/0252879 A1  Oct. 4, 2012

Related U.S. Application Data

(60) Provisional application No. 61/241,853, filed on Sep. 11, 2009.

(51) Int. Cl.
*A61K 48/00* (2006.01)
*C12N 15/113* (2010.01)

(52) U.S. Cl.
CPC ........ *C12N 15/113* (2013.01); *C12N 2310/321* (2013.01); *C12N 2310/345* (2013.01); *C12N 2310/3341* (2013.01); *C12N 2310/341* (2013.01); *C12N 2310/11* (2013.01); *C12N 2310/315* (2013.01); *C12N 2310/346* (2013.01)
USPC .......................................... 514/44; 536/24.5

(58) Field of Classification Search
None
See application file for complete search history.

(56) References Cited

U.S. PATENT DOCUMENTS

| 5,595,756 | A | 1/1997 | Bally et al. |
| 5,700,922 | A | 12/1997 | Cook |
| 5,801,154 | A | 9/1998 | Baracchini et al. |
| 5,998,148 | A | 12/1999 | Bennett et al. |
| 6,043,060 | A | 3/2000 | Imanishi |
| 6,147,200 | A | 11/2000 | Manoharan et al. |
| 6,582,908 | B2 | 6/2003 | Fodor et al. |
| 6,670,461 | B1 | 12/2003 | Wengel et al. |
| 7,320,965 | B2 | 1/2008 | Sah et al. |
| 2001/0053519 | A1 | 12/2001 | Fodor et al. |
| 2003/0109476 | A1 | 6/2003 | Kmiec |
| 2003/0144242 | A1 | 7/2003 | Ward et al. |
| 2003/0228597 | A1 | 12/2003 | Cowsert et al. |
| 2004/0092465 | A1 | 5/2004 | Dobie |
| 2004/0096880 | A1 | 5/2004 | Kmiec |
| 2004/0137471 | A1 | 7/2004 | Vickers et al. |
| 2005/0042646 | A1 | 2/2005 | Davidson |
| 2005/0096284 | A1 | 5/2005 | McSwiggen |
| 2005/0191638 | A1 | 9/2005 | McSwiggen |
| 2005/0255086 | A1 | 11/2005 | Davidson |
| 2005/0255487 | A1 | 11/2005 | Khvorova et al. |
| 2006/0051769 | A1 | 3/2006 | Barts |
| 2007/0031844 | A1 | 2/2007 | Khvorova et al. |
| 2007/0099860 | A1 | 5/2007 | Sah |
| 2008/0015158 | A1 | 1/2008 | Ichiro |
| 2008/0039418 | A1 | 2/2008 | Freier |
| 2008/0274989 | A1 | 11/2008 | Davidson et al. |
| 2009/0092981 | A1 | 4/2009 | Swayze et al. |

FOREIGN PATENT DOCUMENTS

| WO | WO 94/26764 | 11/1994 |
| WO | WO 01/79283 | 10/2001 |
| WO | WO 03/013437 | 2/2003 |
| WO | WO 03/064625 | 8/2003 |
| WO | WO 2004/048601 | 6/2004 |
| WO | WO 2004/101787 | 11/2004 |
| WO | WO 2004/013280 | 12/2004 |
| WO | WO 2005/027980 | 3/2005 |
| WO | WO 2005/045032 | 5/2005 |
| WO | WO 2005/105995 | 11/2005 |
| WO | WO 2005/116204 | 12/2005 |
| WO | WO 2008/018795 | 2/2008 |
| WO | WO 2011/097388 | 8/2011 |

OTHER PUBLICATIONS

Anderson et al. (Current Psychiatry Reports 2001, 3:379-388).*
Chang et al., "Structural Analysis of Complementary DNA and Amino Acid Sequences of Human and Rat Androgen Receptors" PNAS (1988) 85:7211-7215.
Eder et al., "Inhibition of LNCaP Prostate Cancer Cells by Means of Androgen Receptor Antisense Oligonucleotides" Cancer Gene Therapy (2000) 7(7):997-1007.
Sewell et al., "Phase I Trial of ISIS 104838, a 2'-Methoxyexthyl Modified Antisense Oligonucleotide Targeting Tumor Necrosis Factor-Alpha" The Journal of Pharmacology and Experimental Therapeutics (2002) 303(3):1334-1343.
Bennett et al., "Antisense oligonucleoties as a tool for gene functionalization and target validation" Biochimica Biophysica Acta (1999) 1489:19-30.
Boado et al., "Antisense-mediated down-regulation of the human huntington gene" *Journal of Pharmacology and Experimental Therapeutics* (2000)295:239-243.

(Continued)

*Primary Examiner* — Kimberly Chong
(74) *Attorney, Agent, or Firm* — Casimir Jones, S.C.

(57) ABSTRACT

Provided herein are methods, compounds, and compositions for reducing expression of huntingtin mRNA and protein in an animal. Such methods, compounds, and compositions are useful to treat, prevent, delay, or ameliorate Huntington's disease, or a symptom thereof.

8 Claims, 10 Drawing Sheets

(56) References Cited

OTHER PUBLICATIONS

Boffa et al., "Isolation of active genes containing CAG repeats by DNA strands invasion by a peptide nucleic acid" PNAS (1995) 92:1901-5.

Borovecki et al., "Genome-wide expression profiling of human blood reveals biomarkers for Huntington's disease" *Proc. Natl. Acad. Sci. USA* (2005) 102:11023-11028.

Branch et al., "A good antisense molecule is hard to find," TIBS (1998)23:45-50.

Caplen et al., "Rescue of polyglutamine-mediated cytotoxicity by double-stranded RNA-mediated RNA interference" Human Molecular Genetics (2002) 11(2):175-184.

Chin "On the Preparation and Utilization of Isolated and Purififed Oligonucleotides." Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

Davidson et al., "Molecular medicine for the brain: silencing of disease genes with RNA interference" Lancet Neurol. (2004) 3:145-149.

Diaz-Hernandez et al., "Full Motor Recovery Despite Striatal Neuron Loss and Formation of Irreversible Amyloid-Like Inclusions in a Conditional Mouse Model of Huntington's Disease" J. Neurosci (2005) 25:9773-9781.

Gonzalez-Alegre et al., "Technology Insight: therapeutic RNA interference—how far from the neurology clinic?" Nature Clinical Practice 3:394-404, 2007.

Gryaznov et al., "Oligodeoxyribonucleotide N3'->P5' Phosphoramidates Synthesis and Hybridization Properties" *J. Am. Chem. Soc.* (1994) 116:3143-3144.

Haque et al., "Antisense gene therapy for neurodegenerative disease" *Experimental Neurology* (1997) 144:139-146.

Harper et al., "Ten years of presymptomatic testing for Huntington's disease: the experience of the UK Huntington's Disease Prediction Consortium" J. Med. Genet. 37:567-571, 2000.

Harper et al., "RNA interference improves motor and neuropathological abnormalities in a Huntington's disease mouse model" *PNAS* (2005) 102:5820-5825.

Hasholt et al., "Antisense downregulation of mutant huntingtin in a cell model" *Journal of Gene Medicine* (2003) 5:528-538.

Hersch et al., "Translating Therapies for Huntington's Disease from Genetic Animal Models to Clinical Trials" *NeuroRX* (2004) 1:298-306.

Hersch et al., "Neuroprotection for Huntington's disease: Ready, set, slow" Neurotherapeutics (2008) 5(2):226-236.

Liu et al., "Specific inhibition of Huntington's disease gene expression by siRNAs in cultures cells" *Proceedings of the Japan Academy. Series B, Physical and Biological Sciences* (2003) 79B:293-298.

MacDonald et al., "A novel gene containing a trinucleotide repeat that is expanded and unstable on Huntington's disease chromosomes" Cell (1993) 72(6):971-983.

Machida et al., "rAAV-mediated shRNA ameliorated neuropathology in Huntington disease model mouse" *Biochem. Biophys. Res. Commun.* (2006) 343:190-197.

MacMillan et al., "Molecular analysis and clinical correlations of theHuntington's disease mutation" Lancet (1993) 342:954-958.

Maher et al., "Comparative hybrid arrest by tandem antisense oligodeoxyribonucleotides or oligodeoxyribonucleoside methylphosphonates in a cell-free system" *Nuc. Acid. Res.* (1988) 16:3341-3358.

Martin et al., "38. Ein neuer Zugang zu 2'-O-Alkylribonucleosiden and Eigenschaften deren Oligonucleotide" *Helv. Chim. Acta* (1995) 78:486-504.

Nellemann et al., "Inhibition of Huntington synthesis by antisense oligonucleotides" *Molecular and Cellular Neurosciences* (2000) 16:313-323.

New England BioLabs, Inc. Catalogue (1998): 121, 284.

Nikiforov et al., "The Use of Phosphorothioate Primers and Exonuclease Hydrolysis for the Preparation of Single-stranded PCR Products and their Detection by Solid-phase Hybridization" PCR Methods and Applications (1994) 3:285-291.

Nguyen et al., "Clioquinol down-regulates mutant huntingtin expression in vitro and mitigates pathology in a Huntington's disease mouse model" *PNAS* (2005) 102:11840-11845.

Reynolds et al., "Rational siRNA design for RNA interference" Nature Biotechnology (2004) 22:326-330/.

Sanghvi et al., "Heterocyclic Base Modifications in Nucleic Acids and Their Applications in Antisense Oligonucleotides" Antisense Research and Applications (1993) pp. 273-288.

Sheehan et al., "Biochemical properties of phosphonoacetate and thiophosphonoacetate oligodeoxyribonucleotides" *Nucleic Acids Research* (2003) 31:4109-4118.

The Huntington's Disease Collaborative Research Group "A Novel Gene Containing a Trinucleotide Repeat That Is Expanded and Unstable on Huntington's Disease Chromosomes" Cell (1993) 72(6):971-983.

Uhlmann et al., "Antisense oligonucleotides: a new therapeutic principle" *Chemical Reviews* (1990) 90:543-584.

Vickers et al., "Efficient Reduction of Target RNAs by Small Interfering RNA and Rnase H-dependent Antisense Agents. A comparative analysis." J Biol. Chem. (2003) 278:7108-7118.

Wang et al., "Clinico-pathological rescue of a model mouse of Huntington's disease by siRNA" *Neurosci. Res.* (2005) 53:241-249.

Woolf et al., "Specificity of antisense oligonucleotides in vivo" *Proc. Natl. Acad. Sci. USA* (1992) 89:7305-7309.

Yen et al., "Sequence-specific cleavage of Huntingtin mRNA by catalytic DNA" Annals of Neurology (1999) 46(3):366-373.

International Search Report for Application # PCT/US2007/002215 dated Nov. 16, 2007.

International Search Report for Application # PCT/US2007/002171 dated Sep. 26, 2007.

International Search Report for Application # PCT/US2010/048532 dated Jan. 26, 2011.

* cited by examiner

SEQUENCE LISTING

```
<160> NUMBER OF SEQ ID NOS: 58

<210> SEQ ID NO 1
<211> LENGTH: 13481
<212> TYPE: DNA
<213> ORGANISM: H. sapiens

<400> SEQUENCE: 1
gctgccggga cgggtccaag atggacggcc gctcaggttc tgcttttacc tgcggcccag      60
agccccattc attgccccgg tgctgagcgg cgccgcgagt cggcccgagg cctccgggga     120
ctgccgtgcc gggcgggaga ccgccatggc gaccctggaa aagctgatga aggccttcga     180
gtccctcaag tccttccagc agcagcagca gcagcagcag cagcagcagc agcagcagca     240
gcagcagcag cagcagcagc aacagccgcc accgccgccg ccgccgccgc cgcctcctca     300
gcttcctcag ccgccgccgc aggcacagcc gctgctgcct cagccgcagc cgccccgcc      360 gccgccccg ccgccacccg gccggctgt ggctgaggag ccgctgcacc gaccaaagaa       420
agaactttca gctaccaaga agaccgtgt gaatcattgt ctgacaatat gtgaaaacat      480
agtggcacag tctgtcagaa attctccaga atttcagaaa cttctgggca tcgctatgga     540
acttttctct ctgtgcagtg atgacgcaga gtcagatgtc aggatggtgg ctgacgaatg     600
cctcaacaaa gttatcaaag ctttgatgga ttctaatctt ccaaggttac agctcgagct     660
ctataaggaa attaaaaaga atggtgcccc tcggagtttg cgtgctgccc tgtgaggtt      720 tgctgagctg gctcacctgg ttcggcctca gaaatgcagg ccttacctgg tgaaccttct     780
gccgtgcctg actcgaacaa gcaagagacc cgaagaatca gtccaggaga ccttggctgc     840
agctgttccc aaaattatgg cttcttttgg caattttgca aatgacaatg aaattaaggt     900
tttgttaaag gccttcatag cgaacctgaa gtcaagctcc ccaccattc ggcggacagc       960 ggctggatca gcagtgagca tctgccagca ctcaagaagg acacaatatt tctatagttg     1020
gctactaaat gtgctcttag gcttactcgt tcctgtcgag gatgaacact ccactctgct     1080
gattcttggc gtgctgctca ccctgaggta tttggtgccc ttgctgcagc agcaggtcaa     1140
ggacacaagc ctgaaaggca gcttcggagt gacaaggaaa gaaatggaag tctctccttc     1200
tgcagagcag cttgtccagg tttatgaact gacgttacat cataccagc accaagacca      1260 caatgttgtg accggagccc tggagctgtt gcagcagctc ttcagaacgc ctccacccga     1320
gcttctgcaa accctgaccg cagtcgggg cattgggcag ctcaccgctg ctaaggagga     1380
gtctggtggc cgaagccgta gtgggagtat tgtggaactt atagctggag ggggttcctc     1440
atgcagccct gtcctttcaa gaaaacaaaa aggcaaagtg ctcttaggag aagaagagc      1500 cttggaggat gactctgaat cgagatcgga tgtcagcagc tctgccttaa cagcctcagt     1560
gaaggatgag atcagtggag agctggctgc ttcttcaggg gtttccactc cagggtcagc     1620
```

```
aggtcatgac atcatcacag aacagccacg gtcacagcac acactgcagg cggactcagt    1680
ggatctggcc agctgtgact tgacaagctc tgccactgat ggggatgagg aggatatctt    1740
gagccacagc tccagccagg tcagcgccgt cccatctgac cctgccatgg acctgaatga    1800
tgggacccag gcctcgtcgc ccatcagcga cagctcccag accaccaccg aagggcctga    1860
ttcagctgtt acccccttcag acagttctga aattgtgtta gacggtaccg acaaccagta    1920
tttgggcctg cagattggac agccccagga tgaagatgag gaagccacag gtattcttcc    1980
tgatgaagcc tcggaggcct tcaggaactc ttccatggcc cttcaacagg cacatttatt    2040
gaaaaacatg agtcactgca ggcagccttc tgacagcagt gttgataaat ttgtgttgag    2100
agatgaagct actgaaccgg gtgatcaaga aaacaagcct tgccgcatca aggtgacat    2160 tggacagtcc actgatgatg actctgcacc tcttgtccat tgtgtccgcc ttttatctgc    2220 ttcgttttg ctaacagggg gaaaaaatgt gctggttccg gacagggatg tgagggtcag    2280
cgtgaaggcc ctggccctca gctgtgtggg agcagctgtg ccctccacc cggaatcttt    2340 cttcagcaaa ctctataaag ttcctcttga caccacggaa tacctgagg aacagtatgt    2400 ctcagacatc ttgaactaca tcgatcatgg agacccacag gttcgaggag ccactgccat    2460
tctctgtggg accctcatct gctccatcct cagcaggtcc cgcttccacg tgggagattg    2520
gatgggcacc attagaaccc tcacaggaaa tacatttct ttggcggatt gcattccttt    2580
gctgcggaaa acactgaagg atgagtcttc tgttacttgc aagttagctt gtacagctgt    2640
gaggaactgt gtcatgagtc tctgcagcag cagctacagt gagttaggac tgcagctgat    2700
catcgatgtg ctgactctga ggaacagttc ctattggctg gtgaggacag agcttctgga    2760 aaccccttgca gagattgact tcaggctggt gagcttttg gaggcaaaag cagaaaactt    2820
acacagaggg gctcatcatt atacagggct tttaaaactg caagaacgag tgctcaataa    2880
tgttgtcatc catttgcttg gagatgaaga ccccagggtg cgacatgttg ccgcagcatc    2940
actaattagg cttgtcccaa agctgtttta taaatgtgac caaggacaag ctgatccagt    3000
agtggccgtg gcaagagatc aaagcagtgt ttacctgaaa cttctcatgc atgagacgca    3060
gcctccatct catttctccg tcagcacaat aaccagaata tatagaggct ataacctact    3120
accaagcata acagacgtca ctatggaaaa taaccttttca agagttattg cagcagtttc    3180
tcatgaacta atcacatcaa ccaccagagc actcacattt ggatgctgtg aagctttgtg    3240
tcttctttcc actgccttcc cagtttgcat ttggagttta ggttggcact gtggagtgcc    3300
tccactgagt gcctcagatg agtctaggaa gagctgtacc gttgggatgg ccacaatgat    3360
tctgaccctg ctctcgtcag cttggttccc attggatctc tcagcccatc aagatgcttt    3420
gattttggcc ggaaacttgc ttgcagccag tgctcccaaa tctctgagaa gttcatgggc    3480
ctctgaagaa gaagccaacc cagcagccac caagcaagag gaggtctggc cagccctggg    3540
ggaccgggcc ctggtgccca tggtggagca gctcttctct cacctgctga aggtgattaa    3600
catttgtgcc cacgtcctgg atgacgtggc tcctggaccc gcaataaagg cagccttgcc    3660
ttctctaaca aaccccccctt ctctaagtcc catccgacga aagggggaagg agaaagaacc    3720 aggagaacaa gcatcgtgtac cgttgagtcc caagaaaggc agtgaggcca gtgcagcttc    3780
tagacaatct gatacctcag gtcctgttac aacaagtaaa tcctcatcac tggggagttt    3840
ctatcatctt ccttcatacc tcaaactgca tgatgtcctg aaagctacac acgctaacta    3900
caaggtcacg ctgatcttc agaacagcac ggaaaagttt ggagggtttc tccgctcagc    3960
cttggatgtt cttttctcaga tactagagct ggccacactg caggacattg ggaagtgtgt    4020
```

```
tgaagagatc ctaggatacc tgaaatcctg ctttagtcga gaaccaatga tggcaactgt    4080
ttgtgttcaa caattgttga agactctctt tggcacaaac ttggcctccc agtttgatgg    4140
cttatcttcc aacccagca agtcacaagg ccgagcacag cgccttggct cctccagtgt    4200
gaggccaggc ttgtaccact actgcttcat ggccccgtac acccacttca cccaggccct    4260
cgctgacgcc agcctgagga acatggtgca ggcggagcag gagaacgaca cctcgggatg    4320
gtttgatgtc ctccagaaag tgtctaccca gttgaagaca aacctcacga gtgtcacaaa    4380
gaaccgtgca gataagaatg ctattcataa tcacattcgt ttgtttgaac ctcttgttat    4440
aaaagcttta aaacagtaca cgactacaac atgtgtgcag ttacagaagc aggttttaga    4500
tttgctggcg cagctggttc agttacgggt taattactgt cttctggatt cagatcaggt    4560
gtttattggc tttgtattga acagtttga atacattgaa gtgggccagt tcagggaatc    4620
agaggcaatc attccaaaca tcttttcctt cttggtatta ctatcttatg aacgctatca    4680
ttcaaaacag atcattggaa ttcctaaaat cattcagctc tgtgatggca tcatggccag    4740
tggaaggaag gctgtgacac atgccatacc ggctctgcag cccatagtcc acgacctctt    4800
tgtattaaga ggaacaaata aagctgatgc aggaaaagag cttgaaaccc aaaaagaggt    4860
ggtggtgtca atgttactga gactcatcca gtaccatcag gtgttggaga tgttcattct    4920
tgtcctgcag cagtgccaca aggagaatga agacaagtgg aagcgactgt ctcgacagat    4980
agctgacatc atcctcccaa tgttagccaa acagcagatg cacattgact ctcatgaagc    5040
ccttggagtg ttaaatacat tatttgagat tttggcccct cctcctcc gtccggtaga    5100 catgctttta cggagtatgt tcgtcactcc aaacacaatg gcgtccgtga gcactgttca    5160 actgtgata tcgggaattc tggccatttt gagggttctg atttcccagt caactgaaga    5220
tattgttctt tctcgtattc aggagctctc cttctctccg tatttaatct cctgtacagt    5280
aattaatagg ttaagagatg gggacagtac ttcaacgcta gaagaacaca gtgaagggaa    5340
acaaataaag aatttgccag aagaaacatt ttcaaggttt ctattacaac tggttggtat    5400
tcttttagaa gacattgtta caaaacagct gaaggtggaa atgagtgagc agcaacatac    5460
tttctattgc caggaactag gcacactgct aatgtgtctg atccacatct tcaagtctgg    5520
aatgttccgg agaatcacag cagctgccac taggctgttc cgcagtgatg gctgtggcgg    5580
cagtttctac accctggaca gcttgaactt gcgggctcgt tccatgatca ccacccaccc    5640
ggccctggtg ctgctctggt gtcagatact gctgcttgtc aaccacaccg actaccgctg    5700
gtgggcagaa gtgcagcaga ccccgaaaag acacagtctg tccagcacaa agttacttag    5760
tccccagatg tctggagaag aggaggattc tgacttggca gccaaacttg gaatgtgcaa    5820
tagagaaata gtacgaagag gggctctcat tctcttctgt gattatgtct gtcagaacct    5880
ccatgactcc gagcacttaa cgtggctcat tgtaaatcac attcaagatc tgatcagcct    5940
ttcccacgag cctccagtac aggacttcat cagtgccgtt catcggaact ctgctgccag    6000
cggcctgttc atccaggcaa ttcagtctcg ttgtgaaaac ctttcaactc caaccatgct    6060
gaagaaaact cttcagtgct tggagggat ccatctcagc cagtcgggag ctgtgctcac    6120
gctgtatgtg gacaggcttc tgtgcacccc tttccgtgtg ctggctcgca tggtcgacat    6180
ccttgcttgt cgccgggtag aaatgcttct ggctgcaaat ttacagagca gcatggccca    6240
gttgccaatg gaagaactca acagaatcca ggaataccct cagagcagcg ggctcgctca    6300
gagacaccaa aggctctatt ccctgctgga caggtttcgt ctctccacca tgcaagactc    6360
```

-continued

```
acttagtccc tctcctccag tctcttccca cccgctggac ggggatgggc acgtgtcact   6420
ggaaacagtg agtccggaca aagactggta cgttcatctt gtcaaatccc agtgttggac   6480
caggtcagat tctgcactgc tggaaggtgc agagctggtg aatcggattc ctgctgaaga   6540
tatgaatgcc ttcatgatga actcggagtt caacctaagc ctgctagctc catgcttaag   6600
cctagggatg agtgaaattt ctggtggcca gaagagtgcc cttttgaag cagcccgtga    6660
ggtgactctg gcccgtgtga gcggcaccgt gcagcagctc cctgctgtcc atcatgtctt   6720
ccagcccgag ctgcctgcag agccggcggc ctactggagc aagttgaatg atctgtttgg   6780
ggatgctgca ctgtatcagt ccctgcccac tctggcccgg ccctggcac agtacctggt    6840
ggtggtctcc aaactgccca gtcatttgca ccttcctcct gagaaagaga aggacattgt   6900
gaaattcgtg gtggcaaccc ttgaggccct gtcctggcat ttgatccatg agcagatccc   6960
gctgagtctg gatctccagg cagggctgga ctgctgctgc ctggccctgc agctgcctgg   7020
cctctggagc gtggtctcct ccacagagtt tgtgacccac gcctgctccc tcatctactg   7080
tgtgcacttc atcctggagg ccgttgcagt gcagcctgga gcagcagcttc ttagtccaga  7140
aagaaggaca ataccccaa aagccatcag cgaggaggag gaggaagtag atccaaacac    7200
acagaatcct aagtatatca ctgcagcctg tgagatggtg gcagaaatgg tggagtctct   7260
gcagtcggtg ttggccttgg gtcataaaag gaatagcggc gtgccggcgt ttctcacgcc   7320
attgctaagg aacatcatca tcagcctggc ccgcctgccc cttgtcaaca gctacacacg   7380
tgtgccccca ctggtgtgga gcttggatg gtcacccaaa ccgggagggg attttggcac    7440
agcattccct gagatccccg tggagttcct ccaggaaaag gaagtcttta aggagttcat   7500
ctaccgcatc aacacactag gctggaccag tcgtactcag tttgaagaaa cttgggccac   7560
cctccttggt gtcctggtga cgcagcccct cgtgatggag caggaggaga gcccaccaga   7620
agaagacaca gagaggaccc agatcaacgt cctggccgtg caggccatca cctcactggt   7680
gctcagtgca atgactgtgc ctgtggccgg caacccagct gtaagctgct ggagcagca    7740
gccccggaac aagcctctga agctctcga caccaggttt gggaggaagc tgagcattat    7800
cagagggatt gtggagcaag agattcaagc aatggttca aagagagaga atattgccac    7860
ccatcattta tatcaggcat gggatcctgt cccttctctg tctccggcta ctacaggtgc   7920
cctcatcagc cacgagaagc tgctgctaca gatcaacccc gagcgggagc tggggagcat   7980
gagctacaaa ctcggccagg tgtccataca ctccgtgtgg ctggggaaca gcatcacacc   8040
cctgagggag gaggaatggg acgaggaaga ggaggaggag gccgacgccc ctgcaccttc   8100
gtcaccaccc acgtctccag tcaactccag gaaacaccgg gctggagttg acatccactc   8160
ctgttcgcag ttttttgcttg agttgtacag ccgctggatc ctgccgtcca gctcagccag  8220
gaggaccccg gccatcctga tcagtgaggt ggtcagatcc cttctagtgg tctcagactt   8280
gttcaccgag cgcaaccagt ttgagctgat gtatgtgacg ctgacagaac tgcgaagggt   8340
gcacccttca gaagacgaga tcctcgctca gtacctggtg cctgccacct gcaaggcagc   8400
tgccgtcctt gggatggaca aggccgtggc ggagcctgtc agccgcctgc tggagagcac   8460
gctcaggagc agccacctgc ccagcagggt tggagcccttg cacggcgtcc tctatgtgct   8520
ggagtgcgac ctgctggacg acactgccaa gcagctcatc ccggtcatca gcgactatct   8580
cctctccaac ctgaaaggga tcgcccactg cgtgaacatt cacagccagc agcacgtact   8640
ggtcatgtgt gccactgcgt tttacctcat tgagaactat cctctggacg tagggccgga   8700
attttcagca tcaataatac agatgtgtgg ggtgatgctg tctggaagtg aggagtccac   8760
```

```
cccctccatc atttaccact gtgccctcag aggcctggag cgcctcctgc tctctgagca    8820
gctctcccgc ctggatgcag aatcgctggt caagctgagt gtggacagag tgaacgtgca    8880
cagcccgcac cgggccatgg cggctctggg cctgatgctc acctgcatgt acacaggaaa    8940
ggagaaagtc agtccgggta gaacttcaga ccctaatcct gcagccccg acagcgagtc     9000
agtgattgtt gctatggagc gggtatctgt tcttttgat aggatcagga aaggctttcc     9060
ttgtgaagcc agagtggtgg ccaggatcct gccccagttt ctagacgact tcttcccacc    9120
ccaggacatc atgaacaaag tcatcggaga gtttctgtcc aaccagcagc catacccca    9180
gttcatggcc accgtggtgt ataaggtgtt tcagactctg cacagcaccg gcagtcgtc     9240
catggtccgg gactgggtca tgctgtccct ctccaacttc acgcagaggg ccccggtcgc    9300
catggccacg tggagcctct cctgcttctt tgtcagcgcg tccaccagcc cgtgggtcgc    9360
ggcgatcctc ccacatgtca tcagcaggat gggcaagctg agcaggtgg acgtgaacct     9420
tttctgcctg gtcgccacag acttctacag acaccagata gaggaggagc tcgaccgcag    9480
ggccttccag tctgtgcttg aggtggttgc agccccagga agcccatatc accggctgct    9540
gacttgttta cgaaatgtcc acaaggtcac cacctgctga cgccatggt gggagagact     9600
gtgaggcggc agctggggcc ggagcctttg gaagtctgcg cccttgtgcc ctgcctccac    9660
cgagccagct tggtccctat ggcttccgc acatgccgcg gcggccagg caacgtgcgt      9720
gtctctgcca tgtggcagaa gtgctctttg tggcagtggc caggcaggga gtgtctgcag    9780
tcctggtggg gctgagcctg aggccttcca gaaagcagga gcagctgtgc tgcaccccat    9840
gtgggtgacc aggtcctttc tcctgatagt cacctgctgg ttgttgccag gttgcagctg    9900
ctcttgcatc tgggccagaa gtcctcccttc ctgcaggctg gctgttggcc cctctgctgt   9960
cctgcagtag aaggtgccgt gagcaggctt tgggaacact ggcctgggtc tccctggtgg   10020
ggtgtgcatg ccacgccccg tgtctggatg cacagatgcc atggcctgtg ctgggccagt   10080
ggctgggggt gctagacacc cggcaccatt ctcccttctc tcttttcttc tcaggattta   10140
aaatttaatt atatcagtaa agagattaat tttaacgtaa ctctttctat gcccgtgtaa   10200
agtatgtgaa tcgcaaggcc tgtgctgcat gcgacagcgt ccggggtggt ggacagggcc   10260
cccggccacg ctccctctcc tgtagccact ggcatagccc tcctgagcac ccgctgacat   10320
ttccgttgta catgttcctg tttatgcatt cacaaggtga ctgggatgta gagaggcgtt   10380
agtgggcagg tggccacagc aggactgagg acaggccccc attatcctag gggtgcgctc   10440
acctgcagcc cctcctcctc gggcacagac gactgtcgtt ctccacccac cagtcaggga   10500
cagcagcctc cctgtcactc agctgagaag gccagccctc cctggctgtg agcagcctcc   10560
actgtgtcca gagacatggg cctcccactc ctgttccttg ctagccctgg ggtgcgtct    10620
gcctaggagc tggctggcag gtgttgggac ctgctgctcc atggatgcat gccctaagag   10680
tgtcactgag ctgtgttttg tctgagcctc tctcggtcaa cagcaaagct tggtgtcttg   10740
gcactgttag tgacagagcc cagcatccct tctgcccccg ttccagctga catcttgcac   10800
ggtgacccct tttagtcagg agagtgcaga tctgtgctca tcggagactg ccccacggcc   10860
ctgtcagagc cgccactcct atccccaggc caggtccctg accagcctc ctgtttgcag    10920
gcccagagga gccaagtcat taaaatggaa gtggattctg gatggccggg ctgctgctga   10980
tgtaggagct ggatttggga gctctgcttg ccgactggct gtgagacgag gcaggggctc   11040
tgcttcctca gccctagagg cgagccaggc aaggttggcg actgtcatgt ggcttggttt   11100
```

-continued

```
ggtcatgccc gtcgatgttt tgggtattga atgtggtaag tggaggaaat gttggaactc    11160
tgtgcaggtg ctgccttgag accccaagc ttccacctgt ccctctccta tgtggcagct    11220
ggggagcagc tgagatgtgg acttgtatgc tgcccacata cgtgaggggg agctgaaagg    11280 gagccctcc tctgagcagc ctctgccagg cctgtatgag gcttttccca ccagctccca    11340
acagaggcct ccccagcca ggaccacctc gtcctcgtgg cggggcagca ggagcggtag    11400
aaaggggtcc gatgtttgag gaggcccta agggaagcta ctgaattata acacgtaaga    11460
aaatcaccat tccgtattgg ttggggctc ctgtttctca tcctagcttt ttcctggaaa    11520
gcccgctaga aggtttggga acgaggggaa agttctcaga actgttggct gctccccacc    11580
cgcctcccgc ctccccgca ggttatgtca gcagctctga gacagcagta tcacaggcca    11640
gatgttgttc ctggctagat gtttacattt gtaagaaata acactgtgaa tgtaaaacag    11700
agccattccc ttggaatgca tatcgctggg ctcaacatag agtttgtctt cctcttgttt    11760
acgacgtgat ctaaaccagt ccttagcaag gggctcagaa caccccgctc tggcagtagg    11820 tgtccccac cccaaagac ctgcctgtgt gctccggaga tgaatatgag ctcattagta    11880
aaaatgactt cacccacgca tatacataaa gtatccatgc atgtgcatat agacacatct    11940
ataattttac acacacacct ctcaagacgg agatgcatgg cctctaagag tgcccgtgtc    12000
ggttcttcct ggaagttgac tttccttaga cccgccaggt caagttagcc gcgtgacgga    12060
catccaggcg tgggacgtgg tcagggcagg gctcattcat tgcccactag gatcccactg    12120
gcgaagatgg tctccatatc agctctctgc agaagggagg aagactttat catgttccta    12180
aaaatctgtg gcaagcaccc atcgtattat ccaaattttg ttgcaaatgt gattaatttg    12240
gttgtcaagt tttgggggtg ggctgtgggg agattgcttt tgttttcctg ctggtaatat    12300
cgggaaagat tttaatgaaa ccagggtaga attgtttggc aatgcactga agcgtgtttc    12360
tttcccaaaa tgtgcctccc ttccgctgcg ggcccagctg agtctatgta ggtgatgttt    12420
ccagctgcca agtgctcttt gttactgtcc accctcattt ctgccagcgc atgtgtcctt    12480
tcaaggggaa aatgtgaagc tgaacccct ccagacaccc agaatgtagc atctgagaag    12540
gccctgtgcc ctaaaggaca ccctcgccc ccatcttcat ggaggggtc atttcagagc    12600 cctcggagcc aatgaacagc tcctcctctt ggagctgaga tgagcccac gtggagctcg    12660 ggacggatag tagacagcaa taactcggtg tgtggccgcc tggcaggtgg aacttcctcc    12720
cgttgcgggg tggagtgagg ttagttctgt gtgtctggtg ggtggagtca ggcttctctt    12780
gctacctgtg agcatccttc ccagcagaca tcctcatcgg gctttgtccc tcccccgctt    12840
cctccctctg cggggaggac ccgggaccac agctgctggc cagggtagac ttggagctgt    12900
cctccagagg ggtcacgtgt aggagtgaga agaaggaaga tcttgagagc tgctgaggga    12960
ccttggagag ctcaggatgg ctcagacgag gacactcgct tgccgggcct gggcctcctg    13020
ggaaggaggg agctgctcag aatgccgcat gacaactgaa ggcaacctgg aaggttcagg    13080
ggccgctctt ccccatgtg cctgtcacgc tctggtgcag tcaaaggaac gccttcccct    13140
cagttgtttc taagagcaga gtctcccgct gcaatctggg tggtaactgc cagccttgga    13200
ggatcgtggc caacgtggac ctgcctacgg agggtgggct ctgacccaag tggggcctcc    13260
ttgtccaggt ctcactgctt tgcaccgtgg tcagagggac tgtcagctga gcttgagctc    13320
ccctggagcc agcagggctg tgatgggcga gtcccggagc cccacccaga cctgaatgct    13380
tctgagagca aagggaagga ctgacgagag atgtatattt aattttttaa ctgctgcaaa    13440
cattgtacat ccaaattaaa ggaaaaaaat ggaaaccatc a                        13481
```

<210> SEQ ID NO 2
<211> LENGTH: 172001
<212> TYPE: DNA
<213> ORGANISM: H. sapiens

<400> SEQUENCE: 2

```
cctgcagggg cctctccagc tcactggggg tggggtgggg gtcacacttg gggtcctcag      60
gtcgtgccga ccacgcgcat tctctgcgct ctgcgcagga gctcgcccac cctctccccg     120
tgcagagagc cccgcagctg ctccccgca gggctgtccg ggtgagtatg gctctggcca     180
cgggccagtg tggcgggagg gcaaaccccca aggccacctc ggctcagagt ccacggccgg     240
ctgtcgcccc gctccaggcg tcggcggggg atcctttccg catgggcctg cgcccgcgct     300
cggcgccccc tccacggccc cgcccgtcc atggccccgt ccttcatggg cgagcccctc     360
catggccctg cccctccgcg ccccacccct ccctcgcccc acctctcacc ttcctgcccc     420
gcccccagcc tccccaaccc tcaccggcca gtcccctccc ctatcccgtc cgcccctcag     480
ccgccccgcc cctcagccgg cctgcctaat gtcccccgtcc ccagcatcgc cccgccccgc     540
ccccgtctcg ccccgcccct caggcggcct ccctgctgtg ccccgccccg gcctcgccac     600
gcccctacct caccacgccc ccgcatcgc cacgccccccc gcatcgccac gcctccctta     660
ccatgcagtc ccgccccgtc ccttcctcgt cccgcctcgc cgcgacactt cacacacagc     720
ttcgcctcac cccattacag tctcaccacg ccccgtcccc tctccgttga gccccgcgcc     780
ttcgcccggg tggggcgctg cgctgtcagc ggccttgctg tgtgaggcag aacctgcggg     840
ggcagggggcg ggctggttcc ctggccagcc attggcagag tccgcaggct agggctgtca     900
atcatgctgg ccggcgtggc cccgcctccg ccggcgcggc cccgcctccg ccggcgcagc     960
gtctgggacg caaggcgccg tgggggctgc cgggacgggt ccaagatgga cggccgctca    1020
ggttctgctt ttacctgcgg cccagagccc cattcattgc cccggtgctg agcggcgccg    1080
cgagtcggcc cgaggcctcc ggggactgcc gtgccgggcg ggagaccgcc atggcgaccc    1140
tggaaaagct gatgaaggcc ttcgagtccc tcaagtcctt ccagcagcag cagcagcagc    1200
agcagcagca gcagcagcag cagcagcagc agcagcagca acagccgcca ccgccgccgc    1260
cgccgccgcc gcctcctcag cttcctcagc cgccgccgca ggcacagccg ctgctgcctc    1320
agccgcagcc gccccgccg ccgccccgc cgccaccccgg cccggctgtg gctgaggagc    1380
cgctgcaccg accgtgagtt tgggcccgct gcagctccct gtcccggcgg gtcccaggct    1440
acggcgggga tggcggtaac cctgcagcct gcgggccggc gacacgaacc cccggccccg    1500
cagagacaga gtgacccagc aacccagagc ccatgaggga caccgccccc ctcctggggc    1560
gaggccttcc cccacttcag cccgctcccc tcacttgggt cttcccttgt cctctcgcga    1620
ggggaggcag agccttgttg gggcctgtcc tgaattcacc gaggggagtc acggcctcag    1680
ccctctcgcc cttcgcagga tgcgaagagt tgggcgaga acttgtttct ttttatttgc    1740
gagaaaccag gcggggggtt cttttaactg cgttgtgaag agaacttgga ggagccgaga    1800
tttgctcagt gccacttccc tcttctagtc tgagagggaa gagggctggg ggcgcgggac    1860
acttcgagag gaggcggggt ttggagctgg agagatgtgg gggcagtgga tgacataatg    1920
cttttaggac gcctcggcgg gagtggcggg gcagggggggg ggcggggagt gagggcgcgt    1980
ccaatgggag atttctttc ctagtggcac ttaaaacagc ctgagatttg aggctcttcc    2040
tacattgtca ggacatttca tttagttcat gatcacggtg gtagtaacac gattttaagc    2100
```

```
accacctaag agatctgctc atctaagcct aagttggtct gcaggcgttt gaatgagttg   2160
tggttgccaa gtaaagtggt gaacttacgt ggtgattaat gaaattatct taaatattag   2220
gaagagttga ttgaagtttt ttgcctatgt gtgttgggaa taaaaccaac acgttgctga   2280
tggggaggtt aattgccgag ggatgaatga ggtgtacatt ttaccagtat tccagtcagg   2340
cttgccagaa tacgggggt ccgcagactc cgtgggcatc tcagatgtgc cagtgaaagg    2400
gtttctgttt gcttcattgc tgacagcttg ttacttttg gaagctaggg gtttctgttg    2460
cttgttcttg gggagaattt ttgaaacagg aaaagagaga ccattaaaac atctagcgga   2520
accccaggac tttccctgga agtctgtgtg tcgagtgtac agtaggagtt aggaagtact   2580
ctggtgcagt tcaggccttt ctcttacctc tcagtattct atttccgatc tggatgtgtc   2640
ccagatggca tttggtaaga atatctctgt taagactgat taatttttag taatatttct   2700
tgttctttgt ttctgttatg atccttgtct cgtcttcaaa gtttaattag aaaatgattc   2760
ggagagcagt gttagcttat tgttggaat aaaatttagg aataaattat tctaaaggat    2820
ggaaaaactt tttggatatt tggagaaatt ttaaaacaat ttggcttatc tcttcagtaa   2880
gtaatttctc atccagaaat ttactgtagt gcttttctag gaggtaggtg tcataaaagt   2940
tcacacattg catgtatctt gtgtaaacac taaacagggc tcctgatggg aaggaagacc   3000
tttctgctgg gctgcttcag acacttgatc attctaaaaa tatgccttct ctttcttatg   3060
ctgatttgac agaacctgca tttgcttatc ttcaaaatat gggtatcaag aaatttcctt   3120
tgctgccttg acaaggaga tagattttgt ttcattactt taaggtaata tatgattacc    3180
ttatttaaaa aatttaatca ggactggcaa ggtggcttac acctttaatc cgagcacttt   3240
gggaggccta ggtggacgaa tcacctgagg tcaggagttt gagaccagcc tggctaacat   3300
ggtgaaaccc tgtctctact aaaaatacaa aaattagctg gtcatggtgg cacgtgcctg   3360
taatccaagc tacctgggag gctgaggcag gaaaatcgct tgaacccggg aggcagagtc   3420
tgcagtgagt tgagatcacg ccactgcact ccagcctggg tgacagagcg agactctatc   3480
tcaaaaaaaa tttttttaa tgtattattt ttgcataagt aatacattga catgatacaa    3540
attctgtaat tacaaaaggg caataattaa aatatcttcc ttccaccct ttcctctgag    3600 tacctaactt tgtccccaag aacaagcact atttcagttc ctcatgtatc ctgccagata   3660
taacctgttc atattgtaag atagatttaa aatgctctaa aaacaaaagt agtttagaat   3720
aatatatatc tatatatttt ttgagatgta gtctcacatt gtcacccagg ctggagtgca   3780
gtgatacaat ctcggctcac tgcagtctct gcctcccagg ttcaaatgct tctcctgcct   3840
cagccttctg agtagctggg attacaggcg cccaccacca tgtccagcta attttgtat    3900 ttttagtaga gatggggttt caccatgttg gccaggctgg tcttgaactc ctgaccttgt   3960
gatctgtcca cctcggcctc ccaaagtgct gggattacag gtgtgagcca ccatgcctgg   4020
ctagaataat aactttaaa ggttcttagc atgctctgaa atcaactgca ttaggtttat    4080 ttatagttt atagttattt taaataaat gcatatttgt catatttctc tgtatttgc      4140 tgttgagaaa ggaggtattc actaattttg agtaacaaac actgctcaca agtttggat    4200 tttggcagtt ctgttcacgt gcttcagcca aaaaatcctc ttctcaaagt aagattgatg   4260
aaagcaattt agaaagtatc tgttctgttt ttatggctct tgctctttgg tgtggaactg   4320
tggtgtcacg ccatgcatgg gcctcagttt atgagtgttt gtgctctgct cagcatacag   4380
gatgcaggag ttccttatgg ggctggctgc aggctcagca aatctagcat gcttgggagg   4440
gtcctcacag taattaggag gcaattaata cttgcttctg gcagtttctt attctccttc   4500
```

```
agattcctat ctggtgtttc cctgacttta ttcattcatc agtaaatatt tactaaacat    4560
gtactatgtg cctggcactg ttataggtgc agggctcagc agtgagcaga caaagctctg    4620
ccctcgtgaa gctttcattc taatgaagga catagacagt aagcaagata gataagtaaa    4680
atatacagta cgttaatacg tggaggaact tcaaagcagg gaaggggata gggaaatgtc    4740
agggttaatc gagtgttaac ttattttttat ttttaaaaaa attgttaagg gctttccagc    4800
aaaacccaga aagcctgcta gacaaattcc aaaagagctg tagcactaag tgttgacatt    4860 tttatttat tttgttttgt tttgtttttt ttgagacagt tcttgctcta tcagccaggc    4920
tggagtgcac tagtgtgatc ttggctcact gcaacctctg cctcttgggt tcaagtgatt    4980
ctcatgcctc agcctcctgt ttagctggga ttatagacat gcactgccat gcctgggtaa    5040
tttttttttt ttccccgag acggagtctt gctctgtcgc ccaggctgga gtgcagtggc    5100
gcgatctcag ctcactgcaa gctccgcttc ccgagttcac gccattctcc tgcctcagtc    5160
tcccaagtag ctgggactac aggcgcctgc caccacgtcc agctaatttt tttgtatttt    5220
taatagagac ggggtttcac cgtgttagcc aggatgatct tgatctcctg acctcgtcat    5280
ccgccgacct tgtgatccgc ccacctcggc ctcccaaagt gctgggatta caggcatgag    5340
ccactgtgcc cggccacgcc tgggtaattt ttgtattttt agtagagatg ggttttgcc     5400 atgatgagca ggctggtctc gaactcccgg cctcatgtga tctgcctgcc ttggcctccc    5460
aaagtgctag gattacaggc atgagccacc atacctggcc agtgttgata ttttaaatac    5520
ggtgttcagg gaaggtccac tgagaagaca gcttttttt tttttttttt tggggttggg     5580
gggcaaggtc ttgctctttta acccaggctg gaatgcagta tcactatcgt agctcacttc    5640
agccttgaac tcctgggctc aagtgatcct cccacctcaa cctcacaatg tgttgggact    5700
ataggtgtga gccatcacac ctggccagat gatggctttt gagtaaagac ctcaagcgag    5760
ttaagagtct agtgtaaggg tgtatgaagt agtggtattc cagatggggg gaacaggtcc    5820
aaaatcttcc tgtttcagga atagcaagga tgtcatttta gttgggtgaa ttgagtgagg    5880
gggacatttg tagtaagaag taaggtccaa gaggtcaagg gagtgccata tcagaccaat    5940
actacttgcc ttgtagatgg aataaagata ttggcattta tgtgagtgag atgggatgtc    6000
actggaggat tagagcagag gagtagcatg atctgaattt caatcttaag tgaactctgg    6060
ctgacaacag agtgaagggg aacaccggca aaagcagaaa ccagttagga agccactgca    6120
gtgctcagat aagcatggtg ggttctgtca gggtaccggc tgtcggctgt gggcagtgtg    6180
aggaatgact gactggattt tgaatgcgga accaactgca cttgttgaac tctgctaagt    6240
ataacaattt agcagtagct tgcgttatca ggtttgtatt cagctgcaag taacagaaaa    6300
tcctgctgca atagcttaaa ctggtaacaa gcaagagctt atcagaagac aaaaataagt    6360
ctggggaaat tcaacaataa gttaaggaac ccaggctctt tctttttttt ttttttgaaa    6420
cggagtttcg ctcttgtcac ccgggctgga gtgcaatgat gtgatctcag ctcactaaaa    6480
cctctacctc ctgggttcaa gtgattcttc tgcctcagcc tcccaagtaa ctgggattac    6540
aggcgtatac caccatgccc agctaatttt tgtgttttta gtagagatgg ggtttcacca    6600
tgttggccag gctggtctcg aacttctgac ctcaggtgat ccactcgcct cagcctgcca    6660
aagtgctggg attacaggtt tgggccactg cacccggtca gaacccaggc tctttcttat    6720
acttaccttg caaaccccttg ttctcatttt ttcccttttgt atttttattg ttgaattgta    6780
atagttcttt atatattctg gatactggat tcttatcaga tagatgattt gtaaaaactc    6840
```

```
tcccttcctt tggattgtct ttttactttc ttgatagtgt cttttgaagt gtaaaagttt    6900
ttaattttga tgaagtcgag tttatctatt ttgtctttgg ttgctgtgct tcaagtgtca    6960
tatctaagaa atcattgtct aatccaaagt caaaaaggtt tactcctatg ttttcttcta    7020
agaattttag agttttacat ttaagtctga tccattttga gttaattttt atatatggtt    7080
caggtagaag tccaacttta ttcttttcca tgtggttatt cagttgtccc agcactgttt    7140
gttgaagaga ctattctttc cccatggaat tatcttagta cccttgttga aaattaatcg    7200
tccttaattg tataaattta tttctagact gtcagttcta cctgttggtc tttatgtcga    7260
tcctgtgcca gtaccataca gtcttgatta ctgaagtttg tgtcacagtt taaattcatg    7320
aaatgtgagt tctccaactt tgttcctttt caagattgat ttggccatgc tgggtccctt    7380
gcatttccgt acgaattgta ggatcagctt gtcagtttca acaaagaagc caagtaggat    7440
tctgagaggg attgtgttga atctgtagat caacttgggg agtattcgca tcttaacaat    7500
attgtcttcc acctatgaac atgggcaaac tttgtgtaaa tggtcagatt gtaagtattt    7560
cgggctgtgt gggcacagtg tctctgtcac agctacgcgg ctctgccatt gtagcatgaa    7620
agtagccata agcaatatgt atgagtgtct gtgttccaat agaattttat taatgacaag    7680
gaagtttgaa tttcatataa ttttcacctg tcatgagata gtatttgatt attttggtca    7740
accatttaaa aatgtaaaaa catttcttag cttgtgaact agccaaaaat atgcaggtta    7800
tagttttccc actcctaggt taaaatatga taggaccaca tttggaaagc atttcttttt    7860
tttttttttt tttttttttt gagacggagt ttcactcttg ttgcccaggc tggagtgcag    7920
tggcgcgatc tcggctcact gcaacctctg cctcccaggt tcaagacatt ctcctgcacg    7980
gcctccctag tagctgggat tacaggcatg cgccaccaca cccagctaat tttgtatttt    8040
tagtagagac ggggtttctc catgttggtc aggctggtct tgaactcctg acctcaggtg    8100
atccacccgc ctcagcctcc caaagtgctg ggattacagg gtgtgagcca ccacaccctg    8160
ctggaaagca tttctttttt ggctgttttt gttttttttt taaactagtt ttgaaaatta    8220
taaaagttac acatatacat tataaaaata tcttcaagca gcacagatga aaaacaaagc    8280
ccttcttgca agtctgtcat cttttgtctaa cttcctaaga acaaaagtgt tcttgtgtc    8340
ttcttcccag attttaatat gcatatacaa gcatttaaat gtgtcatttt ttgtttgctt    8400
gactgagatc acattacata tgtatttttt tacttaacaa tgtgtcatag atattgttcc    8460
atagcagtac ctgtaattct tattaattgc tatgtaatat tttagaattt cttttttaaaa    8520
gaggactttt ggagatgtaa aggcaaaggt ctcacatttt tgtggctgta gaatgtgctg    8580
gtgacatatt ctctctacct tgagaagtcc ccatccccat cacctccatt tcctgtaaat    8640
aagtcaacca cttgataaac taccttgaa tggatccaca ctcaaaacat ttagtcttat    8700
tcagacaaca aggaggaaaa ataaaatacc ttataaagca ctgtttaata ttgtattaaa    8760
ttggatcaat ttgggggcta gaatgtatgt tagagacatg atatgtccat aggtccttgc    8820
tatcacagtg aggtctcagg gacagtcgtt tggtatcatt tgggatctca taagcagact    8880
ctctctgctt gacctgacaa atcagagtct gtgttttaac aggttcagtg agtgacttac    8940
atgcacattg gagtttggga agctccactg taggtgctta gaccttacct ttgttgttgc    9000
taataacaat gcaagcattt gggaggaaga cctgtgttgc tcatatgtgt ccaggtgtag    9060
ctgaggtggc cttgcttatc tgctgtaggg ccgttgagca tttctgtagc tgtgatgagt    9120
gagctgaggt gagcctgcgg agagctccca gccattggta gtgggactcg cttagatgaa    9180
ctggaaggac cctttcatct gagcagccac tatggagaaa aacaaccgaa tgaggggaga    9240
```

```
gacaatgtgc aatttattt agggcacaaa ggagagctgt ggttagaagg tgacatttga    9300
gtggaaaggg ggcaagccat gtgtatagcg ggagaagaga ggtccaggca gagttaacag    9360
aaggcagaaa tgcttccat gtttgagaac cagtaaggag gccagtggct gaagtaaggt     9420
gaagggcaga ataaggatg aggctgcgag agatgagagg ttagagacga gcgtcttgtg     9480
caccaagata agcttgtgtg gtcaaaacaa gtagtttaat ttatgtttt aaaagatcat     9540
tttggctggg cacaatggtt catgcctgta ataccagtag tttgagacgg tgtggtggga    9600
ggattgcctg aggccagacg accagcatag ccaacatagc agcacctata aggtctctac    9660
aaaaaacttt aaaaaattag ctgggcatag tggtgtgtgc ctgtagtccc agctactcag    9720
gaggctgagg aggctggagg attgcttgag tccaggagtt tgaggctgca gtgagctatg    9780
attatgccac tacactacaa cctgggcaag agagtgagac cctgtctcta aatatacaca    9840
cacacacaca cacacacaca cacacacaca cacacacaca cacacacaca catatatg     9900
tatatatg catttagatg aaagatcac tttgacaata ccacatgctg gtgaggattt       9960
agaaaaacta ggtcacttat tgctggtggg aatataatat agtacggcca ctctggaaaa   10020
cagtttggca gtttgtcata aaactgaaca taccgttagt atacagccca gcagcaacta   10080
caatcctggg cattaatcct agagaaatga aaccttaatg ttcacataaa aacctatact   10140
caagtatgca tagcagcttt acccataata tctaagaact ggaatcagct cagatgtcct   10200
tcaacaggtg aatggttaaa ctactcagta ataaaaagga atgagctact gatagcatgc   10260
aacagtttag gtgaagttat gctaatgaaa aaagccaatc ccaaaaggtt atacatactg   10320
tatgattcta tgttttttg caatggcaca gttttaggga tggagaatag attagtggtt   10380
gcctggggtt agagatgggg tagtagagta ggttagtggt ggcagaggag agaaaagaga   10440
gggaggtgaa tgtggttata aaggacaac acaggggaat acttgtaatg gaaatgctt     10500
gtctttttt tttttttt tttttggcg acagagtctt gctctgttgc ccaggctgga       10560
gtgcagtggc atgatctttt ctcactgcaa cctctgcctc ctgggttcaa gtgatacttg   10620
tgtctcagtc tcccatgttc agagtgaaac aaaccagagg taatgttcat ccaaataatc   10680
caacacacat gacattaaaa catcaagatc aggtcggacg tggtggctca tgcctgtaat   10740
cccagcactt tgggaggcc aaggtgggca gatcacttga ggtcaggagt tcgagaccag    10800
ccgggccaac atgatgaaac cccatcttga ctaaaaatac aaaaattagc cgggcatggt   10860
ggtgtgcacc tgtagtccca gctacttggg aggctgaggc aagagaactg cttgaacccg   10920
aggggcagag gttgcagtga gctgagagtg cgccattgca cttcagcctg tgtgacagag   10980
taagactcca tctccaaaaa aaaaaaacca agatcaatta aaatacagca ttactgggcc   11040
gggtgtggtg gctcacacct gtaatcccag cactttggga ggccgagatg gcagatcac    11100
gaggtcagga gatccagacc atcccggcta acacggtgaa accccgtctc tactaaaaaa   11160
tacaaaaat agccgggta tagtggtggg tgcctgtagt cccagctact ggggaggctg    11220
aagcaggaga atggtgtgaa cccgggaggc agagctggca gtgagctgag atcgcgccac   11280
tgcactccag cctgggcgac agagcaagac tccgtctcgg gggaaaaaaa aaataaata    11340
aatagaatgc tgtagtgtcc ttgagtttac atgcccctcc ttacgcttgt gtgcccgtgc   11400
agattgcttg attacacaat tagaggaggc tggcggagga ttgttttaat ttttttttt   11460
ttgagacagt ctggctctgt tccccaggct agagtgcaat ggcgcaatct tggtgcactg   11520
caacctctgc ctcctgggtt caagcagttc ttctgccgca gcctcccgag tagctgggat  11580
```

```
tataggcgcc cgccaccacg cccaactatt ttttgtattt ttagtagagc agcgtttcac    11640
catgctggcc aggctggtct cgaactcctg acctcagatg atctgctgcc ccagcctccc    11700
aaagtgctgg gattacaggc gtgagccaca cctggccgtt tgttttaatt ttgaaggtga    11760
agtgaaagtg actacattta ccaaaagtga ttgaaaagcc aggactgttc ttaccctgtt    11820
tttccagttc ttgctcagag caaggtggtt tcttttttcac ttaatcacca tacttacttt    11880
tcatgtagaa caagtcagtt tgagttatca gttcatcatc ttaactaaat tccatggggg    11940
aaggaattag ttttagtttc ttaaacttcc aggtttgctt attggacaaa atgagatagc    12000
aaggcagtgt ttttaagtta gattttttat ttctttggta atacaatttt ctcagaaact    12060
tagtagtctt ttagtttagt tgtttttagt tggtcctatg ttttggatca cccctctcta    12120
ctttatttg atagtgccaa ctgtgaagac atctgaagcc ataggtttgg atgggaagga    12180
ggcatcttta gcctgatcat cttcgccagg ctgtttatct ccttttgctt ggctgagaag    12240
tcttaatagg aggcttattc ccagctattt ggggacatag aagcagttag ccattgctta    12300
tattttactg aggtctgtgt ggtatgttga ttgtagtcag ttaacgattt tgagaactga    12360
aggcagcctg gtatatatag agtaggtatt agactgtgtt tcttctaatt gaatttccca    12420
tctcttgtaa tctatgccat catcttctgt actgctgaga aagaaagaaa gtttctaatc    12480
aaactatacc actggttgta agatgcagtt tggctttagt gatgttaaca catgattcaa    12540
acgtgaaatt gattgagtat tggtgaaata cagaggagat ttaaagccag aagacctggg    12600
tttaaatgct ggctgtatga cttcatatct gtgtgatctt gggcatgtca tggttggcac    12660
ttcaatttct tctctctata atgggggaag tgaggccagt catggtggct catacctata    12720
atcccagtgc tttgggaggc caagatggga agatcgcttg aggccaggag tttgagcaat    12780
tgggcaacat cgtgaggccc cgtctctaca aaatattttg aaaaaattag ccaggcccag    12840
tggtgcgtgc ctgtggtccg cgccactcag gaggctgaga cgggaggatc ctttcagcct    12900
aggagtttaa ggctaaagtg agccatgatt gtgctatcgt actccagcct gggcagcaga    12960
gcaagatcct gactctaaaa aaaagtaaaa taaagtaaaa tgggggaaat gaactgcttt    13020
agtaacatca tctgtttttt ctgtgagcag cgtagcttga cagccattgg tgaactcgtg    13080
ccctgtgctt ccctgtccag atccccattc tgcccgcaac atggagtata acggtttatt    13140
catagtagtc gagaaacact cactgaatga atgaatgagg tgtagaacta agtggagtgg    13200
gtaattcaac acatattaat ttccttcttt ttttatttt tagaaagaaa gaactttcag    13260
ctaccaagaa agaccgtgtg aatcattgtc tgacaatatg tgaaaacata gtggcacagt    13320
ctgtcaggta attgcacttt gaactgtcta gagaaaataa gaactttgta tattttcagt    13380
cttaatgggc tagaatattc tttgtgtccc agctatttta aatggattca gaaatccatt    13440
taagatgaag aaggaccctt tccccatatt tctggctata tacaaggata tccagacact    13500
gaaatgaata atgttccctt tttgtaatct tttatgcaaa aattaaaacc attatggtaa    13560
ttgaacaaca tgtttatgtt tagttaacac ccttagcaac tatagttatt ttaaaaccat    13620
ctatggtttg atattttgc atttgttgca atagtaggaa cagcacaaga cagttcagtt    13680
tgtctctctt atttgctttt tcttggcagt ttgctgtcct attgtacctc tgctcctagc    13740
agtggctgga gcccactcct ctgtgcttcg ggattagtgg ggatcgtggg gcattgactg    13800
taggtcagct ttccttgctt gatctttctc actgggatga actagcagca ccttctttg    13860
tagctgcttt gcttttgact atctttctga ccgttgttcc tagtagctgt agatggtaaa    13920
tatatttagg cctgttttcca atggctcagt aggagacata ttcacctatg atatctgaat    13980
```

```
tctgttaccc acatgggcat gcgtgaaata gttgccttgc cttactttcc cttggaataa    14040
ataattcatg ttattctcct ggtagaagct agaaaaagcc tttatagtca gtcagaaaaa    14100
aatttttaga caaataatct tgattttagt actgacaaaa acgtgtggtg attcttttt    14160
taatttttt ttgagacgga gtttcactct tgttgcccag gctggagtgc aatggcgtga    14220
tctcggctca ctgcaacctc tgcctcctgg gttcaagtga ttctcctgcc tcagcctccc    14280
aagtagctgg agttacaggc atgtgctact gtgcccagct aattttgtat ttttagtaga    14340
gatgttggtc aggctgatct cgaactccca accttaggtg atctgcccgc ctcagcctcc    14400
caaagtgctg ggattacagg cgtgagccag gcgcccggt gattcatttg ttttttcaaa     14460
aaatttcctc ttggccattg cttttcactt ttgttttttt tttttttttg agacggagtc    14520
acgatctgtc acccaggctg gagtgcagtg gcatgatctt ggcttactgc aagctctgcc    14580
tcccaggttc acgccattct cctgcttcag cctggcgagt agctgggact acaggtgctc    14640
gccaccacac ccggctaatt ttttgtattt ttagtagaga tggggtttca ccgtggtctt    14700
gatctcctga cctcatgacc cgctcaactc agcctcccaa agtgctggga ttacaggcgt    14760
gagccaccgc gcccggccct ctcttgtctt tttattgtgg taaaatgcac ataaaattga    14820
ctgtcttaac cattttagg ggtacagttc agtatatata ttcgtaatgt tgtacagcca     14880
tcactgccat ctacttcata gttttttctt ctgtcaaaac tgaacatctg tcttcattaa    14940
actccctatc atccattctt tcctgtagtc cctttctact ttctgtctgt atgagtgtaa    15000
ctgctctgga gacctcatgt aagtggattc ctacaggatt tgtgttttt ttttggtgat     15060
ctgcttattt ttaatgcctc tgtgcatttg tattatatac tttcaaagtg atttcacaaa    15120
accgtttcat tttaggttaa ctcatttctg ttgtttgtga aatactgtgt atgattctgt    15180
tctgtttctg tctaatttgt ggaaatgttg tgggaagaaa atgaaataac aaatgagcat    15240
atgtcctgaa aataaaaata taaaaattct aagttagcat gctattgtag aatacaacgc    15300
tatgataaaa gtaggaaaaa aaaggttttg aattctatct ctgctacctg tgtaagctgg    15360
gtgactttag ataagctgta acgtgtttga gccttactgg ctcatttttg aaatgtaatc    15420
cctagttaca cagttcttgt gggatcagat ggtacatgtg aaacactgtg aaaaagcaac    15480
tgcatagata tgttcattag ccacctgagc gggaagcgta tcccattgcg atgcccatca    15540
tccaaagcta tatgttatct ttactttttt tttttgaga cagagtcttg ctctgttgcc    15600
caggctagag tgcagtggtg caatctcagc tcactgcaag ctccacctcc cgggttcacg    15660
ctattctcct gccccagcct cccaagtagc tgggactaca gcacccgcc accatgcctg     15720
gctaaatttt tgtatttta gtagagatgg ggtttcaccg tgttagccag gatggtcttg    15780
atctcctgac ctcgtgatcc gcccgcctcg gcctcccaaa gtgctgggat tacaggcgtg    15840
agccactgcc cctggccatc tttactttt ttgtgaaatg actttaaata cttggcaaac     15900
atttggtcat tgttcatctg atctccacca tccaggtctc agagaacata atttctctct    15960
gaaagcttat tgacccagga aataagatct ctttcaatct gagtgcgtca ggctttattc    16020
ttgtcatttt gtcttttgat aattttcaaa tggaattcat ggaatgttgg cttatattca    16080
tatattagta aagtatgttg agacatctta agattgattt gtggttctat atgccatatt    16140
aaatcaaaat aatagctgtt aatggttttc acattagtct gtctcttgtt tttatggagt    16200
aatgctgaga gttcattatg cttgttctac agaagagcat gttaaaagga gttttttggag    16260
tcagagaggt tattcttggt ttcataggat acactctata ctttttaggg atttcagagt    16320
```

```
atatagctga aggtgatatt ttatgtaaat atgttttatg gaaacttatt gctcatcgct   16380
gtttcctgtt aactctccta aaatataatt aaacttttgg aacttttta tagcttttgt    16440 gctagactaa tttttgtctc taatgaggtt atataaatgg cagcttctga cgttttcaat   16500
gtaggaagtc atttaaaact tcatgtatat tgtgaaaatg tagtctgctt taagctctct   16560
aaagtggtct aagttactgg ttcctaagta tggatgagca tcaaaatcat ctggaaaatt   16620
tgttaaaaat acagtaatga aggcacctca ctgtcctttt tcccaaacat acttctgcat   16680
tctgtttgag taggtaggga ctacacattt ttcacaagta tcctcttggg aatacccagg   16740
aatgcttact tgagcaacct cttactaata tgtaccttga taaggtggct aggtaaacat   16800
aaatatacaa aaatccatag atctcccata tattagcata aatcagctag aaaatataac   16860
gtttaaagat ctagttcaca gtagcaccaa tatatcgaac tctaaggaat cgataaatat   16920
gcaaaaactt tataaaaact tctgttaatg tttctgaaag atataggtga ccactttcta   16980
gataggaaga ttttatatta ctaagttgaa ttttctctaa attaacacag aaatttaaaa   17040
taatcttgat caaaattcta gtagaggtat ttttgaactt gttcactgca agaataaata   17100
cataattgca aagaatatct caaaatcatc accaggcctg gtgtggtggc ccatgcctgt   17160
aatcccagca ctttgggagg ctgaggcagg cagatcacct gaggtcaaga gtttgagacc   17220
agctggacca gtgcggtgaa acactgcctc tactaaaaat acaaaaatta gctgggtgtg   17280
gtggtgcatg cctgtagtcc cagctacttg ggaggctgag gcaggagaat tgcttgaacc   17340
caggaggtac aggttgcggt gagcctagat cgcaccactg cattccagcc tgggcgacaa   17400
gagcaaaatt ctgtctcaag aaaaaagaga aaaagaaaa agaaatcaac actaatatgg    17460
tgagacttaa tgtatgtgac attaaaatag tgattggatg ttaaaacagg tatagaacag   17520
aaagaagagt gtatgtgtgt atctgtatga atttatgatg ggtgtaacat atatgtatta   17580
gggaaatgag ggaaatgata catttctctg actttgggag aacattatat ctctacctca   17640
tattgcaaac aaacataaag ttcagattaa ttacctaaat gtgaaaaaat gaaataattt   17700
ctttaaaaaa tgtaatctta gtttgaggaa ggttaacatt ataaggaaa aaactgtttt    17760 gagtggaata tagttcaata tgtcaaaatc caccttcaac aaaattgaaa gtaaattgaa   17820
cttggggaaa gtattgacag catatagatc aaaggttact agcctgtgta aagagcagtt   17880
ataaatatcg ttaagaaaaa cactgtcgac ctgtcggcac cttgttctcc gactcccagc   17940
ctccagaact gtgacgagta agtgcttatt gtttaaacca cccagtctgt atgtggtatt   18000 ttgtttataga aactcaagct gattaggaca ctagtaatca gtagactgaa actgaaacaa   18060
aaataagaac cttttttacc tgtcaaattg gcaaacatta agaatattca gattttttgtc  18120 agaggtgata caaccttcta agaaggcaat ttgggaaaat ataaagcttt agattattat   18180
atgtctgacc tagcagtttt acctctaggg tgcttacccc taggaaagtg tgtaatgata   18240
ttggtgcagt gcccttcatc ccattagaaa attaaaaata accttaatgg cctaccacta   18300 aaagggggatt gaaaatttaa gatatattta tttatgtgtt tattgagatg gagtcttgca  18360
ctgtccgcct gggccagagt gcaatggtgc gatctcggct cactgcaacc tctgcttccc   18420
gggttcatgt gattctcctg cctcagcctc ctgagtagct gggattacag gctcacacca   18480
ccgcacccgg ctaatttttt gtattttag tagagatggg gtttcactgt gttggccaga   18540
ctggtctcga actcctgacc tcatgatccg cgccctcgg cctcccagtg ttgggattac     18600
aggtgtgagc cactgcgcct ggccagatac atttatacaa gagaatgtta gttaacattc   18660
atagatattt atattttgtt tacttttat taaaaaaatt ttttttagag acaggatctt     18720
```

```
actctgtcac ccaggcagga tgcagttgca caatcatagc ccactgcagc ctgaactcct   18780
gggcttaagt gatccttctg cctcagccct ttgagtacct gggggacttt aggcagtgct   18840
actatacctg gctaattttt aaatgtttta tagatgagat cttgctgtat tgcccaggct   18900
ggtctagaat tcctgggccc aagtgatcct cccaccttgg cctcccaaag cgctgagatt   18960
acaggcatga gccaccactt ctgaccaata gatatttata tttgtgactg gaaaatatat   19020
taacaatgtg ttaaaaaatt cagttaaaaa ataatgaaag atttttgctt ctggctaaga   19080
tagaataaca aggacagcat ttatcttctt gccttgaaat agttgaaaac ggaagaaata   19140
tatgtaacag tggttttcaa gttattgggc atcaggcaaa aagaatagt tatcccagga   19200 aaatgaatgt ggagagccct acaatttcct tacattactg cctggtcatg caagaggaa   19260 aaactgagag gagactgagg ctgagccagt ggtttgctgg gttgaggagg cagagctggg   19320
agtgcagaga tgcaaggtgg tgagagccca tatggaagaa taccagggaa gagagctgca   19380
gagggagctc cggagacctg caccctgccc tctcagtacc ctgtcatgtg tgtagctgag   19440
tactgacgag cacttgcttg tgcggaaatg acccagggct ggaggtagag ccacctgaaa   19500
ggattagaag gaacagttgc tgaaagtcac acagggccag gaagaatttc taatcacacc   19560
agttggagtg gaaaacctca gctctcatag agcaggtagg gtactcagaa gggtttgccc   19620
acctagcccc agactaagtt tcgttactct gaccctacct aatattaaaa agagattaat   19680
taaattgttc gcaacaaaaa taatatattt cagtgtttgt aacacgtaga agtgaattgt   19740
atgacaatag cataaaggct ggaagagcag aaattgacat gtatttgcgc tgggcagaat   19800
aatgctcccc tctttcccca aaagatatca agtcctaatc cctggagcct gtaaatatta   19860
ctttatatgg aaaattgttt tatgatgtga ttaaattcag gatcttgaga tgaggggct   19920 atcttggatg atctgggtag gcactaaatg caatcacata tatataaaaa ggaggcagag   19980
ggagatttta cacacagaga gaaggccctg tgaagatgga acagaaagat ttgaaggtgc   20040
tggccttgaa aattggagtg atgaagctat aagccaagga atgcagcagc caccaaagct   20100
ggaagaggca cggagcagtt ctcatttaga gcctactcca gagggaatgt ggtgctgcca   20160
attccttttt tttttttttt tttaagatat catttaccc tttaagttgg ttttttttt   20220 tttttttttt ttttagtatt tattgatcat tcttgggtgt ttcttggaga gggggatttg   20280
gcagggtcat aggacaatag tggagggaag gtcagcagat aaacatgtaa acaaggtct   20340 ctggttttcc taggcagagg gccctgccac gttctgcagt gtttgtgtcc ctgggtactt   20400
gagattaggg agtggtgatg actcttaacg agtatgctgc cttcaagcat ctgtttaaca   20460
aagcacatct tgcaccgccc ttaatccatt taacccttag tggacacagc acatgtttca   20520
gagagcacgg ggttggggt aaggttatag attaacagca tcccaaggca gaagaatttt   20580
tcttagtaca gaacaaaatg gagtgtccta tgtctacttc tttctacgca gacacagtaa   20640
caatctgatc tctctttctt ttcccacatt tcctcctttt ctattcgaca aaactgccac   20700
cgtcatcatg gactgttctc aatgagctat tgggtacacc tcccagatgg ggtggcggcc   20760
gggcagaggg gctcctcact tcccagatgg ggcggccggg cagaggcgcc ccccaacctc   20820
ccagacgggg cggcggctgg gcgggggctg cccccacct cccggacggg gcgggtggcc   20880
gggcgggggc tgcccaccac ctcccggacg gggcggctgg ccgggcgggg gctgcccccc   20940
acctcccgga cggggcgggt ggccgggcgg ggctgcccc cacctcccg gacggggcgg   21000 ctggccgggc gggggctgcc ccccaccctcc cggacggagc ggctgccggg cggagggct   21060
```

```
cctcacttcc cggacggggc ggctgctggg cggaggggct cctcacttct cagacggggc    21120
ggctggtcag agacgctcct cacctcccag acggggtggc agtggggcag agacattctt    21180
aagttcccag acggagtcac ggccgggcag aggtgctctt cacatctcag acggggcggc    21240
ggggcagagg tgctccccac ttcccagacg atgggcggcc gggcagagat gctcctcact    21300
tcctagatgg gatgacagcc gggaagaggc gctcctcact tcccagactg ggcagccagg    21360
cagaggggct cctcacatcc cagacgatgg gcggccaggc agaaacgctc ctcacttcct    21420
agacggggtg gcggctgggc agaggccgca atcttggcac tttgggaggc caaggcaggc    21480
ggctgggagg tgaaggttgt agtgacccga gatcacgcca ctgcactcca gcctgggcaa    21540
cactgagcac tgagtgagcg agactccgtc tgcaatcccg gcacctcggg aggccgaggc    21600
tggcagatca cttgcagtca ggagctggag accagcccgg ccaacacggc gaaacccgt     21660
ctccaccaaa aaacacgaaa accagtcaga catggcggtg cgtgcctgca atcccaggca    21720
cttggcaggc tgaggcagga gaatcaggta gggaggttgc agtgagtaga gatggtggca    21780
gtacagtcca gccttggctc ggcatcagag ggagactgtg cgagggcgag ggcgagggcg    21840
agggaattcc ttaatttcag tttagtgata ctaattttgg actctggcct ctaaaactgt    21900
gaaagaaaaa attttttgtt tgtttgtttc ttttaagcca catagtttgt ggtaatttgt    21960
tacagcagct gcaggaaact aatttatgct gcatgtgaaa tggtgtaata aggtagattg    22020
tgatgaagat acatagtata aacaattaag caacaactaa aagcacaaca aggaattata    22080
gctaatgaac caaaaaagga gattagaata ataaaaatgg tgaatcccaa agaagccaga    22140
aatagggaa gaggcaaata aaggaaagaa agagcttgat ggtagatttc aacctaacta     22200
tgtcaaaaag gacattacat gtaaaaggca gcgattttc agattgaatg gaaaagtaag     22260
actcggtata tgctgctgcc tgcaagaaac acattctaaa tataaaggca aaaataacct    22320
acaggtaaca gaacggaaag aagttcactg tgcttacaag aattagatgc aagctagact    22380
ggttctgtta atatcagaca aagtggattt caaagcaaag gctcttgccc aggatgagat    22440
ggtcatttca taatgatgaa ggggattcgt tcatcagcct ggcatagcaa gctgaaatgt    22500
ttatgcaccg gactacagag ctaaaataca tgaagcaaag cctgacagaa ctacaagtag    22560
aaacagacaa atccacagtg atagagattt cagtagccgc tctcaatgat tgtagaaca    22620
cgtagccata atatctggat ctagaacact tgaccaacac tgtcccctgt gcaacctcat    22680
tggcatttac aggacactcc acccagcacc agcagaagag acactctctc aagtgctcac    22740
agaatgtttg ccaagataga gcagatgctg ggccataaaa caagtctcta aattaaaagc    22800
attcaaatta ttcagagtat gttttctgac ctcagtatca ttaagttgga atatattata    22860
ggaagataac ctggaaaagc ctcagatatg tggaaaaacc catttccaca tggcccatgg    22920
gtcagaagtg aagtcaaaag ggaaatttga aagtcttttg gattgactga tataaaaaca    22980
atagatttct aaacttgtgg ggtgctgtta cagcatagta aatggaaatt tctagcatta    23040
aatgcctgtt ttaggaaaga aagatttcaa atcaatgacc tcagcttcta cctttggaaa    23100
cttgaaaatg acaagcaaat ggaatccaga gttaccagaa gggccaggta cggtggctta    23160
tgcctgcagt tctgccactt tgggaggccg aggcaggtgg attgtttgag actggcagtt    23220
gaagaccagc ctgggcagcc tagggagacc ccatatctac aaaaaacaaa aaattagcc    23280
aggtgtggtg gcatgtgcct gtagtcccag ctaaccagga gtctaaggtg ggaggattgc    23340
ttgagtctgg gaggttgagg ctgcagtgaa ctgtgattgt gccactgtgt tccatcctgg    23400
gcaacagaat gagaccctgt ctcaaaaaca aaaacagtta ctagaagaat ggacatcata    23460
```

```
aagataggag cagaagtcag taaaatagaa aacaaaaata cataggaaat caataaaacc  23520
aaaagctggt tcatcaagaa catcaataaa ttggtaaagc tgataggaaa aacagtgaag  23580
tcacaaatta gcaatatcag gaatgaggga gatgacagta gtatagatta tatagatatt  23640
aaaaggactg tatgaggcag gtgtggtggt tcacgcctgt aatcccagca ccttgggagg  23700
ccgaggtgga cagatcacct gaggtcagga gtttgggacc agcctggcca acatggtgaa  23760
actctgtctc tactaaaaat acaaaaatta gttggtcgtg gtgctgtgtg cctgtaatcc  23820
cagctacttg ggaggctgag gcaggagaat tgcttgaacc tgggaggcgg aggttgcagt  23880
gagctgagat tgtgccgttg cactccagcc tgggtgacag agcaagactc catctcaaaa  23940
caaataaata aataaaaagg actatatggt aatattatga caactttat gccaataaat  24000 ttgacaactt atagatgaaa tgatgagtt ccttgaaaga cacagaaact attaaagctc  24060
tctcaagaag atatagataa gctgattagc cctatatcta ttttattgaa tttaaatgta  24120
aaaatcaata tttagttact ggaaaacttt taagtgtggt tggaaatggt atacgaactt  24180
tttcaactga attttatgaa gtctaatcac aggtaaaggt tttctgatga aaatttagtg  24240
tctgaattga gatatactgt aaaaaatgtt atatatctta attatttctt cacattaatt  24300
acatgttgaa ataatacttt gggtgtattg ggttaaatta aatattatga aaatcttgcc  24360
tgttttcttt ttacttttga tgcgtcagct aggaaatata aaagtgtagc tcacattctg  24420
tttctgttga cagtactgct ttggagcaca gtgtttgaat gatctatcat ttcaaagacc  24480
tttcctcagt tcgttattca tggctgtctg tattccacat agataaggtc tgaaatactg  24540
ctaagtggca tgttttgttt tatgctttta taagtttgtt gatcattact gatgtggact  24600
tttggtgcct cttaggctca ttgctatctt ccaaccattg tttgcaattt ttacctagag  24660
ataaagagaa agagacattt ggtttcagag tagttagatt gggatcatga aagagcaacc  24720
tcattttgat gcttcaaaaa tagcacatcc cccgtattac tgggatttgc tattcttggg  24780
attacttcaa gaacatcctt gtgttactgg tttggatgct tctgaatgct gtgaagtcag  24840
tttcatgtac atggctcatc agtttagctc tctcttggct ttgtttagac agttggagca  24900
tgatggccta aacagcttct ttcaattaaa cattttaaaa tagtttacaa atagtaaaca  24960
aactccagtt tttgtgactc tttgtctcgc acaacaaaaa cacaatctga ccatgatcat  25020
ctggcatctt agggtgaaat atggttatac tttggcccat accgaaagca agattaaaaa  25080
ggggcaggag agatagactg ctgaactgat tttcaaggtt ccaagaatat tgtaggttaa  25140
gagtaaaagt aaacttttgg tagaaagcag tgggttgtct aggattgaag tatctgaagt  25200
ttttaaacga aaatttaaaa agaaaaatga gaattgcctt acaagtacaa tctcttctt  25260 tttaaaaaat aaactttatt ttgaaatagt tttagattta tagaaaaaaa ttagataggg  25320
taggaagttt tcatataccc tacatccagt taccccagtt attatcatcc taatttagtg  25380
tgagacattt tcatgtttaa tgaatcaata ttgatatgct attaacttaa gtccagactt  25440
tattcagatt ttcttaattt ctatgtaatg tccttttct gttccagaat tccatgcagg  25500
acaccggata cctcattaca tttcattgtc atgtcacctt aggctcctct tgacagtttc  25560
tcttcttttt ttgcttagaa attctccaga atttcagaaa cttctgggca tcgctatgga  25620 acttttctg ctgtgcagtg atgacgcaga gtcagatgtc aggatggtgg ctgacgaatg  25680
cctcaacaaa gttatcaaag taagaaccgt gtggatgatg ttctcctcag agctatcatt  25740
gttgtaggct gagagaagaa gcgatcattg agtgttcttc tgttttgagt ccctgaggat  25800
```

```
gtctgcactt ttttcctttc tgatgtatgg tttggaggtg ctctgttgta tggtttggag    25860
gtgctctgtt gtatggtttg gaggtgctct attgtatggt ttggaggtgc tctgttgtat    25920
ggtttggagg tgctcttgta tggtttggag gtgctcttgt atggtttgga ggtgctctgt    25980
tgtatggttt ggaggtggtc ttgtatggtt tgcaggtgct ctattgcatg gtttgcaggt    26040
gctctattgt atggtttgga agtgctcttg tatggtttgg aggtgctctt gtatggtttg    26100
gagatgctct attgtatggt ttgcaggtgc tctattgtat ggtttggaag tgctcttgta    26160
tggtttggag gtgctcttgt atggtttgga ggtgctctgt tgtatggttt ggaggtgctc    26220
tgttgtatgg tttggaggtg ctcttgtatg gtttggaggt gctctattgt atggtttgga    26280
gatgctctgg tatctgcctg cattgcttgc cacacctgcc cggtcagaag gcgctatgtt    26340
gacaattgtg cctgcacggt gcctaggtca atgaagggaa ccgatggtag ccactggatg    26400
ctcctgggaa aatgtcacta caggcaccag agaagccaga gctatgccca aatttctatg    26460
agtctcagtt ttcttaacca taaaatggga tcaatgtttt tgtggcatgt gtatgagtgt    26520
gtgtctgtgt atgtgtgagg attaaaattgt gtatgtgtga ggactaattg ccactactgg    26580 atccctcaaag tggtaagaag tgttcttatt aataatgaca tccttacact cttacccagc    26640
aagattgatg ggtgtggcac tgcttctctt tttccatcac atggtttcca tggtatcctt    26700
ttgcccaggg aatctttgct ttgtggctag cactttgttg tttggctaat cacgctttct    26760
gtggtcagga cgctggcttc tctggagcca tgggattcta gctccctgtc ttgtccctag    26820
agtggtcact gtcttctctc tccgcttgca attcctgctt tgctcgcatc tcacttatgc    26880
agtgacgtat atcagtttca ccttgttctc cgtgcctgct gatcattggc accacttgca    26940
tggtgccatt tagggcctgc ttccagttaa gcttgcttct ccacaggcct aaatatcctt    27000
gcttgcttct tttattctca ctggcaggac cagggcggtc tgtctttgca tgagacaggg    27060
tctcgctcag tcacccaggc tggagtgcag tggctgatca cggctcattg cagccttgag    27120
ctaccgggct caagctatcc tcctggcttg gccccttgag tagctgggac tacaggcgtg    27180
caccaccatg cccagctaat ttttaaaatt atttgtagag atgggatctc gccaggttgc    27240
ccaggctggt cttgaacgcc tgggctcaag tgatcctccc tccttggttt cccaaagtgc    27300
tgggatcaca ggtgtgagcc actgtgcctg gcccttgatg tttcagttct tgatatttga    27360
tcctcagagt cagaaaatct aaaaagaggg ctatcccagg ttgccttggt tcatggcaaa    27420
tgggacgtta agagggcaga gagaatatga acagaaactg ttctaatatt ggtcatttaa    27480
tgtgtaagta ttgttctttt ttaaacctcc ttcattttt ttccaggaat tgctggacac    27540
agtggcttgg tgtgtgtctg aggactgtag gccatggccc taggttgtgg ttttaggtct    27600
caggtgctct tcctggctgt ctccttgctt ctttcccatg tcctcttctt tgtttccagc    27660
catttctccc ttatgcttaa gtttggtgca gcagggtttg gctgctctca gattcctgct    27720
tcctcagatg ctgtagttgt caggcccagc gggctggcag cgggatcagg atctggctag    27780
gtttgctctc actgtggcag agtaggggga ggcgtgggag agcacgtgtg accccaggcc    27840
agctgtaggg agcataggca tggtcacgta gccttcaggt cctagacttt gtcttctcat    27900
gagtatggct gtgtgtgtat ggtgaaaact aggttctact tagcccaaga aaatgggcac    27960
attttgcatg tggtttctgt agagaaatgc actgggtatc tgacatagcc tggcagcatg    28020
cctccctcag gtaggttagt ctcaggcggt gaagcacgtg tgtccagcaa gaacttcata    28080
tgtggcataa agtctccgtt ctgtgaggtg ctggcaaatc accaccaccg tcaagaggct    28140
gaagtgattt ttgtctaggg aggcaggaaa ggcttcctgg agtcagcagc cagtaggtga    28200
```

```
aagagtagat tggagacctt cttaatcatc accgcctctt gtctcaaggg gtgccaggaa    28260
gctgtggagg ctgaacccat cttatgctgc cagagagtgg gacaccatga gggtcaggtc    28320
aaggggttgt accttgtttg gtagagaatt aggggctctt gaagactttg gatgtggtca    28380
ggggagtgta tcatttagga agagtgaccc ggtgaggacg tggggtagag gaggacaggt    28440
gggagggagt ccaggtggga gtgagtagac ccagcaggag tgcagggcct cgagccagga    28500
tggtggcagg gctgtgagga gaggcagcca cctgtgtgtc tgcggaagca ggggcaagag    28560
ggaagaggcc agcagcgtgc tgccatcacc cagcgactgg cgtagattgt gagagaccat    28620
tccctgctct taggaggggc tgagttttag ttttctcttg ttatacaata agcttggtat    28680
ttgtttacaa aacatttgta aagctaaatc aaggtttgat aaggcttcta gttttatttta   28740 agaagtaatg ttgaaataaa tgtttgtcca attcgctttg ctcatttaag gactttcagt    28800
acaaactgca acaacaggat taggatttaa acgtttctga gatgttttta ctcctcagaa    28860
tttcccagaa tgtgatctgg ttttgatttt caagcttgct gacccaatag gttaacccac    28920
aagttttacg aagaccatct cagtccactt acatcaactg cccatgccac ggttaaagag    28980
atcatcgact gatgtttggc acagcttcct ccctcttggg tggcaagca tttggaagag     29040 aaggctccta tgggtgagag tggggcacca aagtcttccc tgtcccatcc cctagcttga    29100
gaagcccttc tctaatgtgg actttgtgcc gttagcatcg ttactagctt gaagttgacc    29160
atctggacgt actttctggt ttagcctcac aagtgagcaa ggagggttga gagatgtgct    29220
gtgaggaatg tggggcccca gctggcagca ggctctgggt caggggggca gggaccacgg    29280
gcatacctga cagtgaggag gggccacacc tgcagaaaag gatgcaggac tccgccttgg    29340
gaagtgttct aggccagagc gagggtctgt ggtttataag tacacccaca gtgctcggga    29400
ccctgcagat gtccagggtg ccgtctgagc ccgtatcatc caacagaatg ttctgctagt    29460
gaagattaaa gatttactcc aggggcttta ggatttatta tatatatata aatcctatat    29520
atataatttt tttttttttt tttttgaga tggagtttcg ctcttgttgc ccaggctgga    29580
gtgcaatggc gtgatcttgg ctcactgcaa cctccgcctc ccgggttcaa actattctcc    29640
tgcctcagcc tctcgagtag ctgggattac aggcgcccac caccacaccc ggctaatttt    29700
tgtatttttt agtagagacg gagtttctcc atgttggtca ggctggtctt gaactcctga    29760
cctcaggtga tctgcccgcc ttggcctccc aaagtgctgg gattacaggc atgagccacc    29820
ccacctggcc aggatttatt gtatttgaac catctaccat tttaattttg atgttatgta    29880
gtatttgatg ataatgaaag ttaaattgtt tttctttcca ttttttctgtt taagtgaatg    29940 acctgtatct agtttattca gtaacttcct gcatatattt gtttctttca ttcttaatga    30000
atatattctt aatttagttg ctattatgtt ttgctttgcc ccaaaattga aatcttagtt    30060
tccttttagc tcgttttaga actagtgatg ggatgtgtct tccataaatc tcttgtgatt    30120
tgttgtaggc tttgatggat tctaatcttc caaggttaca gctcgagctc tataaggaaa    30180
ttaaaaaggt gggccttgct tttctttttt aaaaatgttt taaattttaa attttttatag    30240 gtacacgtat tttgtaggta catgtaaatg tatatattta tggggtacat gagatatttt    30300
gatacaggta tacaatacat aataatcaca ccatggaaag ttggatatcc atgccctcaa    30360
gcatttatcc tttgtgttac aaacaatcca gttacatgct ttacttattt tattttattt    30420
ttgagacaga gtcttgcttt cacccatgct agagtacagt ggcatgacct tggctcactg    30480
caacctccgc ctcccgggtt caaccgaact ttgggctggt ctcgaactcc tgacctcagg    30540
```

-continued

```
tgatccgccc gcctcggcct cccaaagtgt tgggattaca ggcgtgagcc actgtgccgg   30600
gcctgattgt acatttttaaa ataactaaaa cagtcagggc acagtggctc atgcctgtaa   30660
tcccagcatt ttgggaggct gaggcaggtg atcacctgag atcaggagtt cgagaccagc   30720
ctggccaaca tggagaaacc ctgtctctac taaaaataca aaaattagcc aagtgtggtg   30780
gcgggcgcct gtaatcctgg ctactcggga ggctgaggta ggggaatcgc ttgaacctgg   30840
gggtggaggt tgcagtgagc cgagatcacg ccactgcatt ccagcctgag cgacagagtg   30900
agactttgtc tcaaaaaata aaatgaaat aaaattgggc cgggtgtggt ggctcacacc   30960
ttagtcccag cactttggga acctgaggca ggtggatgct tgagaccagg agtttgagac   31020
cagcatgggc aacatggcaa aacgctgtct gtacagaaat tagctgggtg tggtggtgca   31080
caactatagt ctcagctact tgggagattg aggtgggagg attaattgag cctggaaggt   31140
tgaatctata ggtagctgag attgtgccac tgcccttcag cctgggcgac caagtgagac   31200
cctgtctcaa aagaaaaaca aaaaacaaaa aacaaaacca ctattatcga ctatatatta   31260
ttgtctatga tccctctgct gtgctgtcga ataccaggtc ttgggcccctt atttccatca   31320
ctgagcaaac ttcactctgt taagcagcag gtgtgggatt tcatcgttat tcagtaattc   31380
acaatgttaa aaggaaatgc tgtttggtag acgattgctt tacttttctt caaaaggtta   31440
ctctttatta gatgagatga gaattaaaaa tggtaactta ctttatatct ttataattga   31500
agcccactag accttaaagt agttaccaga tgttttatgc atttaaatgg ccttttctct   31560
aaaattagaa agtaacaagg aaagaaaatg cttcgtttct atgcaaccct cttggtgact   31620
agtatgtgac tcttaatgca accctcattg cacccctca gaatggtgcc cctcggagtt   31680
tgcgtgctgc cctgtggagg tttgctgagc tggctcacct ggttcggcct cagaaatgca   31740
ggtaagttgt acactctgga tgttggtttt tgtcggggggc cagctgctac tgatcctta   31800
tgtctcagct cagatgtcat ttcaaaagtc tgctctgccc tctccaaatt gcagtcgacc   31860
ttgcccgtt tatgtttccc tcatagcact aatccatgtc agaaattgtc acgtacagtc   31920
tatctgtgtg cttgtttatt ttctatccca cccttccgca agagacttat gggatgtgtg   31980
ccccaggaca gcaggggtct tactgtctta tgctctgttg cagcccagca gcgataacag   32040
tgtctgcaca tagtacttgc ttaaaagata cttgccaaat tgttgaaggt tgaggtacca   32100
atttcattat tgctgactat aggagttata gcaaaatatc catttgtctg ttacatgagt   32160
taaaaatatg gttgttgcac tgtgaatagt ttggtttagt caaaacagtt gtatcttaac   32220
ggattgagaa acaaaagcag gaccactttt catcagctcc ctccttctcc ttaaccagca   32280
atacatgctg atgctgatat cccatagacc ctcagctcca tcctgagtca ctgggaatgt   32340
ggtctaaacc ctcactatta atatgaactg agtttcaata agaatcttat atgggtcggg   32400
catagtggct catacctttg atcccagcac ttcaggaggc caaggcaggt ggattgcttg   32460
acccagacta ggcaacatgg tgaaacgccg cctctacaaa aaatacaaaa cttagccagg   32520
catggtggtg cgtgcctgtg gtcacagcca ctcgagaggc tgaggtggga ggatcacttg   32580
agcctgggag gtggaggtcg tgttgagcca agatcgcacc actgcactcc agcctgggca   32640
acagagtgag acctgtctca aaaaaaccaa aatccagaaa agaacttata tggctgcaga   32700
ggtataatca ctaaggaaat ttccttttgt ataatctttt ttctttttact atcatttaaa   32760
aaaatgtgtt atatttctga agcaacacat ccaggttctg cacatagcag ccaaagtgac   32820
cttaaagaat ataactgggt cttgtcattc cctatttaa actcttgtac ccatttccca   32880
gtgccgttta gatagagatt ccagactcgt caatggctct gtcacctcag acaccctgca   32940
```

```
ttgactcatt agtctgatta gagtcaggtt tttcttcctc ctgatggttt ttttttcccc    33000
cttagttctc agcggaacag tcacttcctt agggaggttt ccccagccac cctctgaggc    33060
cgtgcttgtt gccagactct gccactagag ggcagggctg caccactcct ggcacctcgc    33120
acccggcctg ccctgtcact ctgtgtgttg ggtgaattcc tgtgatctgt gactcactgc    33180
tctgtgtcct acacattcgg cttttcttct ctccccacaa ccccatttta taattctcct    33240
ttttcaggaa agctttattc ccatttaaaa attttgttt ttaaaatggt attttcttac     33300
acttattttc taattaaaaa tgagtgtttt aagaagtatt atgatttact gcaaataatt    33360
tttaaaccca gccttttaga tcctctgtga tcataagaga aatgaaggat gtctcccaac    33420
acttgagctt catccacatt tcatcctcct gttctttcag ctgagttttc cccatcccat    33480
tagggactgt tggaatataa aactggcttt tccctaacag ggaatgaatt gcttctgttt    33540
ctcctgaagg agagctggaa gaatgacttg cgttcttttg catacacagg ccttacctgg    33600
tgaaccttct gccgtgcctg actcgaacaa gcaagagacc cgaagaatca gtccaggaga    33660
ccttggctgc agctgttccc aaaattatgg cttcttttgg caattttgca aatgacaatg    33720
aaattaaggt atgattgttg cctcaggtca caaacatgcg agtgatgctg tgagtgagtc    33780
tgtggagggt gagggcttct gaacagggag tcctgtggga gtgcttcttg gggtatgttg    33840
tatgtcgtaa tttagactac catcatttgt gttattttg aggcacctaa ggacttcttt      33900
ccacttctca tttcttactg tggggtgaag agttgaattg ggagatggtt tctagatgca    33960
aattgaaaag gcattttcc agagcagatt tgttttcggc gtactagagt gactctttaa     34020
cctagctgcg ggaagatgac tgtgccaaga ctgcaggtag gagaaagctc actgacgagg    34080
ccttgtgggg ctgaacgtcc tgcagctatc agagcctgtt ggcttcctgt tgtgcattcc    34140
aacaaatcat cttcaaaccc actttagtgt tttgtttata atgtccagaa atagtgaccc    34200
tgtcacatgc tctacagatt acaggattct tagcctcttc cttttggta ggtcagtcct      34260 gggtttgagc ccaagtgacc ctcctgggag gtgatgatac acactgggta gagtggaatc    34320
agatggactt ggattagaat tctgtcctct ttactagtta ttttcctcta ggcaaactgc    34380
ccaacagctc taagctattt ccttcgtatt ctgaaaaata agccttaatg ggacccatat    34440
agggcaactc tgagagtaaa ataaaggaat atgtgttaga gtgtagcata gtcacccacg    34500
ggaagggctt agatgttagc tgctactgct cttattagct gaatgatttg gaataaactg    34560
ttagcctctc tcatgttttt tctcttgagc ttcgaagttt tcttgttaat actaaggaga    34620
tattcaaact agtcatgggg ttttggaatg acgaagggag atgatgaatc taagaatttt    34680
agtgtaatat ttcttcatgc tcagtaaatg gtagtttctg ctgctgttat tttattacc     34740 atctctttgg aatgggagta ggtgctcctt tgtggtcaga ggctgtgaga gctccacagc    34800
gccagtttgc ccatctgtac actggggtct gttgaaggca gtcccctctg tgatatctct    34860
ggctgtcaga gctcagatga tagatggtat ttttgtactc ttagttctca tcattttcat    34920
gatttcgatc accatttgag tatgatgatg ctaacacttt gttgaacgta gaatccgtta    34980
attacttcct tcctgaaacct ttggcattaa aaaaaatcta ttctgctacc tctctgctca   35040
tttatggtta ttcaaattta ttatcaagag cctggtacag tggcttgtgc ctataattgt    35100
agctacttgg gaggctgagg taggaggatt gcttgaggcc aggagtttga gaccagcctg    35160
ggcaagatag tgagacccta tctctaaaaa aactgaaaaa aaattagctg acatgatggg    35220
catgtgcctg tggtcctagc tactcaggag gctgagacag gaggctcggt tgagcccagg    35280
```

```
agttggagtt cgaggctaca ctgagctgtg attgtgccac cacactccag catgggtggt    35340
aaaacaagat gccatttctt aaaaaaaaaa aatatatata tatatattat caatgaaatt    35400
cagtagtacc aacaggatta taaacaaaga tagtagttcc cttcctactt tttctcttaa    35460
tccttgtgtc tcacaggcaa acataactct tagtatttct tccaatattt actttcatgt    35520
ttctttcttt ctttctttt ttttctttga gatggagttt tgctcttgtt gccaaggctg     35580
gagtgcaatg acgcaatctt ggctcaccac aacctctgtc tcccgggttc aagcgattct    35640
cctgcctcag cctcctagta gctgggatta caggcatgca tcaccacgct cggctaattt    35700 tgtacttta gtagagatgg ggtttctccg ggttggtcag gctggtctcg aactcctgac     35760
ctcaggtgat cctcccacct cagcctccca aagtgctggg attacaggcg tgagccactg    35820
cgcccagcaa cttccacatt tctaaataac atgcttctac tgctattttt ttttcaatt    35880 ttagacattt ttttactttc actatagttc tatcagaatt cagtgtgtac gttattatgc    35940
ctaagtaaat agtcatggtt gcttacgtat tatatttctt tgattgtgtt tcttatttga    36000
tgagaaagct gtgttttttg ctctgggttg aaactggaga gaggacctgg ggaggaggag    36060
gaggacagat gaagttggtg actgtacctt catggccata gctgggttct cagcacccgg    36120
ggatctgctg atcacctact cataggccag gcccctatcg aagttctagg tgacccagtg    36180
ctggggacgg gggggccacc tgcaaggtct aatcatggag gtggggcta cagtgttggc     36240 ttgtgctggg gccagcatcc ttaggaaggc atcttggagg tggaggagac agccgccac     36300 ttcttgattg gggccttcag cagcaccagc ttcttgggca ggctggtgct ggctttcatc    36360
accatgtcgt gttcaatctt cttccagatc ctgacttcta ggttcagctt tcctcagacc    36420
ctggttcctt tcagaggcca ttgctgctgc cttgctcttt gctggcttgt gccttgatta    36480
tatgtctttg tacaactttt tgttttcctg gagttaatct tcacatctgt tttcttggag    36540
ttaatcgtta cctctatatc gcttgcttat tattctttgg ccttttgtc ttctcacacc     36600 ttccaacttc tttgtaatat gtgtttagta caattttca tgacaggtag tttactgaat     36660 cagttttcc ccagtgtggt catccaactt gagttatcca gctctctgcc ccagtctggg     36720
caggttgatc ttcaggtctg tagtacactt gtatcctagg acttctcttt gccattagcc    36780
tggaatttcc tttgcagttc tcccgttgga tgcccagttc ctagatgcca tatgttttc    36840 tatcgtctag tagcttcctg agagaagatg aatgggaggg aaattgtatg aggttttgca    36900
ttcataaaaa tgccattttt tttcctgtac acttggctgg gtatggtgtt ctggggtaga    36960
aatcattttc cctcagaaat gcaaagtctt tgccctgttg tcttaaaatc tccaacgtga    37020
cccgattcct taacctatga atgtactttt ctttggaagc tttccatttt tggggaggtg    37080
aagtgctagg tacttagtag gccttttaat ttggaaactt acatccctc agttctggga     37140 aaatttcctt aacatttctc tgagaagttc ttgcctttta ttttctgtgt tctctcctga    37200
aattggttag ttggatgttg gtcctcctag attgactcac atcttacctt tttcttttct    37260
ttttctggta cttttagat atccatctca aactcttcta ttcattgtta tgttttaac     37320 ttctttcttt tctttgtctc ttgatggggt cttgccctgt tgcccaggtt gtggtgcagt    37380
ggtgcgatca tagctcactg cagcctcaaa ttcctgggct caagcagctg ttctgcctca    37440
ccctcccaag tagttgggac tacaggtatg caccaccacg tccagctatt ttctttactt    37500
tttttttttt tttttgaga tggagtccta ctctgtcgcc caggctagag tgcggtggtg    37560
ggattttggc tcacttaagc ctctgcctcc caggttcaag cagttctcct gcctcagcct    37620
ctcaagtagc tgggattaca ggtgtgcacc accatgcccg gctaattttt gtattttag     37680
```

```
tagagccaga gtttcaccat gttggccagg ctggtctcga acgcctgacc tcaggtgatc   37740
cgcctgcctt ggcctccgaa agtgccggga ttacaggcgt gagcccatca ttagatcttt   37800
aaataccagt atctataagt cttttcctct tgagtcagct agtatccctg aaggaaatt    37860 actcattttc ctgcttggag ctataagct tggctatgtt tatcctgcaa ccggggactg    37920
gaagggaggg gactgacagt gttgctggtc agggtgccct cttacttttt gttttctgtg   37980
tgcatctcac gtctgtcctc agcctatgta aacacctctt gagattatcc ctctcaatct   38040
ttgccggagg tgggggaggg gctgcttcct gggctgcctt ggattggagg gaagacctca   38100
ggtgagtggg tgggaatttg cccaaggagc catgagacca gccactattt caccctctcc   38160
atccctccac tttcagatgt atgtggcgcc tccaaagccc gagctcttct tggcgtctgt   38220
ggcttcaata agcttgcttt tgctggtat ccctcctacc ctccctgtc cccagcaaag    38280 cttgcatttg aacttcttcc tacgggctaa caaatcagtc agttatgtag ctcttgttac   38340 ttttagctt ccgaagtttt gttgacaccc gtagtctgct aatgtccctg ttctgttctt    38400
tctgttcgtg taaatatatg ctttatacaa cttctttaca tgattttgt ggggtttctg    38460 ggtagcagag cttcacaagt tcaatccagc gtgttggatt agaaatctcc caccctctgg   38520
tttattctta ttctcaaaat tacctgccaa acactgatac tcccttgttt ttccttttcc   38580
tgacaggaaa tgtacatacc atacaggaca gaaatcatta gtgtatccct tggtgaataa   38640
ccacaaagtg aacttaaccc ttgtaaccgc cacccaggtc aagacagaat attaccaagc   38700
actcagaagc ctctccccta ttccccgtc actgctcctg ccttcctccc caaggtcatg    38760
actgctggct tctaattcca gagtctgttt ttaaattctg tgtacataga ccatggatta   38820
agtgttcttt ttgtctggtt tattttggtc gacattaagt tcatgagagt cttctatatt   38880
atcgtgtgta ttagtattcc tgtagtttta ggagcttcat agcattccat tgtagggata   38940
taccacagtt tattcattgt attatcactg ggttgtttct agttcttggc tattgcgagc   39000
agtgctactg tgaccactct taggtgtgtc ttttggagta catgtgcagg tttccatctt   39060
gcacagctag aggtggagtt gttgggtgat agggtgtgtg catctcagct gcagtagaaa   39120
ctgccaaata gctttccttg agtgcttgta ccagctcacc cttttgccac tgtgtatggg   39180
gattccagga gctctggtcc tcgctagcac ttggaattgc tgatgctttt actcttagcc   39240
ttcctgatgg gtgttttctg gaatcacatt atgatttaa tttccattcc ttaaagtacc    39300
cttggctctg aagtttaatg attcatgcat ctcttccctt ttgaagtact cttacaggta   39360
tgttgtgcat gtgttgaaaa gtggcactat ctattctaaa atacagtatg cctcctctgt   39420
gtttgaacag ttgtagcgtg gccttggggc ctcctgttag ctggcttgga aagggattc    39480 ttgggattgt agagattaga cctgaggagg ccccttggag ctctctgact aaatttttatt  39540 ctttattatt ccaaactatt taagctcacc gtgtgctgac tcatcataat aatgagtagc   39600
tctcattgtg cttgtctatt tggactcata caatgatttt tttttttttct ttgagacaga  39660 gtcttgctct gttgcctagg ctggagtgca gtggcacaat ctcggctcac tgcagcctcc   39720
acctcccagg ttcaagtgat tcttgtgcct cagcttctca agtagctgag actgcaggtg   39780
cgtaccacca tgcctggcta atgtttgtat ttttagtaga cggggttt caccatgttg     39840 gccaggttgg tctcaaactc ctgacctcaa gtgatctgcc ttcttcagcc tcccaaagtg   39900
ctgggattac aggtgtgagc cactgagctt ggccaaagta gttttttaag atgttagtat   39960
cttttcttgc agctaaaaaa gtttgtcaga gatgattcta ctttgttctc caggtgtttt   40020
```

```
ctcagggaga aattggaggc agtaagccac tgggggagtc ctgtggctgg ggggtgggggt    40080
agtcctgtgg ctccttgtca gggagtcctg tggctggcaa ggagagaagt cctgtggctg    40140
ggttgggagg gagtcctgtg gctggggtct catcctgtgc ctaacagtgt ccagaggtgc    40200
cgagaccagc tcagtcgggg agaccctaac ccagcagcgc tagaggaatt aaagacacac    40260
acacagaaat atagaggtgt gaagtgggaa atcagggtc tcacagcctt tagagctgag    40320
agccctgaac agagatttac ccacatattt attaatagca aaccagtcat tagcattgtt    40380
tctatagatg ttaaattaac taaaagtatc ccttatggga aacgagggga tgggccgaat    40440
taaaagaaga ggttgggcta gttaaccgca gcaggagcat gtccttaagg cacagatcgc    40500
tcatgctatt gttgtggct taagaatgcc tttaagcggt tttccaccct gggtgggcca    40560
ggtgttcctt gccctcattc ctgtcaaccc acaaccttcc agtgtgggca ttagggccat    40620
tatgaacatg ttacagtgct tcagagattt tgtttatggc cagttttggg gccagtttat    40680
ggccagattt tgggggggcct gctcccaata cagaggtctc gtgtaaattc cctgggaggc    40740
gataagcctc tgagaaacag actatgctaa ccacgccatg aaagagaaac ttatttataa    40800
atcagatgcc agttactagt ttactgctta tttgcccagg cgtagctctg acagagtccc    40860
cgactcatag tgcttgctca gtgcatgctg aacaatgatt ggaatcaagt catggctcag    40920
agcatagttt tgaataatgg gaaatggatg ttcttaagta acatagtcac caagataatg    40980
cgactagctg ggtcacccct tttcaatttt aggatatttt tatcaagatt taaatggcca    41040
tcattagagt tatagcactt tctcctttgg attgtcctag aggcccatga gaaagtattc    41100
cctaatttct taggagaaca gtttgtgggt agtatgcggt catgtccagt taaattgcag    41160
atatttccga tcgaagatgt tccagtcctg agaacttcgt gacattagca ggacttctac    41220
aagccatctc ttagggtggg gcatttactg cagttggcta gtactctttt ctccttaact    41280
ttgtcatttg ttgattttt tttaactgtc cccaaatact gtgggcagag tgtatctaga    41340
attgaggcct ccaccattgc ggagaggaca tggatgctga gcagtcccct gagtgaaggt    41400
tataaagaag caaatagact acacatgtct gtaaactgct cttgagtgtc ccaaatttgg    41460
ggtacttcag ttcagctgta ggaaaagcct caaactgttt atactttgca agaattggaa    41520
acttctaatt cacgttaagt tttatgtaat acatgataag cttcatagga gcttcatctt    41580
ttatctactt ggacttttgc ttccgtaggt tttgttaaag gccttcatag cgaacctgaa    41640
gtcaagctcc cccaccattc ggcggacagc ggctggatca gcagtgagca tctgccagca    41700
ctcaagaagg acacaatatt tctatagttg gctactaaat gtgctcttag gtaaggtgga    41760
ggcatatgag tggaagagtc tccagcatgt actcaagata gacctttgaa ataaataaaa    41820
ccagatgatc cctcagcttc tagaccaggc tatttggcac tggttgattg aatgtgaact    41880
gcactggggc tgctgtgagc ccgcatgggt ctctgtgacc ctgcagatgc agccgtgccc    41940
agggactggg cagtgggtgt gggctggtgt gagccctgtc tgccacccag ggcctggccc    42000
tctgtctgtg tcggccatga ctatggtgag tcttgtaggc ttgagactgt gcctcgggtt    42060
cctgcgggtt ctctgtaggt cagttgacag tttctcctgt tgtttgggta actgtggaaa    42120
cgaacactgg caagtgctga agcgagcatg tggacgtgcg atatgaaata acgacctggc    42180
tttcaaaggc agtgaggctc tctggaaagg accttgctga gctagggatg tgggtgtgta    42240
gccattccca gtgggcctca tggcgtactc gttcatgatc atgtttgtgc catcttgatc    42300
tctcaggatc tcttcttttt taacagatta agccgggaat ctccaaacag tgagtcagat    42360
gttaagatgt cttgcttcca cccccacagg cttactcgtt cctgtcgagg atgaacactc    42420
```

```
cactctgctg attcttggcg tgctgctcac cctgaggtat ttggtgccct tgctgcagca    42480
gcaggtcaag gacacaagcc tgaaaggcag cttcggagtg acaaggaaag aaatggaagt    42540
ctctccttct gcagagcagc ttgtccaggt aggagcacag ggtttactct aggccctgca    42600
tgtgaatgac tgacattcaa agaaccgatt aatttggaag agaagcggca gaaccgagag    42660
ttagaggtgt ggactctgga gctgcgctgc tcgtttccaa ccctaggtgc tgacctctag    42720
ctgtcttccc tctgtatgtc cctgtcaccg tgagtcaaat gcgggtgatg cctcctcagg    42780
tgccgtgtta cctaagcctc tcagagacca ctgctaccct gtttctaaaa ccagaggtca    42840
cgatatgtgt tcatccaccc agtaaatact gattgagcac ccactgtgtg ctaggctctg    42900 ggatagggc tgggtataca atggtgagta tttcagctgc agcttctgcc ccgtggaggc     42960
tgtggcctag cacactggtc taggcacggt ggtatatgct cactcaagga gatagggacg    43020
tggtcgtttg gggtgtcgga acaaaatgtc ggaacttctc tttccaatgc agagaaacct    43080
tgcagtaatt ctaatgtact gtgattggca gttgacttca gttctttgta gcacgcttac    43140
tcaggttatt tcactaacta tgtaaccatg cagcctcatt ttaagcaatt ggatttttg    43200 aactttactt aaaatgttat gtcagggttt ttattgtgct taatgtgtgc catttagcta    43260
agttttgtag gatacgaaat tgtaagtggc ttaaaatgat tcttaataga atcatgaatt    43320
gaagataatg ctaataattt aagcactgag ttaggtagtg tttgtaaaat gcttagaatg    43380
cttcctggca catgttaagg ccatgtaagt gctgcgtgtt gataaacagc tgagcaaaag    43440
tggactctta agaaagtatt ggggctgaga gttctgttcc aaccagctgc cctttggtta    43500
tttttcagaa taaaagcaga gtctcatggg atatgacatt tatatttcct tcacaaaaaa    43560
cactgctgag tgttttgttg agtaaaaagg gtgtagccat ggtaataata catttaaaat    43620
atagtttatt tcatctttac cttgccttgt tttttttta agctagcttt ttattgagaa     43680
ttccacacat acaaaagtat caactcatga ccagttatat ttcatttata atcctacttc    43740
tccctttttt tattatttga aagcaaaccc caattatcct cttatttcat ctataagtat    43800
ttcagtatct ctatagatga ggactcttct ttatttttaa aactttattt ttaaaatgat    43860
ggtcagatgc agtgttcatg cctgtaatcc cagaactttg ggaggccaag ctgggcggat    43920
cacttgaacc tgggagtttg agaccagccc gggaaacatg gcgaaacccc atgtcttaaa    43980
gaaaaaaatc agccaagtgt ggtgatgcat gcctgtagtc ccagctactt gggaggctga    44040
gatgggaggg tcacatgagc ctggaagatc aaggctgcag tgatccatga ttgtaccact    44100
gcactccatc ctgggtgatg gagcaagatt ctgtctcaaa aaaacaaaac tgcaaaacaa    44160
cgtcacaaaa cagtgccatt gttagacctg aaaatattaa acatttccta catcaaatac    44220
ccaccaactc attatcaatt tttctctcta ctctttggga atcagcatct aaataaaatt    44280
ggtcgataag gattgtaaat ctctttgatg aactggttcc cctccatccc agttttttc    44340 ccttagagtt catttattga gaaccagat tgtttgtctt ctaagttttc ctgtggtctg     44400
atatactgct tccatctcca ctgtgtaaat taacacccttt ttctcttctc tgtatttcct   44460
gtaaatcaat aattggagga aaagccttgt cagatttagt gtatatttta tatctgagtc    44520
cagtatttct tatataatat tttaagataa gtgtactctt ttaaaagta ttgaaactat     44580 atgctcaatt tttttaact gatgctttta agaaggctgc ttgatcataa aagtttagag     44640
atcattggtc tgatgggaaa agcaaataat tactaaaccg tttagcaagg ttgaggtgca    44700
catggtgggg cctggagaag ttcagtcatg agccgtcact tatgggcacg tggaatctga    44760
```

```
cccggcacag agttgggaga agacaggagc tttatagaca gaaaatgtgg tctttgctaa    44820
gtcccaggag tgaaagggtg agacagtgct cacagcacac gagtgtgggt gcgtagacag    44880
agcaagggtg ggtcctgaaa aggcctgcag gctttctcat agattagcaa gagtgctggt    44940
tacggaggtt tctaacattt gtgaacagat cgaaactgtg ttaaattggg attgcagtaa    45000
tcctggaagg acagggatag agggtgaagg ggaaaaaagg gtatggatgt gagacttaat    45060
tgctgatttt cttaagacct ttctccaaag taaataaatg atgtggcaca tttttgaact    45120
ggcaaattct aaactctaga tatgattatc tctataacat atcttactcc atcttctttt    45180
gactaaaaac tgttcttaat taaattacca tgagacgttc aattcagcaa atgtagtttg    45240
gctaaccata tttaattaga atttaatata atcctaggcc tggccaaact attaagcaag    45300
tgtgggcaaa atattgataa ttttagatat gcaggaactt agtttgcttt ccatgtgtgc    45360
ttttcgaaaa aggaataaat tgaaaaatag aggaagccct gaaatccaag aagcaaactc    45420
tctcacctag gcatgcagta aaagcaattc taggatgatt gctgtttggc gcgtagttcg    45480
tattagaaac cattcttctt gaataaatag tatgtttaag aagctgggca gagggaaggc    45540
atatgcatat attatcaaca aggagggaga aaaaggcaat tagtaaccat ccataggagg    45600
gtcagcaaga tttataaagg aaatttgtga tccaagtatg aagcaaaata aggtgcagaa    45660
taaatttttaa gcaagtaata gattagagta agagaaccca tttgaccatt aaccttggga    45720
cattctcttt caaatgacat ggagtagtac tgaaatcttt ctttctttct gagtctaggt    45780
tattgtgact ggactcagaa agaaatattt cattattgca gtgaataaca tttgtgaaca    45840
ttattgttca taaattatgc agtgaataac atttatgaac acgtgatgtg taagatacat    45900
actgtttatt tttagttaag ttttttggct caacttctag gcagagaaca ttaaatgtaa    45960
atagtgttac ctaggagcat gtaaatggaa atctccatag tatgaaagca gtgctgttgc    46020
taacagaatt taggaggggg cagatgaggt gaaggaaatg tgggtgctga tttccttatt    46080
acattgagag gagccaggag attctttgtt caaaatggat ggcttaagaa gtcaaagtat    46140
aagctgatta cgtagagcag gtacccaaaa atgttttgtg taaggggcca gatagtaaat    46200
attttcagtc ttgcaggcca tcccaagtct gtggcagcta ctcaacacta cctttgtagc    46260
atgaaagcag ccacaggcag cccataaatg tggctctgtt ccggtgaaac tttaggtaca    46320
aaagcaggtg caggccagac ctgacctgtg cactgtggtt tgctgacctg ggattcaggg    46380
gtatagaagt taccatcaga agagctaaaa gtgagacttt ttactttata ctcttctaca    46440
ctgtctgatt ttgaaaaaaa gaaacatgta ttttataata ttaaagatag ggttggcaaa    46500
tagcaaataa aaatacagaa taccagtgaa atttgaactt cagatacatt atgagtaatt    46560
ttatggtgta agtatattcc aaatcatgtg ggacatactt acactacaaa attatttgtt    46620
gtttgtttac agtttaaatt tgagtgcctt gtattttatc tggcaactgt aattaaaggg    46680
aaaaagaata aattcattat gttcatataa tgtgatatag caggggtccc caaccccag    46740
gctgcagagt ggtactggtc catgggtccc caaccccag gctgcagagc ggtattggtc    46800
catggcctgt taggaaccag gctgcccagc aggaagtgag cagcaggtga gctggcattc    46860
ccacctgagc accgcctcct gtcagatcag tggcagcatt agattcccat aggagtgcaa    46920
accctattgt gaactgcaca tgtgaggggt ctaggttgtg cgctccttat gagaatctaa    46980
tgcctgatga tctgaggtgg aacagtctcg tcttgaaacc atcccctggc cctgtggaaa    47040
aattgtctcc catgaaacca gtctctggtg ccagaaaggt tgggtagcac tgtgatatag    47100
tattaaaagt gctaataaat atggcatact gcctttaaaa tgtctggtag ctctttctca    47160
```

```
gtggcactca taatagtgtt ttttgatttt taaatgtgtg tcaagctgac tctcccctcc   47220
gtgtatgctg ggctttattt tcccttcct  agtcaccagt tttgggaaat agagatcttc   47280
attctcatgc tgctcctcta gtgcaagtgc tccatttatt tttaaggaat taatataaca   47340
aaaaatcatg ggaatttaga aaacaacatg gaagctaatg atcacattgg tggaagtgat   47400
agggaaatat ttaggggggag aagttaaggt ataaactttg tcaatgaagt cctattaaaa  47460
acaacaaaaa agtgaagctt aggatgcatt ttataaactc tgaccagaac acctgtgttt   47520
ctctgtttct aggtttatga actgacgtta catcatacac agcaccaaga ccacaatgtt   47580
gtgaccggag ccctggagct gttgcagcag ctcttcagaa cgcctccacc cgagcttctg   47640
caaaccctga ccgcagtcgg gggcattggg cagctcaccg ctgctaagga ggagtctggt   47700
ggccgaagcc gtagtgggag tattgtggaa cttataggca agttattagc aaggtctact   47760
cttacaatta actttgcagt aatactagtt acactctatt gattatgggc ctgccctgtg   47820
ctaagcagtc tgcattccat cttccttgcc aaaacttata atacaaattt catctttatt   47880
ttataaatag gggagttggg ctgggtgtgg tggctcacgc ctgtaatttc agcactttgg   47940
aaggatcgct tcagcccagg agtttgagac aacctggcca agtgagaccc tgtctctaca   48000
aaaaaaaaaa aaaaaaaaa  attagctggg catggtggca catgcctgta gtcccagctg   48060
cttttggaggc tgaggtggta ggattgctta agcccaagag gttgaggctg cagtgaatct   48120
tgatggcagc tgcactgagc ctggtgacag agcaagatgc tgtctcaaaa taaatttaaa   48180
aataaaataa gagaattaaa gtttagcagg ttgggtggca aaatgaggcc acacatttaa   48240
agcccctcct cctgattctt ttctctgcct tggctgcctc ctgtggcatt ttaggtgctg   48300
agaaatgaaa acagtaggga aaatagttcc aggatcctca tgttaatttg ccagaaatgg   48360
catcttcaag tcgtcagagg gatctgagag ttccttcctg gcctgacttg agaaaatccg   48420
tctgtcccca gctctgcgtc tgcctccact gcccagtcac ctcctctcca tgctcttggg   48480
gctgggccct accccaccat gcagtgctgc cctggagcag tgagcttggt gggtcctgtc   48540
tggcatgaga gctgccttg  ggagctggat cccagcctct accactgggt ctggtgccta   48600
gcaggctatg gataaacttc tgctgactcc ggcctctcct aagccactgc aacgtggtcg   48660
gtgtagtgca cagtgtgtgt gcagcgtggc cttactcaca gcctccacat tagagagaat   48720
ctgactgaag tcttactgct gcctcgtgtg aacataaatg tttgccagaa ccatgagcag   48780
gaaatgttaa tctgccttgt ttcctgtcct ttacacggaa gaatttttt  ctgtatggaa   48840
tgcgtgcctt acaataatg  agtggaaata cccatcgcta atgaaaagtt atacttgact   48900
gttagtcagc taaataatct gagatttcta atactttta  tttggctttt acaatgcaat   48960
ttatcttagc ttttttgatt tcttaggtca tatctttaga actatatatt tgaatgttaa   49020
tgtaatttc  atattgaaat taaaatgttg aactgcgatg ttaagtgttt cctgtggaaa   49080
aacgttcaca ttttctctag ttttaaagtt gaatcaagct gtttgaagat tttcacatt   49140
cttctagatt ttatcagctt gttactttat ctgtcacttt ctgtgatttg cagctggagg   49200
gggttcctca tgcagccctg tccttcaag  aaaacaaaaa ggtgattatt tcagaaatca   49260
gagtcttgtg ttgaatctta ctgatttct  tgtatttctg taatgtaatg tatccttgtat  49320
ttccttgtaat actgtattgg actctgtgta tatctcttct cagatgagtg attatatgtg   49380
tgaatgttgc tggaatctga taaccaggcc tgaaatagttc tgtagggtgg cttttaaaaa   49440
ttactttcat atcagaattg ctttgtcata aattttgaac gcatcataaa tttctaatgt   49500
```

```
tcggggtcag cagactttt  ttgtaaaggg acagagtgta aacatcttag ctttatgggc  49560
catatggtct cttttgcaac attcagctct gccctgtgac aggaatgcag ttgtaaagac  49620
atgagctact ggccagctat gttccagtag aactttactt acagaaacag acaggctgta  49680
gtttgccaat acctgcctta gggaatgtgt tgttatattt tgtgagttac cttctcagta  49740
aattttattt agtattagtc aggaatatta ttaagtagct tcttttccag cctggtcaac  49800
atagtgagac ccggtctcta ccaaaacaaa acaaaacaaa aaaacagcca cgcatgtggc  49860
atgtgcctgt agcctcagct gctgctcagg gggctgaggc aagaggattg tttgagccca  49920
ggagtttgag gtcacagtga gctgtagtca tgccactgca ctccagccta ggcaacagaa  49980
tgagaccttg tgtcttaaaa aaaaaaagtt tcctttgttg ggttatttta atttggacct  50040
ggttatcatt tttcagccat atttaacttt gtacatatca gaatgttctg ataaaactta  50100
acttttatta aagtgtttgt gatataatct gctagttttg gtacacatta tcttttgcaa  50160
tgccagttat tttctttttcc agtgtgggtt tgcataggaa aagaattgct gtcactttct  50220
attttgaaat cttaaaagac tgatcctttt ttgtgtcatg atttgagtat ttaattgaga  50280
gcctaatgcc taatattatt tgcagtatta aatgggatct taacaggaat agcattctag  50340
ccttcattga attaagtaaa catttcttaa gagaacttgg aatctataat atttgcgtca  50400
tcatagtatg agatacttaa tcaagtttga gattttagtg aaacattgtt tagaagccaa  50460
aaggattcta ggaaaaatta atgtctatat tcttgaatta ggagagattt tgggacgtgt  50520
gactaagtta cgctgacact tgtttgtttc ttagtcgctt tttccagtgg cggtgagaac  50580
gaagatgact gattcacatt gctcagatga gtttatcctc ttctggctgg acatgggat  50640
atatcctgtc tcttttaagc cttttttggta tttttccccc attgagagct gtgtcttcaa  50700
actcttctgt tatagctgga aaatcctttt taagtgaaat ctgcccaaat tataagacag  50760
atgaaggtag agttgtgttg gatataggat tagggtgaaa gtagtggggg tgtcctggag  50820
cctctcttct ggtggcagcc tagctcttgt gcctttgagg aaattacccct ggggacggct  50880
ctgtggaaca tatttgcaaa ccactgattt ggaagataga gatggctttt gttaagatct  50940
gaattcacct ttttggcatt ttatttgatt tctcaaggta aagaacttat tttgtaataa  51000
agtttcctat tatttagtag ataggccaag ttgctgtgtt aattccatgt agattttggg  51060
tttcctttgc tcatttttc actcttaatc tcacatcatt gtaagtttat ggaagttatc  51120
atacttctga cttttttcttt gaagagcaga aattagaaat tcccaataat tattttgata  51180
gtgtcattta atgacactca catgtgatgt agccacaaag atttaatgag ttcagtttta  51240
aatcatatta agactgttgg tttcatttgt tctcattaat gtaattctga agatgaacaa  51300
taaaatgtat ttttagaact ttcaaatgaa atattatttc atccttccag atcatataat  51360
gcttaagttc tgattgttaa tcataaagtc tagaaaatta aagataata aaatgaaagt  51420
gactttttagg tattagagtt ttattataaa ttctggtgtg tcattggagc tatgacatga  51480
atatttcaaa ggccaatagc attggatctt tacagttata acttaccatt tttaagttta  51540
agtagtaata tagattattt aataatcaaa atcaataaat attaattatt aaaatgtttt  51600
gtggtatagt ttgagaatca ttgcttttaa ctttttccat ataggtttat tgactttaat  51660
agcattctaa acataacatc tctacattct ttgtgtttaa tactgtggag gtataaaaat  51720
acttatatat gatgataaac tatattagag taaattaaat attcttatga gtttcatttt  51780
agagtgcatt tacttaattt tgaagtcctt attttagca aactaaaagg aatgttggta  51840
cattatttac taggcaaagt gctcttagga gaagaagaag ccttggagga tgactctgaa  51900
```

```
tcgagatcgg atgtcagcag ctctgcctta acaggtagtt ctcactagtt agccgctggt   51960
gtggaccttc actgtctgcc ttccacccct tgcccttcct gctcgtcccc ctgcacctgg   52020
tggacagcac gactgggggc agcagtggag ccaggttgct taaatggggc atattcgggc   52080 ttctttata  atacttactc tgaagcttgt gtgtctgtgg tgtttgcatc atatatttgt   52140
tgttttccat ggtttaggct gttttaaaat taggtttatg cttgagcat  agggctttgt   52200 gagtagggga tggcaggtcg aaacatctca tgagttggat gggttatgct gggggttggg   52260
aaatgggatg aaaaattatg ggatgaaaaa ttgcctatgg atagtttaac ttgaaagaat   52320
ctgcctttgt ttacagatag ttatctttt  tcttttttga gatagagtct cacactgtca   52380
cccagtgcag atacccagtg tcactggagt gcagtggtgt gctcttggtg cactgcagcc   52440
tccgccttct gggttccagc gattctcctg cctcagcctc caagtagct  gggactacag   52500 gtgcccgcca ccacgcttgg ctaattttg  tattttttg  tggagacggg ttttgccat    52560 gttggtcagg ctggtcttga actcctgacc tcaagtgatc tgcctgcctc agcctcccac   52620
agtgccggga ttacaggagt gagccactgt gcccggccag ttacagatac ttatctaatg   52680
aaattctctg tgtactttat aaaagatgag gattaactga aggtactaat aactggatta   52740
tatgagggtg gttttggttg tataatccta tctaaaagaa tattttagct ataactgaaa   52800
gtaagactta aatatttaga gaggaaaatc tgaataattc tagtagtaat tatttattta   52860
caaaataaaa atagattttt ttttgattac acaaattaaa caacaataaa acatcacagc   52920
aatccggata ctataaagct cacatgctta ccgacccaac tgcccaggaa gtgaccactg   52980
ccaacagctt catgtcgacc tttttgccat aattttata  tagcctttt  tgttttaaa    53040 tggtaattta gaaagtcaac taggaaaatg tgttacaggt ttatcttcca ggagaatagg   53100
actggagtcg agatcttgaa tgtggcttgg aagaaggcaa gcccacccca gagagatgag   53160
ttgacagttg tttctgacca ctgcttgctt agagggcctg cgtgtctgtg accgcctagc   53220
tttgcgcccc tgactaggct gcccttaat  tacaaatgtc tttatatatt gctccagcta   53280
aggcttggag tagtcggtta agaacttgaa cttcggtttt tgcagtgaaa cagcatttga   53340
gaatatcacc ttctgataag ccttatttta taaggtgggt actgtagtgg gaggcagtgt   53400
gagagatgct tgaaggatgc actgctgtcc tgcatttcag catcttcagg atgctgtgca   53460
gctgaaacat ttgataacgg tggaactgtt cgttattttg caagcctgtg attccctatt   53520
gaatgttttc tctcgccatt tgacaaatga gtgtttctct gtcttcagcc tcagtgaagg   53580
atgagatcag tggagagctg gctgcttctt caggggtttc cactccaggg tcagcaggtc   53640
atgacatcat cacagaacag ccacggtcac agcacacact gcaggcggac tcagtggatc   53700
tggccagctg tgacttgaca agctctgcca ctgatgggga tgaggaggat atcttgagcc   53760
acagctccag ccaggtcagc gccgtcccat ctgaccctgc catggacctg aatgatggga   53820
cccaggcctc gtcgcccatc agcgacagct cccagaccac caccgaaggg cctgattcag   53880
ctgttacccc ttcagacagt tctgaaattg taagtgggca gaggggcctg acatcttttt   53940
ttttattttt tatttgagac agagtctcac tccatagtgc agtggaggcc gggcacaggg   54000
gctcatgcct gtaatcccag cactttggga gactgaggca ggcggatcac ttgaggtcag   54060
gagttcgaga ccagcctggc caacatggtg aaaccctgtc tctactaaaa atacaaaaat   54120
tagttgggcg tggtggcaca tgtctgtagt cccagctgtt agggaggctg aggcaggaga   54180
attgcttgag cctgggaggc agaggttgca atgagccgag atcgtgacac tgcactccag   54240
```

```
cccgggcaac agagcaagac tccatttcaa aaaaaataaa aaaataaagt gcagtggctc    54300
gttctcagcc cactgcaact tctgcctccc aggctcgagc gattctcccg cctcagcctc    54360
ctgagtaggt gggattacag gtgggcacca ccacactcag ctaatgtttg tattttcagt    54420
agagacaggg tttcaccatg ttggccaggc tggtctcaaa ctcctgacct tagatgatcc    54480
acccaccttg gcctcctaaa gtattgggat tatagttgtg agccaccatg cccggccctg    54540
ccacctgcca tcttttgagt tcttccctgg agacctagac ctgaaccctc ctgcttgttc    54600
tcttgttatc taatacccct attgacagcg cagcttagat cattaatgga gagcttgacc    54660
tcatctgata ccttcactga aggaaacaac ttagtgtctt ttgtgttgaa cactgaggta    54720
aaaaattgga atagttgatt atatgaactc tgctaaaatt gagtgcattt tacattttt    54780 aaggccttgt tgggccctgg ttaaataatt attttaaaa atccttaagg agcctattat    54840
aaacagatct gtggtcttaa tgaaatgtga ttaatactgt gcattatttt aagaactttt    54900
gacttttcaa aaaacttta caacatttcc catttgatag cggcataggt ttaagcactt    54960
ctcatctcta agttagtgga caaaaaccc tcatggatag tctaataatg tttgctacaa    55020
gtccatgttg agttttatac tccattttat tttcagtttt aaaaactgtg gttaaatatg    55080
tgtaacataa aatttatgtt cttaaccatt ttttgcgtat acagttcgct ggtattaaat    55140
acatttaaat aatgtcatgg aatcattgct accacccatc tctgtaacct tttgatcatg    55200
taacactgaa gctctgttcc cattgaactc tattcctcct ttcccgccaa gtccctggca    55260
accacgattc ttcttctgt cttctgaatt tgactacttt gggttctcat atactttagg    55320
agtcacacag tatttgtttt acttagcata atgtccccaa agctcatgca tgttgtagcc    55380
tatgttagaa cttcctaatg tttcaggcca aatactattc cattgtatgg ataggccaca    55440
ttttgctttt ccattcctct gtccatggac acttgtattg cttcatgttt tagccattgt    55500
gaatcatgct gttatgaacg tgggtgtaca gatagctcct ggagactctg ctttccattt    55560
ttttggctaa atacccagaa atggagttgc ttttacattc caattttaat ttaaaacatt    55620
catatcattg agtgttttac ttaatagtat agtagttaac aaacttaata aaatagtatt    55680
ttggtaataa tttgctggta gtccattgtt cagtttttt aggtaaatta cacaggacat    55740
ttcaagtgga catgaaacat cttgtgatgt ggaatcatgc cccaagctga tggctaaaca    55800
tatgaaatac cataccctaa atttagtaga tttagtcttt gcaatttagg agataacctg    55860
ttatattgtt aggttttgt cgaaaagctt tgtcctcata tttccaactt gctgtaaaat    55920
ttgtttgtga agacaaatat ttttgtatgg gttttttctt tttcatatta aaagaaatg    55980 tccacattgg aattttttg gagttttag agctaataga gcttttcata atgtagtggg    56040
aatgagtgat cagtaagctc ttagcagttt ccatgcgtgc atttctgtgc cttgaaataa    56100
atgacagatg agtacatttg tgttctgtgt gtaaaatgtg ctctttcctc attgcacttc    56160
catgttggag ggcttgtctc ttggtgatca cacttcaaaa ttctcacagc ccccttgaa    56220 ccgtttaggt gttagacggt accgacaacc agtatttggg cctgcagatt ggacagcccc    56280
aggatgaaga tgaggaagcc acaggtattc ttcctgatga agcctcggag gccttcagga    56340
actcttccat gggtatgtgg actacaggtg atgcgctaca aagtggtttg tattcagacc    56400
tggacatctt aattatatct ttgcttccaa gaagaagtcc tttgatactg ttttctgagt    56460
tctgaatagc tgatgaaaat gaccaattga ggaataatca tactttttct tgatctaaat    56520
cttatacttt tgagttatct tagcataaat gtataattgt attttaagtg gaatttgtc    56580 acttaatctt gatttctctg ttttttaaagc ccttcaacag gcacatttat tgaaaaacat    56640
```

```
gagtcactgc aggcagcctt ctgacagcag tgttgataaa tttgtgttga gagatgaagc    56700
tactgaaccg ggtgatcaag aaaacaaggt gagggacata ggcttgagac gacttggtgt    56760
ttctgagctt gtgtgaggat ttaaaatcgc cctggctact gtctacttta ttgctttccc    56820
atccctgggc ctttaaattt cccctttaaa taccagctct tcccaggcct gttgttttct    56880
gcctttccag gtactaccca cagccttgag aattgcctga gttctgcctc ctttgagagt    56940
gtgccccaga caaatctatt ctgtactgaa tgtttccttg tctgatttct tggatcattc    57000
atttgatggt tgcgtatggc ctgcaacgtt tcttgttttg gttctactga actgttctaa    57060
aagtctctct tcatattatc tttttacatg taaatgtaac tgtcttcact tttaattcct    57120
caaggacaag gaatagcgtt tcacagttcg tcccatcaat cagaattata gcctttggca    57180
tctccctatc taccaggccc acttcctctt agatttgggc ttccccaggc tgttgccttt    57240
ccccaagtag cttctgcttg tcctgtagaa gacctttcat gctttgcttc tgcagcagcc    57300
gttcctgaat gccagtgtc aactgccttc ttaccacgcc caccctccct gcatgctgca    57360
tttatcccct gccacagccc tgtgaccctg tgtcctgctg cctctgactt gtctgtttct    57420
gcttggccat ggtctctgtg aggtcaggtg tgcatatggg cacaaaccag ggcatctctt    57480
tatccccagc acctggctta agtgctgctc tggaactatc tgttgaatga actaatgcat    57540
gaatgtattg ttgagtatga gacaaacaag tgtcattgtc tcctttctag ccttgccgca    57600
tcaaaggtga cattggacag tccactgatg atgactctgc acctcttgtc cattgtgtcc    57660
gccttttatc tgcttcgttt ttgctaacag ggggaaaaaa tggtgagtac aaaaggggat    57720
gtgcacagtt gaaggaaata actaggtttc agaggtcagc ttggtggcct gtttttgcct    57780
tgcgtgcagc agaggaagta gaatctgagg atgagtttgg ttttcactag ccgaggggag    57840
ggaggaaatg atgggagcag gtaggttatt gggtctggtt ttgttcattt gaaaacaatc    57900
tgttgtttga ggctgaaggt ggcttgggtg atttcttggc agtgctggtt ccggacaggg    57960
atgtgagggt cagcgtgaag gccctggccc tcagctgtgt gggagcagct gtggccctcc    58020
acccggaatc tttcttcagc aaactctata aagttcctct tgacaccacg gaataccctg    58080
gtatgttaaa agttcacatc ttattttctc agatttaatc attattgtaa aaactatttc    58140
agtattgact attttagttt tagagcagta agtgttttga gttcatttgg gatatttgac    58200
ctgcgttgta gctcttcaga aaacacatga atagtgaagt tctttgtttc atgggttccc    58260
tttagatgaa acccatagag gagaaaagta gaaacctcag cacgtaagag ccaacatata    58320
tacacatcgg atttaaacct aaagcacaaa ttgtgcctgg tcgcagtggc gctgagtcgc    58380
actcagccag gccaggcatt cacactcagg gtgagtggga accaggactg gctgaggcag    58440
cagtggaccc aagtctccat cgcgcccatg cttactatgg agccttctcg ttctctcttt    58500
ttctttgggt gagagggtac acttgtgttt ttgaatttat atgaggtaag tgtgtaatag    58560
ggttttttct aatctttttt aagtggaatc tggaatttta atcagattta ttatctgaca    58620
acctagaatt ataatccaga aagtctgtgg tattgaggac atattggcaa tatgatgaat    58680
ctctaattct taaatcctga aacttttttt tttttaatca cttagggtta ttatagtgaa    58740
gtcatttctg aatttggatc ttctcttcac acctctttttt ctctttcctg agaattaagc    58800
ttttgtttcg agttagaaag ttgatagtag ggaattgttc catggctgag caatttatct    58860
ccacagagga acagtatgtc tcagacatct tgaactacat cgatcatgga gacccacagg    58920
ttcgaggagc cactgccatt ctctgtggga ccctcatctg ctccatcctc agcaggtccc    58980
```

```
gcttccacgt gggagattgg atgggcacca ttagaaccct cacaggtaac ggccagtttt   59040
tcagctgtgt ttttctagt tatgcttact aaggtttaag tttagatgat gatgtttgtt   59100
gcttgttctt ctggttagga aatacatttt ctttggcgga ttgcattcct ttgctgcgga   59160
aaacactgaa ggatgagtct tctgttactt gcaagttagc ttgtacagct gtgagggtga   59220
gcataatctt ctgtggaacc atttcttcac ttagtggaca ttttatcatt gctacaatta   59280
aaattggagc ttaataggaa atatttccat gcactctaaa gctgtaacca gtaatacccca  59340 ccatgtatcc atctctcagc tttagaaaga aaacgttgcc agtaaagtta atgcttcata   59400
aacttcagtt taagttctaa ttctcagaat atttgtttga aatagacctc ttcctaaagg   59460
atatatttag aaataaccta tcattaagtg taaagtctgt tgaatatgct gggcacggtg   59520
actcacacct gtaatctgac cactttggga ggccaaggtg gaaggattgc ttgagcccag   59580
gagttcaaga ctatgggcaa catagttgac cctgtcccta cagaaaatta aaaaaaaaa    59640 aaaaaaagt agctgggtat ggtggtgcat acctgtagtc tcagctactc gggaagctga    59700
ggtggagggg ggattgcttg agccccagag atcaaggctg cagtaaggcg tggttacacc   59760
actgccctct agcctgggca acagagtgag actgtctcaa aataatagt aataataatc    59820 agttgaatta aaaaaaaaa aaaaaaacc actgtgctag gcccatagta tggtaagagt     59880
taaagtgagc cttagggatt atttactcaa cctctgtttc tgtataaagt ggaataggct   59940
caattcttta agtgatagca tgttgaacct ttccatacca actggctcat aagtcacaac   60000
tggccagtca acaagagtaa aaattaactg gtaaaaatca agcaaaaaa cctacaattg    60060 tcaaatttgt gggataactc cccctttttaa aatgtcatgc ctgacagtaa tttctctcta  60120
gtttccaggt tttcagtcag ttgtgtcttt tttgagcaga aggaagcatg ctaagagctc   60180
aatcttgtgg ctagctgggg gtctttgtgt cagccatgca tgtgatggtg cccctggggt   60240
cttggggctg caggggaggg gtacagcagt aggggcctgt tctgttctct cgtgctgtgg   60300
agtacatagt gacatagtgg ggtggtcctt ggtgtaggtc ccttgttcct accccctgggt  60360 ctgagattta tttagaagtg gtgttggggc tgtgcggcag gccccctctgt aactgatcaa  60420 tgtttgtgaa gttgctgttt gagagttgaa accatgacat aagcagaaat ggaaggaaga  60480
aagaaccagt tatgtgaaag ggacacattt acttttaagc ttgtatttac tgagataaag   60540
tattcttaat caatgttctt gagaggtgtg ggaaaaatgc aacatcctgg ttgcagttaa   60600
acccagaaca ttgtgtgttg aagagtgacg gttctcaaac cgtcaagacg cgggtactga   60660
gtgggactaa cctgctgtcc tcttgccttg gaccttgtgt tccagaactg tgtcatgagt   60720
ctctgcagca gcagctacag tgagttagga ctgcagctga tcatcgatgt gctgactctg   60780
aggaacagtt cctattggct ggtgaggaca gagcttctgg aaaacccttgc agagattgac  60840 ttcaggtaag tgagtcacat ccattagatt tcatgaacta agctcaattg aaagttctgg   60900
gatcacttga tgcaaggaat gatgttatca agtaccctgt ccatcagaaa tccgagtggt   60960
ttaggtagat gacagtgatt ttctcctccc agtggctttt tgctgaactt tgccctatgc   61020
ttggaatttt atttattttt attatttatt tagagacaag atcttgctct gtcgcccagg   61080
cttgaatgca gtagcacaat catagctcac tgaagctttg aactctagga ctcaagtggt   61140
cctcctgcct cagcctcccg attagctagg agaataggtg tgtgccgtca cactggctaa   61200 tatttttgt agaaatgggg tcttgctatg ttgcccaggc tggtctcaaa ctcctgggct     61260
tgattgatcc tccatcttgg cctcccaaag tgctgggatt acaggcatga gccactgtgc   61320
ctggcctaga attttaaaat ataagtagaa gagtagattt ttttttttgg tagtcctcgt   61380
```

```
catttaagta ttctggatag tgggaataaa agagcttaga attttcatc tttgtcttaa    61440 acttttaaaa aaatgtagct tatattaatt ctgcttgttt aaaaagaata tactcttcat    61500
tatactgaac ctaggtaaga cagctggttt atattttgtt gcaattaaaa aacgtgagct    61560
gtggttgcag tgagccaaga ttgtggccat tgcacttcag cctggcaaca gagtgagact    61620
tggcctcaaa aaaaaaaaaa taacatgagc tgtgttggca ctttcatttt ctaagagtag    61680
ttttggctgg agaagttttc tttcagtact ttcttttaga agggaaattt tcctttataa    61740
tttagggttt gttttttttt tttccaagcc accttttata gagcccttgt gggttatttc    61800
atttaatcct tagaatgttt ataaatctgg gcttgttctc ggctccaccc acagataggg    61860
acgctgagcg tgcatgagtg ggcagcaaga tagcaggtta tggagggccc agctcacccc    61920
ttctgtggct tgagccaatt ttatagggca cttacagagt cttttgaaat agtatttatt    61980
ttgaagaaaa agaaaaacag tttactgagt actgtcttat tgagtctgga attgtgagag    62040
gaatgccacc tctatttatt taaagccatt ggccttttt gttgttttga gtaagtgctg    62100
cccaaggtcc ttccagggca cctggatgag cctgctctgg agcaagctgg cggtaagtgt    62160
ttactgagta actaaatgat ttcattgtta aatgtgctct tttgttaggc tggtgagctt    62220
tttggaggca aaagcagaaa acttacacag aggggctcat cattatacag gggtaagcgg    62280 tttattttg tgagatgctg ttttaccttc aagaaggtga aagtgaggct ttccttgtgg    62340
aatttctcta aatgcattcg tcatgtttta gatgtttatt tcacagttta tatcatgaaa    62400
gttataatct tgtcatatgg atttaagtct agtaatgttg agttcttct cactagcttt    62460 ccaaaatatc ttacctaaaa tttagtcaaa tacaagatta tgtttatttt tattatcctt    62520
ctctctaaag cttttaaaac tgcaagaacg agtgctcaat aatgttgtca tccatttgct    62580
tggagatgaa gacccagggg tgcgacatgt tgccgcagca tcactaatta ggtatttacc    62640
aatattttat ctcttttcct tttttggttg aagtactaaa agatacgaga atggaaagag    62700
agggaagaat tcaaaggatg tagagcagta ttcctgaatc tgagctcatt tcagccattc    62760
tattcttaaa ctataatgaa aaaaaaatcc aaaaaagtct aaaattataa ttaaaaaaac    62820
aacaaaatac taactgtcca ttgtaaaaag taatgcactt tcattgtaaa aattttggac    62880
tatagagaat agtactaaga agaaaaaaaa aatcaccttc aattctgctg ccacctggag    62940
gtaatcactg ttaatatttt gctatatact ctatgagttt cttgttcaaa atcaggtcaa    63000
aattacatgc aattttgtaa tctgacaatt tccacttaat attttattag cattttcctg    63060
ttatgaaaca gtaattttag ttatgggtcg ttgttttgct atgcggttgg gataaaattt    63120
tatatacttt ttttggcaat tacttattat acataaatgt ttgtgtatag ttttcttttt    63180
ctgagaattc ctggaagttg agttaccagg cccggctttg aattttttt tttattttt    63240 ttttgagaca gagtcctgct ctattgtcca ggtgctatct cggctcactg caacctctgt    63300
ctccctggtt caagcgattc tcctgcctca gcctcccgag tagctgggat tacaggggca    63360
caccaccacg cccaattaat ttttgtattt ttagtagaga cagggtttca cgatattggc    63420
caggctggtc tcgaacttct gacccgtga tccacctgca ttggcctccc aaagtgctgg    63480
gattacaggc gtgagccatg cgcgctgcc aggcttaaa tttaaaacaa atcttctaat    63540
agctttatgg aggttataat ttacattct tgaaatgtac tcactttgag tgtatagtaa    63600
actccaattt tatcacattt ctgtcacccc aaatgtatcc ttgtgcccat tgctgtaac    63660 ctccggttcc tgccccaact cctaggcagc cactcatcta tttctgtcc cttaagattt    63720
```

```
gtgttttcgc caggcgctca tgcctgtaat cccagcactt tgggaggccg aggttggtgg   63780
atcacttgag gtcaggagtt cgagaccagc ctggccaaca tggtgaaacc ttgtctctac   63840
taaaaataca aaaattagtc ggatgtggtg gcacacgcct gtaatcccag ctactcggga   63900
ggctgaggca ggagaatcac ttgaacctgg gaggcggagg ttgcagtgag cagagatcgc   63960
gccactgcct tccaacctgg gcaacagaga gagactgtct caaaacaaac aaagatttgt   64020
attttctgga catttatag tactggggtc atagtataga tggacttttg catttggctt   64080
cttttactta attgtgagat tggttcttgt tgtagcatgt atcagtagtt tgttcatttt   64140
tattggcgaa agtattctat tatatgaata ataccatatt ttatctatcc atcagatgga   64200
tattatagag ttcatgtttt ggctaattta tgaattatgg tactgtgaac atttgcctgc   64260
aagattttgt gtagacatgt cttcatttct cttgagtaga tcacctagaa gtggattttt   64320
aaataatttt ggtacttact gtgaaactgc tcttcaaaaa cataccattg ttccttcctt   64380
ccttccttcc ttccttcctt ccttctttcc ttcctcccttt cctccctccc ttccctactt   64440
ccctctccct ttccctttcc cttcccctttt tcccttcccc ttcccgcctg cctgcctgcc   64500
tgccttcctt ccttccttcc ttcgtttctt tctacatata cacattttttt taaatttcaa   64560 tggttttgg ggtacaagtg gttttggtt acatggctga attttggtta catggtgaag   64620
tctgagattt tagtacacct gtcacccgag tagtgtacct tgtacccaat atgtagtttt   64680
ttgtccctca ccttccagcc ttccgccttg tgagtctcca atgtccatta taccacactg   64740
tatgcccttg cgtacccaca gctcagctcc cacttctgag aacatatagc agaaacatgc   64800
caaagtatac tcccactacc agaatgtgat tgtgcctgat tcttctcacc agtacaaata   64860
tttcaaaaaa agttaaatat gtatcagttt tttgggcaga agttgatact tctctttatt   64920
tatttatttt ttttgagata gggtctcatt ctatgatgcc caggctggag tgtggtggtg   64980
cgatctcggc tcactgcagt ctctgcctcc caggttcaag tgattcccac gtcagcctcc   65040
caggaagctg gaattacagg cgagggccac cactgccagc taattttttgt atttttttggt   65100 agagatgggg tttcaccatg ttggccagac tggtctcaag ctcctgacct caagtgatcc   65160
acctgccttg gccttccaaa gtgctgggat tacaggcgtg agctaccaca cccggctgat   65220 atttctttttt aaaataactt accttctttt gaaagtaata catgtttaat gaacagaatt   65280
taaggaaaat ataaaaaaac gaaataatct ttgtaatcaa actactgaaa agaaaaccaa   65340
agttacattt tggtgcatat tcttttcat tttcatcatt gtaatttgca tttctttgat   65400
tacttgtgag acactccttt catttactta ataggtttat atgacttgcc tattcagaga   65460
ttttgcagct ttaccatttt ctgcaaatga tagcaacttc ttttgtttg tttgtttgtg   65520 gagacagagt ctcgctctgt cactcaggca ggaatgcagt ggtggaatct tggctcattg   65580
caactattgc ctcctggggtt caagcgattt tcctgcctca gcctcccaag tagctgggat   65640
tacaggagtg tgccaccatg cccggctaat ttttgtatct ttagtagaga tggggttttg   65700
ccatgttggc cgggctgatc ttgaactcct ggcctcaagc ggtcccctg tctcggcctc   65760 ccaaagtgct gggattacag gcgtgagcac cgtacccagc cagtagttac ttcttatatt   65820
ctagaaaaaa ttctactcat gatcaagtct ccatgaggaa agagactta attgaagatc   65880 atggggcttg cagaccaata tgataaaata gttcattgtt tctaaaagta ttactgagtg   65940
ttgatggcag atatgaaccc ttttgttttt gtaggaaaat gttacccgta ttctccattt   66000
gaattcagtt tagatttgtt aggaatcgca gcttaagctt tgccatctgg gagtgtttgg   66060
gacagttttg cagacaaaat tgcaaaagtg cctaaggaat gcagctggca ttcagacctg   66120
```

```
ctctgtgctc agtactctgt ggacagacac tgttcagcac ttgttgatca gaaggtttag   66180
aaagagaact ttcaaagttg gtttttaatt aaagcattta atagtgtaaa tagaaaggga   66240
ttaaatttta tgacagacaa aagaaagtac agcacccagc tgggcgtggg ggctcacgcc   66300
tgtaatccag cactatgggg ggctgaggtg ggtggatcac gaggtcagga gttcaagagt   66360
tcaagaacag cctggccaag gtgatgaaac cctgtctcta ctaaaactac aaaaattagc   66420
cgggcgcggt ggcaggcgcc tgtaatccca gctactcagg aggctgaggc aggagaatca   66480
cttgaacctg gacggcagag gttgcagtga gccaagattg caccattgta ctccggcctg   66540
ggccacagag tgacattctg tctcaaaaaa aaaaaaaaaa gaaaaaaaga aagtacagca   66600
cccagttatg tccgagtggg tgcatgagag tgaccctgag attggagaca acgctgtcac   66660
gtgcttgaag aacgccacct gagaaagggg gcgagaagtg gtgtccgctg gtaaccagag   66720
gtgttggctt agccatctgc agggaggagg gtggtctatc acaggtgagt ttcatctact   66780
ttcttaagca aattaacctt acttttgtgt taggcttgtc ccaaagctgt tttataaatg   66840
tgaccaagga caagctgatc cagtagtggc cgtggcaaga gatcaaagca gtgtttacct   66900
gaaacttctc atgcatgaga cgcagcctcc atctcatttc tccgtcagca caataaccag   66960
gtatgctgac ccagtggcat cttcacattg tcgggaaaat gccctttcct gatgcctttc   67020
tttaggcttt aattgaaaac atttttatttt ctagaaaaaa gcttcagctc aggatgtttg   67080
agtgtaggtc agtcctttga taggatatta tcattttgag gattgaccac accacctctg   67140
tatttaagct ctgccacaat cactcagctg tgacactgta aatctcttaa tagtttatta   67200
cattccatgt gctgacagtt gtatttttgt ttgtgacact tacgtattat ctgttaaaac   67260
attttcactt tagttgtgtt acctttaaag aggattgtat tctatcatgc ctgttgattt   67320
tttggtgagc gggctattaa agtcagtgtt atttagggtt atccactagt tcagtgattt   67380
gcgagattat cattcacatt tattgtggag cttttgaata tcgtgtcaaa tggccacata   67440
tatcccattc ttatctgctt cttaggtgag tgggacacag tgctttaatg aagctataat   67500
cttcagaatt ctagcttgca gagaagattg cagaagtgat aagacttgtg cttttttaatt   67560 ttgtctttta aatgttattt taaaaattgg ctttatatga tactcttttt ttctgctgag   67620
taacagtgtt ttacaaaact tggactaaat gacttctaag cttaaatgat cacttgatgc   67680 ttttttctg aattaggaac tcagcttatc aaatatcaaa gtcataattc ctgaataaat   67740
aacgtctttt ttcatgtaaa gactgcttta aaaacacat ggaaggctgg gtgcggtggc   67800
tcacgcctgt aatcctaaca ctttgggagg cccaggtggg caggtcgctt gagctcaggg   67860
gttcaagacc acccagggca acatggcaaa acccacctct actcaaatac aaaaaattag   67920
ccaggcgtgg tggcgggccc ctgtaatccc agctactcgg gaggctgagg gatgagaatc   67980
acttgagccc cggaggcaga ggttgcagtg agccaagatt gtgccattgc actcccagct   68040
tgggctacag agtgagactc tgtctcaaaa aaagacacac acacaaacaa aaaaacatg   68100 gagacatttt tttggccacc ttaatatttc ccctcagata atttcctttg tttaaactca   68160
gaactggcat tttctctctt ggagaagatt caggacaaat actcctttaa gataagtaga   68220
agcagtgaaa gaggatttga ttatcaggaa tttgataagc ttagaataaa ttgttgcttc   68280
ttaatgtcat ttcagaagat gaatatttat taatagatgc caactgagat atcattaaaa   68340
ttgattacta actactactt ggaaaagtct cccagttcca aacttcagca ggcctcttga   68400
caattcagct gtggtcaatt gggtcttgcg tgatagatac aatgaccaat tgtgcagcag   68460
```

```
agtgtgctgc ttagctgcct attctgttag cattcatgtg ttaacttaaa atcataatct    68520
ccttagtttt gttgagtgtc tccgtggaca agacactgtg agggatacaa aatcagattg    68580
gctttattca aaccactggg gtattataat tcatttataa tttattttat tttttgcctt    68640
ttttccatgt gttctaaagg aattagagtt tgtatataac tataatgggg gatagaaatt    68700
gacatgtgcc atgaagggaa tgcaaaaaag tgccgtggga gatgagaagt ggagaaagga    68760
atttcttttt tcttggaagc aggaataact tcatgaagca tgtatttcaa cttaaacaga    68820
tagtaggcaa cgctgtaagg ggagtatggc tgcagcaaaa gtgttcgggg cagactggga    68880
ggaagggagg gaataaattc agccattgtt atggaataat gatcaaaatt tattttcagc    68940
ccgtttcact taaaagttga gactgcttaa ctttttttaa tctttaatct taaactttta    69000
aatgccattt gatctttaaa aatatatgtt ttaatagtgt attttaagtc tctatatttt    69060
tgttattaga atatatagag gctataacct actaccaagc ataacagacg tcactatgga    69120
aaataacctt tcaagagtta ttgcagcagt ttctcatgaa ctaatcacat caaccaccag    69180
agcactcaca gtaagtctct ttcttgatcg gtccttactga cattgtaata gtttttggta    69240
gcttgtatgg ccagttagtt gtatggtcat cttacggtga ggtgcttgtc ttacagctct    69300
tacttatcca tgaggcttgc taagaaattg tgcttctgtg aaaagaatct cagcttactc    69360
caggaatgta aatgactatg ttttttctga ttattaaagt aatacacgcc caaaataaaa    69420
aaattcagcc aatttaggaa gacacaacaa ttaaaataag ccaggcatgg tggctcatgc    69480
ctgtaatccc agcactttgg gaggccaagg ttggggctc acttgaggtc aggagtcgga    69540
taccagcctg gccaacgtgg tgaaacccca tctctactaa aaatacaaaa attagctggg    69600
cgtggtggcg ggcgcctgta atcccagcta ctcaggaggc tgaggcagga gaatcgcttg    69660
aacctgggag gtagaggttg cagtgagctg aggtcaagcc actgcactcc agcctgtgca    69720
atagagcgag actctgtctc aaaaaaaaaa aaaaaaaag aaaagaaaaa agtaaactac    69780
tgtcacctgc attggtaatg tatcagaagt ttaaaatgtc tagattataa ttaactcagt    69840
gacctggtaa tatatactaa gggaaaaata tttataattt acatttttac attttttattt    69900
ttttaatttt attattttttt ttttgagaca gagttttgct cttgttgccc aggctggagt    69960
gcaatggcat gatctcagct caccacaacc tccacctccc gggttcaagc aattctcctg    70020
cctcagcctc ctgagtagct gggattacag gcatgcacca ccatgcccgg ctaattttgt    70080
attttagta gagacagggt ttctccatgt tggtcaggct ggtctcaaac tcccaacctc    70140
aggtgatccg ccctcctcga ccccccaaag tgctgggatt acaggtgtga gccaccatgc    70200
ctggccttac attttataa taagaattta tgttgctgac attagaaaag aaccataata    70260
tccaagaatc caagaataat taaattatgt acatatgcta gtatatagtg tgatgctttg    70320
gagaattttt aacaatatgg agatgtataa tctggattgt aatattgagt gaaaaaaggc    70380
agaatacaaa cctggtgggg gtatagtcgg atttcagtta agaaaaataa tatttacata    70440
tatacatttc tcacactggc agataatcac caagataaat tttgggattg tggatgattt    70500
ttttcttctt tatattttc agatattctc aaattttcta aaatgagcaa gtataacttt    70560
tgttatcaga aaaaaataat atacaaaagt aatgttaatt tgctggtgac caggttaaac    70620
cttttatttt ttattttttg agatggaatc tcactctgtt gcccaggcta gagcacagtg    70680
gcatgatctt ggctcactgc agcctccgct tcctgggttc aaatgattct ctggccccag    70740
cctcctgagt ggctggaatt acaggcgtgt ggcaccacac ctggctaatt tttgtatttt    70800
tagtagaggt agggtttcac caggttggtc aggctggtct cgaactcctg acctcgtgat    70860
```

```
ccacccacct cggcctccca aagtgctggg attacaggcg tgagctactg cgcccagcca   70920 gacctttta ttttatttga caaaagaaat acttccatgt tatagaagac taaatattgt   70980
ttgggctgtc tgcagtatgg tcttcccttg atttgttcaa aatatcgtaa actttgctta   71040 tttatttta ttgtggccga ctgtgtcggg cactgttgta ggcttgggat ggaaaaacag   71100
gattcctgcc cttagggttt ctgcaggctg gtcagggaga cgatgtggta agctggagct   71160
cagctcctaa ggatgtgcag gggcagttga gaggcggaag ggtgggagat cattccaggg   71220
tgtgggcagc acaggaacct ctcttcattg ggatataatt gccattctga taacacgtgt   71280
ttgaggtgtc taaagtagga agttgtacca tggtgggaca gatatcctgt ggttatcata   71340
cacagatctc agttttcttc tcattgtttg tactttttat aaagggtaac aggagatata   71400
attcaataaa cctttgtggt gtttgggtgt gatttttattg tttctttctt ctcagtttgg   71460
atgctgtgaa gctttgtgtc ttcttttccac tgccttccca gtttgcattt ggagtttagg   71520
ttggcactgt gggtatgtat tttcctcagt atatattaat agttgctac aacagtatga   71580 cataaacata gttattagga tgccctttt ctttcttttt aagtctttta tcaatttggc   71640 ttttggaaa aatatctgat ggaatacttg tttctgctat attagctgtg tgagactagt   71700
gacaggagct gtgggaaatg aatgccaaat gttcttaggc attgatggga atttcagggt   71760
gtggtcttca agttcattta agggaatttt catatgctgg caaaaggctt ttctcattag   71820
cttgactctt tccaaaatta tttgctgtga attagaagtt taggaacctt ttttcactta   71880
attgtgacct agcatacgaa atggtgatga tttaggaact actgttcttg tattaacagc   71940 tttatttaa aaatgatttt cctccagtag atggccctac tagcatctgg gaaataattt   72000
caagtcttct ccagcattca ggaataggct ttcattttgt gtatcaatta ctgagaatga   72060
ttttggtgac tcacatcaca tttgagaagt aaacctgcag atttcttgtg tgtgtcagca   72120
aatgaccaac tgatatttgc ttgaagtgga ttacattatc tgctctagaa tgattgcttt   72180
cccaccttcc tcacatacag actgagcagc tacggtttct aatcataggt ctggcactag   72240
acttcacttc tgggcaactt tggcattgga gtaaaatgta ttaatttaaa gaaagttaaa   72300
aatccgttca agtaaacata cagttctaat acttttaca atttaaaata tagatttaaa   72360
tgataaaata aaaagaaaa tatgggtaga caccataatc ctcgtttctg catctgttca   72420
caaggggttg atatttatga gttctattct ccatatccat tctatgttct cttaatgctc   72480
agtcagcacc tcaggtggtt ggagttcaat gcttggtagt ttgacttaca ctgtcttttc   72540 tagggattg agccctgggt agtcctgctt atttgaggtt gcaatttgtc tttcaataac   72600
ttttactaca agatatggcg tgttaaagga taccattggg gaaccaacat aataatatca   72660
ggaaaactaa ccacgtcaga cctgccccat tgtgtatcaa gtacactatt tttccatagt   72720
aataaagagt tcaccccagc caattctctt ttattttgtg cctgtttact caatggcatt   72780
aacatgccca aatgtctggg tagctgtctc atctccagtt cagcagaacc attgtcatat   72840
gccctagtaa aagcattcct tcattggaca cttaggcccc aatactttca ttcagatcta   72900
ctacctgatt tcatttctca aatgattttt atggagctct gatttatagg aaagatgtta   72960
gttgattaaa aataaaacaa tttctgagct ggtataaaat gtattgtgac atgccttcct   73020
cttggaattg caagagaaag gaagactgtt gtttgcttaa aaattgtcta taatttgact   73080
ttgcaaatgt ctgcttccag agtgcctcca ctgagtgcct cagatgagtc taggaagagc   73140
tgtaccgttg ggatggccac aatgattctg accctgctct cgtcagcttg gttcccattg   73200
```

```
gatctctcag cccatcaaga tgctttgatt ttggccggaa acttgcttgc aggtactggt    73260
actgagttga aacagggact ccaggacttg gattttgatt tccttagggg gaatgggggt    73320
ggtgagcata tgaggggaaa atactataag gtcattgcca gtgatggctt gtcccttag    73380 tcaaatttca gatgttacct atatgcataa acacatgcag ttggcagctg ttctgtgctg    73440
agtattttaa agtagcctct tcccaatata gcccctcagt taactacaag taaactcatt    73500
ttgaatttca ttttaatggg caccatatgc cagtactccc tcgggcactg ggatgttaag    73560
aaagtataat gtatggactt cattctcaag ttagttttag attagagggg gatacacgta    73620
aacaaaagtg cagtggtcac acagagtggc cctaatcact ctccttgggc agatttatgg    73680
gctggtagga aagagcacaa cacggagagg gtgtagcacc ttggcgatga taatggagga    73740
tgtggccagc aaggaagacg gagtccattg aaattgattt tgggagaagt tgccaatctc    73800
catgaaagaa ttgggggcctg tgctattgc ttcagggggc tataggagag tttcgtgaaa    73860
gggactaaaa gatgagtatt ttaataagat cattcatcca acttgaacat gggctggagg    73920
agaaggtagg gagactcagg agattaatgt tgatgctaag gcaagataat ggctttggga    73980
ctgtagggaa gacactgatt gtaagagaat gaaggaggca gaattgccag gcctggttca    74040
ccaactgaac ttcggttgtg aagacaaaga aacctgggat gacttcacat cctgggcagg    74100
tgtgtggtgg tgacagtcat ggaaattggg aacacagatt tgtgcgggaa acatcagttt    74160
cagtttgagt ttggcttatc agttgaatat caggcacaga tgtctggcca actctcaaca    74220
tagggtctta aatgacttca gttccccaag caatttgtcc ttcccatgct attggggtgg    74280
agaggtaatg tctgtgccca tatcacagcc agtgctccca aatctctgag aagttcatgg    74340
gcctctgaag aagaagccaa cccagcagcc accaagcaag aggaggtctg gccagccctg    74400
ggggaccggg ccctggtgcc catggtggag cagctcttct ctcacctgct gaaggtgatt    74460
aacatttgtg cccacgtcct ggatgacgtg gctcctggac ccgcaataaa ggtaatgtcc    74520
cacttgggtg ctggattcat acagccttaa tgactatggg tttccagact accttttgttt    74580 agtaatctgt cccttcttta ttctcttttt gctttaaatg aacaaaattg ctcagattgt    74640
gacactaaat ttaacatcaa aatgtgacca tgtggatggg tgcagtggct cgtgcctgtt    74700
attccagcac tttgggagac tgaggcaagt ggatcacttg aggccaagag ttcgagacca    74760
gcctgggcaa catcacgaaa ccccctctct actaaaaata caaaaaatta gatgggttgg    74820
gccgggcgtg gtggctcaag cctgtaatcc cagcactttg ggaggccgag gtgggcggat    74880
cacgaggtca agagatcaag accatcctgg ctaacacagt gaaacccgt ctctactaaa    74940 aatacaaaaa aattatctga gcatggtggc gggcgcctgt agtcccagct gctcgggagg    75000
ctgaggcagg agaatggcgt gaatccggga ggcggagctt gcagtgagcc gagatcgtgc    75060
cactgcactc cagcctgggt gacagagcga gactccgtct caaaaaaaaa attagatggg    75120
catggtggtg cgtgcctgta atcccagcta cttgggaggc tgaggcaaga gagttgcttg    75180
aacctgggag gcggagtttg cagtaagcct tgattgtgcc gctgcactcc agcctgggtg    75240
acagagtcag actctttcca aagaagaaa aaaatgtgac catgtgtttt atagctcttt    75300
tagtatcatc agtcactgtt atccctaaga gggaaatacc tagctttagt tttaggtttc    75360
cagcattagc caagaaagct cagaattgat gttcctggcc aagtacctca ttgctgtctc    75420
cttaaatctt ggttaatggc tactgtcctg gctagcatag ttatggagca tttccatggt    75480
tgtagaatgt tctgccaatc tcagggacag ttttgctttt ctgtgaagca ataaaatcaa    75540
cttcaaaaca aatgttaact atttgtacaa tggatttaag atagaccagt tcacatactt    75600
```

-continued
tttttttttt ttttttttga gatggagttt cattcttgtt gcctgggctg gagtgcaatg 75660
gtgtgatctc agctcactgc aacttctgcc tcctgggttc aaacgattct tctgcctcag 75720
cctctcgagg cagattacag ctgggattac aggcatgcac caccacaccc agctaatttt 75780
tttgtagttt tagtagagac ggggtttcac catgttggtc aggttggtct caaactcctg 75840

acctgaagtg atctatccgc ttcggcctcc caaagtgttg ggattacggg catgagccac 75900
cacgcccagc ctaagataga ccagttcact tactgtttat atctgattac tctctctttg 75960
ccttgtcttc tacctttaaa aatctcccta ctaacttccc attctccttt agctgccatc 76020
agtcttctcc cttctctgca aacatctctg gagagtccca gcctcagccc acagagcttc 76080
ccactgctct gaggtggacc ttgtttgcaa ggcttctttg gctctcttgg cctggaccct 76140
gtctactact tcagccatcc ttccttaacc cctgctggtg gtttctgttg ccacactcca 76200
tagcagcgtt tcccgcccag atcatgtctt tacatctctg ggcactgctc tggtcctgcc 76260
tgcctttccc tctttgtatc ctgcaggctg ctacccccat cttgagtgtc ctcttcagtt 76320
ggctttcaga gggcctcctg ggtgttccct tacccacttg ccactcccca gtcactgggt 76380
tcagtccttc ctgcccacca gcacatgctt tctaggctct gtcctaggcc gtcttctctc 76440
tttgtagtct ctgggccagt gctgttctag agagtggcag aattttctat aaccatggca 76500
gtgctccata gctatgccag gcaagacagt agccactaaa cacatatagc tgttgagccc 76560
ttgaaatgca gctagtgtga ctgaagaact gaaccccgat tcggtttaat tttcattaaa 76620
tttaaattta aataacctta tgtgggtagt ggctccagta ttgggcaggg cagcctgaga 76680
gtcggggctg ttctcctgtc ttcagtgtct agatgaggga cctcagagga cctgtctctg 76740
gagctgcagt tcaatgtagc cagctgcccc gtgacactta catatagctg atttgtggat 76800
atgtcagaca cggtgtgatg agctcagctt tctgtcctcc tccccacatc tgcccctgcc 76860
ccatttaccc cactttgtgt cttatcaagc tagaaacagg tcaccacaag tcttcatttc 76920
cactcaccaa gtcttttgtt tcccctacta aatattttgc gagaagaaag tgtgtacctt 76980
tgtattcaca tacatgtaca tgcacatata catgcacata tgcaggggtc cccaacctct 77040

gttaaaaacc ggactgcagg ccgtgcgtgg tggctcacgc ctgtaattcc agaactttgg 77100
gaggccgaga ccagtgcatc acaaggtcag gagatcgaga ccattccggc tcacacggtg 77160
aaaccccgtc tctactaaaa atacaaaaaa aaattagccg ggtgtggtgg cgggcgccca 77220
tagtcccagc tacctgggag gctgatgcag gagaacggcg tgaacctggg aggcggagct 77280
tgcagtgagc cgagattgtg ccattgcact ccagcctggg cgacagagcg agactctgtc 77340
tcaaaaacaa aacaaaacaa aaaaaaaaaa aaccaggctg cacaggaaga agtgagcaag 77400

cattaccatc tgagctctat ctcctctcag gccagtggtg gcattagatt ctcataggag 77460
cgtgtatgag ttcgttctca cacttctgta aagacatacc tgagacatat aaagaaaaga 77520
ggtttaattg gctcacagtt ctgcaggctg tacaggcttc tgtttctggg aaggcctcag 77580
gaaacttgca gtcatggcag aaggtgaagg ggaagtaggc acatcttcac atggcccaca 77640
ggaaaaagag agaaggagag agagagagag acagagagag agagagaaaa agaaagattg 77700
agagggagag aggagggaga aaggagagtg cctgtagggg gagttgctac acaaaggagc 77760
accaggggga tggtgctcaa ccattagaaa ctacccccat gatccaatca cctcccacca 77820

ggccccacct ccgacactgg agattacaat tcagcatgag atttgggtgg ggacacagag 77880
ccaaaccata tcagagcatg aaccctattg tgaactgcac atttgaggga tctaggttgc 77940

```
atgctcctta tgagaatcta atgcctgatg atgatttgag gtggaacagt tcatcccga    78000 aaccatcccc cgccaaccct ggtttgtgga aaaattgtct tccacagaac cggtccctgg    78060
tgccaaaaag tttggggacc tctgcacata tgcatgcacc tgtacatgga cacataatac    78120
atgtacatat gcatacttta tattctctgc cacttctggt ccagactgat atactatctc    78180
atttggatta ctgcactagc cttttgtttt ggaaacagca ttttttaaaa aatttaattt    78240 aattttttg agatagggtg tcattctgtt gcccagcttg gagtgcagtg tcatgatcat    78300
agctcactgc ggcctcgatc tcccaggctc aagtgatcct tctgcctcag ccttctcagt    78360
agttgggact acaggcatac ccaccatgcc cagctaattt tttgattttt ttttttttt    78420 gagacagagt ctcagcctgt cgcccaggct ggagtgggtt ggcgcgatct cagctcactg    78480
caacttctgc ctcccaggtt caagtgattc tcctgcctca gcctcccgag tagttgggat    78540
tacaggcgcc tgccaccaca cccagctaac tttttgtatt tttagtagag acggggtttc    78600
accatgttgg ccaggctggt ctcgaacttg tgacctcgtg attagcccgc ctcggcctcc    78660
caaagtgctg ggattacagg cgtgagctac cgctcccagc caggaaacag cattcttgag    78720
ataattcata taattcaccc atttaaagta tataattcat tctctttagt atgcccacag    78780
agttgtacag ccatcaccag aatcagtttt agaacccata aaggaactct gtactcttta    78840
cccaaaacct ccatgcctcc agctgcaggc agccactaac ctgccttctg tctctgtgac    78900
tctacgtctt ctggacatta ctgtggatgg gctcatacag tcagtgagct tgtgactggt    78960
gccttctacc aagcagggtt ttcagtgtag cagcctctct gttttctttt ttttttaaa    79020 ttgtgacgga acttctgcct cccggggttca agcgattctc ctgcctcagc ctcccgagtg    79080
gctgggacta caggcccatg tcaccatgcc tggctaattt tttttttttt ttttttagt    79140 agagatgggt ttcaacatgt tagccagggt ggtctcgatc tcctgacttc atgatccgcc    79200
tgcctcggcc tcccaaagtg ctgggattac aggcgtgagc caccatgccc ggctaacctt    79260
tcatttactg tctgcatttc ttccctgatg ccttccagtc catgcacccg attgtagcca    79320
ttcatcctat tatggtttaa ggtgactgtc ttagtcagca tgggttgcca taacaaaata    79380
ccatagcctg ggtggcttca acaacagaat ttacttctca cacttctgga ggttgggaag    79440
tccaagatcc aggactttcg ccttgccctc atgtggtgag ggggtgagga agctctgtgg    79500
ggcctcttat atatggatgc taatctcatt catgaggggt ctgccctcat gacccagtca    79560
cctcccaaag gccccacctc ctaataccat caccctggta attaagtttc agtgtataaa    79620
tttgggggac tatagacatt gaaaccataa caagcacttt tctaagatca gggagtgagt    79680
aagtagcaga gctaggacct caattccaca tgtcagtcat cttgccttca ctctgctcca    79740
tgatggctgc ctcctagagc attgggagtc tcgatgttct atatgctctc atgtgttgtg    79800
tattggagat agttgaggct ttatgaatac atctggattt gttgacttct agctttgctg    79860
gtaaccagct gtgaccttga ataagttact tcatctctga gcctgtttcc tcttttagaa    79920
acaggagttt aaaatgctgc tttgggttgg cacggtggc tcatgcctgt aattccagca    79980
ctttgggagg ctgagatggg aggatcactg gagcttggag ttcgagacca gcctgggcat    80040
catagtgtga tcctgtctct cctcaagaaa ttaaaaaatt agctgggtga tgtggcgtgt    80100
gcctgtggtc ccatctactc tggaggctga ggtgggagga ttgcttgagc ccaggaggtt    80160
gaggctacaa tgaaatatga ttgcacccca tcctgggtga cgagtgagac cctgtctcaa    80220
aaaagaaaaa aaaatgctg ctttgtaccc ctttcatgtc atggcgtcat ggccaacata    80280
gaatgccctg gttgtttgct gttggagggc atgggcctgg gggctccctg agggctcctt    80340
```

```
ccatcttcaa ctcattctct gtgcacctgt taggaagttg tgggccagtc cctaccatgt    80400
atcattgtgt gggtaaaagt aaataaaatg tgtacagtgt ctgaactgta catatcaggg    80460
tccaagaaca aaatgagtga catgggttag ctcttttttaa taaatggtaa aaccaaatat   80520
tctaattttc agttttgtta tacttccatc acatgtttt gttttttgt tttttgtttt     80580 tgttttttcta ttttaggcag ccttgccttc tctaacaaac ccccttctc taagtcccat   80640 ccgacgaaag gggaaggaga aagaaccagg agaacaagca tctgtaccgt tgagtcccaa    80700
gaaaggcagt gaggccagtg caggtaggaa acagcgtggg aagggaggg acatgagtgc    80760 agcatctgtc atgtagaaac ataggattta agtaacttgg tgttttagag aaataaatat   80820
aatacacatc agtaaagtga gagaaagttt ctccaggtgc ggttcaagat attagaaact   80880
aatgactgat gtacacagac cacctttttgg tctgaagcat ttctaagtgc cactggctga  80940
catgcagccc ctacagcctc caggcttcca gccctagcat ggagcatcac tctcctatgc   81000
ttccctggtt gcaggtgatg gctggagagg cctcctgatt ttcagtaagg gaagtggtgt   81060
agatgcttag gaatagatgt agtgagtgaa aaaactgatt ctgatatgtc aaaaattctg   81120
attggaaatg gaatatttac atttggaaga gctaaaggcg agagaaagtg gggataaagt   81180
catctgagtt ggaggagctt aaaccattca caagtttgga ggaccttttt ttacccatga   81240
aaaggtcaga acagaagggg ctaggattta ggtgtgactg cagtttattg aattcccatc   81300
catactgctc tcggtgggca gtggcagggg caggagagga gcctggcaaa gcatgaagtg   81360
actgctgctg cctctgctat ctgggacgcc tggccacctg tctgtacagt ctccctccag   81420
acccattctc acgctgtctc ttggcaccca ggggccagtg atggttctcc catttgtttt   81480
gtgtatatag catttatatc aaggctattt atttatttat ttattttatt tatttatttt   81540
tttgagacag agtctcactc tgtcacccag gctggagtgc agtggtgcaa tctcggctca   81600
gtgcaagctc tgcctcctgg gttcaagcaa ttctcctgcc tcagcctcct gagtagctgg   81660
gactacaggt gtgcaccacc acacctggct aattttttgt atttttttatt agtggagacg   81720 gggtttcacc ttgttggcca ggatggtctt gatctcctga cctcgtgatc cgtccacctc   81780
agcctctcaa agtgctggga ttacaggcat gagtcactgt acccggccta tttatttatt   81840
tttaattgac aaaattgtat atatctgtaa tatacaacat gatgtttgaa atatgtgtac   81900
attggccagg cgtggtggct cacacctttt atcccagcac tttgggaggc tgaggtgggc   81960
ggattacgag gtcggggggtt taaggccaaa ctggccagca tggtgaagag gtgcccctac   82020
taaaaatacc ccaaaaaaaa aaaaaaaaaa aaaagccgg gcatggtggc tcgcgccagt    82080
cgtcccagct acttgggagg ctgaggcagg agaattgctt gaatctggca ggtggaggtt   82140
gcagtgagct gagttcatgc cactgcactc tagcctgggc gatagagcga gactccgtct   82200
caaaaaaaaa aaaaaagaa gaaatacata tgcattgtgg aatggctaat taacctgtgc   82260
atcacctcac gtatcattgt tttgtggtga gaacacttaa aatctactct ttcagtgatt   82320
ttcttgcata tggtacattg ctattaactg cagtcaccat gctatacagt agatctcttg   82380
aactcattcc tcctgtctat aaatgaaatt ttgtatcctt gaccaacaca ttcaaggttt   82440 ttttttgagat ggagtcttct tcacccaggc tggagtacca tggcacgatc tcatctcact  82500
gcaacctccg cctcccaggt tcaagcaatt ctcctgcctc agcctcctga gtagctggga   82560
ttacaggcac atgctactgc acctggctaa ttttttgtatt tttagtagaa gtggagttc   82620 accatgttgg ccaggctggt ctcgaactcc tgacctcaag tgatccgcct gccttggcct   82680
```

```
gccaaagtgc tgggattaca ggtgtgagcc actgcacccg gcctcaagcg tttttaaaaga    82740 tgctctttc taaggattga ctgtagtaca ggaggaagat tgacctgttg aaaagcctca     82800
gcctttacaa gtgtaaaatt atcagtatat tactatcatc tttctgatga attaaataaa    82860
ctaaggactc caagtcaaaa gtcttcaaac tgaagtagaa tagttgtata tagtgcttgg    82920
cactttaata tttagtatcg gtttaatgat aatgtttgtg cctttgccgt ctttaaaaca    82980
tttttacatc atccctgttt gattacttgg tgtgctcatg aagttgttgg ccactaagga    83040
atcttaggct cagagaggtt ctggaattgg ccagtggtcc ttgaatcagc tgctcctatg    83100
attctctaac tgatttctca caaagcaaac aagcaatcat aacaaaacaa ctgtgcacac    83160
tgctcttctt attttgttat ttaaaaagta cttaggctct acttatgttt gttagtcaat    83220
ttctcattac ttctagttaa tcaaaaggtc agaggaaata cttgaatatt ttcatactag    83280
aatactttaa aaaatcatga tttccagtaa tctctttaaa acttggcaag ttattttgat    83340
ctaaaagttt atcttttgtg tgcatatttt taaagcttct agacaatctg atacctcagg    83400
tcctgttaca acaagtaaat cctcatcact ggggagtttc tatcatcttc cttcatacct    83460
caaactgcat gatgtcctga aagctacaca cgctaactac aaggtatggg cctctgcatc    83520
ttttaaaaat atatatgcac acatacttac gtctaatgga tagttgatgt ttttcttatg    83580
atttgtagga tgtataagcc ctttgagata tgagttacat ttagtttttt caagtttgtt    83640
tgtctttcag ctttgtttat gatagcttct atcatacagg tgttttggat tttcatattg    83700
tttgtactca cagctaagat tgattacagt gacagagcta ggatgtgcag ccaggttata    83760 ggggaagtg gccctggtgg agtctggagg gatccgtgta caggcttcct tccctcccgt     83820
gaggctcaca caaaaataca gcaacatgct ggtcctgcag gtaccctctg cctaacatga    83880
gccacaattc cagactcaca gaagaaaagc aggtgttcgg cataaaccat gtgtttcaaa    83940
tagtctgggc atggtgagcc acttgttatc agctagggaa agtttatgtc agcgtaagaa    84000
actgttcacc agataccccc aagagccagc cttctgtct agggatgttt tagttttta     84060 gttcattttt tttttaact ttaaaatttt ctgttcatct gcaatttgtt agatatgaag     84120
tatgtgtcta atttaattt tgtttttggt tgtccccaat aatgtttaca gaagaattt      84180 tctgcactaa ttggcttgag ttacttacat tctcatagtt ctctagtttc agtagtttca    84240
tttattattt tgttatatca atctatctgt ctgctcatct attagaagca tccttgttt     84300 ttttttttct tttttagaca gagtcttgct ctgtcccag gttggagtgc agtggtgcaa     84360
ccatgcctcc ctgcagtctc agggctcaag tgatcctccc acctcagctc ctgagtacct    84420
gggactaccg gcatgtgcca ccacacccag ctaattttta catttttgt agagacaggg    84480 tctcccctaag ttgcctgggc tggtctcaag ctcctggctt aagtaatcct ccctccttgg   84540
cctcccaaag tgctgggatt acaggtgtga gcaactgcac ccggctacaa gtatacttct    84600
taattattgt agcttaatgg tatttatgag gggatcagtt cccctgttgt tctttagaat    84660
tttctggata ttcttcttta ttgatttttgg gatgtgaaca atagaatcaa cttctacttg   84720
tagattgatt tagggagaac ttatacctca gatgttaagt caccctgtcc agaatgtggg    84780
atgctttcct atttgttcag aactttttaa attacctcag aagcacatga aatttaaagg    84840
attttaaaaa aaacttaaag attatttcac atagctcttg cacatttctt gataaatgaa    84900
tcctcaggta ttcctctgtt tttgttacta atagttactt cttatggggtt ttttttcccc   84960 tgaaaatcat ttatcaaacg tatgtggctt attttctgaa ggatgtttga taattttgga   85020
agatatgaaa gtcttcatat tttacaaggt ttgaggtctc tttaagctgc atggttctca    85080
```

```
tgtcagctcc caaagcagaa gacggcatgt tgaaaaatgc cgtagagaag atacttcttt    85140
tccacctgtt ttcaactcat atcatcttga atttcagggc acctttccat gctcctagtg    85200
cttgctatct gtttattatt ttccttcctg aataccctga actccagcat gttctgctgt    85260
aattctggcc tccctggcat cttggactcc tgtttccttt gctctgtcat ccccgcggtc    85320
agctcctgct gcgcagcttc tcagctgaag tgcgtttgga gtgcctggcg tgtcttgctg    85380
gatctttgag tattgcctct ggtttccttg gttccttctg ctgagttgct cagcgtctcc    85440
actccccatt tcttgtgtgg cccttcctgc actcctctga ttccttttgt cttccctggt    85500
ttcttgcttt ggtttcgagt ctccacagaa cttttgcagc tcttctgaag acctggaagc    85560
tttttcatct taattctcat ctcatgacct ctttttccctt ctttgagagc tagaacttcc    85620
catggtgaac ttctctttcc agaattccat gccttctttt ccctcccact tacctgttgt    85680
ccaggagagg tcagattgct gtgcatattg gaggagaacc ctttcttccc tgggctcttc    85740
atctcacatg acatcaccac atcacctcgt tccttggacc ctcagtggtg tcactgctgg    85800 attttcttt cctttggctg gccttagggc acacccaggt tgactagcgt agtcatggta    85860
tttagatcca ctcacatttt cagtttctgt gtctgtctct tgcctgcttc tgacttcgcc    85920
cagagaaagc ttctctttca caagggttct tagatttatg ttcactgagc accttctttt    85980
ctgaggcagt gttttaccaa tatttattttt cctagtcagt ctcgccttac ctttcttgtt    86040
atgcatgtct ttggtcctga cccattctct gagtctgtaa aatagaattg ctgtataatt    86100
taattacatg aaatccttta gaatcttaac acatcttaca cctgatttaa tattttattg    86160
tatccaaatt gaaccaaccc tatgtgaatt tgacagtgat ttctcccagg gatcctagtg    86220
tataaggaat aggacttagt attttctatt ttttgatata ccacatacca gatactgatt    86280
atgatggaca tttaacccctt ttttctcatt atgaaagaaa gttaggaatt atttcttcca    86340
gtagcgccag tgtaacctga aagcctttga aagagtagtt tttgtatagc tatctgaaag    86400
gaatttcttt ccaaaatatt tttccagtgc tgacaacaaa cacgcagaca caccctgcaa    86460
ggtgagtgta cggcgccgca cagtggaggc atctgctgca gccgtcgatg tttgtgtctt    86520
tggttgtaca ttatgagatc gtgacagggc cagtaaccgt gtgttctctc cttcaccttc    86580
ccaaggtcac gctggatctt cagaacagca cggaaaagtt tggagggttt ctccgctcag    86640
ccttggatgt tctttctcag atactagagc tggccacact gcaggacatt gggaaggttt    86700
gtgtcttgtt ttttctcctt gggttgtggc tggcacactt gatgtgcgtc ttctgggctg    86760
agttcatcta ggatggagcc tggttctcca gggtgcctcc gggagactcc tccctgcccc    86820
acgtgcttgc gtcacaggac ccaagtctga ctctgcctta gccatgaagt ttaggggggaa    86880 gtttctattt gtattctatt tttgtctgtt atcatgtatt agcttagacc cagtttagtt    86940
tggaaaatca gtgggtttca aaatgtgttt gtagagtcct ttatttctta acttgacctt    87000
ttcaagtgga aaggggcaaa acagacgggg aaggggggcgg ggcggaggt gtgacttgct    87060 cttttgtgcc tgaggaagta acagagctgg ggttgacagt catattctct gacacagata    87120
gtctctgact tatctcacag aaagtcagcg gcagagcctg agttaaaagt ctcgtagatt    87180 ttcttttct ttttttggt ggctaatttc agttttattt atatttgttt atttatttat    87240
tatactttaa gttctgggtt acatgtgcag aatgtgcagt tttgttacat aggtatacac    87300
gtgccatgat ggtttgctgc acccatcaac ccatcaccta cattaggtat ttctcctaat    87360
gttatccctc ccccagtccc ctcactcccc atgggccccg gtgtgtgatg ttctcctccc    87420
```

```
tgtgcccatg tgttctcatt gttcaatttc cacttgtgag tgagaacatg cggtgtttgg   87480
ttttctgatc ttgtgatagt ttgctgagaa tgatggtttc cagcatcatc catgtgcctg   87540
caaaggacat gaactcatcc tttttatgg ctgtatagta ttccatggtg tatatgtgcc   87600
acattttctt aatccagtct atcattgatg acattcgggt tggttccaa gtctttgcta   87660 ttgtgactag tgccacaata aacatacatg tgcatgtgtc tttatcgtag aatgatttat   87720
aatcctttgg gtatatgccc agtaatggga ttgctgggtc aaatggtatt tctagttcta   87780 gaccttgag gaatcgccag actgtcttcc acaatagttg aactaattta cactcccacc   87840
aacagtgtaa aagtgttcct attttccac aacctctcca gcatctgttg tttcgtgact   87900
ttttaacgat cgccatccta actggcgtga gatggtatct cattgtgatt ttgatctgca   87960
tttctctaat gaccagtggt gatgagcatt ttttcgtatg tctgttggct gcataaatgt   88020
cttcttttgc gaagtgtctg ttcatatcct ttgtccattt tttgatgggg ttgtttgctt   88080
ttttttcgta aatttgttta agttctttgt agattctgga tgttaatctt ttgtcagatg   88140
ggtagattgc aaaaatttta tcccattctg taggttgcct gttcactctg atgatagttt   88200
cttttgctat gcagaagctc tttagtttaa ttagatcccg tttgtcaatt ttggcttttg   88260
ttgccattgc ttttggtgtt ttagacatga agtcttgcc tatgcctatg tcctgaatgt   88320
tatggcccag gttttcttct aggatttta tggtcctagg tcttatgttt aagtctttga   88380
tccatcttga gttgattttt gtgtaaggta taaggaaggg gtccagtttc agttttctgc   88440
atgtggctag ccagttttcc caacaccatt tattaaatag ggaatctttt ccccattgct   88500
tatgtgtgtc aggtttgtca agatcagat gattgtagat gtgtggtggt atttctgagg   88560
cctctgttct gttccattgg tctatatatc tgttttggta ccagtaccat gcagttttgg   88620
ttactgtagt gttgtagtat agtttgaagt caggtagtgt gatgcctcca gctttgttct   88680
tctagcccag gattgtcttg gctatgcagg ctctttttg gttccatatg aagtttaaaa   88740
tagttttttc caattctgtg aagaaagtca gtgatagctt gatgggggga tagcattgaa   88800
tctataaatt actttgggca gcaaggccat tttcacgata ttgattcgtc ctatccatga   88860
acatggaatg ttttttctatt tgtttgtgtc ctctcttatt tccttgagca gtggtttgta   88920
gttctccttg aagaggtcct tcacatccct tgtaagttgt cttcctaggt gtttcattcc   88980
cttagtagca tttgtgaatg ggagttcact catgatttgg ctctctgttt gtctgttatt   89040
ggtgtatagg aatgcttgtg atttttgcac attgattttg tatcctgaga ctttgctgaa   89100
gttgctaatc agcttaagga gattttgagc tgaaccaata gggttttcta aatatacaat   89160
catgtcatct gcaaacaggg acagttttac ttcctctctt cctatttgaa tacccttat   89220 tgctttctct tgcctgattg cgctggccag aacttccaat actatgttga ataggagtgg   89280
tgagagaggg catccttgtc ttgtgccggt tttcgaaggg aatgcttcca gttttgccc   89340 attcagtatg atattagctg tgggtttgtc ataaatagct cttactatgt tgagatacg   89400 tccatcgata cctagtttat tgagagtttt tagcatgaaa ggctgttgaa ttttgtcaaa   89460 ggcctttct gcatctgttg agataatcat atggttttg ttgttggttc tgtttatgtg   89520
atggattacg tttattgatt tgcgtatgtt gaaccagcct tgcattccag ggatgaagct   89580
gacttgattg tggtggataa gctttttgat gtgctgctgg attcagtttg ccagtatttt   89640
attgaggatt ttcacatcga tgttcatcag ggatattggc ctaaaattct cttttttgt   89700 tgtgtctctg ccaggctttg gtatcaggat gatgctggcc tcataaaatg agttaggag   89760 gattctctct ttttctattg attggaatag tttcagaagg aatggtacca tctcctcttt   89820
```

```
gtacctctgg tagaattcgg ctgtgaatcc atcctggact ttttttggtt agtaggctat    89880
taactattgc ctcaagttta gaacctgtta tcagtctatt cagagattca gctttttct    89940 ggtttagtct tgggagggtg tatgtgtcca ggaatttatc catttcttct agattttcta    90000
gtttatttgg gtagagatgt ttatagtatt ctctgatggt agtttgtatt tctgtgggat    90060
cggtggtgat atccccttta tcgtttttat tgagtctatt tgattcttct ctcttttctt    90120
ctttattagt cttgctagcg gtctacctat tttattgatc ttttcaaaaa accagcacct    90180
ggattcattg attttttttg gagggttttt tttcgtgtct ctatctcctt cagttctgct    90240
ctgatcttag ttattttttg tcttctgcta gcttttgaat ttgttgctc ttgcttttct     90300 agttctttta attgtgatgt tagggtgtta attttagatc ttttctgctt tctcttgtgg    90360
gcatttagtg ctataaattt ccctctacac actgctttaa atgtgtccca gagattctgg    90420
tatgttgtgt cttcgttctc attggtttcc aagaaaattt ttatttctgc cttcatttcg    90480
ttatttaccc agtagtcatt caagagcagg ttgttcagtt tccatgtagt tgtgtggttt    90540
tgagtgagat tctcaatcct gagttctaat ttgattgcac tgtggtctga cagacagttt    90600
gttgtgattt ctgttctttt acatttgctg aggagtgttt tacttccaac tatgtggtca    90660
gttttagaat aagtgcaatg tggtgctgag aagaatgtat gttctgttga tttggggtgc    90720
agagttctgt agatgtctat taggtccgct tggtccagtg ctgagttcaa gtcctggata    90780
tccttgttaa ttttctggct cattgatctg cctaatattg acagtggggt gttaaagtct    90840
cccactatta ccgggtggga gtctcttttgt aggtctctaa gaacttgctt catgaatctg    90900
ggtgctcctg tattggggc gtgtatattt aggatagtta gctcttcttg ttgaattgat     90960
cccttaacca ttatgtaatg gccttctttg tctcctttga actttgttga tttaaagtct    91020
gttttatcag agactaggat tgcaatccct gcttttttt tgctttccat ttgcttgtta     91080
gatcttcctc catcccttta ttttgagcca atgagtgtct ttgcatgtga gatgggtctc    91140
ctgaatacag cacaccaatg ggtcttgact ctttatccaa tttgccagtc tgtgtctttt    91200
aattggggca tttagcccat ttacatttaa ggttaatatt gctatgtgtg aatttgatcc    91260
tgtcattatg atcctagttg gttatttgc ccgttaactg atgcagtttc ttcatagcgt     91320
cagtagtctt tacaatttgg catgtttttg cagtggctgg tactggttgt tccttttccat   91380 gtttagtgct tccttcagga gctcttgtaa ggcaggcctg gtggtgacaa aatctctgca    91440
tttgcttgtc tgtaaaggat tttatttctc gttcacttat gaagcttagt ttggctggat    91500
atgaaattct gggttgaaaa tactttttt aaagaatgtt gaatattggc tcccactctt     91560
ttctggcttg taggatttct gcagagagat ctgctgttag tctgatgggc ttcccttttgt   91620 gggtaacccg acctttctct ctggctgccc tttccttcat ttcaatcttg gtggatctga    91680
tgattatgtg tcttggggtt gctcttctcg aggagtatct ttgtggtgtt ctctgtattt    91740
cctgaatttg aatgttggtc tgccttgcta ggttggggaa gttctcctgg ataatatcct    91800
gaagagtgtt ttctaacttg gttctattct ccccatcact ttcaggtaca ccaatcaaac    91860
gtagatttgg tcttttcaca tagtcccata ttcttggag gcttggttca tttctttca     91920 ctcttttttc tctaatcttg tcttctcgct ttatttcatt aatttgatct tcaatcactg    91980
atatcctttc ttctgcttga ttgaatcggc tgtcgaagct tgtgtatact tcacaaaatt    92040
ctcgttctgt ggttttttagc tccatcaggt catttaagct cttctctaca ctggttattc    92100
tagccattag tctaacattt ttttcaaggt ttttagcttc cttgtgatgg gttagaacat    92160
```

```
gctcctttag ctcggagaag tttgttatta ccgaccttct gaagcctact tctgtcaatt    92220
catcaaactc attctccatc cagtttttgtt cccttgctgg tgaggagttg tgatcctttg   92280
gaggagaaga ggtgttctgg ttttttggaat tttcagcctt tctgctatgg tttctcccca   92340
tcattgtggt tttatctacc tttggtctttt gatgttggtg acctacggat ggggttttgg   92400
tgtgggtgtc cttttttgttg atgttgatgc tattcctttc tgtttgttag ttttccttct   92460
aacagacagg cccctcagct gcaggtctgt tggagtttgc tggaggtcca ctccaggccc    92520
tgtttgcctg ggcatcacca gcagaggctg cagaacagca atatattgctg cctgatcctt   92580 cctctggaaa catcgtccca gagcacgaag gtgtctgcct gtatgaggtg tttgttggcc    92640
cctactggga ggtgtctccc agtcaggcta catgggggtc agggaccac ttgaggcagt     92700 ctgttcatta tcggagcttg aatgccgtac cgggagaacc actgctctct tcagagctgt    92760
caggcacgta tgtttaaatc tggagaagct gtctgctgcc ttttgttcag atgtgccctt    92820
cccccagagg tggaatctag agaggcagta ggccttgctg agctgcagtg ggctctgccc    92880
agttcgagct tccctgctgc tttgtttaca ctgtgagcat agaaccacct actctagcct    92940
cagcagtggt ggacacccct cccccagcca agctcctgca tcccaggtcg atttcagagt    93000
gctgcgctag cagtgagcaa ggccccatgg gcgtgggacc cgctgagcca ggcacaggag    93060
agaatctcct ggtctgctgg ttgtgaagac tgtgggaaaa gtgcagtatt tgggcaggag    93120
tgtactgctc cttcaggtac agtcactcat ggcttccttt ggcttggaaa gggaagtccc    93180 ccgaccectt gtgcttccca ggtgaggcaa caccccgccc tgcttcggct gccctccgt     93240 gggctgcacc cactgtccag caagtcccag tgagatgaac taggtacctc agttggaaat    93300
gcagaaatca cctgtcttct gtgtcgatct cactgggagc tgtagactgg agctgttcct    93360
attcggccat tttggaagca tcccttgttt tttgaggtgg agtcttgctc tgtcgcccag    93420
gctgacgtgc atcggcacaa tctcggccca ctgcaacctt gcctcctgg tttcaagcga     93480 ttctcctacc tcagcctccg gagtagctgg gattacaggc acctgccacc atgcctggct    93540
aattttttgt attttttagtg gagatggggt ttcaccacat tggccaggct agtctcgaac    93600
tcctgacctt gtgatccacc cacctcagcc tcctagagtg ctgggatcac aggtgtcagc   93660
caccacgccc agccatattt tcagatctcc ctctcttgc cctaaccac tgtgcttaat      93720 aagtagtttt tagtggccag cagtctccat gtataacaca ttttagcaaa atggaaaata    93780
ctatatgttt taaatttgaa cgtgagatta tactgaaata aaaatcatct aactgggatt    93840
ctttaaatag taagattttc ttttttgtat gtgggttttt ttttaacctt attattatga    93900
ctgtcatata tagaaatggc tgttttttcag ttacagtcag tgaatgtatc aaatgctgcc   93960
ttatccaaat aataaaagta aattattaat aagtcacaat ttaatgaaga ttgatgttag    94020 ttgatctttta tattcttgaa atcagccata tggttgtgtg tgtatgtata tattttaaa    94080 ggtacataaa gataataagc tcatctctga aaatttttac atttggcata agaataactg    94140
gataattaag catcttattc tctggcctgt gtctttacag ttaaaggtag atttactcac    94200
ctctcctttt ttgttttttct aagttcatct ttttttgctgt tcaagacag aggcccattt    94260 tagctttctc gcatatcctt ttgtttgtac tttgaagcc tcacctgctt aattgttgag     94320
tttttatccg tggtcttta gagggggata tgtagggtag aagctttcac aggttcttgt    94380
ttgcacttgg cccctgactg ttttgaggaa tctccctcac tgactcacag catggcaagg    94440
tttcagatct ctttctgcca cacagcagtt ctgaggcagc tggaaagata tccagatgct    94500
tagattgtca ggccaggctt gagatataca aactattgag ccttatctgt gaccttgctt    94560
```

```
aggtgaaggc atcagagccc ctgcaccaac atgcataggc ctctgcatgt gtgcggggct   94620
gggtgttgag gtctgagcac aagtgtagct ggagaggtga gcttgatgtg gcgacgggta   94680
tgagcaggtt ttcttcagac ttctgtgagt ttacctagtt ccaggattta aaggcacaga   94740
gactttagaa ttaaaataga atcattttct ttttctaaat agcaacacta ggaataaaaa   94800
ataataattc cacattcttg acaggtaatg ttttttcttg tcttctaatc cttatttatt   94860
ccatactcat ttttatacat aattgaaatg tattatgcat tggattttc ttttgcatta    94920 tattatagac gattttcat gtaactcctt actgttccat tttatatgtt ttgtctggtt    94980
taagacttta tctgcaaacc gggaaactgt ctctacaaaa agaaaaacaa aaatagttgg   95040
ccgcagtggc atgcgtctgt ggtcccagct actcggggct gaggtgggag gattgcttga   95100
gccttgggag gttgaggctg caaagagcca tgatcatgcc attgcactcc agcatgggtg   95160 acagactta tactgtctgt tttgggtgat ttgataatga tatgccctga tgtagttttt    95220
ttatatcttg tgtttcttgt gcctgggttt attgaggttg ggtctgtggc ttcatagtat   95280
ttttaaagtt tggaaaattt taggccattc tttctttctt tctttctttt ttttttttt   95340 gagacagtgt ctcgctctgt cgcctgcgtt ggagtgcagt gacactatct tggctcactg   95400
caagctctgc ctcctgggtt cacgccattc tcctgcctca gcctcctgag tagctgggac   95460
tacaggcgcc tgccaccacg cctggctaat ttttgtatt tttagtagag acgaggtttc    95520
actgtgttag ccaggatggt ctcaatctcc tgacctcgtg atctgcccgc ctgggcctcc   95580
caaagtgctg ggattacagg cgtgagccac tgcacccagc taggccatta tttcttcaaa   95640 gatttttt ctgccctgcc tcctcctttt tttccctctc ttaaagggc tgtgatttcc      95700 tgaatgattg cttagtgttg tcccatagct tactgatgct cttttcagtg tttgattgtt   95760
ttatgtgttt tctgttttgt atagtttcta ttattgtgtt ttcaagttct ctgatctttt   95820
cttctacagt gtctactctg ttgttaatct gttaatctgt tgttaatcct gtccagcgta   95880
tttttttttt tgttttgaa acagtctcac tctgttgccc aggctggagt ttagtggtgc     95940
gatatcagct cactgcaacc tccacctccc aggctcaagc aattcttctg cctcagcctc   96000
ccgagtagct gggactatag gcacgtgcca ccacacctgg ctaatttgtg tatttttatt   96060
agagatgggg tttcaccatg ttggccaaac tggccttgaa ctcctgacct caggtgattc   96120
atccgcctcg gtctcccaaa gtgttgggat tataggcatg agccaccgtg tctgcccct    96180 gttcagtgta tatcactaat tttgttttta tctctagaag tttgatttag gtcttttaaa   96240
aatgtctccc tgtgtttctg tttagctttg tgaacacaat tgtaataact gttttaatat   96300
ccttctctgc tagttctaag atcttctaat aacttcccag ttcttggtgt ttctcattgg   96360
ttgattgata ctcctcgttt tgggttgtat tttcctgcct ctttgtatgg ctgccaattt   96420
tttattggat gcccaacctt gtgaattta ctttgttgga tgctatatat ttttgtgttc    96480
ccatagatct tcttgagctt tgttctgagg ttagttgagt tacatataga tggtttactc   96540
ttttgggtct tgctttataa tttgtcagat gggttggagc agtgcttagt ttaggactaa   96600 tttttttt ggactaatta ttcctcttta ggaataatta ggtaccatgc ttaggaggca     96660
agaccatcct gagtactcta cctaatgaac cagaaagttt gggttttcca gtccgcctgc   96720
tgagaacagt gactttctag ccctgtgtga gcgctgagct ctgctccttc taatcctttc   96780
caatgcttct ttccctggcc tcagggagtt ttctcacaca catatctctg ctgagtactc   96840
gagagggacc ttccccagat ctccagagct ctctctgtct tgttttctct tctctggtgc   96900
```

```
tctgtcttat gaactgtggc tgtcttggtc tccttagatt ctcagcacct cttcaattca    96960
gagggttgcc tgtccctcct ccttgtgcca cagcctagga actctctcaa agcagcgagt    97020
tggggcagcc atagggctga cttagtctct cgtctcccag ggatcactgt ccttcattgc    97080
tcatgtccag tgtcttgagg actctgggtt ttgtctgttt tgttttttgg tttgctttgg    97140
ttgtctcagg caggagggta aacccagtcc ctcaccctca ttgtgctcag tagtggaagt    97200
ctcactctat tacattagat attagtattt gtagcagagc cctggttccc tggtacttgg    97260
ggagctcttg aaaggccaga acagcatgc tttctcacct tttccagggc ttcagtttct     97320
ggtgcacatc aagcattcca tacacatttg ttaaagtcct tgttagaca agtagtgatt     97380 cacaggttct atttgtaatt ttttcagtta acatgtattg ggtatctgct gggagctagt    97440
aaaaacaaaa agtggtgtgt gacaaattca attctgacaa gaacaaccct aaacacttag    97500
aatatacttt gagcatatca gaattttaaa aatgtgtggc ccttgagtat ttgaaaccaa    97560
caagaatcta ttgcttatta gtagaggata ttttgttaaa caagtggaga gagaggcatt    97620
ttcagtctaa ttggtgttgg cttttagcag ctgatggaaa ccagttcgtg attagccagg    97680
cagtggtgaa acaggctgtg cattctgaat gcctaggtat ctaggcattc agaatggtgg    97740
cgctcttgta gttagcatct tcttctttct tgattctttt tttttttttt ttgagatgga    97800
ctttcgctct tgttgcccag gtaacaactc cagtgcaatg gcgccatctc ggctcactgt    97860
aacctctgcc tccctggttc aagcgattct cctgcctcag cctctcaagt agctgggatt    97920
acaggtgtgc gccaccacgc ctggctaatt ttgtatttt ggtagagatg gggtttcact     97980
atattggtca ggctggtctt gaactcctga cctcaagtga tgcacctgcc tcgatctccc    98040
aaaatgctgg gattacaggc gtgagccacc actcccagcc ccttcttgat tcttgaaaag    98100
gacattgggt gctgtacatc tcgttataga tgttgataaa aatgcttgtg agaagagtaa    98160
cattaaggta gttatttggt cattttttgca gattatttta agacaattct aggactgatt    98220
tgtggtaaat cacacattgc tgtatcatag ttgtgttcac tgaacatatt cagggctct    98280 acagatgcag ggctcttagc tgctttgcac acttctgaat tcctgccctg cgaacaggac    98340
tggataccta atagacaaca ggtacttgat aacagtttat tgaattaatg agtgaatgaa    98400
cagatacata aatgcatgaa agaatggttg taatgtatat aacttggatt tcaagacttt    98460
ttactgactg ttcaaaataa gaaattgaaa actttcctct gattttcctc tactatttac    98520
acaatttaaa tggaagttat cttgtacctt caatttctgt ctaggattcg tacaataacg    98580
ggtcatctct gagtcgctta atgtctcact tgtctttcta cagtgtgttg aagagatcct    98640
aggatacctg aaatcctgct ttagtcgaga accaatgatg gcaactgttt gtgttcaaca    98700
agtaagagct tcattctttt cctcttctgt taagacgttc gggtatgaca gcaaaacgct    98760
gctactcctt aagaggcagg cgctgttggc ataatcagct gggaggattg tggggtccag    98820
cgcagcactt tttggctcag tccatgattg agccaagagg ccatcctcc cttcactccc     98880 caggaggacg aggtctgtca ctgtggaggg cagaggacac cagaagctcc tctgcaacct    98940
cgctagttaa cttccagtcc ctcggagttt ctgtttagaa tgctcaatct catttagaat    99000
tgcaaggaaa cccaaaacgc ctatttaagg tacaaacagc acttcataca atatctcatg    99060
aggtattaat agtgattcac aggaagaatt tcacgctgtg agtctttgct aacatatcca    99120
gttatttaca gatggatttg atatttgtgt gggagattct taaaagtgtt gttcacgcca    99180
cattgttgat gcctcatttt tttcactgta gttgttgaag actctctttg gcacaaactt    99240
ggcctcccag tttgatggct tatcttccaa ccccagcaag tcacaaggcc gagcacagcg    99300
```

```
ccttggctcc tccagtgtga ggccaggctt gtaccactac tgcttcatgg ccccgtacac    99360
ccacttcacc caggccctcg ctgacgccag cctgaggaac atggtgcagg cggagcagga    99420
gaacgcacac tcggggtaac agttgtggca agaatgctgt cgttggtgga agcacgaaag    99480
agcaagcagg aaatactttg taaaagaata aaaacgaaaa atgttagcga acatcttcta    99540
atagtctgct gtattcagag aactctagga gatatatatg gttgatgcaa agatgattta    99600
aggcatagcc cggccttcca agaagtgtgt ggccagtgag tgagatgggc ttgggactta    99660
cacatctcag aggtgggggt agaggaggag gaacactgag tgggctgaga agcagccagc    99720
tctcattgcc aaagtgtgtc agcaaaccag aatgcagttc ataatgtccc cacccattca    99780
aagcacagga cctgtagagt ggtgtggcat gtgttggtgg cacttttcag gcctgtaaca    99840
aggatgaaag aacagcttca tagcagcaca gtagtgctgg tgttcagagg tgtgtgaagg    99900
ccatagaagc atcttggata tattaccttg tgttttgtca gctttatgac tagaagtctc    99960
ttttcactta aatttgtttt tttttttttt gagacggagt cttgctctgt cgcccaggct   100020
ggagtgcagt ggtgcaatct cagctcactg caagctctgc atcctgggtt catgccattc   100080
tcctgcctca gcctcccgag tagctgggac tacaggcgcc tgccatcacg cctggctaac   100140
ttttttttgt attttttagta gagacggggt ttcaccatgt tagccaggat ggtctcgatc   100200
tcctgacctc gtgatctgcc cgtcccggcc tcccaaagtg ctgggattac aggcgtgagc   100260
caccgcgccc ggcctctttt cacttaaatt tatgtttgtg ttttaatgc ctagtataca    100320 ggacttctta aattgcctta agtatgaaca ggtatttgag ttgctaatct gtatagtagc   100380
aataatagaa tcccttgttt ttccttttat aaatttagcg attaaatagc tacaattaaa   100440
acactagagt caggagtcaa ggaaaatacc catgttccag gctgtatgtt agtgatgtac   100500
ttactatata ttggagtttc aggagtaagt ctgtttcaat gctttctgta accatttggg   100560
gtattaataa gcatgtgagt gtgtgcatgt ttgggttaat ttcatatatg tttcttagaa   100620
gggatatcat tgatgtaaat attttaaagg cttgtcctcc aaaaaaatca tgtaatttct   100680
tctaaattac tgatctttta aatgaccttc acctttctct caaatctcac ttaagactgg   100740
gctgagtagt cagtttcctg tagcagaaaa aagctcagac ttgagtagcc ttctgcgagt   100800
gaggagactt gatggctgtc aggcagctgt aaactctaaa tagagtgtca ttatctgaag   100860
agggcgatgc tgccacactg agtggccttt caagttgttt ctcaatctga cacgttctga   100920
tcgtgtgaat gtgaaattgg tttgagcagg agtatatctg agtgcagagg agattattta   100980
aagatattct cattctctgc ttcccttttta ttcccatttg gcagatggtt tgatgtcctc   101040
cagaaagtgt ctacccagtt gaagacaaac ctcacgagtg tcacaaagaa ccgtgcagat   101100
aaggtaaatg gtgccgtttg tggcatgtga actcaggcgt gtcagtgcta gagaggaaac   101160
tggagctgag actttccagg tattttgctt gaagctttta gttgaaggct tacttatgga   101220
ttctttcttt cttttttttct tttttataga atgctattca taatcacatt cgtttgtttg   101280
aacctcttgt tataaaagct ttaaaacagt acacgactac aacatgtgtg cagttacaga   101340
agcaggtttt agatttgctg gcgcagctgg ttcagttacg ggttaattac tgtcttctgg   101400
attcagatca ggtttgtcac ttttatcttt catccatcat acctgttcct aatttagtac   101460 aaattacct aaaagacact gaaatctact ttaaagaaat gtggtctgca tgtttccctc    101520
atcagttgct gctgcttatc ttttttcatgc acctagctgg tgcagaaggc ctggggcata   101580
gccagcctca gcaagtcagc atccttgccc cagctccctg gactcaaggc taacctgggg   101640
```

-continued

```
ttggctgtta gggatttcca aaggtttgtc ccatccactt gcctcccctc caaaataagt   101700
ttgaatttaa attgtgagat acaattaaga tttattgttt ggggaacatt tttgcaaaat   101760
ctagagttag tttaaacaga ttatcaatta ttaccataat tgatcatctg cagtttcaag   101820
ctatctaaca ggttcactta cctctttaaa aaggaatgga atttagcagg acagtaactg   101880
agacccgtgc tcctggagtc catgtgggag ctgtgtggct ctgcacaagc atttgcacgc   101940
ttcccctctt gactgcatta ccttcctcct atagttgctg tgggcaccag attctggcta   102000
gtcctgtccc ttcatgatgc acattttcct caagattcgt cccagttaaa tcactgcaga   102060
tgaaactgcc ttttcatcgt caaaatttaa ctgtcatttt tgagccgtga tcttgggcta   102120
ctttcttatg tggggtagga atatttgtga gttagaaata ttacacttct ctatttcctt   102180
ctagacgtaa atctgttaat cctgtcagca ctgttactca cctgaaaggg tctgtttccc   102240
taggagaact gagggcactc ggtcaacact gattttccac agtgggtatt ggggtggtat   102300
ctgcttgttt tttttgttgt tgttgtttgt tttttttgt tttttttttg agatggagtc   102360
tcgctctgtc acccaggctg gagtgcaggg gtgcgatctc ggctcactgc cagctccgcc   102420
tcagaggttc acgccattct cctgcctcag cctcccgagt agctgggact acaggcaccc   102480
accactacgc caggctaatt ttttgtattt ttagtagaga cgaggtttca ctgtgttagc   102540
caggatggtc tccatctcct gacctcgtga tctgcccgcc tcggcctccc aaagtgctgg   102600
gatgacaggc gtgagccacc gcgcccggcc tggggtctgc ttttaatgaa ggaggcatca   102660
aggggtgggc tttgcgttgg cctgatgctt tcatctttct ttcacaaaac ctgtccgaag   102720
aaaatccgtc taaatgggcc attgctctcc tcaggaaata gtcattggga acttcttttc   102780
ctttcctttg acactaggag gctgactggg gagaagccct ggtctatggc tgtgggcagc   102840
aggggctgag aggagcaggc tctcaggggg gcacgggtac cccaagggaa gccagagccc   102900
tgatttgttc cattctagta agaacaaaga ctgctctggt ttcatgtttg ttctgattgc   102960
ctttcatcaa ccggtcccct ttctcccagt tcttaagatt cagtacagtg acagtttat   103020
gaacaagaat agaacactag aacagacaaa ccattgaact ctatgctgat aaagatttat   103080
tgagctcctg ctgtatgttt gcattctgcc cagaggctct gagaaaacca ggccatatgc   103140
tccatgcttt atccatggaa gctccccgtc aggttgggaa agctgacagc tgcagggaat   103200
acagtgtgac acaaaactgg ctcccatgca gcccttacgt gtcgcctctc agatggttgg   103260
gggacgaagg tcgactcctt tgggtatctt attactaaac cagtttcagg gaatctgtgc   103320
caccctatct gccattaacg tgaacagatg agtcccaag gtgtaatttt gggtattgtc   103380
tgatgtctct tggaatttat tatttgtttt tccaatgaga tttcacctca gggtatagta   103440
aagttgttga ggggattcct ggatgtgttc tgcaattatc taggctgatt tcagaataga   103500
gttatgctta tagtcaaatt tatcagctgt caagaatttt atttaaaatt tatgcagata   103560
agcaggagga aaagaagcct ggtttttaca ttttaatcct attattgatg tgaaatttta   103620
ttttccttcc tgtaggtgtt tattggcttt gtattgaaac agtttgaata cattgaagtg   103680
ggccagttca ggtaatagca ttttattatt ttagattttt ttcttcttct tgtgtactta   103740
catgtaattt aggttattaa gtgaatgttt aaactactgt taggcatttt tgctgttttc   103800
tttaaatgga aatctgacta acatactgtg catttttgct tctcttaaaa attaatgtat   103860
atctcaagac ttgtttggaa gtagttatgt atctgaaaat tccatatgtt gtcagtattc   103920
attgcacatt tcaaagcatt taattgtgtt gacagatggg ggaatgaaat cttgtggtgg   103980
agcactagtt tttaaatctt cttagagaaa gcagttttat ataatgttgt ctttagtaat   104040
```

```
tattatgcat ttgtattctc tgcagctttt tcttgctaga tgttgaggtt ttaatacttc  104100
ttgctagtcc attacaggtt tataattatt aaaagttaaa attcttttag tacctaaaat  104160
gcttaataaa cattgtaatt aggaaaattt agtgcagaag gaaagtgttc ccagattccc  104220
tggggtctgg aaacatagtg tttattctaa ttacatgaca cctccactgt gttttggggc  104280
aagttactgt ttctcttttg agtttcaatt tcttcaagag caaagaggca gaggagagct  104340
aggaagatcg tagctgctgt gccctgtgc cgtcgggtgc cttctacctg ctgcctccga  104400
acctttacac atgtccctgc tctgcgcgag ggcacagatg ggatgcactg tggcaggggt  104460
ggggttagag tagatcacgg acacctgtta gcttgatgtg tgcttgctgt caaggttgaa  104520
tcatgaatta ttttatgttg cttatattga tatgtatctt aattttaaaa gaaaggtcta  104580
aatggatgtt tttgttttta gggaatcaga ggcaatcatt ccaaacatct tttcttctt  104640 ggtattacta tcttatgaac gctatcattc aaaacagatc attggaattc ctaaaatcat  104700
tcagctctgt gatggcatca tggccagtgg aaggaaggct gtgacacatg gtaacgggac  104760
acacctttca ctgtcgtctt cggtgtcgtg atgtgcttgg cagtgttcgt tttcatatac  104820
ccactttgaa cgttgtcagt ggcagccatg tgcttctcag gctctgcatg tgtgtctgtg  104880
tatgtgaagg tactggttag agacgtttca aaagagaaga gagcatattc tttactctca  104940
gcaatttgta atcttctcag ggaaaaaaat tcaagaaaca gtaagataac ctaaggtaca  105000
gatagattct gaatataaag ttcctgttca ttcacatgaa acgctaaaag ttcttcactt  105060
gatcttagcc aaaaggccaa gaagcgatgc aacactaaaa attcttaaat cgaacttgcc  105120
gtgaattaaa ttttgatctc tcatccagtg gtattggaga tatagtttga cttgggttca  105180
gggctttctg ttttgcctga tgattttgct ggagcttaaa taaggaaccc aggagatggc  105240
cagctgtgca agcccccagc ctgtggaagg agctagtgtg gttttatgaa tgagttgcaa  105300
atctttcttt gagcttttg aactgatctt ccagcattgc cctattgacc cctccctgac  105360
tcctttgctg gaatctgtag ctttgaac tttgacaggg acacatccta agacccttgc  105420
aaactcccag atgtgagaat ggcactacta cttagagtct tttcgactca gcgtgtgtgc  105480
agaagagcat caaccgggct gtgttgcgag gcagggcctt ggctgacctc tcagtgttta  105540
catagctaag ccagttagtg tttgccacgg cctcacaagg gcttcagatt cacacagcca  105600
aagtatagat tattaaaggc ataggtgttt ggtttcctgg acttggaggg tctttggaca  105660
gaaaatcagt aggcaaccac acccagtact ttgtgctggg aagcttggtc atctgtgaga  105720
gggtcagaga gtatacccat gcgtgcatgc caccgaaggg tcagtgagta ttcctgtgtg  105780
tgcatgtctc agggccggag agagtatgtg tcactgagag gtcagagtgt ttgtgtgtgt  105840
gtcaaagagg gttgcattgt gcccttcact gaggggtcag agggtgcctc gcgtgtgtgt  105900
gtgtgtacgt gtgtgtgtgt cactgagggg tcagagtgtg cctgtgtgtg tgcttgtgtg  105960
tgcgtacatg tcactgaggg gtcagagtgt gcctctgtgt gtgtgctcat gtgtgtgcat  106020
acgtgtcact gaggggtcag agtgtgcctc tgtgtgtgct catttgtgag cgtatgtgtc  106080
actgaggggg tcagagtgtg cctctgtgtg tgtgctcatg tgtgagcgta tgtgtcactg  106140
agggggtcag agtgtgcctc tgtgtgtgtg ctcatgtgtg agcgtatgtg tcactgaggg  106200
gtcagtgttc ctatgtgctc atgacattga gggtcagagt gtgcctgtgt gccaatgaaa  106260
ggcatttctt atatttttt atatgtggtc atagtagacc agttaattta ttttgactcc  106320
tgtgttagac caaaataaga cttggggga agtcccttat ctatctaatg acagagtgag  106380
```

```
tttacttaaa aaagcataat aatccagtgg ctttgactaa atgtattatg tggaagtctt   106440
tattgtcttt tcagatgaat caagtagatt attcttgaga ccaggaatgt tgctgttttg   106500
gttatttgga aagttttatc attttcaaat tgacttttga atttgagtca ccttttttca   106560
gaagtggtgt taaattatag gagccctagg tttttttttct tttttttagaa gtcatcacaa   106620
aatgatcagt gttcagagga agagctttga ccttccacat ggtataatga ttgataacct   106680
taattcatct cttaccataa accaagtatg tgtaagggtt ttctttattt cttgaaagca   106740
ttttgtagat gttgagagca gttttccaaa tgtaatttcc atgaaatgcc tgataagggt   106800
acccttttgt ccccacagcc ataccggctc tgcagcccat agtccacgac ctctttgtat   106860
taagaggaac aaataaagct gatgcaggaa aagagcttga aacccaaaaa gaggtggtgg   106920
tgtcaatgtt actgagactc atccagtacc atcaggtaag aggaatgtat gttggaactg   106980
tcgtggatac tttattgacc cgtgcagatg aaggaagtg ccatgtggta acgctcactg   107040
ttaactgtgt tactttgaac caggtttggg ctttctgggg cctgggtaga tgccggtgca   107100
gggggatggg gagggaggcg gggggtgggg gggtgtggtg gagttgggga ggtgcagtgg   107160
caggaggtgt tgttggtgtg tatccttttt tttttttttga gatggagtct ctctccgtcg   107220
cccaggctga agtgtggtgg cacgatcttg gctcattgca agctccacct cccgggttta   107280
agcaattctc ctgcctccac ctcccgagta gctgggatta caggcatgca ccaccatgcc   107340
cagcaaattt ttttttttgt attttagta gagatggggt ttcaccatga tggccaagct   107400
gtttcgaact cctgacctca agtgatcctc ctgccttggc ctcccaaagt gctaggatta   107460
caggcgtgag ccaccatgcc cagcctggtg tttatcttta aagtgggcac agccacagga   107520
gttcacctga ctcctggtct gagagtcacg agatcgttca agatagtgag gccctctttt   107580
ccaaaacgag gaccaaaaat caattgacag tgttggtcaa gatggtagaa accttaaaat   107640
gatagaaatc tcaactctga aataaaaact ttatttgtat atttatttac cactatttg    107700
acatagggct aaggtctttt tctttgagct gatttctggt tttgttttct taaagtggca   107760
taagaattca aagacatttt gaggaaggct gagtgcagaa atctctcttt ttaaatgact   107820
tctccttttct tttaacttgc actgttgtct agccctcact tattttgtca attctttta   107880
gctgtttgtc tttgaatctt cataaagcca tagcttttct cataagaagc agcactttct   107940
ttgttcattc atattttaat gaacccctgt agtatttaat taaatactta atgcctaatt   108000
aaatcacata attgcaatgc aaaagtacat gtatcataaa gaggtctgaa aatgagcaac   108060
tgcaagcag gtggtggcag gcagagctgc ttgggtgggt gggtgtcatg gagaggagtt   108120
catcagccac atgttcagtg agctctggat atgtctgttt agaaatgatc actaataaac   108180
ttgtgctcaa ccatgtatac ctctgggaag caggtgctct tcagtagatt gcctctgcag   108240
agaacacaga attgaagtga atgtccacaa aggcaatgag ccacctgcag aatagtttag   108300
tcaaggctgt gtttgaagtt tgccaaagat taatatacat ttgatttttca tgttgtgcct   108360
tttctctgat tgtgaaatat tacaaattct atacaaataa caatgatggc aaatcctcct   108420
gagcaaagtg tgcaccttgt atgtgcccta gaggaacttg tgtttcgttc tgattcccct   108480
acatttctca tgtcatagag tggggttgc attagtgtcc cctgtcctc gctgggatca    108540
catctgtttg gatcctagag tcttccagct gaactgggac aagtataaca gacggacacg   108600
taggggtgga aaggcgtctc ttggcagcag acttttctaat tgtgcacgct cttataggtg   108660
ttggagatgt tcattcttgt cctgcagcag tgccacaagg agaatgaaga caagtggaag   108720
cgactgtctc gacagatagc tgacatcatc ctcccaatgt tagccaaaca gcaggtttgt   108780
```

```
ccccgcagcc ttggcttgtt gttgcatagt gatggtagct taaggtcctt gtgaaaggtg    108840
ggtggctgga atcagctctt ccttcagtcc taatctgtgc cttgatagca gttctccgtg    108900
ctagtcatgg gacagctgac ttcatttctt ctcacaatgc catctcaggt tggtattgcc    108960
cacctacttt acaggggga tcccacagct ccgagaggtt atggaggtga tcaggcagca    109020
cacagcttta gagtgctggg gtgagggcgg gccaaggcta actctaaagc ccgaaccctt    109080
acctcctaca ctgcctcctg cattctggtc aacccagtgt tttatttggt ggttagattt    109140
ttgtttttgt taccttactg cttgtaattt agcagttttc cttccttc ccttcctttc    109200 ctttccgaca gggtctcact ctgtcaccca ggctagagtg cagtcgtgta atctcactgc    109260
aacaacctct gcctcccagg ttcaaccaat tctcccacct cagcctcctg agtagcaagg    109320
accacaggtg tgcaccacta cgcctggcta gttttttgta tttttagtag agatgaggtc    109380
tcgctgtgtt gcccaggctg gttttaaact cctgggcgca agtgatccac caaccttggc    109440
ctgccaaagt gctggcatta caggtgtgag ccacctcgcc tggcctattc atcactaatc    109500
agaatttcta tgatcaaatg acatgaatca ttgtttccac aactgcagtg gaaggaaatg    109560
gcctggcagt gccagtttca gaagcagcct gcccccagtc aggcacaggc cactgtgccc    109620
ccagtgtagc agcacctctg tagctcacag agaagggtgg tggggacctc cttgaggcag    109680
ctctgccaga aaatctcatg agctgcctgg cacagcttga ggttgccttt taagtggact    109740
cagcaaatac atgtttgttc atcttgatta tacacaataa caactactc tgtatagtac    109800 gagtagtccg tggttttgg catttgattt aaacttagag gcatgtgata ttgatgttac    109860
tgccttcatg actgcacccc cattctgatt tcataatgga atgttatctt gagaccagtt    109920
agacaacagg acagggatct tggcttctgg tgagattgac agcagtttta gtgtggtcag    109980
ggtctccctg cctacagatg gttttagaat ggtgccctgg aagctttatc ccattctttt    110040
ctgtgcgtaa tctgagtaga gtggagatcg aaggcctgaa tacatagtaa atacctgact    110100
taatatctgc cgcaatggaa attgtgtgat acaacattta tgaaacgctt agtgcagcac    110160
ctgccaggta gctcaccaca ggtgcatgtt gcattcagaa gtagtgctag atactatcct    110220
gttactggca gtgcatacat cagtgatcaa agcagattaa agaaagaccc cctgccttct    110280
tggagtgaag attttgttgg gatgcgggta aggggacaga caatagaaaa gcaagtgagt    110340
gaagtctata ccatggcggc tgatcaggaa caccgtacag aagaatccag gagggaagag    110400
agttaggtgg tgtctgcggt gggagtggca ttgttcagct ggtgatgaga agaagctttg    110460
gtgatctggt gacatttgag tgaatttgca gaaaggaaag atacaagcct aggagatacc    110520
tggggaagga acattccagg cagagcaaat agcagtgcaa aggccctggc gggggcgga    110580 catgctgtta gggtacaagc aatgagggtg gaggagtggg gcagccatgg ggagggaagg    110640
gagtgaggcc tggtggggtg aggccagtgt ggaggagcct tgagagggtt tgcgctgatg    110700
tggtgtaggt tttagcagga tcattcttat tcctgagttg agaatagcct tgaggggag    110760 gtgagggcag agcagggcca cccatgtgag acccggcact ggagtggaat ggcccaagtc    110820
agcatccctt ggcagcatga aagcaaaacc agcaaggttt gctggtggct tagatgtggc    110880
atgtgagaga gagcagggct ttgggggtga tttcagggtg aggacaggt ggctgtgac    110940 aaggtagggc agacattggg ggcagcagga ggtcagagcc tgtctggatg tagcagttga    111000 gacccccatag gtgcctaatg aggtgaggcc agcatcaggt gtatgagcct ggagttgtcg    111060
agagactgtg gggcaggggg tcagcatctg agatgtccac tcacagtgga cccagactgg    111120
```

```
ctggagagga ggaggagctt gaataccgag cctgctgagt cccagctcca aggtcaggta   111180
ggtgagggga gccagtgctg gggcaggggg agtaggcagg tgtggggttc ctaaagccaa   111240
gatttttttt aaggcatttt gtgcaggagg gcgacatctg ctgtcagcac cttgggaact   111300
tggcccaggt ttggcagcac cgagggcact gatgagtgct tttggaggag caaagggagc   111360
caaaccctaa tgggaatgtg ttcctgaaag gacaggagag agacttggga aaaggtttta   111420
cttgaagagg gaacggagaa atagggcagt agccagagga ggagaggagt cggcaatggg   111480
ttaagttggc agaaatgaag gcctgtttac gcactgaggg cagaagcaac agggaggatc   111540
agttcatgac acaggagaca caaatcgccg ttgtggtgtt cacagacatg ggttaggatt   111600
ggctgcatgg atgacagagc actgtgggtt ctcccagagt tgctgggagg aggcagagt    111660 tggtgagcac aggcgagggt ccaggatgca ggaatcctgg agctcaagtc agttgttccc   111720
ttgttgtaag atgtggccag tgttgtgagc ttcacatctg tgccttgaaa aacaccacat   111780
ctgtttgcag agttgtttac tatgtataca cactcagtag aaacaaaaat tggaaacagt   111840
cagtgcccac catcaataag taatggttga acacactgtg gtataagctt agactatttt   111900
agcttgggct attttgcatg attaaaaatg ttctggccag gtgtggtggc tcatgcctgt   111960
aatcccagca ctttgggagg ccaaggcagg cagattgctt gagctcagga gtttgagacc   112020
agcctgggca acatggtgaa accctgtctc tactagaaat acaaaaagta gctgggtgtg   112080
gtggtgtgcg cctgtagtcc tggctaactc aggaggctga ggtgggagga tcacttgagc   112140
ccattcgtgc gccactgcac tcctggggca cagagtgaga ctctgttaga aagagagaga   112200
gagaaagaag agagagggag ggaggaagga aggaagaaa taaatggaag aaatggaagg   112260
gaggaagggg agggaggaag gaagaaagga agttcagcca gttgccttgg gagttctcca   112320
ttgcactggg ttaagtgaga agagcagaga cgtttatgat tttcaaaac aactaaaaca    112380 aaacctctgt gggtgagggg gcaaggatat ggctatagga acatgggca gattaagaaa    112440 gggatataca cacaccactt agcatttgtt acaactgttg tgggagggat ggagtgcaga   112500
aaaagaaaaa aaaagtgca caccatccca tgtatgtgta tacaaaggga cgcttggaag    112560
actggtcccc aaaatgttgg taatgattgt gtcagggtgc tgcagtgcta gttgatttt    112620 tttcacactt tgtatattt gagtctttta cagaaagcat ttattattta tgtaataaaa    112680
atctaaatga caagatttct gttatgggaa aaatgtagct atacagtgtt gttgtaaaaa   112740
tgtttgcttg gttcaccact gaacttaaaa tgcttttaaa tgagggaagg tgacgatgag   112800
atgattatga tgatttgccc ttgagttaca tagctggtgt acaggaagct gtcgtttctt    112860
ttggcttacg tagaaatgtt tgtggtgtct aattccacag atgcacattg actctcatga   112920
agcccttgga gtgttaaata cattatttga gattttggcc ccttcctccc tccgtccggt    112980
agacatgctt ttacggagta tgttcgtcac tccaaacaca atggtgagtc tctcgcctgg   113040
ctcagcagat gaatctggac ggcttgttca ggctctgatt actgggacca cccccagaat   113100
gtctgagtca gtcagtttgg gtagggcttc ttgagagttt gctttttttt ttttttttt    113160 ttttggtgtg ggggtggtgc ggaacagagt ctcactctgt cgcccaggct ggagtacagt   113220
gtcatgatct cggctcactg caagctctgc cttccagctt cacaccattc tcctgcctca   113280
gcctcccgag ttgctgggac tacaagcgcc caccaccacg cccggctaat tttttgtat    113340 ttttagtaga gatggggttt caccgtgtta gccaggatgg tcttgatctc ctgacctcgt   113400
gacccgccca tctcagcctc ccaaagtgct gggattacag gcgtgagcca ccgcacccgg   113460 ccttttttatt ttttttggag atggagcctt gctctgtcac ccaggctgga gtacagtggc   113520
```

```
gctacctcga ctcactgcaa cctccgcctc ccgggttcaa gcaattttcc tgcctcagcc   113580
tcccgagtag ctgggactac aggtgcgtgc cactgtgccc ggctaatttt ttgtattttt   113640
agtagagacg gggtttcact gtgttagcca ggatggtcgc gatctcctga ccttgtgatc   113700
cgcccgcctc ggcctcccaa agtgttggga ttacaggtgg ctctcgcacc aagccaagag   113760
tttgcatttt tagcaaattc ccaggtgaaa ctaatgcctg cttttctggg agcacacttt   113820
gggactcagt gatagagagg tttattggta ggatagtaaa ataggagtta ttttctttca   113880
caaaattggc aattggggga aatttaatct tccttttttc ttcagctgtg acttatgtat   113940
tatgtttatt ttaggcgtcc gtgagcactg ttcaactgtg gatatcggga attctggcca   114000
ttttgagggt tctgatttcc cagtcaactg aagatattgt tctttctcgt attcaggagc   114060
tctccttctc tccgtattta atctcctgta cagtaattaa taggttaaga gatggggaca   114120
gtacttcaac gctagaagaa cacagtgaag ggaaacaaat aaagaatttg ccagaagaaa   114180 catttcaag gtatgctttc tatctgagcc tataactaac ccatgccttt tgggaagtca   114240
cgtgatgttt cacagtcagt aagtctggaa taatacctgg tcttgcttca cttctgagtt   114300
gggtaaagaa gtctgtatca gtgtaatttt ctaatccgtc ctgcattatc tatggctctt   114360
ggttcatacc tgtcttgaag ttctgtcatg ttctgtctct tgtcctcagt agagatgcta   114420
cagcagtggc tcgcctcagg cagggcaggg cagtggggtg gctgtcctgg gggcaggcag   114480
taggggcacg ctgacgtcag ggaagttgaa acccaagaga agccagtaaa agtgagtctc   114540
agattgtcac catgtgctgg cagttttaca cgctgtcagt aataaaagtc ttctcctgc    114600 agggcagcct gcctccaata aatacgtgta gtatcaaatc ctgtcttccc tcataaattg   114660
tttggaagct ccccaaggac agtgatgagg cactcgtaag tgcttgctgc ctagatgggt   114720
ccctctccac ctttgctaga ttctgagcat tcactgagtt agagctgctt ctgcaaatgt   114780
gctgcttctg ctaagtggct gtgacttcat gcagccttca cttggtttgt catcagtgga   114840
gatgccctgt gttgtcgaag gagataagcc cagtaagcct gctgggcacc ttttggtttg   114900
caggttcagc aggcagccca tggctttccc tgtgtcgcat tgaagcagct ggctaaaatt   114960
gatgatacat taaattcctg tgacagatga tcagcttgta tttgtgtaat ggtgtacagt   115020
tcacaaagct taaaaaaatg ctacctgcca tttcatcctc agtgaggaag gtgatacaca   115080
gagagaccaa gtgactgtgt ccacggcgac ggcgctctgc atttcacttt agcggttaat   115140
gtactctacc tatattttta ctttatattt accatatatc ttttcatgta tacttggcgt   115200
aagtgcttta tagtagtcac ctaattcact gtcatctttt tgtttcttg gaaggtttct    115260 attacaactg gttggtattc ttttagaaga cattgttaca aaacagctga aggtggaaat   115320
gagtgagcag caacatactt tctattgcca ggaactaggc acactgctaa tgtgtctgat   115380
ccacatcttc aagtctggta ggtgaatcac attagtcttc ctggagtgtc tcgttcccca   115440
ttctgcacta tacactctca gagtgtagga gctgtgctgc ccggtagaaa ctctgccttg   115500
cccagtgtgc cagttgaaaa tatttgttgc tgtaagagta cacctgatac catgtgaccc   115560
agcagttcca ctcttgggta tatacccaaa agaatggaaa gcagggtggt gaaaagatat   115620
ttgcatgcca gcattcatag cagcattatt cacgatagct aaaatgtgga accaactgaa   115680
gtgtccctcg atggatgaat ggataagcaa aatctggtgt atatttacag tggaatatta   115740
ttcagcctta aaaaaggac attctgacac atgctacaac atgggtgacc cttaaggaca   115800
ttatgctaaa tgaaataagc cagtcacaaa aggacaaata ctatgtgatt ccacttacat   115860
```

```
gagggacctg gagtagttaa ttcatagata tagaaagtag aatggtggtt gccaggggct  115920
gcaggggagg ggagttattt ttacaagatg aagagagtta ttctagaaat gaatggtggt  115980
gatggttgta taacattatg aatgtactta atgctactga actgtacagt taaaaatagt  116040
taagaggacc aggtgtcatg gctcatgcct gaaatccaag cactttgaga ggccaaggca  116100
ggaggattgc ttgagccaag gagtttgaga ccagcctcag caacatggta ggaccccatc  116160
tgtacaaaca aactagccgg ggatagtggt gtgcatgtgg tcccagctac tcaggagact  116220
gaggctggag gatcgcttga gcccaggagg ttaagtctct agtgagatgt gttcatgcca  116280
ctgcactcca gcctcggcta tagagtaaga ccctgcctca aaaaaacaaa acaaaacaag  116340
acaagagcca aaaatggtta agatgggcca atcacagtgg cttatgcctg taatcccaac  116400
actttgggag gtcaaggtaa aaggatcact tgaagccagg agcttgggac cagcctgagc  116460
aacatatcga ccccctatc tctacaaaga aaatcaaaaa ctagctagat atggtgggca  116520
catgcctgta gtcccagcta cttgggaggc tgaggtggga ggatctcttg agctcaggag  116580
ttcgaggctg cagggagcta ttattgcact ccagcctggg ctacagaatg ataccctgcc  116640
tcttattaaa aaaaaatcca aaaaaaaaaa aaagtaaacc tgagagcttc ctcctcctgt  116700
gttaaatttg gaggccaaga tgttttttgtt acttttacaa atgatcaagg acggtgaagg  116760
ttgggcatgg tagctcacac ctgaaatccc agcactttgg gaggctgagg cggggtgatc  116820
gcttgagctt gagaccagcc tggacaacat agcaagagac cccatctcca caaaaataaa  116880
aaaataaaaa aaaatagcca ggagtagtgg catgagcctg agcccaggag gtcaagctgt  116940
agtgagccat gatcatgcca ctgcactcca gcctgggcga gatcgagacc atgtctctag  117000
agaaagaaaa tgacaaggac agtgaaccca agaaagtcat aagatgccag ctgtgcagca  117060
agcatggaaa gcagccagtc caaattagga cagtgtgttt tccaagaaga acgatcgttt  117120
gtaatgagaa tgctttgctt taaataaatg actaaatagc tagaagccta gttctagggg  117180
ataggcacgt ctttcttctc tcaagaaaat agaaaggcaa ttctaatttc tagtaacagc  117240
aaacagcatt aagtcatggt ccaaatatga ggcaaaccaa aatgtggctt gattgttcag  117300
cagttgatct gttggaagcc cttgatatta aaaaggttct cctttaagcg gcttaggagt  117360
cacgatcaaa gacctataga aagagatgcc atccttctag gatccttggc tctcttggga  117420
actagattca gatagtcata atgtaaatac tgcttgagct ttctttcttt ctttctttct  117480
ttcttttttt ttttgagaca gagtttcact cttgttgccc atcctggagt gcaatggtgc  117540
catctcggct caccgcaacc tctgcctccc aggttcaagc aattctcctg cctcagcctc  117600
ccgagtagct gggattacgg gcatgcacca ccacgcctgg ctaattttt gtattttag  117660 tagagacagg gtttctccat gttgaggctg gtctcgaact cctgacctca ggtgatccac  117720
ccgcctcggc ctcccaaagt gctgggatta caggtgtgag ccaccgcacc cggcccgagc  117780
tttcattttt gaaatcaatg tatgactgaa acactgaaga cttactgact taattatggt  117840
ttcagaacag aatgaaaatg tcttcggttc tgatgaatat aaaaggaaaa ctaaccaagt  117900
taatttggca agtagatggt agagatagag gtggggagtg gaagggaac taaaatcttc  117960 acctagcatt gttgggatta tatggttaca tcatctgaag ttgacagacc aaaatataga  118020
ggcttcagag gtctccaaat agaactaaac atgtaattca gattgttagg aggtagtata  118080
aatgagctaa atctcatctt tattacggta gagttaatgg gtgatgtcta aagttgtctg  118140
aagtctataa atcatgacaa attatgatgt ggtgattgta ttcaacagtc tttcagttgc  118200
agggataaaa ccccagttta aactagagta agagaaagaa tgtgttggtt taagctcctg  118260
```

```
gaaagtgcag gcaagggtag ttggtaggac tgcatctagt gttgtaattc tgtggtctgc    118320
attgtatatt tatgcatctc agctctgctt tcttcttttc atttatataa tttttaaatt    118380
ttattttaaa gatagggtct cactttgtcg cctaggctga agtgcagtgg catgaagtgc    118440
agtgcgaggc tcactctagc ctcgaactcc tgggctctag agttcttcct gcctcagcct    118500
tctaagtagc tgagacaata ggcatgtacc aacatgcctg gataggtttt aaaatttttt    118560
tgtagaaatg gaagtcttgc tgtgttgccc aggcgggtct ttaactctta gcttcaggcg    118620
atcctcctgc ctctgcctcc caaaatgctg aggttatagg tgtcacccac cacgcccagt    118680
ctcatctctg cttcctgtgt tagttttgtt ctctggtggg ctgttttcac atgaccgaag    118740
atgacctcta gcaggctgtg ttctcagccc ctcaagtagg cctatgtgat tggccttgca    118800 tgagtaaatat gggtgaccat aaacccctga atgctctggt ccacatgggc caaatggag    118860 actggacagc attccattga tgaggagtg gggctggtct ccgggagtaa gggagaggag    118920
cacatgcagt aactgatggt ctgctgcaag ggatagcagc acagcagtta gaattttgga    118980
ggtaactacc agaactgaaa acagaaatga taacaagtag ttgccttaaa aagggatggg    119040
agcagggtgc ttttgtgatc aaagctcctt tctcttactg gattttttgta cacattttgc    119100 atacatatct tagagtaaaa gatagcattt tcagccttgg tccatttgag gatactcttg    119160
gcgtggcccg cctccatgct agcaggctct ggttgtgcca agttcagttg agcatcctgg    119220
ctcttgcctg cacggaactt ccagtcagtg cgtcagtatc acaagtcttg atatttccta    119280
tgaagaagaa cagtagtgca gtgacagacg aaatgggtgg gcaggcagag gcaggatttc    119340
tgagggagag aagtagctag cttttttgcag agaagagttc cggcacccaa gagagcagct    119400
gagagtacag gcaggcaggc aggatgccgg tagggcccgg ccgcacggcg ccacagaatc    119460
ctggagaaag gggcctcttc atggcctctg cattcagctg ctgtcaccct ccgcacaggc    119520
catggccaaa atttaatttt catagtggac tctagttttt gagccttact tgctattatt    119580
gaaataattt tcttgtttct ttttaaagat cttcggatta tgcttcactg accactgtaa    119640
taagtttaaa gttgagaaaa tatggcttgt taatgaatga taggtcaatt ttagtatgtt    119700
ggtcatttta atattttgcc accagttggt ttggatttga tgccaggagg agacagcctc    119760
atttctaagg actagtcttg cctttgtggg ataagggtgg tgtgttctgt gtccttctac    119820
atgtccgagc gatctctgtg cagctcaaat gtggtcactg tcttattgcg ctgatttcct    119880
ctccttccat ctcacaattg aggcaaaata ttgttactgt tgaagtgttg tccaatagga    119940
cttccagcag agacaggatg tctgcactgt ctaatttagt tgcctttagc cacatgtggt    120000
gttctgtacc tgaaatgtgg ctggtctgat tggatagctt aatttataat tttatttaat    120060
tttaattaac ttaaatttaa acagctcgt gtggatagtg gctcctgtat gagacagtgc    120120
aggtctgttg agaagcagct ttactggtgg gagtggaggg cttggagagg gcacgtgggt    120180
ttcctgctgt tatctttttga ccttatttaa tctgcccaac atttgcaagt aagttgtgtg    120240
tgtgtgtata tataaatgtg tgtttctgtc ttcttgtttc ctttgactgc atttatttga    120300
aagacactag gtggcagaat tactgtattt gattggtttc aagataagag ttgaaataat    120360
tcatctcgtg ttttttatata agtaaggtgt gtttagcatg taaaattggt aatatgtatt    120420
cacgtactgc ttaaacaaag gctatgaatt ccacccataa accgaaaatg aagacctta    120480 aatttgtcca tttcaggcgt gggtacttct taaataatac ctggttcagg aactagtcag    120540
aatggcaccc ttgactttt gtttcctgct tttcctcttg ttgggagagg agggtattca    120600
```

```
tcccaaagtg gtttgcctat ttcacattcc atctaggata agcagaatag ccaagaaaga   120660
tagctgtcct cctgtttaca acatttgggg taaccagcat ccctctcttt tggtccaaga   120720
tagactggtt tagaaacaga tgatggcacc agaggcccag gaggtggaaa catcagcttt   120780
gtttgttgtc catgtggctg aattagagct gtctggcctt gtagcctcaa cacggccttc   120840
cagctttgct caccgtgatt ttcaaggaca catcttgtgc tcttccctgc ctgccatcca   120900
gactataccc agtcagggtg gcaggagctg ctgccccttc ctccctgagt cctggtcgtg   120960
ggtggtggag atgtgccatg acgctcacgg aggcatgctc accccttcct ctgtggcaga   121020
ggggatggct gcacgacagc tcttccctgt cctttccaaa gcgtctgtgg ttccactttt   121080
tggggcaaag caggaatact ggaagagaga gaaagtggtc cttttctatag taataaagtt   121140
gacattgatt caagttcatg cttggggaaa ggacagggct actaacaatt ataatgctgg   121200
gagcaatgga atttctcat gggtatgtgg taggtttaat tttaattatc ccagttaatt   121260
cttagaactg ctctgtgaag tatttcccgc tttgtgctta agttctaaaa gatcctgtgc   121320
caaaaccaag aatgaaaacc caagcattct ttcttgccca tcgatctttc tctcatcagg   121380
ccacttcttg ggttgatagt ggtgagtgta gccgctgcca cttccagaat acccaccatg   121440
ggccccagtc actgtgtggc gtggagaaga gatggttctc tctgtgtcat agctgaacaa   121500
gcccagccca gagaggtttc tgccctagga gctctcgatg gtggaattgg gatgcgatcc   121560
cacatcctgc ctgttttgaa aacagcattc tttatttcca attcctgctt ccattgttcc   121620
ttttaatatt tctttgttta gctcacaaaa acacggcttg cggagctgct gcgtgcagct   121680
gtagctgttt ctctgggtgc agcctgcatc cgccttcctg cccgcctcct ttcctgcact   121740
gccatcgtgg tctccgggca cttggtccct ttctcttccc ctgagtccct ttggctcccc   121800
tgtgccaccc ttgtgatcca caggctctgc cttctttctg tctcagactg ctgctcatca   121860
ctactcggga ccctaggaag ggaggttcca ccgagaagca tcttctcatc tcagccacgt   121920
tctcagtgcc actgttgtct tgttaggta atggtagcta ctgtaacaaa taaaccaaca   121980
tttccatggc ttcacaccag agaaggttgt ttcttggttt tatgacaatg tattgagggt   122040
gttcttggtt cacggatggt tttcctccat gtgggaattc ggggacccag gctcctttcc   122100
ttcttttggt tctgttctcc aggccttcac atcctctgtg tctggttggg gacaaggaga   122160
gggaaggtaa agaaggcttt gtggccttgg ataagtgaca ggcatgcctt tgctggtgtt   122220
ctctcgtggt gacaggtcac agccccaccc tgtaaagggg gactgagaga cgtcgtcctg   122280
ctgcttccca gcagcagcac tgtggtctct gatgtgtttt ctgtgaggat aaaaacaggt   122340
gattccagga tgaggaaagt cagggaaacc cttgaaggga ggggaccagg cgggtgtcac   122400
catgggatta gtggtggctt cagaatgagc tgcagcgagt gccatgcctt ctaaagcttt   122460
tgctattctg atatgcccac accatgccca gcaggtgtct gccttgctct ccgcagagag   122520
agtgatgaat ccttctcatg agcctctgtc cagttgttcc tccctccacc tggaagggac   122580
cctgggttcc tcataacatc ccagcggaac aggggacctt ctatcctgtc cccaagttca   122640
tcctcatcct cctgccggct tcctggcccc tcttatgtct gcttcctgac gccacatcct   122700
tctgattctc ctggaattga attttgcctt tgatgcttat ttaaaaatat ccattgcagg   122760
ccaggtgtgg tggctcacac ctgtaatcct gtgcactttg ggaagccaag gtgggcagat   122820
tgcttgagcc caggagtttg agattagcct gagcaacatg ttgaaatcct gtttctatag   122880
aaaatacaaa aattagctgg gcatggtggc gcacacctat actcccagct actcaggaac   122940
ctgagacagg aggatcaatt gagccccgga ggccaaagct acagtgggct gtgatcgtgc   123000
```

```
cactgtactc cagtctggtc aaacagagtg agaccctgtc tgaaaaaaaa aaaaaaatcc  123060
attgcatact tcaccgtagc gaaacatgta tgtcttacct ttcctttcct gcctgtagct  123120
gctcttttac acttaacagc cacactaagc cagccttaaa tgaaaaacaa accagcactt  123180
cctgtgccct cctgcttcct tcatgagggg tccctccctc tgtgtacact ccattctcat  123240
tgcccatggt ggtttgtttc cctcttgttt ctcaagccat ggcagcctgc ctcttgccct  123300
ctttactaaa aaggcctttg cagaggctgc ctgtgttctt tctttctagg tctctctcat  123360
cctaggccct ccagcttgat tctgtggagc tgccctcttg tcactcagta gcttgtgggg  123420
tcttctctgt ctagccactt aattgattgt gttcctcgag ttgctgtcca tggtctctcg  123480
ttactgtttt ctctgtgttt ctgcctctct ccttggcctt ggtaggtcca tcccctttgt  123540
gaccttggct gttgctctca tggacaactt tctcttgctg gtccttgtag tcctggcatc  123600
cagcttctcg acacgggact tgtcctgcca gtacctcaga cttgcactta aaattgaact  123660
agcaccactg tcactctcca gggcctcttc ttgttaatta gatcattagg gatgttcaga  123720
atcccagcat catagtatgt tcctcctccc gctaccccag gaaccctaac cttacctcct  123780
cctctctatc tactaggagg tggccctcag agtccgtctc atcttccacc tgaacttccc  123840
taataggctc cagcagctgc caccccgggg gctgagtact tcctccatgc cttgtgcagt  123900
gctgagccct ttacctgggt tctcctgttt gctccttatt acagccctgc gaacagatac  123960
tgctcttaat tccatcttac acctaaggaa gctgaggccc caggtaaggt gcatccaagg  124020
tcacccaggt agtagacagt agagccacga tctgaaccag gcagtctgat tcagagcctg  124080
tgttgacact cagccaccta gaacacagct tggattgtgg gtttctatta cctgttcaaa  124140
acccctacat cccgggtctg tccctgcacg tgctctgtgg cctggctgca tcttccttga  124200
aggcagtgca tgcctcttca ctcagggggc ccatgcagga acagagggcc ccacagaagg  124260
atgaggccag tgcagaatgg gctggagggg acaatgctga ccaggaagca agtgtagaga  124320
aatcccagga aacctggagg agccagagac aaggcattag aactcctcgt cgtgacctgg  124380
tctgcattct ctgagtgtgc tgcttctgtt agctcgcttc cttggtctca ggttatagtt  124440
taaggcattg tggagcccta aaaagcctgt actctgtttt tacctgtttt aggacccttt  124500
cactttgggg atgtgttgat tttttttttt tttttttttt tttttttgag atagagtctc  124560
gctccattgc ccaggctaga gtgcagtggc acgatcttgg ccactgctgc ccctgcctcc  124620
tgggttcaag caattcttgt gctcccgcct cccaaatacc tgggattaca ggcacccgcc  124680
accacactcg gccaattttt gtattttag tggagacagg ttttaccat gttggtcagg  124740 ctggtctcga actcctgacc tcaagtgatc tgcccacctt ggcctcccaa agtgctgtga  124800
ttataggcgt gagccaccac acccggcctg aaatttaaat cagaaataaa attttgatcc  124860
caacagtgat gccaggcagc ccagatctgg gggagagggt ggccttggcc agctgggcct  124920
ttctctgttt cccaagtctt gctgcctctc cctgctgggc tttgcagcct gtgcatgtct  124980
ctgtgccttt gaccttgttt atccaaagga gaggatagaa tgaagtcatg attcctggag  125040
ccctgagaag gatgctgtgg agaaatttgc cggtagaatc tagctgagtg tgttgctgag  125100
gtgccagcat tgtgtgtggg gaggctgacc gcttggcctg cctaggccca ggatgctcca  125160
tggccgggca cagaggccac ttggctgtca ggtgtcagga gcctgcagag ggcacacaga  125220
gcctggaccg cagggggtc ctgctttctc acctggcctc cttcagcatt tctgtccctc  125280
agtccttagc aagcccagga gctgttgagt ttggcaggtg ccgagtgctg ttcctgcctg  125340
```

```
tgtagctgtg gctcagtcct gtgggggccc cgctgtggcc cgagtgcagt gattcgaggc    125400
gctgagtgtt ccctgactcc ttctccagga gctgtgttca gactttcgca gctcttggct    125460
tggagctcct ggagggcttg gcattgccga ccaatgtgga ggtcgacagt gagagaggag    125520
gaatgctagc tttcttgacc agtccattaa ataagtggga tattggccag gcacggcggc    125580
tcacgcctta atcccagcac tttgggaggc tgaggcgggt ggatcacgag ctcaggagtt    125640
caagaccagc ctggccaaca tggtgaaacc ccctctatac taaaaataca aatattagct    125700
gggcgtggtg gcaggcgcct gtaatcctag ctacttggga ggctgaggca ggagaacagc    125760
ttgaaaccgg aaggtggagt ttgcagtgag ccaagattgc gccactgcac tccaacctgg    125820
gcaacaagag caaaactcta tctcaaaaaa aaaaaaaaa gtaggatatc tgtttctgct    125880
tagaaaaatc agaattttct aaatgccagg tgttctgaat acgtaagtat gggagacgac    125940
tcagcctgtt tcatttttat gtaaaatctt cgcgtagcca tgtggcactg gaccgagatg    126000
aaagcaaaga catttctcct taactttgtt tctaggaatg ttccggagaa tcacagcagc    126060
tgccactagg ctgttccgca gtgatggctg tggcggcagt ttctacaccc tggacagctt    126120
gaacttgcgg gctcgttcca tgatcaccac ccacccggcc ctggtgctgc tctggtgtca    126180
gatactgctg cttgtcaacc acaccgacta ccgctggtgg gcagaagtgc agcagacccc    126240
gaagtaggtt cataatgccc cacagcccag ggcgccagcc cagcaccctg tcctgagact    126300
cccagtaacc tgagctttgg ccaccgttaa agcatttttca ttttccattt tttgtgaggg    126360
cttgtgaaat ttctgctgca tattaatatt cctttcatgg acagcatatt attgggacaa    126420
acatgcggtc cagctaaagg cattcaaaat agcagttgct ttctaaatgc gattttcttt    126480
ggcaggttct ttgacaccat tgcatcttgt gggatatgct tgtcatgctc tgtggctcct    126540
actaagttct agtccttaaa ttggttccat agccagacat gttgcaatgt cttaacctca    126600
ttataaagta aatgtggttc tggttatcct tagataatga agtaacagtg tagcaaattt    126660
caaaacctct tggaaatgtt attttaccat tcaaaaaggc ttactaaggt tctcgttatg    126720
ggtggccctc tttttgcaaa aggttttcag gcttaagctc catttctagg tgctccaaca    126780
ctccattatt tgtatatgta tggaaataaa agctgtgacc acccccaacc ctggcccccg    126840
cccagctgaa tcctcagcac agtatttctg gaaggctcaa gatcccacgc tggggaaaag    126900
aagttctgga gacaaaagag ggcaggtgct gccgtgcctc tctgctcagt atggatactg    126960
gaccttgtgc tgccagggct cccagtaggg ccagttcatg gcactcagct ggaaagtcca    127020
ctgttgggag gcattcttaa ccatccactc tgtgccgtat gtagtggggt ctggtcattc    127080
tgttggagga gacagaccag tgacgacatt tgaaatgctt ggtggatgtc ttaggcctgt    127140
tacgatgact gagcactgtg ggggcaggag acagaaagtc agtgtctcct agttctgtgc    127200
tgctttaacg tgcatagaaa tcagctgcgg attcagcaga tcactccttt tctgacagat    127260
gggcctgctt actctgatgt tatatcagaa agctctgaat ctgggaattg tgtccctga    127320 attggagtaa cagaaatgct tagatgatga gtgtttaaaa gaaataaacc aaaggtaaat    127380
ttagtttgga attcagcaag cgtcttcatt cagccctctg agggcaaact acagctttt    127440 gtaaatgtag gtaaattctg tgactgtttc gtgaccccct ctgatccagt tttcctttat    127500
aaccttctgt attgttcctt ctattatcct gaaataacat taatagatta ggctgggcgt    127560
ggtggctcat gcctataatc ccagcacctt gggaagccaa ggcgggcaga tcacctgagg    127620
ccaggacttc gagaccagcc tggccaacat gatgaaatgc tgtctctact gaaaataaca    127680
aaaattagcc gagcatggtg acaggtgcct gtagtccctg ctactcagaa ggctgaggcg    127740
```

```
ggagaatcgc ttgaacctag gaggaaaagg ttgcagtgag ctgagatcgc gccactgcac   127800
tctagcctgg gtgacagagt gagactccat ctcaaaaaaa aaaaaaaaaa aaaaaaatta   127860
atggatcaat ggattttaa cctaataatt aaatttcaaa aaatatcgtt ctttaatggt   127920
aatgtaaagg taaaattaag ataatatgta acaagcatgt gagtgtctaa ggtgtccccg   127980
tggtggaagg aaaaaataaa tccccataag tgtccaagat gcccatagag agcagagctg   128040
ttctggttta aaccctgct cttagcactg tgttttcca gctgtgggtg gtggggatg      128100 agtatctttt tatttccatg agatgagaaa aatgaattac tagaagtgtg aaatacaaaa   128160
cacagctgct ctttttttag ccatagactc agcagccata aaattgctgt atccagttgc   128220
agaaattcct gctgcttact cttgaccctc tctcggtttg tgtgcatctc ctctcaggct   128280
ggctcccaga tgggagctgg ctccaggcga cactgggtgc tctgctccag gaggtcctta   128340
tgtgggtcct gccctagcct agcccctctc ttatggactc tgtcactgtg ggtttatgat   128400
tcactctcaa tctgtcttac ctcttggtga actgttagag tcctgcctat actttggcgc   128460
ttgtgggtgt gttgtggtac acatgatgtg ttggtcactt cccagctcat cttgttctga   128520
gtcaccctag atttgggaca ttcattcgcc accagtaccg gcggtgtat ggcctgagat    128580 ttggggggc ttgtgctgct acaaattggg gctgaatttg agttgacagt ggaccttctt    128640
tatgtctact gctcatattt gaattgcaaa tactgcctct tctctttcag aggctcatta   128700
ccctatagct gtattattgc aaagtgcaca attacagctt gagtgtaagt cacactgcgc   128760
tggcaggacg gcccactgag aaagggcacg tttcctgttc gttagttttc acattgacac   128820
ataatttaca atacagtaaa atgtactttt ctatcaactg tagtcagtaa cagccccct    128880 cccccaacca catcaagata tagaggagtg ctgtcacttc aaacagttcc ctcttcctct   128940
gccacatcct gccctcccc aggtctaacc accaatccgt gctctgtccc tctgttcagc    129000
ccattgcaga aggccataga aatagaatct ataggctagg tgtggtggct catgcctgta   129060
atcccagtat tttgagaggc tgaagtggga ggatgacttg aggctgggag ttcaagacta   129120
gcctgggctg cctagcaaga ccccatctcc agaaaaaaaa aatttaaaaa ttacaatcac   129180
gtccctgtag ttcagctgct tgggaggctg aggcaggagg atcacttgag ctcaggagtt   129240
agaggttaca gtgagctatg atcgtgccac tgtgctccag cctaggtgac acagcaagac   129300
gttgtctctg gggaaaaag aaagaaacgg aaccacgcgg tgtgcagcct tctgagtctg    129360 gccccttcg gtgagcagtg tctaaagttc tgtcgcgtgt tgcccacgcg tcggtggctc    129420
gctccttgca actgctgagc attgtatggc taggctgtag tttgttttca cttcaccagt   129480
tgggaaacag agaaaaggca ctttttaaaa agtttaaatc tgtagaattt tggttttac    129540 cagttctctt ctaaatcctg agggattaca ggaaaagttg ttgtatttca gaatattctt   129600
agcttgatgt gacctctgtc cccgttaagg ccctttgccg caatgggaag gacgtcgctc   129660
ggtcagaccc tgaaggtcag agggcagtt tgggagtgtg tcaacatttt aactgtatgg    129720
actagagcca agagtctcaa ggtttataat tcccacgtat tcaaaagaa aaaaacaata    129780 aagtgagaag tcagtgtaga gtgaaataac ctgtgttagt ggggaagaag tgttttaaa    129840 caggatttcc ataacgtata acatcaacat gtttagagtg gtgatgtttc attgggaaac   129900
gaacagtaaa acatgaaagc agggaggttt tcattctggc agttggcaac tttcacggca   129960
gatggagaat ttcaaaagca attgctcaat tatcaaacat agccagtgtg agttctgaaa   130020
taaaggtgct gattgaatgt gcagctttat ggtggatttt gctattcagg caagcatttt   130080
```

```
aattttctgc ctgttaaatt ctgttttctt tagtttttca tatgtggttt attgtagctt   130140
aggaatagat aactgagagt atatattaca catacaacat tctgatatgg caatatttaa   130200
aacaacttgt ctgttttaga actagaatta aacataatca tcttcagtat tttgcaaata   130260
agctcactgc catccagaaa cattgtcaat gcatctgttg ctccttctag aagacacagt   130320
ctgtccagca caaagttact tagtccccag atgtctggag aagaggagga ttctgacttg   130380
gcagccaaac ttggaatgtg caatagagaa atagtacgaa gaggggctct cattctcttc   130440
tgtgattatg tcgtaagttt gaaatgcctg taaacggggt tgagggaggt ggggaccagg   130500
agaacatcct gtgtagatga cacttgcatg gaccctctgg aacccagacc gcccggtgtc   130560
ctgccaagct ccatcgaaac taaatctaga atgaatgttt acttctgctg tgacatataa   130620
ttggagacca ggcctggcct tccagtcact ggattctaag ttggactgtg agagttttg    130680 cagctgactc atttatcaaa tgcccggcta ttggctcacg cctacatgat gctgggtatg   130740
tttgttaatt tgagggaagc aatgaataaa taataactaa tgatttaaaa aacaaagtaa   130800
gtgcattgac tgtagtgggg ttctgatttt aaatttttt  aaaattaat accaggagca    130860 gtggcttatg cctaaattcc agcaactcga gaggctgagg taggaagatc acttgagccc   130920
aggagtttga gacaagcctg ggctatggtg tgagacaccc atctctaaaa aataaaaaa    130980 taaaaaatta tccaagtgtg gtggctcgtg cctgtaatca cagctctttg agaagctgag   131040
ggcggaggat ggcttgagcc tgggagttcg agaccagcct ggcaacacag agaaaccctg   131100
cctctaccaa aaaagaaag  agaggaagaa agaaaaatta gcctggcgtg gtggtgcatg   131160
cctgtggtcc cagccacctg agagactgag aaggaggat  tgcttgagcc cagaagtttg   131220
aggctgcagt gagctgtgac tgtgtcactg cactccggcc tgggtgacaa ggcgagaccc   131280
ctgctctaaa ataatttttt taagttaatt tgtagaaaag gtgttagatg ttctttgtca   131340 catttatga  tggattcctg tttaaatgcc gttctcttta agaaaaaaa  aataacttgt    131400 gggagttttt aaccataaaa ctagcatcac atatttacca tggagaattt acaaaaaaac   131460
aaataaacgg aggaaaataa aacctcctgt aatcatacta ctcagagata acttgctgtt   131520
agattttggt ctagatttaa tacttttttct atatttatat taaaaatatt taaaacatat   131580
gcatttcttt gtcacaaaca tggtatctta tagatactac tgtcacatag caaaacagtg   131640
ttaaatattc tgaatcagaa aaggaagccg actctccaac tgaaagaggt gttatcctag   131700 agacttttc  tggtgatgac aatttattaa tagtcacttt ttgctttact ttctctattg    131760
aagtagtttt tctattttgt tctacttta  aggataataa aatttataat gctgttttc     131820 acagaaatat aagaaaaaag atactaattt tataagttaa taaagtttga tcatcccaaa   131880
tccaaaaatc tgaaatccaa aatgctccaa attctgaagc tttttgagtg ctgacattat   131940
gttcaaagga aatgttcatt ggaaggtttc agattttcgg atttagggag ctcaacaaat   132000
aagtataatg cacatatttc aaaacctgaa aaaaatccta aattcagaat acttctgatc   132060
ccaaacattt cagataaggg ttattcaacc tgtactgtca gatgatccca aatgaaaaat   132120
attaatcgtt aaccaaatat caaggaattg atcacatttt acagtttctg cctaggatta   132180
tgaatcaaga tgaaaaggct ctgcatgttt aaaaatatat attttttattt tcttataaat    132240 cttaaatatc tacacttaag atttatttga tatgtgggat ccattcatat tttggattca   132300
acagttctgt caaaactgtg gcagtgatag gggattcttt ttttcccact gaactatcac   132360
aaaattggaa aaagagtaat tggagaaccc cactggctta gccggcccga agcccgggag   132420
agggcaggca gtgctgtgga tggggtcatc ccagcgcaac gctgcccctg ctacctgcgg   132480
```

```
atctcgctga ggcctgcctt tgtcctttga cccttggcca tttgttagtg tctctgagag    132540
ctggactgct gtaccctact tccccagggg gcctaacttc acacagcctc tgccgcagtg    132600
cgtggttgga ggtgacggcc ttggtaaatc gagtttccta cctcctcaat tatttgtgct    132660
catacactgt atattttag tgaggttat atttgggatg tgttttctcc ttcttaccct      132720
ttctggcctt tctatggcat taatacctgg tctcttcttg tgtacttgaa aatgaatctc    132780
tcatcatatt tttccttagt gtcagaacct ccatgactcc gagcacttaa cgtggctcat    132840
tgtaaatcac attcaagatc tgatcagcct ttcccacgag cctccagtac aggacttcat    132900
cagtgccgtt catcggaact ctgctgccag cggcctgttc atccaggcaa ttcagtctcg    132960
ttgtgaaaac ctttcaactg tacgtcttca tcctgccgac tattgccagt gcagttttc    133020 cctgccttaa aaatggagta ttgaaatttt taactttaat ttctgatttg caaaatagtc    133080
atcttttgtt cttttccttc ttgctgttag ccaaccatgc tgaagaaaac tcttcagtgc    133140
ttggagggga tccatctcag ccagtcggga gctgtgctca cgctgtatgt ggacaggctt    133200
ctgtgcaccc ctttccgtgt gctggctcgc atggtcgaca tccttgcttg tcgccgggta    133260
gaaatgcttc tggctgcaaa tttacaggta ttgggaagag aaaccctgat attgatttat    133320
attgaaaatt tagcaggcca agcaaaacag gtggctggct ttttcctccg taagtatggt    133380
cttgacatgg tcaccgatag aaacatggaa acatctgcaa acttgccgtt actcgtgtgt    133440
ccgatctgac tgtttcttgt attttttct agtctgccct tactaggatg aactgtacac    133500
atcagttcat ccttttttaaa tgagcatgag gttattttgg gttgttaggt gttacaaaca    133560
cactaatgtg tttttgtcta ttagagcagc atggcccagt tgccaatgga agaactcaac    133620
agaatccagg aataccttca gagcagcggg ctcgctcaga ggtaatgctg gaaacacagg    133680
tcgtccttgt gttaggacaa cccaggatat aaaggatata gatttgtacg ggaataaatt    133740
cacaggacaa gaaatcgatg tgccttatag gtgggtttac tgcagaagtg ccataataga    133800
accttcctac ttttaaaaca accagatctc actttctaaa gagtaaagga tgaccggcag    133860
gatcacgtct gtgacgtgag tggaggcagt ttgcactcct ggtggctgtt tgagaggtag    133920
catttagaat gcctgtattc actgtcctgt gatgagtggg aaaataggtt atcaggttta    133980
tcttagcaaa atcaaagcat gtcatctaat tgctaaacaa gagttggcaa atctgagaga    134040
cattactcaa tccttggcat gcaggactta catctgcatc ctgttgccat tttatgtctt    134100
caaagcattt aatcatttag ttgtgtttgc aaagtctttg agaagccttt gtcagaaatc    134160
cctacatctc ctatgtgagt gtatttccat gactgcagaa taagttaaac ttttacctt     134220 ttccttccct tgcggggcgg ggtgggggc agggattgtg tgtgtgagag ggagagagag     134280
acagcagaga aggagaatat aattatcatg ctgtgtactt tgagctgaaa ctgcaaaaaa    134340
ggaaaaacac acaaaaatta ttatgctttt cagtctttag agtaccttgt ctattatgct    134400
tttcagtctt tagagtacct tgttgatggt gtttttaaat gggattgggc acaattaggt    134460
ggacagtttg ggatgatttt tcagtctgta gggccaagct cttttgtaat ttgcattatg    134520
aagttgtcac tctcatagca gatggcggga gataaactat tattactttt tgaccctaga    134580
cttagtcttc agtccagatg agggagatta aaagattata aatatcttgt gccagatgag    134640
gtgattttat tttgaaatga ccatgaattc ctatcagttg tcttactggg atatttgata    134700
gtggaatttg tgcatttgag tcttagatga tctgttttac atttattaag aaagccttta    134760 ttagcttta tactgtgtat tgcctgttgc agtgtttgag tataaatgaa atttctggaa      134820
```

```
aatattaatg gagtacaaac tgtgatactt aaaagtaaac tagggcctgc atttgtatca    134880
tgacctgttt gagtattgat gagaagatag ctgtgaagaa aaaggtttaa acaagtgtat    134940
tttcctttaa gaagccacta atagtgcatc tccttagagt gtatatttct agaatcctag    135000
tgtgcagagt ttagactaag actaaaaaaa aaaaaaaaca aattatactg taatttcatt    135060
tttatttgta ttttagacac caaaggctct attccctgct ggacaggttt cgtctctcca    135120
ccatgcaaga ctcacttagt ccctctcctc cagtctcttc ccacccgctg acggggatg     135180
ggcacgtgtc actggaaaca gtgagtccgg acaaagtaag tgtccagcgt gtctgcatgg    135240
gaggcacagg gcgctgagtg cctctgtcac ctgtggcaga tacagagagt gcagaggagg    135300
tgccgtggac ccaaggagtt ctggcgctcg gctcggctca gtgaagctgt ggttagagac    135360
gtgggggggcc atcaaggtct gagggagcca agcagtgctg atgtgggacc cttttggtag   135420
gagtgtgggg tgagtagtta gtgggtgaat caaggaatag tcggccgtgg cctgcaggcc    135480
cctgactgca caggccttca agcacatgtc aatgccgtta gcctccctcc atctcctcat    135540
accttctggc cacctgtgag ttgcactgcc actgccagcc attctggtat gttgtcagca    135600
cctccactgc tcatacctca tggttaggga ccacctggag ccttggtaga gccttggtag    135660
agccttggta ctctactttc ctggacaaag ttcagcttat gaatatgaat ttagatttca    135720
aaaaccagca gcccaagtat aagaaagcga aggttcagtc ctgccttctt aggctctatt    135780
cgctaagcac ctgccctgcc ctggttgctg ggagagatg agtaaagcag acaacccagg     135840
agaggatggc aaaggggccg ctaaccctta gtggtttagc tatatttgga aggcctattg    135900
gaagttcacc aggtgaaggg ggaggctgtg agggtgccca ggcaggtaac agaagtccaa    135960
aggggaaaac ctgtggtgtg gtgagccgta tagccacagc ctgccggccg gcagccctct    136020
cagcctagtg cggtgttccc aagcactggc ctaggcctgt agctccaggg atgtgaagtc    136080
cccttgaacg ccgcccatca tgttcccctt atccattttt ttcttcccag gactggtacg    136140
ttcatcttgt caaatcccag tgttggacca ggtcagattc tgcactgctg gaaggtgcag    136200
agctggtgaa tcggattcct gctgaagata tgaatgcctt catgatgaac tcggtacggg    136260
gggagcagtg gaggcaagga atcctcagct tttcttgtga cttccaagtg ggatttgtct    136320
catcatcatg tgacccactt gttgacaaca catgttgggg actccagtct gggcagggac    136380
gggatgtcgg agagactcca ctctgaatgg ggccgggaag tggggaggac tccatttcag    136440
atggggtcgg gacatggggg ttatgctgat cgagacagaa aagcacattg tttcagccac    136500
attagaatcc acgaggtgt tgttttgaaa tccagctggc cccaaggctg ggtgtatggt     136560
ttgggatgag aactatctgg cctccactgg aggaacaaac acaggatgtt atcatctaag    136620
ctccatggcc aagacagaat ggaagtcaag gttgcgtatt tgccgtagac ttcaacacag    136680
tgtcgtaatg cgtgacgtca ataacttgtt tctagtgtct tggaagttga tctttagtcg    136740
taaaagagac ccttggatgc agcgagattt cctctactca cacctctgtt agatgtagtg    136800
aggttcttca ccccccaacc ccagatgtca gagggcaccc tgcgcagagc taggaggcca    136860
tgcaaagcct tggtgtccct gtccctcacc cgtgggcagg tcctgtgagc agtggggggg    136920
ccacctcttg ggtatggtgc agccatggcc caagcagggc ttcttctcag acctactagg    136980
acgggagaaa cctcctggtg ctttagccct gcgttgatat gcagcaaatg ggagggaagt    137040
ggcacctgg gaggacaaat gcctgtagag gccgggagtg acggcaggtg ttcatgaaaa     137100
gagaccttgt ggggagggca acacaacagt gtgttctgat gtactgaaga gctcaactga    137160
aaacaacagg agaattagcc caaaatccat ttactaaaat tgtttatctt tttttttttt    137220
```

```
tttgagacaa agtctcgctg ttgtccccca ggctggagtg caatggcgct atcttggctc 137280
actgcaacct ccgcctcctg ggttcatacg attctcctgc ctcagcctcc caaatagctg 137340
gtattaacag gcatgcacca ccacgcccgg ctaattttg tattttagt agagacggga 137400
tttcaccatg ttggccaggc tggtctcaaa ctcctgacct caggtgatcc gcccacctcg 137460
gcctcccaaa gtgctgggat tataggcctg agccaccacg cccggcctaa aattgtttat 137520
cttaagattc atgcagtgaa agctaactta ctgagtgata aatttgctta gtgatctgtt 137580
tattaggttt tccaaatttg ctaattgggc tttgaacagc tgtaaaagtt ctgactgtaa 137640
aagaaagctt caacttttgg cattcatgat gcttttctga gtattaaact aagatagatg 137700
ttttacctga aggatcggcc accaatcttt aaatggctaa acaaagggt tgctaaaaca 137760
taatccaaat tgacataaga ataccattt ttccaaccaa aattttggca ttcatatggc 137820
tacttttacg tatttcagct gcatttgaac atcttttca aactttaggg tggttggtgt 137880
atcactgagg tcttggatga cactttagct ttgattttgt ttttatgaat taaaattgtc 137940
ataccaaaat ttttatttca agcaaatcca agagcataaa aaattaaaat attacttaaa 138000
atactaagag agaacagata tatttttac taagcatatg ttgaatgaaa ttgttcaaat 138060
atttataaca ggcatagagt agaattttct taaaaatatt tttgatggta taccaatttg 138120
tattttctca gaaacatttg ccttattctt ttttctgttg tgtttttctt acctgattga 138180
aagctcataa tctgttgtta ttgtttgtta acctttaatg ctctgatttc aggagttcaa 138240
cctaagcctg ctagctccat gcttaagcct agggatgagt gaaatttctg gtggccagaa 138300
gagtgccctt tttgaagcag cccgtgaggt gactctggcc cgtgtgagcg gcaccgtgca 138360
gcagctccct gctgtccatc atgtcttcca gcccgagctg cctgcagagc cggcggccta 138420
ctggagcaag ttgaatgatc tgtttggtaa ttaaaattaa aatttatctt attttaaaa 138480
agcattccag ggccagtata gtactttgca ccaagtaaat gtacaataaa ggcagtggat 138540
ctaatacatt gaaagcgttt acagaggtag ctaaagagca gcacgggtgt cctcggctca 138600
gaatttcttc ctgtgtgttt gccactttgc cattcattga catggtcatg gacatagggc 138660
tctaagccct tgaggaaggc tgggccagac ctcaggggag atgcagcccc aaaccacgtg 138720
cagtcctgtg gacggatgtg tagatgtgcc actgaggaac aatgtcttga gctttcatca 138780
gattctcaga gaattgcttg actgcctttc gaagttgatg catctgtgct cacgtttgca 138840
cccacccacg aggtccttct gtttcagggg atgctgcact gtatcagtcc ctgcccactc 138900
tggcccgggc cctggcacag tacctggtgg tggtctccaa actgcccagt catttgcacc 138960
ttcctcctga gaaagagaag gacattgtga aattcgtggt ggcaaccctt gaggtaagag 139020
gcagctcggg agctcagtgt tgctgtgggg aggggcatg gggctgacac tgaagagggt 139080
aaagcagttt tatttgaaaa gcaagatctc tgaccagtcc agtcactttt ccatctcagc 139140
ctggcagtaa gtcttgtcac cgtcaagtta ttgtagccat ccttcaccct cacctcgcca 139200
ctcctcatgg tggcctgtga ggtcagccag gtcccttct catctgcacc taccatgtta 139260
ggtggatcct aattttagag acatgaaaaa taatcatctg gaagtacttt atgtcttaag 139320
ttggcctgga catgtcagcc aaggaatact tacttggttt gtgttagtgc ttgtaattcg 139380
cccccagaat gtgtacacgt tctggatgca ttaaagtctg gcctgtatcc ttaaagggcc 139440
atcgctgtgc tgcctgccct cagcaaggac acacttgca gacccacaga ggctccgcct 139500
ccacctcaca ccaaagaaag ggaggagtcc aaagggcatc agtgccatta ctcacaaaat 139560
```

```
gataaataca cccttattct gaaccacgtg gagtcatatg gtttgtgatc cctgtccttc    139620
aggtttcagc ttagtgggga agtgggaaag tcagcgtgtg atcacagcac agggtgattg    139680
ctgctgatta tattatgtgc ctgctgtatg caggatgaaa tactttatat gcgtcatctt    139740
atttgactct cacaaccccc tgtgagatag gctctgttac tcccatttga caggtgagga    139800
aagcaaggct tagagaattt cagtgacttg cccaggtcct ctgagctagg aagtagccat    139860
tctggcattt gaacccaagg cctgctatcc ctagaaccca cgctctcaaa ttcaacctat    139920
gacagaggca agccctggtg ctgtgggagc cccaaggaag agcctctggc ctggtggcca    139980
cgtagcccag gagagatttc tacaggagcc cacagcgctg aaggagagag aggcagcaga    140040
gtaagggggc tttgtggcag agaggggact ggcactttgg ggaataggtg ggtcaggact    140100
gaatgtaatg gagccatgtc agagctgtcc ttctggaagg gcaagggcac ctggacgcgc    140160
tgcccctcag tgctttggac ggttccacaa ctgtgattca cacggcttcc ccaaacgaag    140220
gtacacgagt gggcattctg tgactcggta cttcccttta ggccctgtcc tggcatttga    140280
tccatgagca gatcccgctg agtctggatc tccaggcagg gctggactgc tgctgcctgg    140340
ccctgcagct gcctggcctc tggagcgtgg tctcctccac agagtttgtg acccacgcct    140400
gctccctcat ctactgtgtg cacttcatcc tggaggccgg tgagtccccg tccatgaacg    140460
gtgggttcct atcatagttc ctgtctgctt caccatgttt ttattttgtg ctgcctgttt    140520
gccaggtact aagctaggaa ttggggatgg agaggtagaa aaatatgca tcaggaaggg    140580
ctgggcccca tctcttactc tccaatatat tggagtctac actggaattt aactggaatt    140640
tgctttttta gtcatttat ttagattttg aagtttcagc tttcatcaaa aatacctcta    140700
aactttatgt ctctgtgatc tttggtctta gctgttttat gtatttagtc ttatatgatc    140760
ataagattaa taacattaca ttcagaagat tatttgtttt ctgtcagagt taaaatgttt    140820
gtttttatac tgcattgtaa tattaacgta ctgtaaaata aaagtggctt gttcttttca    140880
aggaacagta tcctcaacaa gggtcattag ccacaatttt taaaaaattg gacgtcatag    140940
tttacatgtt agagggcgtt ttgaagcttt gtattttaa attaaatgtt atagagtgat    141000
gttttcatgt ttcataattg ttttcatctg tgcatttgta gccaacttga aaacaaagat    141060
ccagggatta ctacttaaaa gccagacttc ttggaggtta tagtgatgat tttgatagta    141120
tcttgagccg tctcataata acctcagggt gagagatggc caacaggaga cagtcgaggg    141180
acttagaaat ctgaatgaaa tctgaagttc aaatcttcag acatatacca ctaaccaaga    141240
gattggtacc tcagtctagt attgtctgtt tgtctaaaat tggttctaag gaatctaggc    141300
tagtctgtct atcccttca acttttgtga ggctgcacaa atgtaaaatg ttgaataaaa    141360
agcactgatg gaagtgtgta gaaattcttc tctttgttct gttgtaattt tagttgcagt    141420
gcagcctgga gagcagcttc ttagtccaga aagaaggaca aatacccaa aagccatcag    141480
cgaggaggag gaggaagtag atccaaacac acagagtaag tctcaggacc catttttttc    141540
ttacatgttg ttcctccagg acttaaaaat cattcacaga gacgtgcacc gcggtgagtg    141600
tggactcctg gaagcgcacc gtagctccgc tgtgtcctgc tgctcctccc tagctgtcag    141660
ggaggctgta gtccattgct ttgccagctc ttttgtttcc gagtgaacac cttatccgta    141720
cacatgcggc tgtctctgac cctacagacc agctgggatg ccactggggg agcgctccct    141780
tccccccgca cttcccacac tctgcagtta ttctgagatc cttgagggca gggaacaggt    141840
ttgtcttctt tgtgttctca gaaattaatg ctcggcctct ggtcagcaag caacaacctt    141900
ttgttgagtg ataatgaata aataaatgtt tcccacatga gtattcagta acctcagtgt    141960
```

```
caggttcagc catctgtttt ggtggatatt taaaagaaaa ttccgctttt cctacagaaa    142020
aaaaaaaaaa tccaaatccc agtgatttaa gccagttata gacttagaca tatactacgg    142080
cttttcatgc actttcctcc caattctaga gtaggtattt tactaggaaa atggtggcag    142140
tgcctgttgg gaggaagatt ctttggccaa gtgtctttg ttcttgccag ggcccctagg     142200
ctgctggggt gcttcagctt ctttagccca gtgtctggtg gggaatggcc cctgttgcct    142260
gtcccacaga ggtgggggtg cctcacctgg agcctgtcca cactttac acagcacgct      142320 tacctggagc atcaggcatc ttttccatgc tctgtggctc aggaaacacg ccttttcaat    142380
catgagtgca ccagtgcttt tgggcttttt ctccccgctt ttgtgcaatc ctggttgtgg    142440
atggagtttt cctgtcttta gtcttctgca tagtactttt ctcttctggt tcccggttca    142500
aggttttgta attagagaat gacccagaag caatggcatt taatgcaca gccaaggact     142560 tctctgaatt tgtatctcaa acctctgtgg gtccttcagg cttcagtttg tgatttcatg    142620
atttcttgtt gctacctaag gaatatgaaa acacccacct ccctactctg catcttccag    142680
ccgagtggca cctcaggctg tggatcctgt gcttctgtgg tgaggataag aatagtgcca    142740
accgtgtgga ttgaaatcaa tcagttaatc cctccatgta aagcacctgg aacggatgac    142800
agtcttgtta tgaatactca acaaatgcta tcatgatttt tagttagatt tccattgctt    142860
taaaacagtt gagacatctt ggcggtttga gttagagcaa cgggccctga agtgggttct    142920
gtttgggtga agatgattat gcttattccc catggccctc tttaggcaag agtgggaagc    142980
tttctttgtt ttttttaatca cctcgatagg acgttacttc ttaaaggtca tccaataaat    143040
attaataggc cgggcgcggt ggctcacgcc tgtaatccca gcactttggg aggccgaggc    143100
gggcggatca cgaggtcagg agatcgagac catcccagct aaaacggtga accccgtctc    143160
ctactaaaaa tacaaaaaat tagccgggcg tagtggcggg cgcctgtagt cccagctact    143220
tgggaggctg aggcaggaga atggcgtgaa cccgggaggc ggagcttgca gtgagccgag    143280
atcccgccac tgcactccag cctgggcgac agagcaagac tccgtctcaa aaaaaaaaaa    143340
aaatattaat aaagccaact cgttagcgtg gggcttaatt gcttaagtcc aatgagaagt    143400
ccttctctat cctaggaagt tgcccaaact gtagaatctc gtggcctgtg ggtaatagcc    143460
acgtaataca cactcactgc ctcaacaaat catattttag taggtatgat attctagact    143520
caagacacca ttctgtggat cttcccaagg gtgtgaagtg tccacagcgt ctgccttggg    143580
agtttccatg cccaccagaa ccatgcccca agcccctcaa gcactctgac ctaggaaagc    143640
cagtgaagca aggatgacaa catggccctt tgatactagc tgagggacag acacaggtcc    143700
tgggagacca gagaaagacg aggggcagag gaggtgtcct aaaggaagtc tgaggctgag    143760
gagccacagg atggcttcca gctgtcacag gctgctgctg gccttatcac agagagtggg    143820
ccagagggct gggaaccaag gccagagctc aggttcagga ccattccagc aatcccagca    143880
gaaaatgggg agaattgtat ggtataggcg gatatgaagg tagaatctgc aggccttcag    143940
tggccaactc agagtctaag tggattccac agttacagct tgagcagctg ttgtaggtc     144000 atgctttcta cactgggcat ataggatgtg ttttttaaaa agtcctctct taaccgttgc    144060
ttgtttagat cctaagtata tcactgcagc ctgtgagatg gtgcagaaa tggtggagtc     144120 tctgcagtcg gtgttggcct tgggtcataa aaggaatagc ggcgtgccgg cgtttctcac    144180
gccattgcta aggaacatca tcatcagcct ggccgcctg ccccttgtca acagctacac      144240
acgtgtgccc ccactggtga gtctgctcgt tccttgcaga agaccaagta cggtgaaagg    144300
```

```
caccggtagg ccctgggctg ggcacacgtg agagggcggg acagaatccc cgcagcccag   144360
aggctgcctg ctgtggttct ggtgcccact gtggttctgg tgccaggctg ctttcctcag   144420
gcaccacgtg tggaggtcgc tagtagaaat actgggtttt ctaaaatgaa ctgaggccct   144480
acatccctaa gagattagtg ttagacctga ttctagagca actagaccac tttgcttaat   144540
agcagaccag aaaccacacc ccctcgagtg agtgagattt cctttggag ataattcatg    144600 tttttctaca cagttttgca gttgtcttca gaattggttt aaagtaggtg ttattgccag   144660
gcgcagtagc tcatgcctgt aatcccagca ctttgggaag ccaaggtggg cggatcactt   144720
gaggtcagga tttcgagacc agcctggcca acatggtgaa accccatctc tactaaaaat   144780
ataaaaatta gccaggtgtg gtggtgtacg cctgtaatcc cagctactca ggagactgag   144840
acaggagaat cgcttgaacc caggaggcga aggttgcagt aagccgagat cgcgccactg   144900
cactctagcc tgggcaacag agcaagactc cgtctcaaaa aaaaaaagg taggtgttat    144960 tgatcagaac ccttgtttca gataacatga ggagcttagc ttgaggagag tgagggttga   145020
tggaggggga ctgacttctg cccagtgaaa tggcatcatc tcccaccagc ccgctgaaat   145080
aagatgatgg ggcctgttcc ttagggcctg cagcatcctc aggcaggaaa gaaaggccga   145140
cctggcaggg tgtgagccag caggtgtagg tcagggagaa tggagccagg tcccaggaa    145200 gaggcttgtg gctgcctgag aagggtgcgt gcctgcctgt gtgtgtgtgt gcacgtgtgt   145260
gtatgtatgc tggagagtct agggaggctt gctccaagga cgcagtattg tttgatcctg   145320
agagataagg attctgccgc agggaatgaa ggtattccag atggcgggct tattccgaag   145380
aagaggccag tgcctggcgg tgctggaagc agttgcagaa cagggagttg taggctttcc   145440
tgggaagaga gcagcagggg tgctggagaa gcaggccaca cttgctgcat ggggttgctc   145500
tcggccccac tcttggtgca cagcgagtca ctgtgggttc attagcatct ggttatgaga   145560
cagtaactgc tccttttggag gggctcgtgg agaccatgca ggagggcacg gtcttgaggt   145620
catgccgtcc agagcacacc tgaggatagg ccaggacggg ctgcacgctg taggtaaaat   145680
tcctccagca agctcttcac tggcattgag gagttccctg agtgcggtca tctggaaggc   145740
agctgtaaca ggcactgcag tctctcccctg ggtgggtacc agagaggagc ataggggagc   145800 ataccgatt taagagagg ctttcctgt ggtgaggtaa gagattagct ggtcattatc       145860
atagagcccc ctctgccttt gtgcagatgg gctgtgggaa tcctgggggtt ccgtgggtc    145920 ctttgtcacc tcactgaagg catgtaagct gagctggcca gaccgtgagc tgatcctgcc   145980
acttgaacag catcaagcct gcctctggat tcttctgtgc atggcacttg tctgagcacc   146040
tcacgcacag agaactggac ttcagagttt acagaaataa gctgtatggt tcattttcat   146100
gcctgcttgc caataaacat atctgagctg aacctcattg aacgcctgcc tttattctag   146160
cacagcacct gctgtttgtg ggcgagggt gctgtctcta actcctgcct gcttctccca    146220
gcactccctg agtggggtgt gccagcagcc tcaggatgag gacaggaagt gggagggcag   146280
agcagatttg ggagggccac ttgatgggga aggaagtccc aggaagcagt tggagctgtt   146340
ttctggggga gaaggtgcca gctctgggac agtgttgggg tagtgaggag ggagcccagt   146400
ggagagaagt cgggcttcct gcttcctcac agtatgtctg tcctgactca actcggatga   146460
tgtcacttcc tttcatctt ctcaggtgtg gaagcttgga tggtcaccca aaccgggagg    146520 ggatttggc acagcattcc ctgagatccc cgtggagttc ctccaggaaa aggaagtctt    146580
taaggagttc atctaccgca tcaacacact aggtactctt ggggcctctc cttcaggtca   146640
ccattgtcgg acatctaccg ggaggaaatc cagagccccc agtactggga tcttctcatt   146700
```

```
tgactccaga aaagatttaa gcatgataat aatacaaacc tatgtgaata cattttgcag   146760
tgttggcaaa actccttta tactgagaaa atagatccca gttcctgtgt tttgtggctt    146820
gaatcccagc tttgtgtatt ccgggcttgt ttgaagtcag gaaaggttca tgtgtagtgg   146880
acaacgtgag accaaattct gccttagatt ttgcatttag gctaaacagt ggcagcactt   146940
gtctcagaat gttttcttgt gttcaccagt ctgatcctgt tgtgtctcag tggtccattt   147000
tctcatatgg gaacaagcag acgggagcag atggagtcag gtttcttggc actcgccttc   147060
cccagagcct agaggcagca tggggagaaa gcaggcttgg ggctcagaca gtcctggtct   147120
gcttccagcc ctcctacctg agcagcgcag ggcaagtccg tctaacctct agagaccctc   147180
agttttgtca tatgtaaaat ggggggtcgtg tctatttcat agaattgttg cagatttaga  147240
aattacattt ctaaacaaat gttacccctt atttctaaat aagtgtctaa atgaataagt   147300
caccactttt gccctatt gatggcaaga ggtgtgatct tgtggtggga ctgtaatcag     147360
tcagttctca gtgactgtgc cctgctgtgg tgtttcctgg aatgttcctg tcttgtccta   147420
gaaagtctgg caggggcacc ctgactccac tgtccagtcc tctccccagt ccctcgggct   147480
tctgcagatt tgaggcttgt ttggatccca gaaggttgtg gcaggagaca ccttgcctct   147540
actttcccct ttataattca atgtccaaag agagccctga gcaggtacct cacgccagct   147600
gcctcacgga gctcctcctc ttcctggctg tgaggatcgg tatcagtggc ctcctgctct   147660
ctcccccttg cctaacacga gcacctttgc ttacttgggt gcccttgctc ttgaactgcc   147720
catcggacgt gcgtgaccca agactgtgcc gcagtccttg ccttgtctgt gctcattttc   147780
tttgttcatt tttttccctg taacgtaaat tgttatattt gtctgtatct gtgtctgaat   147840
cagtcctgca cgctctcctt ctctctgtct cttgttctt ctttaccccg tttatcacgg    147900
ggaccccgat gtccattgct ctagttctcc tgtcctaagc accccatccc gtctctctgg   147960
ccttaccaca agtggcgtgg ctgcctcaga catcatgatg gggacatgaa gcacagctgt   148020
cagaaacaac tgttcgttag atacactcga atgcagctca tcaatagga tggagggtct    148080 gtcggatgta ttttcactga atccccgttc ctaccttgat acactctttt taatctattc   148140
ttctagacag gtcagaggaa ccattacttt gactttaaa ttttagcag ctttattgag     148200 gtagaattca catactacag atttcaccca ctctaagcgg acagcttggt ggccattagt   148260
tttatccaca gagttgtgca gccagctgca cagtctcagg gctggactcc agggaagatt   148320
ttagcccatt tagtgagtgg ggcagaagtg gccctggccc tgcacgaggt tgcctgcatg   148380
ggcgtccctg ccctgtccct gtgtctgctc cactgggggt tgaccaggct gccagggccg   148440
acttgggcct gtgccacctg cctctcatgt gtctcggaca gtgcagccga tgtctatact   148500
tcggtttcct caatgatgaa atggagggga tagtgttccc cgcatcatag aactgtgtga   148560
ggtttaaggg actcactgcc cttggcgtgg agccttctcc aggggccgtg ctgtgtcggc   148620
gtagctgtca gctctccgtt acaggcttga gaagggttga cactctctca tgtaacattt   148680
atatttctag gctggaccag tcgtactcag tttgaagaaa cttgggccac cctccttggt   148740
gtcctggtga cgcagccct cgtgatggag caggaggaga gcccaccaga agtaaggcca    148800
caccctgtgc tggttggcac atgggcagtt atggccgctt gcaggccttt ggtggggaat   148860
aaaataaggc agcaagctgg tgttctttt ttctcttacc ttattttga aagagtagct     148920 gaatggtgtc ttgactgata ttccagagca gggacaaagc ctgctgaggt ctgggggctg   148980
cgattaccaa tggctggaat gcattttatt acggtgcatt ccatgttaag gatcaatacg   149040
```

```
attgtgccct ttctggaaaa tatctttag tttatcaata ttcagaggag tgtaggttga   149100
attaaaatga aaaggcactt tataaaggcc atgagtagta cctggtttca tttttctaat   149160
gtcttgcaga gattttatca ggcttcttga agtgttcacg tacattacgc taacacgata   149220
ttaataataa ctgtgctctg gtacagcgga gccagcagaa tgggaagttg tggaatgcag   149280
gcccttgatt ctgatagaag gtgtggtttg aactcacaga aatgacagtt tggagggtag   149340
acatatgtca caagtcatca agattgtctt taaattcatg catagaagct aacagggtgt   149400
cataagcaag gcctgtaaaa tgtatgaggg aattcaaaga taatttatta aaagtaatt   149460 catgtttgga gttttgtgcc caaaggagtc cttgatttga aaaatgggct tttgcccatc   149520
agattgtttc agggcccgtg tgtgcggagg ccctgccttg tccccgtga gctcagcctg   149580 acagaaatcc tttggtagca cttaaggctc ctcttcctcc cattgaggca gggaagactc   149640
tgggttctgc aggcagaggt ggttgtgggt gtcttgctgc tcttgttgac atgtgggctc   149700
tccttccagg aagacacaga gaggacccag atcaacgtcc tggccgtgca ggccatcacc   149760
tcactggtgc tcagtgcaat gactgtgcct gtggccggca cccagctgt aagctgcttg   149820 gagcagcagc cccggaacaa gcctctgaaa gctctcgaca ccaggtttgc ttgagttccc   149880
acgtgtctct gggacatagc aggtgctggg gacagtgggt tccccgctga agcgtccagc   149940
agcttcaacc aggccgtttt ccttcattgc tagaattgaa acaccgtcc gtgtggcctg   150000 tgcaggagat gcagacccaa aggtggcctc ctggtcagtg agaagctgga acgtgacag   150060 gaactgacgt ggggttattg agcatttagg ggaagacgtt agcagagcag gaatgagcag   150120
gcaactagta gaacacccac ttaagggctc acggacaggg gctcacttag gaagtgagtt   150180
tcatttggta ttacaccagg ttcctttagg caaagcggag ggaaagttct ggtgttttc   150240 acttgtaaga ttttgaagga aacaaaacac tcttaccttt tttttctaaa tgtaggtttg   150300
ggaggaagct gagcattatc agagggattg tggagcaaga gattcaagca atggtttcaa   150360
agagagagaa tattgccacc catcatttat atcaggcatg ggatcctgtc ccttctctgt   150420
ctccggctac tacaggtacc tgagggaaag ggtgcggggg agcggttgta cttgggctag   150480
aatgagagaa gactggcatg ctcaccacac cagtgatgcg ggaagacctg agtgtggtct   150540
gagttggagg ctgtggtgct aaatacgctg cccctttcat aagcaggagt cttagtcagg   150600
cccagggagg aagtaaaatc tggaaatgaa tgagaagcat tctctcctgc cagtcaagaa   150660
atgagaagcg aaagaattct cacgggctgt aagaccagca ggattaaaaa gttgaattag   150720
ttgcttatgt taagaactca accaagttca tctacacaag ctgaatctcc agcttttcct   150780
aagaaaccat gtgtggcagt ggctgcaggg cagggcacag ctgggcctga gcaccccgct   150840
ccctgcacct ctcccctccc tgggccctgc ctgtcactgc ccactctccc accaagcctt   150900
ccggttgtgt gcctgccta tcacaggcat cggagcttgt cacctggttt aaaagaagag   150960
agttgtgtgg ggatttggga tgcacgtttt tcactcaaaa gtattttagc gtagagctct   151020
gtgattccgt agctatttag gagtttaagc accttgaagg ctttaattgc agaaagttct   151080
atgtggacgt gcaatgtgtt atacgcagtg tctatgagac tcaaatgttt attagggcgt   151140
tgaagtaaac tgagcacttg gagggccatg gatccagcct tcaaggagct cataagtcag   151200
gaggacccag gagcaatgac ctgtcataga aggcagaaaa gaggggcaca gaggtgggtg   151260
ggaggcatac acaggcagct cctggagctc caagggggagc aagtgcttcc agggaagggg   151320
gcgtggaggc ccctttggag gaggcaagtt gatctggggt ctggcagagg gttagctggg   151380
gacatttagc gggaggctgg tgcccgggaa ttgggggat gcccagcaga aagacatgag   151440
```

```
gaggctggcc tggggcgtgg gggggtgtga aaggttaagt gggggcatta tcctgctccc   151500
gctcctgccg gctgtatctg gtcagcctgg gcaccgaggt ggggttctgg aaggcactgt   151560
tcaccaaaat gcttatctgg gtcccccaga gagcttgcct gcctggactg tcggctcgcc   151620
tgcaactgct gactcctaag cttttgcagc tcagcccaca accagttcct attcacagag   151680
gtgggagctg aggggtgaca agtgactgct gcagtcttat ttgtcataga gaaaagtga    151740 cagagtccag cttgcccact ggccctgcca gcttaactgg ttataaagtg acaaatcccc   151800
aagacccaca gggctctgca caacctgggc cctcctgcca gtggcggcga gggcaggtgg   151860
ctcacggctg ggtgcctgtc tgggcaggag ctgggctggt atgggtggg  cctgcggccc   151920 tgcccccctg tgcagatcaa gactcagggt gctggtgttc acaggtgccc tcatcagcca   151980
cgagaagctg ctgctacaga tcaaccccga gcgggagctg gggagcatga gctacaaact   152040
cggccaggtc agtctcgcgc ccccgccgcc tggcctctgt ccgtttctgt cctcagactt   152100
tggcgcttga cacacccagg agaaaagctc agtgcacttt ttaaatgaaa ggaagttttc   152160
ctttttttta aaaaaaaatt taatgttcat tgtttttatc tgttttattc ctaggtcccg   152220
caagcagagg aagcattagt tttgttttta tttatgttct gtattccaga aagtagttaa   152280
gagacctcac atgtagcgat agagatgtgt gtaagagaca gtgagagggc gtgacttgga   152340
cttaagcaag gaccgtgaga cacaaaaagg ggggtgagga cagagtggag tcagctgaaa   152400
tgctcaggag gaagtagacg ccatgaaggg ccatggtatg gggggccgca ggcgtggccg   152460
tgagtgtccc tggggccagc tcttgggggg ctccctgagt gtccctgtcc ctgtggccag   152520
ttctgggtgg gagcccgtg  tgcaggcaga cagctcggcc acttcctagc aggtcacatt   152580
ggtctgtgct tctgtttcct cctcagataa gtgaagggat tcaagggtct gggtgtggtg   152640
gctaacacct gtaatctata acattttagg aggctgaggc aggaggctta cctgagctca   152700
ggaggttgag gctgcagtga gccatgattg caccactgca ctccagcctg gcaacagac    152760 cagtactctg tcccttaaaa aaaaatgtaa acagaaacgt agggccattt gcatatgatg   152820
gcacatggcg tggagcccta caggtgtatg ctgggcgggg cccggctgtg ctggccgact   152880 tgcaccttc  cctccacccc ggtgctgtgt ctttcgctca ccgggttcct gatttagtga   152940
aagcagttgt gcaggacagt tctctttgta gcttttgttt ctgtggaaat gggtcagaat   153000
atggtgttta gaaacactta tgagctctga gagtttcctc ttctgagttc ctggcctgca   153060
gccttcacag cagaaaccct gtgatgtcac aagcctgttt ctgttccctg ctctctgcct   153120
gtactgtcct gttttgtgcc tgccggtttc agtgacagga agcagggagc tactggacca   153180
gcctgtattt ttctagacat agttggaaaa agaagtccca ctcttctgtc ctttcacctt   153240
tgacagatgt ttccacccca agataagtga aaatgaccaa taggatgcac tgtatttttc   153300
atgaaagtgt ttctgaaggg caggctgaga gtgagaggcc tggggctcac tgggtgcctc   153360
tggccttgtc ctgggcccag ggacactggt ctgtgcccga ggtattccct atcccccaa    153420 ccccgctgca tttggccaca tccttcaatg tttgcgttgt gtccagcgtc cgcaaaccaa   153480
ctgtcatggg atcatactgg ggctgaagta cggtcccacc cctgccctgt ctggggctga   153540
agtacagtgc caccctgcc  ctgtctgggg ctgaaggaca gtgccacccc tgccctgtct   153600
ggggctgaag tacagtgcca ccctgccct  gtctggggct gaaggacagt gccaccctt    153660 ccctgtctgg ggctgaagga cagtgccacc cctgccctgt ctggggctga aggacagtgc   153720 caccctgcc  ctgtctgggg ctgaaggaca gtgccacccc tgccctgtct ggggctgaag   153780
```

```
gacagtgcca cccctgccct gtctggggct gaaggacagt gccacccctg ccctgtctgg    153840
ggctgaagga cagtgccacc cctgccctgt ctggggctga aggacagtgc acccctgcc    153900 ctgtctgggg ctgaaggaca gtgccacccc tgccctgtct ggggctgaag gacagtgcca    153960
cccctgccct gtctggggct gaaggacagt gccacccctg ccctgtctgg ggctgaagga    154020
cagtgccacc cctgccctgt ctggggctga aggacagtgc acccctgcc ctgtctgggg    154080 ctgaaggaca gtgccacccc tgccctgtct gggatgttta gccctagat gccactggac    154140 tgagccgcta cttgcttttg ggaagaggg gtggggtta ggggtctggg cgaggggagt     154200 gcagggctc ctccttggcc tgagagctgt tcatacagac tcctcgccca ctccctgcag    154260
ggtgctgggt cccaggggg aaatggccct tggtgccaag aacgtgagtt ggggctagtg     154320
ccagtgatga tggagaacag cttttttatgg gcacacagcc cacagcactg tgccaagtgc    154380
tcgaggcttc ccgagaacca ggcagaaagg aggacagtcg aggtgtgctg actgcgtggt    154440
ggctgcgtga tctagagcgc gggtcacaaa ggcgcgaggg agctctggcc ttgggtttac    154500
cgcaatgact gccagtgcgg gagactggaa aaggaatctc acgtattggt tccgtgtttt    154560
ggggactcca ttcagatgtc acttaggagt gaaagcatcc cttcgtagag cctctttctg    154620 tgtcacccte tcagctgct cctggggttg actggccct gattcatgcc tttagcatgt      154680
gctggagctt cccagcagct gtccagcccc tgccccaccc tctctgtggg ctcccttgcc    154740
cgtaacctgg ggtgtctgaa cgacccttgc taaggggcag actgttagac ggtaggcatg    154800
tgctgagtcc cagtggccac acccacccac caggagcctg gcactgtggc cgcagcactg    154860
agcagtgccc cgtttctgtg gcaggtgtcc atacactccg tgtggctggg aacagcatc    154920 acccctga gggaggagga atgggacgag gaagaggagg aggaggccga cgcccctgca     154980
ccttcgtcac cacccacgtc tccagtcaac tccaggtttt ccaatggcct ttttcttttt    155040
aacagaaatt tgaaatttct tatcagtcat ttgatttgtt tgaggtgctt cttgaaatga    155100
gcctctcatc tcatgtactt ggaaaatacc catctcgcat attccacagg aaacaccggg    155160
ctggagttga catccactcc tgttcgcagt ttttgcttga gttgtacagc cgctggatcc    155220
tgccgtccag ctcagccagg aggacccggg ccatcctgat cagtgaggtg gtcagatccg    155280
taagtgagcc ttcccattcc cctcacacct gcacgtgcca cacgcaccac acacgccaca    155340 cacccccacac acacaccg cccacacaca tgccacttgc acacacaccc ctcatgcatg    155400
caacacacac acaggccaca cgcaccatag acaccacaca cacatgccac atgcacacac    155460
atacacggca tgcaccatac acacaacaca cacagcacac atgccacaca cacacgccac    155520
accacatgca ccacacacat gccacatgca cacacactcc acatgcatgc accacacaca    155580
cacacacaca ccacacacac acatgcacc acaccacaca ggttacatgc acacaacaca    155640
cacatgccac gtgcacacac cccacacacc acatgtatgt gccacacaca gcacacaacc    155700
acacacatgc accacacaca tgccacatgt gcatgcacca gacacatggc acacactaca    155760
cacacgccac gtgcacacac cccacacaca tgtacgcacc acacacatgc cacacacaca    155820
tgcaccacac acatgccaca tgtacacaca tgtatataca caccccacac cacacacaca    155880
ccacttgcac accacgcaca cacaccacat gcgcacacac acaccacata cgccacatgt    155940
acacaccata cacacaccat acatgcacca cgtgtaccac gcacccacac agacacagca    156000
cacgcataca ccacacacac acgcacacat gcgtcccgca cagtaatgtc tcttgggtgt    156060
aagaacacga cttgccagta gtagcgttct ggatgcgttg cctggattct aacagcgcga    156120 ttctccccctt gcctcctgg ttttccacat ctccagcttc tagtggtctc agacttgttc    156180
```

```
accgagcgca accagtttga gctgatgtat gtgacgctga cagaactgcg aagggtgcac  156240
ccttcagaag acgagatcct cgctcagtac ctggtgcctg ccacctgcaa ggcagctgcc  156300
gtccttggga tggtaagtga caggtggcac agaggtttct gtgctgaagc cacggggcc   156360
catctgcctt gggacctggt gttggccaga ggtgccgggt gcggctgcct ccttccaaga  156420
gttgacccga accggactcc acggcccacg tgagctgcag tgcttctcag atggagggg   156480
ttcagcgacg gtcagtgcca ttcacaggtc actgtgatgt gggttgtggc ggccaagcca  156540
tggtttgggg tcccgtatcc ctgggcttat gacatcattg tagtagccca tccccacaga  156600
accacggtgt gtggtggcgc tgaggcatcg tagatggtgg aaatgctact ggcttcccca  156660
tgctctgccc tgaggcctga ctgcctcact ccccttctca gttatgttcc aggcccccg   156720
agcttcctgg ctggacagct tctctcctgg gggccgtttt gtcacagtga ccctgtgttt  156780
ctagtcccaa atctgggtgc tatagtctct ttttagcgtg gtggttgtct tagtctttt   156840
tggctgctac cacaagttac cttagactgg gtaatttata aacagtggaa atttacttct  156900
caccgttctg ggggctggaa gttttcatgg tcaaggtgcc agcagatttg gtgtgtgatg  156960
agggctgctc tctgcttcat agatggcatc ttctggctgg gtcctcacgg tggaaggagt  157020
gaacaagctc cctcaggcct tttagaaggg ccccaatcca caagggctct cccatcatga  157080
cctcatcacc tcccaaggcc ccaccttctt gtactgtggc actgcaaatt aggtgtcagt  157140
gtaggagttt caggagggat agaaacattc agaccatccc agcggtcaag tgttcatcct  157200
cttgagttcc tccttattct gcttctggtt tatcaggatt cagccagtgc agcatggtac  157260
ctgtattctg tggcacatca ccacatggta tttgccaagt atccatcacc tgcacacgtg  157320
aaatcattgc ccgtgggtcc cgacatctgg cgaagcatat tcaaggatgg cagaactgtc  157380
agagctggca cctctggttc cttgtcatgt ggcattacct agtaatccat tttatgatag  157440
caatggaaac tcatttcttc aacaaacacc tgagtgcctg ccgtgtgcca gccgtctggg  157500
gcccttggtg agaatggcat ggtggtgccc atcagggcct gcctagcccg tgctctggac  157560
gggctcctgt gtgtcaggaa cgacaatgct gtcatgacgg tgaatgattt ttttttttgc  157620
catcactcca gccgctaaca tttgcggagc tcttcctccc gcaccccac ctgacaaggc   157680
caagggtgac cttggcccca ccctaggcgg ccaaggtcag aggttagctg gcttgtctgg  157740
gtcacacaaa atgcagcaga ggttgaggtg agcacatgtc cgtgacctgg agcctgactc  157800
cctctctgcg agtcttgact gctcttgcct agactctgtc ctccccgagc ccaaacgcca  157860
gtcatcttcc cttgtgggtg tccttcagcc tggtgccatg ctggtgactc agcagccgtc  157920
cagggagtgg aaacaattga gtgtgtgggt tccctgtgtg ggcatctctc ttcacggcga  157980
acaccctctg ggtgttgccc acacgatgtc aaagcggctc ttggaagggg tccttctcct  158040
ttgtgggaag tttcagctgc tgggctaact tgaattgtaa ctgtggtttt gtgctcaggc  158100
ccagatcccc ctaggcaagt gttgtgccat cagtaatcaa atgagaaata atcattttga  158160
aaagcagatc ctaaggcagg atggtcatgg acactcactc ccagctcttt gtgcactcat  158220
gctttctgga agatggccat cctctgtgaa ggttttcagc gcgtcatgct tggtacccac  158280
gtatccagag catgtcgttt tgaggtattt gcccaccgtt gtgaaatccg tgccaccga   158340
gagcaggtcc tgatgtgggg ctttcagaag tgggacctgg ggccgtacgc agtccttagg  158400
gagggccgt gtggcgttgt gcgtgtgagg ggatagcaca gggtgaggtg ggggcccaag   158460
aaggaagtga cccacaaaga acagcctcct ctttggtcc ttgttcctgg gatggctggg   158520
```

```
agtggcttct gtgtcgtccg gccatttccc ctgcggagag gctcctacca ctgccgagaa    158580
cctcatcatt ccacaaaaac aagaggccgc ctggccatcc agcgctccat gggaattctg    158640
tgtccccata gtcttgggct gaaggagggt gacattcctt gctgacttct gcagggtct    158700 cctcactgtt aaagagcaga ttgaaagtga agaacgtggg ctaagtgttt aggtcgatat    158760
ttaaccctgc taggttttgg atactaagtg aaattgaggc cattttggtt gaagttgaca    158820
gaaaccacta tcagggatcc ccaagactac cccaggcttt tctagaaaga ctctcagcta    158880
agatgtgtta tggtaaaagc acacaaaaca aaatcagcaa agaaaattag caagggcaga    158940
ggcccatggg gcgatgtccc gaggacacca ggcttgagct tccagaatcc tctcccagcg    159000
gggtcgtgca ggacgcactt aactccccgc acagtgagcc gtgacagcgc gtgtgcagtg    159060
tcgtcgccag gaaagcacac tagagactcg gtgccagggt ttttactggg ggctgggcac    159120
atgggcaccc tctgcctgcc tcgtgcccag actctggact cccggaggga aggcaagttc    159180
tcagcaccaa ccctggtgcc cacacaagca gctgagcaca gggagcccct cctcagtgag    159240
gatggtgggc accgtcccaa caccagccag gggccagcct tgcacacagg cctctcagga    159300
tggtctccgg cctgctgtgt agtctcttct gcacacaagc gtgagggcag cgcccccgcc    159360
tcggctgtgg ggaggagcca ctgggacgtg agctctggtg gcatgcagca gcttttgtct    159420
gtgtgtgcct aggacaaggc cgtggcggag cctgtcagcc gcctgctgga gagcacgctc    159480
aggagcagcc acctgcccag cagggttgga gccctgcacg gcgtcctcta tgtgctggag    159540
tgcgacctgc tggacgacac tgccaagcag ctcatcccgg tcatcagcga ctatctcctc    159600
tccaacctga aagggatcgc ccagtgagtg ggagcctggc tggggctggg gcggggtct    159660 cagaatgagc tgtgaaggaa gcagcatcac cctctccaag tgcccaggct cctggccaga    159720
tggcaggcca ggtatcagtg ggaacccagg tgggtgccat ggctgaggtc agtgagacgc    159780
aagagcacag gtgcgtccta gaggcttcct cgggcacctc cagcgagctg agctctcgc    159840 ctctgctgct gtctcatgtg gcgcttagca cactctccca cgtgcccatt cctgactctg    159900
ctctcgaggc catcggctct cattctctgc tcccagaacc ctgttattac ccaggctagc    159960
ctcctctctg caccttcccc gccctggccc agtacctccc tcttgtttcc actgtgattc    160020
cgacctcacc ttatcttaaa gctgctggac ggcaggttct gtacacacgt gtccttgaca    160080
aagcacggct ggtgccgcaa cccctcagcg agcaagtcaa gctcttcaca gcgatgtctt    160140
acaagcgcag agggctctgt gacaccctgg tctcaccgcc actcttccaa agtcgcagag    160200
gctttagcag agatgggccc agcctctctg agtcataggc ttctgcacac gggagctgtc    160260
tttagaggga gggtggaatt tcatcagcca cccacatggg ggagttgagg gcaagaatta    160320
ggagcaaaga tgggaagggg tctgggagga atggccagtg atccccttg acaagtgggc    160380 aggaaacggg ggctaggtca aagttgagtg gaagacctgg agggagacgg gaaggtctct    160440
gtaggcacag ttcagacagg agggaggtgt gagccagggc acatgccggt ggccgtctgg    160500
caggatttgg gacatgctgg agcagggaca gcggctcatc aggggccatt gccctcatcc    160560
aggccagagt gtcacaagcc cgtggggagg cccttctcgc ctgtcatcct tgctgggcag    160620
tgggtgctgt gctagcagga caggcggacg gctggcaact gtctctgcat ccctggagcc    160680
tggcataggg ccaagtcaca cggggcacag gcctgcaaat caggcacata tgttggtgca    160740
gtgacgtgat tttgggggc agccccagaa caggccccag acacaggcca aagccctgcc    160800
tgtgctggtg tgttgggctg ttctatggct cttgctgtgg gcatggagga ctcagggaag    160860
gagagttgag gtggtccagg agttgcgttt gggatgcaga gagcttgtgg catccaggta    160920
```

```
gaaatggtgc gtggggctga cctcagcacc atgggcagag gggccgtgtc acgtgcctcc   160980
gaggtggagg tgggaccacg tggtgacaga tatacgcatc actgggcacg tttttgtggg   161040 tgttggggggg catcgtattg gctcctctgt tcacagtggc cactcattca gtccctggct   161100
accaggtcct cactgtgcca tggggaaggc cggcgctgtc gggggatcac agaaggcagc   161160
acgtcatgat ggcatgtgcc atgaaggaaa agcacagggc actcaggaag tagaggggac   161220
tggcctgggg tgtgggaatc tagggcctcg ttgaggggaca gagagaggaa gtgtgtggtg   161280
gccagcatgg aggtggccac aggggaggct gagttaggcc gagagggcag gcgttgggg    161340 aggtagacgg gctcagccac tcagggagtg gtcaagcaga ggctgaaggg tcaggccagg   161400 ttgcagggggc ctgggggagc cactcagggt aggcgctccc gggagcccgc ctggcccata   161460
gctctacact cccgcgtggg gccggacatg ctgtgaagcc ctctccacgt tggatggggg    161520
tggctgagcc tggatgctgt ctcccgtttt cagctgcgtg aacattcaca gccagcagca   161580
cgtactggtc atgtgtgcca ctgcgtttta cctcattgag aactatcctc tggacgtagg   161640
gccggaattt tcagcatcaa taatacaggt gagtgggccc tggctgtctt cctctgcaca   161700
cggggagtgg gcttcccttc tcttttcctt gcaggatcat accagtgggc cagttttgac   161760
ttggtcggga ggaggcatga acacctgaga ctgtgcagcg attctttgac acagaggcct   161820
ttctccctgt gcagatgtgt gggtgatgc tgtctggaag tgaggagtcc accccctcca   161880
tcatttacca ctgtgccctc agaggcctgg agcgcctcct gctctctgag cagctctccc   161940
gcctggatgc agaatcgctg gtcaagctga gtgtggacag agtgaacgtg cacagcccgc   162000
accgggccat ggcggctctg ggcctgatgc tcacctgcat gtacacaggt gagcatgtac   162060
acggtgccca taaggccagc ccaagtcctg ttcaagggag gcaggagcat gctcactcaa   162120
gggacctcga ctaggtgccc tctgatttca cacttctggt gttgccccaa gccggcccca   162180
tcaccttgca agaaaggctc tggagccccc agggctggag tacctggtca gggttgaccg   162240
tccctgtggt cactcatccc atgtggctga gctgggctgg gtcctgggca agcaagggc    162300 tgatatcacc tgcttttcaga tctccaggga ctcactggac ccctgtgtac aaagcactgt   162360
ctacagagcc tattggggttg tatagaggta accttcgtac tgaacacttt tgttacagga   162420
aaggagaaag tcagtccggg tagaacttca gaccctaatc ctgcagcccc cgacagcgag   162480
tcagtgattg ttgctatgga gcgggtatct gttcttttg ataggtaaga agcgaagccc    162540
catccctcag ccgttagctt ccctagaact ttggcctgaa gctgtgcttt tgtgtgtgtc   162600
tgctgatccc ctggcgctgt tgctggagtc ctgccagtga ttccccacca cagcctgacc   162660
atgggctgcc ttggctcagg gttccactgg cgagctggtg gtccttggac cccagcactc   162720
aggtgtagcg ttgaccagtt ccaaggttgt cccagtgcct gcccatctct cctgagggct   162780
cagggacagt acctggcagt tgggggtgtg gcaggggca  ggaatgacca gcctctggga   162840
gggtggggca gaagcctgta cagtgaggag gagctggctc agcctggctg cctatcgtga   162900
gaggggagcc cacggggctg tgggagggg  gccgtggtgc ctgtgagcag ggtgaggagc   162960
agcggcagga ggatgaaggt ggaacccaca catgcatctt tgagacccgt gtggtcagtg   163020
gcttctgccc cccaccaccc cccactgctg tgcgtgcata gaattggctt ccctcacctg   163080
ctctggaagt gggttaggag cttggtaggg cttttttctca aggacaaggg ccctgatttt   163140
gctctcaggc ctcagtcctg gcgacatggt ggatctggag ccttgttgca ctgccttgcc   163200
tgtgctctcc aatcagggtg gccagtgggg agccatttgg ctttttctcaa gagcatactc   163260
```

-continued

```
aggtggacct tgctccactg tttgaccaga tgaggcattc tgaacagcca agcctgtgct    163320
ggtctgtttt catgttgatt ttttttttc ttttcttttt gagatggagt ttttcccttg     163380
tcacccaggc tggagtgcaa tggtgtgatc tcggctcact gcaacctccg cctcccgggt    163440
tcaagtgatt ctcctgcctc agcctccta gtagctggga ttacaggcac acaccaccat     163500
gcccagctaa ttttgtgtt tttagtagag acggggtttc accgtgttgg ctgggctggt     163560
ctcgaactcc tgaactcaag tgatccaccc tccttggcct cccaaagtgc tgggattgca    163620
ggcgtgagcc actgcgcccg gcccccatgt cgatttttaa atgcacctct gcatcgttct    163680
tcagtcccca tatgctcact gagcaccact gcgactggca gacgggcaca gggaggcgcc    163740
acgaccagtc ctggccttca aggggcttgt ggtctagtgg gcccaatgct aggtggcgag    163800
tgctccaaag agtgtggtgc acgccttccg cttgaccgct ctccagacgc cacagggagg    163860
cacctcgcag ctgaccacag atttctctct gtggagcagt gtcttcagag cggctgccat    163920
gccactgctg ggcgagggtc tgcgggcggg tagagccagg agcacctgtg aggaagtgca    163980
ctgccatttt cgtagctgct tcccgtgtgt ctcagttaca cacggctggc atgtgtgcac    164040
tgatgagacg ggaacgtgat ggttgctttt cagcactgaa agggatactg ctcagggggc    164100
gtgtttcagg atctggttag ggaagaagca gcgagagcac agatggggcc ctgtgtgta     164160
acaagaaaaa agtcctggtt gacaacagtg ccacgaagcg ttagaacaca tagggatgtt    164220
tgtggagcat ttgcatgtgg aaagcagcaa aaacataatg ggaacgggtt cttttgttat    164280
gatttttaaa aatctctttt gtaacatcct tcccgctgcg ccgtttctgc atattccttt    164340
atgtagcttt caaactcctc ttaggagttc tggtccctac agggcgtggg agcccaggct    164400
ttacgtagct ttcaaactcc tcttaggagt tctggtccct acagggtgtg ggagcccagg    164460
gcctgtgccg agcagcctgc ctccacgagc tagacagagg aagggctggg gttttgcctt    164520
tttagtctca aaattcgtac tccagttgct taggctctga cttcccac ttggaaagtc      164580
cctcacggcc gagggtccct cccagccctg atttcacatc ggcattttcc ccagtattag    164640
agccaaggcc ctccgcgggc aggtggggca gctgtgggag ctggtgccag tctctgacct    164700
gcgtccctcc tcccaggatc aggaaaggct ttccttgtga agccagagtg gtggccagga    164760
tcctgcccca gtttctagac gacttcttcc caccccagga catcatgaac aaagtcatcg    164820
gagagtttct gtccaaccag cagccatacc cccagttcat ggccaccgtg gtgtataagg    164880
tgaggttgca tgtgggatgg ggatggagtg ggaaagcctg gaggtggagt tgcctccgac    164940
ttcccagcag attcgccagc agagcccagc tcctccgctt taaagcagca atgcctctgg    165000
cccccacccc accccgcca cccaggcgca gcaggtgctt cccgtccccc cagccctgac     165060
actcaggcac ctgcttgctc cttgcaggtg tttcagactc tgcacagcac cgggcagtcg    165120
tccatggtcc gggactgggt catgctgtcc ctctccaact tcacgcagag gccccggtc     165180
gccatggcca cgtggagcct ctcctgcttc tttgtcagcg cgtccaccag cccgtgggtc    165240
gcggcgatgt atcctctctg ggtccctggt gctggccccg tttcccttgt caacaccgag    165300
gctcatgttt catgataagg ttttgaaacc taacctttgc aaaaacccca cagatgccag    165360
ggtgacaggc cctcagcccc aggaagtaa aatgctgaca ggggtacaga aaggagcacg     165420
tccagacatt tgctgaccag ggcctctcag aggggccggt gtatggcagg agggtcgcag    165480
ctgaggggcc tttctgtgga gggcctgggt gaggggagcg agggtgggcg gtggtctctg    165540
cagacgtccc gcccactcgc gggctctgtg tggctgggct tctcctgaca ctgcttctca    165600
ttagctttgg tcattgtgcc tcgatcgccc tctcggggaa aggcttaagt aaagatccag    165660
```

-continued

```
ttcccacccc cagatgctgg ctgccaggag tttcccttc cacagccctt ccccaagaca  165720
gaccacaaga gcctccaagc agcacagttg tcctggtgct gacagcacag ccttgcccgg  165780
cgtgcctggc acggctctgc cctcactgca ttggagcagg gctagtggag gccagcggaa  165840
gcaccggcca ccagcgctgc acaggagcca ggccaggtga gtgctgccga gtgggtgccc  165900
tgcctgcagg gcatccagcc agccaagggt tgcaggaatg gaggtggagg cgctgatgca  165960
gctggaggca tccaggtggc ccttccgggg ctctgctcgc tctccaggct ccctggaccc  166020
ctttgtagac tgtttcagga gaggaactcc caggtgagga cagggaggca gcattcccct  166080
catttgccgg cctttttcct taactcctgc accagcctcc cacatgtcat cagcaggatg  166140
ggcaagctgg agcaggtgga cgtgaacctt ttctgcctgg tcgccacaga cttctacaga  166200
caccagatag aggaggagct cgaccgcagg gccttccagt ctgtgcttga ggtggttgca  166260
gccccaggaa gcccatatca ccggctgctg acttgtttac gaaatgtcca caaggtcacc  166320
acctgctgag cgccatggtg ggagagactg tgaggcggca gctggggccg gagcctttgg  166380
aagtctgcgc ccttgtgccc tgcctccacc gagccagctt ggtccctatg ggcttccgca  166440
catgccgcgg gcgccaggc aacgtgcgtg tctctgccat gtggcagaag tgctctttgt  166500
ggcagtggcc aggcagggag tgtctgcagt cctggtgggg ctgagcctga ggccttccag  166560
aaagcaggag cagctgtgct gcaccccatg tgggtgacca ggtcctttct cctgatagtc  166620
acctgctggt tgttgccagg ttgcagctgc tcttgcatct gggccagaag tcctccctcc  166680
tgcaggctgg ctgttggccc ctctgctgtc ctgcagtaga aggtgccgtg agcaggcttt  166740
gggaacactg gcctgggtct ccctggtggg gtgtgcatgc cacgcccgt gtctggatgc  166800 acagatgcca tggcctgtgc tgggccagtg gctgggggtg ctagacaccc ggcaccattc  166860
tcccttctct cttttcttct caggatttaa aatttaatta tatcagtaaa gagattaatt  166920
ttaacgtaac tctttctatg cccgtgtaaa gtatgtgaat cgcaaggcct gtgctgcatg  166980
cgacagcgtc cggggtggtg gacagggccc ccggccacgc tccctctcct gtagccactg  167040
gcatagccct cctgagcacc cgctgacatt tccgttgtac atgttcctgt ttatgcattc  167100
acaaggtgac tgggatgtag agaggcgtta gtgggcaggg ggccacagca ggactgagga  167160
caggccccca ttatcctagg ggtgcgctca cctgcagccc ctcctcctcg gcacagacg  167220 actgtcgttc tccaccccacc agtcagggac agcagcctcc ctgtcactca gctgagaagg  167280
ccagccctcc ctggctgtga gcagcctcca ctgtgtccag agacatgggc ctcccactcc  167340
tgttccttgc tagccctggg gtggcgtctg cctaggagct ggctggcagg tgttgggacc  167400
tgctgctcca tggatgcatg ccctaagagt gtcactgagc tgtgttttgt ctgagcctct  167460
ctcggtcaac agcaaagctt ggtgtcttgg cactgttagt gacagagccc agcatccctt  167520
ctgcccccgt tccagctgac atcttgcacg gtgaccccct ttagtcagga gagtgcagat  167580
ctgtgctcat cggagactgc cccacggccc tgtcagagcc gccactccta tcccaggcc  167640 aggtccctgg accagcctcc tgtttgcagg cccagaggag ccaagtcatt aaaatggaag  167700
tggattctgg atggccgggc tgctgctgat gtaggagctg gatttgggag ctctgccttgc  167760 cgactggctg tgagacgagg cagggctctg cttcctcag ccctagaggc gagccaggca  167820
aggttggcga ctgtcatgtg gcttggtttg gtcatgcccg tcgatgttt gggtattgaa  167880 tgtggtaagt ggaggaaatg ttggaactct gtgcaggtgc tgccttgaga ccccccaagct  167940 tccacctgtc cctctcctat gtggcagctg gggagcagct gagatgtgga cttgtatgct  168000
```

```
gcccacatac gtgaggggga gctgaaaggg agccctcct ctgagcagcc tctgccaggc    168060
ctgtatgagg cttttcccac cagctcccaa cagaggcctc cccagccag gaccacctcg    168120 tcctcgtggc ggggcagcag gagcggtaga aagggtccg atgtttgagg aggcccttaa    168180
gggaagctac tgaattataa cacgtaagaa aatcaccatt ccgtattggt tggggctcc    168240 tgtttctcat cctagctttt tcctggaaag cccgctagaa ggtttgggaa cgagggaaa    168300 gttctcagaa ctgttggctg ctccccaccc gcctcccgcc tccccgcag gttatgtcag    168360 cagctctgag acagcagtat cacaggccag atgttgttcc tggctagatg tttacatttg    168420
taagaaataa cactgtgaat gtaaaacaga gccattccct tggaatgcat atcgctgggc    168480
tcaacataga gtttgtcttc ctcttgttta cgacgtgatc taaaccagtc cttagcaagg    168540
ggctcagaac ccccgctct ggcagtaggt gtccccacc cccaaagacc tgcctgtgtg    168600
ctccggagat gaatatgagc tcattagtaa aaatgacttc acccacgcat atacataaag    168660
tatccatgca tgtgcatata gacacatcta aattttaca cacacacctc tcaagacgga    168720
gatgcatggc ctctaagagt gcccgtgtcg gttcttcctg gaagttgact ttccttagac    168780
ccgccaggtc aagttagccg cgtgacggac atccaggcgt gggacgtggt cagggcaggg    168840
ctcattcatt gcccactagg atccacatgg cgaagatggt ctccatatca gctctctgca    168900
gaagggagga agactttatc atgttcctaa aaatctgtgg caagcaccca tcgtattatc    168960
caaattttgt tgcaaatgtg attaatttgg ttgtcaagtt ttgggggtgg gctgtgggga    169020
gattgctttt gttttcctgc tggtaatatc gggaaagatt ttaatgaaac cagggtagaa    169080
ttgtttggca atgcactgaa gcgtgtttct ttcccaaaat gtgcctccct tccgctgcgg    169140
gcccagctga gtctatgtag gtgatgtttc cagctgccaa gtgctctttg ttactgtcca    169200
ccctcatttc tgccagcgca tgtgtccttt caaggggaaa atgtgaagct gaacccctc     169260 cagacaccca gaatgtagca tctgagaagg ccctgtgccc taaggacac ccctcgcccc    169320 catcttcatg gagggggtca tttcagagcc ctcggagcca atgaacagct cctcctcttg    169380
gagctgagat gagccccacg tggagctcgg gacggatagt agacagcaat aactcggtgt    169440
gtggccgcct ggcaggtgga acttcctccc gttgcgggt ggagtgaggt tagttctgtg     169500
tgtctggtgg gtggagtcag gcttctcttg ctacctgtga gcatccttcc cagcagacat    169560
cctcatcggg ctttgtccct ccccgcttc tccctctgc ggggaggacc cgggaccaca     169620
gctgctggcc agggtagact tggagctgtc ctccagaggg gtcacgtgta ggagtgagaa    169680
gaaggaagat cttgagagct gctgagggac cttggagagc tcaggatggc tcagacgagg    169740
acactcgctt gccgggcctg ggcctcctgg gaaggaggga gctgctcaga atgccgcatg    169800
acaactgaag gcaacctgga aggttcaggg gccgctcttc ccccatgtgc ctgtcacgct    169860
ctggtgcagt caaaggaacg ccttcccctc agttgtttct aagagcagag tctccgctg    169920 caatctgggg ggtaactgcc agccttggag gatcgtggcc aacgtggacc tgcctacgga    169980
gggtgggctc tgacccaagt ggggcctcct tgtccaggtc tcactgcttt gcaccgtggt    170040
cagagggact gtcagctgag cttgagctcc cctggagcca gcagggctgt gatgggcgag    170100
tcccggagcc ccacccagac ctgaatgctt ctgagagcaa agggaaggac tgacgagaga    170160
tgtatattta attttttaac tgctgcaaac attgtacatc caaattaaag gaaaaaaatg    170220
gaaaccatca gttgttgctg tgtgaggctt gctttgcttc atgagaacct agaccttgct    170280 gagctgagt cttaggaagc agtctcctaa gtgcttctcc agcaggggca gaaactgtcc    170340
caccagctaa catctggcat tatggagggt cccccaggca gctgccagca gggacaggcc    170400
```

```
ccgtgttttc tgtagccagg gatgaggaag tggccccagg gcatgggcct ggctgggtgc    170460
ttctgcaagg gccttcccaa accacagtac aggtggtctt cctgccctgc agatgggagc    170520
tgtgggagct gctggagctg ctggagcctt catggtcaag tgacatcata agcttatatg    170580
acatacacaa gcctcaggac ttggcccatg gcactgaagc aggtcatcag gcccagcaca    170640
gagactagag ctgtgttctc acagggccca ccacccttcc acctccttgg ccattgacac    170700
ctgcgtccct ggcccagctg ctcccaggta accccaaag  cagctggcac atcccacctc    170760
tggtgtggcc ggggctgctg tgtgtccgca gggcctgccc cgtctattct agcttgtttg    170820
tcctgtctga accagcgcct actccaagaa gcctctgctc agcccagcgg ggatgcttct    170880
aagctccgga cgagcctctc ggaagccttg gtgattggtg gtgtagtcat cttgggatgc    170940
agatgtctta ccaacctgca agaacaaaaa ccctgtggct tcctctggtg cagggtattt    171000
agtcaatgtt tgctgaggtc ccgtctggtt ctggctaatt ggcagggtc  gtccacccat    171060 tctttccctg ctctgctgtc tgtgccagga gagacggggg ccagtcggcc aaggggccag    171120
ctcctgctgc ctgctcctct tgggcacgtg cgggggcccc ctttctctga gcagggatag    171180
ggatcagtct gccggaggga tgtggtggac aggcctaaag catttggggc ggggcatgcc    171240
acttgagctc cctaaatctg tctcctcata ggtgacaccg ctccagggcc ccccagtggc    171300
ctctcctttc agagctacct aaattctggt cacttcagag aaatggagca ccccttctc    171360 cctggtccag gtgtggacag cctggcacac tgagcacacc tggcatggct ggtaatttca    171420
gaaagaagag gggccggggt ccagtgggaa gcagcggtga acccctcgtg agtgggcttt    171480
gcagtccctc cccatgccac ggcagagctg ccctcaacac agccttcctc ttcctcatcg    171540
gagagcacac cctgtcccct tgccgagctg tgccctgtgc cttcggtggt atttgatttt    171600
ggctgctact ggctttgttg ggatctggaa gtcgcttccc ctgcgtggtg cgtggagcac    171660
tgtaagtcag atgagggaag tagccagggt gaggtgagta ccgggtggag ccgccactga    171720
agggactggg tagggggggcc ttgcctctac atgatgtgac acagccaacc gaggacagag    171780
gaagccccgt tcctgggggt gtgggggtgca ccccctcaggg aagcctgcag tggggcctga    171840
ggaaaggcat cctccgcgag cccacgagtc tggtccatga gcaccgtgac agtgtctgtg    171900
ggtagaggtg gacccggcct tgtgtcatca ccaggacctc tttttgggaaa ccatgtggac    171960 atcgcttgcg ggtcccccag gctctgcagc cccagcagcc t                       172001
```

<210> SEQ ID NO 3
<211> LENGTH: 10081
<212> TYPE: DNA
<213> ORGANISM: Mus musculus

<400> SEQUENCE: 3

```
gcactcgccg cgagggttgc cgggacgggc ccaagatggc tgagcgcctt ggttccgctt       60
ctgcctgccg cgcagagccc cattcattgc cttgctgcta agtggcgccg cgtagtgcca      120
gtaggctcca agtcttcagg gtctgtccca tcgggcagga agccgtcatg gcaaccctgg      180
aaaagctgat gaaggctttc gagtcgctca agtcgtttca gcagcaacag cagcagcagc      240
caccgccgca ggcgccgccg ccaccgccgc cgccgcctcc gcctcaaccc ctcagccgc       300 cgcctcaggg gcagccgccg ccgccaccac cgccgctgcc aggtccggca gaggaaccgc      360
tgcaccgacc aaagaaggaa ctctcagcca ccaagaaaga ccgtgtgaat cattgtctaa      420
caatatgtga aaacattgtg gcacagtctc tcagaaattc tccagaattt cagaaactct      480
```

| | |
|---|---|
| tgggcatcgc tatggaactg tttctgctgt gcagtgacga tgcggagtca gatgtcagaa | 540 |
| tggtggctga tgagtgcctc aacaaagtca tcaaagcttt gatggattct aatcttccaa | 600 |
| ggctacagtt agaactctat aaggaaatta aaaagaatgg tgctcctcga agtttgcgtg | 660 |
| ctgccctgtg gaggtttgct gagctggctc acctggttcg acctcagaag tgcaggcctt | 720 |
| acctggtgaa tcttcttcca tgcctgaccc gaacaagcaa aagaccggag gaatcagttc | 780 |
| aggagacctt ggctgcagct gttcctaaaa ttatggcttc ttttggcaat ttcgcaaatg | 840 |
| acaatgaaat taaggttctg ttgaaagctt tcatagcaaa tctgaagtca agctctccca | 900 |
| ccgtgcggcg gacagcagcc ggctcagccg tgagcatctg ccaacattct aggaggacac | 960 |
| agtacttcta caactggctc cttaatgtcc tcctaggtct gctggttccc atggaagaag | 1020 |
| agcactccac tctcctgatc ctcggtgtgt tgctcacatt gaggtgtcta gtgcccttgc | 1080 |
| tccagcagca ggtcaaggac acaagtctaa aaggcagctt tggggtgaca cggaaagaaa | 1140 |
| tggaagtctc tccttctaca gagcagcttg tccaggttta tgaactgact ttgcatcata | 1200 |
| ctcagcacca agaccacaat gtggtgacag gggcactgga gctcctgcag cagctcttcc | 1260 |
| gtaccctcc acctgaactc ctgcaagcac tgaccacacc aggagggctt gggcagctca | 1320 |
| ctctggttca agaagaggcc cggggccgag gccgcagcgg gagcatcgtg gagcttttag | 1380 |
| ctggagggg ttcctcgtgc agccctgtcc tctcaagaaa gcagaaaggc aaagtgctct | 1440 |
| taggagagga gaagccttg gaagatgact cggagtccag gtcagatgtc agcagctcag | 1500 |
| cctttgcagc ctctgtgaag agtgagattg gtggagagct cgctgcttct tcaggtgttt | 1560 |
| ccactcctgg ttctgttggt cacgacatca tcactgagca gcctagatcc cagcacacac | 1620 |
| ttcaagcaga ctctgtggat ttgtccggct gtgacctgac cagtgctgct actgatgggg | 1680 |
| atgaggagga catcttgagc cacagctcca gccagttcag tgctgtccca tccgaccctg | 1740 |
| ccatggacct gaatgatggg acccaggcct cctcacccat cagtgacagt tctcagacca | 1800 |
| ccactgaagg acctgattca gctgtgactc cttcggacag ttctgaaatt gtgttagatg | 1860 |
| gtgccgatag ccagtattta ggcatgcaga taggacagcc acaggaggac gatgaggagg | 1920 |
| gagctgcagg tgttctttct ggtgaagtct cagatgtttt cagaaactct tctctggccc | 1980 |
| ttcaacaggc acacttgttg gaaagaatgg gccatagcag gcagccttcc gacagcagta | 2040 |
| tagataagta tgtaacaaga gatgaggttg ctgaagccag tgatccagaa agcaagcctt | 2100 |
| gccgaatcaa aggtgacata ggacagccta atgatgatga ttctgctcct ctggtacatt | 2160 |
| gtgtccgtct tttatctgct tcctttttgt taactggtga aaagaaagca ctggttccag | 2220 |
| acagagacgt gagagtcagt gtgaaggccc tggccctcag ctgcattggt gcggctgtgg | 2280 |
| cccttcatcc agagtcgttc ttcagcagac tgtacaaagt acctcttaat accacggaaa | 2340 |
| gtactgagga acagtatgtt tctgacatct tgaactacat cgatcatgga gacccacagg | 2400 |
| tccgaggagc tactgccatt ctctgtggga cccttgtcta ctccatcctc agtaggtccc | 2460 |
| gtctccgtgt tggtgactgg ctgggcaaca tcagaaccct gacaggaaat acattttctc | 2520 |
| tggtggactg cattcctttta ctgcagaaaa cgttgaagga tgaatcttct gttacttgca | 2580 |
| agttggcttg tacagctgtg aggcactgtg tcctgagtct ttgcagcagc agctacagtg | 2640 |
| acttgggatt acaactgctt attgatatgc tgcctctgaa gaacagctcc tactggctgg | 2700 |
| tgaggaccga actgctggac actctggcag agattgactt caggctcgtg agttttttgg | 2760 |
| aggcaaaagc agaaagttta caccgagggg ctcatcatta tacagggttt ctaaaactac | 2820 |
| aagaacgagt actcaataat gtggtcattt atttgcttgg agatgaagac cccagggttc | 2880 |

```
gacatgttgc tgcaacatca ttaacaaggc ttgtcccaaa gctgttttac aagtgtgacc    2940
aaggacaagc tgatccagtt gtggctgtag cgagggatca gagcagtgtc tacctgaagc    3000
tcctcatgca tgagacccag ccaccatcac acttttctgt cagcaccatc accagaatct    3060
atagaggcta tagcttactg ccaagtataa cagatgtcac catggaaaac aatctctcaa    3120
gagttgttgc cgcagtttct catgaactca ttacgtcaac aacacgggca ctcacatttg    3180
gatgctgtga agccttgtgt cttctctcag cagccttcc agtttgcact ggagtttag     3240 gatggcactg tggagtgccc ccactgagtg cctctgatga gtccaggaag agctgcactg    3300
ttgggatggc ctccatgatt ctcaccttgc tttcatcagc ttggttccca ctggatctct    3360
cagcccatca ggatgccttg attttggctg gaaacttgct agcagcgagt gcccccaagt    3420
ctctgagaag ttcatggacc tctgaagaag aagccaactc agcagccacc agacaggagg    3480
aaatctggcc tgctctgggg gatcggactc tagtgcccct ggtggagcag cttttctccc    3540
acctgctgaa ggtgatcaat atctgtgctc atgtcttgga cgatgtgact cctggaccag    3600
caatcaaggc agccttgcct tctctaacaa accccccttc tctaagtcct attcgacgga    3660
aagggaagga gaaagaacct ggagaacaag cttctactcc aatgagtccc aagaaagttg    3720
gtgaggccag tgcagcctct cgacaatcag acacctcagg acctgtcaca gcaagtaaat    3780
catcctcact ggggagtttc taccatctcc cctcctacct caaactgcat gatgtcctga    3840
aagccactca cgccaactat aaggtcacct tagatcttca gaacagcact gaaaagtttg    3900
gggggttcct gcgctctgcc ttggacgtcc tttctcagat tctagagctg gcgacactgc    3960
aggacattgg aaagtgtgtt gaagaggtcc ttggatacct gaaatcctgc tttagtcgag    4020
aaccaatgat ggcaactgtc tgtgtgcagc agctattgaa gactctcttt gggacaaact    4080
tagcctcaca gtttgatggc ttatcttcca accccagcaa gtctcagtgc cgagctcagc    4140
gccttggctc ttcaagtgtg aggcccggct tatatcacta ctgcttcatg gcaccataca    4200
cgcacttcac acaggccttg gctgacgcaa gcctgaggaa catggtgcag gcggagcagg    4260
agcgtgatgc ctcggggtgg tttgatgtac tccagaaagt gtctgcccaa ttgaagacga    4320
acctaacaag cgtcacaaag aaccgtgcag ataagaatgc tattcataat cacattaggt    4380
tatttgagcc tcttgttata aaagcattga agcagtacac cacgacaaca tctgtacaat    4440
tgcagaagca ggttttggat ttgctggcac agctggttca gctacgggtc aattactgtc    4500
tactggattc agaccaggtg ttcatcgggt ttgtgctgaa gcagtttgag tacattgaag    4560
tgggccagtt cagggaatca gaggcaatta ttccaaatat atttttcttc ctggtattac    4620
tgtcttatga gcgctaccat tcaaaacaga tcattggaat tcctaaaatc atccagctgt    4680
gtgatggcat catggccagt ggaaggaagg ccgttacaca tgctatacct gctctgcagc    4740
ccattgtcca tgacctcttt gtgttacgag gaacaaataa agctgatgca gggaaagagc    4800
ttgagacaca gaaggaggtg gtggtctcca tgctgttacg actcatccag taccatcagg    4860
tgctggagat gttcatcctt gtcctgcagc agtgccacaa ggagaatgag gacaagtgga    4920
aacggctctc tcggcaggtc gcagacatca tcctgcccat gttggccaag cagcagatgc    4980
atattgactc tcatgaagcc cttggagtgt taaatacctt gtttgagatt ttggctcctt    5040
cctccctacg tcctgtggac atgcttttgc ggagtatgtt catcactcca agcacaatgg    5100
catctgtaag cactgtgcag ctgtggatat ctggaatcct cgccattctg agggttctca    5160
tttcccagtc aaccgaggac attgttcttt gtcgtattca ggagctctcc ttctctccac    5220
```

```
acttgctctc ctgtccagtg attaacaggt taaggggtgg aggcggtaat gtaacactag    5280
gagaatgcag cgaagggaaa caaaagagtt tgccagaaga tacattctca aggtttcttt    5340
tacagctggt tggtattctt ctagaagaca tcgttacaaa acagctcaaa gtggacatga    5400
gtgaacagca gcatacgttc tactgccaag agctaggcac actgctcatg tgtctgatcc    5460
acatattcaa atctggaatg ttccggagaa tcacagcagc tgccactaga ctcttcacca    5520
gtgatggctg tgaaggcagc ttctatactc tagagagcct gaatgcacgg gtccgatcca    5580
tggtgcccac gcacccagcc ctggtactgc tctggtgtca gatcctactt ctcatcaacc    5640
acactgacca ccggtggtgg gcagaggtgc agcagacacc caagagacac agtctgtcct    5700
gcacgaagtc acttaacccc cagaagtctg gcgaagagga ggattctggc tcggcagctc    5760
agctgggaat gtgcaataga gaaatagtgc gaagaggggc ccttattctc ttctgtgatt    5820
atgtctgtca gaatctccat gactcagaac acttaacatg gctcattgtg aatcacattc    5880
aagatctgat cagcttgtct catgagcctc cagtacaaga cttttattagt gccattcatc    5940
gtaattctgc agctagtggt ctttttatcc aggcaattca gtctcgctgt gaaaatcttt    6000
caacgccaac cactctgaag aaaacacttc agtgcttgga aggcatccat ctcagccagt    6060
ctggtgctgt gctcacacta tatgtggaca ggctcctggg caccccttc cgtgcgctgg    6120
ctcgcatggt cgacaccctg gcctgtcgcc gggtagaaat gcttttggct gcaaatttac    6180
agagcagcat ggcccagttg ccagaggagg aactaaacag aatccaagaa cacctccaga    6240
acagtgggct tgcacaaaga caccaaaggc tctattcact gctggacaga ttccgactct    6300
ctactgtgca ggactcactt agcccccttgc ccccagtcac ttcccaccca ctggatgggg    6360
atgggcacac atctctggaa acagtgagtc cagacaaaga ctggtacctc cagcttgtca    6420
gatcccagtg ttggaccaga tcagattctg cactgctgga aggtgcagag ctggtcaacc    6480
gtatccctgc tgaagatatg aatgacttca tgatgagctc ggagttcaac ctaagccttt    6540
tggctccctg tttaagcctt ggcatgagcg agattgctaa tggccaaaag agtccctct    6600
ttgaagcagc ccgtggggtg attctgaacc gggtgaccag tgttgttcag cagcttcctg    6660
ctgtccatca agtcttccag ccctttcctgc ctatagagcc cacggcctac tggaacaagt    6720
tgaatgatct gcttggtgat accacatcat accagtctct gaccatactt gcccgtgccc    6780
tggcacagta cctggtggtg ctctccaaag tgcctgctca tttgcacctt cctcctgaga    6840
aggaggggga cacggtgaag tttgtggtaa tgacagttga ggccctgtca tggcatttga    6900
tccatgagca gatcccactg agtctggacc tccaagccgg gctagactgc tgctgcctgg    6960
cactacaggt gcctggcctc tggggggtgc tgtcctcccc agagtacgtg actcatgcct    7020
gctccctcat ccattgtgtg cgattcatcc tggaagccat tgcagtacaa cctggagacc    7080
agcttctcgg tcctgaaagc aggtcacata ctccaagagc tgtcagaaag gaggaagtag    7140
actcagatat acaaaaacctc agtcatgtca cttcggcctg cgagatggtg gcagacatgg    7200
tggaatccct gcagtcagtg ctggccttgg gccacaagag gaacagcacc ctgccttcat    7260
ttctcacagc tgtgctgaag aacattgtta tcagtctggc ccgactcccc tagttaaca    7320
gctatactcg tgtgcctcct ctggtatgga aactcgggtg gtcacccaag cctggagggg    7380
attttggcac agtgtttcct gagatccctg tagagttcct ccaggagaag gagatcctca    7440
aggagttcat ctaccgcatc aacacccctag ggtggaccaa tcgtacccag ttcgaagaaa    7500
cttgggccac cctccttggt gtcctggtga ctcagcccct ggtgatggaa caggaagaga    7560
gcccaccaga ggaagacaca gaaagaaccc agatccatgt cctggctgtg caggccatca    7620
```

```
cctctctagt gctcagtgca atgaccgtgc ctgtggctgg caatccagct gtaagctgct    7680
tggagcaaca gccccggaac aagccactga aggctctcga taccagattt ggaagaaagc    7740
tgagcatgat cagagggatt gtagaacaag aaatccaaga gatggtttcc cagagagaga    7800
atactgccac tcaccattct caccaggcgt gggatcctgt cccttctctg ttaccagcta    7860
ctacaggtgc tcttatcagc catgacaagc tgctgctgca gatcaaccca gagcgggagc    7920
caggcaacat gagctacaag ctgggccagg tgtccataca ctccgtgtgg ctgggaaata    7980
acatcacacc cctgagagag gaggaatggg atgaggaaga agaggaagaa agtgatgtcc    8040
ctgcaccaac gtcaccacct gtgtctccag tcaattccag aaaacaccgt gccggggttg    8100
atattcactc ctgttcgcag tttctgcttg aattgtacag ccgatggatc ctgccatcca    8160
gtgcagccag aaggaccccc gtcatcctga tcagtgaagt ggttcgatct cttcttgtag    8220
tgtcagactt attcaccgaa cgtacccagt ttgaaatgat gtatctgacg ctgacagaac    8280 tacgagagt gcacccttca gaagatgaga tcctcattca gtacctggtg cctgccacct    8340
gtaaggcagc tgctgtcctt ggaatggaca aaactgtggc agagccagtc agccgcctac    8400
tggagagcac actgaggagc agccactgc ccagccagat cggagccctg cacggcatcc    8460
tctatgtgtt ggagtgtgac ctcttggatg acactgcaaa gcagctcatt ccagttgtta    8520
gtgactatct gctgtccaac ctcaaaggaa tagcccactg cgtgaacatt cacagccagc    8580
agcatgtgct ggtaatgtgt gccactgctt tctacctgat ggaaaactac cctctggatg    8640
tgggaccaga attttcagca tctgtgatac agatgtgtgg agtaatgctg tctggaagtg    8700
aggagtccac cccctccatc atttaccact gtgccctccg gggtctggag cggctcctgc    8760
tgtctgagca gctatctcgg ctagacacag agtccttggt caagctaagt gtggacagag    8820
tgaatgtaca aagcccacac agggccatgg cagccctagg cctgatgctc acctgcatgt    8880
acacaggaaa ggaaaaagcc agtccaggca gagcttctga ccccagccct gctacacctg    8940
acagcgagtc tgtgattgta gctatggagc gagtgtctgt tctctttgat aggatccgca    9000
agggatttcc ctgtgaagcc agggttgtgg caaggatcct gcctcagttc ctagatgact    9060
tctttccacc tcaagatgtc atgaacaaag tcattggaga gttcctgtcc aatcagcagc    9120
catacccaca gttcatggcc actgtagttt acaaggtttt tcagactctg cacagtgctg    9180
ggcagtcatc catggtccgg gactgggtca tgctgtccct gtccaacttc acacaaagaa    9240
ctccagttgc catggccatg tggagcctct cctgcttcct tgttagcgca tctaccagcc    9300
catgggtttc tgcgatcctt ccacatgtca tcagcaggat gggcaaactg gaacaggtgg    9360
atgtgaacct tttctgcctg gttgccacag acttctacag acaccagata gaggaggaat    9420
tcgaccgcag ggctttccag tctgtgtttg aggtggtggc tgcaccagga agtccatacc    9480
acaggctgct tgcttgtttg caaaatgttc acaaggtcac cacctgctga gtagtgcctg    9540
tgggacaaaa ggctgaaaga aggcagctgc tgggcctga gcctccagga gcctgctcca    9600
agcttctgct ggggctgcct tggccgtgca ggcttccact tgtgtcaagt ggacagccag    9660
gcaatggcag gagtgctttg caatgagggc tatgcaggga acatgcacta tgttggggtt    9720
gagcctgagt cctgggtcct ggcctcgctg cagctggtga cagtgctagg ttgaccaggt    9780 gtttgtctt ttcctagtgt tccctggcc atagtcgcca ggttgcagct gccctggtat    9840
gtggatcaga agtcctagct cttgccagat ggttctgagc ccgcctgctc cactgggctg    9900
gagagctccc tcccacattt acccagtagg catacctgcc acaccagtgt ctggacacaa    9960
```

```
aatgaatggt gtgtggggct gggaactggg gctgccaggt gtccagcacc attttccttt    10020
ctgtgttttc ttctcaggag ttaaaattta attatatcag taaagagatt aatttttaatg   10080 t                                                                    10081

<210> SEQ ID NO 4
<211> LENGTH: 168001
<212> TYPE: DNA
<213> ORGANISM: Macaca mulatta
<220> FEATURE:
<221> NAME/KEY: misc_feature
<222> LOCATION: (1)...(168001)
<223> OTHER INFORMATION: n = A,T,C or G

<400> SEQUENCE: 4
tacaggcgtg agccaccgca cccagctgga acttaatttt tttaaagatc gtgttgctct      60
atcgcccaag ctggagtgca gtggtgcaac catagctcac ttgcagccac aaattcctgg     120
tttcaggtga tcctcctaca tcagcctccc aagaactggg aactaacggc tgtttctctg     180
ctgtccttct caagagaagg gagggagaca atgctgtggg tccctttggg acaggctctg     240
agacaaggtg gaggtgctgc ttgtggccac agagcagggg actctgggtt gcaggtgtgg     300
cctggcttga gtaggcttta gtgggcttct ctctgcctgc accaccccg ggctgggtgg      360 ttgtctctga ggccaaccct actccctaat gggcaggctg gacagctgcc ctctctgttt     420
gccgctctac cacccaaaag gcgggaggct ctggagacca ggaccctgcc tgcgccggcc     480
tgtgccccag gcgtgagggg gtgcccaca gatctctgct gagctgaggc tgaatggcac      540
cccttggggg tcctgccagg tcagagcagg gtgctttccc atacagaaac gcccccaggt    600
cgggactcat tcctgtggga ggcgtcttgt ggccacaact gcttctcgct gcactaatca    660
cagtgcctct gtgggcagcg ggcgctgacc atccgggcct gcctcagacc ctctcctccc    720
ttccggggcg ctgcgctggg accgatgggg ggcgccaggc ctgtgggcac cgccctgcag    780
gggccgctcc agctcactgg ggggtgggga gggtcacact tggggtcttc agatggcgcc    840
gaccacgcgc aatctctgcg ctctgcgcag gggctcgccc accctctccc cgtgcagcga    900
gtccccagca ggctccccgc agggctgtcc aggtgagcct ggctctggcc gcgggccagt    960
gtggcgggcg ggcaagcccc gaggccacct cggctcagag cccacggccg gctctcgccc   1020
agctccagac gtctgcgagg gttccattcc gcttgggccg gcgccccgcg cgccgcgccc   1080
tggccccgcc cctccctcat cccgcccccct ctgcaccca cccctccctg gccccgccct    1140
ccgcgcccca cctctcatct tcccgcccg ccccagcca cgcccctcac ggtcagcccc      1200
ctcccctatc cgccccgcct ctcatcgtct cgcctcgctc cgccctcag ccgtcccgcc     1260 cctcagccgc cctgcctaat gtccccgccc ccagcctcgc cccgctccgc ccagcctcg    1320 ccccgccccg ccctcaggc gcctgcctg ctgtgccccg cccagcctc gccacgcccc       1380 tcgttaccat gtagtcccgc cccgtccctt ccgcgtcccg cctcgcccct acccttcac    1440 agcttcgccc caccccatta cagtcttgcc acgccccgtc cctgtccgt tgagccctgc    1500 tccttcgccc aggtgggcg ctgcgctgtc agaggctttg gtggctctgt gaggcagaac    1560
atgcgggcgc agggactggc tggctccctg gccagtcatt ggcagagtcc gcaggctagg    1620
gctgtcaatc atgctggccg gcgtggcccc gcctccgccg gcgcagcgtc ttgagacgca    1680
aggcgccgcg ggggctgccg ggacgggtcc aagatggacg gccgcttcgg ttccgctttt    1740
acccgcggcc cagagcccca ttcattgccc cggtgctgag cggcgctgcg agtcggcccg    1800
aggcctccgg ggactgccta gccgggcggg agaccgccat ggcgaccctg gaaaagctga    1860
```

```
tgaaggcctt cgagtctctc aagtccttcc agcagcagca gcagcagcag cagcaacagc    1920
cgccgccgcc gccgccgccg cctcctcctc ctcctcagct tcctcagccg ccgcaggcac    1980
agccgatgct gcctcagccg cagccgcccc cgccgccgcc cccgccacca cccggcccgg    2040
ctgtggctga ggagccgctg caccgaccgt gagtttgggc ccgctgcagc tccctgtccc    2100
ggcgggtccc agcctacggc ggggatggcg gaatcctgca gcctgcgggc cggcgacacg    2160 aaccccccg gccccgcagc gacagagtga cccagcaacc cagagccaat gagggacacc     2220 cgcccctcc tgcggcgaga ccttccccca cttcagcccc ggtcccgcac ttgggtcttg     2280
tcctcccgcg aggggaggca gaacctcgtt gggacctgtc ctgaattcac ggagggagt     2340 cacggcctca gccctctcgc cctttccagg gtgcgaagag ttgggcgaa aacttgtttc     2400 tttttatttg cgagaaacta gggcgggggt ttaactgtgt tctgaagaga acttggaaga    2460
gccgagattt gctcagggcc acttccctca tctagtcaga gagggaagag ggctgggggc    2520
gcgggacacc tcgagaggag gcggggtttg gagctagaga gatgtggggg cagtggatga    2580
cataatgctt ttaggacgcc tcggcgggag tggctggagt gggggcggg gagtgagggc     2640 gcgtccaatg ggagatttat tttccaagtg gcatttaaaa cagcctgaga tttgaggctc    2700
ttcctacatt ctcagggcat ttcatttagt tcatgatcgc ggtggtagta acacgatttt    2760
aagcaccacc taagagacct gctcatctaa gcgcaagtta gtgtgcaggc atttgaatga    2820
gttgtggtcg ccaaataagt ggtgaactta cgtggtatta ataaaattat cttaaatatt    2880
aggaagagtt gattgaagtt tattgcctgt ttgtgttggg aataaaacta acacgttgct    2940 gaggggagg ttaattgccg agggatgaat gaggtataca ttttaccagt attgcagtca     3000
ggcttgccag aatatgggag gtctgcagac tccgtggaca tctcatgtgc cagtgaaagg    3060
gtttctgttc gcctcattgc tgacagcttg ttacttttg gaagctagag gtctctgttg     3120
cttgttcttg gggagaattt ttgaaacaga aaaagagacc attaaaacat ctagcggaac    3180
cccaggacgt gggagtgtgt gctgagtgtt tagcaggatt taggaagtac tccgctgcag    3240
ttcaggcctt tctcttacct ctcagtgttc tatttccgat ctggacgtgt atcagatggc    3300
atttgataag aatatctcta ttaagactga ttaattttta gtaatatttc ttgttctttg    3360
tttctgttat gatccttgcc ttgtcttgaa agtttaatta aagaggagg atttggagag     3420 cagtgttagc ttatttgtta gagtaaaatt taggaataaa ttcttctaaa ggatggaaaa    3480 acttttgga tatttagaga aattttttaaa caatttggct tatctcttca gtaagtaatt    3540
tctcatcctt ccagaaattt aatgtagtgc ctttctagga ggtaggtgtc atagaagttc    3600
acacattgca tgtatcttgt gtaaacacta aactgggctc ctgatgggaa ggaagacctt    3660
tctgctgggc tgcttcagac acttgatcat tctgaaaata tgccgtctct ttcctgtgct    3720
gatttgatag aacctgcgtt tgcttatctt caaaatatgg gtatcaagaa atttcctttg    3780
ctgcctttac aaaggagata gattttgttt cattacttta ttttaaggta atatatgatt    3840
accttatttt aaaaatttaa tcaggcctgg caaggtggct catgccttta atcccagcac    3900
tttgggaggc ttaggcggat gaatcacctg aggtcaggag ttcgagacca gtctggctaa    3960
catggtgaaa ccccatctct actaaaagta caaaaattag ttggtcatgg tggcacgtgc    4020
ctgtaatgcc agctacctgg gaggctgagg caggaaaatc gctggaaccc gggaggcaga    4080
ggctgcagtg agctgagact gcgccactgc actccagcct gggtgacaga gcgagactct    4140
tgtctcaaaa aaaaaaaaat tattatttttt gcataagtaa tacattaaca tgacacaaat    4200
```

```
tccgtaatta caaaagagca atacttaaaa tatcttcctt ccaccccttt catctgagta   4260
cctaactttg tccccaagaa caagcactat tacagttcct cctgtatcct gccagatata   4320
atctatgcat attgtaagat agatttaaaa tgctgtaaaa ataaaagtag tttacagtaa   4380
taatttttt tctttatttt ttttgagatg tagtctcaca ttgtcaccca ggctggagtg   4440
cggtggtatg atcttggctc actgcaacct ccacctccca ggttcaaacg attctcctgc   4500
ctcagcctcc agagtagctg ggattacagg tgctcaccac catgtccagc tgattttgt    4560
attttagta gagatggggt ttcaccatgt tggccaggct ggtcttgaac tcctgacctc    4620
ggaatccatc cacctcggcc tcccaaagtg ctggggttac aggtgtgagc cactgcccct   4680
ggctagaata ataactttta aaggttctta gcattctctg aaatcaactg cattaggttt   4740
atttatagtt attttaaata aaatgcatat ttgtcatatt tgtatgtatt ttgctgttga   4800
gaaaggaggt attcgctaat tttgagtaac aaacactgct cacaaagttt ggattttggc   4860
atttctgttc atgtgcttca gccaaaaaat cctcttctca aagtaagatt gactaaagca   4920
atttagaaag tatctgtttt tatggctctt gctcttttgt gtggaactgt ggtgtcatgc   4980
catgcatggg cctcagtcta agtatgagcg tatgtgctct gctcagcata caggatgtgg   5040
gagttccgtg tggggctggc cacagtctca gcaaatctag catgcttggg agggtcctca   5100
cagtaattag gaggcaactg atacttgctt ctggcaattc cttattctcc ttcagattcc   5160
tatccggtgt ttccctgact ttattcattc atcagtaaat atttactaaa catgtactat   5220
gtacctagca ctgttctaga tgcagggctc agcagtgagc agacaaagct gtgccctcat   5280
gaagctttca ttctaatgaa ggacatagac aataagcaag atagataagt aaaatataca   5340
gtatgttaat aagtggagga atgtcaaagc agggaagggg atagggaaat gtcagggtta   5400
atcaattgtt aacttatttt tattaaaaaa aaatttttt aagggctttc cagcaaaacc    5460
cagaaagcct gctggacaac ttccaaaaaa actgtagcac taagtgttga catttttatt   5520
ttattttatt ttatttttgtt ttgttttgtt ttttgaggca gtcttgcttt gtcagccagg   5580
ctgcagtgca ctggtgtgat cttagctcac tgcaacctct gcctgttggg ttcaagcgat   5640
tcttatgcct cagcctcctg attagctggg attatagaca tgcaccgtcc cgcctgggta   5700
attttttttt tttcccctg agacagagtc ttgctctgtc gcccaggctg gagtgcagtg    5760
gcacaatctt ggctcactgc aagctccgcc tcccaggttc atgccattct cctgcctcag   5820
cctcccaggt agctgggact acaggcgcct gccaccacgc ccagctaatt ttttgtattt    5880
ttagtagaga tggggtttca ctgtgtcagc caggatggtc ttgatctcct cacctcgtag   5940
tccgcccccc ttggcctccc aaagtgctgg gattacaggc gtgagccacc gcgcccggcc   6000
tgtaattttt tttttttttt tttgagacag agtcttgctt tgttgctagg ctggactgca   6060
gtggtgtgat cttggcacac tgcaacctct gcctcccggg ttcaagcgat tctcctgcct   6120
cagcttcccg agtagctggg actacaggca cgtgccatca cgcttggcta ctttttgtat   6180
atttagtaga acggggtttt caccatgtta gctgagatga tctcgatctc ttgacctcgt   6240
gatccgcccg cctcggcctc ccagagtgct gggattacag gtgtgagcca ctgtgcctga   6300
ccacgcctgg gtaattttg tattttagt agagacggga tttcaccacg atggccagac    6360
tggtctcgaa ctcccagcct catgtgatct gcctgcctag gcctcccaaa gtgctaggat   6420
tacaggcatg agccaccatg actggccagt gttgatattt taaatagggt gttcaggaa    6480
ggtccactga ggtgacagct gttttttgg ggggagtggt gggacagggc cttgctcttt    6540
aacccaggct ggaatacagc atcacaatcg tagcttactg cagccttgaa ctcctaggct   6600
```

```
caagtgatct tcccaccttg acctcacaac gtgttgggac tgtaggtgtg agtcaccatg    6660
cctggccaga tgatggcttt gagtaaagac ctcaggcgag ttaagagtct agcgtaaagg    6720
tgtatggagt aggggtattc cagatagggg gaacaggtcc aaagtcttcc tgtttgagga    6780
atagcaaggg tgccatttta gttgggtgaa ttgagtgagg cgacatttg tagtaagagg     6840 taaagtccaa gaggtcaagg gagtgccata tcagaccaat actacttgcc ttgtagatgg    6900
aataaagata ttggcattta tgtgagtgag atgggatgtc actggaggat tagaggagag    6960
gagtagcatg atctgaattt cattcttaag tgaactctgg ctgacaacag agtgaagggg    7020
aacatggaca aaagcagaaa ccagttagga agccactgca gtgctcagat aagcgtggtg    7080
ggttctgtca gggtaccggc tgtgggcagt gtgaggaatg actggatttt gaatgcagaa    7140
gcaactgtac ttgttgaact ctgctaagta taactattta gcagtagctg cattatcag     7200 ttaggtttgt attcagctgc aagtaacaga aaattctgct gcaatagctt aaactggtaa    7260
caagaaagag cttatcagaa gacaaaaata agtctgtttg gggaaattca acaataagtt    7320
aaggaaccca ggctctttct tttttttttt gaaatggagt tttgctcttg tcacccaggc    7380
cggagtgcaa tgatgcgatc ttggctcact ataacctccg cctcctaggt tccagtgatt    7440
cttctgcctc agccttccag gtatctggga ttagaggcgc acgcacacca ccatgcccag    7500 ctaattttg tatttttagt aggcacgggg tttcatcatg ttggccaggc tggtctcgaa      7560
ctcctgacct taggtgatca acccgcctca gcctgccaaa gtgctgagat tacaggtgtg    7620
agccactgca ctcggtcaga acccaggctc ttttttacac ttagcttgca aacccttgtt    7680
ctcattcttt tcccttgta ttttattgt cgaattgtaa cagttctttg tgtattctgg       7740
atactggatt cttatcagat agatgatttg tgaaaacatt ctctcttcct ttggattgtc    7800
tttttacttt cttgatcatg tcttttgaag tgtgaaagtt tttaattttg atgaagtcta    7860
gtttatctag tttgtccttg gttgctatgc tttgagtgtc atatctaaga aatcattgtc    7920
taatccaaag tcaaaaaggt ttacccgtat gtttttcttct aagaattttta gagttttaca  7980 tttaggtctg atccattttg agttaatttt tatatgtggt tcaggtagaa gtccaacttc    8040
attcttttgc atgtggttat tcagttgtcc cagcacagtt tgttgaagag actgtacttt    8100
ccccatggaa ttgtcttagc atccttgttg aaaattcatt gtccttgatt gtatagattt    8160
atttcttgac tctcagttct acctattggt ctttatgttg atcctgtgcc agtaccatac    8220
agtcttgatt actgaagttt gtgtcacaat ttaaattcat gaaatgtgag ttctccaact    8280
ttgttctttc tcaagattga tttggccatg ctgggtccct tgcatttcca tatggattgt    8340
aggatcaact tgtcagtttc tacaaagaag ccaaggagga ttctgagagg gattgtgttg    8400
aatctgtaga tcaacttggg gagtattacc atcttaacag tattgtcttc catctctgaa    8460
ctgggcaaac tttgtgtaaa tggtcagatt taggtatttc aggctgtgtg ggcacaatgt    8520
ctctgtcaca gctactcagc tctgccattg tagcgtgaaa tagccataag caatatgtat    8580
gagtgtctgt gttccagtat aatttttatta atgacaagga aatttgaatt tcgtgtaatt    8640
ttcacctgtc atgaaatatt atttggtttt tttggtcaat catttaaaaa tgtaaaaact    8700
tttcttagct tttgaactgg ccaaacatat gcaggttata atttttcccac tcctagatta   8760 aaatatgata ggaccacctt tgaaaagcat gtnnnnnnnn nnnnnnnnnn nnnnnnnnnn    8820
nnnnnnnnnn nnnnnnnnnn nnnnnnnaac actttgggag gccgagccag gtggatcact    8880
tgaggccagg agttcgagac cagcctaacc aacatggtga acccccatct ctactaaaaa    8940
```

```
taaaaaaatt agctgggggt ggtggtgggt gtagggtcca gccctatggg gcttagcggg     9000
tgttctcccc gtgcggggag acgagagatc ttaagaaata aagacacggc cgggcgcggt     9060
ggctcacgcc tgtaatccca gcactttggg aggccgaggc gggcggatca caaggtcagg     9120
agatcgagac cacggtgaaa ccccgtcttt actaaaaata caaaaaatta gcggggcgcg     9180
gttgtgggcg cctgtagtcc cagctactcg ggaggctgag gcaggagaat ggcgtgaacc     9240
cgggaggagg agcttgcagt gagccgagat cgcgccactg cactccagac ggggcgacag     9300
agcgagactc ctgtctcaaa aaaaaaaaaa aaaaaaaaa gaaaagcatg ttttttttt      9360 tttgagatgg agtttcgctt tgttgccca  ggctggagtg cagtggcgcg atctcgggtc     9420
accacaacct ctgcctccca ggttcaagcg attctcctgc ctcagcctcc cttgtagctg     9480
ggattacagg catgtgccac catgcccggc taattttgta ttttagtag  agacggggtt     9540 tctccaggtt ggtcaggctg gtctcgaact cctgacctca ggtgatctgc ctgcctcggc     9600
ctcccgaagt gctgggatta caggcgtgag ccactctgcc cagccagaaa gcatttcttt     9660
tttggctgtt ttttgttgt  ttttttaat  taactagttt tgaaaattat agaagttaca     9720
catatatgtt ataaaaacat ctccaagcag cacagaagat gaaaaacaaa gcccttcttg     9780
caagtctgtc atctttgtct aacttcctaa gaacaaaagt atttcttgtg tcttcttccc     9840
agattttaat atgcatatac aagcatttaa atatgtcatt ttttgttggc ttgactgaga     9900
tcacattaca tacgtatttt tttacttaac aatttgagta caatgtgtca tggaaattgt     9960
tccatagcag tatctgtaat tcttattaat tgctgtgtaa tattgtagaa tttctttta     10020 aaagaggact tttggagatg taaaggcaaa ggtctcccat tattctggct gtacaacgtt     10080
ctggtgacat attctctcta ccctgagagg tccccatacc catcacctcc atttcctgta     10140
aataagtcaa ccacttggta aactaccttt gaatggatcc acactcaaaa catttagtct     10200
tattcagaca acaaggagga aaaataaaat accttataaa gcactgtttc atatgtatta     10260
aattggatca atttgcgtgc tagaatgtat gttagagaca tgatatgccc ataggtcctt     10320
gctatcacgg tgaggtctca gggacagcag tttggtatca tttggtatct cataagcaga     10380
ctctgtctgc ctgacttaac aaatcagagt ctgcgtttta acaggttcag tgagtgactt     10440
acatgcacat tggagtttgg gaagctccac tataggtgct tagaccttac ctttgttgtt     10500
gctaataaca atgcaagcat ttgggaggaa gacctgtgtt gctcgtatgt gtccaggtgt     10560
agctgaggtg gccttgcttg tctgctgtag ggccattgag catttgcgta gctgtgatga     10620
atgagctgag gtgagcctgc ggagagctcc cagccattgg tagtgggact tgcttagatg     10680
aactagaagg acctgagcat ccactttggg gaaaaacaac cgaatgaagg gagaggcaac     10740
atgcagtttt atttagggta cgaaggagag ctgtggttag aaggtgacat ttgagtggaa     10800 aggggcaac  ccatgtgtgg agcgggagaa gagcggtcca ggcagagtta acagaaggca     10860
gaaatgcttt ccatctttga aaactaggaa ggatgccagt ggctgaagta agatgaagga     10920
cagaaatagg ggatgaggct tcgagagatg agaggttaga gacgagggtc ttgtgcacca     10980
agataagctt gtgtggtcaa acaagtagt  ttcgtttttg tttttaaaag atcactttgg     11040
ctgggtgcaa tggttcatgc ctgtaatacc agtactttga gaggctgtgg tgggaggatt     11100
gcctgaagcc aggggaccag cgtagccaac atagcagcac ctataaggtc tctacaaaaa     11160
acttttaaaa agtagctggg tgtagtggtg tgtgcctgta gtcccagcca cccaggaggc     11220
tgaggaggct ggagggttgc ttgagtccag cagtttgagg ctgcagcgag caatgattgt     11280
gccactgcac tacagcctgg gcatgagagt gagaccctgt ctctaaatat atgtgtatat     11340
```

```
ataaaagaaa agatcacttt gacaacacca catgctggtg aggatttaga aaaactaggt    11400
cacttattgc tggtgggaat ataatatagt acggccactc tggaaaacag tttggcagtt    11460
tctcataaaa ctgaatgtac aattagtata caacccagca actcctgcaa tcctgcgcat    11520
taatcctaga gaaatgaagc cttcatgttc acataaaaac ctatactcaa gcgtgcatag    11580
cagctttacc cataatatct aagaactgga atcagctcag atgtccttct gcaggtgaat    11640
ggttaaacta ctcagtaata aaaggaatg atctactgat agcatgcaac agtgtaggtg    11700
aagttatgct aatgaaaaaa gccaatccca aaaggttaca tattatatga ttctatgtat    11760
ataacgtttt ggcagtgaca cagttttagg gatggagaat agattagtgg ttgcctgggg    11820
ttagagatgg ggttgtagag taggttaggg gtggcagagg agagaaaaga gagggaggcg    11880
agtgtggtta taaaaggaca acacagggg atacttgtaa cagaaatgct ttgtcttttt    11940 ttttttttt  nnnnnnnnnn nnnnnnnnnn nnnnnnnnnn nnnnnnnnnn nnnnnnnnnn    12000
nnnnnnnnnn nnnnnnnnnn nnnnnnnnnn nnnnnnnnnn nnnnnnnnnn nnnnnnnnnn    12060
nnnnnnnnnn nnnnnnnnnn nnnnnnnnnn nnnnnnnnnn nnnnnnnnnn nnnnnnnnnn    12120
nnnnnnnnnn nnnnnnnnnn nnnnnnnnnn nnnngctcac tgcagcctct gcctctgggg    12180
ttcaagcgat tcttctgcct cagcctcctg agtagctggg actacaggtg cacgccacca    12240
tgcccggcta attttgtat ttttagtaga cagggtttt catcatgttg gccaggctgg    12300
tcttgatctc ctcacctcat gatccgccca cctcgcccac ctcggcctcc cagagtgctg    12360
ggattacagg cttgagccac cgcgtccggc ctatttatt ttttttgaga cagagtctca    12420
ctctgtatcc cagactggag tacagtggcg cgatcttggc tcactgcagc ctctgcctct    12480
ggggttcaag cgattctcct gcctcagcct cctgagtagc tgggactaca ggtgcacgcc    12540
accatgcccg gctaattttt gtatttttag tagagacggg gtttcaccat gttggccagg    12600
gtggtcttga tctcctcacc tcatgatccg cccacctcgg cctcccaaag tgctgggatt    12660
acagggattt ttgtgttttt cgtagagaca gggtttcatt atgatggcca ggttggtttt    12720
gaactcctga cctcctgtga tctgctggcc tcgcctccca aagtgttggg attatagacg    12780
ttgagccact gcactcggcc aaggaaagag atgcttgtc ttgagtgtgg tggtgtatag    12840
aaattgtata gaactaaggc tgggcacggt ggctcactcc tgtaatccca gcattttggg    12900
agaacgaggt gggcagatcg tgagttcagg agattgagac catcctggct aacatggtga    12960
aaccctgtcc ctgctaaaaa taccaaaaat tggccgggcg tggtggctca cgcctataat    13020
cccagcactt tgggaggctg aggcgggtgg atcacgaggt caggagatcg agaccatcct    13080
ggctaacaca gtgaaaccct gtctctacta aaaatacaaa agcaaaatta gccgggcgtg    13140
gtggcgggcg cctgtagtcc cagctacttg ggaggctgag acaggagaat ggcgtgaacc    13200
tgggaggtgg aggttgcagt gagctgagat cgcgccactg cactccagcc tgggcaacag    13260
agtgagactc tgtctcaaaa aaaaaaaaa aaagaaatt gtatagaact aaatacacaa    13320
atgaacaaca ataaaacttg aaactctaag taagatcact ggattgtatc agtgtcaata    13380
ttctggttgt gataatgtag tatattaaat agttttgcaa agtgttacca ttggggaaaa    13440
ctggataaag ggcacactgg atctctgtta tttcttacaa ctgcacgtga accaataatt    13500
atcttaaaaa aacttcaatt caaaaaagtc tgccctgatc cagttgggag gctactgaag    13560
taatcaaagc tagacatgct ggtgtcttgt gactggtagc agtggtgatg gtaagtggtc    13620
agattctgga tctcttggag aaagatctga caagatttgc agattcttta aaaaaatga    13680
```

```
gattaggctg ggcacggtgg ctcacgcttg ggaggctgag gagggcggat cnnnnnnnnn   13740
nnnnnnnnnn nnnnnnnnnn nnnnnnnnnn nnnnnnnnnn nnnnnnnnnn nnnnnnnnnn   13800
nnnnnnnnnn nnnnnnnnnn nnnnnnnnnn nnnnnnnnnn nnnnnnnnnn nnnnnnnnnn   13860
nnnnnnnnnn nnnnnnnnnn nnnnnnnnnn nnnnnnnnnn nnnnnnnnnn nnnnnnnnnn   13920
nnnnnnnnnn nnnnnnnnnn nnnnnnnnnn nnnnnnnnnn nnnnnnnnnn nnnnnnnnnn   13980
nnnnnnnnnn nnnnnnnnnn nnnnnnnnnn nnnnnnnnnn nnnnnnnnnn nnnnnnnnnn   14040
nnnnnnnnnn nnnnnnnnnn nnnnnnnnnn nnnnnnnnnn nnnnnnnnnn nnnnnnnnnn   14100
nnnnnnnnnn nnnnnnnnnn nnnnnnnnnn nnnnnnttga taatttataa aatgtgatta   14160
tagaatgctg tagtgtcctt gagtttacat gcccttcctt acacttgtgt gcctgtgcag   14220
atgccttgat ttcacaatta gaggaggctg actgagattt gtttaatttt tttttttttt   14280
gaggcagagt cttgttatgt cccccaggct agagtacagt agcgcaatct tggtgcactg   14340
caacatccgc ctcctgggtt caagcaattc ttctgcctca gcctcccgag tgcctgggat   14400
aacaggtgcc agcccccacg cccagctatt ttttgtattt ttagtagaga cgggatttca   14460
ccatgttgac tggctggtc tcaaactcct gacctcagat atctgccgcc ccagcctccc   14520
aaagtgctgg gattacaggc gtagccacac ctggccgttt gttttaattt ttaaggtgac   14580
gttaaagtga ctgcatttac caaaagtggt tgagaagcca ggactgttct tatcctgttt   14640
ttccagttct tgctcagagc aaggtggttt atttttcact taattaccat acttactttt   14700
catgtagaac aagtcagttt gagttatcag ttcatcatct aactaaattc catggggaa   14760
ggaatagttt tagtttctta aacttccaag gttgcttatt ggacaaaatg agatagcaag   14820
gcggtgtttt taagttagat ttttttatttc tttggtaata taattttctc aaaaacttag   14880
tagtctttta gtttagttgt ttttagttgg tcctatgttt tgcatccccc ctctctactt   14940
ttattttgat agtgccaatt gcgaagacat ctgaagccat aggtttgggt gggaaggcgg   15000
cacctttagc ctgattatct ttgccaggct gtttatctcc ttttgcttgg ctgagaagtc   15060
ttaataggag gcttattccc agctacttgg ggacatagaa gcggttagct attgttcatg   15120
ttttactgag gtctgtgtgg tatgttgact gcagtcagtt actggttttg agaattgaag   15180
gcagcctggt atatagagta ggtattatat tgtgtttctt tgaattgaat ttcctatctc   15240
ttgtaatctt tgccatcatc ttctgtgaaa gaaaaaagt ttctatcaaa ctataccatt   15300
ggttgtaaga tgcagttcgg ctttagtgat gctaacacat gatccaaacg tgaaactgag   15360
tattggtgaa atacagagga gatttaaagc cagaagacct gggtttaaat gctggctcta   15420
tgacttcaaa tctgtgtgtt cttgggcacg tcatggttgg cacttcaatt tcttctctct   15480
gtaatggggg aaatgaggcc agtcatggtg gctcatacct atgatcccag cactttgggg   15540
gccaagatgg gaagatcgct tgaggccagg aggttgagca attgggcaac atagtgaggc   15600
cccgtctcta caaaacattt aaaaaaaatt agccaggccc agtggtgcat gcctgtggtc   15660
cccaccactc aggaggctga gatgggagga tcctttcagc ccaggagttt aaggctaaag   15720
tgagccatga ttgtgctact gtactctagc ctgggcagta gagcaagatc ctgactctaa   15780
aaaaaagtaa aatgaaataa aatggggaa atgaactgct ttagtaacat catctgtttt   15840
ttctgtgagc agtgtagctt gaaagccatt ggtgaactca tgcactgtgc ttccctgtcc   15900
agatccccat tctgcccca gcatggagta taacagttta ttagtagtag tcgagaaacc   15960
ctcattgaat gaatgaatga gatgtagaag taagtggagt gggtaattga acacatattc   16020
atttcctttt cttttttctt attttttagaa agaaagaact ttcagctacc aagaaagacc   16080
```

```
gtgtgaatca ttgtctgaca atatgtgaaa acatagtggc acagtctgtc aggtaattgc   16140
actttgaact gtctagagaa aataagaact ttgtatattt tcagtcttaa tgggctagaa   16200
tattctgtgt cccagttatt ttaaatggat tcaaaaatcc ttgaagaagg acccttttcc   16260
catatttctg gctatataca aggatatcca gacactaaaa tgaataatgt tcccttttcg   16320
taatctttta tgcaaaaatt aaaaccatta tggtaattga acaacatgtt tatgtttagt   16380
taacacccct agcaactata gttattttaa aatcctgtgt ggtttgatat ttttgcgttt   16440
attgtaacag tgggaacagc acaaggcggt ccactttgtc tctctcattt tgcagtttgc   16500
tgtcctgttg tgctggtgct cctagcagtg gctggagccc acttctctgt gctttgggat   16560
tagtggggtc atggggcatt gactggaggt cagcttttcct tgcttgatct ttctcactgg   16620
ggtgaactag cagcacccttc tttttgtagct gctttgctttt tggctatctt tctgaccgtt   16680
gttcctagca gctgtagatg gtaaatatgt ttaggcctgt ttccaatggc tgagtaggag   16740
acatatgcac ctatgatatc tgaattctgt tacccagatg ggcgtgtgtg aaatagttac   16800
cttgctttac tttcccttgg aataaataat tcatgttatt ctcctggtag aagctagaaa   16860
aagctcttta tagtcagtca gaaaaaaatt tttagacaaa taatcttgat tttagtactg   16920
acaaaaatgt gtggtgattc ttttttttag tttttttttga gatggagttt cactcttgtt   16980
gcccaggctg gagtgcaatg gtgcgatctc ggctcactgc aacctccgcc tcctgggttc   17040
aagcgattct cctgccttag tctcctgagt agctggggtt acaggcatgt gccaccacgc   17100
ccagctaatt ttgtattttt agtagagaca gggtttctcc atgttggtca ggctgatctc   17160
aaactcccaa cctcaggtga tccgcccgcc tcagcctctc aaagtgctgg gattacaggc   17220
gtgagccatg gcacctggtg attcatttgt tttttttaaaa atttcctctt ggccattgct   17280
tttcactgtt ttcttttnnn nnnnnnnnnn nnnnnnnnnn nnnnnnnnnn nnnnnnnnnn   17340
nnnnnnnnnn nnnnnnnnnn nnnnnnnnnn nnnnnnnnnn nnnnnnnnnn nnnnnnnnnn   17400
nnnnnnnnnn nnnnnnnnnn nnnnnnnnnn nnnnnnnnnn nnnnnnnnnn nnnnnnnnnn   17460
nnnnnnnnnn nnnnnnnnnn nnnnnnnnnn nnnnnntgta gaaatattgt gggaagaaaa   17520
tgaaataaca aatgagcatg tgtcctgaaa ataaaaatat aaaaattcta agttagcatg   17580
ctattgtaga atacaacact atgataaaag tagggaaaaa aaagtttgaa ttccacgtct   17640
gctgcctgtg taagctgggt gactttagat aagctttaac gtgtttgagc cttactggct   17700
catgtttgaa gtgtaatccc tcgttacaca gttcttgtgg gatcagacga tgcatgtgaa   17760
acactgtgaa gaagtaactg cgatagatgt gttcattagc cgcctgaacg ggaagcacat   17820
cccattgcga tgcccatcat ccaaagctat atgttatctt tacttttttt gttttttttga   17880 gacagagtct cactctgtcg cccagactgg agtgcagtgg cgccatctcg gctcactgca   17940
gtttctgcct cctgggttca cgccattctc ctgcctcagc ctcccaagta gctgggacta   18000
caggtgcccg ccaccacacc tggccaaatt tttgtatttt tagtagagac agggtttcac   18060
tgtgttagcc aggatggtct cgatctcctg acctcgtgat ccgcccacct cagcctctca   18120
aagtgctggg attacaggcg tgagacactg tgcccagcca tcttcacttt tcttgtgaaa   18180
tgatgactct aaatgtttgg caaacatttg gtgattgttc atctgatttc cactatccag   18240
gtctcagaga atataaattta tctctgaaag cttattgacc caggaaacaa gatctcttcc   18300
aatctgagta catcaggctt tattcttgtc attttgtctt ttgagaattt tcaaatggaa   18360
ttcatggaat gttggctcat attcacatat tagtaaagta cgctgagaca tcttaagatt   18420
```

```
gatttgtggt tctatttgcc atattaaatc aaaataataa ctgttaatgg tttcttttt     18480
tttttttttt tttttttgaga cggagtcttg ctctgtcgcc caggccggag tgcagtggcc   18540
cgatctcagc tcactgcaag ctccgcctcc cgggtttatg ccattctcct ccctcagcct   18600
cccgagtagc tgggactaca ggcgcccgct acctcgccca gctagttttt ttgtattttt   18660
tttagtagag acggggtttc gcccgtgtta gccaggatgg tctcgatctc ctgagctcgt   18720
gatccgcccg tctcggcctc ccaaagtgct gggattgagc caccgcgccc ggcctgttaa   18780
tggttttcac attagtctgt ctcttgtttt tatggagtaa tgctgagagt tcattatgct   18840
tcttgttcta cagaagagca tgttaaaagg attttttggg atcagagagg ttatccatgg   18900
tttcatagga tactctgtac tttgcaggga tttcagggta tatagccaaa ggtgatattt   18960
tatataaata tgttttatgg aaacttactg annnnnnnnn nnnnnnnnnn nnnnnnnnnn   19020
nnnnnnnnnn nnnnnnnnnn nnnnnnnnnn nnnnnnnnnn nnnnnnnnnn nnnnnnnnnn   19080
nnnnnnnnnn nnnnnnnnnn nnnnnnnnnn nnnnnnnnnn nnnnnnnnnn nnnnnnnnnn   19140
nnnnnnnnnn nnnnnnnnnn nnnnnnnnnn nnnnnnnnnn nnnnnnnnnn nnnnnnnnnn   19200
nnnnnnnnnn nnnnnnnnnn nnnnnnnnnn nnnnnnnnnn nnnnnnnnnn nnnnnnnnnn   19260
nnnnnnnnnn nnnnnnnnnn nnnnnnnnnn nnnnnnnnnn nnnnnnnnnn nnnnnnnnnn   19320
nnnnnnnnnn nnnnnnnnnn nnnnnnnnnn nnnncctgta gtcccagcta ctcagaaggc   19380
tgaggcagga gaatagcgtg aacccgggag gcagagcttg cagtgagccg agatcgcccc   19440
actgcactcc agcctaggtg acagagtgag actctgtctc aaaaaaaaaa aaaaacaaaa   19500
aaacaaaaaa accaaaacct tatgtatatt gtgaaaatgt agtctgcttt aagctctcta   19560
aagaggtcta agttactggt tcctaagtat ggatgagcat caaaatcatc tggaaaattt   19620
gttaaaaata caataatgaa ggtacctcac tgtccttttt cccaaacaca cttctgcatt   19680
ctgtttgagt aggtagggcc tacacatttt tcacaagtat tctcttggga atacccagga   19740
atgctcactt gagcaacctc ttactaatac catatacttt gataaagtgg ctaggtaaaa   19800
ataaatatat aaaaatccat caatctccca tatattagca taaatcagct agaaaacagt   19860
aatgtttaaa gatctagttc acagtagcac tgaagtattg aattccaaga aattgataag   19920
aaatatgcag aaactttata aaaacttctg ttaatgtttc tgaaagatat aggtgaccac   19980
tttctagaca ggaagatttt tatcattaa gttgactttt ctctaaatta acacagaaat   20040
ttaaaataat cttgattaaa attctagtag aggtattttt gaacttgttc actgtaagaa   20100
taaatacata actgcaaaga atatcttaaa atcatcacta ggcccggtgt ggtggcccac   20160
gcctgtaatc ccagcacttt tggaggccaa ggcaagcgga tcacctgagg tcaggagttt   20220
gagcccagcc tgaccaatgt ggtgaaaccc tgtctctact aaaaatacaa aaattagctg   20280
ggtgtggtgg tgcatgcctg tagtcccagc tacttgggag gctgaggcag gagaatcgct   20340
tgaatccagg aggtggaggt tgtggtaagc ctagatggca ccactgcacc actgcctggg   20400
tgacgagcaa aattgtgtct caaaaaaaaa aaaaaaaag aaaaaagaa aaagaaatca    20460
acgctaatat ggtgagactt gatatatgtg acattaaaat agtgattgga cattagaaca   20520
ggtatagaac agaagaagaa gtgtgtgtat ctgtgtggat ttatgatggg tgtagcatat   20580
tgtattagta gggaaatgag ggaaatgata tatttctttg actttgggac aacattatat   20640
ctctacctca tattgcaaac aagcataaaa ttctgattaa ttacctaaat gtgaaaaat    20700
gaaatacttt cttcaaaaaa tgtaatctta gtttgaggaa gactaacatt atgaaggaaa   20760
aacctgtttt gactggaata tagttcaata tgtcaaaatc caccttcaac aaaattgaaa   20820
```

```
gtaaattgaa cttggggaaa gtattgatag catgtagatc aaaggttact agcctgtgta   20880
aagagcaatt ataaatcatt aagaaaagac tgtcaacccg tcggcacctt gttctccgac   20940
tcccagcctc cagaactgtg acgagtaagt gcctgttgtt taaaacacct agtctatatg   21000
tactattttg ttatagcaac tcaagctgat taggaccctaa gtaatcagta gactgagact   21060
aaaacaaaaa taagaacctt ttttacctgt caagttggca aacattaaga atatgcagat   21120
ttttgtcaga ggtgatacaa cctttaagaa ggcaatttgg gaaaacataa agctttagat   21180
tattaatgtg tctgatctag ggcacttacc ctaggaaagt gtgtaatgat attggtgcac   21240
tgctgttcat cccattagaa aataaaaata accttaatag cttaccacta aaaggggat    21300
tgaaaaatta agatacattt atttatttat ttattgagac agagtcttgc actgttgcct   21360
gggccggaat gcaatggtgc gatctcagct cactgctacc tccgcctcct gggttcacat   21420
gattctcctg cctcagcctc ccgagtagct gggaatacag gctcacacct ccacacccag   21480
ctaattttt gtattttag tagagatggg gtttcactgt gttgaccaga ctggtctcga    21540
actcctgacc ttgtgatcca tccccctcgg cctcccaaag tgtcaggatt agaggcgtga   21600
gccattgtac ctggccagat acatttatac aagagagtgt tagttaacat tcatagattt   21660
ttttttttctt gtttactttt tattaaaaaa atttttttt agagacaggg tcttactctg    21720
tcacccaggc tgaatgcagt tgcacaatcg tagcccactg cagcctgaac tcctgggcgg   21780
aagtgatcct tctgcctcag ccttttgagt acctggggga ctttaggcag tgctgctata   21840
tatacctggc taagttttaa atgttttata gatgggatct tgctatgttg cccaggctgg   21900
tctagaattc ctgggcccaa gcaatcctcc caccttggcc tcccaaagca ctgagattac   21960
aggcattgag ccaccacttc tgatcaatag atatttatat ttgtgactgg aaaatatatt   22020
aacaatgtgt taaaaattc agttaaaaaa taatgaaaga ttttttgcttc tagctaagat    22080
agaataacaa ggacagcatt tatcttcttg ccttgaaata gttgaaaatg gataaaatat   22140
atgtaacagt ggttttcaag ttattgggca ttaggcaaag aagagtagtt atcacaggaa   22200
aattaatgtg gagagcccta caatttcctt acattgctgc ctggccatgg caagaggaaa   22260
aactgaaagg aaactgaggc tgagccagtg gtttgctggg ttgaggaggc agagctggga   22320
gtccagagat gcaaggtggc tagagcccgt atggaaaaat accagggaag agagctgcag   22380
agggagctcc ggagaactgc acagtaccct ctcatgtgtg tagctgagta ttgatgagca   22440
catgctggtg aggaaatgac ccagggctgc aggtagaacc acttaaaagg attagaagga   22500
acaattgctg caactcacac agggccagga agaattcttt tttttttttt tttttttttg   22560
tattttagt agagatgggg tttcaccatg ttagccagga tggtctcgat ctcctgacct    22620
cgtgatccgc ccgtctcggc ctcccaaagt gctgggatta caggcttgag ccaccgcgcc   22680
cggccaaagg gccaggaaga atttctaatc acacaagtcg gagtggaaaa cctcggctct   22740
catagagcag caggtagagt actcagaagg gtttgcctgc ctagcccag actaagtttc     22800
gttactctga ccccgcctaa tattaaaaaa agattaatta aattaattgt ttgcaacaaa   22860
agtaatatat ttcagtgttt ataacgtgta gaagtgaatt gtatgacaat agcataaagg   22920
ctggaagagc agaaattgac atgtatttgt gctggacaga ataatgttcc cctcttttcc   22980
caaaagatat cgagtcctaa tccctggaac ctgtaaatgt tactttataa ggaaaatggt   23040
ttcatggtgt gattaaattc aggatcttga gatgaggggg ctgtcttgga tgatttgggt   23100
aggcactaaa tgcaatcaca tgtgtatgca aaggaggcag agggagattt tacatacaca   23160
```

-continued

```
gagaaggcca tgtgaagata gaacagaaag atttgaaggt gctggccttg aaaattggag    23220
tgatgaagct ataagccaag gaatgcagta gccaccaaag ctggaagagg taggagcaat    23280
tctccttcag agcctactcc agagggaacg tggtgctgcc agttccttaa tttcagctca    23340
gtgatactaa ttttggactc tggtctctga aactgtgaaa gaataaattt tttttgtttg    23400
tttgtttaag ccacacagtt tgtggtaatt tgttacagca gctgcaggaa actaatttat    23460
gctgcatgtg aaatggcata atatcattaa gatagattgt gataaaggta catagtataa    23520
acaattaagc aacaactaaa agcacaacaa ggagttatag ctaatgaacc aaaaaaggag    23580
attagaatca taaaaatagt gaatcccaaa gaagccagaa ataggggaag aggcaaataa    23640
aggaaagaaa gagcttgatg gtagatttaa acctagttat gtcaaaaagg acattaaatg    23700
taaaagatat ttttcggatt gaatggaaaa gtaagaccca gtatatgctg ctgcctgcaa    23760
gaaacatatt ctaaatgtaa aggcaaaaat agcctacaag taacagaaca gaaagaagtt    23820
caccgtgctt acaagaatta gatgcaagct agactggttc tgttaatatc agacaaagtg    23880
gatttcagag caaaggctat tgcctaggat gagatggtcg tttcataata acgaagggga    23940
ttcgttcatc agccgcacat aacaaactga aatatttatg cacctgacta cggagctaaa    24000
atacacgaag caaagcctaa caactacgag tagacacagg caaatccaca gtgagagaga    24060
tttcagtggc ttctctcagt gatttgtaga acacgtagcc ataatatctg gatctagaac    24120
agttgaacaa cactgtccct atgcaacctg attggctttt acaggacact ccacccggca    24180
ccagcagaag agacactctc tcaagtgctc acagaatgtc tgccaagata gagcagatgc    24240
tgggccataa aacaagtctc taaattaaac gcattcaaat tattcagagt acgttttccg    24300
acctcagtat cattaagttg gaatatatta taggaagata acctggaaaa gcctcagata    24360
tgtgaaaaaa ctcatttcta agtggcccat gggtcagaag tgaagtcaaa agggaaaact    24420
gaaaatcttt tggattgact gatatgaaaa caatagatgt ctatacttgt ggggtgctgt    24480
tacagtatag taaagggaaa tttctagcat taaatgcctg ttttagtaaa gaaagatttc    24540
aaatcaatga cctcagcttc taccttggga aacttgaaaa tgacaagcaa atggaatcca    24600
gagttaccag aaaggccagg tacagtggct catgcctgca attctgccac tttgggaggc    24660
caaggcaggc ggattgtttg agactggcag ttcaagacca gcctgggcag catagggaga    24720
ctccatatct acaaaaaaca cagaaaatta gccaggtgtg gtggcatgtg cctgtagtcc    24780
cagctaacca ggagtctaag gtgggaggat tgcttgagcc tgggaggttg aggctgcagt    24840
gaactgtgat tgtgccactg cgctccaccc tgggcaacag aatgagaccc tgtctcaaaa    24900
acaaaaacag ttactagaag aatggacatc atagagataa gagcagaagt cagtaaaata    24960
gaaaacaaaa atacatagaa aatcaataaa accaaaagct agttcatcaa gaacatcaat    25020
aaattggtga gactaatagg aaaaaaagtg aagtcacata ttatcaatat caggaatgag    25080
ggagatgaca gtagtataga ttatatagat attaaaaggg ctatatgagg caggtgcggt    25140
ggctcacgcc tgtaatccca gcactttgga aggccgaggt ggacagatca cctgaggtca    25200
ggagtttgag accagcctgc ccaacatggt gaaactccgt ctctactaaa aatacaaaaa    25260
ttagctggtc atggtgccat gcgcctgtag tcccagctac tcgggaggct gaggcaggag    25320
aattgcttga acctgagagg cagaggttgc agtgagctga gatggcgcca ttgtgctcca    25380
gcctgggtga cagagtgaga ctccgtctca aaaataata ataataaaaa ggactatatg    25440
ggaatattat gaacaacttt atgccaataa atttgataac ttatagatta aatggataag    25500
ttccttgaaa gacacacaaa ctattaaagc tctctcaaga agaaatagat aaactgatta    25560
```

```
gccctatatc tattttatta aatttaaatg taaaaatcaa tatttagtta ctggaaaact    25620
tttaagtgtg gttggaaatg gtatatgaac tttttcaact gaattttatg aaggctaatc    25680
acaggtaaag gttttctgat gaaaatttag tgtctgaatt gagatgtgct gtaaaaaatg    25740
ttgttatgta tcttaatcat ttcttcacat taattacatg ttgaaataat actttgggtg    25800
tattgggtta aatgaaatat tatgaaaatc ttgcctgttt tcttttttact tttgatgtgt    25860 cacctgggaa ataaaaaagt gtgacttaca ttctgtttct gttgacagta ctgctttgga    25920
gtgcagtgtt ggaatgatct agcatttcga agacctttcc tcccttcgtt attcagggct    25980
gtattccaca tagataagtc tgaaatactg ctaagtggca cgttttgttt tgtgcttttg    26040
taagtttgtt gatcgttact gatgtggacc tttggtgcct cttaggctca tggctatctt    26100
ccaaccattg tttgcaattt ttacctagag ataaagagaa aaagagattt ggtttcagag    26160
taagttagat tgagatcatg aaagagcaat ctcattttga tgcttcaaaa atagcacatc    26220
ccccgtatta ctgggatttg ctattcttgg gcttacttca agaacatcct tgtgttgctg    26280
gtttggatgc ttccgaatgc tgtgaagtca gtttcatgga cgtggctcat cagtttagct    26340
ctcttggctt tgtttaggca gttggagcat gatagcctga acagcttctc tcaattaaac    26400
atttacaaat cgtttacgaa tagtaaacaa actccaggtt ttgtgactct ttgatagttc    26460
atctagcaca acaaaaacac aatgtgacca tgatcacctg gcatcttagg gtgaaatact    26520
ttggcccaga ctgaaagcaa aattaaaaag gggcaagaga gatatactgc tgaactgatt    26580
ttcaaggttc caagaatatc ataggttaag agtaaaagta aacttttgac agagagcagc    26640
gggttttctg ggattgaagt atctgaagtt ttcaaacgaa aatttaaaaa gaaaaaatga    26700
gaattgcctt ataagtacaa tctcttcttt tttaaaaaat aaactttatt ttggaatagt    26760
tttaggttta tcgaaaaaaa ttagggtaga gagttttcat ataccctaca tccggttacc    26820
ccagttatta tcttaattaa gtgtgagaca ttttcatgtt taatgaatca gtatcgatat    26880
gctgttaact aaagtgcaga cttattaag attttcttaa tttctatgta atgtcctttt    26940
tctgttccag aattccgtgc aggacaccgg ataccctcatt acatttcatt gtcatgtcac    27000
cttaggctcc tcttgacagt ttctcttctt ttttgcttag aaattctcca gaatttcaga    27060
aacttctggg catcgctatg gaactttttc tgctgtgcag tgatgacgca gagtcggatg    27120
tcagaatggt ggctgatgaa tgcctcaaca aagttatcaa agtaagagcc gtgtggatgg    27180
tgttctcaga aatgtcattg ttgtaggcta agagaagcag ccatcgttga gtgttcttct    27240
gtttggagcc cctgaggatg tctgcacttt ttttcctttct ggtgtgtggt ttggaggtgc    27300
tctggtatct gcccgcattg cttgccacac ctgcctggtc agaaggaact gtgttgaccc    27360
ttgtgcctgc atggtgccta ggtcaatgaa gggaaccaat ggtgaccact ggatgctcct    27420
gggaaaatgt cactacaggt accagagaag ccagagctat gcccacattt tttttttttt    27480 tttttgaga cggagtctca ctctgtcgcc caggctggag tgcagtggcg cgatctcagc    27540
tcactgcaag ctccgcctcc tgggttcacg ccattctcct gcctcagcct cccgagcagg    27600
tgggactaca ggcacctgcc accgcgcccg gttaattttt tgtatttta gtagagacag    27660 ggtttcacta tggtctcgat ctcctgacct cgtgatccgc cgcctcagc ctcccaaagt    27720 gctgggatta caggcgtgag ccaccgcgcc cggcgctatg cccacatttc tatgagtctc    27780
agttttctta actataaaat gggatcaaag ttttgtggc atgcgtatga gtgtgtgtct    27840
gtgtgaggat taaatgcact aattgccact accggatcct caaagtggta agaagtattc    27900
```

```
ttattaatca tgacatcctc acactcttat gcagcaagat tgatgggtgt ggcactgctt    27960 ctcttttttcc atcacatgga ttccatgcta tccttttgcc cagggaatct ttcctttgtg   28020
gccagcactt tgttgtttgg ctcatcacgc tttctgtggg caggacgctg gcttctctgg    28080
agtcttggga ttctagctcc ctctcttgtc cctagagtgg tcactgtctt ctctctctgc   28140
ttgcaattct tgctttgctc gcatctcact catgcggtga cctgtatcag tttcaccttg    28200
ttctccgtgc ctgctggtcg ttggcaccac ttgcctgtgg atggcatccc atagcgtatt   28260
tagggcctgc ttccccagtt aagcttgctt ttccacaggc ctgaatatcc ttgcttgctt   28320
ctgttattcc cactggcagg accacggcgg tctttttttgg atgagacagg gtcttgctca   28380
gtcacccagg ctggagtgca gtggctgatc acggctcact gcagccttga gctactgggc    28440
tcaagctatc atcctggcct ggcttcttga gtagctggga ctacaggcgt gcaccaccat    28500
gcccagctaa ttttaaaaat tatttgtaga tatgggatct cgccaggttg cccaggctgg    28560
tcttgaacac ctgggctcaa gtaatcctcc ctccttggtt tcacaaagtg ccgggatcac    28620
aggtgtgagc cactgtgcct ggcccttgat gtttcagttc ttgatatttg atcctcagag    28680
tcagaaagtc taaaaagagg actatcccag gttgccttgg ttcacggcaa atggacgtt    28740 aagagggcag agaaaacaat atgaccagaa acgcttctaa tattggtcat ttaacgtgta    28800
agtattgttc tttttttaaac ctccttcatc tttttctagg gattgctgga cacagtggct   28860
tggtgtgtct gagggctgta ggccatggcc ctggttgtg gttttaggtc tcaggtgctc     28920
ttcctggttg tctccttgct tctttcccat ttcctcttct ttgtttccag ccatttctcc    28980
cttttgctta agtttggtgc agcagggttt ggctgctctc agattgctgc ttcctcagat    29040
gatgcagttg ccaggcccag tgggctggca gtgggatcag gatctgacta ggtttgctct    29100
cactgtggca gaggaggggc aggcgtggga gagcacgtgt gaccccaggc caggtgtagg    29160
gagcccaggc atggtcactt agccttcagg tcctagactt tgtcttctca tgagtgtggc    29220
tgtgtgtgta tggtgagaac caggttctac gtagcccaag aaaatgtaga gaaatgcact    29280
gggtatctga catagcctgg cagcacgcct ccctcaagta ggttagtctc aggcggtgaa    29340
gcatgtatgt ccagcaagaa cttcatatgt ggcataaagt ctccgttctg tgcggcactg    29400
acaaatcacc accgtcagga ggctgaagta atttctgtct agggaggcag ggaaggcttc    29460
ctggagacag tagccaatag gtgaaagggt agattggaga ccttcttaat catcaccgcc    29520
tcttggttcg agggggtgcca ggaagctgtg gaggctgaga ggaggggaa cccatcttat   29580 gctgccagag agtgggacac cctgagggtc aggtcaaggg gttgtacctt gttgggtgga    29640
gaattagggg ctcttgaaga cttttgatgt ggtcagggga gtgtatcatt taggaagagt   29700
gacctggtaa ggacgtggga tagaggagga cagaggtggg agggagtcta ggtgggagtg    29760
agtgggccca gcaggagtgc agggcctcga gccaggatgg tggcagggct gtgaggagag    29820
gcagccacct gtgtgtctgc ggaagcaggg gcaagagaga agaggccagc ggcgcgccgc    29880
catcacccag caactggcgt agattgtgag agcccattcc ctgcttttag gagggccga    29940 gttttagttt tctcttataa aataaacttg gtatttgttt acaaaacatt tgtaaagcta    30000
aatcaaggtt tgataaggct tctagtttta tttaagaagt aatgtttaaa taatgtcca    30060 attcgctttg cttatttaag gactttcagt acaaacttca acaacaggat caggatttaa    30120
acatttctga gatgttatta cccctcagaa tttcccagaa cgtgatctgg ttttgatttt    30180
caagcttgct gacccagtag gttaacccac aaatttttact aagatacacc tcagtccatt   30240
tatatcgact gcccatgtca cggtcaaaga gatcatcgac tgatgtttgg cacagcttcc    30300
```

```
tccctcttgg gtgggcaagc atttggaaga gaaggctccc atgggtgaga gtggggcacc    30360
agagtcttcc ccgtcctgtc ccctggcttg agaaacccct ctctaatgtg gactttgtgc    30420
cgttagcatc gttactggct tgaagttgac catgtggaca taattctggt tttagcctca    30480
caagtgagca aggaggggttg agagatgtgc tgtgaggaac atggggcccc cgctggccgt    30540
gggctctggg tcaggggggc aggggaccat ggcatacct gacagtgagg aggggccaca     30600
cctgcagaaa gcatgcggga ctcggcnnnn nnnnnnnnnn nnnnnnnnnn nnnnnnnnnn    30660
nnnnnnnnnn nnnnnnnnnn nnnnnnnnnn nnnnnnnnnn nnnnnnnnnn nnnnnnnnnn    30720
nnnnnnnnnn nnnnnnnnnn nnnnnnnnnn nnnnnnnnnn nnnnnnnnnn nnnnnnnnnn    30780
nnnnnnnnnn nnnnnnnnnn nnnnnnnnnn nnnnnnnnnn nnnnnnnnnn nnnnnnnnnn    30840
nnnnnnnnnn nnnnnnnnnn nnnnnnnnnn nnnnnnnnnn nnnnnnnnnn nnnnnnnnnn    30900
nnnnnnnnnn nnnnnnnnnn nnnnnnnnnn nnnnnnnnnn nnnnnnnnnn nnnnnnnnnn    30960
nnnnnnnnnn nnnnnnnnnn nnnnnnnnnn nnnnnnnnnn nnnnnnnnnn nnnnnnnnnn    31020
nnnnnnnnnn nnnnnnnnnn nnnnnnnnnn nnnnnnnnnn nnnnnnnnnn nnnnnnnnnn    31080
nnnnnnnnnn nnnnnnnnnn nnnnnnnnnn nnnnnnnnnn nnnnnnnnnn nnnnnnnnnn    31140
nnnnnnnnnn nnnnnnnnnn nnnnnnnnnn nnnnnnnnnn nnnnnnnnnn nnnnnnnnnn    31200
nnnnnnnnnn nnnnnnnnnn nnnnnnnnnn nnnnnnnnnn nnnnnnnnnn nnnnnnnnnn    31260
nnnnnnnnnn nnnnnnnnnn nnnnnnnnnn nnnnnnnnnn nnnnnnnnnn nnnnnnnnnn    31320
nnnnnnnnnn nnnnnnnnnn nnnnnnnnnn nnnnnnnnnn nnnnnnnnnn nnnnnnnnnn    31380
nnnnnnnnnn nnnnnnnnnn nnnnnnnnnn nnnnnnnnnn nnnnnnnnnn nnnnnnnnnn    31440
nnnnnnnnnn nnnnnnnnnn nnnnnnnnnn nnnnnnnnnn nnnnnnnnnn nnnnnnnnnn    31500
nnnnnnnnnn nnnnnnnnnn nnnnnnnnnn nnnnnnnnnn nnnnnnnnnn nnnnnnnnnn    31560
nnnnnnnnnn nnnnnnnnnn nnnnnnnnnn nnnnnnnnnn nnnnnnnnnn nnnnnnnnnn    31620
nnnnnnnnnn nnnnnnnnnn nnnnnnnnnn nnnnnnnnnn nnnnnnnnnn nnnnnnnnnn    31680
nnnnnnnnnn nnnnnnnnnn nnnnnnnnnn nnnnnnnnnn nnnnnnnnnn nnnnnnnnnn    31740
nnnnnnnnnn nnnnnnnnnn nnnnnnnnnn nnnnnnnnnn nnnnnnnnnn nnnnnnnnnn    31800
nnnnnnnnnn nnnnnnnnnn nnnnnnnnnn nnnnnnnnnn nnnnnnnnnn nnnnnnnnnn    31860
nnnnnnnnnn nnnnnnnnnn nnnnnnnnnn nnnnnnnnnn nnnnnnnnnn nnnnnnnnnn    31920
nnnnnnnnnn nnnnnnnnnn nnnnnnnnnn nnnnnnnnnn nnnnnnnnnn nnnnnnnnnn    31980
nnnnnnnnnn nnnnnnnnnn nnnnnnnnnn nnnnnnnnnn nnnnnnnnnn nnnnnnnnnn    32040
nnnnnnnnnn nnnnnnnnnn nnnnnnnnnn nnnnnnnnnn nnnnnnnnnn nnnnnnnnnn    32100
nnnnnnnnnn nnnnnnnnnn nnnnnnnnnn nnnnnnnnnn nnnggtggga gaatcacttg    32160
aacctgggcg gtggaggttg ccttgagccg tgatcacgcc actgcactcc agcctgggca    32220
acaaagtgag acttcgtctc aaaaaataaa aataaaaatg aaataaaatc agtccgggtg    32280
tggtggctcg tacctgtagc cccagcactt caggaagctg aggcaggtgg attgcttgag    32340
accaggagtt tgagaccagc ataggcacca tggcaaaacg ctgtctgtac agaaatgagc    32400
taggtgcggt ggtgcacaac tatagtccca gttacttgcg aggtggaggt gggaggataa    32460
atggagcctg gaaggttgaa tctacagtga gctgagattg taccactgcc cttcagcctg    32520
ggcgagcaag taagaccctg tctcaaaaaa aaaaattatt gactatatct tattgtctat    32580
aatccctcct ctgtgctatt gaataccagg ttttgggccc ttatttccat cactgaacaa    32640
```

```
acttcactct attgagcagc atgtgtggaa tttcatctttt attcaataat taacagctag    32700
gaggaaatgc tgtttgctag actattgctt tacttttctt caaaaggtta ctctttatta    32760
gatgagatgg gaattaaaaa tggtaactta ctttatgtct ttataattga agcccgctag    32820
atcttaaagt agttaccaga tgttttatgc atttaaatgg ccttttctct aaaaatagaa    32880
agtaacaatg aaagaaaatg cttcgtttct atgcaacct cttggtgact agtgtgtgtg     32940
actcttaatg tgacactcat tgcacccct cagaatggtg ccctcggag tttgcgtgct      33000 gccctgtgga ggtttgccga gctggctcac ctggttcggc ctcagaaatg caggtaagtt    33060
gtacattctg gatgttgatt tttgttgggg gccagctgct actgatcctt tatgtctcag    33120
ctcagatgtc atttcagaaa tctgctctgc cccttccaaa ttgcagtcga ccttgccctg    33180
tttatgtttc cgtcatagca ctaatccgtg tcagaaagtg tcacgtacag tctgtgtgct    33240
tgttcatttt ctatcccacc ctcccccaag agacttatgg gatgtgtgcc ccaggacagc    33300
aggggtctta ctgtcttatg ctctgttgca gcctaaacag cagtaacagt gtctgcacat    33360
agtacttgct taaatgattc ttgccaaatt gttgaaggtt gaggtaccag tttcattatt    33420
gctgactata ggagttacag caaaatatcc atttgtctat tacatgagtt aaaaatatgg    33480
ttgtttcact atgaatagtt ttgtctagtc aaaacagttg tgtcttaacg gattgagaaa    33540
caaaagcagg accacttttc atcagctccc tcctccttaa cctgcagtat acgctgatgc    33600
tgatgtcctg tagaccctca gctccatcct gagtcactgg gaacgtggtc taaaccctca    33660
ttattagtat gaactgagtt tcaataagaa tctcacatgg gtcgggtgta gtggctgata    33720
cctgtaaccc cagcacttca ggaggccaag gcaggtgaat ggcttgatcc agactaggca    33780
atatggtgaa accccgcctc tacaaaaaat acaaaaatta gctgggcatg tggtgcgtg     33840 cctgtaatca cagctactgg agaggctgag gtgggaggat cagttgagcc tgggaggtgg    33900
aggtcgtgtt gagccaagat cacatcactg cactccagcc tgggcaacag agtgagacct    33960
gtctcaaaaa acaaaaaac aaagaaacaa aaaaagctt atatgggtgc agaggtataa      34020
tcactaagga aatttctttt tgtgtagtct ttttttcttt actgtcattt caaaaaatgt    34080
gttatatttc tgaagtaaca catccaggtt ctccacatag cagccaaagt gaccttaaag    34140
aacataattg ggtcttgtca ttcccttatt taaactcttg tgcccgtttc ccagtgccgt    34200
ttagattgat tccagactgg taactggctc cgtcacctca gacactctgc attgactcat    34260
tagcctgatc agttcttcag atgagtcagg ttttcttcc tcctgatggt ttgtttgttt     34320
tgtttattcc cctcagttct cagcaaaaca gtcatttcct tagggaggtt tccctagcct    34380
ccctgtcttt ccctgtccca ggagcctggt ggtgtggtca ctgccctctg aggccctgct    34440
tgttgccagg ctctgccact agagggcagg gctgcaccac tcctggcacc tcacacctgg    34500
cctgccctgt cagtgtttgt tgggtgaatt cctgtgatct gtgactcact gctctgtgtc    34560
ctacacattc tgcttttcctt ctcccctcac aataccattt ataattctcc tttttcagga   34620
aagctttatt tccattaaaa catttttgtt tttaaaatgg tattttctta cactattatt    34680
ttctaattaa aaatgagtgt tttggcaggg cgtggtggct caccctgta atcctagcac      34740 tttgggaggc ccagatgggc ggatcacaag gtcaggagat agagaccatc ctggctaaca    34800
tggtgaaacc ccgtctctac taaaaataca aaaaaaatt aggcgagtgt ggtggtgggc     34860
gcctgtagtc ccagctacgt gggaggctga agcaggagaa tggtgtgaac ccggagggtg    34920
gagcttgcag tgagccgaga tcacgccact gcactccagc ctgggcgaca gagcgagact    34980
ccgtctcaaa aaaaataaa aataaaaaaa aaaaaataaa taaaaagtaa aaaaaaaaaa     35040
```

```
gagtatttta agaagtatta cgatttactg caaataattt ttaaacccag cctttagat    35100
cctctgtgat cataagagaa atgaaggatg tctcccgaca cttgagcttc atccacattt    35160
cattctctcg ttctttcagc tgagctttgc ccatccccat tagggaccgt ttggcatatg    35220
aaactggctt ttccctaaca gggaatgaat tgcttctatt tctcctgaag gagagctgga    35280
ggaatgactt gcgttctttt gcatacacag gccttacctg gtgaaccttc tgccgtgcct    35340
aagtcgaaca agcaagagac ccgaggaatc agtccaggag accttggctg cagctgttcc    35400
caaaattatg gcttctttcg gcaattttgc aaatgacaat gaaattaagg tacgattatt    35460
gcctcagatc acaaacatgt gagtgacgct gtgagtgagt ctgtggaggg ttacggcttc    35520
tgagcaggga gtcatgtggg agcgcttctt agagtatgtt gtatgtcgta atttagacta    35580
ccgtcatttg tgttattttt gaggcaccta aagacttctt tccacttctg atttcttact    35640
gtggggtgaa gagttgaatt gggagatggt ttatagatgc acattcaaaa ggcatatttc    35700
cagagcagat tggttttcag tgtattagag tgactgttta acctagctgt ggaaagatgg    35760
ctgtgccagg actgcaggta ggagaaagct cactgacgag gccttgtggg tctgaacatc    35820
ctgcagctat cagggcctgt tggctccctg ttgtgcattc caacaaacca ccttcaaacc    35880
cactttagtg tttgtttata atgtccagaa atagtgaccc tgtcacatgc tctacagatt    35940
acaggattcc tagcctcttc cttttggtg ggtcagtcct gggttgagc ccaagtggcc    36000
ctcttggaag gtgatgatac acagtgggta gagtggaatc agatggactt ggattagaat    36060
tctgtccgct ttactggttc ttttcctcta ggcaaactat ccaacagctc taagctattt    36120
ccttcgtatt ctgaaaacta agccttaatg ggacccatat cgggcaattc tgagagtgaa    36180
ataaatgaat atgtgttagc gtgtagcata gtcgcccaca ggaagggctt agatgttagc    36240
tgctactgct cttattagct gaatgacttg gaataaagtg ttagcctctc tcatgttttt    36300
ttctctgagc tttgaagttt tcttgttaat actaaggaga tattcaaact agtcatgggg    36360
ttttggaatg acgaagggag atcatgaatc taaagaattt agtgtggtaa ttcatcatgc    36420
tcagtaaatg gtagctgctg cttgctgtta tttttattac catctctttg gagtgggagt    36480
aggtctcctt tgtggtcaga ggctgtgaga gctccgcagc gccagtctgc ccgtcagtac    36540
accgggctct gatgaaggca gttccctctg tggtatctct ggctgtcaga gctcagatga    36600
tagatggtgt ttttgtactc tcagttctca tcattttcat gatttcgatc actatttgag    36660
tatgatgatg ctaacacttt gttgaacata gagtccatta attacttcct tcctgaacct    36720
taggtattta aaaaaatcta ttctgctacc tctctgctca tttatgatta ttcagattta    36780
ttatcaagag cctggtacag tggcttgtgc ctataattgt agctacatgg gaagctgagg    36840
taggaggatt gctggaggcc aggagtttga ccagcctg gtaacatgg tgagaccct a    36900
tcgctaaaaa atgaaaaaag ttagctgggc atgatggcac gtgcctgtgg tcctagctac    36960
tcaggagact gaggcaggag gattgcttga gcccaggagt tggagttcga ggctatactg    37020
agctgtgatt gtgccaccac actctgggat gggtggcaaa agaagatgcc atttcttcaa    37080
aacaaaacaa aacaaaaaaa ggtattatcg gtgaaattca atagtaccaa caggattata    37140
aacaaagata gttctcttcc tacttttct cttaatcctt gtgtctcaga ggcaaacata    37200
actcttagtg tttcttccaa tatttacttc gannnnnnnn nnnnnnnnnn nnnnnnnnnn    37260
nnnnnnnnnn nnnnnnnnnn nnnnnnnnnn nnnnnnnnnn nnnnnnnnnn nnnnnnnnnn    37320
nnnnnnnnnn nnnnnnnnnn nnnnnnnnnn nnnnnnnnnn nnnnnnnnnn nnnnnnnnnn    37380
```

```
nnnnnnnnnn nnnnnnnnnn nnnnnnnnnn nnnnnnnnnn nnnnnnnnnn nnnnnnnnnn    37440
nnnnnnnnnn nnnnnnnnnn nnnnnnnnnn nnnnnnnnnn nnnnnnnnnn nnnnnnnnnn    37500
nnnnnnnnnn nnnnnnnnnn nnnnnnnnnn nnnnnnnnnn nnnnnnnnnn nnnnnnnnnn    37560
nnnnnnnnnn nnnnnnnnnn nnnnnnnnnn nnnnnnnnnn nnnnnnnnnn nnnnnnnnnn    37620
nnnnnnnnnn nnnnnnnnnn ggagtacaat gacatgatct tggctcacca caacctccgc    37680
ctcccgggtt caagcgattc tcctgcctca atctcctgag tagctgggat tacaggcacg    37740
caccaccatg ctcggctaat tttgtatttt tagtagagac ggggtttctc cagattggtc    37800
aggctggtct caaactcctg acctcaggtt atccacccac ttcagcctcc caaagtgctg    37860
ggattacagg catgagccac tgcacccggc aacttccaca tttctcagta acatgcttct    37920
actgcttttt ttttttttt tttttcaatt ttagacattt tttactttca cactataatt    37980
ctatcagaat tcagtatgta cattattata cctaagtaaa tagtcatggt tggttgtgta    38040
ttatatttct ttgtatttct tatttgatga gagagctgtg ttttttgctg tgggttgaaa    38100
ctgtggagag aggacatggg gaggggaagg aagacagatg aagttggtga ctgtaccttc    38160
ctggccatag ctgggttctc agcaccctgg gatctgctga tcacctgctc gtaggccaag    38220
cccctagcga agttctaggt gacccagtgc tggggatggg ggggtcacct gcaaggtcta    38280
gtcatggagg tgggggctac agtgttggct tgtgctgggg ccagcatcct taggaatgca    38340
tcttggagga ggaggagaca gccacccact tcttgactgg ggccttcagc agtgccagct    38400
tcttgggcag actggtgctg gctttcatca ccacatcgtg ttcaatcttc ttccagatcc    38460
tgacttctag gttcaccttt ccttagaccc cggttccttt cagaggctgt cgctctgcct    38520
tgctctttgc tggcttgtgc cttgattata tgtctttgta caacttttg ttttcctgga    38580
gttaatcctc acatctgttt tcctagagtg aattgttacc tttatatcac ttgcttatta    38640
ttctttgacc tttttttctt ctcacacctt ccaacttctt tgtaaaatgt gtttagtaca    38700
attttcatg acaggtaatt taccaaatca gttttttcccc agtgcagtca tccatcttga    38760
gttacccagc tcgctgcccc agtctgggcg gattgctctt caggtctgtt gtacacttgt    38820
atcctaggac ttctcttgc catcagcctg gaatttcctt tgcagttctc ctgttggatg    38880
cccagttcct acatgccata tgtttatctt tctatcctct agtagctttg tgagagaaga    38940
tgaatgggag gtaaattgtt tggagttttg cattcataaa aatgccattt tttctcgcgt    39000
acacttggct gagtatagtg ttctggggta gaaatcattt ttcctcagaa atgtgaagtc    39060
tttccccgtt gtcttaaagt ctccaacata acccaattcc ttaacccatg aatgtgcttt    39120
tctctggaag cttttccattt tggggaggt gaagtgctag gtacttagta ggccttttat    39180
tttttatttt tatttgtttt ttgaggcgga gtctcacttt gtcgccgagg ctggagtgca    39240
gtggcatgat ctcggctcac tacaagctct gcctcccagg ttcacgccat tctcctgcct    39300
cagcctccaa gtagctggga ctacaggcgc acaccaccac gcccggctag ttttttttt    39360
gtattttag tggagacggg gtttcaccgt gttagccagg atggtctcga tctcctgacc    39420
tcgtaatccg cctgcctcgg cctcccaaag tgctgggatt acaggcgtga gccaccgcgc    39480
ccagccagta ggccttttaa tttggaaact tatatacttc agttctggga aaattttctt    39540
acatttctct gataaattct tgcctttat tttctgtgtt ctctccttct gaaattagtt    39600
agttggatgt tggtcctcct gggttgactc acatcttacc ttttcttttt tctggtactt    39660
tttagatatc catctcaaac tcttctattc agtgttatgt ttttaacttc tttctttct    39720
ttgtctcttg atggggtctt gctttgttgc ccaggttgag gtgcagtggt gcaatcatag    39780
```

```
ctcactgcag cctccaactc ctgggctcaa gcaaccgttc tgccttagcc tcccaagtag    39840
ttgggactac aggtatgcac caccatgtcc agctattttc tttactttct ttctttttt    39900 tttttttttt tgagatggag tgctgctctg ttacccaggc tggagtgcag tgatgcgatt    39960
ttggctcact taagcctctg cctcccaggt tcaagcaatt ctcctgcctc agcctcctaa    40020
gtagctggga ttataggtgt gcaccaccac gcccggctaa ttttgtatt tttagtagag    40080 acggggtttc gccatgttgg ccaggctggt ctcaaacacc tgacctcagg tgatccacct    40140
gcctcagcct cccacagttc tgggattaca ggcgtgagcc catcattaaa tctttaaata    40200
ctagtatctg taagtctttt cctcttgagt cagccagtat ccctggaagg aaattcctca    40260
ttttcctgct tggagactat aagcttggct gtgtttatcc tgcaaccggg gactggaagg    40320
ggatggaagg ggactgacac tgttgctggt cagggcgccc tcttttttgtt ttctgtatgc    40380 atctcacatc tgtcctcagt tatgtaaaca cctcttgaga ttatccctct cagtctttgc    40440
tggaggtggg gaaggggctg cttcctgggc tgccttggat tggaggggag acctcaggcg    40500
agtgggtggg aatttgccca aggagccatg agacaagcca ctgttccacc ctctccgtcc    40560
ctccactttc agatgtatgt ggtgcctcca aagcccgagt gcttcttgga gttctgtggc    40620
ttgaataagc ttgcttttca ctggtatccc tcatacctt tcccccatcc ccagcaaagc    40680
ttgcatttga acttcttccc atgggctaac aaatcagtca gttatgtagc ccttgttact    40740
ttttagcttc cgaagttttg ttgacacacg tagtctgcta gtgtccctgt tctgttcttt    40800
ctgtccgtgt acatttatgc tttatacaac ttctttacat gattttcgtg gggtttctgg    40860
gtagcagagc ttcacatgtt caatccagca tgttggatta gaagtctccc accctctggt    40920
gtattctcat tctcagaatt acctgccaaa caccgatact cccttgtttt tccttttcct    40980
gacaggaaat gtacatacca gacaggacag aaatcattag tgtatcccctt ggtgaataac    41040 cacaaagtga tcttaccctc gtaaccacca cccaggtcaa gacagagtat taccagcact    41100
cagaagcctc accccatcc tcccatcact gcttcttcct tcctcccaa ggtcatgact    41160 gtcctggctt ctaatgccag agtctgtttt taaattctgt gtacatagac catatagtat    41220
gtattctttt tgtctggttt cttttgctcg acagtaattt cttaagagtc ttctatatta    41280
tcgtgtgtat tagtagttcc tgtagtttta ggagcttcat agcattccat tgtaggtata    41340
taccacagtt tattcattgt gttatcactg ggttgtttct agttcttggc tattgtgagc    41400
aatgctactg tgaccactct caggtgtttt ttttggagca catgtgcagg tttccatcat    41460
gcgcagctag aggtggagtt gttgggtgat agggtgtatg catgtcagct gcagcagaaa    41520
ctgccaaata gctttcctga gtgcttgtac cagctcaccc tttggttgct gcgtatgggg    41580
actccgggag ctctggtcct cgctagcact tggaattgct gatgctttta cttttagcct    41640
tcctgatggg tattttctgg aatcacatta tgattttaat ttccgttcct taaagtaccc    41700
ttgactctga agtttaatga ttaatgcatc tcttcctttt tgaagtactc tgaaaggtat    41760
gttgtgcatg tgttgaaaac tggagctatc tagtctaaaa tacagtgtac ctcctccctg    41820
tttgaagagt tgtagcatgg cctcggggcc tcctgttagg tgccttggag aagggattct    41880
tgggattgta gagattagac ctgaggaggc cccttggagc tctcagacta aattttgttc    41940
tttattattc caaactattt aagctcaccg tgtgctgact catcataata atgagtagct    42000
ctcattgtgc ttgtatattt ggaccaatag aatgattttt tttttttgag acatagtctt    42060
gctctgtcac ctaggctgga gtgcaatggc acaatcttgg ctcactgcag cctctgcctc    42120
```

```
ccaggttcaa gcgattcttg tgcctcagct tctcgagtag ctgggactgc aggtgtgtac    42180
caccatgcct ggctaatgtt tgtattttta gtagaaacgg ggtttcacca tgttggccaa    42240
gttggtctca aactcctgac ctcaagtgat ctacccgctt aagcctccca aagtgctggg    42300
attacaggcg tgagccgctg cgcttggcca aagtagtttt ttaagatgtg aatatctttt    42360
cttgcagcta aaaagtttg tcagagataa ttctacttta ttctccaggt ggttttttcag    42420 ggagaaattg gaggcagtaa accacggggg gagtcctgtg gcttggtggg tgggtggggg    42480
aggtgtggct ggggtgggga gaagtcctgt ggctcgctgg gtttgggggg agctgtggct    42540
ggggtgggga gaagtctagt ggctggggtg gggagaagtc ctatggctcg gtgggtggtg    42600
ggggagctgt ggctggggtg gggagaagtc ctgtggctcg gtgggtggtg ggggagctgt    42660
ggctggggtg gggagaagtc ctgtggctcg gtgggtggtg ggggagctgt ggctggggtg    42720
gggagaagtc ctgtggctcg gtgggtggtg ggggagctgt ggctggggtg gggagaagtc    42780
ttgtggctgg ggtgggggc agtcctgtgg ctggtgtctc atcatgtgcc taacagtgtc    42840
cagaggtctc gtgtaaattc cctgggagtc gataagcctc tgagaaacag atgatgctaa    42900
ccacgctgtg gaagagaaac ttgttttataa atcagatgtc cgttactggt ttactgcttg    42960
tttgcccagg catagctccg acagagtccc cgactcatag tgattgctca gtgcgtgctg    43020
aacaatgatt ggaatcaagt catggctcag agcatagttt tgaataatgg gaaattgatg    43080
ttcttaagta acatagtcac caagataatg caactagatg agtcacccct tttcaattt    43140 aggatatttt tatcaagatt taagtggtca tcattagaat tatagcagtt tctcctttgg    43200
attgttctag aggcccagtg agaaagtatt ccctaatttc tcaggagaac agttgtgggt    43260
agtgtgctgt catgtccagt taaattgcag acgtttccgg ttgaagatat tccagtcctg    43320
agaactttgt gacattagca ggacttttac aagccatctc ttagggtggg gcattactgt    43380
agttggctgg tactcttttc tccttaactt tgtcatttgt tgattttttt tttttaactg    43440
tccccaaaca ctgtgggcag acagtatcta gaattgaggc ctccaccct gcagagagga    43500 cgtggatgct gagcagtccc cgagtgaaga ttataaagaa gcaaatagag tacacgtgtc    43560
tgtgaactgt tcttgagtct cccaaattcg gggtacttct gttcagctat aggaaaagcc    43620
tcaaactgtt tatactttgc aagaattgga aacttctaat tcaagttaag ttttacggaa    43680
tgcatggtaa gcttcatagg agcttcatct tttatctgct tggactttg cttctataagg    43740 ttttgttaaa ggccttcata gcgaacctga agtcaagctc ccccactatt cggcggacag    43800
ctgctggatc agcagtgagc atctgccagc actcaagaag gacacagtat ttctatagct    43860
ggctactaaa tgtgctctta ggtaaggtgg aggcatacag gtggaagggt ctccagcatg    43920
tattcatgat agacctttga aataattaaa atcagatgat ccctcagctt ctagaccagg    43980
ctatttggca ctggttgact gaatgtgaac tgcattggga ctgctgtgag cacgcatggg    44040
tctctgtgac cctgcagatg cagccatgcc cagggacacc tagctgggca gtgggtgtgg    44100
gctggtgtga gccctgcctg ccacccaggg cctggtcctc cgtctgtgcc ggccctgact    44160
acggtgagtc tgtgaggctt gagactgtgc cttgggtccc tgtgggttct ctgtaggtca    44220
gttgacagtt tctcctgttg tttgggtaac tgtgaaatg aacactggca agtgctgaag    44280
tgagcactgg acgcgtgata tggaccctgc caagccaggg atatgggtgt gtagccactc    44340
ccagtgggcc tcatggtgta ctcgttcacg gtcatgtttg tgccatattg atctcttggg    44400
atctcttctt tttaacaaa ttaagcgggg aatctccaaa cagtgagttg gatgttaaga    44460
tatcttgctg ctgcccccac aggcttactg gttcctgtcg aggaggagca ctccaccctg    44520
```

```
ctgattcttg gcgtgctgct caccctgagg tatttggtgc ccttgctgca gcagcaggtc    44580
aaggatacaa gcctgaaagg cagcttcgga gtgacacgga agaaatgga ggtctctcct    44640 tctgcagagc agcttgtcca ggtaggagca cagggtttac tctaggcctg gcatgtgaac    44700
aactgacatt tgaagaactg attactttgg aagagaagcg gcagaaccga gggttagagg    44760
tgtggactct ggagctgtgc tgctcggttc cgaccctagg tgctgacctc tagctgcctt    44820
ccttctgtat gccattgtca ccgtgagtca gatgcaggtg atgcctcttc aggtgccact    44880
ctgtttctaa aaccagaggt cacgatatgt gttcatacac ccagtaaata ctgattgagc    44940
acccactgtg tgctcgggtc tggggtaggt gctgggggtc ctgtggtgaa tatttccgct    45000
gcagcctctg ccctgtggag cctgtggcct ggtgcactgg tcgaggcagg gtggtatgcc    45060
ccctcaggga ggtggggacg tggtccttcg gggtgtcaga acaaaatgtt ggaacttctc    45120
tttccaatgc agagaaaccc tgcagtaatt ctaatgtact gtgattggca gttgacttca    45180
gttctttgta gcgtgcttac tcaggttatt ttcactaact gtgtaacagt gcagcctcat    45240
tttaagcaat tgaattttt gaactttact taaaatatta ggtcagggtt tttattgtgc    45300
ttaacatgtg ccatttagct aaattttgta ggatataaaa ttgtaagtga cttaaaatga    45360
ttcttgcata gaatcatgaa ttgaagataa tgctaataat ttaagcactg agttaggtag    45420
tgtttgtgaa gtgcttagaa tgcttcctgg cacatgtgaa ggccatgtaa gtgctgctta    45480
ttgataaaca gctgagcaag agtgaactct aagaaatgaa tggggctgag agttctattc    45540
cacccagctg ccctttggtt attttacaga ataaaagcag agtctcatgg gatatgacat    45600
ttaattatat ttccttcaca aaaaacactg ctgaatattt tgtggagtaa aaagggtgta    45660
gccatggcaa taatacattt aaaatatagt ttatttcatc tttaccttac ctgtttttt    45720 tttttaagct agctttatat tgagaattgc atacatgcaa aagtatcaag tcatgaccag    45780
ttacatttca tttataatcc tacttctccc ttttttttt tattatttgg aagcaaacca    45840
caatcatcct cttacttcat ctataggtat ttcagtatct ctatagatga ggactctttt    45900
ttatttttaa aacttaatga tggtcaggcg cagtggctca tgcctgtagt cccagaactt    45960
tgggaggcca aggcgggcag atcacttgag cctaggagtt tgagaccaac ctgggaaaca    46020
tggtgaaacc ccatgtcttt aaaaaaaaaa aacaaagtca gccaagtgtg gtgatgcatg    46080
cctgtagtcc cagctacttg ggaggctgag atggaggat cacatgagcc tggaaggtcg    46140
aggctgcagt aagccatgat tgtaccactg cactccagcc tggttgatgg agcaagattc    46200
tgtctcaaga aaacaaaacg aaactccaaa acaatgtcac aaaacagtgc cattgttaga    46260
cctgaaaata ttaaacattt cctacatcaa atacccacta actcattgtc aattttctc    46320 tctactcttt tggaatcagc atataaataa aattggttga taaggattgt aaatctcttt    46380
gatcaactgg ttctcctcca tccgaatttt ttttcccctt tagagttcat ttattgagaa    46440
accagattat ttgtcttcta agttttcctg tggtctgata tactgcttac atctccattg    46500
tgtaaattaa cacctttttc tgttctctgt atttcctgta catcaataat tggaggaaaa    46560
acctggtcag atttagtgta tattttatat ctgagttcag tatttcgtat ataatatttt    46620
aaggtaagag tatactcttt taaaaagtgt tgagactata tgctcaattt tttttaacag    46680
atgcttttga aaaggctgct tgatcataaa agtttagaga ccattggtct gttgggagaa    46740
gcaaataatt acgaaacagt ttagcaaggt taaggtgcac atggtagggc ctggagaggt    46800
tcagtcgtga gccgtcactg atgggcacgt ggaatctgac ccggcacaga gagctgggag    46860
```

```
aagacaggag ctttatagac agaaaacgtg gtctttgcca agtcccggga gtgaaagagt   46920
gagagaatgc tcacagcaca tgagtgtggg tgcgtagaca gagcaacggt gggtcctgaa   46980
aaggcctcca ggctttctca tagattagca agagtgttgg ttatggaggt cagaaggagg   47040
tcgaaactgt gttaaattgg gattgcagta atcctggaag gacagagata gagggtgaag   47100
gggaaaaaag ggtatggatg tgagacttaa ttgctgattt tcttaatacc tttctccaaa   47160
gtaaataaat gatatggcac attttttgaac tagcaaactc tagatatgat tatctgtata   47220
acatatctta ctccatcttc ttttgactaa taactgttct taattaaatt actgtgagat   47280
gttcaattca gcaaatgtag tttggctaac tatatttaat tagaatttaa tataatccta   47340
ggcctggcca aactattaag caagtgtggg caaaatattg ataattttag atatgcagga   47400
gctcagtttc tttctatgtg tgcttttttga aaaagaaaga aattgaaaaa tagaggaagc   47460
cctgaaatcc aagaaacaaa gtctctcatc taggcatgca ataaaagcaa ttctaggatg   47520
attgttgttc ggcatgtagt ttgttagaaa acattcttct tgaataaaata gtatgcctaa   47580 gaaagtgggc agagggaagg catatgcata tattattaac aaggagggag aaaaaggcaa   47640
ttagtaacca tccataggag agccagcaag atttataaag gaaatttgtg atccaagtat   47700
gaagcaaaat aagatgcata ataaaatttta agcaagtaat agattacagt aagagaaccc   47760
atttgaccat taattttggg gcattttctt tcaaatgaca tggagtagta atgaaatatt   47820
tctttctttc tgagtctagg ttattgtgac tggactcaga aagaaagatt tcattattgc   47880
agtgaataac attttttgaac attattcata aattatgcag tgaataacat ttatgaacac   47940
atgatacata agatacatac tgtttatttt taattaagtt tttcagctca acttctcggc   48000
agggaacatt aaatgtaaat agtgttacct agtagcatgt aaatggaaat ctccatagta   48060
tgaaagcagt gctgttgcta acagaattta ggaggcgaca gatgaggtga aggaaatgtg   48120
ggtgccgatt tccttattac attgagagga gccaggagat tctttgttca aaatagatgg   48180
cttaagaagt caaggtataa gctgattacc tagagcaggt acccacaaat gttttgtgta   48240
aggggccaga tagtaaatat tttcagtctt gcaggccatt ccaagtctgt ggcaactagg   48300
ccccactacc ttcgtagcac gaaagcagcc acaggcagcc cataaacgtg gctgtgttcc   48360
agtgaaactt tatgtacaaa agcaggtgcg ggccagacct gacctgtgta ctgtggtttg   48420
atgacctggg attcagggt ataggagtta ccatcagagg agctgaaagt gagcttttt   48480 actttatact cttctacact gtctgatttt ttaaaaaga aacatatgta ttttataata   48540
ttgaagatgg ggttggcaaa tagcaaataa aaatacagga tgccagtgaa atttgaactt   48600
cagataaatt atgagtaatt ttatgatgta agtatattcc aaatcctgtg ggacatacac   48660
tacaaaatta tttgttgttt ctttacaatt taaatttaac tgggtgccct tgtcttttat   48720
ctggcaactc taattaaagg gaaaaagaat aaattcatta tgttcatata atgtgataca   48780 gcagggtcc ccagccccca cgctgcggag cggtattggt ccatggcctg ttaggaacta   48840
ggctgcccag caggaggtga gcagcaggtg agctggcatt cccacctgag ctccgcctcc   48900
tgtcagatca gtggcagcat ttgattctca tagtgcaaac cctattgtga acagcacatg   48960
taagggatct agattgtgtg ctccttatga gagtctactg cctgatgatc tgaggtagaa   49020
cagtctcatc ttgaaaccat cccctggccc tgtggaaaaa ttgtctccca tgaaaccagt   49080
ctctggtgcc agaaaggttg gggagcactg tgatatagta ttgaaagtgc tgataaatgt   49140
ggctactgcc tttaaaatgt ctggtagctc tttctcagtg gcactcataa tagtgttttt   49200
tgatttttaa atgtgtgtca agctaactct cccctcagtg tatgctggac tttatttcc   49260
```

```
ctttcctagt caccagtttt gggaaataga gatcttcatt ctcatgctgc ttctctagtg   49320
gaagtgctcc atttattttt aaggaatgaa tataacaatg aaaaaatcat gggaattcag   49380
aaaacaacat ggaaggtaac gatcacattg gtagaagtga tagggaaata tttaggggga   49440
gaaattaagg tgtaaacttt gccaacgaag tcctgttaaa aaaaaaaaag tgaagcttag   49500
gatgcatttt ataaactctg accagaacac ctgtgtttct ctgtttctag gtttatgaac   49560
tgacgttaca tcatacacag caccaagacc acaatgttgt gaccggagcc ctggagctgt   49620
tgcagcagct cttcagaacg cctcccccg agcttctgca agccctgacc acagtggggg   49680
gcattgggca gctcaccgcc gctaaggagg agtctggtgg ccgaagccgt agtgggagta   49740
ttgtggaact tataggcaag ttattagtaa ggtctactct tacagttaac ttttcagtga   49800
tactagttac cctctattga tgatgggcct gccctgtgct aagcagtctg cattgcatct   49860
tccttgccaa aacttataat acagatttca tctttatttt ataaataggg gagttgggct   49920
gggtgtggtg gctcaggcct gaaatttcag cactttggaa ggatcacttc agcccaggag   49980
tttgagacag cctggccaag tgagaccctg tctctccaaa aaaaaaaaa aaaacaaaaa   50040 ctgggcatgg cggcacgtgc ctgtagtccc agctgctttg gaggctgagg tggtaggatt   50100
gcttaagccc aaaaggttga ggctgcagtg agttgtgatg gcagctgcac tgcagcctgg   50160
tgaccgagca agatgctgtc tcaacaaaat ttaaaaatca agaagagaaa ttaaagttta   50220
gaaggttagg tggcaaaatg aggccacaca tttaaagccc ctcctcctga ttctttctct   50280
accttgactg cctcctgtgg tggttcagtt gctgagaaat gaaaacagta gggaaggccg   50340
ggtgcggtgg ctcaagcctg taatcccagc actttgggag gccgagacgg gcggatcacg   50400
aggtcaggag atcgagacca tcctggctaa caccgtgaaa ccccgtctct actaaaaaat   50460
acaaaaaact agccgggcgc cgtggcgggc gcctgtagtc ccagctactc gggaggctga   50520
ggcaggagaa tggcgtaaac ctgggaggcg gagcttgcag tgagctgaga tccgccact   50580 gcactccagc cggggcaaca gagcgagact ccgtctcaaa aaaataaaaa caaaacaaaa   50640
caaaaaaaaa aaaaaaaaga aaatccatct gtccccagct ctgcatctgc ctccactgcc   50700
cagtctgctc ctctccatgc gcttgggggct gggccctgtc ccaccatgca gtgctgccct   50760
ggagcagtga gcttagtggg tccttttctgg catgagagct gcctttggga gctggagtgg   50820
gtgggaatct ctgaatccca gcctctaccg ctgggtctgg tgcctagcag gctatggata   50880
agcttttgct gactctagcc tccctaggc cactgcagcg tggtcggtgt agtgcactgc   50940
gtgtgcagca tggcctttac tcacagcctc cacattagag agaatctgac tgaagtctcg   51000
ttgctgcctc gtgtgagcat aaatgtttgc cggaaccatg agcaggaaat attaatctgc   51060
cttgtttcct gtcctttaca ctgaagaatc tttttctgta tgggatgcat gccttacaaa   51120
taatgagtgg aaatactcat cgctaatgaa aagttatacc tgattgttag tctaccaaat   51180
aatctgagat ttctaatact tttaatttgg cttttaaaat gcaatttatc ttagcttttt   51240
tgacttctta ggtcatatct ttagaactat gtatttgaat gttaatgtaa ttttcatatt   51300
gaaattaaaa tgttgaactg tgatgttaag tgcttcctgt ggaaatacat tcacatttga   51360
ttcaactttg aatcaagctg tttgaagatt ttcacatttc ttctagattt tatcagcttg   51420
ttactttatc tgtcactttc tgtgatttac agctggaggg ggttcctcat gcagccctgt   51480
cctttcaaga aaacaaaaag gtgattattt cagaaatcag agtcttgtgt tgaatcttac   51540
tgatttcctt gtatttctgt aatgtaatgt atcttgtatt tcttgtaata ctgtattgga   51600
```

```
ctctgtgtat gtatatatct tctcagtgga gtgattgtat gtgtgaatgt tgctggaatc    51660
tgataacaag gcctgaatag ttttataggg tggcttttaa cagttacttt catatcagaa    51720
ttgctttgtc atacattttg aatgcatcat aaatttctaa tgttcggggt cagcagactt    51780
tttctgtaaa gggacagagt gcaaacatct tagcttatg agccatatgg tctcttttgc     51840
aaccattcag ctctgccctg tggcaggaat gcagttgcag acaatacacg agctactggc    51900
cagccatgtt ccagtagaac tttacttaca ggaacaggca ggctgtagtt tgcccatacc    51960
tgccttaggg aatgtgttgt tatatttat gaagttaact taccttccca gtgaattttg      52020
tttagcatta gtcaggaata ttattaagta gcttcttttc cagcctgggc aatgtcatga    52080
gacccggtct ctaccaaaac aagaccaaac aaaaaaacag ccaggcatgg tggcatgtgc    52140
ctgtagcctc agctgctgtt ctggaggctg aggcaagagg attgtttgag cccaggagtt    52200
tgaggtcaca gtgagctgtg atcatgccac tgcactccag cctgggcaac agaatgagac    52260
ctcgtgtcgt taaaaaaaac aacaaaaaaa gtttcctttg ttggactgtt ttaatttgga    52320
cctggttatc atttttcagc catatctaac tttgtacata tcagaatgtt ctgataaagc    52380 ttaacttttta ttaaagtgtt tctgatagtt ttggtacaca ttatcatttg caatgccagt   52440
tattttcttt tccagtgggg atttgcatag gaaaaaaatt gctgtcactt tctattttga    52500
aatcttaaaa gactgatcct tttttgtgtc atgatttgag tgtttaattg agagcctaat    52560
gcctaatatt atttgcagta ttgaatggga tcttaacagg aataacattc tagccttcat    52620
tgaattaagt aaacatttct tgaaagaact tggaatctat aatatttggg tcatcacagt    52680
atgagatact taatcaaatt tgagatttta gtgaaacatt gttgaaaagc caaaagatt     52740 ctaggaaaaa ttcatctcta tattcttgaa ttaggagaga ttttcggacc tgtgactaag    52800
ttactctgac acttgtttgt ttcttagtca ctcttcccag tggcagtgaa aaagaagatg    52860
actggttcac attgttgaga ttagtttatc ctcttctggc taggacatgg gatatatcct    52920 gtctcttttta gcccttttg gtattttttc ccccatttag agctgtgtct tcaaactgtt   52980
ttgttatagc tggaaaatcc ttttttttaag tgaaatctgc ccaaattata agacagatga   53040
aagtagagtt gtgttggata taggattagg gtgcaagtgg cggggggtgtc ctggagcctc   53100 tcttctgagg gcagcctagc gcttgtgcct ttgaggaaat taccctgggg atggtctatg    53160
gaacatattt gcaaaccact gatttgaaag atagagatgg cttttgttaa gatctgaatt    53220 caccttttttg gcatttttatt tgatttctca agggaaagaa cttattttgt aataaagttt   53280 cctttttattt agtagatagg ccaagttgct gtgttaattt aacctagagt ttgggtttcc   53340
tttgctaatt tttttccacct ttaatgtcac atcattgtaa atttgtggaa gttatacttc   53400
tgacttattc tttgaagagc agaaattaga aatttccaat aattatttttg atagtgtcat   53460 ttaatgacat taatatgtaa tgtagccaca aagatttaat gagttcagtt aagtcatatt    53520
aagactgttg gtttcatttg ttttcattaa tgtaattctg aagatgaaca ataaaatgta    53580
tttttagaac tttcaagtga aatattattt catccttcca gatcatataa tgcttgagtt    53640
ctgattgtta atcataaagt caagaaaatt aaaagataat aaaatgaaag tgacttttag    53700
gtgttagagt tttatgtaca aattctggtg tgtcattgga gctatcacat gaatatttca    53760
aaggccaata gcattgggtc tttacagtta aaacttacta tttttaagtt taagtagtac    53820
tatagattat ttaataatcg aaatcaataa atattaatta ttaaaatgtt ttgtggtata    53880
ctttgagaat cattgctttt aacttttttcc atataggttt attaacttta atagcattct    53940
aaacataaca tctctacatt ctttgtgttt aatactgtag aggtataaaa atacttatat    54000
```

```
atgatgataa accatattag agtaaattaa atattcttat gagtttcatt ttagagtgca    54060
tttacttaat tttgaaatcc ttattttttag caaactaaag gaatgttggt acattattta   54120
ctaggcaaag tgctcttagg agaagaagaa gccttggagg atgactctga atcgagatcg    54180
gatgtcagca gctctgcctt tgcaggtagt tctcactagt tagccactga tgtggacctt    54240
cactctctgc cgtccacccc atgcccttcc tgcctgtccc cctgcacctg gtggacagca    54300
caactggggg cagcagtgga cccaggttgc ttaaatgggg gatatttggg cttctttcat    54360
aatacttact ctgaagcttg tgtgtctgtg gtgtttgcat catatatttg ctgttttctg    54420
tggtttagac tgttttaaaa ttaggtttat gctcccttgag catagggctt tgtgagtagg    54480
gatggcacgt tgaaacgtct catgagttgg atgggttatg ctgggggttg gaaatgggat    54540
gaaaaattgt gggatgaaaa attgcctatg gatagtttaa cttgaaagaa tctgcctttg    54600
tttacagata gttatctttt ttttttttttt ttgagataaa gagtctcact ctgtcaccca    54660
gtgccgatac ccaatgtcac tggcatggag tggtgtgctc ttggcgcact gcagcctccg    54720
ccttctgggt tccagccgtt ctcctacctc agcctcccaa gtagctggga ctacaggtgc    54780
ccgtcaccac ggctggctaa gttttgtatt ttttgtagag acgaggtttt accatgttga    54840
ccaggctggt cttgaagtcc tgacttcaag tgatccgcct gtctcagcct cccacagtgc    54900
tgggattaca ggcgtgagcc actgtgcctg gccagttaca gacagttatc taatgaaatt    54960
ctctgtgtac tttataaaag ataaggatta acttaaggta ctaataactg gattatatga    55020
gggtggtttt ggttgtataa tcctatctaa aagaatattt tagctgtaac tgaaagtaag    55080
acttaaatat ttagggagga aaatctgaat aattctagta gtaattattt acaaaataaa    55140
aatagatttt attttttgatt acacaaatta aacaacaata aaacatcaca gcgatctaga    55200
ctagtataaa ggtcacacgc ttaccaaccc aaccgcccca ggagtgacca ctgccaacag    55260
cttcgtgttg accttttttgc catgatttct atatagtctt ttttgttttt aaatggtaat    55320
taaaaaagtc aactaggaaa atgtgttaga agtttatctt ccaggagaat aataggactg    55380
gagtcgagat cttgaacgtg gcttggaaga aggcaagccc accccagaga gattacagtt    55440
gttcgggacc actgcttgct tagaggacct gcgtgtctgg gaccgcctag ttttgtgccc    55500
ctgactaggc tgccccttaa ttacgaacgt ctttataaat tgccctagcc agggcttgga    55560
gtagttggtt aagaacttga acttcagttt ttgcagtgaa acaccgtttg agaatattac    55620
cttctgataa gccttatttt attaagatgg gtactgtagc gagaggcagt gtgagtggta    55680
catgagggat gcactgctgt cctgcatttc actgtcttca ggatgctatg cagtgatgac    55740
atttggaaac atttcatcaa acattccatc aaatggaaac attggatgac agtggaactt    55800
tgtgttattt tgcaagcctt tgattccata ttgaatgttt tctctcgcca tttgacaaat    55860
gagtgtttct ctgtcttcag cctcagtgaa ggatgatatc agtggagagc tggctacttc    55920 ttcagggggtt tccactccag ggtcagcagg tcacgacatc atcacggagc agccacggtc    55980
acagcacacg ctgcaggcgg actcagtgga tctggccagc tgtgacttga caagctctgc    56040
cacggatggg gatgaggagg atatcttgag ccacagctcc agccaggtca gcgccgtccc    56100
atctgaccct gccatggacc tgaatgatgg gacccaggcc tcctcgccca tcagcgacag    56160
ctcccagacc accaccgaag ggcctgattc agctgtcacc ccttcagaca gttctgaaat    56220
tgtaagtgtg cggaggggcc tgccatcttt tattttttat ttgagacaga gtctcactct    56280
atagtgcagt ggaggccggg cacagtggct cacgcctgta atcctagcac tttgggaggc    56340
```

```
cgaggtgggc agatcnnnnn nnnnnnnnnn nnnnnnnnnn nnnnnnnnnn nnnnnnnnnn   56400
nnnnnnnnnn nnnnnnnnnn nnnnnnnnnn nnnnnnnnnn nnnnnnnnnn nnnnnnnnnn   56460
nnnnnnnnnn nnnnnnnnnn nnnnnnnnnn nnnnnnnnnn nnnnnnnnnn nnnnnnnnnn   56520
nnnnnnnnnn nnnnnnnnnn nnnnnnnnnn nnnnnnnnnn nnnnnnnnnn nnnnnnnnnn   56580
nnnnnnnnnn nnnnnnnnnn nccacccatc ttggcctcct aaagtattgg gattatattt   56640
gtgagctacc atgcccaacc ctactgtctg ccatcttttg agctcttccc tggagaccca   56700
gacctgaacc ctcctgcttg ttctcttctt gtctaatacc cctaatgaca gcgcagctta   56760
gatcactagt ggagagcttg acctcatctg ataccttcac tgaagggaac agcttagtgt   56820
cttttccact gaacactgag gtaaaaaatt ggaatagttg attatgtgaa ctctgctaaa   56880
attgagtgca ttttacattt tttaaggcct ttttaggccc tggttaaata attatttta    56940 aaaatcctga aggagcctat tataaacaga tctgtggtct taatgaaatg tgattaatac   57000
tgtgcattat tttaagaact tttgactttt caaaaaactt ttacaacatt tcccatttta   57060
tagcagcata ggtgtaagta cctctcatcc ctgagttagt ggacaagaaa ccctcatgga   57120
tagtctaata acgtttggta caagtctatg ttgttttata ctccatttta ttttcagttt   57180
taaaaactgg ttaaatatgt gtaacataaa atctaccttc ttaaccattt tttacgtatg   57240
cagcttgctg gaataaataa ttaaataatg tcatggaatc atcgctccac ccatctgtgt   57300
aaccttttga tcatgtgaca ctgaagctct gttcccattg aactctctat tcctccttcc   57360
ccgccaagtc cctggcaacc accattcttc tttctgtctt ctgaatttga ctactttagg   57420
ttctcatata ctttagggtc acaccgtatt tgttttagtt agcataacgt ccgcaaagct   57480
catgcatatt gtagcctgtg ttgaacttcc taatgtttca ggccaaatgc tattccattg   57540
tatgGatagg ccacatttg cttttccatt tctctgtcca tggacacttg tattgctttc   57600
atgctttagc tattgtgaat cgtgctgtta tgaacatgcg tgtacaaatg tctcctggag   57660
actctgcttt ccatttttt ggctaaatac ccagaattgg agttgctttt acattctgat   57720
tttaatttaa acatttata tcattgagtg ttttacttaa tagtataata gttagcaaac   57780
taatattttg gtaataattt gctggtagtt ttagagtcca ttgctcagtt tttttaggta   57840
aattacacag gacatttcaa gtggacgtgg aacaacttgt gatatggaat catgccccaa   57900
gctgatggct aaacatacga aataccatgc cctaaattta gtagatttag tctttgcaat   57960
ttaggagata acctgttata ttgttaggtt tttgtctaaa agctttgtcc tcatatttcc   58020
aacttgctgt aaaatttgtt cgtgaagaca aatattttg tatgggtttt ttcttttttta  58080 tattaaaaag aaatgtccac attggaattt ttttggagtt tttagagcta atagagcttt   58140
tcataatgta gtgggaatga gtgatcagta agctcttagc agtttccatg cacacatttc   58200
tgtgcattga aataaatgac agatgagtac atttgtgttc tgtgtgtaaa acgtgctctt   58260
tcttcgttgc atttccatgt tggagggctt gtctcttggt gatcacactt caaaattctc   58320 acagccccc ttgaaccgtt taggtgttag acggtaccga caaccagtat ttgggcctgc    58380
agattggaca gccccaggat gaagatgagg aagccacagg tgttcttcct gacaaagcct   58440
cggaggcctt caggaactct tccatgggta tgtggaccac aggtgacgcg ctacaaagtg   58500
gtcttgtatt caggcctgga catcttaatt atatctttgc tctcaagaag aaatcctttg   58560
atattgtttt ctgagttctg aatagctgat gaaaatgacc aattgaggaa taatcatact   58620
ttttcttcat ctaaatctta cgcttttgag ttatcttagc ataaatgtat aattgtattt   58680
taagtggaaa tttgtcactt aatcttgatt tctctgtttt taaagcccctt caacaagcac   58740
```

```
atttattgaa aaacatgagt cacagcaggc agccttctga cagcagtgtt gataaatttg   58800
tgttgagaga tgaagctact gaaccgggtg atcaagaaaa caaggtgagg gacataggct   58860
tgagacaact tggtgtttct gagcttgtgt gaggatttaa aatcgccctg gctactatct   58920
actttattgc tttcccatcc ctgggccttt aaatttcccc tttaaatacc agctcttccc   58980
aggcctgttg ttttccgcct ttcaggtgct actgacagcg ttaagaattg cctgagttct   59040
gcctcctttg agagtgtgcc ccagagaaat ctattctgta ctgagtgttt ccttgtctga   59100
tttcttgggc cattcatttg atggctgcgt atggccttgc accatgtttt ggttctattg   59160
aactgtttta aaagtctctg tttatattac cttttacat gtaaatgtaa ctgtcttcac   59220
ttttaattgc tcaagggcaa ggaatagcgt ttcacagttt ctcccagcaa tcagaattac   59280
agcctttggc atctccctgt ctaccaggcc cagttcgtct tagctttggg cttccccagg   59340
ctgttacctt tccctgagta gcttctgctt gtcctgtaga agaccactca tgctttgctt   59400
ccagagcagc cttttctgaa tgcctggtgt caggtgcctt cttactgtgc ccaccctccc   59460
tgcatgctgc atttatcccc tgccacagcc ctgggaccct gtgtccagct gcctctgact   59520
tgtctgtttc tgcttggtca tggtctctgt gaggtcaggt gtgcatatga gcacagacca   59580
gggcatctct ttatccccag cacccagtgt aagtgctact ctaggactat tgttgaatg   59640 aactaatgca tgaatgtatt ggttgagtat gagacaaaca agtgtcactg tctcctttct   59700
agccttgccg catcaaaggt gacatcggac agtccactga tgatgattct gcacctcttg   59760
tccattgtgt ccgcctttta tctgcttcgt ttttgctaac aggggaaaa aatggtgagt   59820 acaaaggggg acgtgcagag ttgaaggaaa taactaggtt tcagaggtca acttggtgcc   59880
cgtttagtac tgtgtgtagc agaggcagta gaatctgagg atgagtttgg ttttcactag   59940 ccaagggaa gggaggaaat gatgggagca ggtaggttac tgggtctggt tttgttcatt   60000
tgaaaacaat ctgttgtttg aggctgaagg tggcttgggt gatttctttg cagtgctggt   60060
tccggaccgg gatgtgaggg tcagcgtgaa ggccctggcc ctcagctgtg tgggagcagc   60120
tgtggctctc cacccagaat ctttcttcag caaactctat aaagttcctc ttgacaccac   60180 agaatacct ggtatgttaa aagttcacat cttatttct cagatttaat cattattgta   60240 aaacgatt cagtattgac tattttagtt ttagagcggt gttttgagtt tatttgggat   60300
tttttttttt ttttgagacg gagtctcacg ctgttgccca ggctggagtg cagtggcgcg   60360
atctcggctc actgcaagct ccgcctcctg ggttcacgcc attctcctgc ctcagcctcc   60420
tgagtagcta ggactacagg cgcccgccac tgcgcccggc taattttttg tattttttagt   60480 agagatgggg tttcactgtg gtctcgatct cctgaccttg tgatccgccc gccttggcct   60540
cccaaagtgc tgggattaca ggcttgagcc accgcacccg gcctatttgg gatatttgac   60600
ccgcgttgta gctcttcaga aaacacatga atagtgaagt tctttgtttc atggtttctc   60660
tttagatgaa atccgtagag gaaaaaaata gaaacctcag cacgtaagag ccaacttata   60720
tacgcatcgg atttaaacct aaagcacaaa ttgtgcatgg tcacggtggc gctgagtcac   60780
actcagccag gccaggcatt cacactcagg gtgagtgggc accaggactg gctgaggcag   60840
cagtggaccc gtgtctgcac cctgcccatg cttattgtgg agccttctcg ctcgctctct   60900
ttctttgggt gagagggtac acttgtgttt ttgaatttat atgaggtaag ggtttatata   60960
tagggttttt tctaatcttt ttttaagtgg aatctggaat tttaatcaga tttactatct   61020
gacagcctag aattataatc cagaaagtct gtggtattga ggacatattg gcaatatgat   61080
```

```
gaatctgtaa tccttaaatc ctgaaacttt tttttttttt taatcactta gggttattat   61140
agtgaagtca tttctgaatt tggatcttct cttcatacct cttttctct ttcctgagaa   61200 ttaagctttt gttttgagtt agaaagttga tagtaggaaa ttgttccatg gctgggcaat   61260
ttatctccac agaggaacaa tatgtctcag atatcttgaa ctacatcgat catggagacc   61320
cacaggttcg aggagccact gccattctct gtgggaccct catctgctcc atcctcagca   61380
ggtcccgctt ccacgtggga gattggatgg gcgccattag aaccctgaca ggtagtggcc   61440
agtttttcag ctgtgttttt tctagatatc cttactaagg tttccgtttc catgacgatg   61500
tttgtttctg ttcttctgtc aggaaacaca ttttctttgg cggattgcat tcctttgctg   61560
cggaaaacac tgaaggacga gtcttctgtc acttgcaagc tggcctgtac agctgtgagg   61620
gtgagcgcga tctctgtgga gccattgctt cacttagtgg gcattttatc attgctgcaa   61680
ttacaattgg agcttaatag gaaatatttc catacactct aaagctgtaa ccagtaatat   61740
ccaccatgta tccatctctt agctttagaa agaaaacatt gccagtaaag ttaatgcttc   61800
ataaacttca gtttaagttt taattctcag aatatttgtt tgaaatagac ttcttcctaa   61860
aggatatatt tagaaataac ctatcattac atgtaaagtc tgttgaatat gctgggcacg   61920
gtgactcatg cctgtaaact gagcactttg ggaggccaag gtggaaggat tgcttgagcc   61980
caggagttca agactatggg caacatggtt gatcctgtct ctacagaaaa ttaaaaagaa   62040
aaaaaaaaat taactgggcg tggtggtgca tacctgtagt ctcagctact cgggaggctg   62100 aggtggggggg attacttgag ccccggagat gaaggctgca gtgaggcatg gctgcatcac   62160
tgccctctag cctgggcaac agagtgagac tgtctcaaaa ataatagtaa taataatccg   62220
ttgaattaaa aaaaacccca aaaaccactg tgttaggccc atggtgtagt aagagttaaa   62280
gtgagcctta gggattattt actcaacctc tgtgtttgta tgaagtggaa tggcccccagt   62340 tctttaagtg atagcatgtt gaacctttcc ataccagctg gctcgtaagt cacaactggc   62400
cagtcaacaa gagtcaaaat taactagtaa aaatcaaagc aaaaaactta gaattgtcga   62460
atttgtgcga tacctccccc ttttaaaatg tcatgcctga cagtaatttt tccctagttt   62520
ccaggttttg tttcagtcaa ttgtgtctgt cttgagcaga aggaagcgtg ctaacagctc   62580
agtctcatgg ctagctgggg gtctatgtgt cagccatgca tgtgatggtg cccctgggtg   62640
cctgaggctg caggggaggg gtacagcagt aggggcctgt tctgttctcc cgtgccttgg   62700
agtacatagt gatatagtgg ggtggtcctt ggtgtaggtc cctcgttcct accctgggtc   62760 tgcgattat ttagaagtgg tgttggagct gtgcggcagg cccctttgta actgatcaat   62820
gtttgtgaag ttgccgtttg agaattgaaa ccatgacata agcagaaatg gaagaaaaga   62880
accagttatt tgaaagggac acattccactt ttaagcttgt atttactgag ataaaatata   62940
taccatcagt gttcttgaga ggtgtgggaa aagtgcaaca tcctggttgc agttaaaccc   63000
agaacgttgt gtgttgaaga ctgacagttc tcaaaccgtc aagacgcggg tactgagtgg   63060
gactaacctg ctgccctctt gcctcggacc ttgtgttcca gcattgtgtc atgagtctct   63120
gcagcagcag ctacagtgag ttaggactgc agctgatcat cgatgtgctg actctgagga   63180
acagttccta ttggctggtg aggacagagc ttctggaaac ccttgcggag attgacttca   63240
ggtaagtgag tcacgtccat tagatttcat gaactaagct caattgaaag tcctggggtc   63300
acttggtata aggaatgatg ttatcaagta ccctgcccat cagaaatctg agcggtttag   63360
gtagatgaca gtgattttct cccccccagtg gcttttttgct gaacctcgcc ctatgcgtgg   63420
attttatttt attttattat ttatttagag acatgatctt gctctgttgc ccaggcttgg   63480
```

-continued

```
atgcagtagc acagtcatag ctcactgtag ctttgaactc caggactcga gtggtcctcc   63540
tgcctcagac tcccggttag ctaggacaat aggtgtgtgc catcacactg ctaatattt    63600 tattttttgt agaaatgggg tcttgctctg ttgcccaggc tagtctcatc tcctgagctc   63660
aattgatcct ccaatcatgg cctcccaaag tgctgggatt acaggcatga gccactgtgc   63720
ctggcctaga attttaaaag ataaatagaa gagtagtttt ttttttttt ttggatagtc    63780 ctagtcattt aagtgttctg gatagtagga ataaagagc ttagaatttt tcatctttgt    63840
cttaaacttt ttaaaaaatg tagcttatgt taattctgct tgttttaaaa gaatatactc   63900
atcattatac tgaacctagg taagacagct ggtttatatt ttgttgcaat taaaaaatgt   63960
gagctgtggt tgcagtgagc caagatcgtg gccattgcac ttcagcctgg cgacagagcg   64020
agactccgtc tcaaaaaaaa aacaaaccaa aaaacgtgag ctgtgttgga actttcattt   64080
tctaagagta aagttttggc aggagaagtt ttctgtcagt actttatttt agaagggaaa   64140
tttttataat tcaggtgttt tgttttgtt tttgtttttc cccccaagcc acctttata    64200 gagcccttgt gggttatttt atttaatcct tagaatgttt ataaatctgg gactgttctc   64260
ggctccaccc acagataggg gcgctgagca tgcgtgagtg ggcagcaaga tagcaggtta   64320
tggagggccc agctcgcccc ttctgtggtt tgagccagtt ctgtacggga cttacagagt   64380
gttttgaaat agtatttatt ttgaagaaaa agaaaaacag tttactgagt gctatcttat   64440
tgagtctgga gttgtgagag gaatgccacc cctatttgtt tgaagccatc ggccttttct   64500
gttgtcttga gtaagtgctg cccaaggggcc ttccagggcg cctgactgag cctgctctga   64560
agcaagctgg cggaaagtgt ttactgagta actaaatgat ttcattgtta aatgtgctct   64620
tttgttaggc tggtgagctt tttggaggca aaagcagaaa acttacacag aggggctcat   64680
cattatacag gggtaagcgg cttattttg tgagatactg ttttacctta aggaggtgaa    64740
agtgaggctt tccttgtgga atttctctaa atgcattcat cgtatttttag atctgtttat   64800 ttcacagttt atatcatgaa agttataatt gtgtcacatg gatttaagtc tagcaatgtt   64860
gagttctttc tcactagctt tccaaaatat cttacctaaa atttagtcaa atacaagatt   64920
atgtttattt ttattatcct tctctctaaa gcttttaaag ctgcaagaac gagtgctcaa   64980
taatgttgtc atccatttgc ttggggatga agaccccagg gtgcgacatg ttgctgcagc   65040
atcattaatt aggtatttac cagtatttta tctcttttac ttttttggtt gaagtactaa   65100
aaggtatgaa catggaaaga gagggaagaa ttcaaaggat gtagagcagt attcctgaat   65160
ctgagctcat ttcagctatt ctgttcttaa actatcaaga aaaaaaaatc caaaaagtc   65220 taaaattata attaaaaaaa caaaatacta accatccatt gtaaaaagta atgcattttc   65280
attgtaaaaa tttggactat agagaatagc actaagaaga aaaaaaatca ccttcaattc    65340
tgctaccacc tggaagtaat cgctgttaat attttgctgt atactttta tgagtttctt    65400 attcaaaatg gggtcaaaat tacatgcaat tgtgtaaccc aatttccact gaatattta    65460 ttagcatttt tctgttatga aacagtaatt ttagttatgg gtcattgttt tactatgtga   65520
ttgtgataaa attttacata aattttttt ggaaattaac tattgtacat aaatgtgtat    65580
aattttcttt ttccgagaat tcctggaagt tgagttagca gcccaggctt tgaatttttt   65640 ttttttttg agacagagtc ttgttcgttt gcctaagcgc gatctcggct cactgcaacc   65700
tccgcctccc aagctattct cctgcctcag ccccccgagt agccgggatt acaggtcac    65760 accaccacac ccagctaatt tttgtatttt tagtagagac agggtttcac cagattggcc   65820
```

| | |
|---|---|
| aggctggtct caaactcctg accccatgat ccacctgcct cggcctccca aagtgctggg | 65880 |
| attacaggtg tgaaccacca tgcctggcca ggctttgaat ttaaaaaaaa ttttctaata | 65940 |
| gctttatggc ggtataattt acatttcttg aaacctactc gttttgagtg tatagtaaac | 66000 |
| ttcaatttta tcacatttct atcaccccaa aggtccttgg gcccattgca gtaacctccg | 66060 |
| gttcccgccc ccattcctag gcagccactc atctattttc tgtcccttaa gatttgtgtt | 66120 |
| ttcgtcaggc acggtggctc acgcctttac tcccaccact tgggaggcc gaggcaggtg | 66180 |
| gatcatgggg tcaggagttt gagaccnnnn nnnnnnnnnn nnnnnnnnnn nnnnnnnnnn | 66240 |
| nnnnnnnnnn nnnnnnnnnn nnnnnnnnnn nnnnaccctg tctgtactaa caatacaaaa | 66300 |
| attagtcagg tgtggtggcg ggcatctgta atcctagcta cttgggaggc tgaggcagga | 66360 |
| gaatcgcttg aacgtgggag gcgaagttga cagtgagcag agatcgtgcc actgcattcc | 66420 |
| agcctgggca gcagagagag actctgtctg aaaacaaaga tttgtatttt ctggacattt | 66480 |
| tatagaactg gggtcatagt ataaatggac ttttgcattt ggcttctttc acttaatttt | 66540 |
| gagattgggt cttgtagcat gtatcggtag tttgttcatt tttattggtg agagtattat | 66600 |
| atgaataata ccatattta tctatccatc agatggatat tattgagttc atgttttggc | 66660 |
| caatttatga attatggtac tgtgaacatt tgcctacaag atttgtatag gcatgttttc | 66720 |
| atttctcttg agtggataac ctagaagtgg atttttaaat aattttggt acttactgtg | 66780 |
| aaactgctct tcagaaacat accatcgttt gtcctttctt tcttgtcttt ctctttcttt | 66840 |
| ctttctttct ttctttcttt ctttctttct ttctttcttt ctttcttct ttctttcttt | 66900 |
| ctttctacat agacacattt taagaaaaat ttcagtagtt tttggggtac aagtggtttt | 66960 |
| tggttacatg gctgaatttt ggttgcatgg tgaagtctga gattttagta tacttgtcac | 67020 |
| ccaagtagtg tatcttgtac ccaatatgta gttttctgtc cctcaccttc ctcccagcct | 67080 |
| cccgccttgt gagtctccaa tgtgcattat accactctgt atgcccttgc gtactcacag | 67140 |
| cccagctccc acttctgaga acatactgca gaaacatacc aaaggatact cccactgcca | 67200 |
| gaatgtgatt gtgcctgatt cttctcacca ataaatattt caaaaaaagt taaatatata | 67260 |
| tcagttttt gggcagaagt tgatacttct ctttattttt tatttttttt tgagataggg | 67320 |
| tctcactcta tgatgcccag actggagtgc ggtggtgcca tctagcttac tgcagtctct | 67380 |
| gcctcccagg ttcaagtgat tctcccacct cagcctccca agaagctgga attacagggg | 67440 |
| agagccacta ctgccagcta attttgtat tttttggtag agatggggtt tcaccatgtt | 67500 |
| ggccagactg tctcaaaact cctgacctca agtgatctac ctgccttggc cttccaaagt | 67560 |
| gctgggatta caggcgtgag ctaccacacc cggctgatat tcttttttaa aataacttac | 67620 |
| cttcttttga agtaaataca tgttaaatga acaaaattta aggaaaatat aaaaaaggaa | 67680 |
| ataatctttta taatgaaact actgaaagaa aaccaaaatt acattttggt gcatattctt | 67740 |
| tttcgttttc atcattgtaa tttgcatttc tttgattact tgtgagacac acttttcatt | 67800 |
| tacttaaagg ttcgtatgac ttgcctgttc agaaattttg cagctttacc attttctgca | 67860 |
| aatgatagca acttcttttt attttttat ttttattttt attttatt ttttttttga | 67920 |
| gacggagtct cgctctgtcg cccaggctgg agtgcagtgg ctggatctca gctcactgca | 67980 |
| agctccgcct gctgggttca cgccattctc ctgcctcagc ctcccgagta gctgggacta | 68040 |
| caggcgccgc cacctcgccc ggctagtttt tgtattttt agtagagacg gggtttcacc | 68100 |
| gtgttagcca ggatggtctc gatctcctga cctcgtgatc caaccgtctc agcctcccaa | 68160 |
| agtgctggga ttacaggctt gagccaccgc gcccggccgc aacttctttt tatttgtttg | 68220 |

```
tttgtggtga cagagtctcg ctctgtcacc caggctggag tgcagtggtg aatcttggc    68280 tcattgcaac tattgcctcc tgggttcaag cgattttcct gcctcagccc ccaggtagc    68340 tgggattaca ggaatgtacc accatgcccg gccaatttt atatctttag tagagatggg     68400
gtttcgccat gttggccagg ctggtcttga actcctggtc tcaagcggtt ccctgtctc     68460 ggcttcccaa agtgctggga ttacaggtgt gagccaccct acccagccaa tagttacttc    68520
ttatattcca gaaaaaattg tactcatgat caagtctcca tgaggaaaaa gactttaatt    68580
aaagatattg cagtttgcag accaatatga taaaatagtt gattgtttct aaaagtatta    68640
ctgagtaatg atggcagata taagccctt tgttttgta ggaaaatgtt acccatgttc      68700
tgcatttgaa ttcagtttag atttgttagg aatctcagct taagctttgc catctgggag    68760
tgtttgggac aattttgcag acagaattgc aaaagtgcct aagggatgca actggcactc    68820
agacctgctc cttgctcagt actctgtgga cagatgttca gcgcttgttg atgttgatta    68880
aaaggtttag aaagagaact ttcaaagttg gttttaatt aaagcattta atagtgtgaa     68940
taaaaaggga cttaatttta tgacagacaa agaaagtac agcacctggc ggggcgcggg     69000
ggctcacgcc tgtaatccca gcactttggg aggctgaggc aggtggatca tgaagtcagg    69060
agttcaagag ttcaagacca gcctggccaa ggtggtgaaa ccccgtctct actaaaacta    69120
caaaaattag ccaggtgcgt tggcaggcac ctgtaatccc gctactcagg aggctgagac    69180
aggagaatca cttgaacctg gatggcagag gttgcagtga gccaagattg tgccactgca    69240
ctccagcctg ggcaacagag tgagagtcta tctcaaaaaa agaaaaaaga aaatacagca    69300
cccagttatg tcagagtggg tgcatcagag agtgaccctg agattggaga cgatgctgtc    69360
acgtgcttga agaatgctac ctgagaaagg gggcgagaag tggtgttttgc tggtaaccag    69420 aggtgttggc ttagccacct gcagggaggg tggtctatca caggtgagtt tcatctactt    69480
tcttaagcaa atcaacctta cttttgtgtt aggcttgtcc caaagctgtt ttataaatgt    69540
gaccaaggac aagctgaccc agtagtggcc gtggcaagag atcaaagcag tgtttacctg    69600
aaacttctca tgcatgagac gcagcctcca tctcatttct ccgtcagcac aataaccagg    69660
tatgctgacc cagtggcgtc ctcacattgt tgggaaaatg ccctttcctg atgcctttct    69720
ttaggcttta attgaaaaca ttttattttc tagaaaaaag ctttagctca ggatgtttga    69780
gtgtaggtca ttcctttgat aggatattgt cattctgagg attgaccaca ccacctctgt    69840
atttaagccc tgccacaatc acacagctgt gacactataa atcttttaat cgtttattac    69900
atttaatgtg ctgacagtta tatttttgtg tgtgacactt acgtattatc tgttaaaaaa    69960
ttttcacttt agttgtgtta cctttaaaga ggattgtatt ctatcatgcc tgttgatttg    70020
taggtgagcg ggctattaaa gtcagtgtta tttagggcta tccactagtt ctgtgatttg    70080
caatgactct ccttcacatt tgttgtggag cttttgaata tagcgtcaaa tggccacata    70140
tatcccatgc ttacctgatt cttaggtgag taggacagag tgctttaatg aagctataat    70200
cttcagaatt ctagcttgca aaggagattg cagaaggata agacttgtgc ttttcaattt    70260
tgtcttttaa atgttatttt aaaaattggc tttatatgat actctttttc tgctgagtaa    70320
cggtatttta cagaacttgg actagatgac ttctaagctt aaatgatcac ttgatgcttt    70380
ttttctgaat taggaactca gcttacacat ttcaaagtca taattcctga atacataaca    70440 tcttttttc atgtaaagac tgctttaaaa aacacatgga aggtcgggcg tggcggctca    70500
cacctgtaat cctagcactt tgggaggccc aggcgggcag gttgcctgag ttcaagagtt    70560
```

```
caagaccacc ctggacaaca tggcaaaacc tgcctctact aaaacataaa aaattagccg    70620
ggcgtggtgg tgggcacctg taatcccagc tacttgggaa gctggggat gagaatcact    70680
tgagccctgg aggcagaggt tgcagtgagc caagatggtg ccattgcact ccagcttggg    70740
ctacagagtg agactgtgtc tcaaaaaaaa aaaaaaaaaa aaaaaaagc cacaaaacaa    70800
caacaacaaa aacacacgga aacattttat ttggccacct tagtatttcc ccttcagata    70860
attcctttgt ttaaactcag aactggcatt ttctctcttt gaaagattc aggacaaata    70920
ctcctttaag ataagcagaa acagtgaaag agtatttgat tatcaggaat ttgataggct    70980
tagaataaat tgttgcttct taatgtcatt tcagaagatg aatattaata gatgccaact    71040
gagatatcat taaaattggt tactactact ttgaaaagtt tcccagttcc aaacttcagc    71100
aggcctcttc acaattcaac agtgcttaat tgggacttgt gtgatagata cgattcccaa    71160
ttgtgtagca gagtgtgctg cttagctacc tattctgtta gcattcgtgt gttaacttaa    71220
aatcataatc tccttagttt tgttgagtgt ctctgtggat gagacactgt gagggataca    71280
aaatcagatt ggctttattc aaaccattgg ggtattattt ttatttttg cctttttcc    71340
atgtgttcta aaggaattag agtttgaata taactataat ggggataga aatttacatg    71400
tgccatgaag ggaatgcaga aaagtgccat gggagctcag aagtggagaa aggaattttt    71460
tttcttggaa gcaggagtaa cttcatgaag catttatttc aacttagaga tagtaggcaa    71520
tgctgtaagg ggagtgtggc tgcagcgaaa gtgtttgggg cagactggga ggaagggagg    71580
gaataaattc agccattgtt atggcataat gatcaaaatt tattttcagc ccctctttca    71640
cttaaaagtt gagactgctt aacttctttt aatctttaat cttaaacttt taaatgccat    71700
ttgatcttta aaagatatg ttttaatagt atattttaag tctctgtatt tttcttatta    71760
gaatatacag aggctataac ctactgccaa gcataacaga tgtcactatg gaaataacc    71820
tttcaagagt tattgcagca gtttctcatg aactgatcac atcaaccacg agagcactca    71880
ctgtaagtct ctttcttgat tggtcttaat gaaattataa taattttcg tgacttgtat    71940
ggccagttag ttttatggtc atcttatggt gaggtgcttg tattagagct cttacttatc    72000
tgtgggctt gctaagaaat tgtgtttctg tgaaaaggat cttagcttac tccaggaatg    72060
taaataacta ttttttttctg attattaaag taatacatgc caaaagttaa aaaattcagc    72120
caatttagga agacataaaa atgaaaataa gccaggcgtg gtggctcaca cctgtaatcc    72180
cagcactttg ggaagccgag gtgggggct cacttgatgt caggagttcg agaccagcct    72240
ggccaacatg gtgaaaccca tctctactga aaatacaaaa attagctggg catggtggcg    72300
ggcgcctgta atcccagcta ctcgggaggc cgaggcagga gaatcacttg aacgtgggag    72360
gcagagcttg cagtgagccg agatcgagcc actgcactcc agcctgtgca acagagcgag    72420
actttgtttc caaaaaaaaa aaagagaaag aaaactactg tcacctgcat nnnnnnnnnn    72480
nnnnnnnnnn nnnnnnnnnn nnnnnnnnnn nnnnnnnnnn nnnnnnnnnn nnnnnnnnnn    72540
nnnnnnnnnn nnnnnnnnnn nnnnnnnnnn nnnnnnnnnn nnnnnnnnnn nnnnnnnnnn    72600
nnnnnnnnnn nnnnnnnnnn nnnnnnnnnn nnnnnnnnnn nnnnnnnnnn nnnnnnnnnn    72660
nnnnnnnnnn nnnnnnnnnn nnnnnnnnnn nnnnnnnnnn nnnnnnnnnn nnnnnnnnnn    72720
nnnnnnnnnn nnnnnnnnnn nnnnnnnnnn nnnnntttag tagagatggg gtttctccat    72780
gttggtcagg ctggtctcaa actcctgacc tcaggtgatc cacccgcctt ggtcacccaa    72840
agtgctggga ttacaggcgt gagccaccac accgtctttt acattttat aataataatt    72900
tatgttgctg atattagaaa agaaccataa tatccaagaa ttcaagaaca attaaattat    72960
```

```
gtacatatgc tagtgtatag tgtgatgctt tggagaattt ttaacaatgt ggagatatat    73020
aatctgaatt gtagtattga gtgaaaaaag gcagaataca aacctagtag ggggtatagt    73080
cggatttcag ttaagaaaaa taatatttac atatatacat tcctcacatt ggcagataat    73140
caccaagata cattttggga ttgtggatga ttttgtgtt ctttatattt ttcaggtatt    73200
ctcaaatttt ctaaaatgag caagtataac ttttgtcatc agaaaaaata atatgcaaaa    73260
gtaatgttaa tttgttggtg accaggttaa acctttttat ttttattatt atttttgag    73320 atagagtctc gctctgttgc ccaggctgga acgcagtggt gtgatcttgg ctcactgcag    73380
cctctgcttc ccgggttcaa acgattctcc agccccagcc tcctgagtgg ctggaattac    73440
aggtgcaggg caccacacct ggctaatttt tgtattttta gtagaggtgg ggtttcacca    73500
ggttggtcag gctggcctcg aactcctgac ctcgtgatcc accctcctcg gcctcccaaa    73560
gtgctgggat tacaggtgtg agccgctgca cccagccaaa ccttttatt ttatttgaca    73620 aaagaaatac ttgcatgtta tagaaaacta aatattgttt gggctgtctg cagtatggtc    73680
ttctcttgat ttgttcaaaa tattgtaaac tttgatttgt tcaaaatatt gtaaactttg    73740 cttattttt ttgttcttcc cttgcttgt tcaaaatatt gtaaacttta cttatttttt    73800
tttgttcttc ccttggtttg ttcaaaatat tgtaaacttt gcttatttat ttttattgtg    73860
gctgacatgt gtcagacact gttgtaggcc tgggatgtaa aaacaggatt cctgccctta    73920
cggtctctgg aggctggtca gggagatgat gtggtcagct ggagctccgc tcctaaggtt    73980
gtgcaggggc agttgagagg cggaagggtg ggacagcatt tcaaggtgtg ggcagcacag    74040
gagtctctct tcattgggat ataattgcca ttccgataac atgtatttga gttgtctaaa    74100
gtaggaagtt gtaccatggt gggacagata tctcatggtt atcatacaca gatctcagtt    74160
ctcattgttt gtactttta taagggtaa aaggagatat aattcaataa acctttgtgg    74220
tgtttgggtg tgatttatt gtttctttgt tctatagttt ggatgctgtg aagctttgtg    74280
tcttctttcc actgccttcc cagtttgcat ttggagttta ggttggcact gtgggtatgt    74340
attttcctca gtatgtatta atagttgtct acaacagtat aatataaacg tagttattag    74400
gatgcccttt ttctttcttt ttaagtcttt tatcagtttg gcttttgcaa aaatatctga    74460
tagaatactt gtttctgctg tattagttgt gtgagactag tgacaggagc tgtgggaatt    74520
gaatgccaaa tgttcttagg cattttggg aatttgaggg tgtgatcttc aagttcatct    74580
agggaatttt tcatatgctg gcaaaatact tttctcatta gcttgattct ttccagaatt    74640
atttgctgca tattagaagt ttaggaacct tttttcactt aaatgtgatc taacatatga    74700
aatggtgatg atttaggaac tactgtactt acattaacag ctttactta aaatgatttt    74760 tcccccagta gatgacccta ctcacatctg ggaataatt tcaagtcttc tccagcattc    74820
aggaataagc tttcattctg tgtatcaatt actgagaatg attttggtga ctcacatcac    74880
atttgagaag taaacctgta gatttcttgt gtgtgtcagt gaataaccag ctgacatttg    74940
cttgaagtgg attacattct ctgctctaga atgattgctt tcccgccttc ctcacatata    75000
gactgagcaa ctatggtttc tagtcatagg tccggcacta gacttgactt ctgagcaact    75060
ttggcattgg agtaaaatgt attaatttaa agaaagctaa aaattcattc aagtaaacat    75120
acagttctaa tacttttaa agtttaaaat atagataggt ttaagtgata aaaaaatatg    75180
agtagacacc ataatcctca tttctgtatc tgttcacaag gggttgatat ttatgagttc    75240
tattctccat acccattctg tgttctctta atcctcagtc agcacctcag gtggttggga    75300
```

```
ttcagttctt ggtagtttga cttatactct cttttctagg ggattgagcc ctgggtagtc    75360
ctccttatat gagattgcaa tttgtcttcc aataacttt actacaagat atggggtatt    75420
aaaggatgcc attggggaac caagataata ttagtatcag gaaaactaac cacgtcagac    75480
ctgccccatt gggtatcaag tatactattt ttccatagta ataaagagct caccccagcc    75540
aattctcttt tattttggac ctgtttattc aatggcatta agatgcccaa atgtctgggt    75600
agctatctca tctccaattc agcagaacca ttgtcatatg ccctagtgga agcattcctt    75660
cattggacac ttaggcccca gtactttat tcagatctac tacctgattt catttctcaa    75720
atgattttta tggagcttta atttatagga aagttgttag ttgattaaca gtaaaacagt    75780
ttctgagctg gtataaaaca tattgtgaca cgcttttctc ttggaattgc aagagaaagg    75840
aagactgttg tttgcttgaa attttttctat aatttgacct tgcaaatgtc tgcttccaga    75900
gtgcctccac tgagcgcctc cgatgagtct aggaagagct gtaccgttgg gatggccacg    75960
atgattctga ccctgctctc gtcagcttgg ttcccattgg atctctcagc ccatcaagat    76020
gctttgattt tggccggaaa cttgcttgca ggtactgagt tgaagcaggg actccgaggc    76080
ttggattttg atttccttag ggggaatggg ggtggtgagc atatgagggg aaaatactaa    76140
aaggtcatcg ccagtgatgg cttgtccctt tagtcaaatt tcagatgtta cctatatgca    76200
caaacacatg cagctgttct gtgctgagta ttttaaagtg gcctcttccc agtatggccc    76260
ctcagttaac tacaaataaa ctcattttga atttcatctt agtgggcacc atatgccagt    76320
actgcctcag gcactgggat ggtaagaaag tataaagtat ggactccatt ctcaagttgg    76380
ttttagatta gaggggatac atgtaaacag aagtgcagtg gtcacacaga gtggccatga    76440
tcactctcct tgggcagatt tatgggctga taggaaaggg cacaacaggg agagggtgca    76500
gcaccgtggc gatgataatg gaggatgtgg ccagcaagga agacgcagtc cattgaaatt    76560
gattttggga gaagttgcca atctccatga aagaatcggg acctgtgttc tttgctttag    76620
gaggctatag gagagtttcg tgaaagggac taaaagatga gtattttaat aagatcattc    76680
agccaacttg aatgtgggct ggaggagaag gtagagagac tcaggagatt aatgttgacg    76740
ctaaggcaag agatggggag tctaaaccaa gataatggct ttgggattgt agggaagaca    76800
ctgatcgtaa gagaatgaag gaggcagaat tgccaggcct gggtcaccaa ctgaacttcg    76860
gttgtgaaga ccaagaaacc tgggatgact tcacatcctg ggcaggtgtg tggtagtgac    76920
agtcatggaa attgggaaca cagatttgtg gggaagacat cagtttgagt ttgagtttga    76980
gtttgagttt ggcttatccg ttgaatatca gacacagatg tctggccaac tctcaacata    77040
gattagggtc ttaaatgact tcagttcccc aagcaatttg tccttcccat actgttgggc    77100
tagagaggta atatctatgc ccatatcaca gccagtgctc ctaaatctct gagaagttca    77160
tgggcctctg aagaagaagc caacccagca gccaccaagc aagaggaggt ctggccagcc    77220 ctggggacc gggccttggt gcccatggtg gagcagctct tctcccacct gctgaaggtg    77280
atcaacattt gtgcacatgt cctggacgac gtggctcctg gaccggcaat aaaggtaatg    77340
tcccacttag gtgctggatt aatatagcct taatgactgt gggtttccag actatcttta    77400
tttagtaatc tgtctcttct ttattctctt ttactttaaa tgaacaaaat tgctcagatt    77460
gtgacactaa atttaacatc aaaatgtgac catgtggccg ggtgcagtgg ctcatgcctg    77520
ttattccagt actttgggag actgaggtgg gcagatcact tgaggccaag agttcaagac    77580
cagcctggcc aacatcacaa aaccccatct ctactaaaaa tacaaaaaaa ttagttgggc    77640
gtggtggcac atgcctgtag tcccagctac ttgggaggct gaggcaagag aattgcttga    77700
```

-continued

```
acctgagagg tggagtttgc agtgaacctt gattgtgcca ctgcattcca gcctggatga   77760
cagagtcagg ctctgtctca aaagaaaaaa aaaatgtgac catgtgtttt acagctcctt   77820
tggtatcatc agtcactgtt acccctaaga gggaaataca tagctttagt tttaggtttc   77880
catcattagc caagaaagct cagaattggt tttcctggct aaagtacctc attgctgtct   77940
ccttaaatct tagttaatgg ctactgtcct ggctagcata gttatagagc atgtccatgg   78000
ttgtagaatg ttctgccaat ctcagggaca gttttgcttt tctgtgaagc aataaaatca   78060
acttcaaaac aaatgttaac tgtttgcaca atggatttaa gatagaccag ttcacatact   78120
tttttttttt tttgagacgg agtttcactc ttgttgccta ggctggagtg caatggtgcg   78180
atctcaggtc actgcaactt ctgcctcctg ggttcaaacg attctcctgc ctcagtctct   78240
agagtagctg ggattacagg catgcaccac cacacccagc taatttttttt gtattttag   78300 tagagacggg gtttcaccat gttggtcagg ctggtctcaa actcctgacc taaagtgacc   78360
tacccgcctt ggcctcccaa agcgttgaga ttacgggcat gagccaccac gcccagccta   78420
agatagacca gttcacttac tgttatatct gtttactctc tctttgctgt gtcttctacc   78480
tttaaaaatc tccccactaa cttcccattc tcctttagct gccatcagtc acttcccttc   78540
tctgcaaaca tctctggaga gtctcagcct cagcccacag agcttccac tgctctgagg    78600 tggaccttgt ttgtaagact tcttggcct cttggcctgg accctgtcta ctacttcagc    78660
catccttcct taaccatcgc tagtggtttt tgttgccacc ctccatagca gcgtttccct   78720
tccagatcat gtctttacat ctctgggcac tgctctggtc ctgcctgcct ttccctctct   78780
gtaccctgca ggccgctgcc gccatcttga gtgtcctctt cacttggctt tcagagggcc   78840
cacagagttt cccactgctc tgaggtgggc cttgtttgca atacttcttg gccctcttgg   78900
attactgcac tagccttttg ttttggaaac agcattttta aaaaaattta attttatttt   78960
tttgagatag gatgtcactc tgttgcccag gctggagtgc agtgtcatga tcgtagctcg   79020
ctgtggcctt gatctcccag gctcaagtga tccttctgcc tcagcctcct cagtagttgg   79080
gagtacaggt gtgcaccacc atgcccagct agttttttga ttttttttct tttttctttt   79140
tttttgagac agagtctcac actgtcgccc ggactggcac aatcttggct cactgcaaca   79200
acctccacct cccaggttca ggtgattctc ctgcctcagc ctcctgagta gttgggatta   79260
caggcgcctg ccaccacaac ttttttgtatt tttaggagag acggggtttc accatgttgg   79320
ccagtctggt ctcgaactcc tgatctcgtg attcgcctac ctcagcctcc caaagtgctg   79380
ggattacagg catgagccac tgctcccagc caggaaacag cattcttgag ataattcata   79440
taattcaccc atttaaagta tataattcat tctctttagt atgcccacag agttgtgcag   79500
ccatcaccag aatcagtttt agaacccaca aaggaactct gtaccttca cccaaaacct    79560 tccatgcccc cagctgcagg cagccactga cctaccttct gtctctgtga ctctgcatct   79620
tctggacatt actgtggatg ggctcataca gtcagtgagc ttgtgactgg tgccttctac   79680
caagcagggt tttcagtgca gtagcctttc tttcttttt ttttttttaa attgagacgg    79740
agcttctgcc tcccaggttc aagcgattct cctgcctcag cctcccaagt agctgggact   79800
acaggcccat gccaccatgc ctggctaatt ttttttttt ttttgtattt ttagtagaga    79860
tggggtttca ccatgttagc caggatggtc ttgatctcct gacctcatga tccgcccacc   79920
ttggcctgcc aaaatgctgg aattacaggc gtgaaccacc acacctggct aacctctcat   79980
gtactgtctg cggttcttcc ctgatgcctt ccagtccatg cacccgattg tagcccctca   80040
```

```
tcctattatg gtttaaggtg actgtcttag tcaccatggg ttgccataac aaaataccat    80100
agcctgggtg gcttcaacaa cagaatttac ttctcacagt tctagaggtt aggaagttca    80160
agatctagga cttttcacctt gccctcacat ggtgaggggg tgagggagct ctctggtgcc    80220
tcttatatgt ggacgctaat ctcattcatg agggtctgcc ctcatgcccc agtcacctct    80280
caaaggcccc acctcctaat accatcaccc tggtaattaa gtttcagtgt atgaatttgg    80340
gggactatag acattgaaac cataacaagc acttttctaa aagatcaggg agtgagtaag    80400
taccagagct aggacctcaa ttccacctct cggtcatctt gccttcactc tgctccatga    80460
tggctgcctc ctagagtgat gggagcctcc atgttttata ttctctcatg tgttgtgtat    80520
tggagagagt tcagacttta tgaatacatc tggatttgtt gacttctagc tttgctggta    80580
accagctgtg accttgagta aattacttca tctctgagcc tgtttcctct tttgaaaag    80640 ggagtttaaa atgctgtttt gggttgggca tggtggctca tgcctgtaat ccagcactt    80700 tgggaggctg agatgggagg atcacttgag cttggagttc gagaccagcc tgtgcatcat    80760
agtgtgagat cctgtctcct caagaaatta aaaaattaac tgggtgaggt aacgtgtgcc    80820
tgtgggccca tctactctgg aggctgaggt gggaggatta cttgagcctg ggaggttgag    80880
gctgcagtga actatgattg cgccccatcc cgggtggcga gtgagaccct atctcaaaaa    80940
aaagaaaaaa aaatgctgct ttgcacccct ttctcatgtc atggtgtcat ggctaacatc    81000
gaatgccctg gttgttgct gttggaaggc gtgggcctag gggctccctg aggactcctt    81060
ccatcttcaa ttcgttctct gtgtacctgt tagcaagttg tgggccagtc cctgccatgt    81120
accattgtgt gggtaaaagt aaataaaatg tgtacagtgt ctgaactgta catataggg    81180 tccaagaaca aaatgaatga catgggttag ctctttctaa taaatggtaa aaccaaatat    81240
tctaattttc agttttgtta tacttccatc acatgttttt gttttttgtt tttgtttttc    81300
tattttaggc agccttgcct tctctaacaa acccccttc tctaagtccc atccgacgaa    81360 agggggaagga gaaagaacca ggagagcaag catctgtacc gttgagtccc aagaaaggca    81420
gtgaggccag tgcaggtagg aaacagtgtg gggaagggag ggacaggagt gcagcatctg    81480
tcatgtagca acataggatt taagtaactt ggtgttttag agaaatataa tacacatcag    81540
taaagtgaga gaaggtttct ccaggtgcgg ttcaagatat tagaaactaa tgactaatat    81600
acacagacca ccttttggtc tgaagcatct ctaagtgcca cctgctgaca cgcagccct    81660 gcagcctcca ggcttccagc cccagcacgg agcctcactc tcctgtgctt ccctggttgc    81720
gggtgagggc tggagaggcc tcctgatttt cagtaaggga agtggtgtag atgcttagga    81780
atagatatag tgagtgaaaa aattgattct gatatgtcaa aatttctgat tggaaatgga    81840
atatttacat ttggaagaac taaggagag agaaagtggg gataaagtca tctgagttgg    81900
aggagcttaa accatgcaca agtttggagg accttttttt aacccatgaa aaggtcagaa    81960
cagaaggggc taggatttag ttgtgactgc agttttcga attcccatcc atactgctct    82020
tggagggcag tggcaggggc aggagaggag cctggcaaag catgaagtga ctgctgctgc    82080
ctctgctatc tgggtcgcct ggctgcctgt ctgtacagtc tccctccaaa cccattctct    82140
cgctgtctct tggtgcccag gggccagtga tggttctccc gtttgttttg tgtatatagc    82200
atttatatca aggctattta tttatttaga gacagagtct tgctctgtcg cccaggctgg    82260
agtgtagtgg tgcaatctcg gctcattgca agctccgcct cccaggttca gcaattctc    82320 ttgcctcagc ctcccaagta gctgggacta caggtgtgca ccactacacc tggctaattt    82380
tttgtatttt ttttagtaga cagggtttt caccatgttg gccaggatgg tcttgatctc    82440
```

```
ctgaccttgt gatccaccaa cctcagcctc tcaaagtgct ggaattacag gcatgagcca    82500
ctgcacctgg cctatttatt tatttttaat tgacaaaatt gtatatgtct gtagtataca    82560
acatgatgtt tgaaatatgt atacattggc caggcgcagt ggctcannnn nnnnnnnnnn    82620
nnnnnnnnnn nnnnnnnnnn nnnnnnnnnn nnnnnnnnnn nnnnnnnnnn nnnnnnnnnn    82680
nnnnnnnnnn nnnnnnnnnn nnnnnnnnnn nnnnnnnnnn nnnnnnnnnn nnnnnnnnnn    82740
nnnnnnnnnn nnnnnnnnnn nnnnnnnnnn nnnnnnnnnn nnnnnnnnnn nnnnnnnnnn    82800
nnnnnnnnnn nnnnnnnnnn nnnnnnnnnn nnnnnnnnnn nnnnnnnnnn nnnnnnnnnn    82860
nnnnnnnnnn nnnnnnnnnn nnnnnnnnnn nnnnnnnnnn nnnnnnnnnn nnnnnnnnnn    82920
nnnnnnnnnn nnnnnnnnnn nnnnnnnnnn nnnnnnnnnn nnnnnnnnnn nnnnnnnnnn    82980
nnnnnnnnnn nnnnnnnnnn nnnnnnnnnn nnnnnnnnnn nnnnnnnnnn nnnnnnnnnn    83040
nnnnnnnnnn nnnnnnnnnn nnnnnnnnnn nnnnnnnnnn nnnnnnnnnn nnnnnnnnnn    83100
nnnnnnnnnn nnnnnnnnnn nnnnnnnnnn nnnnnnnnnn nnnnnnnnnn nnnnnnnnnn    83160
nnnnnnnnnn nnnnnnnnnn nnnnnnnnnn nnnnnnnnnn nnnnnnnnnn nnnnnnnnnn    83220
nnnnnnnnnn nnnnnnnnnn nnnnnnnnnn nnnnnnnnnn nnnnnnnnnn nnnnnnnnnn    83280
nnnnnnnnnn nnnnnnnnnn nnnnnnnnnn nnngcacttt aatatttagt atcggtttaa    83340
tgataatgtt tgtgccctta ctgtctttaa aacattttta cgtcatccct gtttgattac    83400
ttggtgtgct catgaagttg ttggccacta gggaatctta ggctcagaga ggttctggaa    83460
ttggtcagtg gtccttgaat tagccgctcc tatgattctc taactgattt ctcaaaaagc    83520
aaacaagcaa ccacagcaaa acagctgtgc acaccactct tcttattttg ttattgtttt    83580
agtacttagg ccgtacttat gtttgttagt cagtttctca ttacttctag ttaatcaaaa    83640
gatcagaggc aatatttgag tatttcata ctagaatgct ttaaaaaag tcattattgg    83700 ccgggcgcgg tggctcaagc ctgtaatccc agcactttgg gaggccgaga cgggtggatc    83760
acgaggtcag gagatcgaga ccatcctggc gaacacggtg aaaccccgtc tctactaaaa    83820
aatacaaaaa actagccggg cgagatggcg ggcgcctgta gtcccagtta cttgggaggc    83880
tgaggcagga gaatggcgta aacccgggag gcggagcttg cagtgagctg agatccggcc    83940
actgcactcc agcccgggcg acagagcgag actccatctc aaaaaaaaaa aaaaaaaaaa    84000
aaaagtcatt atttccagta atctctttaa aacttggcaa gttattttga tctaaaagtt    84060
tatcttttgt gtgcacattt ttaaagcttc tagacaatct gataccctcag gtcctgttac    84120 aacaagtaaa tcctcatcac tggggagttt ctatcatctt ccttcatacc tcaaactgca    84180
tgatgtcctg aaagctacgc acgctaacta caaggtatgg gcctctgcat cttttgaaaa    84240
tatatatgcc cacatactta tgtctaatgg atcgttgatg tttttcttat gatttgtagg    84300
acgtataagc cctttgagat atgagttaca attcgtgttt tcaagtttgt ctttcagctt    84360
tgtttatgat agcatctgtc atacaggtgt tttggatttt catattgttt gtactcacag    84420
ctaagattga ttacgtgaga gagctaggat gtgcagccag gttattgggg gaagtggcct    84480
cggtggagtc tggagggatc tgtgtacagg cttccttccc tcctgtgagg ctcacacaaa    84540
aatacagcaa cctgctggtc ctgcaggtcc cctctgccta acatgagcca caattccaga    84600
ctcacagaag caggcgttca gcataaacca cgtgtttcaa atagtctggg cgttgtgagc    84660
cacttgttat cagctaggga aagttttat gtcagtgtaa ggaactgttg accagataac    84720
cccaagagcc ggcctttctg tctagggatg ttttagtttt ctagttcatt ttttttttt    84780
```

```
taactttaaa attttctatt catctgcaat ttgttagata tgaagtacgc atctaattta   84840
attttggttt tggttgtccc caatgctgtt tacagaagaa ttttttttgca ctaattggct   84900
taagttactt acattctcat agttctctag tttcatttgc cattttgtta tatcaatcta   84960
tctgtctgct catctattag aagcatcctt tttttcctgt tgtagacagt ctcgctctgt   85020
ccccaggctg gagtgcagtg gtgcaaccat gcctcactgc agtctcaacc tccagggctc   85080
aagtgatcct cccacctcag ctcctgggta cctgggacta caggcatgtg ccaccatagc   85140
cagctgcttt ttacattttt tgtagagaca gggtctccct aagttgcctg ggctggtctc   85200
aagttcctgg cttaagtaat ccttcctcct tggcctccca aagtgctggg attacaggcg   85260
tgagcaactg cacctggcta gaagtatact tcttagttat tatagcttca tggtatttat   85320
gatgggatca gttctcctgt tctttagaat tttctggata ttcttctttg ttgattttgg   85380
gatgtgaaca atagaatcaa cttctacttg taggttgatt tagggagaac ttatacctca   85440
gatgttaagt taccctgtcc agaatgtggg atgctttcct atttgttcaa aacgttttaa   85500
attacctcag aagcacatga aatttaaagg attttaaaaa aaactttaaa gattatttca   85560
catagctctt gcacattttct tggtaaatga atcctcaggt gttcttctgt ttttgttact   85620
aatagatact tctcatggtt gttttttttt tttttttcct gaaaatcatt tgtcaaactt   85680
atgtggcttc ttttctgaag gatgtttgat aattttggaa gatataaaag tcttcatatt   85740
ttacaaggtt tggagtctct ttaagctgcg tggttctcac gtcagctccc aaagcagaag   85800
acggcatgtc gaaaaatgcc atagagaagc tacttctttt ccacctgttt tcagctcata   85860
tcatcttgaa tttcggggca cctttctatg ctcctagtgc ttgctgtctg tttattattt   85920
tccttcctga ataccctgaa ctccagcatg ttctgctgta attctggcct ccctggcgtc   85980
ttggactcct gtttcctttg ctctgtcatc cccacggtca gctcctgctg cgcagcttct   86040
cagctgaact gtttggagtg gctggcgggt cttgctggat ctttgagtat tgcctctggt   86100
ttccttggtt ccttctgctg agttgctcag cgtctccact ccccatttct cgtgtggccc   86160
ttcctgctct cctctgattc cttttgtctt ccctggtttc ttgctttggt tttcagtctc   86220
cgcagaactt tgccactct tctgaaaacc cggaggcttt tcatcttaa ttctcatttc   86280
atgacctctt ttcccttatt tgagaggtag accttcccat ggtgagcttc tctttccaga   86340
attccatgtc ttcttttccc tcccacttac ctgttgtcca ggagaggtca gattgctgtg   86400
cgcattggag aagaacccctt tcttccctgg gctcttcatt tcacatgaca tcaccacatc   86460
acctcatccc ttggaccctc agtggtggca ctgctggatt tttctttcct ttggctggcc   86520
ttggggcaca cccaggttga ccctagctta gtcatggtat ttagatcaac tcacattttc   86580
agttctgtg tctgtctctt gcctgcttct gactttgccc agagaaagct ttttcacaag   86640
ggttcttaga tttacgagca ccttctttcc tgaggcagtg tttttgccaa tatttatttt   86700
cctagtcagt ctcgccttac ctttcttgtt atacatgatg tctttggtcc tgacccattc   86760
tctgagtctg taaaatagaa ttgctgtata atttaattac atgaaatcct ttagaatctt   86820
aatacatctt acaccaggtg taacatttta tgatatccaa attgaacaac cctgtgtgaa   86880
tttgacagtg atttctccca gggatcctaa tgtataagga ataggacttt gtattttcta   86940
tttttttgata taccacatac cagatactga tcatgatgga catttaaccc ttttttttctc   87000
attaggaaag aaagttagga attacatctt tcagtagtgc cagtgtgacc tgaaagatgc   87060
ctttgaagaga gtagtttttg tatagctatc tgaaaggaat ttcttccaa gatattttcc   87120
cagtgctgac aacaaacacg cagacacgcc ctacaaggtc aatgtacagc gccgcacagt   87180
```

```
ggaggcgtct gccgcagccg ttaatgtttg tatctttggt tgtactttac gagatcttga   87240
cggggccagt aaccgtgtgt tctctccttc accttctcaa ggtcaccttg gatcttcaga   87300
acagcacgga aaaatttgga gggtttcttc gctcagcctt ggacgttctc tctcagattc   87360
tagagctggc cacactgcag gacattggga aggtctgtgt cttgttttga cgtgcgtcct   87420
ctgggctgag ttcatctagg atggagtccg gttctccagg gtgcctccgg gagactcctc   87480
cctgcgccac ggacttgcat cacaggaccc gagtctgact ctgccttagc catgaagttt   87540 gggggggaagg ttctatttgt attctgtttt tgtctgttat cacgtattag cttagaccca   87600
gtttagttta gaaaattggt gggtttaaaa atgtgtttat agagtccttt atttcttaat   87660 ttgaccttt caagtggaaa ggggcaaaac agacagatga ggggcgggg cgggaggtgt   87720 gacttgctct tttgtgcctg aggaagtaac agagctgggg ttgacagtta tattctctgg   87780
ttttatgtcc aggaatttcc cctgccgcac ccctagttga tagcgaaaat gttcaaaact   87840
atgagaaagt tagaatgctg tggtaaacac tctattatgt acacacaacc cagcttctgc   87900
agttgtttgc gtttggctac gtttcctttc tatgtatata gccatctctc catttaccag   87960
tacatcttac tttataatgc attttaaaag gagtgacaga tgcctccctc caccaaatgt   88020
gtgtcttcac gtgaaataca gtatgtctga tgcacttcat ttgttcttat gtctttgaat   88080
ctttttatct ggacatggac acaaggttac ctagttttaa tcgttacata tgttagtgct   88140
tcttctctgt tattcctcat gttttttccca tgtatctatt tagtgtgcgc agttgtcatt   88200
tttaatggct atctagtgtc ctgctgtgtt gatactccat cgttcccttc gagtaaaact   88260
tgttgagact tcagtaatgt cacctgctca gtgagacttt cctggccatc ctttcaaaac   88320
ttgcttctct ctgtactctc ttttcctgtt cattttttctc tttgacccat agcatcgtct   88380
aacagtcaac cttaaaataa ataaataaat aaagacttca gagaaatgtc caaatacatg   88440
gagtcagttt gggaatgaga aatgaggatt ataatccggg atgcacggca tgtccggctg   88500
ccagtgcctc tggtgaagga aggggaaggg gaagctgtta ttgtcagaaa gggagagaat   88560
cacataggct ccctggaagc agagttcgtt ggctccagag gctgaaagcc agagttgtcg   88620
tcattcactg gtggaattgt aggcaccggg caggtgttca gttgagagta ttttaactga   88680
attgctgcag tcctccagaa tggctagtga taaatctggt catagaaaca tgtattcacg   88740
tggaacatgc aagccatgca cagcagatat gtaaaggatg tacgggaagg gtttcttcta   88800
gggttgttgg aaagtctttg gaaacagctc taacctgggg cacataagca tgaaccccat   88860 ctcccttgt gctttcctag tccaatttg tctgggtctg acaaagtgat tgatccctg   88920 tatctgcaac tttcacaaaa catactattt atttatttta cttccttgtc ttttcagtgc   88980
ctatagcagt gcctggaaga ttgtggaatt tagtgaacat tgttgaatg aatagatgtt   89040 cttgttaaaa atgagtttta gtgtctcatt tatcttacat ccacactgtg gtggagccat   89100
attagcccat ttcacgccat aactggaagc tgaaagatgt gacattcttg gggccagata   89160
agtcagtggc agagcctgag ttaagtctca tagatttct tttttctttt tcgttttgg   89220 tggctagctt tggttttatt tttatttatt tatttatttt tattatactt taagttctgg   89280
gttacatgtg cagaacgtgc agttttgtta tataggtata catgtgccat gatggtttgc   89340
tgcacccatc aacctgtcac ctacattagg tatttctcct aatgttatcc cttccctagt   89400
ccctcacccc cgatgggccc cggtatgtga tgttcccctc cctgtgtcca tgtgctctca   89460
ttgttcaact cccacttgtg agtgacaaca tgcagtgttt ggttttctga tcttgtgata   89520
```

```
gtttgctgag aatgatggtt tctggcttca tccatatccc tgcaaaggac attaactcat   89580 cctttttat  ggctgtatag tattccatgg tgtatatgtg ccacatttct taatccagtc   89640
tatcatcgat ggacatttgg gttggttcca agtctttgct gttgggacta gtgccacaat   89700
aaacatacgt gtgcatttgt ctttattgta gaatgatata atcctttggg tatatgccca   89760
gtaatgggat tgctgggtca aatggtattt ctagttctag atctttgagg aattgccaca   89820
ctatcttcca caatggttga actaatttac actcccacca acagtgtaaa agtgttccta   89880 ttttccaca  acctctccag catctgttgt ttcattaatt tttaatgatc gccattctag   89940
ctggtgtgag atggtatctc attgtgattt tgatttgcat ttctgtaatg aacagtgacg   90000
atgagcattt attcatatgt ctgttgactg cataagtgtc ttcttttgag aagtgtctgt   90060
tcatatcctt tgtccatttt tagatggggt tgtttgcttt tttttttttt ttgtaaattt   90120
gtttaagttc tttgtagatt ctggatatta gcccttttgtc agatggttag attgcaaaaa   90180
ttttctccca ttctgtaagt tgcctgttta ctctgatgat agtttctttt gctgtgcaga   90240
agctctttag tttaattaga tcccatttgt caattttggc ttttgttgcc attgcttttg   90300
gtgttttaga cattaagtct ttgcccatgc ctatggcctg aatgttattg cccaggtttt   90360
cttctaggat ttttatagtc ctaggtcttaa tgtttaagtc tttgatccat cttgagttga   90420
tttttgtata aggtgtaagg aaggggtcca gtttcagttt tcagcatgtg gctagccagt   90480
tttcccaaca ctatttatta aatagggaat cttttcccca ttgcttatgt gtgtcagatt   90540
tgtcaaagat cagatgctgg tagatgtgtg gtgttatttc tgaagcctct gttctgttcc   90600
attggtctat atatctgttt tggtaccatg ctgttttggt tactgtagcc ttgtagtata   90660
gtttgaagtc aggtagcgtg atgcctccag cttttgttctt cttgcccagg attgtcttgg   90720
ctatgcaggc tctttttgg  ttccatatga agtttaaagt agttttttcc aattctgtga   90780
agaaagtcag tggtagcttg atggggatag cattgaatct ataaattact tgggtagta   90840 aggccatttt cacaatattg gttcttccta tccatgaaca tggaatgttt ttccatttgt   90900
ttgtgtcctc tcttatttcc ttgagcagtg gttttgtagt tctccttgaag aggtccttca   90960 catctcttat aagttgtatt cccaggtatt ttattctctt agtagcaatt gtgaatggga   91020
gttcactcat gatttggcac aatctcagcc cactgcaacc tttgcctcct gggttcaagg   91080
aattctcctg cctcagcctc cagagcagct gggattacag gcacctgcca ccatacctgg   91140
ctaatttttt gtattttag  tggaaacggg gttttaccac attggccggg ctagtctcga   91200
actcctgacc tcgtgatcca cccacctcag cctcccagag tgctgggatt acaggcttca   91260
gcaactgcgc ccagccagat tttcagatct ccctctcttt gccctaaacc actgtgctta   91320
ataagaattc tttagtggcc agcagtctcc atgtgtaaca cattgtagca aaatggaaaa   91380
tattacatgt tttaaatttg agtgtgagat atactgaaat aaaaatcatc taaatgagat   91440
tctttaaata ataagatttt cttttttgta tgtgggtttt ttttaacat  tattattatg   91500 actgtcgtat atagaaatgg ctgttttcaa ctacagtcag tgaatgtatc aaatgctgcc   91560
ttatccaaat aataaaagta aatgattaac aagtcacaat ttagtgaaga ttgatgttag   91620
ttgatcttta tattcctgaa ttagccacat ggttgtgtgt gtgtatatat gtttagaggt   91680
acatatagat aataagctca tctctgaaaa ttttttacatt tggcataaga ataactggat   91740
aattaagcat cttattctct ggcctgtgtc tttacagtta aaggtagatt tactcacctc   91800
tccttttttg tttttctcag ttcatctttt ttgctatttc atgacggagg cccatttac   91860 ctttctcgta tatcctttg  tttgtacttt ggaagcctca cctgcttaat tgttgagttt   91920
```

```
ttaatctgtg gtcttttaga ggaggatgtg tagggtagaa gctttcacag gttcttcttt    91980
gcacttggcc cttggctgtt ttgaggaatc tccctcacta actcacagca tagcaaggtt    92040
tgagatctct tctgccacac agcagttccc aggcagctgg aaagatatgc agatgctcag    92100
attgtcaggc cagccttgag atatacaaac tactgagcct tatctgtgac cttgcttagg    92160
tgaaggcatc agagcccctg caccgacatg tgtaggcctc tggatgtgtg cggggctggg    92220
tgttggggtc tgagcacaag tgtagctgga gaggtgagct tgttgtggtg acgggtatga    92280
gcaagttttc ttcagacttc tgtgagttta cctcgttcca ggatttaaag gcacagagac    92340
cttagaatta aaatagaatc attttctttt tctaaatagc aacactagga ataaaaaata    92400
ataattccac attctttaca ggtaatgttt tgttttctt gtcttctaat ccttatttat    92460
tctgtactta ttttttatacg tatttgaaat gtattatgtg ttggagtttt cttttgcat    92520 tatattatac acggttttc atgtaactcc ttactgttcc attttatatg ttttgtctgg    92580 tttatttaa gactttatca gcaaatcggg aaaccgtctc tacaaaaaca aaaacaaaag    92640
caaaaatagt tggccacagt ggcatgcgtc tgtggtccca gctactcggg gctgaggtgg    92700
gaggattgcc tgagcccggg aggttgaggc tgcagacaac catggtcgtg tcactgcact    92760
ccagcgtggg tgacagactt tatactgtct gtttggggtg atttggtaat gatatgccct    92820
gatgtagttt ttttatatct tgtgtttctt gtgcctgggt ttattgagct tgggtctgtg    92880
gcttcatagt atttttaaag tttggaaaat tttagggcat tatttcccca aagatttttt    92940
tctgccctgt tcccctcctt ttttcctct cttaaagggg ctgtgatttc ctgaatgatt    93000
gcttagtgtt gtcccatagc ttattgatgc tcttttcagt gtttttgtg ttttctgttt    93060 tctatagttt ctattattgt atttgcaagt tctctaactt ttcttctacg atgtctaatg    93120
tgttgtttat ctgttaatct attgttaatc ctgtccagta ttttttttt tttttgaaa    93180 cagtctcact ctgttgccca tgctggagtt tagtggtaca atctcggctc actgcaacct    93240
ccacctccca ggctcaagca attgttctgc ctcagcctcc caagtagctg ggactacagg    93300
cacgtgccac cacacctagc taattttgt atttttatta gagatggggt ttccccatgt    93360
tggccagact ggccttgaac tctgatctca ggtgattcat ccacctcggc ctcccaaagt    93420
gctgggatta taggcatgag ctaccttgac tggcccctgt tcagtgtata tcactaattg    93480 tgttttatc tatataagtt tgatttaggt cttttaaaaa tttctccctg tgtctctact    93540
tagctttgtg aacacagttg taataactgt tttaatatct ttctctgcta gttctaagat    93600
cttctaataa cttcctggtt ctcggtgttt ttgattggtc tattgatgct ccttgttgtg    93660
gattgtgctt tcctgcctct ttgcatcgct gccaattttt ggttggatgc ccaacattgt    93720 gaatttact ttgctggatg ctagacattt ttgtgttcac agagatcttc ttgagttttg    93780
ctctgaggtt agttgagtta catgtagatg gtttactctt ttgggtcttg ctttataatg    93840
agtactctac ctaatgaacc agaaagttcg ggttttccag tctgcctgct gagaacggtg    93900
actgtttcta gccctgtgtg agtgcccgag cgccgctccc tctgatcctt tctgatgctt    93960
ccctctgtgg cctcaggag tttcctcaca cacacagttc tgctgagtac tcgagggtc    94020 cttccccgat ctccaaggct ctctctgtct tgttctctct tctctggtgc tctgtcctat    94080
aaactgtggc tatcttggtc tccttagatt ctcagcacct cttcaattca gagggttgcc    94140
tgtccctcct ccttgtgcca cagcctagga actctcttaa agaagtgagg tggggcagct    94200
gtggggctca ctttgtctct cgtctcccag ggatcactgt ccttcatggc tgatgtccaa    94260
```

```
tgtcttaagg actctggatt ttgtctgttt tgtttttgg ttggctttgt ttgtttcaaa   94320
caggagggta aacccagttc ctcactctca ttgtgctcag tactggaagt ctcgctctgt   94380
tatattggat attagtattt gtagcagagc cctggttccc tggtacttgg ggagctcttg   94440
aaaggccaga acagcatgc tttctcacct ttcccagggc ttccgttttct ggtgcacaca   94500 aagcattcca tacacatttg ttaaagttct ttgttagaca aatagtgatt cacaggctct   94560
atttgtaatt ttttcagtaa gcatgtatta gatatctgct gggagctagt agaaacaaaa   94620
agtgacatgt gacaaattca attctgacaa gaacaacctt aaacatttag aatataattt   94680
gagtaaatca gaattttaaa aatgtgtggc ccttgaatat ttgaaaccaa caagaatcta   94740
ttgcttatta gtagaggata ttttgttgaa caagtggaga gagaggcatt ttcagtctaa   94800
ctggtgttgg cttttagcag ctgttggaaa ccggttcatg attagccagg cagtggtgaa   94860
acaggctgtg cattctgaat gcctagattg gtggcactct tcgagttagc atcttcttct   94920
ttcttctttt ttttgagatg gactttcact cttgttgccc aggtaacaac tccagtgcaa   94980
tggtgccatc tcggctcact gcaacctctg cctcccgggt tcaagcgatt ctcctgcctc   95040
agcctcccaa gtagctggga ttacaggtgt gcgccaccat gcctgactaa ttttgtgttt   95100
ttagtagaga tgggggtttca ctatattggt cagactggtc ttgaactcct gacctcaagt   95160
gatccacctg cctcgacctc ccaaaatgct gggattacag gtgtgaacca ctgctcccag   95220
ccccttcttg attcttgtaa aggacattgg gtgctgtaca ccttgttata gatgttgata   95280
aaaattcttg tgagaatagt aacgttaagg tagttgtttg gtcattttg tctatcagta   95340 taagataatt ctaggactga tttgtggtaa atcacacatt gctgtatcat agttgtgttc   95400
actgaacata ttcaggggct ttacagatgc agggctctta gctgctttgc gcacttctga   95460
attcctgccc tgagaacagg actggatacc tagtagacga taggtatttg ataacagttt   95520
aatgaattaa tgagtgaatg aacagatacg taggtatgtg aaagaatggt tgtaatgtat   95580
gtaacttgga tttcaagact tactctgttc aaataagaaa tggaaaactt tcctctgatt   95640
ttgctctact atttacactc tttaaatgga agttatcttg tacctttgat ttctgtctag   95700
gattcgtaca ataatgggtc atctctgagt cacttacggt ctcactgttc tttccacagt   95760
gtgttgagga gatcctagga tacctgaaat cctgctttag tcgagaacca atgatggcaa   95820
ctgtttgtgt tcaacaagta agagcttcat tcttttccta ttctgttaag actttcaggt   95880
atgacgacaa aatgctgcta ctccttaagc agcaggtgct ggtggcgtaa tcagctggga   95940
ggattgtggg gtccagcata gcactttttcg gctcattcca tgattgagcc aagaggccga   96000
ccttcccgtc attccccagg aggacgaggt ctgtcattgt ggagagcaaa ggacatcaga   96060
agctcccctg catcctcact cgttaacttc cagtccctcg gggttttgt ttagcgtgct   96120 caatctcatt tagaatcgca aggaaaccca aaactcttat ttaaggtaca aacagcactt   96180
catacaatat ctcgccgagg taataatagt gattcacagg aagaatttca cattgtgaat   96240
ctttgctaat gtatccagtt atttacagat ggatttgata tttgtgtggg agattcttaa   96300
agtgttgttc atgccacgtt gtttgtgctt caattttttc actatagttg ttgaagactc   96360
tctttgggac aaacttggcc tcccagtttg acggcttatc atccaacccc agcaagtcac   96420
aaggccgagc acagcgcctt ggctcctcca gtgtgaggcc aggcttgtac cactactgct   96480
tcatggcccc gtacacccac ttcacccagg ccctcgctga cgccagcctg aggaacatgg   96540
tgcaggcgga gcaggagcac gacacctcgg ggtaacagtt gtggcaagaa tgctgtcgtt   96600
ggtggaagca caaaagagca agcaggaaat actttgtaaa agaataaaaa cgaaaaatgt   96660
```

```
tagccaacat cttctaatag tctgctgtat tcaaagaact ctaggaaata tggttgatgc   96720
aaagatgatt taaggcatag cccggccttt caagaagtgt gtggccagtg agtgagatgg   96780
gcttgggact tacacatctc agaggtgggg gtagaggagg aggaacactg agtgggctga   96840
gaagcagcca gctttcattg ccaaagtgtg tcagcaaacc agaaggcagt tcataatgtc   96900
cccacccgtt caaagcacag gccctgtaga gtggtgtggc atgtgttggt ggcactttc    96960 aggcctgtaa caaggatgaa agaacagctt cattgcagca cagtagtgct ggtattcaga   97020
ggtatatgaa ggtcatggaa gcatcttgga tatgttacct tgtgttttgt caactttatg   97080
actagaaatc tcttttact  taaatttatg tttgtgtctt taatgcctgg aatacaggac    97140
ttcttaaatt gccataagta tcaacaggta tttgagttac taatctgtat agtagcaata   97200
atagaatccc ttgttttcc  ttttataaat gtaatgatta aatagctaca attgaaacac    97260
tagagtcagg agtcaaggaa aatacccatg ttccaggctg tatgttagtg atgtactcac   97320
tgtgtattcc agtttcagga ataagtctgt ttcaatgctt tctgtaacca tttgggtat    97380 taataagcaa gtgagtgtat gcatgtttgg gttaatttca tatatgtgtc ttagaaagga   97440
tatcattgat gtaaatattt tcaaggctta tcctccaaaa aaatcctgtg atttcttcta   97500
aattactgat cttttaaatg accttcacct ttctctcaag tctcacttaa gactgggctg   97560
agtagtcagt ttcctgtagc agtaaaaagc tcagacttga gtagccttcc acaggtgacg   97620
agacttgatg gctgtcaggc agctgtaaac tgtaaataga gtgtcattat ctcgagaggg   97680
tgatgctgcc acactgagtg gcctttcaag ttgtttctca gtctgacatg ttctgatcgt   97740
gtgaatgtga aattggtttg aacaggagta tatctgagtg cagaggagat tatttaaaga   97800
tattctcatt gtctgcttcc cttctattcc catttggcag atggtttgat gtcctccaga   97860
aagtgtctac ccagttgaag acgaacctca caagtgtcac aaagaaccgt gcagataagg   97920
taaatggtgc cgtttgtggc gtgtgaactc aggcgtgtca gtgctagaga tgaaactgga   97980
gctgagactt cccaggtatt tgcttgaag  cttttggttg aaggctcact tacggattct    98040
ttctttcttt cttttgtttt tttatagaat gctattcata atcacattcg tttgtttgaa   98100
cctcttgtta taaaagcttt aaaacagtac acgacaacaa catctgtgca gttacagaag   98160
caggttttag atttgctggc gcagctggtt cagttacggg ttaattactg tcttctggat   98220
tcagatcagg tttgtcgctt ttaatctttc atccatcata cctgtaccta atttagtaca   98280
aattaccctg aaagacactg aaatctactt taaagaaatg tgaactgtgt ttccccaccc   98340
cccatcaatt gctgctgctt atgttttca  tgcacttagc tagtacaagg cccggggcat    98400
agccagcctc agcaagtcgg catccttgcc ccagctccct ggactcaagg ctaacctggg   98460
gttggctgtt agggatttcc aaaggtttgt cccatccact cgcctcccct ccaaaataag   98520
tttgaattta aattgtgaga tttaattaag atttattgtt tggggaacat ttttgcaaaa   98580
tctagagagt tagtttaaat ggattatcaa ttatgactat aattgatcat ctgcagtttc   98640
aggctatcta acaggttagc ttacctcttt aaaaaggaat ggaatttagc cggacagtaa   98700
ctgagaccca cgctcctgga gtccacgtgg gagccgcgtg gctctgcaca aacaagcatt   98760
tgcactcttc ccctcttggc tgcgttgccc tcctcctgca gttgctgtgg gcactagatt   98820
ctggctagtc atgtcccttc atgatgcaca gtttcctcaa gattcgtgcc agttaaatca   98880
ctgccttttc atagtcaaaa tttaactgtc atctttgacc catgatcttg ggctacttcc   98940
ttatgtgggg taggaatatt tttgagatag aaatattaca cttctctgtt tccttctaga   99000
```

```
caaaaatctg ttaattctgt tagtaccgtg actcatctga aagggtctgt ttccctagga    99060
gaactgaggg cacgtggtca acactgattt cccaccatgg gtattgaggt ggggtctgct    99120
tttttttgtt ttgtcttttt tttttttgaga cggagtcttg ctctgtcgcc caggctggag   99180
tgcaatagtg ccatctcagc tcactgcaac ctccacctcc cgggttcacg ccattctcct    99240
gcctcagcct cccaagtagc tgggactaca ggcacccacc acttcgcctg gcttattttt    99300
tgtagagacc gggtttcacc atgttagcca ggatggtctc tatctcctga cctcatgatc    99360
cacctgcctc ggcctcccaa agtgctagga ttacaggcgt gagccaccgt gcccggcctg    99420
gggtctgctt ttaatgaaag aggcatctag gggtgggctt tgccttggct tgatgctttg    99480
aacctttgtt cacaaaacct atctgaagaa aatctgtctc agtgggccat tgctctcctc    99540
aggaaacatg cattgggaac ttcttttcgt ttcctttgac actaggaggc tgcctgggga    99600
gaagccctgg tctatggcta tgggcaagca ggggctgaga ggagcaggct ctcagtgggg   99660
cagggtaccc caaggaagc cagaaccctg atttgttcca ttctagtgag aacaaagact    99720
acagtctacc ttttcttcag aatttcccag ttctaactgg gcatggtggc acacctctgt   99780
agtcctagtt actgaggagg ctgaggcggg aggatcactt gagtccagga gtttgagtcc    99840
agcctgcaca acatggcaag gcctgtctct aaaataatag taataatcat aatctctagt    99900
tctagccggg cacagtggct catgcctgta atcccagcac tttgagaggc cgaggcaggt    99960
aaatcatttg agctcaggag tttgagaaca gcctggccaa catgatgaaa ccccatcttt    100020
actaaaagta caaaaatatt agctgggtgt ggtggcaggt gcctgtaatc ccagttactt    100080
gggaggctga ggcaggagaa tcacttgaac ccgggagatg gaggttgcag tcagctgaga    100140
ttgtgccact gtcctccagc ctgggcgaga cagagcgaga ctgtgtctca aaataataat    100200
aacaacctgt ggttctgact cgtcatgggt aggaactgat tttctcatgt ggtagttaca    100260
gactatggtc tccttgggcc tgtctttagt agggaaaaaa ggcaactccc cactctaaca    100320
taaaatgggg ggacttgaat gttttatcaa attctttctt tagtcgttct actggagctt    100380
tttcttcaat gtagaatatt ctgttgcttt attatatttg tctgcaatct ccatgtgata    100440
tttccatgtt gagggaggac agccttgagg ctcccccgtg ctgcctgcgg ccctgcaggc    100500
atgtggaatt catctttggc ctgtgctttc ttctgggtcc cggtgcccct gcccgcgagg    100560
ctcatgtcca gctgcccctt tgtggtggtg tgaggtcatt cctgctgtga gcgctctggt    100620
ttcatgtttg ttccgattgc ctttcatcag ccgatcccct ttctcccagt tcttaagatt    100680
caatacagtg acagttttat gaacaagaat agaactagaa cagacaagcc attgaactct    100740
atgctgataa tgatttaccg agcacctgct gtatgtttgc attccgcgca gaggctctga    100800
gaaagccggg ccatgtgctc catgctttat cggtggaagc tcctcatcag gttgggaaag    100860
ctgacagctg cgtagaatac cagtgtgaca caaagctggc tcccgtgcgg cccttgcgtg    100920
ttgcctctca gatggtggga ggaagaaggt cgactccttt ggggatctta ctaccaaacc    100980
agtttcaggg aatctgctac cctgtctgcc attaatggga acagatgagt ccccaaggtg    101040
tacttctggg tattgtctga tgtcgcttgg aatttattac ttgttttcc aatgaggttt     101100
cacctcagtg tgtagtaaag ttgttgaggg gattcctgga ggtgttctac agttatctag    101160
gctgatttca gaatagagtt atgcttatag tccaatttat cagctgtcaa gaaattcatt    101220
taaaatttgt gcagataagc aggaggaaaa gaaacctggt ttttacgttt taatcctatt    101280
attgatgtaa aattttactt tccttcccgt aggtgtttat tggctttgta ttgaaacagt    101340
tcgaatacat tgaagtgggc cagttcaggt aatagcattt tgttatttta gagttttttc    101400
```

```
tccttcttgt gtacttacat gtaatttagg ttattaagat gaatgtttaa actactgtta 101460 ggcattttg ctgttttctt taaatggaaa tctgattaac atgctgtgca tttttgcttc 101520
tcttaaaaat taatgtatat ctcaagactt gtttggaagt agttacatat ctgaaaattc 101580
catatgttgt cagttttcat tgcacatttc aaagcattta attatgttga cagatggcgg 101640
aatgaaatct tgtggtggag cactagtttt taaatcttct tagagaaagc agtttttata 101700
taaggttgtc tttagtaatt attatgcact tgtattctct gcagcttttt tttgctagat 101760
gttgaggttt taatacttct tgctagtcca ttacaggttt ataatgattg aaagttaaaa 101820
ttctttagta cctgaaatac ttaataaata ctgtagttag gaaaacttag tgcagaagga 101880
aagtgttccc agattccctg gggtctggaa gcatagcgtt tgttctaatc acgtgacacc 101940
tccactgtgt tttggggcaa gttacttttt ctcttttgag tttcaatttc tacaagagca 102000
aaggggcaga gagagctagg gagattgtag ctgctgtgcc tctgtgccgt caggtgcctt 102060
ctacctgctc cctctgaacc tttacacctg tcccggctct gcacaagggc acagatggga 102120
tgcactgtgg cagggatggg cttagagtag atcactgaca cctgttagct tcatgtgccc 102180
tcatgaatta ttttatgttg cttatattga tatgtatctt aattttaaaa gaaaggtcta 102240
aatggatgtt tttgtttcta gggaatcaga ggcaatcatt ccaaacatct ttttcttctt 102300
ggtattactg tcttatgaac gctatcattc aaaacagatc attggaattc ctaaaatcat 102360
tcagctctgt gatggcatca tggccagtgg aaggaaggct gtgacacacg gtaatgggac 102420
acatctttca ctgtcgtctt cagtgtcacg atgtgcttgg cagtgttcgt tttctttttt 102480
ttgttgttgt tgttttttttt tttttgagac ggagtctcgc tgtgtctccc aggctggagt 102540
gcagtggcgt gatctcggct cactgcaagc tccgcctccc gggttcacgc cattctcccg 102600
cctcagcctc ccaagtagct gagactacag gcgcccgcca ccacgcccgg ctagtttttt 102660
gtatttttag tagagacggg gtttcaccat gttagccagg atagtctcga tctcctgacc 102720
tcgtgatcca cccgcctcgg cctcccaaag tgctgggatt acaggcttga gccaccgcgc 102780
ccggccggca gtgttcgttt tcatacaccc actttcaact ttgtcagtgg cggccgtgtg 102840
cgtctcaggc tctgcatatg tgtctgtgtg tctgtgtatg tgaatgtact ggttagagac 102900
gtttcaaaag agaagagagc atattcttta ctctcagcaa tttgtaatct tctcagggaa 102960
aaaaagttca agaaacagta agatagccta aggtacagat agattctgaa tataaagttc 103020
ctgttcattc acacgaaaca ctaaaagttc ttcacctgat cttagcccaa aggccgagaa 103080
gcgatgaaac actaaaaatt cttcagtcga acttgctgtg aattaaattt tgatctctca 103140
tccaggtggt attggagata cagtttgact tgggttcagg gctttctgtt ttgcctgatg 103200
attattttgc tggagcttaa ataaagacag ggctccagga gatggccagc tgtgcaagcc 103260
cccagcctgt ggaaggagct agcctggttt tatgaatgag ctgtaaatct ttctttgagc 103320 ttttgaact ggtcttccag cattgcccta ttgacccctc cctgactcct ttgctggaat 103380
ccgtaggctt ttgaactttg acagggacac atcctaagac ccttgcaaac ccctagatgt 103440
gagaatggca ctactacata gagtcttttc cactcagcgt gtgtgcagaa gaacatcaac 103500
catgctgtgt ggcgaggcag ggccttggct gacctctcag tcaaggcctt agctttacag 103560
agctaagcca gttagtcttt gccatggctt cacaatggct tcaggttcac actgccaaag 103620
tatagattat taaaggcata ggtgtttggt ttcctgcact tggagggtct ttggacagaa 103680
aatcagtagg cagccaaagc cagtactttg cgctgggaag cttggtcgtc tgtgagaggg 103740
```

-continued

```
tcagagagga tacccatgtg tgcgcaccac cgaagggtca gtgagtctca gggctctgcg 103800
tgcatgtctc agggctggag agagtgtgtc actgagaggt cagagtgttt gtgcgtgtgt 103860
gtcaaagagg gttgcagtgt gcccttcact gaggggtcag agggtgcctc acgtgtgtgt 103920
atgtgtgtgt gtcactgggt cagtgagtgt cttgtgtgt gcatgtcact gagaggtcag 103980
agggtgcctt tgtgtgtgtg tgctcatgtg tgtgtgcgtg tcactgaggg gtcagtgttc 104040
ctgtgtgcac atgacattga gggtcagagt gtgcctctgt gtgcgtgtgc tcgtgtgtgc 104100
atgcgtgaca cctccactgt gttttgggggc aagttacttt ttctctttct cttttacttg 104160
gtcatctgtg agagggtcag agaggatatg gtcctgtgtg cgcatgacac tggggcagag 104220
tgtgcctctg tgtgtgtgtg tgctcctgtg tgtgtacgtg tcactgaggg gtcagtgttc 104280
ctgtgtgcgc gtgacactga ggggcagagt gtgcctctgt gtgtgtgtgt gtgctcctgt 104340
gtgtgtacgt gtcactgagg ggtcagtgtt cctgtgtgcg cgtgacactg aggggcagag 104400
tgtacccgtg tgccaatgaa aggcatttct tattttttttt tatatgtggt cacagtagac 104460
caattaattt attttgactc ctgttttaga ccaaaataag acctggggga aagtccctta 104520
tctatctaat gagagagtga gtttacttaa aaaagcataa taatccagtg gctttgacta 104580
aatgtattac gtggaagttt ttattgtctt ttcagatgaa tcaaatagat tattctcgag 104640
accaggaatg gtgctgtttt ggttattttgg gaagttttat cattttcaaa ttgacctttg 104700
aatttgagtc accttttttc agaagtggtg ttaaattaca ggagccctag gttttttttc 104760
cttttttaga agccatcaca aaatgatcgg tgttcagagg aaaagctttg atcttccaca 104820
atggtataat gattgataac cttaattcat ctcttaccat aaaccaagta tgtgtaaggg 104880
ttttctttat ttcttgatat cattttgtag atgttgagag cagttttcca aatgtaattt 104940
ccatgaaatg cctgatgagg gtacccttttt gtccccacag ccataccggc tctgcagccc 105000
atagtccatg accttttttgt attaagagga acaaataaag ctgatgcagg aaaagagctt 105060
gaaacccaaa aagaagtggt ggtatcaatg ttactgagac tcatccagta ccatcaggta 105120
agaggaatgt gtgttggaac tgtcgtggat actttattga cccgtacaga tggaaggaag 105180
tgccatgtgg taacactcac tgttaaccgt gctactttga actaggtttg agctttctga 105240
ggcctgggga gatgctgggg cagcggcggg tgcagggga ggtgggggcg ggggacaggc 105300
gtggtggcag gaggtatcat tggtgtttat ccttcctttt ttttttttt ttttgagatg 105360 gagtctcact ccgttgccca ggctggagtg cggtggcatg atcttggctc actgtaagct 105420
ccatctcccg ggtttaagcg attctcctgc ctccacctcc cgagtagctg ggattacaga 105480
catgcaccac catgcccagc taattttttt ttttttttttt ttgtattttt agtagagatg 105540
gggtttcacc atgatggcca agctggtttc aaactcctga cctcaagtga tccgcctgcc 105600
tcggcctccc aaagtgctgg gattacaggc gtgagccacc gcgcccggcc tggtgtttat 105660
ctttaaagtg ggtacagcca caggggttca cctgactcct ggtctgagag tcacaagatc 105720
gttcaagata gtgaggccct cttttccaaa acaaggacca aaaatcagtt gacagtgttg 105780
gtcaagatgg tagaaaccta aaatgataga aatctcaact ctgaaataaa aactttattt 105840
gcatatttat ttaccactat tttgacatag ggctaaggtc ttttttcttttg agctagtttc 105900 tggttttgtt ttcttaaggt ggcataagaa ttcaaagaca ttttgaggaa aactgagtgt 105960
agaaatctct cttttttaat gacttctctt ttctttcagc ttgtactgtt gtgtagccct 106020
cgcttatttt gtcaattctt tttagctgtt tgtcttgaa tctttatgaa gccatagctt 106080
ttctcataag aagcagcact ttctttgttc attcatattt taattaactc ctgtagtatt 106140
```

```
taaatactta atgcctaatt aaatcacata attgcaatgc aaaagtacat gtatcataaa   106200
gaggtctgaa aatgagcaac tggcaagcag gtggctgcag gcagagctgg ctgggtgggt   106260
gggtgtcctg gagaagagct catcagctgc atgttcagtg agctctggat atctctgtgt   106320
aaaaatgatc actaataaac ttgtgctcaa ctgtgcacac ttccggaaag gagatgcgtgt  106380 tcagtagatt gcctctgcag agaacacaga attgaaggga atttccacaa aggcggtgag   106440
ccgcctgcag aatagtttag tcaaggctgt gtttgaattt tgccaaagat taatatacat   106500
ttattttttt catgctgtgc cttttctctg attgtgaaat attataaatt ctatccaaat   106560
aacaatgatg gcaagtcctc ctgagcaaag tgtgcagctt gcatgtgtcc tagaggaact   106620
cgtgtttcgt tctgattccc ctgcatttct catgtcatag agtggggatt gcatccgtgt   106680 cccccctgtcc tcgtggggat cacatctgtt tggatcctag agtcttcaag ctgagctggg   106740
acaagtgtaa cagatggaca catgggggtg gaaaggcgcc tctaggcagc agactctcta   106800
attgtgcaca ctcttatagg tgttggagat gttcattctc gtcctgcagc agtgccacaa   106860
ggagaatgaa gacaagtgga agcgactgtc tcgacagata gctgacatca tcctcccaat   106920
gttagccaaa cagcaggttt gtccccgcag ccttggctcg ttgttgcata gtgatggtag   106980
cttaaggtcc ttgtgaaagg tgggtggctg gaatcagctc ttccttcaat cctaatctgt   107040
gctttgatag cagttctcca tgctagtcat ggggcaactg acttcatttc ttctcataat   107100
gccatctcag gttggtattg cccacctcct ttacggggggg aactcatgac tcagagaggt   107160
tatggaggcg atcaggcagc acacagcttt agagtgctgg ggtgagggcg ggccaagtct   107220
gactctaaag cccgaacccct tacctcctat actgcctcct gcattctggt caacgcagtg   107280
ttttatttgg tggttacatt tttgtttttg ttaccttact acttgtaatt tagcagtttt   107340 ccttttccttt ccttttccctt ccttttccttt ttccttcttt ctttccttc tgacagggtc   107400 tcgctctgtc actcaggcta gagtgcagtc gtgtaatctc actgcaactt ccgcctccca   107460
ggttcaagca attctcccac ctcagtctcc cgagtagcaa ggaccacagg tgtgcaccac   107520
tacacctggc tagttttttg tattttagt agaggcgagg tcttgctgtg ttgcccaggc   107580
tggttttaga ctcctgggtg caagtgatcc accaaccttg gcctcccaaa gtgctggcat   107640
tacaggtgtg agccacctca cctggcctat tcatcactaa tcagaattc tatgatcaaa   107700 tgacatgaat tgttgtttcc acaaatgcag tggaaggaaa tggcctggca gtaccaattt   107760
tggaagcaac aggcccccag tcaggcacag gacactgtgc ccccagtgta gcagcatctc   107820
tatctcacag agaaggtggt gcgtcctcct caaggcagct ccgccagaaa atctcatgag   107880
cggcctggca cggcttgagg ttgccttta aatggactca gcaaatacat gtttgttcat   107940
cttgattata cacaataaac aactactctg tatagtacaa gtagtccgtg gttttttgca   108000
tttgatttaa accagagaca tgtgatattg atggttactg ccttcatgac tgcaccccca   108060
tcctgatttc ataatagaat gttatcctga gaccagttag acaatggaac agggatcttg   108120
gcttctggtg agactgacag cagtttttagc gtggtcaggg tctccctgcc cacagatggt   108180
gttagaatgg tgctctggaa gctttattcc attatcttct gtgcataatc tgagtagagt   108240
ggagattgaa ggcctgaatg catagtaaat atctgactta atttctgccg caatggaaat   108300
tgtgcgataa acatttatg aaatgcgtag cacagccccg gccaggtagc tcagcacagg   108360
agcctgttgc attcagaagt agtgctagat actatcctgt tactggcagt acatacatca   108420
gtgatcagag cagattcaag aaagacccccc tgccttcttg gagtgaaggt tttgttggga   108480
```

```
tggggtgagg ggacagacaa tagaaaaacc agtgagtgaa gtctctacca tggcagctga   108540
tcagggacgc tgtacagaag aatcccggag ggaagagagt taggtggttt cggcggcgga   108600
gtggcattgt tcagttggtg atgagaaacg ttgtggtgat ctggtgacat ttgagtgaat   108660
ttgcagaaag gaaagataca agcctaggag atacctgggg gaggagcatt ccaagaagag   108720
caaacagctg caaaggccct gggggaacg tgctgttagg gtaaaagcaa tgggggtgga    108780
ggagtggggc agctatgcgg agggaaggga gcgaggcctg gtggggtgag gccagcatgg   108840
aggagcctga gaggnnnnnn nnnnnnnnnn nnnnctccca aagtgctggg attacaggtg   108900
tgagccactg caccccggcc tgtttttttt agagacggag tcttgctctg tcgcccaggc   108960
tggagtatag tggtgcgatc tcggctcact gcagcctccg cctcccggat tcaagcgatt   109020
ctcctgcctc agcctcctga gtagctggga ctacaggcgt gtgccactgt gcctggctaa   109080
ttttttgtag agacggagtt tcaccgtgtt agccaggatg gtctcaatct cctgaccttg   109140
tgatccgccc gtctcagcct cccaaagttt acaggtggat tacaggtggc tcccacaccg   109200
agccaagagt ttgcattttt aacaaattcc caggtgatac taatgctgct tttctgggac   109260
cacactttga gactcagtga tagaaagatt tattggtagg atagtaaaat aggagtaatt   109320 tttttttcc acaaaattgg caattggggg aaatttaatc ttccttttt ctttagctat     109380 gacttattta ttctgtttat tttaggcatc tgtgagcact gttcaactgt ggatatcagg   109440
aattctggcc attttgaggg ttctgatttc ccagtcaact gaagatattg ttctttctcg   109500
tattcaggag ctctctttct ctccatattt aatctcctgt ccagtaatta ataggctaag   109560
agatggggac agtaattcag cactagaaga acacagtgaa gggaaacaaa taagaatttt   109620
gccagaagaa acattttcaa ggtatgcttt ctatctgagc ctgtaactaa cccatgcctt   109680
ttgggaagtc acttggtatt tcatgatcag ttaagtctgg aataacacct ggtctcgctt   109740
cagttctgag ctgggtaaag aagtctgtat cagtgtaatt ttctaatcca tcctggctta   109800
tctgtggctc ctgtttcata cctctcttga ggttctgtca tgttctgtct cttgtcctca   109860
gcagagatgc tacagcagtg gcttgctcag gtaggacagg gcagtggggt ggctgtcctg   109920
ggggcaggca gtaggcgtgc attgccttca gggaagttaa aacccaagag aagccacaga   109980
aagtgaatct tatattctca ccatgtgccg gcagttttac acgctgtcag taataaaata   110040
cttctccctg caaggcagac tgcctccagt aaatacctgt agtatcaaat cctgtcttcc   110100
ctcataaatt gttgggaagc tccctcagga cagtggtcag gcactcgtaa atgcttgctg   110160
cctagatggg tccctctcca cctctgctgg attctgagca ttcactgagt tagagctgct   110220
gctgcaaatg tgctacttct gcctgagtgg ctgtgacttc atgcagccgt catttggttt   110280
gtcgtcagta aagatgccct gtgttgtcga tggagataag cccagtaagc ctgctgggca   110340
cctttttgtt tgcgggttca gcaggcagcc cgtggctttc cctctgttgc attgaagcag   110400
ctggctaaaa ctgatggtac attaaattcc tatgacagat gatcagcttg tatttgtgta   110460
atggtgtaca gtttacaaag cttaaaaaaa tactacctgc catttcatcc tcagcgagga   110520
aggtgataca cagagaggaa aagtgactgt atccaaggcg atggtgttac gcgtttcact   110580
ttaacggttt aatgtacttt acttctattt ttactttata tttaccacat atattttcat   110640
atatacttgg cataagtgct ttatagtagt cacctaattc actgtcaccc ttttgtttc    110700 ttggaaggtt tctattacaa ctggtgggta ttcttttaga agacattgtt acaaaacagc   110760
tgaaggtgga aatgagtgag cagcaacata ctttctattg ccaagaacta ggcactctgc   110820
taatgtgtct gatccacatc ttcaagtctg gtaggtaaat cacattagtc ttcctcgagt   110880
```

```
atctcaattc cccattctgc actgtacgct cttagagtgt aggagctatg ctgcccggta  110940
gaaactctgt cttgcccaga gtgccagttg aaaatgtttg ttgctataag agtcagcctg  111000
atccatatga cccagcagtt ctactcttgg gtatgtaccc aaaagaatgg aacgcagggt  111060
ggtgaaaaga tgtttgcatg ccagcgttca tagcagcgtt attcacagca gctaaaatgt  111120
ggaagcaact gaagtgtcca ttgatggacg aatggataag caaatctgg tgtatactta  111180 gagtggaata ttattgaacc ttaatattca ataaccttaa aggacattct gacacgtgct  111240
acaacatggg tgaccccta ggacattatg ctaaatgaaa taagccagtc acaaaggac  111300 aaatactatg tgattcctct tatatgaggg acctggagta cttaattcat agatacggac  111360
agtagagtgg tggttgccag gggctgcggg ggaggggagt tgttttaca agatgaaaag  111420 agttattcta gaaacgaatg gtggggatgg ttgtataaca gtgtgaatgt atttaatgct  111480
actgaactct acagttaaaa atagttaaga tgagccaggt gtaatggctc atgcctgtaa  111540
tccaagcact ttgagaggcc aaggcaggag gactgcttga gccaaggagt ttgagaccag  111600
cctcagcaac atgcaagac cccatctgta caaacagact agccagggat agtggtgtgc  111660
ctgtggtccc aactactcag gacactgagg ctggtggacc gcttgagctc aggaggtcaa  111720
ggctctagtg aagtatgttc atgcctctgc actccagcct cgactacaga gtaagaccct  111780
gcctcaaaaa aacaaagcaa gacaagaccc aaaaatggtt aagacgggcc aatcacactg  111840
gcttactcct gtaatcccaa cacttcgggg ggtcaaggtg aaggatcac ttgaagccag  111900 gagcttgaaa ccagcctgag caacatagtg agaccctat ctctacaaag aaaataaaaa  111960
actagctagg tatggtaggc acatgcctgt agtcccagct acttgggagg ccgaggcggg  112020
atgatcgctt gagcttgaga ccagcctgga aaacatagga agagactcca tctccacaaa  112080
aataaaaaaa ataaaaaaat tatccagggg tagtgacgtg agcctgagcc caggaggtca  112140
agctgtagtg agccacgatc gtgccactgc actccaacct gggcgagaga tcgaccat  112200 gtctctaaag aaagaaaatt acaaggacag tgaacccaag aaagtcagtt gtgcagcaag  112260
catagaaagc aaccagtcca aattaggaca gtgtgttttc caagaagaac gatcatttgt  112320
catgagaatg ctttgcttta aataaatgag taaataggta gaagactagt tctaggggat  112380
aggcacgtct ttcttctctc aacaagaaaa aagaaaggca attctaatct ctaggaaaag  112440
caaatagcat taagtcatgg tccaaatatg aggcaaacca aaatatggct tgatttttca  112500
gcagttgatc tgttggaagc ccttgatatt aaaaggttc tcctttaagc agtttagggg  112560
tcatgatcaa agaccatag aaagagatgc catccttta ggatccttgg ctctcttggg  112620
aactgtattc acgtagtcat aatgtaagta ttgcttgagc tttcatttt ggaatcaata  112680 tgtgactgaa acactgaaga cttactgact taattatggt ttcagaacag aatgaaaatg  112740
tcttcagttc tgatgaatat aaaaggaaaa ctaaccaagt taatttggca agtagatggt  112800
agagatgggg tgggaatgga aggggcacta aaatccttac ctagcattgt tggagttaca  112860
tgattacatc atctgaagtt gacagaccaa aatatagagg cttcaaaggt atccagatag  112920
agctaaacat gtaactcaga ttgttaggag gtagtataaa tgagccaaat ctcctcttta  112980
ttaccgtaga gttaatgggt aatgtctaaa gttgtctgaa gtctgtaaat catgacaaat  113040
tatgatgtgg tgattgtatt caacagtctt tcagttgcag ggataaaacc ccaatttaaa  113100
ctagagtaag agaaagaatt tgttggtttg agctcctgga aagtgcaggc aagggtagtt  113160
ggtaggactg catctagtgt tataattcta tggtctgcat tgtatattta tgcatatcag  113220
```

```
ctctgctttc ttctcttaat ttgtatactt ttaaaatttt attttaaaga tagggtctca 113280
ctttgtcggc tacgctgaag tgcagtggtg tgaagtgcag tgcgaggctc gctctagcct 113340
cgaactcctg ggctctagag ttcttcctgc ctcagccttc taaggagctg agacaatagg 113400
cattcaccac catggctgga taggttttaa aattcttttg tagaaatgga ggccttgtta 113460
tgttgcccag gctggtcttt aactcctagc ttcaggcgat cctcctgcct ctgcttccca 113520
aaatgctgag gttataggtg tgagccaccg cgcccagtct catctctgct tcctgtctta 113580
gcccctcaag taggcatgtg attggccttg cataagtcat atgggtgacc ataaaccgct 113640
gaatgctctg gtccacctgg gccaaatggg agactggaca gcattccatt gacgaggagg 113700
tggggcttgt ctccgggagt aagggagagg agcgcatgca gtaactgatg gtctgctgca 113760
cgggatagcg gcgcatcagt tagaattttg aaggtaacta ccagaactga aaacagaaaa 113820
gataacaagt agttgcctta aaagggatg gggcagggtg cttttgtgat cagaaactcc 113880
tttctcttat tggattttg tacacatttt gcggacatac ccttagagta aagataatta 113940
gcattttcag ccttggtcca tttgaggagt ggcccgcctc cctgctagca ggctctgggt 114000
ctgctaggtt cagttgagca tcctggctct tgcctgcatg gaacttacag tcagtgcgtc 114060
agtatcacaa gtcttaatat ttcctatgaa ggaaaacaat agtgcagtga cagacaaaat 114120
gggtgggcgg gcagaggcag gatttccgag ggggagaagt agctagcttt ttgcagagaa 114180
atgttccggc acccgagaga gcagctgaga gtgcaggcag gcaggaggcg agtggggcct 114240
ggccgcacag cgtcacagag tcccagagaa aggggcctct tcatggccac tgcattcagc 114300
tgctgtcacc ctccacacaa gccatggcca aaatttaatt ttgataatgg actctagttt 114360
ttgagcctta cttgctatta ttgaaagaat tttcttgttt cttttttaaag atcttcagat 114420 tatgcttcac tgaccactgt aataagttta aagttgagaa aatatgcctt gttaatgaat 114480
gataggtcaa ttttagtata ttggtcattt taatattttg ccaccagttg gtttgaatct 114540
gatgccagga ggagacagcc tcatttcttt ttttttttt gagacggagt ctcgctctgc 114600
cgcccaggct ggagtgcagg ggccggatct cagctcactg caagctccgc ctcccgggtt 114660
cacgccgttc tcctgcctca gccgcccgag tagatgggac tgcaggtgcc caccatctcg 114720
cccggctagt ttttttgtatt ttttcagtag agacggggtt tcaccgtgtt cgccaggatg 114780
gtctcgatct cctgacctcg tgatgcgccc gtctcggcct cccaaagtgc tgggattaca 114840
gacttgagct accgcgcccg gccgagacag cctcatttct aaggactagt cttgcctttg 114900
tgggataagg gtggtgtgtt ctgtgtcttt ctacatgtcc gagcgatctc tgcagctcaa 114960
aggtgttcac tgtcttattg tgctgatttc ctcttcttcc atctcaaaat tgaggcaaaa 115020
tactttcact attgaagtgt tgtccagtag aacttccagc agagacggga tgtctgcact 115080
gtctaattta gttgccttta gccacgtgtg tgttccata cctgaaatgt ggctggtctg 115140
attgggtagc ttaatttata atttttattta atttttaatta agtttgaaca gctctgtgtg 115200
gatagtggct cctgtatgaa actgcaggtc tgttgagaag catctttact ggagagagtg 115260
gagggcttgg agggggcaca tgggtttcct gctgctatct ttgaccttat ttaattggcc 115320
caacatttgc aagtaagttg tctgtgcgtg tatatataaa tgtctgtttc tgtcttcttg 115380
tttcgtttga ctgcatttat ttgaaagaca ctaggtggca gaattactgt atttggttgg 115440
tttaaagata agagttgaag taatccgtct tgtgttttta tatcggtaag gtgtgtttag 115500
catgtaaaat tggtaattcg tattcacgta ctgcttaaac aaaggctaag aattccaccc 115560
atacactgaa aatggagacc tttgaatttg tccatttcag gcattacttc ttaaacaata 115620
```

```
cctggttcag gaactagtca gaatggcacc cttgactttt agtttcctgc tttctctttt   115680
gttgggggag gagggtattt agctcaaagg tgtgtgccta tttcagattc catctaggag   115740
aagcagaata gccaagacag atacctgtcc tcctgtttac aacatttggg gtaaccagca   115800
tccctctcct ttggtccaag atagacgggt ttagaaacag atgatggtac cagaggcccc   115860
gggggtggaa gcatcagctt tgtttgttgt ccatgtggct ggattagagc tgtctggctt   115920
tgtagcctca acacggccgt ccagctttgc tcagtatgat tttcaaggac acatcttgtg   115980
cccttccctg cctgccatcc agaccatacc cagtcagggt ggcaggaact gctgcccctt   116040
cctccctgag tcctggtcgt gggtggtgga gaggtaccat gaccctcacg gaggcctgct   116100 caccctcct  ctgcggcaga ggcgatggct gcacgacagc tctttccctg tcctttccaa   116160
agcgtccatg gttccacttg atggggcaaa gcaggaatac tggaagagaa agtggtcctt   116220
tctatagtaa taaagttgac attgattcaa gttcacccct ggggaaagga cagggccact   116280
aacaattata atgctggaag cagtggaatt ttctcatggg tatatagtag gtttaatttt   116340
aattatccca gttaattctt agaacagctc tgtgaagtat ttccccctttt ctgcttgagt   116400 tctaaaagat cctatgccaa aaccaagaat gaaaacccaa gcattctttc ttgctcatcg   116460
atctttctct catcgggcca cttcttgggt tgttagtggt gaatgtagcc gctggcaatt   116520
gcagaatacc caccatgggc cccagtcact gtgtggcgtg gattagaggt ggttctctcc   116580
atgtcatagc cgaacaagcc cagcccagag aggtttctgc cctaggagct cttgatggtg   116640
gaattgggat gcgatcccac atcctgcctg tgttttgaaa gcagcattct tcatttccag   116700
ttcctgcttc cgttgttcct tttagtattt ctttgtttaa ctcacgaaat caggacttgg   116760
ggagctgctg cgtgcagctg tagctgtttc tctgggtgca gcctgcatcc accttcctgc   116820 cccctcctt  actgccatcg tggtctctgg gcacttggtc cctttctctt ccccgagtc    116880 cctttggctc ccctgtgcca cccttgtgat ccacaggctc tgccttcttt ctgtctgaga   116940
ctgctgctca tcactacccg ggaccttagg aagggaggtt cctccgagaa gcatcttcta   117000
atctcagcca cgttctcaat gccgctgttg gctttgttaa ataatggtag ctactgtaac   117060
aaataaacca acatttccat ggcttcacac cagagaaggt tgtttcttgg ttttatgaca   117120
atgtgttgag ggtgtttctg gttcacggat ggttttcctc catgtgggaa ttcggggacc   117180
caggctcctt tccttctttt ggttctcttc tctgggcctc cacatcctct gtgtctagtt   117240
ggggacaagg agagggaagg tagagaagaa ggctctgtgg ccttggacaa gtgacatgca   117300
tgcctttgct ggtgttctct gctggtggtg ggtcacagcc ccaccccgta cgagggggact   117360 gggagacgtc gtcctgctgc ctcccagcag caagcagcac tgtggtctct gatgtgtttt   117420
ctatgaggat aaaaacaggc gattccagga tgagtaaagt cagggaaacc cttgaagga    117480 ggtgaccagg caggtgtcac catgggatta gtggtggctt cagaatgagc cgccaagagt   117540
gcagtgcctt ctaaagcttt tgctattctg atatgcccac accatgccca gcaggtgtct   117600
gccttgctct ccgcagagag agtgatgaat ccttctcgtg aacctctgtc ccgttcttcc   117660
tccctccacc tggaagggac cctgggttcc ttgaaacatc ccggtggaac agggggacctt  117720 ctgtcctgtc cctaagctca gcctcatcct cctgccagct tcccaacccc tcttatgtct   117780
gcttcctcac gccacatcct tctggattct ctggaattga atttttgcctt tgatgcttat   117840 ttaaaaatat ccattgcagg ccaggtatgg tggctcacac ctgtaatcct gtgcactttg   117900
ggaagccaag gcgggcagat tgcttgaacc caggagtctg agattagcct gagcaacatg   117960
```

```
gtgaaatcct gtttatagag aatacaaaca gggcatggtg gcgcacacct atactcccag 118020
ctagacagga tcgactgagc cctggaggcc ctggaggccg aagctgcagt gggctgtgat 118080
cgtgccactg tattcccgtc tgggcaacag agtgagaccc tgtctttaaa aaaaaaaaa  118140 aatccattgc atacttcacc acagtgaaac gtgtgtctta tctttccttt ccggcctgta 118200
gctgctcttt tgcacttata gccgcactaa gtcaaccttaa aattaaaagc aaaccagcac 118260
ttcctgtgct cttctgcttc cttcatgagg gtccctccct ctgtgtacgc tccattctca 118320
ttgccccggt ggtttgtttc cctcttggtt ctcaagctgt ggcagcctgc ctcttatcat 118380
ctttactgaa aagtcctttg cagaggctgc ctgtgttctt tctttctcgg tccctctcat 118440
cctgggcccc ccagcttgat gctgtggggc tgccctctcc tcactcagta gcttgcaggg 118500
tcttctctgt ctagccactt aattggttgt gttccccgag ttgctgtccg tggtctctcg 118560
tcactgtttt ctctgtgtct ctgcctctct cctcggcctt ggtaggtctc tcccctttgt 118620
gaccctggct gttgctctcg tggacaactt tctcttgctg gtccgcgtag tcctggcatc 118680
cagcttctca acatgggact tgtcctgcca gtacctcaga cttacgctga aaattgaact 118740
agcaccactg tcactctcca ggacctcttc ttgttaatta ggtcattagg gatgttcgaa 118800
atcccagcat cattgtccat tcctcctcct gccagcccag ggaccctgac cttacctcct 118860
cctctccatc taccgggagg tggctctcag agtccgtctc atcttccacc cgaacttccc 118920
tacagactcc ccgctgccgc cccaggggct gagcacttcc tccgtgcctc gtgcagcgct 118980 gagccctttta cctgggttct cctgtttgct ccttattgca accctgtgga cagatactgc 119040
tcttaattcc atcttaaacc tgaggaagct gaggccccag gtaaggtgca tccaaggtca 119100
ctcaggtagt aaactgtaga gccacgatcc gaaccaggca gtctgattcg gagcctgtgt 119160
tgacactcag ccacctagaa cacagctcag attgtgggtt tctattacgt gttcaaaacc 119220
gccacatccc gggtctgtcc ctgcacgtgc cctgtggcct ggctgcatct tcttgaaggc 119280
agcgcatgcg tcttcactca aggggcccat gcaggaaaga gggccccaca gaaggacgag 119340
gccagtgcag aatgggctgg aggggacgat gctgactgtg aagcaagtgt agagaaatcc 119400
caggaaacct ggaggaacca gagacagggc attagaactc atcgttgtga cctggtctgt 119460
attctctgag tgtgctgctg cttttagctc gcttccttag tctcaggttg tagtttaagg 119520
cattgtggag ccctaaaaag cctctactct gtttttgcct gtttcgggac cctttcactt 119580
cggggatgtg ttgaattttt tgttttttgtt ttttaattttt ttgagataga gtcttgctcc 119640
attgcctagg ctgagtgca atggcacaat cttggcccac tgcagcccct gcctcctggg 119700
ttcaagcgat tcttgtgcct ctgcctccca agtacctggg attacaggcg cccgccacca 119760
cgcctgacca attttttatat ttttagtgga gacagagttt tgccatgttg gccaagctgg 119820
tctcgaactc ctgacctcaa gtgatccacc cacctcggcc tcccaaagtg ctgggattat 119880
aggcatgagc caccatgccc ggcctgaaat ttaatcagaa ataaaatttt gaccccaaca 119940
atgatgctag gaggcccaga tctgggggag agggcaacct tggccagatg ggcctgtctc 120000
tgtttcccaa gtcttgctgc ctctcctgc tgtgctttgc agcctgtgca tgtctctgtg 120060
cctctgatct tgttcatcca gaggagagga tagaatcaag tcatgattcc tggagccctg 120120
agaagaatgc tgtggagaaa cttgcaggta gactctaact gagtgtgtgg ctgaggtgcc 120180
agcattgtgt gtggggaggc tgaccgcttg gcctgcccag gcccaggatg ctccatggcc 120240
gggcacagag gcaacttggc tgtcaggtgt caggagcctg cagagagcac acagcctgga 120300
ccgcagggcg ctgcccatgt tcttccagca cctgtcctgc ttgctcacct ggcctcttac 120360
```

```
agcatttctg tccctcagtt cttagcaagc ccaggagctg ttcaggttgg caggtgccga  120420
gtgctgttcc tgcctgtgta gctgtggctc agtcctgtgg ggggcccgc tgtggcctga  120480 gtgcagtgat tcgaggtgcc gagtgttccc tgactcgttc tgcaggagct gtgttcagac  120540
tttcacagct cttggcttgg agcttctgga gggcttggca ttgccaacca gtgcaggggt  120600
ggacagtggg agaggaggaa tgctagcttt cttgaccagt ccattaaata aatgggatat  120660
tggccgggca cggtggctca cgcctgaatc ccagcacttt gggaggctga ggcgggtgga  120720
tcacgaagtc aggagttcga ccagcctg gccaacatgg ggaaaccccc tctattctaa  120780
aaatacaaaa attagctggg cgtggtggca gacacctgta atcctagcta ctcgggagac  120840
tgaggcagga gataggttg aaaccagaag gcggaggttg cagtgagcca agatcatgcc  120900
actgtactcc cacctgggca acaagagtga aactccatct cacaaaaaaa aaagcagaat  120960
gtctgtttct gcttagaaaa atcagaattt tctaaatgcc aggtgctttg aatatgtaag  121020
tatgggaaac aactcagcct gtttcatttt tatgtaaaat ctccacgtag ccatgtggca  121080
ctggaccgag atgaaagcaa agacatttct ccttctgaac tttgtttcta ggaatgttcc  121140
ggagaatcac agcagctgcc actagactgt tccgcagtga tggctgtggc ggcagtttct  121200
acaccctgga cagcttgaat ttgcgggctc gttccatgat caccacccac ccggccctgg  121260
tgctgctctg tgtcagatc ctgctgcttg tcaaccacac cgactaccgc tggtgggcag  121320
aagtgcagca gaccccgaag taggttcata atgcccacag cccagggcgc tggcccagca  121380
ctctgtcctg agactcccag taacctgaga ttgggccacc gttacagcat tttcattttc  121440 catttttgt gagggcttgt aaaatttctg ctgcatatta atattccttt catggacagc  121500
atattgtaga gacaaacatg cggtccagcc aaaggcattc agaatagcaa ttgctttcta  121560
aatgtgattt tctttggcaa gttctttgac accattccat cttgtggatt atgcttgtca  121620
tgctgtgtgg ctcctactaa gttctagtcc ttcagttggt tccatagcca gacatgttgc  121680
aatgtcttaa cttcattata aattaaatgt ggttctggtt attcttagat aatggagtaa  121740
cgatttagca aatttcaaaa cctcttggaa atattatttg accattcaaa aagacttact  121800
aagtctctca ttatgggtgg ccctctttt gtaaaaggtt ttcaggctta agctccattt  121860
ctaggtgctc caacactctg ttatttgtat acacgtggaa ataaaagctg tgacatcccc  121920
gccctagctg aatcctcagc acagtgtttc tggaaggctc aagatcccac actggggaaa  121980
agaagttcca gagagaaaag agggcaggtg ctgccgtgcc tctctgctca gtatggatac  122040
tgggccatgt gcggccaggg cttgcagtag ggccagttca tggcactcag ctggaaagtc  122100
cactgttggc gggcattcgt aaccatccac tctgtgccgt atgtagtggg gtgtggcatc  122160
caagtatttg aaatcagccg cgtgcagaga aatcagccgc ggatgcagca gatcactctt  122220
tttctgacag gcctgctcac tctgatgtta tatcagaaag ctctgaatct gggaattgtg  122280
ttccctgaat tggaataaca gaaatgctta gatgatcagt gtttaaaaga aataaaccaa  122340
aggtaaattt agtttggaat tcagcaagcg tcttcattca gccctctgag ggcaaactac  122400
agcttttcat aaatgtaggt aaattctctg tttcttgacc ccttctgacc cagttttcct  122460 ttataaacctt ctgtattgtt ccattatcct gaaataacat taatagatta ggctgggtgt  122520
ggtggctcat gcctataatc ccagcacctt gggaggccaa ggcgggagga tcacctgagg  122580
ccaggacttc gagaccagcc cagcctggcc aacatggtga aaccctgtct ctactgaaaa  122640
taacaaaaat tagccaagcg tggtgacagg tgcctgtagt cccagctact cagaaggctg  122700
```

```
aggcaggaga attgcttgaa cccaggaggc aaaggttgca gcgagctgag atcacgccac 122760
tgcactctag gctgggtgac agagtgagac tccatctcaa aaaaaaaaaa aaaaattaat 122820
ggatcaatgg attttttaacc taatagttaa attaaaaaaa tatcattctt taatggtaat 122880
gtaaaggtaa aattaagaga agataatatg taacaagcat tttagtatgt gagtgtccaa 122940
ggtctccctg tggtggaagg aaaaaataaa tccccataag tgtccacgat gctcatagag 123000
agcagagctg ttccggttta aaccgctgct cttaggactg tgttttttcca gctatgggtg 123060 gtgggggatg agtacctttt tatttccatg agatgagaaa aatgaattac tagaagtatg 123120
aagcacaaaa cacagctgct cttttttttat ctggactcag cagctataaa attgctctat 123180
ccagttgcag aagttcctgc tgcttaccct tgatgccccc tcggttagtg tgcatctcct 123240
ttcaggctgg ctcccagatg ggagctggct ccaggcgaca ctgggtgctc tgctccagga 123300
ggtccttgtg tgggccctac cccggcctag cccctctctt atggactctg tcaccatggg 123360
tttgattcac tcaatctgtc ttacctttttg gtgagctgtt agagtcctgc ctatacttca 123420
gcacttgtgg gtgtgttgtg gtacacatga catgttggtc acttcccagc tcatcttgtt 123480
ctgagtcacc ctggatttgg tacgttcatt cgccactagt agctggcggt atatggcctg 123540
cgatttggag gacttgtgct gctacaaatt ggggctgaat ttgagttgac actggccctt 123600
ctttatgtct actgctaata tttgaattgc aaatgctgcc tcttctcttt cagaggctca 123660
ttaccctata gctgtattat tgcaaagtac ataattacag cttgagtgta agtcacgctg 123720
ggctggcagg acagccaact gagaaagggc aagtttcctg ttagttttca cattgacaca 123780
taatttacaa tacagtagaa tgtacttttg tatcaactgt agtcagtaac agcccctcc 123840 cccaaccaca taagatatag agcagtgctg tcgcttcaca tagttccctc ttcctctgcc 123900
atgtcccgcc ctccccaggt ctaaccacca atccgtgctc tattcagccc attgcagagg 123960
gtcatagaaa tagaatctac aggctgggtg tggtggctca tgcctgtaat cccagtgctt 124020
tgagaggctg aagtggaagg atcacttgag gctaggagtt cgagactagc ctgggctacc 124080
tagcaagacc ccatctccag aaaaaaaaaa tttgaaaatt acaagcatgt ccctgtagtt 124140
ccagctgctt gggaagctga ggcgggagga tctcttgttg aggttacagt gagctatgat 124200
cgtgccactg tgctccagcc tgggtgacac agcaagacct tgtctttggg aaaaaaatta 124260
agaaagagat ggaaccacac agtgtgcagc cttttgagtc tggcccccttg cagtgagcgg 124320 tgtctaccgt catgcgttgc acacgtgttg gtggctggct tcttgtgact gctgagcatt 124380
atatggctgg gctgtagatt gctttcactt caccagttgg gaaacagaga aaaggcagtt 124440
tttaaaaagt ttaaatctgt agaattttgg ttttttaccag ttctcttcta aatcctgagg 124500
gattacagga aaagttgttg tatttcagaa tattcttagc ttgatgtgac ctctctccct 124560
gttaaggccc tttgctgcaa tgggaaggac gtcgtcctcg gtcagaccct gaaggtcaga 124620
ggggcacttt gggagtgtgt caacatttta actgtatgga ctagagccaa gagtctcaag 124680
atttataatt cccacctatt caaaagaaa aataataat aataaagtga gaagaagtca 124740
atgtaaagtg aaataaccctg tgttggtggg gaagaagtgt ttttaaacag aatttccata 124800
atgtataccc tgaacgtgtt tagagtggtg atgtttcatt gggaaacgaa cagtaaaaca 124860
tgaaagcagg gagattttct ttctggcagt tggcaacttt catggcagat ggggaatttg 124920
aaaagcaatt gctcaattat caaacatagc cagtgtgagt tctgaaataa aggtgctgat 124980
tgaatgtgca gctttatggt ggattttgtc attcaggcaa gcattttaat tttctgcctg 125040
ttaaattctg ttttctttag tttttcatat gtggtttatt gtagcttggg aatagataac 125100
```

```
tgagagtata tattacacat acaacattct gatatggcaa tatttaaacc aacttgtctg   125160
ttttagaact agaattaaac ataatcatct tcagtatttt gcaaataagc tcactgccat   125220
ccagaaacat tgtcaatgca tctgttgctc cttctagaag acacagtctg tccagcacaa   125280
agttacttag tccccagatg tctggagaag aggaggattc tgacttggca gccaaacttg   125340
gaatgtgcaa tagagaaata gtacgaagag gggctctcat tctcttctgt gattatgtcg   125400
taagtttgaa atgcctgtaa acggggttga gggaggtggg gaccgggaga acatcctgag   125460
tagatgacac ttgcctggac cctctggaac ccagactgcc cagtgtcctg ccagctccat   125520
caaaactaaa tctggaatga atgtttactt ctgctctgac atataattgg agaccgggcc   125580
tggccttcca gtcactggat tctaagctgg actgtgagag ttgatgcagc tgactcattt   125640
atcaaatgcc cagctattgg cttcacgcct acacgatgct gggcatattt gttaattcaa   125700
gggaagcaat ggaataataa taactaatga tttgaaaaac aagataagtg cattgactat   125760
agtggggttc tgattttaaa ttttttaaaa agtaatacc aggagcagtg gcttacgcct    125820
aaattctagc aactcgagag gctgaggtgg aaagatcact tgagcccagg agtttgagac   125880
aagcctgggc tacggtgtaa gacccccatc tctaaaaaaa taaaaaatga aaaattatcc   125940
aagtgtggtg gctcgtgcct gcaatcacag cttcttgaga agctgaggcc agaggatggc   126000
tagagcgtgg gagttcgaga ccagcctggc aacacagaga aaccctgccc ctaccgaaag   126060
aaagaaaaat tagcctgatg gtggtgcgtg cctgtggtcc cagctacctg agagactgag   126120
aagggaggat tgcttgagcc cagaagtttg aggctgcggt gagccgtgac tgtgtcactg   126180
cactttagcc tgggtgacaa ggcgagaccc ctgctctaaa aaacaatttt tttaagttaa   126240
tttgtagaaa aggtgttaga tgttcattgc cgtattttat gatggattcc tgtttaaatg   126300
ccattctctt aaaaaaaaaa aaataacttg taggagtttt taaccgtaaa attagcatca   126360
catgtttacc atgagagaatt tacaaaaaac aaacagagga aaataaaacc tctgtaatca   126420
tactactcag agataacttg ctgttagatt tcggtgtaga tctaatactt tttctgtatt   126480
tatattaaaa atacttaaaa catatacatt tctttgttac aaacatggta tcttatagat   126540
agtgctgtca catagcaaaa cagtgttaaa tattctgaat cagaaaagga agccgactct   126600
ccaactgaaa gaggtgttat cctagagact ttttctggtg atggcaattt gttaatattc   126660 acttttgct ttacattctg tattgaaata gttttctgt tttgttctac ttttaaggat    126720
aatataattg tatcatgctg tttttcacag aaatgtaaga aaaaagata ttaattttgt    126780 aagttaatag aggttgagca tcccaaatcc aaaaatctga atcccagat gctccaaatt    126840 ctgaagcttt ttgagtgctg acattatgtt caaggaaat gttcattgga agatttcaga    126900
ttttttgatt tagggagctc aacaaataag tataatgcac atattccaaa acctgaaaaa   126960
aatcctacat tcagaatact tctgatccca acatttcag ataagggtta ttcaaccttt    127020
actgtcagat gatcccaaat gaaaatatt atcgttaac caaatgtcaa ggaattgatc     127080
acattttaca gtttctgcct aggattatga atcaagatga aaaggctctg cgtgtttaaa   127140
aatatatata ttttttatttt cttataaatc ttaaatgtat caacacttaa gatgtatttg   127200
atatgtggaa tccattcata ttttggatta acaattctg tcaagaccgt ggcagtgata    127260
gaggattttt ttttcccact gaactatcac aaaattggaa aaagagtaat tggagaaccc   127320
cactggcttg gccagctcga agccccggag ggggcaggca gtgctgtgga tgggagcgtc   127380
gcagtaccac gctgcccctc ctgcccatgg atctctgagg cctgcctttg tcctttgacc   127440
```

```
cttggccatt tgttagtgtc tctgagagct ggactgctgt accctacttc cccagggggg   127500
cctgacttca cacagcctct gctgcagtgc gtggttggag gtgacggcct tggtaaatcc   127560
agtttcctgc ctcctcaatt atttgtgctc atacactgta tattttttag tgaggtttat   127620
atttgagatg tgttttctcc ttcttaccct ttctggcctt tctatggatt aatacctggt   127680
ctcttcttgt gtacttgaaa gtgaatctct catcgtattt ttccttagtg tcagaacctc   127740
catgactccg agcacttaac gtggctcatt gtaaatcaca ttcaagatct gatcagcctt   127800
tcccacgagc ctccagtaca ggacttcatc agtgctgttc atcggaactc cgctgccagc   127860
ggcctcttca tccaggcaat tcagtctcgt tgtgaaaacc tttcaactgt acgtcttcat   127920
cctgccaaca attgccagtt gcagttttct ctgccttaaa aatggagtat tgaaattttt   127980
aactttaatt tctgactggc aaaatagtca tcttttgttc ttttccttct cgctgttagc   128040
caaccactct gaagaaaact cttcagtgct tggagggggat ccatctcagc cagtcgggag   128100
ctgtgctcac gttgtatgtg gacaggctgc tgtgcacccc tttccgtgtg ctggctcgca   128160
tggtcgacat ccttgcttgt cgccgggtag aaatgcttct ggctgcaaat ttacaggtat   128220
tgggaaaaga aaccctgata ttgatttata ttgaaaattt agcaggccaa gcaaaacagg   128280
tggctgcctt tttcctccat aggtgtggtc ttgacacggt caccaataga aacatggaaa   128340
tatctgcaaa cttgccattc ctcgtgtgtc tgatctgttt cttgaacttt tttctagtct   128400
gtccttacta ggatgaactg tacacatcag tttatccttt ttaaatgagc atgaggttat   128460
tttgggttgt acagtgtcac aaacacacta atgtgttttt gtctattaga gcagcatggc   128520
ccagttgcca atgaagaac tcaacagaat ccaggaatac cttcagagca gcgggctcgc   128580
tcagaggtaa tgctggaaac acaggtcatc cttgtgttag gagaacccag gatataaaag   128640
atatagattt gtgcgggaat aaattcacag gacaagaaat tgatgtgcgt tataggtggg   128700
tttgctgcag aagtgccata atagaaagct tcctactttt aaaacaacca gatctcactt   128760
tatatggagt aaaggacaac cagcaggatc acgtctatga catgagtgga ggcagtttgc   128820
actcctttg gctgtttgag aggtagtatt tagaatgcct gtattcactg tcctgtgatg   128880
agtgggaaaa taggttatca gctttatctt agcaaaatca aagcatatca tctaattgct   128940
aaacaagagt tggcaaatct gaaagacatt actgaatcct tggcatgcag gacttacatc   129000
tgcatcccgt tgccattttt tctcttcaaa gcatttaatc acttagttgt gtttgcaaag   129060
tcttttagaa gcctttatca gaaatcctta catctcctat gtgagtgtat ttccatgact   129120
gcaaataag ttaaacttttt acctttttttc ttcccttggt gggggcggaa attgtgtgtg   129180
tgaaagggaa agagagacag cagagaagga gaatataatt atcatgctgt gtccctttgag  129240
ctgaaattgc aaaaaagaaa acacacacac acatgctttg atttcagtct taagagtacc   129300
ttgttgatgg tgttttttaaa tgggattggg cacaattagg tggacagttt ggggcgattt   129360
ttcggtctgt agggccaagc tgttttgtaa tttgctttat aaagttgtca ctctcatagc   129420
atatggtggc agataaacta ttattacttt ttgaccctag acttagtctt cagtccgat   129480
gagggagatt aaaagattat aaatatcttg tgccagatga ggtgatttta ttttgaaatg   129540
accataaatt cctatcagtt gtcttactgg gatatttgat agtggagttt gtgcatttga   129600
gtcttagatg atctgtttta cgtttattaa gaaagccttt attagctttt ataccatgta   129660
tggactgttg caatgtttga gtataaatga aatttctgga caatattaat ggagtacaaa   129720
ctgtgatacc ttgaagtaa actagggcct gcgtttatat catgacctgt ttgagtgttg   129780
atgagaaaat agctgtgaag aaaaagttttt aaacaagttt cattttcctt taagaagcca   129840
```

```
ctaatagtgc atccttaggg tgtatatttc tagaatccta gtgtgcagag tttagactaa 129900
gactaaaaaa aaaattgcac tgtaatttcc tttttgtttg tattttagac accagaggct 129960
ctattccctg ctggacaggt ttcgtctctc caccatgcaa gactcactta gtccctctcc 130020
cccagtctct tcccacccgc tggacgggga tgggcacgtg tcactggaaa cagtgagtcc 130080
ggacaaagta agtgtccagc gtgtctgcat gcgaggcaca gggcagagtg cctctgtcac 130140
ctgaggcaga tacagagagt gcagaggagg tgcggtggac ccaaggagtg ctggcgctct 130200
gctcggctca atgaagccgt ggttagagac ctgggggac catcaatgtc cgagggagca 130260
aagcagtgct gatgtgggac cgtttcggta ggagtgcgag gtgagtcgtt agtgggtgac 130320
tcaagggaaa gtcaattgtg gcctgcaggc ccctgactgc acaggccttc aagcacatgt 130380
cagtgcattt agcctccctc catcgcctca taccttctgg ccacctgtga gttgcactgc 130440
cactgccagc catactggta tgttgtcagc acctccactg ctcataccctc accgttaggg 130500
accacttggg gccttggtag agccttggta ctctactttc ctggagagag ttcagcttat 130560
gaatatgaat ttagatttca aaaccagca gcccaagtat aagaaagcga aggttcagtc 130620
ctgccgcctt aggctctatt tgctaagcat ctgccctgcc ctgccctggt tgctgggaag 130680
agatgagcaa agcagacagc ccaggagagg atggcaaagg ggccgctaac ccttagtagt 130740
ttagctatat ttggaaggac tattagaaat tcaccaggtg aaggggaggg ccgtgagagt 130800
acccaggtag gtaacagaag tccaaagagg aagacctgtg gtgtggtgag ctgtatagcc 130860
acaacatgcc ggccggaggc cctctcagtt agcctagtgc agtgttccca agcactggcc 130920
taggcctgta gctccaggga tgtgaagtcc ccttgaacgc cacccatcat gttccccta 130980
ttcatctttt tcttcccagg actggtacat tcatcttgtc aaatcccagt gttggaccag 131040
gtcagattct gcgctgctgg aaggtgcaga gctggtgaat cggattcctg ctgaagatat 131100
gagtgccttc atgatgaact cggtacgggg ggagcagcgg aagcaaggaa tcctcagctt 131160
ttcttgtgac ttccaagtgg gatttgtctc ctcatgtgac ccacttgttg acaacacatg 131220
ttgaggactc cactctggat ggggacggga tgacggagag actccactct gaatggggct 131280
gggaactggg gaggactcca tttcagggg ccggacatg ggggatatgc tgatcgagat 131340
tgtttcagcc acattagaat ccaaggaggc aagtcgattt cactcaacct ttcatgcatt 131400
taaagaaaat ggaggtggtc ttagattaca gtcatttcac tggtttgttc tcatggcagt 131460
gaggaagggt attgggattg gtgtctgtct taattcagga tctttgagaa gatggagagc 131520
actccctcag ggattaggag agactcgaga tggaaatgaa gattttacta cttacaggtc 131580
ctggcgggta catggcatgc ccagaggccc ctcacacgtg gaagttgggg gcatgtgagg 131640
gaatgaagtg tggtcctggg cactagggtg ggggacctga gcggnnnnnn nnnnnnnnnn 131700
nnnnnnnnnn nnnnnnnnnn nnnnnnnnnn nnnnnnnnnn nnnnnnnnnn nnnnnnnnnn 131760
nnnnnnnnnn nnnnnnnnnn nnnnnnnnnn nnnnnnnnnn nnnnnnnnnn nnnnnnnnnn 131820
nnnnnnnnnn nnnnnnnnnn nnnnnnnnnn nnnnnnnnnn nnnnnnnnnn nnnnnnnnnn 131880
nnnnnnnnnn nnnnnnnnnn nnnnnnnnnn nnnnnnnnnn nnnnnnnnnn nnnnnnnnnn 131940
nnnnnnnnnn nnnnnnnnnn nnnnnnnnnn nnnnnnnnnn nnnnnnnnnn nnnnnnnnnn 132000
nnnnnnnnnn nnnnnnnnnn nnnnnnnnnn nnnnnnnnnn nnnnnnnnnn nnnnnnnnnn 132060
nnnnnnnnnn nnnnnnnnnn nnnnnnnnnn nnnnnnnnnn nnnnnnnnnn nnnnnnnnnn 132120
nnnnnnnnnn nnnnnnnnnn nnnnnnnnnn nnnnnnnnnn nnnnnnnnnn nnnnnnnnnn 132180
```

-continued

```
nnnnnnnnnn nnnnnnnnnn nnnnnnnnnn nnnnnnnnnn nnnnnnnnnn nnnnnnnnnn    132240
nnnnnnnnnn nnnnnnnnnn nnnnnnnnnn nnnngagaaa cctcctggtg ctttagccgt    132300
gcgttgatac acagcagatg ggagggaagt gggcacccgg gaggacaaat gcatgtagag    132360
gctgggggtg gaggcaggtg ttcatgaaaa gagaccttac agggagggca acacaacagt    132420
gtgttctgat gtactgaaga gctagactga aaagaacagg agaattcacc caaaatccat    132480
ttactaaaat tgtttatcct tttttttttt gagacgaagt ctcgctcttg tcccccaggc    132540
tggagtgcga tggtagatct tggctcactg caacctctgc ctcctggatt taaacaattc    132600
tcctgcctca gcctcccgag tacaggcatg cgcccaccac gcccggctaa ttttttgtatt   132660 tttagtagag acgcggtttc accgtgttgg ccaggcttgt cttaaactcc tgacctcagg    132720
tgatctccct gcctcagcct cccaaagtgc tgggattaca ggcctgagcc actgcgcccg    132780
gcctaaaatt gtttatctta agattcatgc agtgaaaact aacttactga gtgataaatt    132840
tgcttagtga tctgtttatt aggttttcta aatttgctaa ttgggctttg aacagctgta    132900
aaagttctga ctgtaaaaga aagctgcaac ttttggcatt catgatgctt ttctgaatat    132960
taaactaaga tagatgtttt acctgaagaa ttggccccca atcttataaa tggctaaaca    133020
aaaaaggttg ctaaaacata atccaaattg tcataggaaa taccattttt ccaaccaaaa    133080
ttttgtcatt catatggcta cttttactta tttcagctgc atttgaccat cttttttcaaa   133140 cttcagggat ggctggtgta tcaccgagat cttggatgac actttagctt tgattttctg    133200
tttttatgaa ttaaaattgt cataccaaaa tttttacttc aagcaaatcc aagagcataa    133260
aaaattaaaa tatcacttaa agtaccaaga gagaacagaa atatatttta ctaagcgtac    133320
gttgaatgaa gttgttcaaa tatttgtaac aggcatagag tagaattttc ttaaaaacat    133380
ttttgatggt ataccaatct gtgttttctc agaaacattt gccttattct tttttctgtt    133440 gtgttttttct tacctgattg aaagctccta atctgttgtt attgtttgtt taacctttaa   133500
tgctctgatt tcaggagttc aacctaagcc tgctagctcc atgcttaagc ctagggatga    133560
gtgaaatttc tggtggccag aagagtccgc ttttttgaagc agcctgtgag gtgactctgg   133620
cccgcgtgag cagcaccgtg cagcagctcc ctgctgtcca ccacgtcttc cagtccgacc    133680
tgcctgcaga gccggcggcc tactggagca agttgaatga tctatttggt aattaaaatt    133740
aaaatttatc ttatttttag aaaggttcca gggccagtat agtactttgc accaagtaaa    133800
tatacaataa aggcggtgga tctaatacag cgaaagcgtt tacagaggca gctaaagagc    133860
agcactggtg gcctcagcgc agaatttctt cctgcgtgtt tgccactttg ccgttcattg    133920
acgtggtcac ggacataggg ctctaagccc ttgaggaagg ctgggccaga cctcagggga    133980
gatgcagccc caaactacat gcagtcatgt ggatggatgc gtagatgtgc cattgaggag    134040
caatgtcttg tgctttcatc agattctcaa agaattgctt gactgccttt cgaaggtgtt    134100
gcatctgtgc tcatgtttgc acccacccac gagggcctttc tgtttcaggg gatgctgcgc   134160
tgtatcagtc cctgaccact ctggcccggg ccctggcaca gtacctggtg gcggtctcca    134220
aactgcccag tcacttgcac cttcctcctg agaaagagaa ggacaccatg aaattcgtgg    134280
tggcaaccct tgaggtaaga ggcagctccg gagctcattg ttgctgtggg aggggacacg    134340
gggctgacac tggagagggt aaagcagttt tatttgaaaa gcaagagctc tgaccaatcc    134400
agtcactatt ctgtctccagc ctggcagtaa gtcttgtcac cgtcaagtta ttgtagccag    134460
ccttcaccct tgcctcgcca ctcctcacgg tggcctgtga ggtcagccag gtccccttct    134520
catctgcacc tccagtgtta tgtggatcgt aattttagag acttgaaaaa taaccatctg    134580
```

```
taggtacttt gtgtcttaag ttggcctgga catgtcagcc aaggaatact tggtttgtgt   134640
tagtgcttgt aattagcccc caaaacatgt acacattctg gatgcattaa actcaggcct   134700
gtatccttaa agggccatct ctgtgctgcc tgccctcagc agggacacac tttgcagacc   134760
cacagaggct ccgcctccac ctcacaccaa agaaagggag gagtccaaag ggcatcagtg   134820
ccgttactca caaaatgata aatacaccct tattctgaac caggtggagt cagatggttt   134880
gtgatccctg tcctttaggt ttcagcttag tggggaagtg ggaaagccag cgtgtgatca   134940
cagcacaggg tgattgctgc cgattatatt atgtgcctgc tgtgtgcagg acaacatact   135000
ttacacgcat catcttattt gactctcaca actccctgtg agataggctc tgttactccc   135060
atttgacagg tgaggagagc aaggcttaga gaatttcagt gacttgccca ggtccactga   135120
gctaggaagt agccattctg gcgtttgaac tcaaggcctg ctatccctag aacccacgct   135180
ctcaaattca acctctgagg ctatgccaga ggcaagcccc agtgctgtgg gcgccccagg   135240
gaagaacctc tggcctggtg gccacgtagc ccaggagaga tgtctacagg agcccacagc   135300
gctgaaggag agaagggcag cagagttaag ggggcattct ggcagagagg ggactggcac   135360
cttggggaat agctgggtca ggactgaatg tcatggagtc aggtcagagc tgtccttctg   135420
gagggcaagg gcatctggac ctgcttcccc tcaatgcttt ggacggttcc accacaactg   135480
attcacacgg cctccccaaa tgaaggtaca cgagcgggca ttctgtgact tggtacttcc   135540
ctttaggccc tgtcctggca tttgatccat gagcagattc cgctgagtct ggatctccag   135600
gcagggctgg actgctgctg cctggccctg cagctgcctg gcctctggag cgtggtctcc   135660
tccgcagagt ttgtgaccca cgcctgctcc ctcatccact gtgtgcactt catcctggag   135720
gccggtgagt ccccatccgt gaacaatggg ttcctatcct agttcctgtc tagttcacca   135780
tgtttatatt ttgtgctgcc tgtttgccag gtactaagct aggaattggg gatggagagg   135840
tagataaaat acgcattagg aagggctggg ctccatctct tttttttttt ttttttttt    135900 gagacggagt ctcgctctgt cgcccaggct ggagtgcagt ggccagatct cagctcactg   135960
caagctccgc ctcccgggtt cacgccattc tcttgcctca gcctcccgag tagctgggac   136020
tacaggtgcc cgccacctcg cccagctagt ttttcgtatt ttttagtaga cgcggggttt   136080
caccgtgtta gccaggatgg tctcgatctc ctgacctcgt gatccgcccg tctcggcctc   136140
ccaaagtgct gggattacag gcttgagcca ccgcgcccgg ccggctccat ctcttactct   136200
ccaatatatt ggagtctaca ctggaattta acttgaattt gcttttttag tcattttatt   136260
tagattttgg aatttcagct ttcatcaaaa ttacttctaa atttatgtc tctgtgatct    136320 ttggtcttag ctgactgttt tatgcattta gtcttatatg atcgaaaggt tagtaagatt   136380
acgttcagaa gattgttttc tgttcaaatg cttgtttcta tactgcacta taatattaac   136440
gtactgtaaa ataaaagtgg cttattcttt tcaaggaaca gtatcctcaa caagggttat   136500
tagccacaat ttttaaaaaa ttggacatca tggtttacat gttggagggc attttgaagc   136560
tttgtatttt caaattaaac attatagagt gatgtttga tgtttcataa ttgttttcat    136620
ctgtgcattt gtggccagct tgaaaacaaa gatccaggga ttaatactta aaagccagac   136680
ttcttggggg ttatagagat gattttggta gtaatgaatc ttgagccgtc tgataataac   136740
ctcggggtga gagatggcca acaggagaga gtcgagggac ttacaaatct gaatgaaatc   136800
tgaagtacaa atcttcagac atatgccact aaccaagaga ttggtacctc agtctaatat   136860
tgtctgtttg tctaaaattg gttctaagaa atctaggctc atctgtctat cccttttgaac  136920
```

```
ttttgtgagg ctgcacaaat gtaaaatttt gaatgaaaag cactgatgga agtctgtgga   136980
aattcttctg tttgttctgt tgtaatttta gttgcagtgc agcctggaga gcagcttctt   137040
agtccagaaa gaaggacaaa taccccaaaa gtcatcagag aggaggagga ggaaatagat   137100
cctaacacac agagtaagtc tcaggaccca ttctttctta catgtggttc ctccaagact   137160
taaaagtcat tcacagagac gtgcgccgtg gtgagtgtgc actcctggaa gcgcaccgta   137220
gctcggctgt gtcctgctgc tcctccctcg ccgtgggagg ctttagtcca ttgctttgcc   137280
acactctttt gtttcaccgt atccctgtgc atgcggctgt ttctgaccct acagagcagc   137340
tgggatgcct ctgggggagc ccttccccgc tccagcactt ccacatgcgg ttactctggg   137400
ctcctggagg gcagggagca ggtttgtctt ctctgtgttc tcagaaatta atgcttggcc   137460
cctggtcagc aagcagcaac cttttgttga gtgatactga ataaatacat gtttcccaca   137520
tgagtattca gtaacctcag tgtcaggttc aggcatctgt tttggtggat atttaaaaga   137580
aaattccact tttcctacag aaaaaaaaaa ataaataaat ctaaatccca gtgatttaag   137640
ccagttatag acttagacat atactacggc ttttcatgcc ctttcctccc agttctagag   137700 tagtattttta ctaggaaaat ggtggcaatg cctgttgaga ggaaaagttt ttggccaagt   137760
gtctttcgtt cttgccaggg gccctaggct gctggggcta cttcagtttc tttagcccag   137820
tgtctggcag ggaatgctcc ctgtagcctg tcccacagag gcaggggtgc ctcacctggg   137880
gcctgtccac gcattttaca cagcacccctt acttggagca tcaggcatct tttccgcgtt   137940
ccgtggctca ggaaacacac cttttcaatc atgagttcgc cagtgctttt gggctttttc   138000
tcccagcttt tgtgcaatcc tagttatgga tggagttttc ctgcctttag tcttctgcat   138060
agtacttttt tcttctggtt cccggttcga ggttttgtaa ttaaagaatg acccagaagc   138120
agtggcattt tcttttcttt tctttctttt ttttttttga cacagagtct ggctctgtcg   138180
tccaggctgg agtgcagtgg ccggatctca gctcactgca agctccgcct cccgggttca   138240
cgccattctc ccgcctcagc ctcccgagta gctgggacta caggcgcccg ccacctcgcc   138300
cggctagttt tttgtatttt ttagtagaga cggggtttca ccgtgttagc caggatggtc   138360
tcgatctcct gacctcgtga ttcacccgtc ttggcctccc aaagtgctgg gattacaggc   138420
ttgagccacc acgcctggcc agcagtggca ttttcataca cagccaaggt cttctctgaa   138480 ttttatctc gaacctctgt gggtccttca ggcttcagtt tgtgatttca tgatttcttg   138540
ttgctaccta aggaatatga aaacacccac ctccctactc tgcgtcttcc agccgatggc   138600
acctcaggct cttggtcctg tgcttctgtg gcgaggataa gaatagtgcc aaccatgtgg   138660
attgagatag atcagttagt ccatccatgt caagcacctg gaatggatga cagtcttgtt   138720
gtgaatactc aacagatgct accatgactt tagttagatt tccattgctt tgaaacagtt   138780
gagacatctc agagctttga gccagagcag tgggccctga tgcaggttct gtttggttga   138840
agatgattgt gcttattccc tgtgcccctt gtagaccgga gtgggaagct tgcttgattt   138900
taatcacctc gataggatct tacttcttaa aggtcatcca ataaataatg agccaactca   138960
ttagcctggg gcttaattgc ttaagtccaa tgagaagtca ttctctatcc taggaagttg   139020
cccaaactgt agaatctcgt ggcctgtggg tagtagccac ttactacaca ttcactgact   139080
caacgaatca tatttttagt agatacaata ttctagactc aagacaccat gatgtggatc   139140
ttcccagggg tgtgacgtgt tcctcggcgt ctgccttggg agtttccatt tccatcagaa   139200
ccatgcccca gggccctcaa acactctgat ctaggaaagc cagtgaagca aggatgacag   139260
cgtggccctt tgataccagc tgagggacag acacaggtcc tgggagacca gagaaagaca   139320
```

```
aggggcagag gaagtgtcct agagggtggg ccagagggct gggaacgaag gccagagctc 139380
aggttcagga ccattccagc aatcccagca gaaaatgggg aggattgtat ggtataggcg 139440
gatatgaagg aggtagactc tgcaagcttt cagtggccaa ctcattctag gtgattccac 139500
aattacagct tgagcagctg cttgtcggtc atgcttctta cactgggcaa gtagaatgtg 139560
ttttttaaaa agtcttctct taaccattgc ttgtttagat ccgaagtata tcaccgcagc 139620
ctgtgagatg gtggcagaaa tggtggagtc tctgcagtcg gtgttggctt tgggtcataa 139680
aaggaatagt ggcgtgccgg cgtttctcac gtcagtgctc aggaacatcg tcgtcagcct 139740
ggcccgcctg ccccttgtca acagctacac acgtgtgccc ccactggtga gtctggtcgt 139800
tccgtgtaga agaccaagta cggtgaaacg catgggtaag ccctgggctg gcacaccgg 139860 agagggcagg gcagagtccc cgcggcccag aggctgccag ctgtggttct ggtgccagct 139920
gtggttctgg tgccagctgt ggttctggtg ccagctgtgg ttctcgtgcc aggctgcttt 139980
cctcaggcac cgtatgtgga ggtcgctagt agaaatactg ggttttctaa aatgaagtga 140040
ggccccacat ccctaagaga ttagtgttag acttgattct aaagcaacta gaccactttg 140100
cttactggta gaccagaaac cacactccct cgagtgagtg agattttcct ttggaaataa 140160
ttcatgtttt tctacacaat tttgctgttg tcttcagaat cggtttaaag taggtgttat 140220
tgctgggcac agtaactcat gcctgtaatc ccagcacttt gggaagccaa ggcgggcaga 140280
tcacttgagg tcaggagttt gagaccagcc tggccaacat ggtgaaaccc cgtctctact 140340
aaaaatacaa aaattagcca ggtgtggtgg tgtgcacctg taatcccagc tactcaggag 140400
actgagacag gagaatggct tgaacccagg aggcggaggt tgcagtgagc cgagatcacg 140460
ctactgcact ccagcctggg caacagagca atattttgtt tcaaaaaaaa aaaaaaaaa 140520 aaaaaaaaa aagtaggtgt tattgatcag gatgcttgtt tcagataacg aagagcttag 140580
cttgaggaga gtgagggttg atggaagggg actggcttct gctcagtgaa atggcatcat 140640
cccccaccag cctgctgaag taagatgatg ggacctgttc cttagggact gcagcatcct 140700
caggcaagaa agaaaggccg accggcaggg tgtgagccag caggtatagg tcagtgacaa 140760
tggagctggg tcccagggaa gaggcttgtg gctgcttgag aagggcgcgt gcccgtctgc 140820
gtgcgcgtgt gtgtatgtac gctggagagt ctggggaggc ttgctccaag gacacagtat 140880
ttgatcctga gacatgagga gggttctgcc gcaggcgatg aagtattca gatggagagc 140940 tcattcggaa gaagaggcca gggcctggtg gtgctggaag cagttgcaga acaggggagtt 141000 gtaagctttc ctaggaagag cagcaggagt gctggagaag caggccaccc ttgctgcatg 141060
ggggttgctc ttggccccac tcttggtgca cggcgagtca ctgtgagttc gttagcatct 141120
ggttctgaaa cagtaactgc tccttttggag gggctcgggg agaccatgta ggagggcaca 141180
gtcaagaggt catgctatct ggaacacact tgaggatatg ccaggacgga ctgcatgctg 141240
tagataaaat tcctctagca agctcttaac cggcattgag gagttccctg agtgcggtca 141300
tctggaaggc agctgtgaaa ggcactgcag tctcccccg ggcaggtacc aggagcacag 141360
gggagcagaa ctgatttaaa gagagggctt tcctgtggtg aggtgagaga tgagctggtc 141420
attatcatag aacccctctg cctgtgtgca gatgcgctgt gggaatcctg ggttccgtt 141480 gggtcctctg tcacctcact gaaggcatgt cagctgagct ggccagacct tcagctgatc 141540
ctgccacttg aacagcatca agcctgcctc tggattcttc tgtgcacggt gcttgtctaa 141600
tcacctcatg cacagagaac tgtacttcag agtttacaga aataagctgt atggttcatt 141660
```

```
ttcgtgcctg cttgccaaca acatatctg agctgaactt cattgaacgc ctgcctttat   141720
tctaacacac catctgctgt ttgtgggcga ggggtgctgt ctctaactcc tgcctgcctc   141780
tcccagcatc cctgagtggg gtgtgccagc agcctcaggg tgaggacagg aagtgggagg   141840
gcagagcaga tttggaaggg ccacttgatg gggaaggaag tcccaggaag cagttggagc   141900
tgttttctgg gggagaaggt gccagcttgg ggacagtgtt gtagtgagga ggaagcccag   141960
tggagagaag tggggcttcc tgcttcctca cagtgtgtct gtcctgactc agctcgggtg   142020
atgtcacttc cttttcatct tctcaggtgt ggaagcttgg atggtcaccc aaaccgggag   142080
gggattttgg cacagcattc cctgagatcc ccgtggagtt cctccaggaa aaggaagtct   142140
ttaaggagtt catctaccgc atcaacacgc taggtactct tggggcctct ttcaggtcac   142200
catcgtcggg catgtaccgg gaggaaatcc agagccccag tactgggatc ttctcatttg   142260
actccagaaa agatttaagc atgataataa tacaaacctg tgtgaataca ttttgcagtg   142320
tcagcaaaac tccttttact gagaaaatag atcccagttc ctgtgttttg tggcttgaat   142380
cccagctttt tatattctgg gcttgtttga agtcaggaaa gattcatgtg taacagacaa   142440
cgtgaggcca aattctgcct tcgattttgc atttaggctc aacagtggca gcgcttgtct   142500
cggagtgtgt tctcgtgttc accagtctga tcctgttgtg tctcactggt gcgttttctc   142560
acatgggaac aagcagacgg gagcagatgg agtcaagtct cttagcactc gccttcctca   142620
gagcctagag gcagcatggg gagaaagcgg gcttggggct cagacagtcc tggtctgctt   142680
ccagccctct gtagctgagc agcgcggaac aagtccttct aacctctaga gaccctcagt   142740
tttgtcaaat gtaaaatggg agtcacgtct atttcataga attgttgcag atttagaaat   142800
tacatttctt tttttttttt gagacggagt ctcggctctg tcacccaggc tggagtgcag   142860
tggcgcgatc tcggctcact ccaaactccg cctcctgggt tcacgccatt ctcctgcctc   142920
agcctcccga gtagctggga ctacaggcgc ccgctgccac gcctggctaa ttttttgtat   142980
ttttagtaga cagggtttt cattgtatta accaggatgg tctcgatctc ctgacctcgt   143040
gatccgccca cctcggtctc ccaaagtgct gggattacag gagtgagcca ccgtgcctgg   143100
cctagaaatt gcatttctaa acaagtgtta gcccttattt ctaaataagt gtcgaaatga   143160
ataagtcacc actttcgccc ctatttgatg gcaagaggtg tgatcttgtg gtgggattgt   143220
aatcagtcag tcctcagtga ctgtgccctg ctgtggtgtt tcctgaaaag ttcttgtctt   143280
gtcctagaaa gtctggcagg ggcaccctgt ctccactgtc cagtcttctc cccaggccct   143340
tcaggcttct gcaaatttga ggcttgtttt catcccagaa ggttctggca gcagacgcct   143400
tgcgtctact gtcccctta gttaattaga taattcaatg tccaaaggga accctgagca   143460
ggaacctcaa gccagctgcc tcacggagct cctcctcttc ctcactgtga agattggtgt   143520
cagtggcctc ctggtctccc ccttgcctaa cacgagctcc tttgcttact tgggtgccct   143580
tgcccttgaa ctccccggca gacgtgcgtg acccaagact gtgctacagt ccttgttttt   143640
gttcatgctc atcttcttct tggttcattg ttttccctgt aatgtcaatt gttttatttg   143700
tctgtatctg tgtctgaatc agtcctgcac gctctccttc tctctgtctt tgttctttc    143760
tttacccagt ttatcacagg gaccccgat gtccatttct ctagttctcc tgtcctaagc   143820
accccatcct gtctttctgg ccttatcaca agtggcgtgt ctgcctcaga catcatgatg   143880
ggggcatgaa gcacagctgt cagaaacaac tgttcgttag gtacactcga attcagctca   143940
tcaataggaa tggagggtct atcagatgtg ttttcactga atccctgttc nnnnnnnnnn   144000
nnnnnnnnnn nnnnnnnnnn nnnnnnnnnn nnnnnnnnnn nnnnnnnnnn nnnnnnnnnn   144060
```

| | | | | | |
|---|---|---|---|---|---|
| nnnnnnnnnn | nnnnnnnnnn | nnnnnnnnnn | nnnnnnnnnn | nnnnnnnnnn | nnnnnnnnnn 144120 |
| nnnnnnnnnn | nnnnnnnnnn | nnnnnnnnnn | nnnnnnnnnn | nnnnnnnnnn | nnnnnnnnnn 144180 |
| nnnnnnnnnn | nnnnnnnnnn | nnnnnnnnnn | nnnnnnnnnn | nnnnnnnnnn | nnnnnnnnnn 144240 |
| nnnnnnnnnn | nnnnnnnnnn | nnnnnnnnnn | nnnnnnnnnn | nnnnnnnnnn | nnnnnnnnnn 144300 |
| nnnnnnnnnn | nnnnnnnnnn | nnnnnnnnnn | nnnnnnnnnn | nnnnnnnnnn | nnnnnnnnnn 144360 |
| nnnnnnnnnn | nnnnnnnnnn | nnnnnnnnnn | nnnnnnnnnn | nnnnnnnnnn | nnnnnnnnnn 144420 |
| nnnnnnnnnn | nnnnnnnnnn | nnnnnnnnnn | nnnnnnnnnn | nnnnnnnnnn | nnnnnnnnnn 144480 |
| nnnnnnnnnn | nnnnnnnnnn | nnnnnnnnnn | nnnnnnnnnn | nnnnnnnnnn | nnnnnnnnnn 144540 |
| nnnnnnnnnn | nnnnnnnnnn | nnnnnnnnnn | nnnnnnnnnn | nnnnnnnnnn | nnnnnnnnnn 144600 |
| nnnnnnnnnn | nnnnnnnnnn | nnnnnnnnnn | nnnnnnnnnn | nnnnnnnnnn | nnnnnnnnnn 144660 |
| nnnnnnnnnn | nnnnnnnnnn | nnnnnnnnnn | nnnnnnnnnn | nnnnnnnnnn | nnnnnnnnnn 144720 |
| nnnnnnnnnn | nnnnnnnnnn | nnnnnnnnnn | nnnnnnnnnn | nnnnnnnnnn | nnnnnnnnnn 144780 |
| nnnnnnnnnn | nnnnnnnnnn | nnnnnnnnnn | nnnnnnnnnn | nnnnnnnnnn | nnnnnnnnnn 144840 |
| nnnnnnnnnn | nnnnnnnnnn | nnnnnnnnnn | nnnnnnnnnn | nnnnnnnnnn | nnnnnnnnnn 144900 |
| nnnnnnnnnn | nnnnnnnnnn | nnnnnnnnnn | nnnnnnnnnn | nnnnnnnnnn | nnnnnnnnnn 144960 |
| nnnnnnnnnn | nnnnnnnnnn | nnnnnnnnnn | nnnnnnnnnn | nnnnnnnnnn | nnnnnnnnnn 145020 |
| nnnnnnnnnn | nnnnnnnnnn | nnnnnnnnnn | nnnnnnnnnn | nnnnnnnnnn | nnnnnnnnnn 145080 |
| nnnnnnnnnn | nnnnnnnnnn | nnnnnnnnnn | nnnnnnnnnn | nnnnnnnnnn | nnnnnnnnnn 145140 |
| nnnnnnnnnn | nnnnnnnnnn | nnagaaaata | aggcagcaga | ctggtgtttc | tttctttttt 145200 |
| tttttctcc | taccttattt | tgagagagta | gccagatggt | gtcttgactg | atattccaga 145260 |
| gcagggacaa | agcccactga | ggtttggggg | ctgcaattac | caatggctgg | aatgcatttg 145320 |
| attacggtgc | gttccatgtt | aaggatcaat | aagattgtgc | tctttctgga | aagtatcttt 145380 |
| tagttttatt | tattggtatt | cagaggagtg | taggttgaat | taaaatgaaa | aggcatttta 145440 |
| taaaggccgt | gagtagtaca | tggtttcatt | tttctaatgt | cttgcagaga | ttttattagg 145500 |
| cttctcgaag | tgttcacgta | cattacgtta | atgtgatact | aagagtaact | gtactctggc 145560 |
| acagcgaagc | cagcagaatg | ggaagttgtg | gaatgcaggc | ccttgattct | gatagaaggt 145620 |
| gtggtatgaa | ctcgcagaaa | tgacagtttg | gagggtagac | atatgtcaca | agtcatcaag 145680 |
| attgtcttta | aattcatcca | tagaagctaa | caggttgtca | taagcaaagc | ctctaaaatg 145740 |
| tatgagggaa | ttcaaggata | atttatcaaa | aagtaattca | tgtttggagt | tttgtgccca 145800 |
| aaggagtcct | tgatttgaaa | atgggtgtt | tgcccatcag | attgtttcag | ggtccgtatg 145860 |
| tgcagaggcc | gtgcctcgtg | ccccgtgagc | tcagcctgac | agaagtccct | tggtagcact 145920 |
| tagggacttg | gttagcactt | cttcccttg | aggcagggtg | gactctgggt | tctgcattca 145980 |
| gagctggctg | tgggtgtctt | gctgttcttg | ttgacctgtg | ggctctcctt | ccaggaagac 146040 |
| acagagagga | cgcagatcaa | cgtcctggcc | gtgcaggcca | tcacctcact | ggtgctcagt 146100 |
| gcaatgaccg | tgcctgtggc | cggcaaccca | gctgtgagct | gcttggagca | gcagcctcgg 146160 |
| aacaagcctc | tgaaagctct | ggacaccagg | tttgcctgaa | ttcccacgtg | tctccaggac 146220 |
| atcatggtg | ctgcggacag | tggggtcccc | gctgaagcat | ccagcagctt | ccccaggct 146280 |
| gttttccttt | gttgctagaa | ttgaaaacgc | tgtccatgtg | gcctgtgcag | gaggtgcaga 146340 |
| cccaaaggtg | gcctcttggc | cattgaggag | ctggaaacgc | gacgggaact | gacatgggt 146400 |

```
tattgggcat ttaggggtaa acattagcag agcaagaatg agcgggcaag tggtagaaca    146460
cccacctaag ggctcatgga caggtgctca cttaggaagt gagtttcgtt tggtattaca    146520
ccaggttcct ttaggcaggg cggagggaaa gttctggcgt ttttcacttg taagattttg    146580
aaggaaacaa aacactcttt accttttttc tgaaatgtag gtttgggagg aagctgagca    146640
ttatcagagg gattgtagag caagagattc aagcaatggt ttcaaagaga gagaacatcg    146700
ccacccatca tttataccag gcgtgggatc ctgtcccttc tctgtccccg gctaccacag    146760
gtacctgagg gagagggtgg ggggtggctg tacttgggct gggatgagaa aagactggcg    146820
tgctcaccac accagttatg caggaagacc tgagtgtggt ttgagttgga ggctgtggtg    146880
ctaaatagct gcccccattca taagcaggag tcttattcag gcccagggag gaaataaaat    146940
ctggaaatga attaggagca ttatctcctg ccagtcaatt ctcacgggct gtaagaacag    147000
caggatttaa aagttgaatg agttccttat gttaagaact caaccgagtt catctacaca    147060
agctgaatct ccagcttttc ctaagaaacc aggtgtggca gtggctgcag gcggggcac     147120
agctgggcct gagcaccccg ctccctgcac ctctcccctc cctgggccct gtctgtcggt    147180
gcccactctc ccaccaagcc tgccagttgt gtgcctgccc tatcacaggc atcagagttt    147240
gtcacctggt ttaaaagaag ggagttgtgt agggatctgg ggatgcacat ttttcactga    147300
acagtatttt agcatagagg tttgtgattc cctggttatt taggagttta agcaccttaa    147360
aggctttaat tgcagaaagg tctatgtgga catgcaatgt gttatacgca gtgtctatga    147420
ccctcaaatg tttattaggg tattgaaata aactgagcac ttggagggcc atggatccag    147480
cttcaaggag ttcataggtc aggaggaccc aggagcaatg acctgtcgta gacgcagaa     147540
aagaggggca cagaggtggg ttgggggcat acacaggcag ctcctggagc tccaaggaga    147600
gcaagtgctt ccaggaagg gggtgtggag gctccttggg aggaggcgag ttgatgctgg     147660
ggtctggcag agggttagct ggggacattc ggctggaggc tgttgtctgg gaattggggg    147720
gatgcccagc agaaagacat gcggaggttg tttggcctgg ggcgtggggg gtgtgagagg    147780
tcgagtgggg gcattatcct gctcccgctc ctgctggctg tatctggtca gcctgggcac    147840
cgaggcgggt tctggaaagc actgttcaca gatgcttatc tgagtccccc agannnnnnn    147900
nnnnnnnnnn nnnnnnnnnn nnnnnnnnnn nnnnnnnnnn nnnnnnnnnn nnnnnnnnnn    147960
nnnnnnnnnn nnnnnnnnnn nnnnnnnnnn nnnnnnnnnn nnnnnnnnnn nnnnnnnnnn    148020
nnnnnnnnnn nnnnnnnnnn nnnnnnnnnn nnnnnnnnnn nnnnnnnnnn nnnnnnnnnn    148080
nnnnnnnnnn nnnnnnnnnn nnnnnnnnnn nnnnnnnnnn nnnnnnnnnn nnnnnnnnnn    148140
nnnnnnnnnn nnnnnnnnnn nnnnnnnnnn nnnnnnnnnn nnnnnnnnnn nnnnnnnnnn    148200
nnnnnnnnnn nnnnnnnnnn nnnnnnnnnn nnnnnnnnnn nnnnnnnnnn nnnnnnnnnn    148260
nnnnnnnnnn nnnnnnnnnn nnnnnnnnnn nnnnnnnnnn nnnnnnnnnn nnnnnnnnnn    148320
nnnnnnnnnn nnnnnnnnnn nnnnnnnnnn nnnnnnnnnn nnnnnnnnnn nnnnnnnnnn    148380
nnnnnnnttg cagtgagcca agatcacgcc attgcactcc agcctgggcg gcagagcgag    148440
actctgtttc aaaaaaaaaa aaaaaaaaaa aaaaatcttt aatgttcatt gttttttgtcc   148500
tttttattcc taggtcccac aagcagagaa aatattactt ttgttttat ttatgttctt     148560
tattctagaa agtagttaag agacctcaca tgtagtgata gagatgtata taagagacag    148620
tgagagggcc tgagctggac ttaagcaagg accgtgagac accaaagggg gtgaggacag    148680
agtggagtta gctgagatgc tcaggaggaa gtagatgcca tgaagggctc tgttgtgggg    148740
ggctgcaggc ttggccctga gtgtccctgt ggccagttgt tgggggggc ccagtgtgca     148800
```

```
ggcagacagc tcggccactt tgtggcaggt cacgttggtc tgtgcttctg tttcctcctc  148860
aggtaagtga agggatttaa gggtccaggt gtggtggctc acacctgtaa tgtataacat  148920
tttaggaggc tgaggccgga ggctcacctg agctcaggcg gttgaggctg cagtgagcca  148980
tgattgcacc actgcactcc agcctgggca acagaccaat actctgtcac ttaaaaaaag  149040
tgtaaacaga aacacagggc catttacata tgatggcaca tggcaggagc cccacaggtg  149100
tatgctcagg ggagggccca gctttgctgg ctgacttgca cctatccctc caccctgtgc  149160
tgtgtctttc gctcactggg ttcctggttt agtgaaacca gttgtgcagg acggttccct  149220
tggtagcttt tgttgcagtg gaaatgggtc aggatatggt gtgtagaagc acttatgagc  149280
tctgagagtt tcctcttatg acttcctggc ctgcagcctt cacagcagaa accccatgat  149340
gtcacacgcc tgtttctgtt ccctgctctg tgccctgtac tgtcctgttc tgtgcctgct  149400
ggtttcagtg acaggaggca gggagctgct ggaccagcct gtattttctct agacatagtt  149460 ggaaaaagaa gtcacgctct tctgtcctct cacctttgac agatgtttcc acctcaagat  149520
aagtggacat ggccaatagg acgcactgta cttttcctgg atgtgtttct gaagggcagg  149580
ctgagagtga gaggcctgga gctcactggg tgcctgtggc cttgtcctgg ccccggggac  149640
actggtctgt gcccgagata ctccctattc cccacgcccc actgcatttg cccacatcct  149700
tcgatgtttg ccctgtgtcc aatgtctgca aaccgactgt catgggatta tactgggct  149760 gaagtatagt gccacccctg ccctgtcggg gacgttcagc cccagatgcc actggactga  149820
gccactgctt gcttttagga aaggggtgg gggttatggg tctgggcttg gggagcacag  149880
gggctgctcc ttggcctgag aattgttcat acagactccc tgcccactcc ctgcagggt  149940 gctgggtccc aggggggaaa tggcccttgg tgccaagaac gtgagttggg cctagggcca  150000
gtgatgatgg agaacagctt tttatgggca cacagcccat agcactgtgc caagtgctcg  150060
aggctcccag agaagcaggc agaaaggagg acagtcgagg tgtgctgagc acgtggtggc  150120
tgtgtgatct ggagcgcggg tcacagaggc gcgggacgc tctggcctgg ggtttaccac  150180
aatgactgcc agtggcggag atcggaaaag aaatctcacg cgttggttcc gtgttttggg  150240
gggttccgtg ttttgggggg ttccgtgttt tgggggttc cgtgttttgg ggactgcatt  150300
gagatctcac ttacgagtga gagcgtcccc ttcgtagagc ctctttctgt gtcgcctcct  150360
cagccgctcc tggggctggc tgactcctga tccaggccct tagcgtgtgc tggagcttcc  150420
cagcagcagt ccagccccca ccccaccctc tctgtggact cccttgcctg taagctgggg  150480
tgtctgaacg acccttgcaa aggggcagac tgttcaacgg taggcatgtg ctgagtcccg  150540
gcggccgcac ccgcccacca ggagcctggc actgtggctg cagcgctgag cagcaccctg  150600
tttctgtggc aggtgtccat acactctgtg tggctgggga acagcatcac accccctaagg  150660 gaggaggaat gggacgagga ggaggaggag gaggccgacg cccctgcacc ttcatcacca  150720
cccacgtctc cagtcaactc caggtttttcc aatggccttt ttcttttcta cagaaatttg  150780
aaatttctta tcagtcattt gatttgtttg aggtgcttct tgaaatgagc ctctcatctt  150840
ctgtacccag aaaacaccca tcttgcatat tctacaggaa acaccgggct ggagttgaca  150900
tccattcctg ttcgcagttt ttactcgagt tgtacagccg ctggatcctg ccatccaact  150960
cagccaggag gaccccggcc atcctgatca gtgaggtggt tcgatccgta agtgagcctt  151020
cccattcccc tcacactggc acatgccaca cgcaccacac acgctgcaca cacagacacg  151080
ccacaccaca cgtaccacat gcaccacaca cacgtcacat cacacatacc ccacatgcac  151140
```

-continued

```
ggaacacaca cacgccacat gcacacgtac cccacatgca tgcaccacac acacacacca   151200
catgcacacg taccccaaat gcacgcccca tacacctcac atgcacacat accccacatg   151260
cacacaacac acacatgcca catgcacacg taccccgcat gcacacaaca cacacatgcc   151320
acatgcacac ataccccaca tgcacacaac acacacacgc cacacgtgca cacacataca   151380
ccacatgcac cacgcacagc acacatgcca cacgcacaca cacaccacac acacccacac   151440
cagcccatac accactttca tgcaacacac accacacaca atgccacact cgccacatgc   151500
acacacacca catgtacata ccacacacat gccacacgca ccacacacat gccacatgca   151560
ccacacacat gccacaccac acaccacaca caatgccaca cactcaccac atgcacacac   151620
accacatgta cataccacac acatgccaca tgcaccacac acatgccaca tgcaccacac   151680
acaccacaca catcacatac atgcaccacg tgtactatgt acacacacag acacaccaca   151740
cgcgtacacc acacacagac gcacacacgc gtcccgcgca gtcatgtctc ttaggtgtaa   151800
gaacacgact tgccagtagc ggcgttctgg atgtgttgcc tggattctaa ctgcgctact   151860 ctcccctttgc tttcctggtg ttccacatct ccagcttctg gtggtctcag acttgttcac   151920
tgagcgcaac cagtttgagc tgatgtatgt gacgctgaca gaactgcgaa gggtgcatcc   151980
ttcagaagac gagatcctcg ctcagtacct ggtgcccgcc acctgcaagg cagctgccgt   152040
ccttgggatg gtaagtgaca ggtggtacag aggttcctgt cctgaagcca tgtgggccca   152100
tctgccttgg gacctggtgt tggcagagg tgccaggtgc ggctgcctcc ttccaagagt   152160
tgacccgagc cggactccac agcccacgtg agctgcagtg cttctcagct ggaggggtt    152220 cagcgacggt cagtgccatc cacaggccac cgtgatgtgg gtcgtggcgg ccaagccatg   152280
gtttggggtc ccgtgtccct gggcttgtga catcattgta gtagcccatc cccacagaac   152340
catggtgtgt ggtagcactg aagcatcgta gatggtggaa acgcgactgg cttccccatg   152400
ctctgccctg aggcctgact gcctcactcc ccctcagtta tgttccaggc ccccgaact    152460 tcctgactgg acagcttctc tcctgggggc cattttgtca cagtgaccct gcgtttccag   152520
tcccaagtct gggtgctata gtgtcttctt agcatggtgt ttctcttagt ctatttcggc   152580
tgctaccaca aggtaccta gactgggtga tttataaaca gtggaaattc acttctcata    152640
gttctggggg ctggaagttc atggtcaagg tgccaacaga tttggtgttt ggtgagggct   152700
gctctctgct tcatagatgg catgttctca ctgggtcctc acggtgaaag gagtgaacaa   152760
gctccctcag gccttttcaaa agggcccaaa tccacaaggg ctcaccctc atgacttcat   152820 caccacccga ggccccacct tctagtactg tggcactgca aattagttgt cagtgtaaga   152880
gtttcggggg ggatacattc attcagacca tcccaagggt caagtgttca tcctcttgag   152940
ctcctcctta ttctgcttct ggtttatcag gattcagccc gtgcagcacg gtacctgtgt   153000
tctgtgggca catcaccaca tggcatttcc caagcatcca tcagctgtac acatgaaatc   153060
gctacctgtg ggccccgact gctggcaaag cctattcaag gatgtcagaa ctgtcagagc   153120
tggagcctct gggtctttgt catgtggcat tacctagtaa tccatttat gatagcaata    153180 gaaacgcgtg tcttcaacaa acacctcagt ggctgccgtg tgccagccgt ctggagccct   153240
tggtgagaat ggcatggtag tgcccatcag ggcctgctta ccccatgctc tggatgggct   153300
cctgtcagta acaacgctgt cgtgacagtg atgatgtttt tttgccgtca ctccagctgc   153360
taacatttgc ggagctcttc ctcctgcacc ccacctgaca aaggcaccct aggcggccag   153420
cgtcagaggt tagctggctt gtctgggtca cacaaaatgc ggcagaggtg ggactgagcc   153480
catgtctgtg acctgaagcc tgactccctg cgagtcttga ctactcttgc ctggactctg   153540
```

```
tcctccccga gcccaaactc cagtcatctt cccttgtggg tggccgtcag cctggtgccg 153600
tgctggtgac ttggcagcca tccagggagt ggaaacaatg aacgcgtggg ctccctgtgt 153660
gggcatctct cttcactgcg agcaccctct gggtgttgcc cacatgatgt caaagcggct 153720
ctcggaaggg gtccttctcc tttatgggga gtttcagctg ctgggctaac ttgaattgta 153780
atgtggtttt gtgctcaggc ccagagctcc ttaggcaagt gttgtgccat cagtaatcaa 153840
atgagaaata atcattttga aaagcagatc ctaaggcagg atggtcatgg cactaattc 153900 ccagctctgt gcatctttct tgaagacggt gatcctctgt gaaggttttc agcatgtcat 153960
gcttggtacc agcgtatcca gagcatgtca ttttgaggta tttgcctcct gttgtgaaat 154020
ccgtgccacc tgagagcagg tcctgatgtg ggactttcag aggtgggacc aggggccgtg 154080
ggagcgcagt ccttagggag gtgccgcgtg gcgttgtgtg tatgagggga tagcacaggg 154140
tgaggtgggg gcccaagaag gaagtgatcc accaaagaac agcctctttc ggtcctcatt 154200
cctgggatgg gtgggagcgg cttctgtgtc ttccggtcat ttcccctgcg gagaagctcc 154260
tgccactgcc aagaacctca tcttgttcca caacaagaag aggctgcctg gccatccagc 154320
gctccatggg aattctgtgt ccccatagtc ttgggctgaa agagagcgac ataccttggt 154380
gacttctgca ggggtctcct cactgttaaa gagcagattg aaagtgaaga atgtgggcta 154440
agtgtttagg tcgatattta accccattag gttttggata ctaagtgaaa ttgaggccat 154500
tttggttgaa ggttggcata aactactatc agggatcccc aagactaccc ccaggctttt 154560
ctagaaggac tctcagctaa gatgtaatac agtaaaagca cacaaaacac aatcagcaaa 154620
ccaaatcagc aagggcagag gcccatgggg cggtgtcccg aggaaaccag gcccgagctt 154680
ccagaatcct ctcccggcgg ggtcgtgcag gacacactga gctcccccag agtgagccgt 154740
gacagcgtgt gcagtgtcgt caccaggctc aagcttccag aatcctctcc cagtggggtc 154800
gtgcaggacg cactgagctc ccccagagtg agctgtgaca gtgtgtgcag tgttgtcacc 154860
agggaagccc actagagact cggtgccagg gttttgactg cgggctgggc acgtgggcac 154920
cttctgcctg cttcgtgccc atactctgga ctcccagagg gaaggcagat tctcagcaca 154980
aacaccgttg cccacacaag cagctgagca cagagagccc ctcctcagtg aggatggtgg 155040
gcaccgtccc gacaccagcc aggggccagc cttgcacaca gacctctcag gatggtcttg 155100
ggccgtgcac acaagcatga gggcagcgca ccgcccccgc cctccttgg ctgtggggag 155160 gagccactgg ggcgtgagct ctggtggcat cagcagcttt tgtctgtgtg tgtctaggac 155220
aaggtcgtgg cggagcctgt cagccgcctg ctggagagca cactcaggag cagccacctg 155280
cccagcaggg tcggagccct gcacggcatc ctctatgtgc tggagtgcga cctgctggac 155340
gatactgcca agcagctcat cccagtcatc agtgactatc tcctctccaa cctgaaaggg 155400
atcgcccagt gagtgggagc ctggctgggg ctaggacggg ggtctcggaa tgagctgcga 155460
aggaagcagc atcaccctct ccaagtgccc aggtccctgg ccagatggca ggcaggtgtc 155520
agtgggaacc caggtgggcg ccatggctga ggttggtgag acgcaagggc acaggtgtgt 155580
cctagaggct tcctcgggca cccccagtga gctagagctc ctgcctctgc tgctgtctca 155640
tgtggcgctg agcacatttc cccatgtgcc cattcctgac tctgctcgcg aggccagcgg 155700
ttctcattct ctgctctcag aaccctctcc tcattaccca ggccagcctc ctctctgcac 155760 cttcccgcc ctggcccagc acctccctcc tgtttccact gtgactccga cctcactta 155820 tcttaaagct gctgggcggc aggttctgca cagatgtgtc cttgacaaag cacggctggt 155880
```

-continued

```
gccacaaccc cttaacgagc aagtcaagct cttcacaacg atgtcttgtg agtgcggagg 155940
gctctgtgac accctggtct cacctccgct ctcccgaagt cgcagaggct ttagcagaga 156000
tgggcccagc ctctctgagt cacaggcttt agagctgtct gtagagggag ggtagaattt 156060
catcagccac ccacatgggg gagttgaggg caagaatttg gagcaaagat gggaaagggg 156120
ctgggaagaa tggccagtga tcccctttga caagtgggca ggagatgggg gccgggtcaa 156180
agttgagtgg aagacttgga gggagatggg aagatctctg taggcacagt tcagacagga 156240
gggaggtgtg agccagggca ctggctggtg gctgtctggc aggatttggg acatcctgga 156300
gcagggacag tggctcaaca ggggccattg ccctcatcca ggccagagtg gcacaagctt 156360
gtggggaggc ccttctcgtc tgtcatcctt gctgggcggt gggtgctgtg ctagcaggac 156420
gcaggacagg cggacagctg gcaactgtct ctgcatccct ggagcctggc atagggcaag 156480
tcacacgggg gacacaggcc tgcaaatcag gcacatgcgt tggtgcagcg aggtgatttt 156540
ggggggcagc cccacaacag gccccaggca caggccaaag ccctggctgt gctggcgtgt 156600
tgggccgtct atggctcttg ctgtgggcat ggaggactca ggaaaggaga gttgaggtgg 156660
cccaggagtt gcgtttggga tgcagagagc ttgtggcatc caggtagaaa tggtgtgtgg 156720
ggctggcctc agtgccatgg gcacgggctg tgtcacatgc ctccgaggta gaggtgggac 156780
cacgtggtga tggatataag catcactggg cacatttctg tgggtggagg ggggcatctt 156840
actggctcct ctgttcacag tggccactca ttcagtccct ggctaccggg tccccattgt 156900
gccatgggga aggcaggtgc tgtcggggga tcacacaagg cagcacgtca tggtggaatg 156960
tgccacgaag gaaaagcaca gggcactcag gaagtagagg ggactggcct ggggtgtggg 157020
aatccagggc ctctttgagg gacagagaga ggaagtctgt ggtggccagt atggaggtgg 157080
ccacagggga ggctgggcca ggccgagagg gcagggcgtg gaggaggtag acgggctcag 157140
ctatccaggg aggggtcgag cagaggctga agggtcaggc caggttacag gggcctgggg 157200
agccacacag ggtaggtgct tccgggagcc agcctggccc gcagctcttc actcccgcgt 157260
ggggccgggc atgctgcgaa gccctctcta cgttggatgg gggcggctga gcctggctgc 157320
tgtctcccgt tttcagctgc gtgaacattc acagccagca gcacgtactg gtcatgtgtg 157380
ccactgcgtt ttacctgatt gagaactatc ctctggacgt agggccagaa ttttcagcat 157440
caataataca ggtgagtggg ccctggctgt cttcctctgc acacggggag tgggcttccc 157500
ttctcttttc cttgcgggat cataccagtg ggccagtttt gacttggtgg ggaggaggca 157560
tgaacacctg agaccatgca gcgacagaaa cctttctccc tgtgcagatg tgtggggtga 157620
tgctgtccgg aagtgaggag tccaccccct ctatcattta ccactgtgcc ctcagaggcc 157680
tggagcgcct cctgctctct gagcagctct cccgcctgga tgcagaatcc ctggtcaagc 157740
tgagtgtgga cagagtgaac gtgcacagcc cgcaccgcgc catggcggct ctgggcttga 157800
tgctcacctg catgtacaca ggtgagcagg tacacagtgc ccgcaaggcc agcccaagtc 157860
ctgttcaagg gagacaggag catgctcgct caaggaacct agactaggtg tcctctgatt 157920
tgacactttt agtgttgccc caagctggcc ccatcacctt gcaagagagg ctctggagcc 157980
cccagggctg gagtacctgg tcagggttga ccacccctct ggtcactcat ccatgtggc 158040 tgagctgtgc tgggtcctgg gctagcgagg ggctcacatc acctgctgtc aggtcttctc 158100
cagtgattca ttggactcct gtgtacaaag cactatctac agagcctgtt gggttgtata 158160
gatgtaacct tcgtactgaa cacttttatt acaggaaagg agaaagtcag tccgggtaga 158220
acttcagacc ctaatcctgc agccccagac agcgagtcgg tgattgttgc tatggagcgg 158280
```

```
gtgtctgttc tttttgatag gtaagaaacg aagccccatc cctcagccgt tagcttccct 158340
agaattttgg cctgaagctg agcgtttgtg tgtgttggct gatcccctgg cgctgttgct 158400
ggagtcccgc cagtgattcc tgaccacagc ctgaccgtgg gctgccttgg ctcagggttc 158460
cactggcgag ctggtggtcc ttggaccccca gcgctcaggt gtagtgttga ccagttccaa 158520
ggttgtccca gcgcctgccc atctctcctg agggctcagg caccgcacct ggccgtgtgg 158580
ggtatggcag ggggcaggaa tgaccagtct ctgggagggt gcggcagaag cctgcgcagt 158640
gatgaggagt tggctcagcc tggctgcctg tcgtgagagg ggagcccacg ggggtctgtg 158700
ggaggggtc catggtgcct gtgagcaggg tgaggggcag cagcaggagg aggaaggtga 158760
aacccacaca tgcatctttg agacccgtgt ggtcagtggc ttctcctcgc taccccctccg 158820
ccccactgct gtgcgtgaat tggtgttgag aattggcttc gctcccctgc tctgaaagtg 158880
ggttaggagc ttcgtagggc ttttctcaa ggacaaggct ccctgattgc tctcaggcct 158940
cagtcctggc gacatggcgg atctgggcg ttgttgtgct gccttgcctg tgctctccaa 159000
tcagggtgtc ccagtcctgg cgacatggcg gatctgggc gttgttgcac tgccttgcct 159060
gtgctctcca atcagggtgt ccagtgggga gccatttggc ttttctcaag agcatactca 159120
ggtggacttt gctctattct ttggccagat gaggtgttct gaacagctga gcctgtgctt 159180
gtctgttttc atgttttttt tttttttga gatggagttt gccccttgtc acccaggctg 159240
gagtgcaatg gcgcgatctc ggctcactgc aacctccacc tcccgggttc aagcgattct 159300
cctgcctcag cctcccaagt agctgggatt acaggcacgt gccaccacgc ccagctaatt 159360
tttgtgtttt tagtagagac agtgcttcac cgtgttggcc gaactggtct cgaacttctg 159420
aactcaagtg atccaccctc ctcggcctcc caaagtgctg ggattgcagg catgagccac 159480
cgtgcctggc ccccatgtcg attttaaaac gcacctctgc atcattcttc agttcccaca 159540
tgctcactga gcaccaccac agctggcaga cggacacagg gaggcgccac gaccagtcct 159600
ggccttcaag gggcttgtgg tctagtggac ccagtgctag gtggcgagtg ctccagagag 159660
cgtggtgtat gccttccgct ctaccgcccct ccagacgccg cagggaggca ccttggagct 159720
gaccacagat ctccctccgt ggagcactgt cttcagcgca gccgcatgc cactgctggg 159780
cgagggtctg cgggcgggta gagccaggag cacctctgag aaagtgcact gccgtttctt 159840
ggctgcttcc tgtgcatctc agttacacac agctggcatg tgtgcactga tgagacagga 159900
acatgatggt tgcttttcag cactaaaaag gatactgctc aggggcgtg tttcaggatc 159960
tggttaggga aaagcagcg agagcacaga tggggccctg tttggtaaca agaaaaaagt 160020
cccggttgac aacagtgcta caaagtgtta gaacacatag aaatgtttat ggagcatttg 160080
gatgtggaaa gcagcaaaaa cataatgaga agggggttctt ttgttaggat ttttaaaaat 160140
ctcttttgta acatccttcc ggctgcacca tttctgcata ttcttttatg tagctttcag 160200
actcttagga tttctggtca ctgcaggcg tgggagccag acagagccta tgcctagcag 160260
cctgtcttca cgagctggac agaggaggag ctggggtttt gccttttag cctcaaattt 160320
catactccag ttgcttaggc tctgactttc cccacttgga aagtccctca cggccaaggg 160380
tacctcccag ccctgatttc acatcagcat ttttcccaga gccaaggccc tccgcgggca 160440
ggtggggcag ctgtgggagc tggtgccagg ctctgacctg tgtccctcct cccaggatca 160500
ggaaaggctt tccttgtgaa gccagagtgg tggcgaggat cctgccccag tttctagacg 160560
acttcttccc accccaggac atcatgaaca aagtcatcgg agagtttctg tccaaccagc 160620
```

```
agccatacccc ccagttcatg gccaccgtgg tgtataaggt gaggttgcat gtgggatggg  160680
gatggagtgg ggaagcctgg aggtggaatt gacccccgact tgccagcaga ttcgccagaa  160740
gaacccagct cctcccttt aaagcagcaa tgcctctggc ccccacccca ccccaccac   160800 ccgggcacag caggtgcttc ccgcccccca gccctgacac tcaggcgccc gcttgctcct  160860
ggcaggtgtt tcagactctg cacagcaccg ggcagtcatc catggtccgg gactgggtca  160920
tgctgtccct ctccaacttc acacagagga ccccagtcgc catggccaca tggagcctct  160980
cctgcttctt cgtcagcgcg tccaccagcc catgggttgc ggcgatgtat cctctctggg  161040
tccctggtgc tggccccgtt tccctcgtca acaccgaggc tcatgtttca tgataaagtt  161100
ttgaaaccta acctttgcaa agccccaca gatgccaagg tgacaggccc tcagcccag   161160 ggaagtacaa tgctgacagg gatacagaaa ggagcacatc cagacatttg ctgaccaggg  161220
cctctcagag gggcccgtgt atggcagaag ggtcgaagct gctaaggggc ccttctgtgg  161280
agggcctggg tgaggggagc gagggtgggc ggcggtctct gcagacctcc cgcccactcg  161340
cgggctctgt gtggctgggc ttctcctgac actgcttctc attagctttg gtcattgtgc  161400
ctcgatcacc ctctcgggga aaggcttaag taaagatcca gttcccaccc ccagatgctg  161460
gctgccagga gtttcccttt ccacagccct cccccaagac agaccacaag agcctccgag  161520
cagcacggtt gtcctggtgc tgacagcaca gcctcgccca gtgtgcctgg cgtggctctg  161580
cccgcactgt actggagcag ggctcgtggg ggccagcagg acagcaggag catcggccac  161640
cagcgctaca caggagccag gccaggtgag tgctgccgag tgggtgcctg cctgcaggcc  161700
tcctgcttcc ttggccagct ctgcccagct cacttctgcc ctgctggcct tccagcaggg  161760
tgtccagcca gccaagggtt gcaggaatga aggtggaggc gctgctgcag ctggagccat  161820
ccaggtagcc cttccggggc tctgctggct ctccaggctc cctgggcccc ttcgtaggct  161880
gtttcaggag aggagctccc aggtgaggac agggaggcag cattcccctc atttgccggc  161940 cttttttcctt aactcctgca ccagcctccc acatgtcatc agcaggatgg gaaagctgga  162000
gcaggtggac gtcaacccttt tctgcctggt tgccacagac ttttacagac accagataga  162060
ggaggagctc gaccgcaggg ccttccagtc tgtgtttgag gtggttgcag ctccaggaag  162120
cccatatcac cggctgctga cttgtttacg aaatgtccac aaggtcacca cctgctgagc  162180
gccatggtgg gagagactgt gaggcggcag ctggggctgg agcctccaga aatctgcgcc  162240
ctgtgccctg cctccaccga gccagcttgg tccctgtggg cttccgcaca tgccgcgggc  162300
ggccaggcaa cgtgcgtgtc tctgccatat ggcagaagtg ctctttgtgg tacagtggcc  162360
aggcaaggag tatctgcagt cccggtgggg ctgagcctga ggccttccgg agagcaggag  162420
cagctgtgct gcacgccatg tgggtgacca ggtcctttct cctgatgctc acctgttggg  162480
tgttgccagg ctgcagctgc tcttgcatct gggccggaag tcctccctcc tgcaggctgg  162540
ctgtgggccc ctctgctgtc ctgcagtaga aggtgccgtg agcaggcttt gggaacactg  162600
gcctgtgtct tcctggtggg gtgtgcatgc cacgccctgt gtctgtatgc acagatgcca  162660
tggcatgtgc tgggccagtg gctgggggtg ctagacaccc agcaccattc tcccttctct  162720
cttttcttct caggatttaa aatttaatta tatcagtaaa gagattaatt ttaacgtaac  162780
tctttctatg cccgtgtaaa gtatgtgaat tgcaaggcct gtgctgcatg cgacagtgtt  162840
cggggaggtg ggcagggccc ctggccacgc tccctctcct gtagccactg gcatagcctt  162900
cctgagcacc cgctgacatt tccgttgtac atgttcctgt ttatgcattc acaaggtgac  162960
tgggatgtag agaggcgcta gtgtgcaggt ggccacagca ggactaagga caggccccca  163020
```

```
ctgtcctagg ggcatgctcg cctgcagccc ctccttcttg ggcacagaca actgttgttc 163080
tccacccaca ttagggacag cagcctccct atcagctgag aaggccagcc ctccctggct 163140
gtgagcagcc tccgctgtgt ccagagacat gggcctccca ctcctgttcc ttgctagccc 163200
tggggcggtg tctgcccagg agctggctgg ccggtgatgg gatctgccgt tccatggatg 163260
catgccccaa gggtgtcact gagctgtgtt ttgtctgagc ctctcttggt caacagcaaa 163320
gcttggcgtc ttggcactgt tagtgacaga gcctggcatc ccttctgccc ccgttccagc 163380
tgacatcttg cacggggacc ccttttagtc aggagagtgc agatctgtgc tcattggaga 163440
ctgccccact gccctgtcag agccgccact cctatcccca ggccaggtcc ctggaccagc 163500
ctcttgtttg caggcccaga ggagccaagt cattaaaatg gaagtggatt ctggatggcc 163560
ggctgctgct gacataggag ctggatttgg gagctctgag atggggcagg agctctgctt 163620
cctcagccct tgaggcgagc caggcgaggt tggcgactgt catgtggctt ggtttgctca 163680
tgcctgttga tgttttgggt attgaatatg gtaagtggag gaaatgcttt tctggagtct 163740
gtgcaggtgc tgccttgaga ccctcaagct tccacctgtc cctctcctat gtggcagctg 163800
aggagcagct gacatgtgga cttgtgtgct gcccacatac atgaggggc gctgaaaggg 163860 agcccctgct caaagggagc ccctcctctg agcagccttt gacaggcctg tatgaggctt 163920
ttcccaccag ctcccaacag aggcctcccc cagccaggac cacctcgtcc tgtggcagg 163980 gcagcaggag cggtagaaag gggtctgatg tttgaggagg cccttaaggg aagctactga 164040 atttttaacaa gaaagccacc attcttccgt attggttggg ggctcctgtt tctcatccta 164100
gcttcttcct ggaaagcctg ctagaagctt tgggaatgag gggaaagttc tcagaaccgt 164160
tgctgctccc cacccacctc ccctgcagta agttatgtca acagtcgga gacagaagta 164220 tcacaggcca gatgttgttc tgctagatgt ttacatttgt aagaaataac actgtgaatg 164280
taaaacggag ccattcccct tggaatgcat atcgctgggc tcaacacaga gtttgtcttc 164340
cttttgttta cgacgtgatc taaaacagtc cttagcaagg ggctcagaac accccgctct 164400
ggcagtgggt gtcccccact cccaaaggcc tgcctgtgtg ctccagagat gaatatgagc 164460
tcattagtaa aatgacttta cccatgcgta agtcaagtac acgtgcacgt gcatatggac 164520
acatctgtag ttttatacac gcacatctca agacagagat gcatggcctc caagagtgcc 164580
cgtgtcggtt cttcctggaa gttgactttc ctcagacctg ccaggtaaag ttagctgtgt 164640
gacgggcgtc caggcgcggg gcttggtcag agcagggctc attcatggct cactaggatc 164700
ccaccggaga aaacggtctc catatcaact ctgccgaagg gaggaagact tgtcgcgtt 164760 cctaaaaaac ctatggcaag caccaatcat attatccaaa ttgtgttgaa aatgtgatta 164820
atttggttgt caagttttgg gggtgagctg cggggagact gcttttgttt tgctgctggt 164880
aatatcagga aagactttaa tgaaaccagg gtagaattgt ttggcaatgc actgaagcgc 164940
gtttctgtcc caaacgtgc ctcccttccg ctgcgggccc agctgagtct gtgtaggtga 165000
cgtttccggc tgccaagcgc tctttgttac tgtccacccc catttctgcc agcacacgtg 165060
tcctttcagg aggaaaatgt gaagctgaaa ccctccaga cacccagaat gtagcatctg 165120
agaaggcccc gtgccctaaa ggacacccc gcccccacct tcatggaggg gtcattccag 165180
agccctcgga gccgatgaac agctcgtcct cttggagctg agctgagccc cccacggagc 165240
tcgggacgga tagtaaacag caataactcg gtctgtggct gcctggcagg tggaagttcc 165300
tccccctgag gggcggagtg aggttagttc tgtgtgtctg tggggtggag tcagcctgct 165360
```

-continued

```
cctgctacct gtgagcatcc tgcccagcag acatcctcac ccggctttgt ccctccccac   165420
ttcctccctc tgcggggagg acccaggacc acagctgctg gccagggtag gcttggagct   165480
gtgctccgga ggggccacct gtgggagcga gaagaaggaa gatcttgaga gctgccgagg   165540
caccctggag agctcaggat ggtccaggcg agaagaggac actcgctcgc caggcctggg   165600
cctcctggga aggagggagc cgctcagagc gccgcatgac aactgaaggc aacctggaag   165660
gttcagaggc cactcttccc ccgtgtgcct gtcacgctct ggtgcagtcc aaggaacgcc   165720
ttcccctcag ttgtttccaa aagcagagtc tcccgctgca atctgggtgg tgattgccag   165780
ccttggagga ttgtggccaa cgtggacctg cctacggagg gtgggctctg acccacgtgg   165840
ggcctccttg tccaggtctc attgctttgt gctgtggtca gagggactgt cagctgagcc   165900
tgagctcccc tggagccagc agggctgtga tgggcgagtc ccggagcccc acccagacct   165960
gactgcttct gagagcaaag ggaaggactg acgagagatg tatatttaat ttttttaact   166020
gctgcaaaca ttgtacatcc aaattaaagg aaaaacattg aaaccatcag ttgttgctgt   166080
gtgaggcttg ctttacttca tgagaaccta gaccttgctg agctggagtc ttaggaaact   166140
gtctcctaag tgcttatcca gcaggggcag aaactgtccc accagctaac atctgacatt   166200
acggagggtc ccgcaggcag ctgccagcaa ggacaagccc tgtgttttct gtagccaggg   166260
atgaggaagt ggccccaggg gcctggctgg gtgctgcttc aagggccttc gcaaaccaca   166320
gtacaggtgg tcttcctgca ctgcagatgg gagctgtggg agctgctgga tccttcatgg   166380
tcaagtgaca tcataagctt atatgacaca cacaagcctc aggacttggc ccatggcact   166440
ggagcaggtc atcaggccca gcagactaga gctgtgttct cacagggccc atgacccttc   166500
tagctccttg gccattgaaa cctgtgtccc tgacccagct gctcccaggt accccccaaa   166560
gcagctggca catcccacct ctggtgtggc ctgggctgct gtgtgtccgc agggcctgcc   166620
ccgtctgttc tagcttgttt ctcctgtctg aaccagcgcc tactccaaga aggctctgct   166680
cagcccagcg gggatgcttc taagctcggc ccagcctctg ggaagccttg gtggtcggtg   166740
gtgtagtcat cctgggatgc agaacgaaaa cctgcaagaa caaaactgtg gcttcgtctg   166800
gtgcagggta tttagttact gtttgctgag gtcctgtctg gttctggcga atgggcaggg   166860
gtcgcccacc cattctttcc ctgctctgct gtccgtgcca ggagagacgg gggcctgttg   166920
gccaaggggg cagctcctgc tgcctgctgt ccttaggcac gtgcagggac cccctttctc   166980
tgagcaggat ggggatcagt ctgccagagg gatgtggtgg acaggcccag ccgggtaaaa   167040
aattcccca gttgctcaaa gcatttgggg cggggcatgc cacttgagct ccttaaatct   167100
gtctcatagg tgacaccgct ccagggcgcc ccaggggctt ctcccttcag agctaccaaa   167160
gttctggtca cttcagaaaa atggagcacc cccttctccc tggtccagat gtggacagcc   167220
agacccttgg cacacctagc acacctggca tggctggtaa tttcagaaag aaaaggggcc   167280
ggggtccagt gggaagcagt ggcgaacccc tcatgcgtgg gctttgcgat ccctcccct   167340
gccacggcag agctgccctc agcacagcct tcctcttcct catcggagag cacaccctgt   167400
cccccttgccg gggctgtgct ctgtgcctgc agtggtattt ggttttggct gctactggct   167460
ttgttccaaa gaggatctgg aagtcgcttc cctgtgtgg agcgtggagc actgtgagtc   167520
agatgaggga agtagccagg gggaggtgag taccggcgg agccgccaca gaaaggactg   167580
ggtaggggc cttgcctcca cgtgatgtga cacggccagc cgaggacaga ggaagcccg   167640
ttcctggggg tgtggggtgc acccctcagg gaagcctgca gtgggcccca aggaaaggcg   167700
ttctctgcga gcccacgagt ctgctctgtg ggcaccgtga caatgcccgt gggcagaggt   167760
```

```
gggcccggcc ttgtgtcgtc accaggacct cttttgggaa accatgtggg catcccttgc    167820
gggtccccca ggttctgcag tcccagcggc ctggctgcct gttgggcaca tggcttgagc    167880
cgcccagagg gcccagccct gttggcagcc acatcctctg gaggccctgc cggtggggct    167940
ggctttctct accccacacc aggcctccaa gtatactggt cggggtgtc tgggccctgg    168000 g                                                                   168001
```

<210> SEQ ID NO 5
<211> LENGTH: 10295
<212> TYPE: DNA
<213> ORGANISM: Rattus norvegicus

<400> SEQUENCE: 5

```
gcactcgccg cgagggttgc cgggacgggc ccaagatggc tgggagcttt ggttccgctt      60
cggtctacct cgtagagccc cattcattac cttgctgcta agtggcgctg cgtagtgcga     120
ataggctcca agccttcagg gtctgtcctg tcgggcagga ggccgtcatg caaccctgg      180 aaaaactgat gaaggctttc gagtcgctca agtcgttcca gcagcaacag cagcagcagc    240
agccgccgcc gcaggcgccg ccaccaccgc cgccgccgcc gcctcaaccc cctcagccgc    300
cgcctcaggg gcagccgccg ccaccaccgc cgctgccagg tccggccgag gagccgctgc    360
accgaccaaa gaaggaactc tcagccacca agaaggaccg tgtgaatcac tgtctaacaa    420
tatgtgaaaa cattgtggca cagtctctca gaaattctcc agaatttcag aaactcttgg    480
gcattgctat ggaactgttt ctgctgtgca gcgacgatgc ggagtcagac gtcagaatgg    540
tggctgatga gtgcctcaac aaagtcatca agctttgat ggactctaat cttccaaggc     600
tacagttaga actctataag gaaattaaaa agaatggtgc tcctcgaagt ttgcgtgcag    660
ctctgtggag gttgctgag ctggctcacc tggttcgacc tcagaagtgc aggccttatc     720
tggtgaatct tcttccatgt ttgacccgaa caagcaaacg accggaggag tcagttcagg    780
agactttggc tgcagctgtt cctaaaatta tggcctcttt tggcaatttc gcgaatgaca    840
atgaaattaa ggttctattg aaagctttca tagcaaatct gaagtcaagc tctcccactg    900
tgcggcggac agcagctggg tcagcagtga gtatctgcca gcactctagg aggacacagt    960
acttctacaa ctggctcctg aatgtgctcc taggtttgct ggttcccatg gaggaagacc   1020 acccccactct cctgatcctt ggtgtgttgc tcacactgag gtgtctagtg cccttgctcc   1080
agcagcaggt caaggacaca gtctaaagg gcagctttgg ggtaacacgg aaagaaatgg    1140
aagtctctcc ttctgcagag cagcttgtcc aggtttatga actgactttg catcacacac   1200
agcaccaaga ccataatgtg gtgacagggg cattggagct cctgcagcag ctcttccgta   1260 ccctccacc tgagctgctg caagcactga ccacaccagg agggctcggg cagctcactc     1320
tggttcgaga ggaagccggg ggccgaggcc gcagcgggag tatcgtggag cttttagctg   1380
gagggggttc ctcatgcagc cctgttctct caagaaagca aaaaggcaaa gtgctcttag   1440
gagaggaaga agccttggag gatgactcgg agtccaggtc agatgtcagc agctcagcct   1500
ttgcagcctc tgtgaagagt gagattggtg gagagctcgc tgcttcttct tcgggtgtct   1560
ccactcccgg ttctgtaggt cacgacatca tcactgagca gcctcgatcc cagcacacac   1620
ttcaagcaga ctctgtggat ttgtcaggct gtgacttgac cagtgctgct actgatggag   1680
atgaggaaga catcttgagc cacagctcca gccagttcag tgctgttcca tccgaccctg   1740
ccatggacct gaatgatggg acccaggcct cctcacccat cagtgacagt tctcagacca   1800
```

-continued

```
ccactgaagg acctgattca gctgtgactc cttctgacag ttctgaaatt gtcttagatg   1860
gtgctgacag ccagtattta ggcgtgcaga taggacagcc acaggaggaa gacgaggagg   1920
aagctgcagg tgttctttct ggtgaagtct cagacgtttt cagaaactct tctctggccc   1980
ttcagcaggc acacttgttg aaagaatgg gtcatagccg gcagccttct gacagcagtg   2040
ttgataagtt tgtttcaaaa gatgaggttg ctgaagctgg ggacccagaa agcaagcctt   2100
gccgaatcaa aggtgacata ggacagccta atgatgatga ttctgctcct ctggtacatt   2160
gtgtccgtct tttatccgct tccttttgt taactggcga aaagaaagca ctggttccag   2220
acagagatgt gagagtcagt gtgaaggccc tggccctcag ctgtattggt gcagctgtgg   2280
cccttcatcc agagtcgttc ttcagcaaac tctacaaagt acctctcagt accatggaaa   2340
gtactgagga acagtatgtc tctgacatcc tgaactacat cgatcatgga acccctcagg   2400
tgcgaggagc tactgccatt ctctgtggga cccttgtcta ctccatcctc agcaggtccc   2460
gtctccgtgt tggtgactgg ctgggcacca tcagggccct gacaggaaat acattttctc   2520
tggtggactg cattcctta ctgcagaaaa ctttgaagga tgaatcttct gttacttgca   2580
agttggcttg tacagctgtg aggcactgtg tcctgagtct ttgcagcagc agctacagtg   2640
acttgggatt acaactgctt attgacatgc tgcctctgaa aacagctcc tactggctgg   2700
tgaggactga actgctggaa actcttgcag agattgattt caggctggtg agttttttgg   2760
aggcaaaagc agaaagttta caccgagggg ctcatcatta tacagggttt ctaaaactac   2820
aagaacgagt actcaataat gtggtcattt atttgcttgg agatgaagac cccagggttc   2880
gacatgttgc tgcgacgaca ttgacaagac ttgtcccaaa gctgttttat aagtgtgacc   2940
aaggacaggc tgacccagtc gtggctgtag caagagatca agtagtgtt tacctgaagc   3000
tcctcatgca tgagacccag ccaccatccc acttctccgt cagcaccata accagaatct   3060
atagaggcta cagcttacta ccaagtgtaa cagatgtcac catggaaaac aacctctcaa   3120
gagtcgttgc cgcagtttct catgaactca ttacgtcaac tacacgggca ctcacatttg   3180
ggtgctgtga agccttgtgt gttctttcag ccgccttttcc agtttgcact tggagtctag   3240
gatggcactg tggagtgccc ccactgagtg cctctgatga gtccaggaag agctgcactg   3300
ttgggatggc ctccatgatt ctcaccttgc tttcatcagc ttggttccca ctggatctct   3360
cagcccatca ggatgccttg attttggctg gaaacttgct agcagcgagt gcccccaagt   3420
ctctgagaag ctcatgggcc tcggaagaag aaggcagctc agcagccacc agacaggagg   3480
agatctggcc tgccctgggg gatcggactc tggtgcccat ggtggagcag cttttctccc   3540
acctgctgaa ggtgatcaat atctgtgctc atgtcttgga tgacgtgact cctggaccag   3600
caatcaaggc agctttgcct tctctcacaa acccccttc tctaagtcct attcgacgga   3660
aagggaagga gaaagagccc ggagaacaaa catccactcc gatgagtccc aagaaaggtg   3720
gagaggccag tacagcctct cgacagtcag acacctcagg acctgtcaca gcgagtaaat   3780
catcttcact tgggagtttc taccatctcc cttcctacct cagactgcat gatgtcctga   3840
aagccactca cgccaactat aaggtcacct tagatcttca aacagcact gaaaagtttg   3900
gggggttcct gcgctctgcc ttggacgtcc tttctcagat tctagagctg gcgacactgc   3960
aggacattgg aaagtgtgtt gaagaggtcc ttggatactt gaaatcctgc tttagtcgag   4020
aaccaatgat ggcgactgtc tgtgttcagc agctattgaa gactctcttt gggacaaact   4080
tagcctcaca gtttgatggc ttatcttcca accccagcaa gtctcagtgc cgagcacagc   4140
gccttggctc ttccagtgtg aggcccggct tatatcacta ctgcttcatg gcaccataca   4200
```

```
cgcacttcac gcaggctttg gctgatgcca gcctgaggaa catggtacag gcggaccagg    4260
agcacgatgc ctcagggtgg tttgatgtac tccagaaagt gtctgctcag ttgaagacga    4320
accttacaag tgtcacaaag aaccgtgcag ataagaacgc tattcataac cacattaggt    4380
tatttgagcc tcttgttata aaagcattga agcagtacac cacgacaaca tcagtacaac    4440
tgcagaagca ggttttggat ttgctggcac agctggttca gctacgggtc aattactgtc    4500
tactggattc agatcaggtg ttcatcgggt ttgtgctgaa gcagtttgag tacattgaag    4560
tgggccagtt cagggaatca gaggcaatta ttccaaatat attttctttc ctggtactat    4620
tatcttatga gcgctaccat tcaaaacaga tcattgaatt cctaaaatc atccagctgt     4680 gtgatggcat catggccagt ggaaggaagg ctgtcacaca tgctattcct gcgctgcagc    4740
ccattgtcca tgacctcttt gtgttaagag aacaaataa agctgatgca gggaaagagc     4800
ttgaaaccca aaggaggtg gtggtctcaa tgctgttacg actcatccag taccatcagg      4860
tgctagagat gttcatcctc gtcctgcagc agtgccacaa agagaatgag acaagtggaa    4920
aacggctctc tcggcaggtc gcagacatca tcctgcccat gttagccaag cagcagatgc    4980
atattgactc tcatgaagcc cttggagtat aaatacctt gtttgagatt ttggctcctt      5040
cctccctacg tcctgtggac atgcttttgc ggagtatgtt catcactcca agcacaatgg    5100
catctgtaag cactgtgcag ctgtggatat ctggaatcct agccattctg agggttctca    5160
tttcccagtc aaccgaagac attgttcttt ctcgtattca ggagctctcc ttctctccat     5220
atttaatttc ctgtccagta attaacaggt taagggatgg agacagtaat ccaacactag    5280
gagaacgcag tgaagggaaa caagtaaaga atttgccaga agatacattc tcaaggtttc    5340
tcttacagct ggttggtatt cttctggaag acattgttac aaaacagctc aaagtggaca    5400
tgagtgaaca gcagcataca ttctattgcc aagagctcgg cacactgctc atgtgtctga    5460
tccacatatt caaatctgga atgttccgga gaatcacagc cgctgccact agactcttca    5520
ccagtgatgg ctgtgaaggc agcttctata ctctagatag cctgaatgca cgggtgcgag    5580
ccatggtgcc cacacaccca gctctggtac tgctctggtg tcagatccta ctgctcatca    5640
accacactga ccaccgatgg tgggccgagg tgcagcagac gcccaagaga cacagtctgt    5700
cctgcacgaa gtcactaaac ccccagatat ctgctgaaga ggattctggc tcagcagctc    5760
agcttggaat gtgcaataga gaaatagtac gaagaggggc ccttattctc ttctgtgatt    5820
atgtctgtca gaatctccat gactcagaac acttaacatg gctcattgtg aatcacattc    5880
aagatctgat cagcttgtcc cacgagcctc cagttcaaga cttattagt gccattcatc     5940 gtaattctgc agctagtggt cttttatcc aggcaattca gtctcgctgt gaaaatcttt      6000
caactccaac cactctgaag aaaacacttc agtgcttgga aggcatccat ctcagccagt    6060
ctggtgctgt gctcacactg tatgtggaca ggctactggg caccccttc cgtgcgctgg      6120 ctcgcatggt cgacaccctg gcctgtcgcc gagtagaaat gcttttggct gcaaatttac    6180
agagcagcat ggcccagttg ccagaggagg aactgaacag aatccaggaa cacctccaga    6240
acactgggct tgcacaaaga caccaaaggc tctattcact gctggacaga ttccgactct    6300
ctactgtgca ggactcactt agccccttgc ccccagtcac ttcccaccct ctggatgggg    6360
atgggcacac atccctggaa acagtgaatc cggacaaaga ctggtacctc cagcttgtca    6420
gatcccagtg ttggaccagg tcagattctg cactgctgga aggtgcagag ctggtgaacc    6480
gtatccctgc tgaagatatg agtgacttca tgatgagctc ggagttcaac ctaagccttt    6540
```

```
tggctccctg cttaagcctt ggcatgagcg agattgctaa tggccaaaag agtccccttt    6600
ttgaagcggc tcgtagggtg actctggacc gggtgaccaa tgtggttcag cagctgcctg    6660
cagtccatca agtcttccag cctttcctgc ctacagaacc cacagcctac tggagcaagc    6720
tgaatgatct ctttggtgat accacatcat accagtctct gaccacactt gcccgtgccc    6780
tggcacagta cctggtggtg ctctccaaag tgcctgctcc tttgcacctt cctcctgaga    6840
aggaggggca cacggtgaag tttgtggtaa tgacacttga ggccctgtca tggcatttga    6900
tccatgagca gatcccactg agtctggacc tccaagccgg cctagactgc tgctgcctgg    6960
cactgcaggt gcctggcctc tgggggggtgc tgtcctcccc agagtacgtg actcatactt    7020
gctcccttat ccactgtgtg cgattcatcc tggaagccat tgcagtacaa cctggagacc    7080
aacttcttgg tccggaaagc aggtcacata ctccaagggc tgtcagaaag gaggaagtag    7140
actcagatat acaaaacctc agtcacatca cttcggcctg cgagatggtg gcagacatgg    7200
tggaatccct gcagtcggtg ctggccctgg gccacaagag gaacagcacc ctaccttcat    7260
ttctcacagc tgtgctgaag aacattgttg tcagtctggc ccgcctcccc ctcgttaaca    7320
gctatactcg tgtgcctcct ctggtatgga aactcgggtg gtcacccaag cctggagggg    7380
atttcggcac agtgtttcct gagatccctg tagagttcct ccaggagaag gaggtcctca    7440
aggagttcat ctaccgcatc aacaccctag ggtggaccag tcgtactcaa ttcgaagaaa    7500
cttgggccac cctccttggt gtcctggtga ctcagccctt ggtgatggaa caggaagaga    7560
gcccaccaga ggaagacacc gaaaggaccc agatccacgt cctggctgta caggccatca    7620
cctctctagt gctcagcgca atggctgtgc ctgtggctgg caatccagct gtaagctgct    7680
tggagcaaca gccccggaac aagccactga aggctctcga taccagatttt ggaagaaagt    7740 tgagcatgat cagagggatt gtagaacaag aaatccaaga gatggtttcc caaagagaga    7800
atactgccac tcatcattct caccaggcat gggatcctgt cccttctctg ttaccagcta    7860
ctacaggtgc tcttatcagc catgacaagc tgctgctgca gatcaactca gagcgggagc    7920
caggcaacat gagctacaag ctgggccagg tgtccataca ctccgtgtgg ctggggaaca    7980
acatcacacc cctgagagag gaggaatggg atgaggagga ggaggaagaa gcggatgccc    8040
ctgcgccaac atcaccacct gtgtctccag tcaattccag aaaacaccgt gctggggttg    8100
atattcactc ctgttcgcag tttctgcttg aattatacag ccgttggatc ctgccatcca    8160
gtgcagccag aaggaccccct gtcatcctga tcagtgaagt ggttcgatct cttcttgtgg    8220
tgtcagactt attcactgaa cgtacccagt ttgaaatgat gtatctgacg ctgacagaac    8280
tacggagagt gcacccttca gaagatgaga tcctcattca atacctggtg cctgccacct    8340
gtaaggcagc tgctgttctt ggaatggaca aaactgtggc agagccggtc agccgcctac    8400
tggagagcac actcaggagc acccacctgc ccagccagat cggagccctg catggcatcc    8460
tctatgtgtt ggagtgtgac ctcttggatg acactgtaaa gcagctcatt ccagttgtta    8520
gtgactatct gctgtccaac ctcaaaggaa tagcccactg cgtgaacatt cacagccagc    8580
agcatgtgct ggtgatgtgt gccactgcat tctacctgat ggaaaactac cctctggatg    8640
tgggccagag attctcagca tctgtgatac agatgtgtgg agtaatgctg tctgaagtg     8700 aggagtccac cccctccatc atttaccact gtgccctccg gggtctggaa cggctcctgc    8760
tgtctgagca gctctctcgg ctagacacgg agtccttggt caagctaagt gtggacagag    8820
tgaatgtaca aagcccacac agggccatgg cagccctagg cctgatgctt acctgcatgt    8880
acacaggaaa ggaaaaagcc agtccaggca gagcttctga ccccagccct gctacccctg    8940
```

```
acagcgagtc tgtgattgta gctatggagc gagtgtctgt gctctttgac aggatccgca    9000
agggatttcc ctgtgaagcc agggtcgtgg caaggatcct gcctcagttt ctagatgact    9060
tctttccacc tcaagatgtc atgaacaaag tcattggaga gttcctgtcc aaccagcagc    9120
catacccaca gttcatggcc actgtagtat acaaggtttt tcagactctg cacagtgctg    9180
ggcagtcatc catggtccgg gactgggtta tgctgtctct gtccaacttc acacaaagaa    9240
ctccagttgc catggccatg tggagcctct cctgcttcct tgtcagtgca tctaccagcc    9300
catgggtttc tgcaatcctt ccacacgtca tcagcaggat gggcaaactg agcaggtgg     9360 atgtgaacct tttctgcctg gttgccacag acttctacag acaccagata gaggaggaat    9420
tcgaccgcag ggctttccag tctgtgtttg aggtggtggc agcaccagga agtccatacc    9480
acaggctgct tgcttgtttg caaaatgttc acaaggtcac cgcctgctga gtagtacctg    9540
tggaacaaga ggctgagagg aggcaactgc tgtggctaca gcctccaggg gcctgcacca    9600
agcttctgct aaggctgcct tggacgtgca ggcttccact tgtgtcaagt ggacagccag    9660
gcaatggcag gagtgctttg caatgagagc tatgcaggga acatgcacta tgttggggtt    9720
gagcctgagt cctgggtcct ggcatcactg cagctggtgg cagtgctagg ttgaccaggt    9780
gtttgtcttt ttcttagtgt tgccctggcc atagttgcca ggttgcagct gccctggtat    9840
gtggaacaga atccgagctc ttgtaagatg gttctgagcc ccctgtccc actgggctgg     9900 agagctccct cccacattta cccagcaggt gtacctgcca caccagtgtc tggacacaaa    9960
gtgaatggtg tgggggctgg gaactgggac tgccaggtgt ccagcatcat tttcccttc    10020 tctgttttct tctcaggagt taaaatttaa ttatatcagt aaagagatta attttaatgt    10080
aactcttcct atgcccgtgt aaagtgtgtg acttggcaag gcctgtgctg catgtgacaa    10140
agtttatgga agtggatgcg ccttctggcc accactctct ctcctgtagc tactcagtct    10200
agtcgggcag gtccctcatg tagccctccc aacaccctat ggcacttgca cttcacacgg    10260 ctccttttc ttatgcattc catttgacta gcaca                                10295
```

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 6
tagcattctt atctgcacgg                                                20

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
acccgtaact gaaccagctg                                                20

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligonucleotide

```
<400> SEQUENCE: 8
ttccctgaac tggcccactt                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 9
ctctgattcc ctgaactggc                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 10
gcctctgatt ccctgaactg                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 11
tgcctctgat tccctgaact                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 12
ttgcctctga ttccctgaac                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13
attgcctctg attccctgaa                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
tggaatgatt gcctctgatt                                               20

<210> SEQ ID NO 15
<211> LENGTH: 18
```

```
<212> TYPE: DNA
<213> ORGANISM: Artificial Sequence
<220> FEATURE:
<223> OTHER INFORMATION: Synthetic Oligonucleotide

<400> SEQUENCE: 15
gtttggaatg attgcctc                                            18

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
ccaatgatct gttttgaatg                                          20

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 17
gccttccttc cactggccat                                          20

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 18
ctgcatcagc tttatttgtt                                          20

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 19
cctgcatcag ctttatttgt                                          20

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
agctcttttc ctgcatcagc                                          20

<210> SEQ ID NO 21
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 21
```

```
gtaacattga caccacca                                              18

<210> SEQ ID NO 22
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 22
ctcagtaaca ttgacaccac                                            20

<210> SEQ ID NO 23
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 23
atgagtctca gtaacattga                                            20

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 24
tccttgtggc actgctgcag                                            20

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 25 ttctcccttgt ggcactgctg                                           20

<210> SEQ ID NO 26
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 26
tcattctcct tgtggcactg                                            20

<210> SEQ ID NO 27
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 27
attctccttg tggcactg                                              18

<210> SEQ ID NO 28
<211> LENGTH: 20
<212> TYPE: DNA
<213> ORGANISM: Artificial Sequence
```

```
<220> FEATURE:
<223> OTHER INFORMATION: Synthetic Oligonucleotide

<400> SEQUENCE: 28
cgagacagtc gcttccactt                                              20

<210> SEQ ID NO 29
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 29
tgtcgagaca gtcgcttc                                                18

<210> SEQ ID NO 30
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 30
ttgcacattc caagtttggc                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 31
tctctattgc acattccaag                                              20

<210> SEQ ID NO 32
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 32
tttctctatt gcacattcca                                              20

<210> SEQ ID NO 33
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 33
tctctattgc acattcca                                                18

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 34
gcagggttac cgccatcccc                                              20
```

<210> SEQ ID NO 35
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 35
accttatctg cacggttc                                                 18

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
ctctctgtgt atcaccttcc                                               20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
ctccgtccgg tagacatgct                                               20

<210> SEQ ID NO 38
<211> LENGTH: 23
<212> TYPE: DNA
<213> ORGANISM: Artificial Sequence
<220> FEATURE:
<223> OTHER INFORMATION: Primer

<400> SEQUENCE: 38
ggaaatcaga accctcaaaa tgg                                           23

<210> SEQ ID NO 39
<211> LENGTH: 29
<212> TYPE: DNA
<213> ORGANISM: Artificial Sequence
<220> FEATURE:
<223> OTHER INFORMATION: Probe

<400> SEQUENCE: 39
tgagcactgt tcaactgtgg atatcggga                                     29

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40
gtctgagcct ctctcggtca a                                             21

<210> SEQ ID NO 41
<211> LENGTH: 19
<212> TYPE: DNA
<213> ORGANISM: Artificial Sequence
<220> FEATURE:
<223> OTHER INFORMATION: Primer

```
<400> SEQUENCE: 41
aagggatgct gggctctgt                                            19

<210> SEQ ID NO 42
<211> LENGTH: 30
<212> TYPE: DNA
<213> ORGANISM: Artificial Sequence
<220> FEATURE:
<223> OTHER INFORMATION: Probe

<400> SEQUENCE: 42
agcaaagctt ggtgtcttgg cactgttagt                                30

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
cagagctggt caaccgtatc c                                         21

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
ggcttaaaca gggagccaaa a                                         21

<210> SEQ ID NO 45
<211> LENGTH: 26
<212> TYPE: DNA
<213> ORGANISM: Artificial Sequence
<220> FEATURE:
<223> OTHER INFORMATION: Probe

<400> SEQUENCE: 45
acttcatgat gagctcggag ttcaac                                    26

<210> SEQ ID NO 46
<211> LENGTH: 25
<212> TYPE: DNA
<213> ORGANISM: Artificial Sequence
<220> FEATURE:
<223> OTHER INFORMATION: Primer

<400> SEQUENCE: 46
aggagaaaaa caaagaacac cagaa                                     25

<210> SEQ ID NO 47
<211> LENGTH: 25
<212> TYPE: DNA
<213> ORGANISM: Artificial Sequence
<220> FEATURE:
<223> OTHER INFORMATION: Primer

<400> SEQUENCE: 47
caattagggc aactcagaaa tagct                                     25

<210> SEQ ID NO 48
```

-continued

```
<211> LENGTH: 22
<212> TYPE: DNA
<213> ORGANISM: Artificial Sequence
<220> FEATURE:
<223> OTHER INFORMATION: Probe

<400> SEQUENCE: 48
ccaactggtc ccccagccaa ga                                              22

<210> SEQ ID NO 49
<211> LENGTH: 21
<212> TYPE: DNA
<213> ORGANISM: Artificial Sequence
<220> FEATURE:
<223> OTHER INFORMATION: Primer

<400> SEQUENCE: 49
cagagctggt gaaccgtatc c                                               21

<210> SEQ ID NO 50
<211> LENGTH: 21
<212> TYPE: DNA
<213> ORGANISM: Artificial Sequence
<220> FEATURE:
<223> OTHER INFORMATION: Primer

<400> SEQUENCE: 50
ggcttaagca gggagccaaa a                                               21

<210> SEQ ID NO 51
<211> LENGTH: 26
<212> TYPE: DNA
<213> ORGANISM: Artificial Sequence
<220> FEATURE:
<223> OTHER INFORMATION: Probe

<400> SEQUENCE: 51
acttcatgat gagctcggag ttcaac                                          26

<210> SEQ ID NO 52
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 52
tcctagtgtt acattaccgc                                                 20

<210> SEQ ID NO 53
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 53
ctcgactaaa gcaggatttc                                                 20

<210> SEQ ID NO 54
<211> LENGTH: 17
<212> TYPE: DNA
<213> ORGANISM: Artificial Sequence
<220> FEATURE:
<223> OTHER INFORMATION: Primer

<400> SEQUENCE: 54
```

```
tggtcccca gccaaga                                                17

<210> SEQ ID NO 55
<211> LENGTH: 18
<212> TYPE: DNA
<213> ORGANISM: Artificial Sequence
<220> FEATURE:
<223> OTHER INFORMATION: Primer

<400> SEQUENCE: 55
cccaccgtgt gacatcca                                              18

<210> SEQ ID NO 56
<211> LENGTH: 26
<212> TYPE: DNA
<213> ORGANISM: Artificial Sequence
<220> FEATURE:
<223> OTHER INFORMATION: Probe

<400> SEQUENCE: 56
agctatctcc gagctgccct gattgg                                     26

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 57
gctgattaga gagaggtccc                                            20

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
tcccatttca ggagacctgg                                            20
```

MODULATION OF HUNTINGTIN EXPRESSION

This application is the national stage entry of international patent application No. PCT/US2010/048532, filed Sep. 10, 2010, which claims priority benefit of U.S. provisional application No. 61/241,853, filed Sep. 11, 2009, each of which is incorporated herein by reference in its entirety.

SEQUENCE LISTING

The present application is being filed along with a Sequence Listing in electronic format. The Sequence Listing is provided as a file entitled BIOL0113WOSEQ.txt created Sep. 8, 2010, which is 456 Kb in size. The information in the electronic format of the sequence listing is incorporated herein by reference in its entirety.

FIELD OF THE INVENTION

Provided herein are methods, compounds, and compositions for reducing expression of huntingtin mRNA and protein in an animal. Such methods, compounds, and compositions are useful, for example, to treat, prevent, or ameliorate Huntington's disease.

BACKGROUND

Huntington's disease (HD) is a devastating autosomal dominant, neurodegenerative disease caused by a CAG trinucleotide repeat expansion encoding an abnormally long polyglutamine (PolyQ) tract in the huntingtin protein. The Huntington disease gene was first mapped in 1993 (The Huntington's Disease Collaborative Research Group. Cell. 1993, 72:971-83), consisting of a gene, IT15, which contained a polymorphic trinucleotide repeat that is expanded and unstable on HD chromosomes. Although CAG repeats in the normal size range are usually inherited as Mendelian alleles, expanded HD repeats are unstable through meiotic transmission and are found to be expanded beyond the normal size range (6-34 repeat units) in HD patients.

Both normal and variant huntingtin protein are localized chiefly in the cytoplasm of neurons (DiFiglia et al., Neuron 1995, 14:1075-81). As a result of excessive polyglutamine length, huntingtin protein forms aggregates in the cytoplasm and nucleus of CNS neurons (Davies et al., Cell 1997, 90:537-548). Both transgenic animals and genetically modified cell lines have been used to investigate the effects of expanded polyQ repeats on the localization and processing of huntingtin. However, it is still unclear whether the formation of aggregates per se is the essential cytotoxic step or a consequence of cellular dysfunction.

HD is characterized by progressive chorea, psychiatric changes and intellectual decline. This dominant disorder affects males and females equally, and occurs in all races (Gusella and MacDonald, Curr. Opin. Neurobiol. 1995 5:656-62). Symptoms of HD are due to the death of neurons in many brain regions, but is most apparent in the striatum, particularly in the caudate nucleus, which suffers a progressive gradient of cell loss that ultimately decimates the entire structure. Although the gene encoding huntingtin is expressed ubiquitously (Strong, T. V. et al., Nat. Genet. 1995, 5:259-263), selective cell loss and fibrillary astrocytosis is observed in the brain, particularly in the caudate and putamen of the striatum and in the cerebral cortex of HD patients (Vonsattel, J-P. et al., Neuropathol. Exp. Neurol. 1985, 44:559-577), and, to a lesser extent, in the hippocampus (Spargo, E. et al., J. Neurol. Neurosurg. Psychiatry 1993, 56:487-491) and the subthalamus (Byers, R. K. et al., Neurology 1973, 23:561-569).

Huntingtin is crucial for normal development and may be regarded as a cell survival gene (Nasir et al., Human Molecular Genetics, Vol 5, 1431-1435). The normal function of huntingtin remains incompletely characterized, but based upon protein-protein interactions, it appears to be associated with the cytoskeleton and required for neurogenesis (Walling et al., J. Neurosci Res. 1998, 54:301-8). Huntingtin is specifically cleaved during apoptosis by a key cysteine protease, apopain, known to play a pivotal role in apoptotic cell death. The rate of cleavage is enhanced by longer polyglutamine tracts, suggesting that inappropriate apoptosis underlies HD.

Antisense technology is emerging as an effective means for reducing the expression of specific gene products and may therefore prove to be uniquely useful in a number of therapeutic, diagnostic, and research applications for the modulation of huntingtin expression. (See U.S. Patent Publication Nos. 2008/0039418 and 2007/0299027)

Antisense compounds for modulating expression of huntingtin are disclosed in the aforementioned published patent applications. However, there remains a need for additional such compounds.

SUMMARY OF THE INVENTION

Provided herein are methods, compounds, and compositions for modulating expression of huntingtin and treating, preventing, delaying or ameliorating Huntington's disease and/or a symptom thereof.

Figure 1:
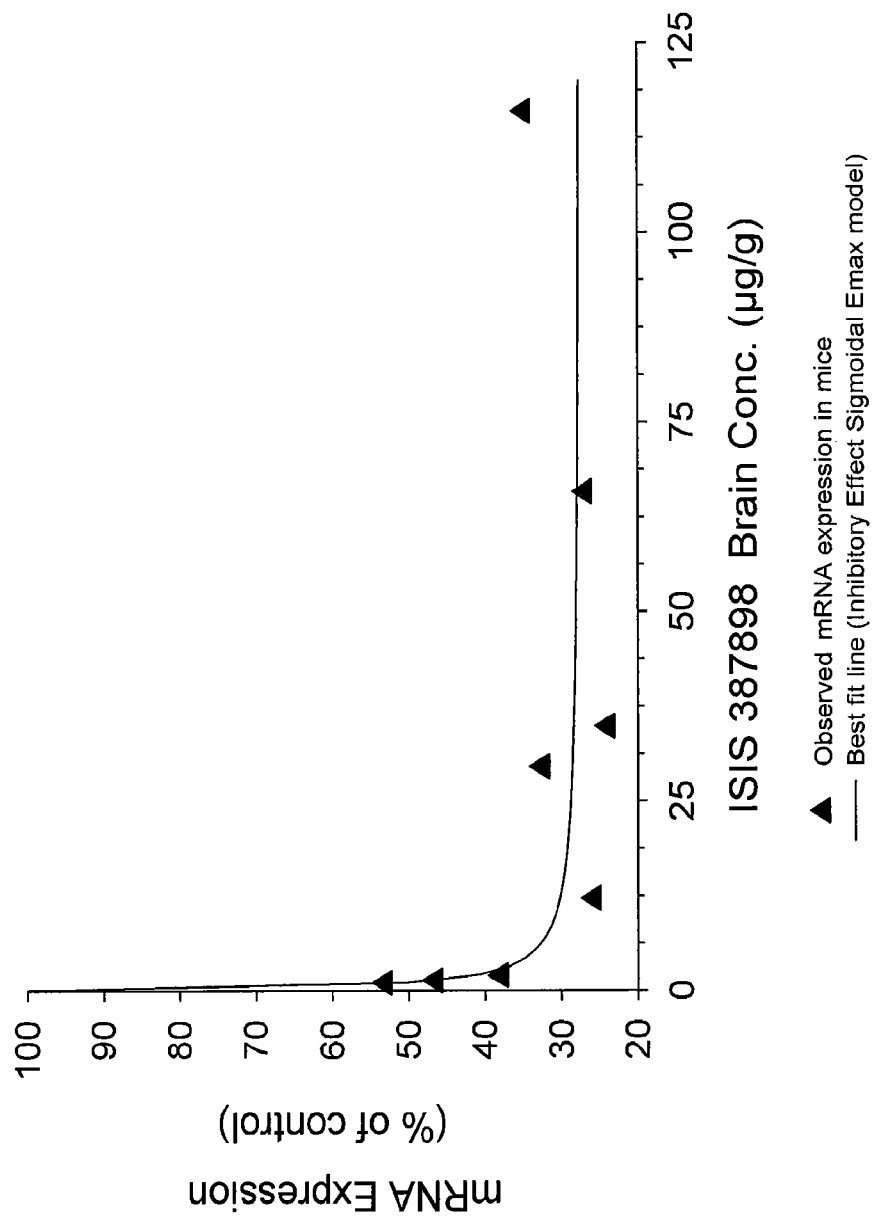
FIG. 1:
The PK/PD relationship of huntingtin mRNA expression in intrastriatal tissue with ISIS 387898 concentration in mouse brain. C57/BL6 mice were administered a single bolus of 50 µg of ISIS 387898 and huntingtin mRNA expression as well as the concentration of the antisense oligonucleotide in the tissue were measured. The $EC_{50}$ of ISIS 387898 was also calculated.

The duration of action (as measured by htt mRNA expression) of ISIS 387898 (dashed line) was observed to be longer even after the concentration of the oligonucleotide (solid line) in the tissue.

FIG. 5:

Comparison of huntingtin mRNA expression in posterior cortex tissue and ISIS 388241 concentrations at various time points. BACHD mice were administered intracerebroventricular infusion of 50 µg of ISIS 388241 for 2 weeks, and huntingtin mRNA expression as well as the concentration of the antisense oligonucleotide in the tissue were measured. The duration of action (as measured by htt mRNA expression) of ISIS 388241 (dashed line) was observed to be longer even after the concentration of the oligonucleotide (solid line) in the tissue.

FIG. 6:

Comparison of huntingtin mRNA expression in posterior cortex tissue and ISIS 443139 concentrations at various time points. BACHD mice were administered intracerebroventricular infusion of 50 µg of ISIS 443139 for 2 weeks, and huntingtin mRNA expression as well as the concentration of the antisense oligonucleotide in the tissue were measured. The duration of action (as measured by htt mRNA expression) of ISIS 443139 (dashed line) was observed to be longer even after the concentration of the oligonucleotide (solid line) in the tissue.

FIG. 7.

Effect of antisense oligonucleotide treatment on the motor performance of BACHD mice using the Rotarod assay. BACHD mice were treated with 50 µg/day ICV of ISIS 388241 or PBS for two weeks. Control groups of non-transgenic littermates were similarly treated with ISIS 388241 or PBS. The accelerating Rotarod assay was then performed. Animals were placed on the Rotarod at a speed of 2 RPM; the Rotarod accelerated to 40 RPM over 5 minutes. The duration to fall was recorded. Baseline values at 6 months age were taken before the treatment and the time points given are the age of the mice at which the assay was conducted. The bars represent the duration to fall in seconds by BACHD mice treated with ISIS 388241 (black); by BACHD mice treated with PBS (hashed); and by non-transgenic littermates treated with PBS (white). ISIS 388241-treated mice displayed increased duration of fall and, therefore, improved motor performance on the Rotarod, compared to the PBS control.

FIG. 8.

Effect of antisense oligonucleotide treatment on brain weight of R6/2 mice. Six-month old R6/2 mice were treated with 50 µg/day ICV of ISIS 388817 or control oligonucleotide ISIS 141923 or PBS for 4 weeks. Control groups of non-transgenic littermates were similarly treated with ISIS 388817 or PBS. A control group of eight-week old pre-symptomatic R6/2 mice were included in the study and not given any treatment. The bars represent the brain weights of eight-week old untreated R6/2 mice; R6/2 mice treated with ISIS 141923; R6/2 mice treated with PBS; R6/2 mice treated with ISIS 388817; non-transgenic littermates treated with PBS; and non-transgenic littermates treated with ISIS 388817. There was an increase in brain weight of R6/2 mice treated with ISIS 388817 compared to the PBS control.

FIG. 9

Behavioral characterization of antisense oligonucleotide-treated YAC128 mice using the Open Field assay. Five month old YAC128 mice were treated with 50 µg/day ICV of ISIS 388241 or control oligonucleotide ISIS 141923 or PBS for 14 days. A control group of non-transgenic FVB/NJ littermates were included in the study and not given any treatment. Mice were placed in an open field arena that uses photobeam breaks to measure horizontal and vertical movement over a 30 min test session. Data was analyzed using Activity Monitor software to examine total ambulatory movement within the arena and movement within the center of the arena as a measure of anxiety. The bars represent time in seconds spent at the center of the field by FVB/NJ mice, YAC128 treated with PBS, and, YAC128 mice treated with ISIS 388241. YAC128 mice treated with ISIS 388241 spent more time in the center and were therefore deemed less anxiety-prone than the PBS control.

FIG. 10

Behavioral characterization of antisense oligonucleotide-treated YAC128 mice using the Elevated Plus Maze assay. Five month old YAC128 mice were treated with 50 µg/day ICV of ISIS 388241 or control oligonucleotide ISIS 141923 or with PBS for 14 days. A control group of non-transgenic FVB/NJ littermates were included as untreated control. Mice were placed in the center of an apparatus which consisted of two open arms and two closed arms each measuring 65×6.25 cm and elevated 50 cm above the ground. The location of the mice on the apparatus and amount of time spent in the open arms was recorded over a 5 minute test session as a measure of anxiety. The bars represent the percentage of time spent in the open arms by FVB/NJ control, YAC128 treated with PBS, and YAC128 mice treated with ISIS 388241. YAC128 mice treated with ISIS 388241 spent more time in the open arms and were therefore deemed less anxiety-prone than the PBS control.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

DEFINITIONS

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"5-methylcytosine" means a cytosine modified with a methyl group attached to the 5' position. A 5-methylcytosine is a modified nucleobase.

"Active pharmaceutical agent" means the substance or substances in a pharmaceutical composition that provide a therapeutic benefit when administered to an individual. For example, in certain embodiments an antisense oligonucleotide targeted to huntingtin is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Amelioration" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Contiguous nucleobases" means nucleobases immediately adjacent to each other.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Huntingtin nucleic acid" means any nucleic acid encoding huntingtin. For example, in certain embodiments, a huntingtin nucleic acid includes a DNA sequence encoding huntingtin, an RNA sequence transcribed from DNA encoding huntingtin (including genomic DNA comprising introns and exons), and an mRNA sequence encoding huntingtin. "Huntingtin mRNA" means an mRNA encoding a huntingtin protein.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap segment" and the external regions may be referred to as "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Hybridization" means the annealing of complementary nucleic acid molecules. In certain embodiments, complementary nucleic acid molecules include an antisense compound and a target nucleic acid.

"Immediately adjacent" means there are no intervening elements between the immediately adjacent elements.

"Individual" means a human or non-human animal selected for treatment or therapy.

"Internucleoside linkage" refers to the chemical bond between nucleosides.

"Linked nucleosides" means adjacent nucleosides which are bonded together.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising at least one modified nucleotide.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA). A nucleic acid may also comprise a combination of these elements in a single molecule.

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleotide" means a nucleoside having a phosphate group covalently linked to the sugar portion of the nucleoside.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, or chronic, or short or intermittent.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition may comprise one or more active pharmaceutical agents and a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e. under physiological conditions in the case of in vivo assays and therapeutic treatments.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Certain embodiments provide methods, compounds, and compositions for inhibiting huntingtin expression.

Certain embodiments provide antisense compounds targeted to a huntingtin nucleic acid. In certain embodiments, the huntingtin nucleic acid is any of the sequences set forth in GENBANK Accession No. NM_002111.6 (incorporated herein as SEQ ID NO: 1), GENBANK Accession No. NT_006081.17 truncated from nucleotides 462000 to 634000 (incorporated herein as SEQ ID NO: 2), GENBANK Accession No. NM_010414.1 (incorporated herein as SEQ ID NO: 3), the complement of GENBANK Accession No. NW_001109716.1 truncated at nucleotides 698000 to 866000 (incorporated herein as SEQ ID NO: 4), and GENBANK Accession No. NM_024357.2 (incorporated herein as SEQ ID NO: 5).

Certain embodiments provide compounds comprising a modified oligonucleotide consisting of 12 to 30 linked nucleosides wherein the linked nucleosides comprise at least 8 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the modified oligonucleotide comprises at least 9, at least 10, at least 11, or at least 12 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the nucleobase sequences are those recited in SEQ ID NOs: 24, 25, 26, 6, 12, 28, 21, 22, 32, 13. In certain embodiments, the modified oligonucleotide comprises at least 9, at least 10, at least 11, or at least 12 contiguous nucleobases of a sequence selected from among the nucleobase sequences recited in SEQ ID NOs: 12, 22, 28, 30, 32, and 33.

Certain embodiments provide compounds comprising a modified oligonucleotide consisting of 15 to 25 linked nucleosides wherein the linked nucleosides comprise at least 8 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the modified oligonucleotide comprises at least 9, at least 10, at least 11, at least 12, at least 13, at least 14 or at least 15 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the nucleobase sequences are those recited in SEQ ID NOs: 24, 25, 26, 6, 12, 28, 21, 22, 32, 13. In certain embodiments, the modified oligonucleotide comprises at least 9, at least 10, at least 11, at least 12, at least 13, at least 14 or at least 15 contiguous nucleobases of a sequence selected from among the nucleobase sequences recited in SEQ ID NOs: 12, 22, 28, 30, 32, and 33.

Certain embodiments provide compounds comprising a modified oligonucleotide consisting of 18 to 21 linked nucleosides wherein the linked nucleosides comprise at least 8 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, and 32. In certain embodiments, the modified oligonucleotide comprises at least 9, at least 10, at least 11, at least 12, at least 13, at least 14, at least 15, at least 16, at least 17 or at least 18 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 and 32. In certain embodiments, the nucleobase sequences are those recited in SEQ ID NOs: 24, 25, 26, 6, 12, 28, 21, 22, 32, 13. In certain embodiments, the modified oligonucleotide comprises at least 9, at least 10, at least 11, at least 12, at least 13, at least 14, at least 15, at least 16, at least 17, or at least 18 contiguous nucleobases of a sequence selected from among the nucleobase sequences recited in SEQ ID NOs: 12, 22, 28, 30, 32, and 33.

Certain embodiments provide compounds comprising a modified oligonucleotide consisting of 12-30 linked nucleosides wherein the linked nucleosides comprise at least an 8 contiguous nucleobase portion that is complementary within the region selected from nucleotides 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828, 4928-4947 of SEQ ID NO: 1. In certain embodiments the region is selected from 4384-4403, 4609-4628, 4610-4629, 4860-4877, 4862-4881, 4925-4944, 4928-4947, 4931-4950, 4955-4974, and 5809-5828 of SEQ ID NO: 1. In certain embodiments the region is selected from 4862-4881, 4609-4628, 5809-5828, 5809-5826, 5801-5820, and 4955-4974. In certain embodiments, the modified oligonucleotide has at least a 9, at least a 10, at least an 11, or at least a 12 contiguous nucleobase portion of which is complementary within a region described herein.

Certain embodiments provide compounds comprising a modified oligonucleotide consisting of 15-25 linked nucleosides wherein the linked nucleosides comprise at least an 8 contiguous nucleobase portion that is complementary within the region selected from nucleotides 4384-4403, 4609-4628, 4610-4629, 4860-4877, 4862-4881, 4925-4944, 4928-4947, 4931-4950, 4955-4974, and 5809-5829 of SEQ ID NO: 1. In certain embodiments, the modified oligonucleotide has at least a 9, at least a 10, at least an 11, at least a 12, at least a 13, or at least a 15 contiguous nucleobase portion of which is complementary within a region described herein.

Certain embodiments provide compounds comprising a modified oligonucleotide consisting of 15-25 linked nucleosides wherein the linked nucleosides comprise at least an 8 contiguous nucleobase portion that is complementary within the region selected from nucleotides 4862-4881, 4609-4628, 5809-5828, 5809-5826, 5801-5820, and 4955-4974. In certain embodiments, the modified oligonucleotide has at least a 9, at least a 10, at least an 11, at least a 12, at least a 13, or at least a 15 contiguous nucleobase portion of which is complementary within a region described herein.

Certain embodiments provide compounds comprising a modified oligonucleotide consisting of 18-21 linked nucleosides wherein the linked nucleosides comprise at least an 8 contiguous nucleobase portion that is complementary within the region selected from nucleotides 4384-4403, 4609-4628, 4610-4629, 4860-4877, 4862-4881, 4925-4944, 4928-4947, 4931-4950, 4955-4974, and 5809-5829 of SEQ ID NO: 1. In certain embodiments, the modified oligonucleotide has at least a 9, at least a 10, at least an 11, at least a 12, at least a 13, at least a 14, at least a 15, at least a 16, at least a 17, or at least an 18 contiguous nucleobase portion of which is complementary within a region described herein.

Certain embodiments provide compounds comprising a modified oligonucleotide consisting of 18-21 linked nucleosides wherein the linked nucleosides comprise at least an 8 contiguous nucleobase portion that is complementary within the region selected from nucleotides 4862-4881, 4609-4628, 5809-5828, 5809-5826, 5801-5820, and 4955-4974. In certain embodiments, the modified oligonucleotide has at least a 9, at least a 10, at least an 11, at least a 12, at least a 13, at least a 14, at least a 15, at least a 16, at least a 17, or at least an 18 contiguous nucleobase portion of which is complementary within a region described herein.

In certain embodiments, the modified oligonucleotide consists of a single-stranded modified oligonucleotide.

In certain embodiments, the modified oligonucleotide consists of 20 linked nucleosides.

In certain embodiments, the nucleobase sequence of the modified oligonucleotide is at least 90% complementary over its entire length to a nucleobase sequence of SEQ ID NO: 1, 2, 3, 4 or 5. In certain embodiments, the nucleobase sequence of the modified oligonucleotide is at least 95% complementary over its entire length to a nucleobase sequence of SEQ ID NO: 1, 2, 3, 4 or 5. In certain embodiments, the modified oligonucleotide is at least 99% complementary over its entire length to SEQ ID NO: 1, 2, 3, 4 or 5. In certain embodiments, the nucleobase sequence of the modified oligonucleotide is 100% complementary over its entire length to a nucleobase sequence of SEQ ID NO: 1, 2, 3, 4 or 5.

In certain embodiments, the compound has at least one modified internucleoside linkage. In certain embodiments, the internucleoside linkage is a phosphorothioate internucleoside linkage.

In certain embodiments, the compound has at least one nucleoside comprising a modified sugar. In certain embodiments, the at least one modified sugar is a bicyclic sugar. In certain embodiments, the at least one bicyclic sugar comprises a 4'-CH(CH$_3$)—O-2' bridge. In certain embodiments, the at least one modified sugar comprises a 2'-O-methoxyethyl.

In certain embodiments, the compound comprises at least one at least one tetrahydropyran modified nucleoside wherein a tetrahydropyran ring replaces the furanose ring. In certain embodiments, the at least one tetrahydropyran modified nucleoside has the structure:

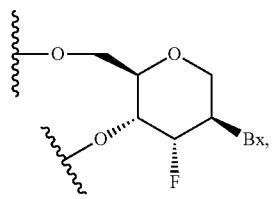

wherein Bx is an optionally protected heterocyclic base moiety.

In certain embodiments, the compound has at least one nucleoside comprising a modified nucleobase. In certain embodiments, the modified nucleobase is a 5-methylcytosine.

In certain embodiments, the modified oligonucleotide of the compound comprises:
(i) a gap segment consisting of linked deoxynucleosides;
(ii) a 5' wing segment consisting of linked nucleosides;
(iii) a 3' wing segment consisting of linked nucleosides, wherein the gap segment is positioned between the 5' wing segment and the 3' wing segment and wherein each nucleoside of each wing segment comprises a modified sugar.

In certain embodiments, the modified oligonucleotide of the compound comprises:
(i) a gap segment consisting of ten linked deoxynucleosides;
(ii) a 5' wing segment consisting of five linked nucleosides;
(iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the modified oligonucleotide of the compound comprises:
(i) a gap segment consisting of eight linked deoxynucleosides;
(ii) a 5' wing segment consisting of six linked nucleosides;
(iii) a 3' wing segment consisting of six linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the modified oligonucleotide of the compound comprises:
(i) a gap segment consisting of eight linked deoxynucleosides;
(ii) a 5' wing segment consisting of five linked nucleosides;
(iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

Certain embodiments provide a composition comprising a compound as described herein, or a salt thereof, and a pharmaceutically acceptable carrier or diluent. In certain embodiments, the composition comprises a modified oligonucleotide consisting of 12 to 30 linked nucleosides and having a nucleobase sequence comprising at least 12 contiguous nucleobases of a nucleobase sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 and 32 or a salt thereof and a pharmaceutically acceptable carrier or diluent.

Certain embodiments provide a composition comprising a compound as described herein, or a salt thereof, and a pharmaceutically acceptable carrier or diluent. In certain embodiments, the composition comprises a modified oligonucleotide consisting of 12 to 30 linked nucleosides and having a nucleobase sequence comprising at least 12 contiguous nucleobases of a nucleobase sequence selected from among the nucleobase sequences recited in SEQ ID NOs: 12, 22, 28, 30, 32, and 33 or a salt thereof and a pharmaceutically acceptable carrier or diluent.

Certain embodiments provide methods of treating, preventing, or ameliorating Huntington's disease.

Certain embodiments provide methods comprising administering to an animal a compound as described herein to an animal. In certain embodiments, the method comprises administering to an animal a modified oligonucleotide consisting of 12 to 30 linked nucleosides and having a nucleobase sequence comprising at least 8 contiguous nucleobases of a nucleobase sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 and 32.

Certain embodiments provide methods comprising administering to an animal a compound as described herein to an animal. In certain embodiments, the method comprises administering to an animal a modified oligonucleotide consisting of 12 to 30 linked nucleosides and having a nucleobase sequence comprising at least 8 contiguous nucleobases of a nucleobase sequence selected from among the nucleobase sequences recited in SEQ ID NOs: 12, 22, 28, 30, 32, and 33.

In certain embodiments, the animal is a human.

In certain embodiments, the administering prevents, treats, ameliorates, or slows progression Huntington's disease as described herein.

In certain embodiments, the compound is co-administered with a second agent.

In certain embodiments, the compound and the second agent are administered concomitantly.

In certain embodiments, the administering is parenteral administration. In certain embodiments, the parenteral administration is intracranial administration. In certain embodiments, the intracranial administration is intrathecal or intracerebroventricular administration.

Certain embodiments further provide a method to reduce huntingtin mRNA or protein expression in an animal comprising administering to the animal a compound or composition as described herein to reduce huntingtin mRNA or protein expression in the animal. In certain embodiments, the animal is a human. In certain embodiments, reducing huntingtin mRNA or protein expression prevents, treats, ameliorates, or slows progression of Huntington's disease.

Certain embodiments provide a method for treating a human with Huntington's disease comprising identifying the human with the disease and administering to the human a therapeutically effective amount of a compound or composition as described herein. In certain embodiments, the treatment reduces a symptom selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, sleep disturbances, impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination, dementia, a anxiety, depression, blunted affect, egocentrisms, aggression, compulsive behavior, irritability, suicidal ideation, reduced brain mass, muscle atrophy, cardiac failure, impaired glucose tolerance, weight loss, osteoporosis, and testicular atrophy.

Further provided is a method for reducing or preventing Huntington's disease comprising administering to a human a therapeutically effective amount compound or composition as described herein, thereby reducing or preventing Huntington's disease.

Further provided is a method for ameliorating a symptom of Huntington's disease, comprising administering to a human in need thereof a compound comprising a modified oligonucleotide consisting of 12 to 30 linked nucleosides, wherein said modified oligonucleotide specifically hybridizes to SEQ ID NO:1, 2, 3, 4 or 5, thereby ameliorating a symptom of Huntington's disease in the human.

Further provided is a method for reducing the rate of progression of a symptom associated with Huntington's Disease, comprising administering to a human in need thereof a compound comprising a modified oligonucleotide consisting of 12 to 30 linked nucleosides, wherein said modified oligonucleotide specifically hybridizes to SEQ ID NO: 1, 2, 3, 4 or 5, thereby reducing the rate of progression a symptom of Huntington's disease in the human.

Further provided is a method for reversing degeneration indicated by a symptom associated with Huntington's disease, administering to a human in need thereof a compound comprising a modified oligonucleotide consisting of 12 to 30 linked nucleosides, wherein said modified oligonucleotide specifically hybridizes to SEQ ID NO:1, 2, 3, 4 or 5, thereby reversing degeneration indicated by a symptom of Huntington's disease in the human.

In certain embodiments, the symptom is a physical, cognitive, psychiatric, or peripheral symptom. In certain embodiments, the symptom is a physical symptom selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, and sleep disturbances. In certain embodiments, the symptom is a cognitive symptom selected from the group consisting of impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination and dementia. In certain embodiments, the symptom is a psychiatric symptom selected from the group consisting of anxiety, depression, blunted affect, egocentrisms, aggression, compulsive behavior, irritability and suicidal ideation. In certain embodiments, the symptom is a peripheral symptom selected from the group consisting of reduced brain mass, muscle atrophy, cardiac failure, impaired glucose tolerance, weight loss, osteoporosis, and testicular atrophy.

Also provided are methods and compounds for the preparation of a medicament for the treatment, prevention, or amelioration of Huntington's disease.

Certain embodiments provide the use of a compound as described herein in the manufacture of a medicament for treating, ameliorating, or preventing Huntington's disease.

Certain embodiments provide a compound as described herein for use in treating, preventing, or ameliorating Huntington's disease as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating Huntington's disease as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating Huntington's disease as described herein in a patient who is subsequently administered an additional agent or therapy as described herein.

Certain embodiments provide a kit for treating, preventing, or ameliorating Huntington's disease as described herein wherein the kit comprises:
(i) a compound as described herein; and alternatively
(ii) an additional agent or therapy as described herein.

A kit as described herein may further include instructions for using the kit to treat, prevent, or ameliorate Huntington's disease as described herein by combination therapy as described herein.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 6, 9, 10, 11, 12, 13, 14, 15, 18, 19, 20, 21, 22, 23, 24, 25, 26, 27, 28, 29, 30, 32, 33, 35, or 36, for use in treating an animal having a disease or condition associated with huntingtin by administering to the animal a therapeutically effective amount of the compound so that expression of huntingtin is inhibited. In certain embodiments, the disease or condition is a neurological disorder. In certain embodiments, the disease or condition is Huntington's Disease. In certain embodiments, the animal is a human.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 6, 9, 10, 11, 12, 13, 14, 15, 18, 19, 20, 21, 22, 23, 24, 25, 26, 27, 28, 29, 30, 32, 33, 35, or 36, for use in an animal having a disease or condition associated with huntingtin by administering to the animal a therapeutically effective amount of the compound to prevent, treat, ameliorate, or slow progression of Huntington's disease.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 12, 22, 28, 30, 32, or 33, for use in an animal having a disease or condition associated with huntingtin by administering to the animal a therapeutically effective amount of the compound so that expression of huntingtin is inhibited. In certain embodiments, the disease or condition is a neurological disorder. In certain embodiments, the disease or condition is Huntington's Disease. In certain embodiments, the animal is a human.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 12, 22, 28, 30, 32, or 33, for use in an animal having a disease or condition associated with huntingtin by administering to the animal a therapeutically effective amount of the compound to prevent, treat, ameliorate, or slow progression of Huntington's disease.

Certain embodiments provide compounds comprising a modified oligonucleotide consisting of 12-30 linked nucleosides, wherein the linked nucleosides at least an 8, at least a 9, at least a 10, at least an 11, at least a 12, at least a 13, at least a 14, at least a 15, at least a 16, at least a 17, at least a 18, at least a 19, or at least a 20 contiguous nucleobase portion complementary within the region selected from nucleotides 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828 and 4928-4947 of SEQ ID NO: 1, for use in an animal having a disease or condition associated with huntingtin by administering to the animal a therapeutically effective amount of the compound so that expression of huntingtin is inhibited.

Certain embodiments provide compounds comprising a modified oligonucleotide consisting of 12-30 linked nucleosides, wherein the linked nucleosides comprise at least an 8, at least a 9, at least a 10, at least an 11, at least a 12, at least a 13, at least a 14, at least a 15, at least a 16, at least a 17, at least a 18, at least a 19, or at least a 20 contiguous nucleobase portion complementary within the region selected from nucleotides 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828 and 4928-4947 of SEQ ID NO: 1, for use in an animal having a disease or condition associated with huntingtin by administering to the animal a therapeutically effective amount of the compound to prevent, treat, ameliorate, or slow progression of Huntington's disease.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a huntingtin nucleic acid is 12 to 30 nucleotides in length. In other words, antisense compounds are from 12 to 30 linked nucleobases. In other embodiments, the antisense compound comprises a modified oligonucleotide consisting of 8 to 80, 12 to 50, 15 to 30, 18 to 24, 19 to 22, or 20 linked nucleobases.

In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobasis in length, or a range defined by any two of the above values.

In certain embodiments, the antisense compound comprises a shortened or truncated modified oligonucleotide. The shortened or truncated modified oligonucleotide can have a single nucleoside deleted from the 5' end (5' truncation), or alternatively from the 3' end (3' truncation). A shortened or truncated oligonucleotide may have two nucleosides deleted from the 5' end, or alternatively may have two subunits deleted from the 3' end. Alternatively, the deleted nucleosides may be dispersed throughout the modified oligonucleotide, for example, in an antisense compound having one nucleoside deleted from the 5' end and one nucleoside deleted from the 3' end.

When a single additional nucleoside is present in a lengthened oligonucletide, the additional nucleoside may be located at the 5' or 3' end of the oligonucleotide. When two or more additional nucleosides are present, the added nucleosides may be adjacent to each other, for example, in an oligonucleotide having two nucleosides added to the 5' end (5' addition), or alternatively to the 3' end (3' addition), of the oligonucleotide. Alternatively, the added nucleoside may be dispersed throughout the antisense compound, for example, in an oligonucleotide having one nucleoside added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a huntingtin nucleic acid have chemically modified subunits arranged in patterns, or motifs, to confer to the antisense compounds properties such as enhanced the inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, T-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-$(CH2)_n$—O-2' bridge, where n=1 or n=2). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers include, but are not limited to, for example 5-10-5, 4-8-4, 4-12-3, 4-12-4, 3-14-3, 2-13-5, 2-16-2, 1-18-1, 3-10-3, 2-10-2, 1-10-1, 2-8-2, 6-8-6 or 5-8-5.

In certain embodiments, the antisense compound as a "wingmer" motif, having a wing-gap or gap-wing configuration, i.e. an X-Y or Y-Z configuration as described above for the gapmer configuration. Thus, wingmer configurations include, but are not limited to, for example 5-10, 8-4, 4-12, 12-4, 3-14, 16-2, 18-1, 10-3, 2-10, 1-10, 8-2, 2-13, or 5-13.

In certain embodiments, antisense compounds targeted to a huntingtin nucleic acid possess a 5-10-5 gapmer motif.

In certain embodiments, antisense compounds targeted to a huntingtin nucleic acid possess a 6-8-6 gapmer motif.

In certain embodiments, antisense compounds targeted to a huntingtin nucleic acid possess a 5-8-5 gapmer motif.

In certain embodiments, an antisense compound targeted to a huntingtin nucleic acid has a gap-widened motif.

In certain embodiments, a gap-widened antisense oligonucleotide targeted to a huntingtin nucleic acid has a gap segment of ten 2'-deoxyribonucleotides positioned immediately adjacent to and between wing segments of five chemically modified nucleosides. In certain embodiments, the chemical modification comprises a 2'-sugar modification. In another embodiment, the chemical modification comprises a 2'-MOE sugar modification.

In certain embodiments, a gap-widened antisense oligonucleotide targeted to a huntingtin nucleic acid has a gap segment of eight 2'-deoxyribonucleotides positioned immediately adjacent to and between wing segments of five chemically modified nucleosides. In certain embodiments, the chemical modification comprises a 2'-sugar modification. In another embodiment, the chemical modification comprises a 2'-MOE sugar modification.

In certain embodiments, a gap-widened antisense oligonucleotide targeted to a huntingtin nucleic acid has a gap segment of eight 2'-deoxyribonucleotides positioned immediately adjacent to and between wing segments of six chemically modified nucleosides. In certain embodiments, the chemical modification comprises a 2'-sugar modification. In another embodiment, the chemical modification comprises a 2'-MOE sugar modification.

Target Nucleic Acids, Target Regions and Nucleotide Sequences

Nucleotide sequences that encode huntingtin include, without limitation, the following: GENBANK Accession No. NM_002111.6, first deposited with GENBANK® on May 31, 2006 incorporated herein as SEQ ID NO: 1; GENBANK Accession No. NT_006081.17 truncated from nucleotides 462000 to 634000, first deposited with GENBANK® on Aug. 19, 2004, and incorporated herein as SEQ ID NO: 2; GENBANK Accession No. NM_010414.1, first deposited with GENBANK® on Mar. 23, 2004, incorporated herein as SEQ ID NO: 3; the complement of GENBANK Accession No. NW_001109716.1 truncated at nucleotides 698000 to 866000, first deposited with GENBANK® on Jun. 14, 2006, incorporated herein as SEQ ID NO: 4, and GENBANK Accession No. NM_024357.2, first deposited with GENBANK® on Jun. 5, 2008, incorporated herein as SEQ ID NO: 5.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for huntingtin can be obtained by accession number from sequence databases such as NCBI and such information is incorporated herein by reference. In certain embodiments, a target region may encompass the sequence from a 5' target site of one target segment within the target region to a 3' target site of another target segment within the target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in huntingtin mRNA levels are indicative of inhibition of huntingtin expression. Reductions in levels of a huntingtin protein are also indicative of inhibition of target mRNA expression. Further, phenotypic changes are indicative of inhibition of huntingtin expression. For example, increase in brain size to normal, improvement in motor coordination, decrease in continual muscular spasms (dystonia), decrease in irritability and/or anxiety, improvement of memory, or an increase in energy, among other phenotypic changes that may be assayed. Other phenotypic indications, e.g., symptoms associated with Huntington's disease, may also be assessed as described below.

Hybridization

In some embodiments, hybridization occurs between an antisense compound disclosed herein and a huntingtin nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a huntingtin nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a huntingtin nucleic acid).

An antisense compound may hybridize over one or more segments of a huntingtin nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a huntingtin nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound may be fully complementary to a huntingtin nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a huntingtin nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a huntingtin nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a huntingtin nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity or some other beneficial biological property to the antisense compounds. In certain embodiments, nucleosides comprise a chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or C(R1)(R)2 (R=H, C1-C12 alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH3 and 2'-O(CH2)2OCH3 substituent groups. The substituent at the 2' position can also be selected from allyl, amino, azido, thio, O-allyl, O—C1-C10 alkyl, OCF3, O(CH2)2SCH3, O(CH2)$_2$—O—N(Rm)(Rn), and O—CH2-C(=O)—N(Rm)(Rn), where each Rm and Rn is, independently, H or substituted or unsubstituted C1-C10 alkyl.

Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-(CH2)-O-2' (LNA); 4'-(CH2)-S-2; 4'-(CH2)-O-2' (LNA); 4'-(CH2)2-O-2' (ENA); 4'-C(CH3)2-O-2' (see PCT/US2008/068922); 4'-CH(CH3)¬-O-2' and 4% C¬H(CH2OCH3)¬-O-2' (see U.S. Pat. No. 7,399,845, issued on Jul. 15, 2008); 4'-CH2-N(OCH3)-2' (see PCT/US2008/064591); 4'-CH2-O—N(CH3)-2' (see published U.S. Patent Application US2004-0171570, published Sep. 2, 2004); 4'-CH2-N(R)—O-2' (see U.S. Pat. No. 7,427,672, issued on Sep. 23, 2008); 4'-CH2-C(CH3)-2' and 4'-CH2-C¬(=CH2)-2' (see PCT/US2008/066154); and wherein R is, independently, H, C1-C12 alkyl, or a protecting group. Each of the foregoing BNAs include various stereochemical sugar configurations including for example α-L-ribofuranose and β-D-ribofuranose (see PCT international application PCT/DK98/00393, published on Mar. 25, 1999 as WO 99/14226).

In certain embodiments, nucleosides are modified by replacement of the ribosyl ring with a sugar surrogate. Such modification includes without limitation, replacement of the ribosyl ring with a surrogate ring system (sometimes referred to as DNA analogs) such as a morpholino ring, a cyclohexenyl ring, a cyclohexyl ring or a tetrahydropyranyl ring such as one having one of the formula:

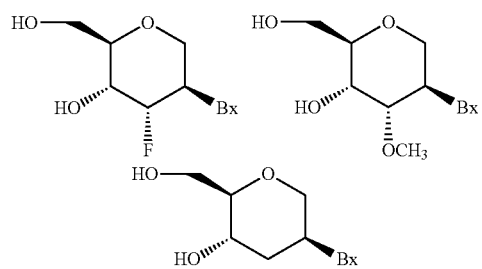

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry*, 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds targeted to a huntingtin nucleic acid comprise one or more nucleotides having modified sugar moieties. In certain embodiments, the modified sugar moiety is 2'-MOE. In certain embodiments, the 2'-MOE modified nucleotides are arranged in a gapmer motif Modified Nucleobases Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to a huntingtin nucleic acid comprise one or more modified nucleobases. In certain embodiments, gap-widened antisense oligonucleotides targeted to a huntingtin nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to a huntingtin nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a huntingtin nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of huntingtin nucleic acids can be tested in vitro in a variety of cell types. Cell types used for such analyses are available from commercial vendors (e.g. American Type Culture Collection, Manassus, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells, Hep3B cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE2000®, Lipofectin or Cytofectin. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of a huntingtin nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invitrogen, Inc. Eugene, Oreg.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a huntingtin nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of huntingtin nucleic acids can be assessed by measuring huntingtin protein levels. Protein levels of huntingtin can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of human and rat huntingtin are commercially available.

In Vivo Testing of Antisense Compounds

Antisense compounds, for example, antisense oligonucleotides, are tested in animals to assess their ability to inhibit expression of huntingtin and produce phenotypic changes. Testing may be performed in normal animals, or in experimental disease models. For administration to animals, antisense oligonucleotides are formulated in a pharmaceutically acceptable diluent, such as phosphate-buffered saline. Administration includes parenteral routes of administration. Following a period of treatment with antisense oligonucleotides, RNA is isolated from tissue and changes in huntingtin nucleic acid expression are measured. Changes in huntingtin protein levels are also measured.

Certain Compounds

About seventeen hundred newly designed antisense compounds of various lengths, motifs and backbone composition were tested for their effect on human huntingtin mRNA in vitro in several cell types. The new compounds were compared with about two hundred and fifty previously designed compounds including ISIS 387916 which had previously been determined to be one of the most potent antisense compounds in vitro (see e.g., U.S. Patent Publication Nos. 2008/

0039418 and 2007/0299027. Of the about seventeen hundred newly designed antisense compounds, about sixty compounds were selected for further study based on in vitro potency compared to ISIS 387916. The selected compounds were tested for systemic tolerability (see Example 3) and activity and tolerability in the brain of BACHD mice (see Example 4) compared to previously designed ISIS 388241 and ISIS 387916. From these studies, compounds having a nucleobase sequence of a sequence recited in SEQ ID NO: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 or 32 were selected as having high tolerability and high in vivo potency. By virtue of their complementary sequence, the compounds are complementary to the regions 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828 or 4928-4947 of SEQ ID NO: 1. In certain embodiments, the compounds targeting the listed regions, as further described herein, comprise a modified oligonucleotide having some nucleobase portion of the sequence recited in the SEQ ID NOs, as further described herein. In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif as indicated by the ISIS NOs: ISIS 419628, ISIS 419637, ISIS 419640, ISIS 419641, ISIS 451541, ISIS 419642, ISIS 436665, ISIS 436671, ISIS 436684, ISIS 436689, ISIS 436754, ISIS 437168, ISIS 437175, ISIS 437441, ISIS 437442, ISIS 437507, ISIS 437527, ISIS 443139, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661, or ISIS 444663.

Compounds described above as having high in vivo potency and tolerability were then tested by CNS bolus injection in rat to further assess neurotoxicity (see Example 5) along with several additional compounds having a nucleobase sequence of a sequence recited in SEQ ID NO: 7, 8, 11, 16, 17. Of these, ten compounds having a nucleobase sequence of a sequence recited in SEQ ID NO: 24, 25, 26, 6, 12, 28, 21, 22, 32 or 13 were selected as having high tolerability. By virtue of their complementary sequence, the compounds are complementary to the regions 4384-4403, 4609-4628, 4610-4629, 4860-4877, 4862-4881, 4925-4944, 4928-4947, 4931-4950, 4955-4974, or 5809-5829 of SEQ ID NO: 1. In certain embodiments, the compounds targeting the listed regions, as further described herein, comprise a modified oligonucleotide having some nucleobase portion of the sequence recited in the SEQ ID NOs, as further described herein. In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif as indicated by the ISIS NOs: ISIS 419640, ISIS 419641, ISIS 419642, ISIS 436665, ISIS 436671, ISIS 436689, ISIS 437507, ISIS 443139, ISIS 444591, and ISIS 444661. Selected compounds were compared with previously designed compound ISIS 388241 by ICV administration in BACHD mice.

Additional studies were then run on compounds described above as having high in vivo potency and tolerability. The additional studies were designed to further assess neurotoxicity. Studies included ICV administration in wild-type mouse (see Example 16) and bolus administration in rat (see Example 17). SEQ ID NOs: 12, 22, 28, 30, 32, and 33 were selected as having high neurotolerability. By virtue of their complementary sequence, the compounds are complementary to the regions 4862-4881, 4609-4628, 5809-5828, 5809-5826, 5801-5820, and 4955-4974 of SEQ ID NO: 1. In certain embodiments, the compounds targeting the listed regions, as further described herein, comprise a modified oligonucleotide having some nucleobase portion of the sequence recited in the SEQ ID NOs, as further described herein. In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif as indicated by ISIS 388241, ISIS 443139, ISIS 436671, ISIS 444591, ISIS 437527, ISIS 444584, ISIS 444652, and ISIS 436689.

Accordingly, provided herein are antisense compounds with improved characteristics. In certain embodiments, provided herein are compounds comprising a modified oligonucleotide as further described herein targeted to or specifically hybridizable with the region of nucleotides of SEQ ID NO: 1.

In certain embodiments, the compounds as described herein are efficacious by virtue of having at least one of an in vitro IC50 of less than 7 uM, less than 6 uM, less than 5, uM, less than 4 uM, less than 3 uM, less than 2 uM, less than 1 uM when delivered to a human fibroblast cell line as described herein or an ED50 of less than 10 µg, less than 9 µg, less than 8 µg, less than 7.5 µg, less than 7.4 µg, less than 7.0 less than 6 µg, less than 5 µg, less than 4 µg, less than 3 µg, or less than 2 µg by bolus injection. As described herein, ICV infusion can result in 3 to 4 fold higher ED50 values for the compounds described herein. In certain embodiments, the compounds as described herein are highly tolerable as demonstrated by having at least one of an increase an ALT or AST value of no more than 4 fold, 3 fold, or 2 fold over saline treated animals; an increase in liver, spleen or kidney weight of no more than 30%, 20%, 15%, 12%, 10%, 5% or 2%; or an increase AIF1 levels by no more than 350%, 300%, 275%, 250% 200%, 150% or 100% over control.

Certain Indications

In certain embodiments, provided herein are methods of treating an individual comprising administering one or more pharmaceutical compositions as described herein. In certain embodiments, the individual has Huntington's disease.

As shown in the examples below, compounds targeted to huntingtin as described herein have been shown to reduce the severity of physiological symptoms of Huntington's disease. In certain of the experiments, the compounds reduced rate of degeneration, e.g., the animals continued to experience symptoms, but the symptoms were less severe compared to untreated animals. In other of the experiments, however, the compounds appear to result in regeneration of function over time; e.g., animals treated for a longer period of time experienced less severe symptoms than those administered the compounds for a shorter period of time. As discussed above, Huntington's disease is a degenerative disease with a progression typified by increased severity of symptoms over time. The ability of the compounds exemplified below to restore function therefore demonstrates that symptoms of the disease may be reversed by treatment with a compound as described herein.

Accordingly, provided herein are methods for ameliorating a symptom associated with Huntington's disease in a subject in need thereof. In certain embodiments, provided is a method for reducing the rate of onset of a symptom associated with Huntington's disease. In certain embodiments, provided is a method for reducing the severity of a symptom associated with Huntington's disease. In certain embodiments, provided is a method for regenerating neurological function as shown by an improvement of a symptom associated with Huntington's disease. In such embodiments, the methods comprise administering to an individual in need thereof a therapeutically effective amount of a compound targeted to a huntingtin nucleic acid. Huntington's disease is characterized by numerous physical, neurological, psychiatric, and/or peripheral symptoms. Any symptom known to one of skill in the art to be associated with Huntington's disease can be ameliorated or otherwise modulated as set forth above in the methods described above. In certain embodiments, the symptom is a physical symptom selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, and sleep disturbances. In certain embodiments, the symptom is a cognitive symptom selected from the group consisting of impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination and dementia. In certain embodiments, the symptom is a psychiatric symptom selected from the group consisting of anxiety, depression, blunted affect, egocentrisms, aggression, compulsive behavior, irritability and suicidal ideation. In certain embodiments, the symptom is a peripheral symptom selected from the group consisting of reduced brain mass, muscle atrophy, cardiac failure, impaired glucose tolerance, weight loss, osteoporosis, and testicular atrophy.

In certain embodiments, the symptom is restlessness. In certain embodiments, the symptom is lack of coordination. In certain embodiments, the symptom is unintentionally initiated motions. In certain embodiments, the symptom is unintentionally uncompleted motions. In certain embodiments, the symptom is unsteady gait. In certain embodiments, the symptom is chorea. In certain embodiments, the symptom is rigidity. In certain embodiments, the symptom is writhing motions. In certain embodiments, the symptom is abnormal posturing. In certain embodiments, the symptom is instability. In certain embodiments, the symptom is abnormal facial expressions. In certain embodiments, the symptom is difficulty chewing. In certain embodiments, the symptom is difficulty swallowing. In certain embodiments, the symptom is difficulty speaking. In certain embodiments, the symptom is seizures. In certain embodiments, the symptom is sleep disturbances.

In certain embodiments, the symptom is impaired planning. In certain embodiments, the symptom is impaired flexibility. In certain embodiments, the symptom is impaired abstract thinking. In certain embodiments, the symptom is impaired rule acquisition. In certain embodiments, the symptom is impaired initiation of appropriate actions. In certain embodiments, the symptom is impaired inhibition of inappropriate actions. In certain embodiments, the symptom is impaired short-term memory. In certain embodiments, the symptom is impaired long-term memory. In certain embodiments, the symptom is paranoia. In certain embodiments, the symptom is disorientation. In certain embodiments, the symptom is confusion. In certain embodiments, the symptom is hallucination. In certain embodiments, the symptom is dementia.

In certain embodiments, the symptom is anxiety. In certain embodiments, the symptom is depression. In certain embodiments, the symptom is blunted affect. In certain embodiments, the symptom is egocentrism. In certain embodiments, the symptom is aggression. In certain embodiments, the symptom is compulsive behavior. In certain embodiments, the symptom is irritability. In certain embodiments, the symptom is suicidal ideation.

In certain embodiments, the symptom is reduced brain mass. In certain embodiments, the symptom is muscle atrophy. In certain embodiments, the symptom is cardiac failure. In certain embodiments, the symptom is impaired glucose tolerance. In certain embodiments, the symptom is weight loss. In certain embodiments, the symptom is osteoporosis. In certain embodiments, the symptom is testicular atrophy.

In certain embodiments, symptoms of Huntington's disease may be quantifiable. For example, osteoporosis may be measured and quantified by, for example, bone density scans. For such symptoms, in certain embodiments, the symptom may be reduced by about 15, 20, 25, 30, 35, 40, 45, 50, 55, 60, 65, 70, 75, 80, 85, 90, 95 or 99%, or a range defined by any two of these values.

In certain embodiments, provided are methods of treating an individual comprising administering one or more pharmaceutical compositions as described herein. In certain embodiments, the individual has Huntington's disease.

In certain embodiments, administration of an antisense compound targeted to a huntingtin nucleic acid results in reduction of huntingtin expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to huntingtin are used for the preparation of a medicament for treating a patient suffering or susceptible to Huntington's disease.

In certain embodiments, the methods described herein include administering a compound comprising a modified oligonucleotide having a contiguous nucleobases portion as described herein of a sequence recited in SEQ ID NO: 6, 9, 10, 11, 12, 13, 14, 15, 18, 19, 20, 21, 22, 23, 24, 25, 26, 27, 28, 29, 30, 32, 33, 35, 36, 10, 11, 12, 13, 18, 22 or 32. In certain embodiments, the methods described herein include administering a compound comprising a modified oligonucleotide having a contiguous nucleobases portion as described herein of a sequence recited in SEQ ID NOs: 12, 22, 28, 30, 32, and 33.

Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, compounds and compositions are delivered to the CNS. In certain embodiments, compounds and compositions are delivered to the cerebrospinal fluid. In certain embodiments, compounds and compositions are administered to the brain parenchyma. In certain embodiments, compounds and compositions are delivered to an animal by intrathecal administration, or intracerebroventricular administration. Broad distribution of compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

The median effective concentration ($EC_{50}$) of an antisense compounds for inhibiting huntingtin mRNA expression was calculated after either ICV infusion or bolus injection (see Examples 9 and 10). The $EC_{50}$ for the compound after intrastriatal injection was determined to be 0.45 µg/g. The $EC_{50}$ after ICV administration was determined to be 26.4 µg/g.

Therefore, in certain embodiments, delivery of a compound or composition described herein can affect the pharmacokinetic profile of the compound or composition. In certain embodiments, injection of a compound or composition described herein, to a targeted tissue improves the pharmacokinetic profile of the compound or composition as compared to infusion of the compound or composition. In a certain embodiment, the injection of a compound or composition improves potency compared to broad diffusion, requiring less of the compound or composition to achieve similar pharmacology. In certain embodiments, similar pharmacology refers to the amount of time that a target mRNA and/or target protein is down-regulated (e.g. duration of action). In certain embodiments, methods of specifically localizing a pharmaceutical agent, such as by bolus injection, decreases median effective concentration (EC50) by a factor of about 50 (e.g. 50 fold less concentration in tissue is required to achieve the same or similar pharmacodynamic effect). In certain embodiments, methods of specifically localizing a pharmaceutical agent, such as by bolus injection, decreases median effective concentration (EC50) by a factor of 20, 25, 30, 35, 40, 45 or 50. In certain embodiments the pharmaceutical agent in an antisense compound as further described herein. In certain embodiments, the targeted tissue is brain tissue. In certain embodiments the targeted tissue is striatal tissue. In certain embodiments, decreasing EC50 is desirable because it reduces the dose required to achieve a pharmacological result in a patient in need thereof.

The half-life of MOE gapmer oligonucleotides in brain tissue is about 20 days (see Examples 9-11). The duration of action as measured by inhibition of huntingtin mRNA is prolonged in the brain (see Examples 9 and 10). Intracerebroventricular infusion of antisense oligonucleotides for 2 weeks results in inhibition of huntingtin mRNA by at least 50% in striatal tissue of BACHD mice for at least 91 days after termination of dosing. Administration by bolus injection, resulted in a similar duration of action.

In certain embodiments, delivery of a compound or composition, as described herein, to the CNS results in 47% down-regulation of a target mRNA and/or target protein for at least 91 days. In certain embodiments, delivery of a compound or composition results in at least 25%, at least 30%, at least 35%, at least 40%, at least 45%, at least 50%, at least 55%, at least 60%, at least 65%, at least 70%, or at least 75% down-regulation of a target mRNA and/or target protein for at least 20 days, at least 30 days, at least 40 days, at least 50 days, at least 60 days, at least 70 days, at least 80 days, at least 85 days, at least 90 days, at least 95 days, at least 100 days, at least 110 days, at least 120 days. In certain embodiments, delivery to the CNS is by intraparenchymal administration, intrathecal administration, or intracerebroventricular administration.

In certain embodiments, an antisense oligonucleotide is delivered by injection or infusion once every month, every two months, every 90 days, every 3 months, every 6 months, twice a year or once a year.

Certain Combination Therapies

In certain embodiments, one or more pharmaceutical compositions are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions as described herein. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, one or more pharmaceutical compositions and one or more other pharmaceutical agents are administered at the same time. In certain embodiments, one or more pharmaceutical compositions and one or more other pharmaceutical agents are administered at different times. In certain embodiments, one or more pharmaceutical compositions and one or more other pharmaceutical agents are prepared together in a single formulation. In certain embodiments, one or more pharmaceutical compositions and one or more other pharmaceutical agents are prepared separately.

In certain embodiments, pharmaceutical agents that may be co-administered with a pharmaceutical composition of include antipsychotic agents, such as, e.g., haloperidol, chlorpromazine, clozapine, quetapine, and olanzapine; antidepressant agents, such as, e.g., fluoxetine, sertraline hydrochloride, venlafaxine and nortriptyline; tranquilizing agents such as, e.g., benzodiazepines, clonazepam, paroxetine, venlafaxin, and beta-blockers; mood-stabilizing agents such as, e.g., lithium, valproate, lamotrigine, and carbamazepine; paralytic agents such as, e.g., Botulinum toxin; and/or other experimental agents including, but not limited to, tetrabenazine (Xenazine), creatine, conezyme Q10, trehalose, docosahexanoic acids, ACR16, ethyl-EPA, atomoxetine, citalopram, dimebon, memantine, sodium phenylbutyrate, ramelteon, ursodiol, zyprexa, xenasine, tiapride, riluzole, amantadine, [123I]MNI-420, atomoxetine, tetrabenazine, digoxin, detromethorphan, warfarin, alprozam, ketoconazole, omeprazole, and minocycline.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

Antisense Oligonucleotides Targeted to Human Huntingtin Gene Sequences

About seventeen hundred newly designed antisense compounds of various lengths, motifs and backbone composition targeting the human huntingtin gene sequence were tested for their effect on human huntingtin mRNA in vitro in several cell types. These gapmers were further designed with internucleoside linkages that are either only phosphorothioate linkages (described in Table 1) or that are phosphorothioate and phosphodiester linkages (described in Table 5). A number of the newly designed oligos and two benchmark oligonucleotides (previously designed and disclosed) are provided in Tables 1 and 5.

Gapmers with Fully Phosphorothioate Internucleoside Linkages

Certain of the compounds presented in Table 1 have a motif of 5-10-5 MOE, 6-8-6 MOE, or 5-8-5 MOE. The 5-10-5 gapmers have twenty linked nucleosides, wherein the central gap segment has ten 2'-deoxynucleosides and is flanked on both sides (in the 5' and 3' directions) by wings having five nucleosides each. The 6-8-6 gapmer has twenty linked nucleosides, wherein the central gap segment has eight 2'-deoxynucleosides and is flanked on both sides (in the 5' and 3' directions) by wings having six nucleosides each. The 5-8-5 gapmers have eighteen linked nucleosides, wherein the central gap segment has eight 2'-deoxynucleosides and is flanked on both sides (in the 5' and 3' directions) by wings having five nucleosides each. For all gapmers listed in Table 1, each nucleoside in the 5' wing segment and each nucleoside in the 3' wing segment has a 2'-MOE modification. The internucleoside linkages throughout each gapmer are phosphorothioate (P=S) internucleoside linkages. All cytosines throughout each gapmer are 5-methylcytosines. Each gapmer in Table 1 is targeted to SEQ ID NO: 1 (GENBANK Accession No. NM_002111.6) or SEQ ID NO: 2 (GENBANK Accession No. NT_006081.17 truncated from nucleotides 462000 to 634000). 'Start site' indicates the 5'-most nucleotide to which the gapmer is targeted in the human gene sequence. 'Stop site' indicates the 3'-most nucleotide to which the gapmer is targeted in the human gene sequence.

TABLE 1

Chimeric antisense oligonucleotides with phosphorothioate internucleoside linkages targeting human huntingtin gene sequences (SEQ ID NOs: 1 and 2)

| Start Site | Stop Site | Target SEQ ID NO. | ISIS No. | Sequence (5' to 3') | Motif | SEQ ID NO. |
|---|---|---|---|---|---|---|
| 4384 | 4403 | 1 | 436665 | TAGCATTCTTATCTGCACGG | 5-10-5 | 6 |
| 4511 | 4530 | 1 | 436668 | ACCCGTAACTGAACCAGCTG | 5-10-5 | 7 |
| 4599 | 4618 | 1 | 419627 | TTCCCTGAACTGGCCCACTT | 5-10-5 | 8 |
| 4605 | 4624 | 1 | 419628 | CTCTGATTCCCTGAACTGGC | 5-10-5 | 9 |
| 4607 | 4626 | 1 | 444607 | GCCTCTGATTCCCTGAACTG | 5-10-5 | 10 |
| 4608 | 4627 | 1 | 419629 | TGCCTCTGATTCCCTGAACT | 5-10-5 | 11 |
| 4608 | 4627 | 1 | 444578 | TGCCTCTGATTCCCTGAACT | 6-8-6 | 11 |
| 4609 | 4628 | 1 | 436671 | TTGCCTCTGATTCCCTGAAC | 5-10-5 | 12 |
| 4610 | 4629 | 1 | 444608 | ATTGCCTCTGATTCCCTGAA | 5-10-5 | 13 |
| 4617 | 4636 | 1 | 444615 | TGGAATGATTGCCTCTGATT | 5-10-5 | 14 |
| 4622 | 4639 | 1 | 437168 | GTTTGGAATGATTGCCTC | 5-8-5 | 15 |
| 4679 | 4698 | 1 | 419630 | CCAATGATCTGTTTTGAATG | 5-10-5 | 16 |
| 4733 | 4752 | 1 | 419636 | GCCTTCCTTCCACTGGCCAT | 5-10-5 | 17 |
| 4813 | 4832 | 1 | 444618 | CTGCATCAGCTTTATTTGTT | 5-10-5 | 18 |
| 4814 | 4833 | 1 | 419637 | CCTGCATCAGCTTTATTTGT | 5-10-5 | 19 |
| 4823 | 4842 | 1 | 444627 | AGCTCTTTTCCTGCATCAGC | 5-10-5 | 20 |
| 4860 | 4877 | 1 | 437507 | GTAACATTGACACCACCA | 5-8-5 | 21 |
| 4862 | 4881 | 1 | 388241 | CTCAGTAACATTGACACCAC | 5-10-5 | 22 |
| 4868 | 4887 | 1 | 436684 | ATGAGTCTCAGTAACATTGA | 5-10-5 | 23 |
| 4925 | 4944 | 1 | 419640 | TCCTTGTGGCACTGCTGCAG | 5-10-5 | 24 |
| 4928 | 4947 | 1 | 419641 | TTCTCCTTGTGGCACTGCTG | 5-10-5 | 25 |

TABLE 1-continued

Chimeric antisense oligonucleotides with phosphorothioate
internucleoside linkages targeting human huntingtin
gene sequences (SEQ ID NOs: 1 and 2)

| Start Site | Stop Site | Target SEQ ID NO. | ISIS No. | Sequence (5' to 3') | Motif | SEQ ID NO. |
|---|---|---|---|---|---|---|
| 4931 | 4950 | 1 | 419642 | TCATTCTCCTTGTGGCACTG | 5-10-5 | 26 |
| 4931 | 4948 | 1 | 437442 | ATTCTCCTTGTGGCACTG | 5-8-5 | 27 |
| 4955 | 4974 | 1 | 436689 | CGAGACAGTCGCTTCCACTT | 5-8-5 | 28 |
| 4960 | 4977 | 1 | 437175 | TGTCGAGACAGTCGCTTC | 5-8-5 | 29 |
| 5801 | 5820 | 1 | 444584 | TTGCACATTCCAAGTTTGGC | 5-10-5 | 30 |
| 5807 | 5826 | 1 | 387916 | TCTCTATTGCACATTCCAAG | 5-10-5 | 31 |
| 5809 | 5828 | 1 | 444591 | TTTCTCTATTGCACATTCCA | 5-10-5 | 32 |
| 5809 | 5826 | 1 | 437527 | TCTCTATTGCACATTCCA | 5-8-5 | 33 |
| 1446 | 1465 | 2 | 388817 | GCAGGGTTACCGCCATCCCC | 5-10-5 | 34 |
| 101088 | 101105 | 2 | 437441 | ACCTTATCTGCACGGTTC | 5-8-5 | 35 |
| 115066 | 115085 | 2 | 436754 | CTCTCTGTGTATCACCTTCC | 5-10-5 | 36 |

The complementarity of the gapmers in Table 1 with mouse, rhesus monkey and rat huntingtin gene sequences is further described in Tables 2, 3, and 4.

The gapmers of Table 2 are complementary with mouse huntingtin mRNA (GENBANK Accession No. NM_010414.1, designated herein as SEQ ID NO: 3). 'Mouse target start site' indicates the 5'-most nucleotide to which the gapmer is targeted in the mouse mRNA. 'Mouse target stop site' indicates the 3'-most nucleotide to which the gapmer is targeted in the mouse mRNA. 'Human Target Start Site' indicates the 5'-most nucleotide to which the gapmer is targeted in the human gene sequence. 'Human Target Stop Site' indicates the 3'-most nucleotide to which the gapmer is targeted in the human gene sequence. 'Number of mismatches' indicates the number of mismatches between the human oligonucleotide and the mouse mRNA sequence.

TABLE 2

Complementarity of antisense oligonucleotides having phosphorothioate
linkages with murine mRNA (SEQ ID NO: 3)

| Human Start Site | Human Stop Site | Human Target SEQ ID NO. | ISIS No. | Mouse Start Site | Mouse Stop Site | No. of mismatches | SEQ ID NO. |
|---|---|---|---|---|---|---|---|
| 4384 | 4403 | 1 | 436665 | 4343 | 4362 | 0 | 6 |
| 4511 | 4530 | 1 | 436668 | 4470 | 4489 | 1 | 7 |
| 4599 | 4618 | 1 | 419627 | 4558 | 4577 | 0 | 8 |
| 4605 | 4624 | 1 | 419628 | 4564 | 4583 | 0 | 9 |
| 4607 | 4626 | 1 | 444607 | 4566 | 4585 | 0 | 10 |
| 4608 | 4627 | 1 | 419629 | 4567 | 4586 | 0 | 11 |
| 4608 | 4627 | 1 | 444578 | 4567 | 4586 | 0 | 11 |
| 4609 | 4628 | 1 | 436671 | 4568 | 4587 | 0 | 12 |
| 4610 | 4629 | 1 | 444608 | 4569 | 4588 | 0 | 13 |
| 4617 | 4636 | 1 | 444615 | 4576 | 4595 | 1 | 14 |
| 4622 | 4639 | 1 | 437168 | 4581 | 4598 | 2 | 15 |
| 4679 | 4698 | 1 | 419630 | 4638 | 4657 | 0 | 16 |
| 4733 | 4752 | 1 | 419636 | 4692 | 4711 | 0 | 17 |
| 4813 | 4832 | 1 | 444618 | 4772 | 4791 | 0 | 18 |
| 4814 | 4833 | 1 | 419637 | 4773 | 4792 | 0 | 19 |
| 4823 | 4842 | 1 | 444627 | 4782 | 4801 | 1 | 20 |
| 4925 | 4944 | 1 | 419640 | 4884 | 4903 | 0 | 24 |
| 4928 | 4947 | 1 | 419641 | 4887 | 4906 | 0 | 25 |
| 4931 | 4950 | 1 | 419642 | 4890 | 4909 | 0 | 26 |
| 4931 | 4948 | 1 | 437442 | 4890 | 4907 | 0 | 27 |
| 4955 | 4974 | 1 | 436689 | 4914 | 4933 | 3 | 28 |
| 5807 | 5826 | 1 | 387916 | 5763 | 5782 | 1 | 31 |
| 5809 | 5826 | 1 | 437527 | 5765 | 5782 | 1 | 33 |
| 5809 | 5828 | 1 | 444591 | 5765 | 5784 | 1 | 32 |
| 101088 | 101105 | 2 | 437441 | 4340 | 4357 | 2 | 35 |

The gapmers of Table 3 are complementary with the rhesus monkey huntingtin genomic sequence (the complement of GENBANK Accession No. NW_001109716.1 truncated at nucleotides 698000 to 866000, designated herein as SEQ ID NO: 4). 'Rhesus monkey target start site' indicates the 5'-most nucleotide to which the gapmer is targeted in the rhesus monkey gene sequence. 'Rhesus monkey target stop site' indicates the 3'-most nucleotide to which the gapmer is targeted in the rhesus monkey gene sequence. 'Human Target Start Site' indicates the 5'-most nucleotide to which the gapmer is targeted in the human gene sequence. 'Human Target Stop Site' indicates the 3'-most nucleotide to which the gapmer is targeted in the human gene sequence. 'Number of mismatches' indicates the number of mismatches between the human oligonucleotide and the rhesus monkey gene sequence.

TABLE 3

Complementarity of antisense oligonucleotides having phosphorothioate linkages with rhesus monkey gene sequence (SEQ ID NO: 4)

| Human Start Site | Human Stop Site | Human Target SEQ ID NO. | ISIS No. | Rhesus monkey Start Site | Rhesus monkey Stop Site | No. of mismatches | SEQ ID NO. |
|---|---|---|---|---|---|---|---|
| 4511 | 4530 | 1 | 436665 | 98182 | 98201 | 0 | 6 |
| 4599 | 4618 | 1 | 419627 | 101353 | 101372 | 1 | 8 |
| 4609 | 4628 | 1 | 436671 | 102256 | 102275 | 3 | 12 |
| 4610 | 4629 | 1 | 444608 | 102257 | 102276 | 2 | 13 |
| 4617 | 4636 | 1 | 444615 | 102264 | 102283 | 0 | 14 |
| 4622 | 4639 | 1 | 437168 | 102269 | 102286 | 0 | 15 |
| 4679 | 4698 | 1 | 419630 | 102326 | 102345 | 0 | 16 |
| 4733 | 4752 | 1 | 419636 | 102380 | 102399 | 0 | 17 |
| 4813 | 4832 | 1 | 444618 | 105030 | 105049 | 0 | 18 |
| 4814 | 4833 | 1 | 419637 | 105031 | 105050 | 0 | 19 |
| 4823 | 4842 | 1 | 444627 | 105040 | 105059 | 0 | 20 |
| 4860 | 4877 | 1 | 437507 | 105077 | 105094 | 1 | 21 |
| 4862 | 4881 | 1 | 388241 | 105079 | 105098 | 1 | 22 |
| 4868 | 4887 | 1 | 436684 | 105085 | 105104 | 0 | 23 |
| 4925 | 4944 | 1 | 419640 | 106844 | 106863 | 0 | 24 |
| 4928 | 4947 | 1 | 419641 | 106847 | 106866 | 0 | 25 |
| 4931 | 4950 | 1 | 419642 | 106850 | 106869 | 0 | 26 |
| 4931 | 4948 | 1 | 437442 | 106850 | 106867 | 0 | 27 |
| 4955 | 4974 | 1 | 436689 | 106874 | 106893 | 0 | 28 |
| 4960 | 4977 | 1 | 437175 | 106879 | 106896 | 0 | 29 |
| 5801 | 5820 | 1 | 444584 | 125331 | 125350 | 0 | 30 |
| 5807 | 5826 | 1 | 387916 | 125337 | 125356 | 0 | 31 |
| 5809 | 5826 | 1 | 437527 | 125339 | 125356 | 0 | 33 |
| 5809 | 5828 | 1 | 444591 | 125339 | 125358 | 0 | 32 |
| 101088 | 101105 | 2 | 437441 | 97904 | 97921 | 0 | 35 |
| 115066 | 115085 | 2 | 436754 | 110518 | 110537 | 0 | 36 |

The gapmers of Table 4 are complementary with rat huntingtin mRNA (GENBANK Accession No. NM_024357.2, designated herein as SEQ ID NO: 5). 'Rat target start site' indicates the 5'-most nucleotide to which the gapmer is targeted in the rat mRNA. 'Rat target stop site' indicates the 3'-most nucleotide to which the gapmer is targeted in the rat mRNA. 'Human Target Start Site' indicates the 5'-most nucleotide to which the gapmer is targeted in the human gene sequence. 'Human Target Stop Site' indicates the 3'-most nucleotide to which the gapmer is targeted in the human gene sequence. 'Number of mismatches' indicates the number of mismatches between the human oligonucleotide and the rat mRNA sequence.

TABLE 4

Complementarity of antisense oligonucleotides having phosphorothioate linkages with rat mRNA (SEQ ID NO: 5)

| Human Start Site | Human Stop Site | Human Target SEQ ID NO. | ISIS No. | Rat Start Site | Rat Stop Site | No. of mismatches | SEQ ID NO. |
|---|---|---|---|---|---|---|---|
| 4384 | 4403 | 1 | 436665 | 4343 | 4362 | 1 | 6 |
| 4511 | 4530 | 1 | 436668 | 4470 | 4489 | 1 | 7 |
| 4599 | 4618 | 1 | 419627 | 4558 | 4577 | 0 | 8 |
| 4605 | 4624 | 1 | 419628 | 4564 | 4583 | 0 | 9 |
| 4607 | 4626 | 1 | 444607 | 4566 | 4585 | 0 | 10 |
| 4608 | 4627 | 1 | 419629 | 4567 | 4586 | 0 | 11 |
| 4608 | 4627 | 1 | 444578 | 4567 | 4586 | 0 | 11 |
| 4609 | 4628 | 1 | 436671 | 4568 | 4587 | 0 | 12 |
| 4610 | 4629 | 1 | 444608 | 4569 | 4588 | 0 | 13 |
| 4617 | 4636 | 1 | 444615 | 4576 | 4595 | 1 | 14 |
| 4622 | 4639 | 1 | 437168 | 4581 | 4598 | 2 | 15 |
| 4679 | 4698 | 1 | 419630 | 4638 | 4657 | 0 | 16 |
| 4733 | 4752 | 1 | 419636 | 4692 | 4711 | 0 | 17 |
| 4813 | 4832 | 1 | 444618 | 4772 | 4791 | 0 | 18 |
| 4814 | 4833 | 1 | 419637 | 4773 | 4792 | 0 | 19 |
| 4823 | 4842 | 1 | 444627 | 4782 | 4801 | 1 | 20 |
| 4925 | 4944 | 1 | 419640 | 4884 | 4903 | 1 | 24 |
| 4928 | 4947 | 1 | 419641 | 4887 | 4906 | 1 | 25 |
| 4931 | 4950 | 1 | 419642 | 4890 | 4909 | 1 | 26 |
| 4931 | 4948 | 1 | 437442 | 4890 | 4907 | 1 | 27 |
| 4955 | 4974 | 1 | 436689 | 4914 | 4933 | 3 | 28 |
| 5801 | 5820 | 1 | 444584 | 5757 | 5776 | 3 | 30 |
| 5807 | 5826 | 1 | 387916 | 5763 | 5782 | 0 | 31 |
| 5809 | 5826 | 1 | 437527 | 5765 | 5782 | 0 | 33 |
| 5809 | 5828 | 1 | 444591 | 5765 | 5784 | 0 | 32 |
| 101088 | 101105 | 2 | 437441 | 4340 | 4357 | 2 | 35 |

Gapmers with Mixed Phosphorothioate and Phosphodiester Internucleoside Linkages

The chimeric antisense oligonucleotides in Table 5 were designed as 5-10-5 MOE gapmers. The 5-10-5 gapmers have twenty linked nucleosides, wherein the central gap segment has ten 2'-deoxynucleotides and is flanked on both sides (in the 5' and 3' directions) by wings having five nucleosides each. Each nucleoside in the 5' wing segment and each nucleoside in the 3' wing segment has a 2'-MOE modification. The internucleoside linkages within the central gap segment, the linkages connecting the gap segment to the 5' or 3' wing segment, and the linkages for the 5'-most and 3'-most nucleosides of each wing segments are all phosphorothioate (P=S) linkages; the internucleoside linkages connecting the rest of the nucleosides of both the 5' and 3' wing segments are phosphodiester linkages; i.e. the gapmer has a mixed backbone. All cytosines throughout each gapmer are 5-methylcytosines. Each gapmer in Table 5 is targeted to the human mRNA sequence (GENBANK Accession No. NM_002111.6, designated herein as SEQ ID NO: 1). 'Start site' indicates the 5'-most nucleotide to which the gapmer is targeted in the human mRNA. 'Stop site' indicates the 3'-most nucleotide to which the gapmer is targeted in the human mRNA.

TABLE 5

Chimeric antisense oligonucleotides with phosphorothioate and phosphate internucleoside linkages targeting human huntingtin mRNA (SEQ ID NO: 1)

| Start Site | Stop Site | Target SEQ ID NO. | ISIS No. | Sequence (5' to 3') | Motif | SEQ ID NO. |
|---|---|---|---|---|---|---|
| 4607 | 4626 | 1 | 444658 | GCCTCTGATTCCCTGAACTG | 5-10-5 | 10 |
| 4608 | 4627 | 1 | 444659 | TGCCTCTGATTCCCTGAACT | 5-10-5 | 11 |
| 4609 | 4628 | 1 | 444660 | TTGCCTCTGATTCCCTGAAC | 5-10-5 | 12 |
| 4610 | 4629 | 1 | 444661 | ATTGCCTCTGATTCCCTGAA | 5-10-5 | 13 |
| 4813 | 4832 | 1 | 444663 | CTGCATCAGCTTTATTTGTT | 5-10-5 | 18 |
| 4862 | 4881 | 1 | 443139 | CTCAGTAACATTGACACCAC | 5-10-5 | 22 |
| 5809 | 5828 | 1 | 444652 | TTTCTCTATTGCACATTCCA | 5-10-5 | 32 |
| 4928 | 4947 | 1 | 451541 | TTCTCCTTGTGGCACTGCTG | 5-10-5 | 25 |

The complementarity of the gapmers in Table 5 with mouse, rhesus monkey and rat huntingtin gene sequences are further described in Tables 6, 7, and 8.

The gapmers of Table 6 are complementary with mouse huntingtin mRNA (GENBANK Accession No.

NM_010414.1; SEQ ID NO: 3). 'Mouse target start site' indicates the 5'-most nucleotide to which the gapmer is targeted in the mouse mRNA. 'Mouse target stop site' indicates the 3'-most nucleotide to which the gapmer is targeted in the mouse mRNA. 'Human Target Start Site' indicates the 5'-most nucleotide to which the gapmer is targeted in the human mRNA (GENBANK Accession No. NM_002111.6). 'Human Target Stop Site' indicates the 3'-most nucleotide to which the gapmer is targeted in the human mRNA (GENBANK Accession No. NM_002111.6). 'Number of mismatches' indicates the number of mismatches between the human oligonucleotide and the mouse mRNA sequence.

TABLE 6

Complementarity of antisense oligonucleotides having mixed phosphorothioate and phosphate linkages with murine mRNA (SEQ ID NO: 3)

| Human Start Site | Human Stop Site | Human Target SEQ ID NO. | ISIS No. | Mouse Start Site | Mouse Stop Site | No. of mismatches | SEQ ID NO. |
|---|---|---|---|---|---|---|---|
| 4607 | 4626 | 1 | 444658 | 4566 | 4585 | 0 | 10 |
| 4608 | 4627 | 1 | 444659 | 4567 | 4586 | 0 | 11 |
| 4609 | 4628 | 1 | 444660 | 4568 | 4587 | 0 | 12 |
| 4610 | 4629 | 1 | 444661 | 4569 | 4588 | 0 | 13 |
| 4813 | 4832* | 1 | 444663 | 4772 | 4791 | 0 | 18 |
| 5809 | 5828 | 1 | 444652 | 5765 | 5784 | 1 | 32 |

The gapmers of Table 7 are complementary with the rhesus monkey huntingtin genomic sequence (the complement of GENBANK Accession No. NW_001109716.1 truncated at nucleotides 698000 to 866000; SEQ ID NO: 4). 'Rhesus monkey target start site' indicates the 5'-most nucleotide to which the gapmer is targeted in the rhesus monkey gene sequence. 'Rhesus monkey target stop site' indicates the 3'-most nucleotide to which the gapmer is targeted in the rhesus monkey gene sequence. 'Human Target Start Site' indicates the 5'-most nucleotide to which the gapmer is targeted in the human mRNA (GENBANK Accession No. NM_002111.6). 'Human Target Stop Site' indicates the 3'-most nucleotide to which the gapmer is targeted in the human mRNA (GENBANK Accession No. NM_002111.6). 'Number of mismatches' indicates the number of mismatches between the human oligonucleotide and the rhesus monkey gene sequence.

TABLE 7

Complementarity of antisense oligonucleotides having mixed phosphorothioate and phosphate linkages with rhesus monkey gene sequence (SEQ ID NO: 4)

| Human Start Site | Human Stop Site | Human Target SEQ ID NO. | ISIS No. | Rhesus monkey Start Site | Rhesus monkey Stop Site | No. of mismatches | SEQ ID NO. |
|---|---|---|---|---|---|---|---|
| 4609 | 4628 | 1 | 444660 | 102256 | 102275 | 3 | 12 |
| 4610 | 4629 | 1 | 444661 | 102257 | 102276 | 2 | 13 |
| 4813 | 4832 | 1 | 444663 | 105030 | 105049 | 0 | 18 |
| 4862 | 4881 | 1 | 443139 | 105079 | 105098 | 1 | 22 |
| 5809 | 5828 | 1 | 444652 | 125339 | 125358 | 0 | 32 |

The gapmers of Table 8 are complementary with rat huntingtin mRNA (GENBANK Accession No. NM_024357.2; SEQ ID NO: 5). 'Rat target start site' indicates the 5'-most nucleotide to which the gapmer is targeted in the rat mRNA. 'Rat target stop site' indicates the 3'-most nucleotide to which the gapmer is targeted in the rat mRNA. 'Human Target Start Site' indicates the 5'-most nucleotide to which the gapmer is targeted in the human mRNA (GENBANK Accession No. NM_002111.6). 'Human Target Stop Site' indicates the 3'-most nucleotide to which the gapmer is targeted in the human mRNA (GENBANK Accession No. NM_002111.6). 'Number of mismatches' indicates the number of mismatches between the human oligonucleotide and the rat mRNA sequence.

TABLE 8

Complementarity of antisense oligonucleotides having mixed phosphorothioate and phosphate linkages with rat mRNA (SEQ ID NO: 5)

| Human Start Site | Human Stop Site | Human Target SEQ ID NO. | ISIS No. | Rat Start Site | Rat Stop Site | No. of mismatches | SEQ ID NO. |
|---|---|---|---|---|---|---|---|
| 4607 | 4626 | 1 | 444658 | 4566 | 4585 | 0 | 10 |
| 4608 | 4627 | 1 | 444659 | 4567 | 4586 | 0 | 11 |
| 4609 | 4628 | 1 | 444660 | 4568 | 4587 | 0 | 12 |
| 4610 | 4629 | 1 | 444661 | 4569 | 4588 | 0 | 13 |
| 4813 | 4832 | 1 | 444663 | 4772 | 4791 | 0 | 18 |
| 5809 | 5828 | 1 | 444652 | 5765 | 5784 | 0 | 32 |

Example 2

Dose-Dependent Antisense Inhibition of Human Huntingtin mRNA In Vitro

About seventeen hundred newly designed antisense compounds of various lengths, motifs and backbone composition were tested for their effect on human huntingtin mRNA in vitro in several cell types. These compounds were compared to about two hundred and fifty previously designed compounds including the compound ISIS 387916 which was previously determined to be a compound of considerable potency in vivo. As shown in this example, ISIS 419640, ISIS 419641, ISIS 419642, ISIS 436665, ISIS 436671, ISIS 436689, ISIS 437507, ISIS 443139, ISIS 444591, ISIS 444661, ISIS 437527, ISIS 444584, and ISIS 444652 and previously designed ISIS 388241 were found to have similar or better potency than the benchmark compound ISIS 387916 in vitro.

A. GM04281 Fibroblasts

Cultured GM04281 fibroblasts at a density of 25,000 cells per well were transfected using electroporation with 500 nM, 1000 nM, 2000 nM, 4000 nM, or 8000 nM of antisense oligonucleotide. After a treatment period of approximately 16 hours, RNA was isolated from the cells and huntingtin mRNA levels were measured by quantitative real-time PCR. Human primer probe set RTS2617 (forward sequence CTCCGTC-CGGTAGACATGCT, designated herein as SEQ ID NO: 37; reverse sequence GGAAATCAGAACCCTCAAAATGG, designated herein as SEQ ID NO: 38; probe sequence TGAG-CACTGTTCAACTGTGGATATCGGGAX, designated herein as SEQ ID NO: 39) was used to measure mRNA levels. Huntingtin mRNA levels were adjusted according to total RNA content, as measured by RIBOGREEN®. Results are presented in Table 9 as percent inhibition of huntingtin mRNA, relative to untreated control cells and demonstrate antisense oligonucleotide-mediated dose-dependent reduction of huntingtin mRNA levels.

The half maximal inhibitory concentration ($IC_{50}$) of each oligonucleotide is also presented in Table 9 and was calculated by plotting the concentrations of oligonucleotides used versus the percent inhibition of huntingtin mRNA expression achieved at each concentration, and noting the concentration of oligonucleotide at which 50% inhibition of huntingtin mRNA expression was achieved compared to the control. The $IC_{50}$ is expressed in μM.

TABLE 9

Dose dependent reduction of huntingtin mRNA in GM04281 fibroblasts

| ISIS No. | 500 nM | 1000 nM | 2000 nM | 4000 nM | 8000 nM | $IC_{50}$ (μM) |
|---|---|---|---|---|---|---|
| 387916 | 33 | 73 | 90 | 96 | 97 | 1.00 |
| 388241 | 44 | 70 | 82 | 95 | 97 | 0.61 |
| 419641 | 26 | 32 | 71 | 90 | 93 | 1.06 |
| 436665 | 56 | 67 | 87 | 95 | 96 | 0.32 |
| 436671 | 12 | 35 | 68 | 82 | 91 | 1.55 |
| 436689 | 10 | 34 | 61 | 80 | 91 | 1.89 |

ISIS 387916, ISIS 388241, and ISIS 437507 were further tested for their effect on human huntingtin mRNA in vitro. Cultured GM04281 fibroblasts were tested in a similar procedure, as described above. The results are presented in Table 10 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 10 expressed in μM.

TABLE 10

Dose dependent reduction of huntingtin mRNA in GM04281 fibroblasts

| ISIS No. | 500 nM | 1000 nM | 2000 nM | 4000 nM | 8000 nM | $IC_{50}$ (μM) |
|---|---|---|---|---|---|---|
| 387916 | 56 | 84 | 94 | 98 | 99 | 0.34 |
| 388241 | 58 | 75 | 94 | 98 | 99 | 0.23 |
| 437507 | 61 | 74 | 85 | 93 | 93 | 0.22 |

ISIS 387916, ISIS 388241, and ISIS 437507 were further tested for their effect on human huntingtin mRNA in vitro. Cultured GM04281 fibroblasts were tested in a similar procedure as described above. The results are presented in Table 11 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 11 expressed in μM.

TABLE 11

Dose dependent reduction of huntingtin mRNA in GM04281 fibroblasts

| ISIS No. | 500 nM | 1000 nM | 2000 nM | 4000 nM | 8000 nM | IC$_{50}$ (µM) |
|---|---|---|---|---|---|---|
| 387916 | 40 | 61 | 85 | 94 | 97 | 0.70 |
| 388241 | 51 | 72 | 86 | 94 | 98 | 0.41 |
| 437507 | 30 | 55 | 71 | 79 | 82 | 1.07 |

ISIS 387916, ISIS 388241, ISIS 419641, and ISIS 436754 were further tested for their effect on human huntingtin mRNA in vitro. Cultured GM04281 fibroblasts were tested in a similar procedure as described above. The results are presented in Table 12 as percent inhibition of huntingtin mRNA, relative to untreated control cells and demonstrate antisense oligonucleotide-mediated dose-dependent reduction of huntingtin mRNA levels. The IC$_{50}$ of each antisense oligonucleotide is also presented in Table 12 expressed in µM.

TABLE 12

Dose dependent reduction of huntingtin mRNA in GM04281 fibroblasts

| ISIS No. | 500 nM | 1000 nM | 2000 nM | 4000 nM | 8000 nM | IC$_{50}$ (µM) |
|---|---|---|---|---|---|---|
| 387916 | 58 | 75 | 93 | 98 | 98 | 0.22 |
| 388241 | 40 | 68 | 85 | 95 | 98 | 0.73 |
| 419641 | 37 | 58 | 86 | 92 | 95 | 0.80 |
| 436754 | 44 | 62 | 63 | 84 | 93 | 0.59 |

ISIS 387916, ISIS 388241, and ISIS 437507 were further tested for their effect on human huntingtin mRNA in vitro. Cultured GM04281 fibroblasts at a density of 25,000 cells per well were transfected using electroporation with 250 nM, 500 nM, 1000 nM, 2000 nM, 4000 nM or 8000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 13 as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 13 expressed in µM.

TABLE 13

Dose dependent reduction of huntingtin mRNA in GM04281 fibroblasts

| ISIS No. | 250 nM | 500 nM | 1000 Nm | 2000 nM | 4000 nM | 8000 nM | IC$_{50}$ (µM) |
|---|---|---|---|---|---|---|---|
| 387916 | 10 | 9 | 61 | 85 | 97 | 99 | 0.79 |
| 388241 | 0 | 18 | 42 | 90 | 98 | 99 | 1.08 |
| 437507 | 1 | 0 | 32 | 71 | 92 | 98 | 1.30 |

ISIS 387916, ISIS 388241, ISIS 419628, ISIS 419629, ISIS 419637, ISIS 436684, ISIS 443139, ISIS 444584, ISIS 444615, ISIS 444627, ISIS 444652, ISIS 444658, ISIS 444659, ISIS 444660, and ISIS 444661 were further tested for their effect on human huntingtin mRNA in vitro. Cultured GM04281 fibroblasts at a density of 25,000 cells per well were transfected using electroporation with 156.25 nM, 312.5 nM, 625 nM, 1250 nM, or 2500 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 14 as percent inhibition of huntingtin mRNA, relative to untreated control cells, and demonstrate antisense oligonucleotide-mediated dose-dependent reduction of huntingtin mRNA levels. The data presented is the average of two experiments. The IC$_{50}$ of each antisense oligonucleotide is also presented in Table 14 expressed in µM.

TABLE 14

Dose dependent reduction of huntingtin mRNA in GM04281 fibroblasts

| ISIS No | 156.25 nM | 312.5 Nm | 625 nM | 1250 nM | 2500 nM | IC$_{50}$ (µM) |
|---|---|---|---|---|---|---|
| 387916 | 19 | 22 | 44 | 62 | 85 | 0.73 |
| 388241 | 3 | 13 | 24 | 42 | 71 | 1.42 |
| 419628 | 56 | 45 | 59 | 71 | 83 | 0.20 |
| 419629 | 42 | 38 | 67 | 70 | 89 | 0.33 |
| 419637 | 24 | 17 | 32 | 61 | 77 | 0.91 |
| 436684 | 15 | 28 | 55 | 73 | 85 | 0.59 |
| 443139 | 13 | 45 | 50 | 64 | 81 | 0.61 |
| 444584 | 0 | 0 | 25 | 50 | 74 | 1.28 |
| 444615 | 36 | 35 | 37 | 38 | 70 | 0.12 |
| 444627 | 40 | 38 | 48 | 73 | 87 | 0.43 |
| 444652 | 15 | 28 | 55 | 73 | 85 | 0.59 |
| 444658 | 50 | 54 | 75 | 84 | 96 | 0.18 |
| 444659 | 47 | 61 | 69 | 79 | 93 | 0.18 |
| 444660 | 41 | 61 | 65 | 84 | 95 | 0.22 |
| 444661 | 47 | 59 | 72 | 84 | 96 | 0.19 |

ISIS 387916, ISIS 436671, ISIS 444661, ISIS 419641, and ISIS 436665 were further tested for their effect on human huntingtin mRNA in vitro. Cultured GM04281 fibroblasts at a density of 25,000 cells per well were transfected using electroporation with 13.6719 nM, 27.3438 nM, 54.6875 nM, 109.375 nM, 218.75 nM, 437.5 nM, 875 nM, 1750 nM, 3500 nM, or 7000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 15 as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 15 expressed in µM.

TABLE 15

Dose dependent reduction of huntingtin mRNA in GM04281 fibroblasts

| ISIS No. | 13.6719 nM | 27.3438 nM | 54.6875 nM | 109.375 nM | 218.75 nM | 437.5 nM | 875 nM | 1750 nM | 3500 nM | 7000 nM | $IC_{50}$ (μM) |
|---|---|---|---|---|---|---|---|---|---|---|---|
| 387916 | 0 | 31 | 14 | 43 | 44 | 68 | 86 | 89 | 97 | 97 | 0.31 |
| 436671 | 0 | 0 | 21 | 31 | 54 | 73 | 77 | 83 | 88 | 97 | 0.31 |
| 444661 | 0 | 10 | 25 | 53 | 66 | 73 | 87 | 96 | 99 | 99 | 0.16 |
| 419641 | 5 | 23 | 33 | 48 | 44 | 75 | 79 | 90 | 94 | 98 | 0.17 |
| 436665 | 26 | 37 | 47 | 44 | 65 | 83 | 89 | 94 | 98 | 98 | 0.07 |

ISIS 387916, ISIS 388241, ISIS 437168, and ISIS 437175 were further tested for their effect on human huntingtin mRNA in vitro. Cultured GM04281 fibroblasts at a density of 25,000 cells per well were transfected using electroporation with 250 nM, 500 nM, 1000 nM, 2000 nM, 4000 nM, and 8000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 15.1 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 15.1 expressed in

TABLE 15.1

Dose dependent reduction of huntingtin mRNA in GM04281 fibroblasts

| ISIS No. | 250.0 nM | 500.0 nM | 1000.0 nM | 2000.0 nM | 4000.0 nM | 8000.0 nM | $IC_{50}$ |
|---|---|---|---|---|---|---|---|
| 387916 | 22 | 63 | 70 | 83 | 95 | 96 | 0.62 |
| 388241 | 17 | 45 | 65 | 87 | 96 | 97 | 0.56 |
| 437175 | 47 | 31 | 56 | 60 | 79 | 91 | 1.19 |
| 437168 | 32 | 46 | 64 | 81 | 89 | 95 | 0.59 |

ISIS 387916, ISIS 388241, ISIS 437441, and ISIS 437442 were further tested for their effect on human huntingtin mRNA in vitro. Cultured GM04281 fibroblasts were tested in a similar procedure as described above. The results are presented in Table 15.2 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 15.2 expressed in μM.

TABLE 15.2

Dose dependent reduction of huntingtin mRNA in GM04281 fibroblasts

| ISIS No. | 250.0 nM | 500.0 nM | 1000.0 nM | 2000.0 nM | 4000.0 nM | 8000.0 nM | $IC_{50}$ |
|---|---|---|---|---|---|---|---|
| 387916 | 26 | 47 | 58 | 79 | 91 | 95 | 0.65 |
| 388241 | 30 | 52 | 60 | 81 | 94 | 97 | 0.55 |
| 437441 | 25 | 37 | 56 | 69 | 86 | 47 | 0.81 |
| 437442 | 39 | 43 | 47 | 70 | 85 | 50 | 0.59 |

ISIS 387916, ISIS 388241, ISIS 437175, and ISIS 437527 were further tested for their effect on human huntingtin mRNA in vitro. Cultured GM04281 fibroblasts were tested in a similar procedure as described above. The results are presented in Table 15.3 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 15.3 expressed in μM.

TABLE 15.3

Dose dependent reduction of huntingtin mRNA in GM04281 fibroblasts

| ISIS No. | 250.0 nM | 500.0 nM | 1000.0 nM | 2000.0 nM | 4000.0 nM | 8000.0 nM | $IC_{50}$ |
|---|---|---|---|---|---|---|---|
| 387916 | 40 | 45 | 47 | 76 | 92 | 96 | 0.50 |
| 388241 | 40 | 37 | 50 | 90 | 96 | 97 | 0.80 |
| 437175 | 48 | 55 | 55 | 63 | 80 | 93 | 0.37 |
| 437527 | 33 | 52 | 61 | 80 | 86 | 95 | 0.52 |

B. A549 Cells

Some of the antisense oligonucleotides described in Example 1 were tested for their effect on human huntingtin mRNA in vitro. Cultured A549 cells at a density of 4,000 cells per well were transfected using lipofectin transfection reagent with 7.4074 nM, 22.222 nM, 66.667 nM, or 200 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. Results are presented in Table 16 as percent inhibition of huntingtin mRNA, relative to untreated control cells and demonstrate antisense oligonucleotide-mediated dose-dependent reduction of huntingtin mRNA levels. The $IC_{50}$ of each antisense oligonucleotide is also presented in Table 16 expressed in nM.

TABLE 16

Dose dependent reduction of huntingtin mRNA in A549 cells

| ISIS No. | 7.4074 nM | 22.222 nM | 66.667 nM | 200.00 nM | $IC_{50}$ (nM) |
|---|---|---|---|---|---|
| 387916 | 12 | 37 | 76 | 92 | 33 |
| 419640 | 21 | 45 | 73 | 93 | 27 |
| 419641 | 34 | 60 | 83 | 96 | 15 |
| 419642 | 30 | 58 | 85 | 95 | 16 |

ISIS 387916, ISIS 388241, and ISIS 437507 were further tested for their effect on human huntingtin mRNA in vitro. Cultured A549 cells at a density of 20,000 cells per well were transfected using electroporation with 250 nM, 500 nM, 1000 nM, 2000 nM, 4000 nM or 8000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 17 expressed as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 17 expressed in µM.

TABLE 17

Dose dependent reduction of huntingtin mRNA in A549 cells

| ISIS No. | 250 nM | 500 nM | 1000 nM | 2000 nM | 4000 nM | 8000 nM | $IC_{50}$ (µM) |
|---|---|---|---|---|---|---|---|
| 387916 | 15 | 17 | 25 | 36 | 52 | 75 | 3.09 |
| 388241 | 12 | 22 | 38 | 58 | 77 | 91 | 1.43 |
| 437507 | 25 | 28 | 38 | 57 | 58 | 76 | 1.84 |

C. LLC-MK2 Cells

Some of the antisense oligonucleotides described in Example 1 and targeted to a human huntingtin nucleic acid were tested for their effect on rhesus monkey huntingtin mRNA in vitro. Cultured LLC-MK2 cells at a density of 25,000 cells per well were transfected using electroporation with 625 nM, 1250 nM, 2500 nM, 5000 nM, 10,000 nM, or 20,000 nM of antisense oligonucleotide. After a treatment period of approximately 16 hours, RNA was isolated from the cells and huntingtin mRNA levels were measured by quantitative real-time PCR. Human primer probe set RTS2686 (forward sequence GTCTGAGCCTCTCTCGGTCAA, designated herein as SEQ ID NO: 40; reverse sequence AAGGGATGCTGGGCTCTGT, designated herein as SEQ ID NO: 41; probe sequence AGCAAAGCTTGGTGTCTTG-GCACTGTTAGTX, designated herein as SEQ ID NO: 42) was used to measure mRNA levels. Huntingtin mRNA levels were adjusted according to total RNA content, as measured by RIBOGREEN®. Results are presented in Table 18 as percent inhibition of huntingtin mRNA, relative to untreated control cells and demonstrate antisense oligonucleotide-mediated dose-dependent reduction of huntingtin mRNA levels. The $IC_{50}$ of each antisense oligonucleotide is also presented in Table 18 expressed in µM.

TABLE 18

Dose dependent reduction of huntingtin mRNA in LLC-MK2 cells

| ISIS No. | 625 nM | 1250 nM | 2500 nM | 5000 nM | 10000 nM | 20000 nM | $IC_{50}$ (µM) |
|---|---|---|---|---|---|---|---|
| 388241 | 21 | 12 | 35 | 46 | 46 | 94 | 4.1 |
| 444591 | 37 | 46 | 51 | 52 | 82 | 96 | 1.9 |
| 419641 | 32 | 52 | 69 | 87 | 94 | 97 | 1.2 |
| 444661 | 45 | 59 | 66 | 85 | 91 | 95 | 0.8 |
| 419642 | 6 | 3 | 56 | 81 | 91 | 98 | 2.9 |
| 436665 | 40 | 43 | 70 | 73 | 84 | 89 | 1.2 |
| 436671 | 31 | 51 | 68 | 82 | 90 | 97 | 1.2 |
| 436689 | 24 | 37 | 59 | 74 | 89 | 98 | 1.9 |
| 437507 | 21 | 15 | 11 | 33 | 55 | 92 | 6.4 |
| 443139 | 31 | 36 | 37 | 56 | 76 | 97 | 2.6 |

ISIS 387916, ISIS 388241, ISIS 436684, ISIS 437168, ISIS 437175, ISIS 437441, ISIS 437507, ISIS 437527, ISIS 444578, ISIS 444584, ISIS 444591, and ISIS 444607 were further tested for their effect on rhesus monkey huntingtin mRNA in vitro. Cultured LLC-MK2 cells were tested in a similar procedure as described above. The results are presented in Table 19 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 19 expressed in µM.

TABLE 19

Dose dependent reduction of huntingtin mRNA in LLC-MK2 cells

| ISIS No. | 625.0 nM | 1250.0 nM | 2500.0 nM | 5000.0 nM | 10000.0 nM | 20000.0 nM | $IC_{50}$ |
|---|---|---|---|---|---|---|---|
| 387916 | 23 | 42 | 57 | 81 | 88 | 96 | 1.95 |
| 388241 | 6 | 12 | 37 | 43 | 62 | 84 | 5.32 |
| 437168 | 72 | 47 | 60 | 78 | 83 | 92 | 1.43 |
| 437175 | 27 | 48 | 36 | 56 | 68 | 78 | 3.58 |
| 437441 | 29 | 34 | 50 | 67 | 56 | 85 | 2.43 |
| 437507 | 18 | 29 | 18 | 33 | 45 | 66 | 6.12 |
| 437527 | 36 | 36 | 48 | 57 | 81 | 90 | 2.71 |
| 436684 | 0 | 12 | 24 | 29 | 36 | 49 | n.d. |
| 444578 | 34 | 40 | 65 | 74 | 82 | 87 | 1.70 |
| 444584 | 28 | 38 | 68 | 75 | 90 | 94 | 1.69 |
| 444591 | 25 | 45 | 55 | 74 | 85 | 94 | 1.84 |
| 444607 | 41 | 54 | 76 | 87 | 92 | 94 | 0.96 | n.d. = $IC_{50}$ could not be measured for that compound

ISIS 387916, ISIS 388241, ISIS 444608, ISIS 444615, ISIS 444618, ISIS 444627, ISIS 444652, ISIS 444658, ISIS 444659, ISIS 444660, and ISIS 444661 were further tested for their effect on rhesus monkey huntingtin mRNA in vitro. Cultured LLC-MK2 cells were tested in a similar procedure as described above. The results are presented in Table 20 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 20 expressed in µM.

TABLE 20

Dose dependent reduction of huntingtin mRNA in LLC-MK2 cells

| ISIS No | 625.0 nM | 1250.0 nM | 2500.0 nM | 5000.0 nM | 10000.0 nM | 20000.0 nM | IC50 |
|---|---|---|---|---|---|---|---|
| 387916 | 35 | 44 | 68 | 74 | 90 | 96 | 1.35 |
| 388241 | 23 | 37 | 54 | 56 | 68 | 89 | 2.64 |
| 444608 | 43 | 50 | 64 | 83 | 90 | 95 | 1.07 |
| 444615 | 29 | 45 | 55 | 76 | 90 | 97 | 1.67 |
| 444618 | 30 | 34 | 57 | 73 | 89 | 95 | 1.66 |
| 444627 | 35 | 56 | 76 | 90 | 97 | 98 | 1.00 |
| 444652 | 32 | 55 | 66 | 55 | 92 | 98 | 1.23 |
| 444658 | 50 | 62 | 80 | 90 | 95 | 97 | 0.55 |
| 444659 | 31 | 56 | 68 | 86 | 95 | 97 | 1.17 |
| 444660 | 38 | 49 | 62 | 86 | 89 | 96 | 1.26 |
| 444661 | 41 | 50 | 75 | 68 | 95 | 97 | 0.95 |

ISIS 387916, ISIS 419627, ISIS 419628, ISIS 419629, ISIS 419630, ISIS 419636, ISIS 419637, ISIS 419640, ISIS 419641, and ISIS 419642 were further tested for their effect on rhesus monkey huntingtin mRNA in vitro. Cultured LLC-MK2 cells at a density of 3,000 cells per well were transfected using lipofectin transfection reagent with 6.25 nM, 12.5 nM, 25 nM, 50 nM, 100 nM, or 200 nM of antisense oligonucleotide. After a treatment period of approximately 16 hours, RNA was isolated from the cells and huntingtin mRNA levels were measured by quantitative real-time PCR. Human primer probe set RTS2686 was used to measure mRNA levels. Huntingtin mRNA levels were adjusted according to total RNA content, as measured by RIBOGREEN®. Results are presented in Table 21 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 21 expressed in nM.

TABLE 21

Dose dependent reduction of huntingtin mRNA in LLC-MK2 cells

| ISIS No. | 6.25 nM | 12.5 nM | 25.0 nM | 50.0 nM | 100.0 nM | 200.0 nM | $IC_{50}$ |
|---|---|---|---|---|---|---|---|
| 387916 | 1 | 37 | 37 | 53 | 84 | 90 | 35 |
| 419627 | 0 | 9 | 18 | 45 | 58 | 72 | 75 |
| 419628 | 9 | 30 | 49 | 63 | 73 | 77 | 31 |
| 419629 | 9 | 16 | 40 | 56 | 80 | 85 | 36 |
| 419630 | 17 | 8 | 43 | 58 | 71 | 81 | 40 |
| 419636 | 23 | 25 | 38 | 55 | 72 | 78 | 37 |
| 419637 | 10 | 35 | 31 | 62 | 78 | 76 | 33 |
| 419640 | 3 | 28 | 39 | 59 | 74 | 87 | 36 |
| 419641 | 11 | 34 | 51 | 65 | 85 | 87 | 26 |
| 419642 | 25 | 30 | 49 | 65 | 85 | 88 | 24 |

ISIS 387916, ISIS 419641, and ISIS 436689 were further tested for their effect on rhesus monkey huntingtin mRNA in vitro. Cultured LLC-MK2 cells at a density of 3,000 cells per well were transfected using LipofectAMINE2000 transfection reagent with 6.25 nM, 12.5 nM, 25 nM, 50 nM, 100 nM, or 200 nM of antisense oligonucleotide. After a treatment period of approximately 16 hours, RNA was isolated from the cells and huntingtin mRNA levels were measured by quantitative real-time PCR. Human primer probe set RTS2686 was used to measure mRNA levels. Huntingtin mRNA levels were adjusted according to total RNA content, as measured by RIBOGREEN®. Results are presented in Table 22 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 22 expressed in nM.

TABLE 22

Dose dependent reduction of huntingtin mRNA in LLC-MK2 cells

| ISIS No | 6.25 nM | 12.5 nM | 25 nM | 50 nM | 100 nM | 200 nM | $IC_{50}$ (nM) |
|---|---|---|---|---|---|---|---|
| 387916 | 0 | 50 | 31 | 68 | 83 | 90 | 47 |
| 419641 | 28 | 23 | 28 | 51 | 65 | 81 | 74 |
| 436689 | 16 | 30 | 29 | 48 | 67 | 83 | 69 |

ISIS 387916, ISIS 388241, ISIS 436665, ISIS 436671, and ISIS 436689 were further tested for their effect on rhesus monkey huntingtin mRNA in vitro. Cultured LLC-MK2 cells at a density of 3,000 cells per well were transfected using lipofectin transfection reagent with 4.6875 nM, 9.375 nM, 18.75 nM, 37.5 nM, 75 nM, or 150 nM of antisense oligonucleotide. After a treatment period of approximately 16 hours, RNA was isolated from the cells and huntingtin mRNA levels were measured by quantitative real-time PCR. Human primer probe set RTS2686 was used to measure mRNA levels. Huntingtin mRNA levels were adjusted according to total RNA content, as measured by RIBOGREEN®. Results are presented in Table 23 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 23 expressed in nM.

TABLE 23

Dose dependent reduction of huntingtin mRNA in LLC-MK2 cells

| ISIS No. | 4.6875 nM | 9.375 nM | 18.75 nM | 37.5 nM | 75.0 nM | 150.0 nM | $IC_{50}$ (nM) |
|---|---|---|---|---|---|---|---|
| 387916 | 7 | 6 | 38 | 59 | 82 | 91 | 32 |
| 388241 | 0 | 0 | 5 | 35 | 62 | 81 | 60 |
| 436665 | 7 | 0 | 36 | 59 | 64 | 69 | 37 |
| 436671 | 21 | 7 | 35 | 59 | 80 | 86 | 31 |
| 436689 | 38 | 45 | 45 | 59 | 76 | 86 | 15 |

D. BACHD Transgenic Mouse Hepatocyes

Some of the antisense oligonucleotides described in Example 1 and targeted to a human huntingtin nucleic acid were tested for their effect on human huntingtin mRNA in vitro. Cultured BACHD mouse hepatocytes at a density of 10,000 cells per well were transfected using cytofectin transfection reagent with 7.4074 nM, 22.222 nM, 66.667 nM, or 200 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. Results are presented in Table 24 as percent inhibition of huntingtin mRNA, relative to untreated control cells, and demonstrate antisense oligonucleotide-mediated dose-dependent reduction of huntingtin mRNA levels. The data presented is the average of two experiments. The $IC_{50}$ of each antisense oligonucleotide is also presented in Table 24 expressed in nM.

TABLE 24

Dose dependent reduction of huntingtin mRNA in BACHD transgenic murine hepatocytes

| ISIS No. | 7.4074 nM | 22.222 nM | 66.667 nM | 200.00 nM | $IC_{50}$ (nM) |
|---|---|---|---|---|---|
| 387916 | 8 | 19 | 58 | 89 | 40 |
| 419640 | 15 | 30 | 64 | 93 | 33 |
| 419641 | 20 | 35 | 73 | 97 | 31 |
| 419642 | 3 | 29 | 70 | 96 | 43 |

ISIS 387916, ISIS 388241, and ISIS 419641 were further tested for their effect on human huntingtin mRNA in vitro. Cultured BACHD mouse hepatocytes at a density of 10,000 cells per well were transfected using cytofectin transfection reagent with 12.5 nM, 25 nM, 50 nM, 100 nM or 200 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. Results are presented in Table 25 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 25 expressed in nM.

TABLE 25

Dose dependent reduction of huntingtin mRNA
in BACHD transgenic murine hepatocytes

| ISIS No. | 12.5 nM | 25 nM | 50 Nm | 100 nM | 200 nM | IC$_{50}$ (nM) |
|---|---|---|---|---|---|---|
| 387916 | 0 | 37 | 51 | 78 | 91 | 51 |
| 388241 | 0 | 10 | 45 | 70 | 92 | 68 |
| 419641 | 17 | 38 | 70 | 88 | 96 | 34 |

ISIS 387916, ISIS 388241, ISIS 419641, ISIS 436665, ISIS 436671, and ISIS 436689 were further tested for their effect on human huntingtin mRNA in vitro. Cultured BACHD mouse hepatocytes were tested in an identical manner as described above. The results are presented in Table 26 as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 26 expressed in nM.

TABLE 26

Dose dependent reduction of huntingtin mRNA
in BACHD transgenic murine hepatocytes

| ISIS No. | 12.5 nM | 25 nM | 50 nM | 100 nM | 200 nM | IC$_{50}$ (nM) |
|---|---|---|---|---|---|---|
| 387916 | 19 | 48 | 64 | 86 | 93 | 32 |
| 388241 | 20 | 34 | 54 | 81 | 93 | 38 |
| 419641 | 38 | 54 | 70 | 85 | 95 | 21 |
| 436665 | 32 | 40 | 67 | 84 | 93 | 29 |
| 436671 | 32 | 42 | 58 | 78 | 91 | 32 |
| 436689 | 35 | 44 | 70 | 88 | 96 | 25 |

ISIS 387916, ISIS 419640, ISIS 419641, and ISIS 419642 were further tested for their effect on mouse huntingtin mRNA in vitro. Cultured BACHD mouse hepatocytes at a density of 20,000 cells per well were transfected using cytofectin transfection reagent with 6.667 nM, 20 nM, 60 nM, or 180 nM of antisense oligonucleotide. After a treatment period of approximately 16 hours, RNA was isolated from the cells and huntingtin mRNA levels were measured by quantitative real-time PCR. Murine primer probe set RTS2633 (forward sequence CAGAGCTGGTCAACCGTATCC, designated herein as SEQ ID NO: 43; reverse sequence GGCTTAAA-CAGGGAGCCAAAA, designated herein as SEQ ID NO: 44; probe sequence ACTTCATGATGAGCTCGGAGT-TCAACX, designated herein as SEQ ID NO: 45) was used to measure mRNA levels. Huntingtin mRNA levels were adjusted according to total RNA content, as measured by RIBOGREEN®. Results are presented in Table 27 as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 27 expressed in nM.

TABLE 27

Dose dependent reduction of huntingtin mRNA in BACHD transgenic
murine hepatocytes

| ISIS No. | 6.667 nM | 20 nM | 60 nM | 180 nM | IC$_{50}$ (nM) |
|---|---|---|---|---|---|
| 387916 | 15 | 15 | 68 | 94 | 37 |
| 419640 | 4 | 39 | 73 | 94 | 32 |

TABLE 27-continued

Dose dependent reduction of huntingtin mRNA in BACHD transgenic
murine hepatocytes

| ISIS No. | 6.667 nM | 20 nM | 60 nM | 180 nM | IC$_{50}$ (nM) |
|---|---|---|---|---|---|
| 419641 | 16 | 45 | 81 | 96 | 24 |
| 419642 | 23 | 39 | 75 | 93 | 25 |

Example 3

Systemic Administration of Antisense Oligonucleotides Against Huntingtin mRNA in BACHD Mice Of the about seventeen hundred newly designed antisense compounds, sixty six compounds were selected based on in vitro potency compared to ISIS 387916 for testing in systemic tolerability screens.

BACHD mice were treated with ISIS oligonucleotides and evaluated for changes in the levels of various metabolic markers as well as inhibition of huntingtin mRNA in the liver. Antisense oligonucleotides which caused adverse changes in body weight, organ weight or in the levels of metabolic markers were deemed unsuitable for utilization in further studies.
Study 1.
Treatment Nineteen groups of four BACHD mice each were injected intraperitoneally with 12.5 mg/kg of ISIS 387916, ISIS 388241, ISIS 419629, ISIS 419637, ISIS 436684, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661, or ISIS 444663 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.
RNA Analysis RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 28 and 29 and were calculated as percent inhibition of human and murine huntingtin expression levels respectively, relative to the PBS control. All the antisense oligonucleotides effect significant inhibition of human huntingtin mRNA levels. ISIS 388241 has more than three mismatches with the murine huntingtin mRNA (SEQ ID NO: 3) and therefore did not show significant inhibition of murine mRNA levels compared to the control.

TABLE 28

Percent inhibition of human huntingtin mRNA in BACHD mice

| ISIS No. | % inhibition |
|---|---|
| 387916 | 82 |
| 388241 | 52 |
| 419629 | 80 |
| 419637 | 83 |
| 436684 | 55 |

TABLE 28-continued

Percent inhibition of human huntingtin mRNA in BACHD mice

| ISIS No. | % inhibition |
|---|---|
| 444578 | 70 |
| 444584 | 62 |
| 444591 | 54 |
| 444607 | 76 |
| 444608 | 61 |
| 444615 | 89 |
| 444618 | 91 |
| 444627 | 92 |
| 444652 | 79 |
| 444658 | 62 |
| 444659 | 74 |
| 444660 | 66 |
| 444661 | 72 |
| 444663 | 77 |

TABLE 29

Percent inhibition of murine huntingtin mRNA in BACHD mice

| ISIS No. | % inhibition |
|---|---|
| 387916 | 77 |
| 419629 | 75 |
| 419637 | 87 |
| 436684 | 32 |
| 444578 | 64 |
| 444584 | 20 |
| 444591 | 32 |
| 444607 | 76 |
| 444608 | 66 |
| 444615 | 60 |
| 444618 | 88 |
| 444627 | 58 |
| 444652 | 66 |
| 444658 | 53 |
| 444659 | 62 |
| 444660 | 47 |
| 444661 | 67 |
| 444663 | 60 |

Organ Weight Measurements

Liver, spleen and kidney weights were measured at the end of the study, and are presented in Table 30 as a percent of the saline control normalized to body weight.

TABLE 30

Percent change in organ weight of BACHD mice after antisense oligonucleotide treatment

| ISIS No. | Liver | Spleen | Kidney |
|---|---|---|---|
| 387916 | −5 | −13 | +6 |
| 388241 | −1 | +14 | −5 |
| 419629 | +5 | +13 | −12 |
| 419637 | −6 | −17 | −25 |
| 436684 | −2 | −3 | +6 |
| 444578 | +11 | +18 | +1 |
| 444584 | +8 | +54 | +1 |
| 444591 | +4 | −4 | −3 |
| 444607 | +3 | +22 | −8 |
| 444608 | +6 | +18 | −3 |
| 444615 | +6 | +1 | +3 |
| 444618 | +11 | +0 | −2 |
| 444627 | +3 | −14 | +14 |
| 444652 | −11 | −4 | −18 |
| 444658 | −1 | 0 | −16 |
| 444659 | +1 | +15 | −2 |
| 444660 | −5 | +4 | −6 |
| 444661 | −1 | +7 | −1 |
| 444663 | +7 | +10 | +8 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of alanine transaminase (ALT) and aspartate transaminase (AST) are expressed in IU/L and the results are presented in Table 31.

TABLE 31

Effect of antisense oligonucleotide treatment on markers of liver function

| | ALT | AST |
|---|---|---|
| PBS | 40 | 69 |
| 387916 | 69 | 84 |
| 388241 | 42 | 76 |
| 419629 | 51 | 71 |
| 419637 | 59 | 86 |
| 436684 | 60 | 87 |
| 444578 | 62 | 93 |
| 444584 | 48 | 76 |
| 444591 | 39 | 53 |
| 444607 | 51 | 111 |
| 444608 | 48 | 75 |
| 444615 | 74 | 95 |
| 444618 | 687 | 908 |
| 444627 | 105 | 127 |
| 444652 | 54 | 64 |
| 444658 | 46 | 59 |
| 444659 | 90 | 138 |
| 444660 | 34 | 64 |
| 444661 | 49 | 99 |
| 444663 | 90 | 164 |

Study 2

Treatment

Fourteen groups of four BACHD mice each were injected intraperitoneally with 12.5 mg/kg or 50 mg/kg of ISIS 419581, ISIS 419602, ISIS 419628, ISIS 419629, ISIS 419640, ISIS 419641, or ISIS 419642 twice a week for 2 weeks. A group of four BACHD mice was injected intraperitoneally with 12.5 mg/kg of ISIS 387916 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 32 and 33 and were calculated as percent inhibition of human and murine huntingtin expression levels respectively, relative to the PBS control.

TABLE 32

Percent inhibition of human huntingtin mRNA in BACHD mice

| ISIS No. | Dose (mg/kg) | % inhibition |
|---|---|---|
| 387916 | 12.5 | 71 |
| 419581 | 12.5 | 54 |
|  | 50 | 68 |
| 419602 | 12.5 | 72 |
|  | 50 | 77 |
| 419628 | 12.5 | 65 |
|  | 50 | 76 |
| 419629 | 12.5 | 87 |
|  | 50 | 93 |
| 419640 | 12.5 | 69 |
|  | 50 | 79 |
| 419641 | 12.5 | 61 |
|  | 50 | 80 |
| 419642 | 12.5 | 76 |
|  | 50 | 83 |

TABLE 33

Percent inhibition of murine huntingtin mRNA in BACHD mice

| ISIS No. | Dose (mg/kg) | % inhibition |
|---|---|---|
| 387916 | 12.5 | 70 |
| 419581 | 12.5 | 42 |
|  | 50 | 86 |
| 419602 | 12.5 | 77 |
|  | 50 | 85 |
| 419628 | 12.5 | 67 |
|  | 50 | 86 |
| 419629 | 12.5 | 90 |
|  | 50 | 93 |
| 419640 | 12.5 | 63 |
|  | 50 | 84 |
| 419641 | 12.5 | 52 |
|  | 50 | 81 |
| 419642 | 12.5 | 56 |
|  | 50 | 83 |

Organ Weight Measurements

Liver, spleen and kidney weights were measured at the end of the study, and are presented in Table 34 as a percent of the saline control normalized to body weight.

TABLE 34

Percent change in organ weight of BACHD mice after antisense oligonucleotide treatment

| ISIS No. | Dose (mg/kg) | Liver | Spleen | Kidney |
|---|---|---|---|---|
| 387916 | 12.5 | −9 | 3 | −4 |
| 419581 | 12.5 | −2 | −6 | −1 |
|  | 50 | 14 | −1 | −11 |
| 419602 | 12.5 | 10 | 1 | −2 |
|  | 50 | 28 | 9 | −3 |
| 419628 | 12.5 | −2 | −7 | −2 |
|  | 50 | −3 | 7 | −9 |
| 419629 | 12.5 | −7 | −5 | −10 |
|  | 50 | 16 | 0 | −8 |
| 419640 | 12.5 | −5 | −2 | −8 |
|  | 50 | 1 | −20 | −4 |
| 419641 | 12.5 | −7 | −10 | −11 |
|  | 50 | −2 | −13 | −9 |
| 419642 | 12.5 | −11 | −21 | −19 |
|  | 50 | −1 | −8 | −9 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of ALT and AST are expressed in IU/L and the results are presented in Table 35.

TABLE 35

Effect of antisense oligonucleotide treatment on markers of liver function

| | Dose (mg/kg) | ALT | AST |
|---|---|---|---|
| PBS |  | 44 | 80 |
| 387916 | 12.5 | 44 | 75 |
| 419581 | 12.5 | 56 | 101 |
|  | 50 | 390 | 281 |
| 419602 | 12.5 | 86 | 108 |
|  | 50 | 240 | 229 |
| 419628 | 12.5 | 52 | 110 |
|  | 50 | 51 | 73 |
| 419629 | 12.5 | 104 | 118 |
|  | 50 | 1262 | 1150 |
| 419640 | 12.5 | 36 | 65 |
|  | 50 | 38 | 55 |
| 419641 | 12.5 | 56 | 103 |
|  | 50 | 57 | 172 |
| 419642 | 12.5 | 40 | 64 |
|  | 50 | 47 | 101 |

Study 3

Treatment

Eighteen groups of four BACHD mice each were injected intraperitoneally with 12.5 mg/kg or 50 mg/kg of ISIS 388250, ISIS 388251, ISIS 388263, ISIS 388264, ISIS 419641, ISIS 436645, ISIS 436649, ISIS 436668, or ISIS 436689 twice a week for 2 weeks. A group of four BACHD mice was injected intraperitoneally with 12.5 mg/kg of ISIS 388241 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 36 and 37 and were calculated as percent inhibition of human and murine huntingtin expression levels respectively, relative to the PBS control. All the antisense oligonucleotides effect significant inhibition of human huntingtin mRNA levels. ISIS 388241, ISIS 388250, ISIS 388251, ISIS 388263, ISIS 388264, and ISIS 436645 have more than three mismatches with the murine huntingtin mRNA (SEQ ID NO: 3) and therefore did not show significant inhibition of murine mRNA levels compared to the control. ISIS 436649 and ISIS 436689 have three mismatches with the murine huntingtin mRNA (SEQ ID NO: 3) and therefore did not show significant inhibition of murine mRNA levels compared to the control.

TABLE 36

Percent inhibition of human huntingtin mRNA in BACHD mice

| ISIS No. | Dose (mg/kg) | % inhibition |
|---|---|---|
| 388241 | 12.5 | 32 |
| 388250 | 12.5 | 21 |
|  | 50 | 45 |
| 388251 | 12.5 | 30 |
|  | 50 | 34 |
| 388263 | 12.5 | 29 |
|  | 50 | 35 |
| 388264 | 12.5 | 35 |
|  | 50 | 42 |
| 419641 | 12.5 | 71 |
|  | 50 | 73 |
| 436645 | 12.5 | 43 |
|  | 50 | 48 |
| 436649 | 12.5 | 40 |
|  | 50 | 38 |
| 436668 | 12.5 | 45 |
|  | 50 | 69 |
| 436689 | 12.5 | 62 |
|  | 50 | 78 |

TABLE 37

Percent inhibition of murine huntingtin mRNA in BACHD mice

| ISIS No. | Dose (mg/kg) | % inhibition |
|---|---|---|
| 419641 | 12.5 | 68 |
|  | 50 | 77 |
| 436668 | 12.5 | 41 |
|  | 50 | 62 |

Organ Weight Measurements

Liver, spleen and kidney weights were measured at the end of the study, and are presented in Table 38 as a percent of the saline control normalized to body weight. Mice treated with ISIS 388263 and ISIS 436645 suffered increases in liver weight at the 50 mg/kg dose compared to the PBS control.

TABLE 38

Percent change in organ weight of BACHD mice after antisense oligonucleotide treatment

| ISIS No. | Dose (mg/kg) | Liver | Spleen | Kidney |
|---|---|---|---|---|
| 388241 | 12.5 | 1 | 6 | 9 |
| 388250 | 12.5 | 2 | 1 | -2 |
|  | 50 | 1 | 30 | 3 |
| 388251 | 12.5 | 4 | -8 | 1 |
|  | 50 | 19 | 19 | 2 |
| 388263 | 12.5 | 4 | 8 | 9 |
|  | 50 | 23 | 52 | 1 |
| 388264 | 12.5 | 2 | -2 | 3 |
|  | 50 | 12 | 9 | 6 |
| 419641 | 12.5 | -1 | -9 | 3 |
|  | 50 | 2 | -4 | 3 |
| 436645 | 12.5 | 8 | 6 | 5 |
|  | 50 | 26 | 25 | 9 |
| 436649 | 12.5 | 1 | 0 | 6 |
|  | 50 | 0 | 1 | 3 |
| 436668 | 12.5 | 1 | 5 | 10 |
|  | 50 | -2 | 3 | 11 |
| 436689 | 12.5 | -3 | -5 | 4 |
|  | 50 | 6 | 11 | 5 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of alanine transaminase (ALT) and aspartate transaminase (AST) are expressed in IU/L and the results are presented in Table 39.

TABLE 39

Effect of antisense oligonucleotide treatment on markers of liver function

| | Dose (mg/kg) | ALT | AST |
|---|---|---|---|
| PBS |  | 43 | 76 |
| 388241 | 12.5 | 43 | 88 |
| 388250 | 12.5 | 37 | 55 |
|  | 50 | 44 | 89 |
| 388251 | 12.5 | 42 | 98 |
|  | 50 | 67 | 91 |
| 388263 | 12.5 | 51 | 90 |
|  | 50 | 55 | 93 |
| 388264 | 12.5 | 31 | 59 |
|  | 50 | 65 | 90 |
| 419641 | 12.5 | 39 | 70 |
|  | 50 | 42 | 83 |
| 436645 | 12.5 | 43 | 82 |
|  | 50 | 179 | 143 |
| 436649 | 12.5 | 35 | 47 |
|  | 50 | 38 | 76 |
| 436668 | 12.5 | 36 | 73 |
|  | 50 | 28 | 57 |
| 436689 | 12.5 | 31 | 52 |
|  | 50 | 49 | 164 |

Study 4

Treatment

Eighteen groups of four BACHD mice each were injected intraperitoneally with 12.5 mg/kg or 50 mg/kg of ISIS 388241, ISIS 437123, ISIS 437132, ISIS 437140, ISIS 437442, ISIS 437446, ISIS 437477, ISIS 437478, or ISIS 437490 twice a week for 2 weeks. A group of four BACHD mice was injected intraperitoneally with 12.5 mg/kg of ISIS 387916 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 40 and 41 and were calculated as percent inhibition of human and murine huntingtin expression levels respectively, relative to the PBS control. ISIS 388241 and ISIS 437490 have more than three mismatches with the murine huntingtin mRNA (SEQ ID NO: 3) and therefore did not show significant inhibition of murine mRNA levels compared to the control. ISIS 437132 has three mismatches with the murine huntingtin mRNA (SEQ ID NO: 3) and therefore did not show significant inhibition of murine mRNA levels compared to the control. ISIS 437123 and ISIS 437140 have two mismatches with the murine huntingtin mRNA (SEQ ID NO: 3) and do not show significant inhibition of murine mRNA levels compared to the control.

TABLE 40

Percent inhibition of human huntingtin mRNA in BACHD mice

| ISIS No. | Dose (mg/kg) | % inhibition |
|---|---|---|
| 387916 | 12.5 | 51 |
| 388241 | 12.5 | 47 |
|  | 50 | 67 |
| 437123 | 12.5 | 0 |
|  | 50 | 21 |
| 437132 | 12.5 | 31 |
|  | 50 | 33 |
| 437140 | 12.5 | 7 |
|  | 50 | 32 |
| 437442 | 12.5 | 42 |
|  | 50 | 85 |
| 437446 | 12.5 | 39 |
|  | 50 | 70 |
| 437477 | 12.5 | 52 |
|  | 50 | 75 |
| 437478 | 12.5 | 54 |
|  | 50 | 78 |
| 437490 | 12.5 | 42 |
|  | 50 | 44 |

TABLE 41

Percent inhibition of murine huntingtin mRNA in BACHD mice

| ISIS No. | Dose (mg/kg) | % inhibition |
|---|---|---|
| 387916 | 12.5 | 48 |
| 437442 | 12.5 | 27 |
|  | 50 | 76 |
| 437446 | 12.5 | 38 |
|  | 50 | 71 |
| 437477 | 12.5 | 63 |
|  | 50 | 87 |
| 437478 | 12.5 | 60 |
|  | 50 | 89 |

Organ Weight Measurements

Liver, spleen and kidney weights were measured at the end of the study, and are presented in Table 42 as a percent of the saline control normalized to body weight.

TABLE 42

Percent change in organ weight of BACHD mice after antisense oligonucleotide treatment

| ISIS No. | Dose (mg/kg) | Liver | Spleen | Kidney |
|---|---|---|---|---|
| 387916 | 12.5 | 1 | 6 | 12 |
| 388241 | 12.5 | −3 | 16 | −2 |
|  | 50 | −6 | 10 | 0 |
| 437123 | 12.5 | −4 | 0 | 4 |
|  | 50 | 4 | 0 | −4 |
| 437132 | 12.5 | −2 | −3 | −5 |
|  | 50 | 2 | −6 | −2 |
| 437140 | 12.5 | −4 | 11 | −3 |
|  | 50 | 4 | 5 | −5 |
| 437442 | 12.5 | −10 | 9 | 3 |
|  | 50 | −3 | −20 | −10 |
| 437446 | 12.5 | −6 | 7 | 2 |
|  | 50 | −4 | 1 | −1 |
| 437477 | 12.5 | 1 | −2 | 0 |
|  | 50 | 25 | −9 | −6 |
| 437478 | 12.5 | −7 | −4 | −9 |
|  | 50 | 22 | 4 | 3 |
| 437490 | 12.5 | −5 | 0 | −5 |
|  | 50 | −7 | 3 | −9 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of alanine transaminase (ALT) and aspartate transaminase (AST) are expressed in IU/L and the results are presented in Table 43.

TABLE 43

Effect of antisense oligonucleotide treatment on markers of liver function

| | Dose (mg/kg) | ALT | AST |
|---|---|---|---|
| PBS |  | 32 | 58 |
| 387916 | 12.5 | 40 | 122 |
| 388241 | 12.5 | 39 | 93 |
|  | 50 | 28 | 62 |
| 437123 | 12.5 | 38 | 88 |
|  | 50 | 34 | 66 |
| 437132 | 12.5 | 34 | 52 |
|  | 50 | 30 | 52 |
| 437140 | 12.5 | 30 | 62 |
|  | 50 | 40 | 63 |
| 437442 | 12.5 | 40 | 106 |
|  | 50 | 63 | 119 |
| 437446 | 12.5 | 35 | 119 |
|  | 50 | 35 | 89 |
| 437477 | 12.5 | 39 | 68 |
|  | 50 | 52 | 162 |
| 437478 | 12.5 | 37 | 53 |
|  | 50 | 55 | 71 |
| 437490 | 12.5 | 48 | 71 |
|  | 50 | 34 | 59 |

Study 5

Treatment

Eleven groups of four BACHD mice each were injected intraperitoneally with 12.5 mg/kg of ISIS 388241, ISIS 419640, ISIS 419641, ISIS 419642, ISIS 436665, ISIS 436671, ISIS 436689, ISIS 437507, ISIS 443139, ISIS 444591, or ISIS 444661 twice a week for 2 weeks. A control group of four mice was injected intraperitoneally with phosphate buffered saline (PBS) twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 44 and 45 and were calculated as percent inhibition of human and murine huntingtin expression levels respectively, relative to the PBS control. All the antisense oligonucleotides effect significant inhibition of human huntingtin mRNA levels. ISIS 388241, ISIS 437507, and ISIS 443139 have more than three mismatches with the murine huntingtin mRNA (SEQ ID NO: 3) and therefore do not show significant inhibition of murine mRNA levels compared to the control. ISIS 436689 has 3 mismatches with the murine huntingtin mRNA (SEQ ID NO: 3) and does not show significant inhibition of murine mRNA levels compared to the control.

TABLE 44

Percent inhibition of human huntingtin mRNA in BACHD mice

| ISIS No. | % inhibition |
|---|---|
| 388241 | 53 |
| 419640 | 34 |
| 419641 | 63 |
| 419642 | 55 |
| 436665 | 63 |
| 436671 | 66 |
| 436689 | 57 |
| 437507 | 54 |
| 443139 | 39 |
| 444591 | 48 |
| 444661 | 50 |

TABLE 45

Percent inhibition of murine huntingtin mRNA in BACHD mice

| ISIS No. | % inhibition |
|---|---|
| 419640 | 24 |
| 419641 | 51 |
| 419642 | 34 |
| 436665 | 49 |
| 436671 | 63 |
| 444591 | 41 |
| 444661 | 46 |

Body Weight and Organ Weight Measurements

The body weights of the mice were measured at the onset of the study and subsequently twice a week. The body weights of the mice are presented in Table 46 and are expressed as a percent change over the weights taken at the start of the study. The results indicate that treatment with these oligonucleotides did not cause any adverse change in body weight of the mice throughout the study.

TABLE 46

Percent change in body weight of BACHD mice after antisense oligonucleotide treatment

| | day 4 | day 7 | day 10 | day 12 |
|---|---|---|---|---|
| PBS | −3 | 0 | +2 | +1 |
| ISIS 388241 | −2 | −1 | −1 | +1 |
| ISIS 419640 | +1 | 0 | +3 | +4 |
| ISIS 419641 | +1 | +1 | +2 | 0 |
| ISIS 419642 | −3 | −2 | +1 | −5 |
| ISIS 436665 | +1 | +4 | +5 | +1 |
| ISIS 436671 | +1 | +2 | +5 | +4 |
| ISIS 436689 | +1 | +3 | 0 | −1 |
| ISIS 437507 | −1 | −2 | +2 | −2 |
| ISIS 443139 | −2 | +6 | +4 | +1 |
| ISIS 444591 | −1 | +1 | +2 | 0 |
| ISIS 444661 | +1 | +3 | +2 | 0 |

Liver, spleen and kidney weights were measured at the end of the study, and are presented in Table 47 as a percent of the saline control normalized to body weight.

TABLE 47

Percent change in organ weight of BACHD mice after antisense oligonucleotide treatment

| ISIS No. | Liver | Spleen | Kidney |
|---|---|---|---|
| 388241 | +2 | +13 | −7 |
| 419640 | −2 | +12 | −12 |
| 419641 | +4 | +3 | −13 |
| 419642 | +5 | +19 | −8 |
| 436665 | −3 | +3 | −13 |
| 436671 | 0 | +1 | −18 |
| 436689 | −6 | −10 | −12 |
| 437507 | −5 | −5 | −14 |
| 443139 | −2 | −9 | −13 |
| 444591 | −2 | −10 | −12 |
| 444661 | 0 | −16 | −12 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of ALT and AST are expressed in IU/L. Plasma levels of bilirubin and albumin were also measured using the same clinical chemistry analyzer and expressed in g/dL. The results are presented in Table 48.

TABLE 48

Effect of antisense oligonucleotide treatment on markers of liver function

| | ALT | AST | Bilirubin | Albumin |
|---|---|---|---|---|
| PBS | 42.5 | 86.5 | 0.2 | 3.1 |
| ISIS 388241 | 39.3 | 54.5 | 0.3 | 3.0 |
| ISIS 419640 | 36.8 | 85.8 | 0.2 | 2.9 |
| ISIS 419641 | 50.0 | 71.8 | 0.2 | 3.0 |
| ISIS 419642 | 42.8 | 77.0 | 0.1 | 3.0 |
| ISIS 436665 | 51.5 | 123.0 | 0.2 | 3.0 |
| ISIS 436671 | 52.0 | 71.0 | 0.1 | 3.0 |
| ISIS 436689 | 38.3 | 75.3 | 0.2 | 3.1 |
| ISIS 437507 | 37.0 | 77.5 | 0.1 | 3.0 |
| ISIS 443139 | 41.3 | 124.8 | 0.2 | 3.0 |
| ISIS 444591 | 46.5 | 61.3 | 0.2 | 3.0 |
| ISIS 444661 | 67.5 | 109.8 | 0.2 | 3.1 |

Measurement of Kidney Function

To evaluate the impact of ISIS oligonucleotides on the kidney function of mice described above, plasma concentrations of blood urea nitrogen (BUN) and creatinine were measured using an automated clinical chemistry analyzer (Hitachi Olympus AU400e, Melville, N.Y.). Results are presented in Table 49 expressed in mg/dL.

TABLE 49

Effect of antisense oligonucleotide treatment on markers of kidney function

| | BUN | Creatinine |
|---|---|---|
| PBS | 24.0 | 0.17 |
| ISIS 388241 | 22.6 | 0.17 |
| ISIS 419640 | 21.4 | 0.16 |
| ISIS 419641 | 19.9 | 0.16 |
| ISIS 419642 | 23.6 | 0.18 |
| ISIS 436665 | 20.2 | 0.17 |
| ISIS 436671 | 22.6 | 0.17 |
| ISIS 436689 | 19.2 | 0.18 |
| ISIS 437507 | 19.9 | 0.16 |
| ISIS 443139 | 23.3 | 0.16 |
| ISIS 444591 | 23.5 | 0.18 |
| ISIS 444661 | 25.4 | 0.18 |

Measurement of Other Metabolic Parameters

To evaluate the impact of ISIS oligonucleotides on other metabolic functions in mice described above, plasma concentrations of glucose, cholesterol and triglycerides were measured using an automated clinical chemistry analyzer (Hitachi Olympus AU400e, Melville, N.Y.). Results are presented in Table 50 expressed in mg/dL and demonstrate that treatment with these oligonucleotides did not cause any adverse changes in the levels of these metabolic markers between the control and treatment groups.

TABLE 50

Effect of antisense oligonucleotide treatment on metabolic markers

|  | Glucose | Cholesterol | Triglycerides |
|---|---|---|---|
| PBS | 198 | 142 | 225 |
| ISIS 388241 | 197 | 133 | 185 |
| ISIS 419640 | 198 | 132 | 189 |
| ISIS 419641 | 188 | 140 | 219 |
| ISIS 419642 | 184 | 128 | 192 |
| ISIS 436665 | 199 | 134 | 152 |
| ISIS 436671 | 196 | 148 | 174 |
| ISIS 436689 | 194 | 132 | 174 |
| ISIS 437507 | 198 | 139 | 155 |
| ISIS 443139 | 178 | 122 | 239 |
| ISIS 444591 | 202 | 145 | 263 |
| ISIS 444661 | 180 | 140 | 247 |

Example 4

Bolus Administration of Antisense Oligonucleotides Against Huntingtin mRNA to the Striatum of BACHD Mice BACHD mice were treated with ISIS oligonucleotides via bolus administration to a defined mouse brain area, the striatum, for the purpose of screening the activity of the oligonucleotides in brain tissue against human and mouse huntingtin mRNA expression.

Treatment and Surgery

Groups of four BACHD mice each were administered with ISIS 388241, ISIS 419628, ISIS 419637, ISIS 419640, ISIS 419641, ISIS 419642, ISIS 436665, ISIS 436671, ISIS 436684, ISIS 436689, ISIS 436754, ISIS 437168, ISIS 437175, ISIS 437441, ISIS 437442, ISIS 437507, ISIS 437527, ISIS 443139, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661 or ISIS 444663 delivered as a single bolus injection at 3 µg, 10 µg or 25 µg concentrations into the striatum.

A control group of 4 BACHD mice were similarly treated with PBS. ISIS 388241 was administered in seven groups of 4 mice each and the results presented are the average of the data derived from the 28 mice. ISIS 419628 was administered in 2 groups of 4 BACHD mice each and the results presented are the average of the data derived from the 8 mice. Seven days after the bolus administration, the mice were euthanized using isoflurane and the organs were removed. The animals were decapitated and the brain was removed for dissection of the striatal tissue.

RNA Analysis

RNA was extracted from striatal tissue for real-time PCR analysis of huntingtin mRNA levels. Human mutant huntingtin mRNA levels were measured using the human primer probe set RTS2617. Mouse normal huntingtin mRNA levels were measured using the murine primer probe set RTS2633.

The results for human huntingtin mRNA levels are presented in Table 51 and are expressed as percent inhibition compared to the PBS control group. All the antisense oligonucleotides effect dose-dependent inhibition of human huntingtin mRNA levels. The results for murine huntingtin mRNA levels are presented in Table 52 and are expressed as percent inhibition compared to the PBS control group.

The effective doses ($ED_{50}$) of each oligonucleotide for human huntingtin mRNA and mouse huntingtin mRNA were calculated by plotting the concentrations of oligonucleotides used versus the percent inhibition of huntingtin mRNA expression levels of either species and noting the concentrations at which 50% inhibition of huntingtin mRNA expression was achieved for each species compared to the corresponding controls. The $ED_{50}$ (4 for each antisense oligonucleotide is also presented in Tables 51 and 52 for human and murine huntingtin mRNA respectively.

ISIS 388241, ISIS 436684, ISIS 436754, ISIS 437175, ISIS 437507, ISIS 443139, and ISIS 444584 are each mismatched by 8 base pairs or more with murine huntingtin mRNA (SEQ ID NO: 3) and therefore do not show significant inhibition of murine mRNA levels compared to the control. ISIS 437168 and ISIS 437441 have 2 mismatches each with the murine huntingtin mRNA (SEQ ID NO: 3) and do not show significant inhibition of murine mRNA levels compared to the control. ISIS 436689 has 3 mismatches with the murine huntingtin mRNA (SEQ ID NO: 3) and does not show significant inhibition of murine mRNA levels compared to the control.

TABLE 51

Percent inhibition of human huntingtin mRNA levels in vivo and $ED_{50}$ of the antisense oligonucleotides

| ISIS No. | 3 mg | 10 mg | 25 mg | $ED_{50}$ |
|---|---|---|---|---|
| 388241 | 33 | 55 | 68 | 7.4 |
| 419628 | 49 | 58 | 83 | 5.1 |
| 419637 | 40 | 62 | 79 | 6.1 |
| 419640 | 52 | 64 | 77 | 4.8 |
| 419641 | 71 | 77 | 89 | 2.2 |
| 419642 | 67 | 70 | 83 | 3.0 |
| 436665 | 52 | 71 | 60 | 5.8 |
| 436671 | 68 | 80 | 84 | 2.4 |
| 436684 | 2 | 18 | 37 | 36.9 |
| 436689 | 27 | 63 | 81 | 7.0 |
| 436754 | 31 | 54 | 61 | 10.5 |
| 437168 | 2 | 49 | 60 | 15.2 |
| 437175 | 0 | 53 | 64 | 12.9 |
| 437441 | 3 | 32 | 38 | 35.3 |
| 437442 | 38 | 50 | 56 | 11.9 |
| 437507 | 38 | 59 | 79 | 6.6 |
| 437527 | 37 | 47 | 59 | 11.9 |
| 443139 | 39 | 61 | 70 | 6.7 |
| 444578 | 51 | 66 | 75 | 4.6 |
| 444584 | 30 | 63 | 71 | 7.8 |
| 444591 | 60 | 54 | 70 | 5.6 |
| 444607 | 57 | 69 | 75 | 3.2 |
| 444608 | 67 | 68 | 82 | 3.1 |
| 444615 | 47 | 55 | 91 | 5.2 |
| 444618 | 57 | 64 | 83 | 4.0 |
| 444627 | 47 | 70 | 61 | 5.0 |
| 444652 | 36 | 62 | 66 | 7.8 |
| 444658 | 60 | 66 | 79 | 3.6 |
| 444659 | 61 | 67 | 84 | 3.4 |
| 444660 | 55 | 62 | 66 | 4.2 |
| 444661 | 48 | 57 | 70 | 6.4 |
| 444663 | 42 | 60 | 80 | 5.5 |

TABLE 52

Percent inhibition of murine huntingtin mRNA levels in vivo and ED$_{50}$ of the antisense oligonucleotides

| ISIS No. | 3 mg | 10 mg | 25 mg | ED$_{50}$ |
|---|---|---|---|---|
| 419628 | 50 | 55 | 83 | 5.1 |
| 419637 | 63 | 79 | 86 | 2.6 |
| 419640 | 51 | 60 | 86 | 4.9 |
| 419641 | 65 | 80 | 87 | 2.7 |
| 419642 | 69 | 73 | 88 | 2.5 |
| 436665 | 68 | 82 | 66 | 2.7 |
| 436671 | 75 | 87 | 90 | 2 |
| 437442 | 30 | 53 | 82 | 9 |
| 437527 | 67 | 73 | 90 | 2.7 |
| 444578 | 50 | 65 | 74 | 4.9 |
| 444591 | 69 | 69 | 81 | 2.8 |
| 444607 | 57 | 70 | 75 | 3.8 |
| 444608 | 70 | 72 | 90 | 2.5 |
| 444615 | 30 | 37 | 88 | 9.5 |
| 444618 | 66 | 71 | 90 | 2.8 |
| 444627 | 41 | 60 | 57 | 8.8 |
| 444652 | 47 | 62 | 66 | 4.7 |
| 444658 | 60 | 62 | 85 | 3.9 |
| 444659 | 54 | 62 | 85 | 4.2 |
| 444660 | 42 | 48 | 64 | 9.5 |
| 444661 | 49 | 57 | 74 | 5.9 |
| 444663 | 42 | 65 | 84 | 5.1 |

The ten compounds marked with an asterisk had an improved ED50 over ISIS 388241.

Example 5

Assay for Neurotoxic Effects of Bolus Administration of Antisense Oligonucleotides in the Striatal Tissue of Rats About 30 compounds were selected as having high tolerability and high potency. Compounds were then tested by CNS bolus injection in rat to further assess neurotoxicity. Sprague-Dawley rats each were treated with ISIS oligonucleotides via bolus administration to a defined brain area, the striatum, for the purpose of screening for the induction of the microglial marker AIF1 as a measure of CNS toxicity.

Treatment and Surgery

Groups of four Sprague-Dawley rats were administered with ISIS 387916, ISIS 388241, ISIS 419627, ISIS 419628, ISIS 419629, ISIS 419630, ISIS 419636, ISIS 419637, ISIS 419640, ISIS 419641, ISIS 419642, ISIS 436665, ISIS 436668, ISIS 4196671, ISIS 436684, ISIS 436689, ISIS 436754, ISIS 443168, ISIS 437175, ISIS 437441, ISIS 437442, ISIS 437507, ISIS 437527, ISIS 443139, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661, or ISIS 444663 delivered as a single bolus injection at 50 µg concentration into the striatum.

A control group of 4 rats were similarly treated with PBS. A group of 4 rats were similarly treated with ISIS 104838, an antisense oligonucleotide against TNF-α, as a negative control group. ISIS 387916 was administered in four groups of 4 rats each and the results presented are an average of the data derived from the 16 rats. ISIS 419628 was administered in two groups of 4 rats each and the results presented are the average of the data from the 8 rats. ISIS 419629, ISIS 444584 and ISIS 444618, which had toxic indicators in the systemic administration study (Example 3) were also tested in this study. Seven days after bolus administration, the rats were euthanized using isoflurane and the organs were removed. The animals were decapitated and the brain was removed for dissection of the striatal tissue.

RNA Analysis of AIF1 Expression Levels

RNA was extracted from striatal tissue for real-time PCR analysis of AIF1 mRNA levels. Rat AIF1 levels were measured using the rat primer probe set rAif1_LTS00219 (forward sequence AGGAGAAAAACAAAGAACACCAGAA, designated herein as SEQ ID NO: 46; reverse sequence CAATTAGGGCAACTCAGAAATAGCT, designated herein as SEQ ID NO: 47; probe sequence CCAACTGGTCCCCCAGCCAAGAX, designated herein as SEQ ID NO: 48). Results were calculated as the percentage of AIF1 expression over that of the PBS control and are presented in Table 53. ISIS 419629, ISIS 444584, and ISIS 444618, which had toxic indicators in the systemic administration study (in Example 3), also had toxic indicators in this study (greater than 300% above saline control). Later studies showed that ISIS 444584 is neurotolerable and exhibits negligible toxic indicators (see Example 16 and 17).

TABLE 53

Percent expression of AIF1 mRNA levels in vivo as a measure of neurotoxicity

| ISIS No. | % expression |
|---|---|
| 104838 | 111 |
| 387916 | 870 |
| 388241 | 236 |
| 419627 | 168 |
| 419628 | 497 |
| 419629 | 247 |
| 419630 | 227 |
| 419636 | 464 |
| 419637 | 275 |
| 419640 | 305 |
| 419641 | 206 |
| 419642 | 173 |
| 436665 | 217 |
| 436668 | 447 |
| 436671 | 239 |
| 436684 | 700 |
| 436689 | 149 |
| 436754 | 125 |
| 437168 | 130 |
| 437175 | 131 |
| 437441 | 158 |
| 437442 | 157 |
| 437507 | 133 |
| 437527 | 184 |
| 443139 | 143 |
| 444578 | 352 |
| 444584 | 317 |
| 444591 | 194 |
| 444607 | 362 |
| 444608 | 476 |
| 444615 | 645 |
| 444618 | 547 |
| 444627 | 377 |
| 444652 | 336 |
| 444658 | 364 |
| 444659 | 319 |
| 444660 | 411 |
| 444661 | 249 |
| 444663 | 448 |

RNA Analysis of Huntingtin Expression Levels

RNA was extracted from striatal tissue for real-time PCR analysis of huntingtin mRNA levels. Rat huntingtin mRNA levels were measured using the rat primer probe set rHt_LTS00343 (forward sequence CAGAGCTGGTGAACCG-TATCC, designated herein as SEQ ID NO: 49; reverse sequence GGCTTAAGCAGGGAGCCAAAA, designated herein as SEQ ID NO: 50; probe sequence ACTTCATGAT-GAGCTCGGAGTTCAACX, designated herein as SEQ ID NO: 51). Results were calculated as the percentage reduction of huntingtin expression over that of the PBS control and are presented in Table 54. ISIS 388241, ISIS 436684, ISIS 436754, ISIS 437175, ISIS 437507, and ISIS 443139 are each mismatched by 6 base pairs or more with the rat gene sequence (SEQ ID NO: 5) and therefore do not show significant inhibition of rat mRNA levels compared to the control. ISIS 419640, ISIS 419641, ISIS 419642, ISIS 436665, ISIS 436668, ISIS 437442, ISIS 444615, and ISIS 444627 have 1 mismatch each with the rat gene sequence (SEQ ID NO: 5) and do not show significant inhibition of rat mRNA levels compared to the control. ISIS 437168 and ISIS 437441 have 2 mismatches each with the rat gene sequence (SEQ ID NO: 5) and do not show significant inhibition of rat mRNA levels compared to the control. ISIS 436689 and ISIS 444584 have 3 mismatches each with the rat gene sequence (SEQ ID NO: 5) and do not show significant inhibition of rat mRNA levels compared to the control.

TABLE 54

Percent reduction of rat huntingtin mRNA levels in rats

| ISIS No. | % reduction |
|---|---|
| 387916 | 70 |
| 419627 | 67 |
| 419628 | 57 |
| 419629 | 85 |
| 419630 | 11 |
| 419636 | 53 |
| 419637 | 84 |
| 436671 | 77 |
| 437527 | 86 |
| 444578 | 72 |
| 444591 | 35 |
| 444607 | 57 |
| 444608 | 68 |
| 444618 | 56 |
| 444652 | 75 |
| 444658 | 61 |
| 444659 | 55 |
| 444660 | 63 |
| 444661 | 52 |
| 444663 | 59 |

Example 6

Intracerebroventricular Administration of Antisense Oligonucleotides Against Huntingtin mRNA-Tolerability Study in BACHD Mice Selected compounds were compared with previously designed compound ISIS 388241 by ICV administration in BACHD mice.

Selected compounds plus the benchmark 388241 were selected based on in vitro and systemic potency and systemic tolerability as well as CNS potency and tolerability.

BACHD mice were treated with ISIS oligonucleotides via intracerebroventricular (ICV) administration to a defined mouse brain area, the right lateral ventricle, for the purpose of evaluating the tolerability of ICV dosing in mice.

Treatment and Surgery

Groups of five BACHD mice each were administered ISIS 388241, ISIS 437507, ISIS 443139, ISIS 419640, ISIS 419641, ISIS 419642, ISIS 444591, ISIS 436665, ISIS 436671, ISIS 444661, or ISIS 436689 at 150 μg/day delivered ICV with Alzet 2002 pumps at the rate of 12 μL/day for 2 weeks. A control group of 4 BACHD mice were similarly treated with PBS. The mice were surgically implanted with the pumps in the following manner: Mice were individually anaesthetized with 3% isoflurane for pump implantation. After two weeks, the mice were anesthetized again and the pump was surgically removed. The animals were then allowed to recover for two more weeks before being euthanized.

The body weights of the mice were taken weekly during the treatment and recovery periods. After 4 weeks, the mice were euthanized using isoflurane and decapitated. The brain was removed for tissue acquisition from the anterior and posterior sections.

RNA Analysis

RNA was extracted from the right hemisphere of the anterior cortex and the posterior cerebellar section of the cannulation site for real-time PCR analysis of huntingtin mRNA levels. Human mutant huntingtin mRNA levels were measured using the human primer probe set RTS2617. Mouse normal huntingtin mRNA levels were measured using the murine primer probe set RTS2633. Results were calculated as percent inhibition of human and murine huntingtin mRNA expression compared to the control and are presented in Tables 56 and 57 respectively. All the antisense oligonucleotides effect significant inhibition of human huntingtin mRNA levels. ISIS 388241, ISIS 437507, and ISIS 443139 are each mismatched by 8 base pairs or more with the murine huntingtin mRNA (SEQ ID NO: 3) and therefore do not show significant inhibition of murine mRNA levels compared to the control. ISIS 444591 has 1 mismatch with the murine huntingtin mRNA (SEQ ID NO: 3) and does not show significant inhibition of murine mRNA levels compared to the control. ISIS 436689 has 3 mismatches with the murine huntingtin mRNA (SEQ ID NO: 3) and does not show significant inhibition of murine mRNA levels compared to the control.

TABLE 56

Percent reduction of human huntingtin mRNA levels in BACHD mice via ICV administration of antisense oligonucleotides

| ISIS No. | Number of mice | Anterior cortex | Posterior cortex |
|---|---|---|---|
| 388241 | 3 | 82 | 70 |
| 419640 | 1 | 60 | 46 |
| 419641 | 2 | 75 | 66 |
| 419642 | 3 | 29 | 42 |
| 436665 | 5 | 62 | 38 |
| 436671 | 3 | 69 | 77 |
| 436689 | 3 | 49 | 40 |
| 437507 | 3 | 77 | 66 |
| 443139 | 5 | 93 | 90 |
| 444591 | 5 | 79 | 78 |

TABLE 57

Percent reduction of murine huntingtin mRNA levels in BACHD mice via ICV administration of antisense oligonucleotides

| ISIS No. | Number of mice | Anterior cortex | Posterior cortex |
|---|---|---|---|
| 419640 | 1 | 22 | 34 |
| 419641 | 2 | 40 | 26 |
| 419642 | 3 | 63 | 71 |
| 436665 | 5 | 72 | 56 |
| 436671 | 3 | 80 | 71 |

Body Weight Measurement

The body weights of the mice were measured at the onset of the study and subsequently once a week. The body weights of the mice are presented in Table 58 and are expressed as a percent change over the weights taken at the start of the study. The body weights were considered a measure of the tolerability of the mice to the ICV administration of antisense oligonucleotide. 'n.d.' means that there was no data available for that time period.

TABLE 58

Percent change in body weight of BACHD mice during antisense oligonucleotide treatment

|  | week 1 | week 2 | week 3 | week 4 |
| --- | --- | --- | --- | --- |
| PBS | −1 | +2 | +6 | +6 |
| ISIS 388241 | +3 | +11 | +15 | +7 |
| ISIS 437507 | +21 | +10 | +13 | −4 |
| ISIS 443139 | +10 | +10 | +16 | +12 |
| ISIS 419640 | +21 | +11 | −10 | +9 |
| ISIS 419641 | +24 | +3 | −5 | −12 |
| ISIS 419642 | +45 | +39 | +12 | +1 |
| ISIS 444591 | +18 | +38 | +27 | +17 |
| ISIS 436665 | +34 | +43 | +23 | +9 |
| ISIS 436671 | +19 | +17 | +11 | 0 |
| ISIS 444661 | +19 | −10 | −21 | n.d. |
| ISIS 436689 | +49 | +40 | +2 | −17 |

Survival of the Mice

The survival of the mice was assessed throughout the entire study period. Table 59 below shows the survival pattern in the groups of mice treated with ISIS oligonucleotides as well as the control.

TABLE 59

Number of survivals during antisense oligonucleotide treatment

|  | week 1 | week 2 | week 3 | week 4 |
| --- | --- | --- | --- | --- |
| PBS | 5 | 5 | 5 | 5 |
| ISIS 388241 | 4 | 3 | 3 | 3 |
| ISIS 437507 | 5 | 5 | 4 | 4 |
| ISIS 443139 | 5 | 5 | 5 | 5 |
| ISIS 419640 | 5 | 5 | 4 | 1 |
| ISIS 419641 | 5 | 5 | 4 | 2 |
| ISIS 419642 | 5 | 5 | 4 | 2 |
| ISIS 444591 | 5 | 5 | 5 | 5 |
| ISIS 436665 | 5 | 5 | 5 | 5 |
| ISIS 436671 | 4 | 4 | 3 | 3 |
| ISIS 444661 | 5 | 5 | 1 | 0 |
| ISIS 436689 | 4 | 4 | 4 | 3 |

Example 7

Intracerebroventricular Administration of Antisense Oligonucleotides Against Huntingtin in C57/BL6 Mice Wild-type C57/BL6 mice were treated with ISIS oligonucleotides via intracerebroventricular (ICV) administration to a defined mouse brain area, the right lateral ventricle, for the purpose of evaluating the potency of the oligonucleotides against mouse huntingtin in these mice.

Treatment and Surgery

Groups of ten C57/BL6 mice each were administered ISIS 408737 (5' TCCTAGTGTTACATTACCGC 3' (SEQ ID NO: 52), start site 5263 of SEQ ID NO: 3) at 50 µg/day delivered ICV with Alzet 2002 pumps at the rate of 0.5 µL/day for 7 days or 14 days. A control group of six C57/BL6 mice were similarly treated with PBS. The mice were surgically implanted with the pumps in the following manner: Briefly, Alzet osmotic pumps (Model 2002) were assembled according to manufacturer's instructions. Pumps were filled with a solution containing the antisense oligonucleotide and incubated overnight at 37° C., 24 hours prior to implantation. Animals were anesthetized with 3% isofluorane and placed in a stereotactic frame. After sterilizing the surgical site, a midline incision was made over the skull, and a subcutaneous pocket was created over the back, in which a pre-filled osmotic pump was implanted. A small burr hole was made through the skull above the right lateral ventricle. A cannula, connected to the osmotic pump via a plastic catheter, was then placed in the ventricle and glued in place using Loctite adhesive. The incision was closed with sutures. Antisense oligonucleotide or PBS was infused for 7 or 14 days, after which animals were euthanized according to a humane protocol approved by the Institutional Animal Care and Use Committee. Brain and spinal cord tissue were harvested and snap frozen in liquid nitrogen. Prior to freezing, brain tissue was cut transversely into five sections (S1, S2, S3, S4, and S5) using a mouse brain matrix. Sections 1 to 5 were approximately 2 mm apart from each other with S1 being most rostral and S5 most caudal.

RNA and Protein Analysis

Total RNA was extracted from mouse brain and spinal cord with RNeasy Protect Mini Kit (Qiagen, Mississauga, ON, Canada) for real-time PCR analysis of huntingtin mRNA levels using an RNeasy Mini prep kit (Qiagen). Q-PCR reactions were conducted and analyzed on an ABI Prism 7700 Sequence Detector (Applied Biosystems). Mouse huntingtin mRNA levels were measured using the murine primer probe set ABI #Mm01213820_m1 (Applied Biosystems) and normalized to peptidylprolyl isomerase A mRNA levels. Protein lysates were prepared from mouse brain slabs as described previously (Li S. H. and Li X. J., *Methods in Molecular Biology* (2008), 217:1940-6029). Lysates were run on 3-8% tris-acetate gel and transferred using the iBlot dry blotting system (Invitrogen). Blots were probed with anti-beta tubulin (Chemicon) and monoclonal MAB2166 antibody (Millipore) that reacts specifically with murine huntingtin protein. Immunoblots were quantified using Odyssey V3.0 software. The results are presented in Table 60 as percent reduction compared to the PBS control and demonstrate significant inhibition of huntingtin mRNA and protein levels by the antisense oligonucleotide both at day 7 and day 14.

TABLE 60

Percent inhibition of murine huntingtin mRNA in C57/BL6 mice

|  | day 7 | day 14 |
| --- | --- | --- |
| mRNA | 66 | 68 |
| protein | 21 | 49 |

Example 8

Intracerebroventricular Administration of Antisense Oligonucleotides Against Huntingtin mRNA in Cynomologous Monkeys Cynomologous monkeys were treated with ISIS oligonucleotides via intracerebroventricular (ICV) administration to a defined brain area, the lateral ventricles, for the purpose of screening the activity of the oligonucleotides in brain tissue against huntingtin mRNA expression.

Treatment and Surgery

Two groups of 3 cynomologous monkeys each were administered either 0.635 mg/ml (1.5 mg/day) or 1.67 mg/ml (4 mg/day) of ISIS 436689 delivered ICV with individual ambulatory pumps (Pegasus Vario) at the rate of 0.05 ml/hr for 4 weeks. A control group of 2 cynomologous monkeys were administered with PBS in a similar manner. The groups were administered ISIS 436689 bilaterally. One animal was administered ISIS 436689 at the 4 mg/day dose unilaterally to the right ventricle.

Animals were allowed 10 days to recover from surgery prior to infusion being performed. During the post surgery recovery period, the animals were maintained on PBS ICV infusion at a flow rate of 0.05 mL/h using one ambulatory infusion pump per ventricle. At the end of the recovery period, each cannula was connected to an individual ambulatory pump (Pegasus Vario) placed within a primate jacket (Lomir, PJ-02NB). The pumps remained connected until completion of the infusion period. After 4 weeks administration, the animals were euthanized and the brain, liver and kidney were harvested.

RNA Analysis of htt mRNA

RNA was extracted from the anterior caudate, posterior caudate, temporal cortex, parietal cortex, hypothalamus, midbrain, hippocampus, and spinal cords, as well as the liver and kidney for real-time PCR analysis of huntingtin mRNA levels. Huntingtin mRNA levels were measured using the human primer probe set RTS2617 and normalized to monkey cyclophilin A levels. Results were calculated as percent inhibition of huntingtin mRNA expression compared to the PBS control and are presented in Table 61. ISIS 436689 effected significant inhibition of human huntingtin mRNA levels in the CNS.

TABLE 61

Percent reduction of huntingtin mRNA levels in cynomologous monkeys via ICV administration of antisense oligonucleotides

| Tissue | Dose (mg/day) | | | |
|---|---|---|---|---|
| | 1.5 (bilateral) | 4 (bilateral) | 4 (right unilateral) | 4 (left unilateral) |
| Anterior caudate | 59 | 49 | 85 | 12 |
| Posterior caudate | 52 | 81 | 63 | 0 |
| Temporal cortex | 10 | 34 | 41 | 31 |
| Parietal cortex | 22 | 38 | 46 | 24 |
| Hypothalamus | 59 | 71 | 35 | 100 |
| Mid-brain | 32 | 38 | 2 | 0 |
| Hippocampus | 18 | 18 | 28 | 10 |
| Cervical cord | 58 | 65 | n.d. | n.d. |
| Thoracic cord | 50 | 67 | n.d. | n.d. |
| Lumbar cord | 49 | 62 | n.d. | n.d. |
| Liver | 0 | 13 | n.d. | n.d. |
| Kidney | 0 | 13 | n.d. | n.d. | n.d. = no data

Example 9

Measurement of Half-Life of ISIS 387898 in the Striatum of C57/BL6 Mice Via Single Bolus Administration C57/BL6 mice were administered ISIS 387898 as a single bolus to the striatum for the purpose of measuring half-life and duration of action of the antisense oligonucleotide against huntingtin mRNA expression in that tissue.

Treatment

Forty C57/BL6 mice were treated with ISIS 387898 (5' CTCGACTAAAGCAGGATTTC 3' (SEQ ID NO: 53); start position 4042 of SEQ ID NO: 1 and start position 4001 of SEQ ID NO: 3) delivered as a single bolus of 50 µg in a procedure similar to that described in Example 5. Eight control C57/BL6 mice were treated with PBS in a similar procedure. Groups of 4 mice each were euthanized at various time points and striatal tissue extracted in a procedure similar to that described in Example 5.

RNA Analysis

RNA was extracted from striatal tissue for real-time PCR analysis of huntingtin mRNA levels. Mouse normal huntingtin mRNA levels were measured using the murine primer probe set RTS2633. The results are presented in Table 62 and are expressed as percent inhibition compared to the PBS control group at day 7. The inhibitory effect of ISIS 387898 was observed to be prolonged for at least 91 days.

TABLE 62

Effect of ISIS 387898 as a single bolus administration on murine huntingtin mRNA expression at various time points in C57/BL6 striatum

| Treatment | Days after dosing | % inhibition |
|---|---|---|
| ISIS 387898 | 1 | 66 |
| | 7 | 74 |
| | 14 | 68 |
| | 21 | 77 |
| | 28 | 75 |
| | 50 | 63 |
| | 73 | 55 |
| | 91 | 48 |
| PBS | 50 | 5 |

Analysis of Antisense Oligonucleotide Concentration in the Brain:

Brain tissues were minced, weighed, homogenized, and extracted using a phenol/chloroform liquid-liquid extraction method. This was followed by solid phase extraction of the supernatant on a phenyl-bonded column before capillary gel eletrophoresis electrokinetic injection. A P/ACE MDQ capillary electrophoresis instrument (Beckman Coulter, Fullerton, Calif.) was used for gel-filled capillary electrophoretic analysis. Oligonucleotide peaks were detected by UV absorbance at 260 nm.

Figure 2:
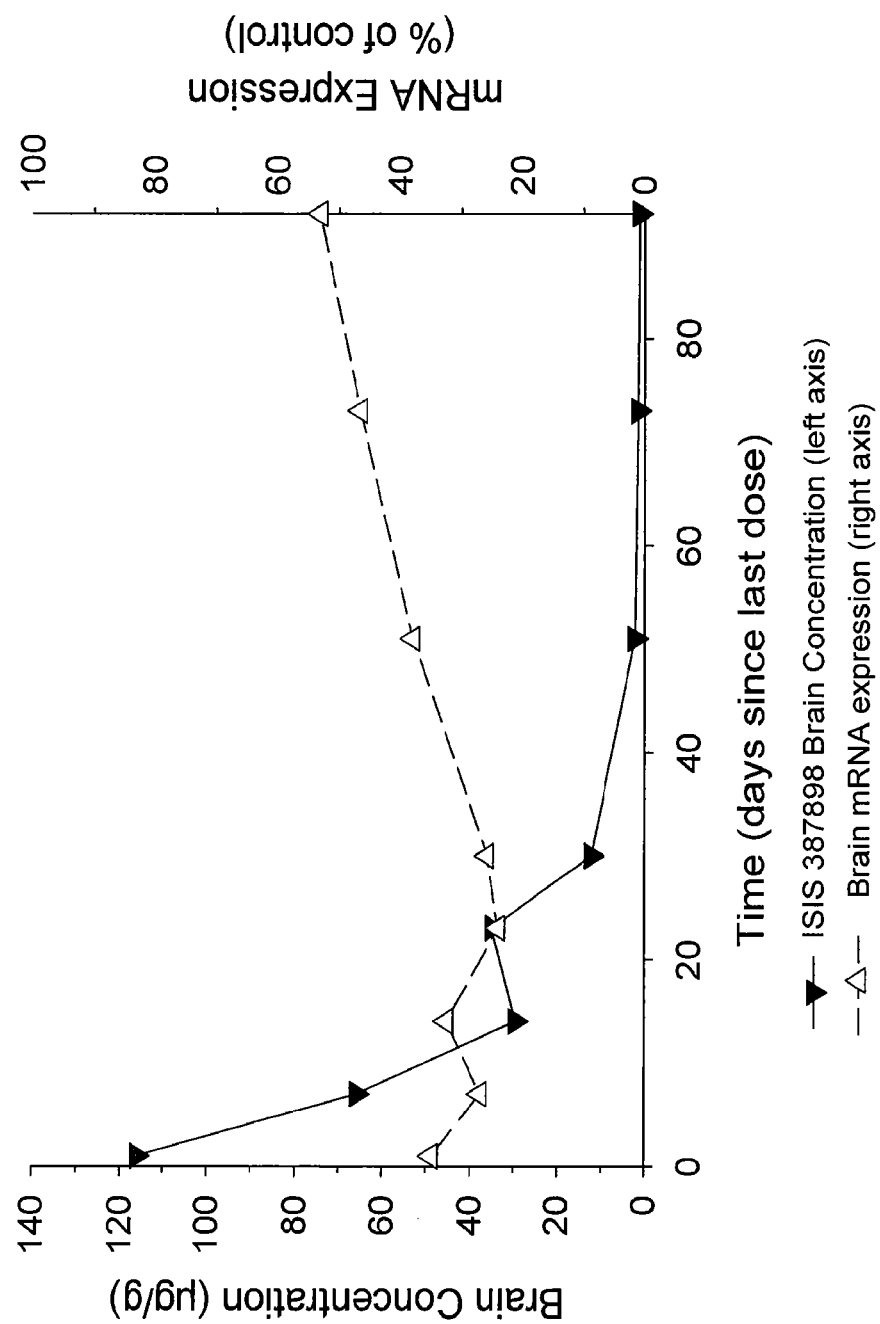
FIG. 2:
Comparison of huntingtin mRNA expression in intrastriatal tissue and ISIS 387898 concentrations at various time points. C57/BL6 mice were administered a single bolus of 50 µg of ISIS 387898 and huntingtin mRNA expression as well as the concentration of the antisense oligonucleotide in the tissue were measured. The duration of action (as measured by htt mRNA expression) of ISIS 387898 (dashed line) was observed to be longer even after the concentration of the oligonucleotide (solid line) in the tissue.

The concentration of ISIS 387898 in the brain (µg/g) was plotted against the expression of human huntingtin as a percentage of the PBS control (Table 63 and FIG. 1). The concentration of ISIS 387898 which achieves 50% inhibition of huntingtin mRNA expression ($EC_{50}$) was calculated. The $EC_{50}$ was determined to be 0.45 µg/g. The time-dependent concentration of ISIS 387898 in the brain tissue and corresponding percentage huntingtin mRNA expression was also plotted (Table 64 and FIG. 2) and the half-life of the oligonucleotide was calculated as 21 days.

TABLE 63

Concentration of ISIS 387898 in brain tissue and its effect on htt mRNA expression as a percentage of the control

| concentration (µg/g) | % mRNA expression |
|---|---|
| 0 | 105.0 |
| 25 | 28.8 |
| 50 | 28.2 |
| 75 | 27.9 |
| 100 | 27.8 |
| 125 | 27.8 |

TABLE 64

Time-dependent concentration of ISIS 387898 in brain tissue and its effect on htt mRNA expression as a percentage of the control

| Time (day) | Conc (µg/g) | mRNA % expression |
|---|---|---|
| 1 | 116 | 35 |
| 7 | 65.7 | 27 |
| 14 | 30 | 32 |
| 23 | 34.9 | 24 |
| 30 | 12.2 | 26 |
| 51 | 2.1 | 38 |
| 73 | 1.4 | 47 |
| 92 | 1.1 | 53 |

Example 10

Measurement of Half-Life of ISIS 387898 in the Lateral Ventricles of BACHD Mice Via ICV Administration BACHD mice were administered ISIS 387898 by ICV to the lateral ventricles of the brain for the purpose of measuring half-life and duration of action of the antisense oligonucleotide against huntingtin mRNA expression in that tissue.

Treatment

Twenty eight BACHD mice were treated with ISIS 387898 delivered by ICV administration at 75 µg/day for 2 weeks in a procedure similar to that described in Example 9. Twenty eight control BACHD mice were treated with PBS in a procedure similar to that described in Example 9. Groups of 4 mice each from both the treatment and control groups were euthanized at biweekly time points and anterior cortical tissue extracted in a procedure similar to that described in Example 9.

RNA Analysis

RNA was extracted from the right hemisphere, both anterior and posterior to the cannulation site for real-time PCR analysis of huntingtin mRNA levels. Human mutant huntingtin mRNA levels were measured using the human primer probe set RTS2617. Mouse normal huntingtin mRNA levels were measured using the murine primer probe set RTS2633. Human mutant huntingtin mRNA expression levels are presented in Table 65 and are expressed as percent inhibition compared to the average of that measured in the PBS control groups. Murine normal huntingtin mRNA expression levels are presented in Table 66 and are expressed as percent inhibition compared to the average of that measured in the PBS control groups. The inhibitory effect of ISIS 387898 was observed to be prolonged for 91 days.

TABLE 65

Effect of ISIS 387898 administered ICV on human huntingtin mRNA expression at various time points

| Treatment | Days after dosage | anterior | posterior |
|---|---|---|---|
| ISIS 387898 | 14 | 74 | 65 |
|  | 28 | 67 | 61 |
|  | 42 | 70 | 61 |
|  | 56 | 57 | 52 |
|  | 70 | 57 | 43 |
|  | 91 | 41 | 61 |
|  | 127 | 28 | 16 |
| PBS | 14 | 0 | 0 |
|  | 28 | 0 | 0 |
|  | 42 | 1 | 0 |
|  | 56 | 9 | 10 |
|  | 70 | 13 | 10 |
|  | 91 | 13 | 25 |
|  | 127 | 11 | 0 |

TABLE 66

Effect of ISIS 387898 administered ICV on murine huntingtin mRNA expression at various time points

| Treatment | Days after dosage | anterior | posterior |
|---|---|---|---|
| ISIS 387898 | 14 | 85 | 81 |
|  | 28 | 81 | 69 |
|  | 42 | 86 | 79 |
|  | 56 | 74 | 69 |
|  | 70 | 73 | 58 |
|  | 91 | 39 | 63 |
|  | 127 | 39 | 0 |
| PBS | 14 | 0 | 0 |
|  | 28 | 0 | 0 |
|  | 42 | 0 | 0 |
|  | 56 | 17 | 14 |
|  | 70 | 5 | 24 |
|  | 91 | 9 | 17 |
|  | 127 | 32 | 0 |

Figure 3:
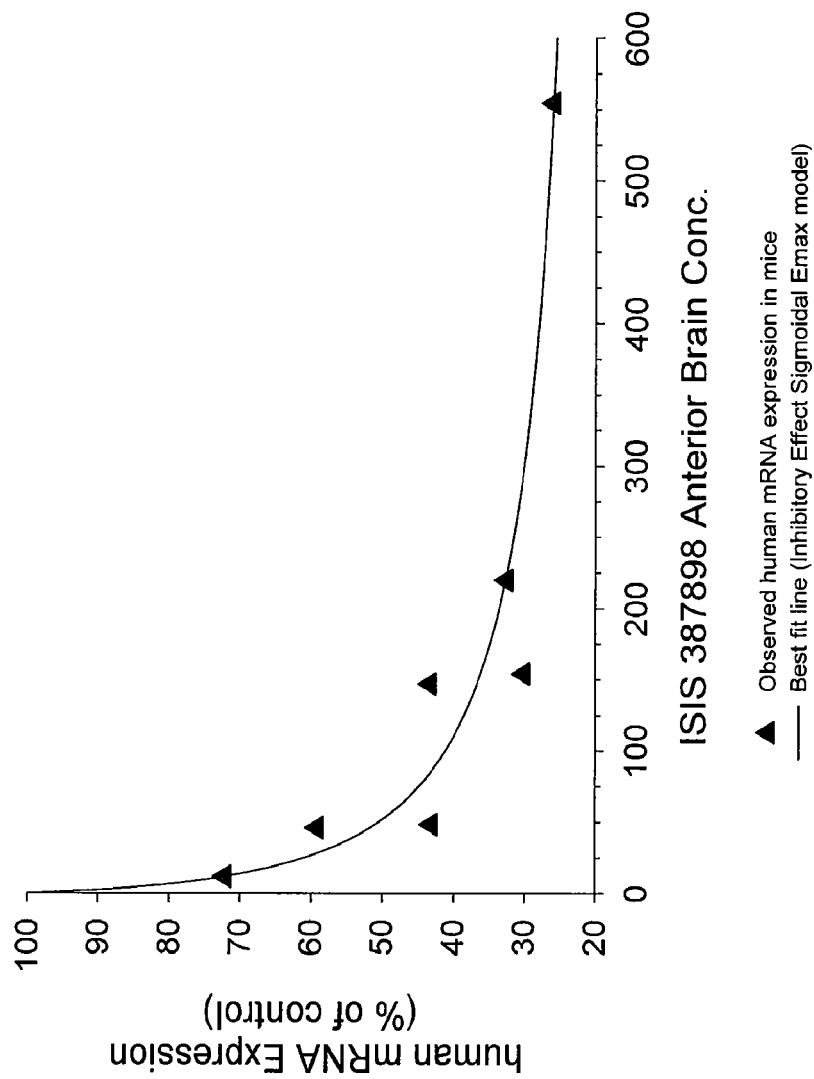
FIG. 3:
The PK/PD relationship of huntingtin mRNA expression in the anterior cortex tissue with ISIS 387898 concentration in mouse brain. BACHD mice were administered an intracerebroventricular infusion of 75 µg of ISIS 387898 for 2 weeks and huntingtin mRNA expression as well as the concentration of the antisense oligonucleotide in the tissue were measured. The $EC_{50}$ of ISIS 387898 was also calculated.
Figure 4:
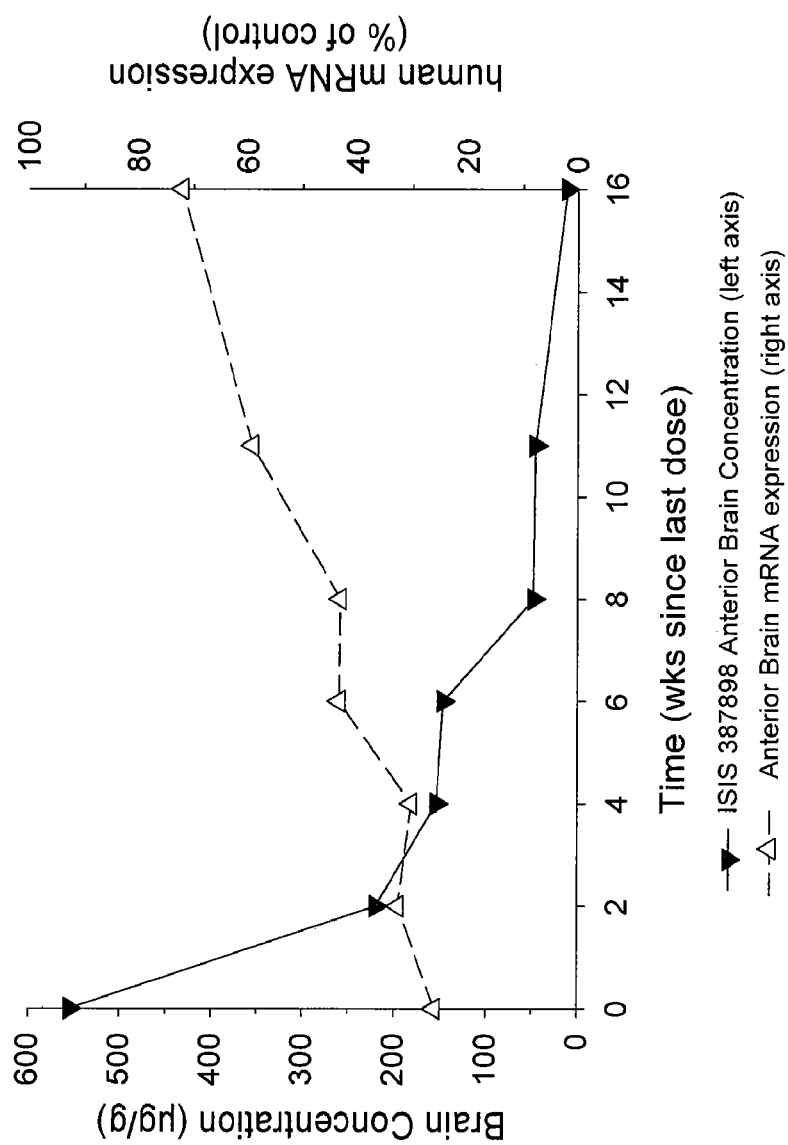
FIG. 4:
Comparison of huntingtin mRNA expression in anterior cortex tissue and ISIS 387898 concentrations at various time points. BACHD mice were administered intracerebroventricular infusion of 75 µg of ISIS 387898 for 2 weeks, and huntingtin mRNA expression as well as the concentration of the antisense oligonucleotide in the tissue were measured.

Analysis of Antisense Oligonucleotide Concentration in the Brain:

Brain tissue was processed in a procedure similar to that described in Example 9. The concentration of ISIS 387898 in the anterior cortex of the brain (µg/g) was plotted against the inhibition of human huntingtin as a percentage of the PBS control (Table 67 and FIG. 3), and the $EC_{50}$ was calculated to be 26.4 µg/g. The time-dependent concentration of ISIS 387898 in the brain tissue was also plotted (Table 68 and FIG. 4) and the half-life of the oligonucleotide was calculated as 21 days.

TABLE 67

Concentration of ISIS 387898 in brain tissue and its effect on htt mRNA expression as a percentage of the control

| Concentration (µg/g) | % mRNA expression |
|---|---|
| 0 | 105 |
| 10 | 90.7 |
| 100 | 19.3 |
| 200 | 14.3 |
| 300 | 13.2 |
| 400 | 12.7 |
| 500 | 12.5 |
| 600 | 12.4 |

TABLE 68

Time-dependent concentration of ISIS 387898 in brain tissue and its effect on htt mRNA expression as a percentage of the control

| Days after last dose | Conc (mg/g) | % mRNA expression |
|---|---|---|
| 14 | 554.3 | 12 |
| 28 | 219.8 | 15 |
| 42 | 154 | 13 |
| 56 | 146.9 | 32 |
| 70 | 48.3 | 28 |
| 91 | 46.1 | 66 |
| 127 | 11.8 | 90 |

Example 11

Measurement of Half-Life of ISIS 388241 and Isis 443139 in the Lateral Ventricles of BACHD Mice Via ICV Administration BACHD mice were administered ISIS 388241 or ISIS 443139 by ICV to the lateral ventricles of the brain for the purpose of measuring half-life and duration of action of the antisense oligonucleotide against huntingtin mRNA expression in that tissue.

Treatment

Twenty BACHD mice were treated with ISIS 38241 delivered by ICV administration at 50 µg/day for 2 weeks in a procedure similar to that described in Example 9. Twenty BACHD mice were treated with ISIS 443139 delivered by ICV administration at 50 µg/day for 2 weeks in a procedure similar to that described in Example 9. Twenty control BACHD mice were treated with PBS in a procedure similar to that described in Example 9. Groups of 4 mice each from both the treatment groups and control group were euthanized at biweekly time points and tissue extracted in a procedure similar to that described in Example 9.

RNA Analysis

RNA was extracted from the right hemisphere, both anterior and posterior to the cannulation site for real-time PCR analysis of huntingtin mRNA levels. Human mutant huntingtin mRNA levels were measured using the human primer probe set RTS2617. The results are presented in Table 69 and are expressed as percent inhibition compared to the average of that measured in the PBS control groups. The inhibitory effects of both ISIS 388241 and ISIS 443139 were observed to be prolonged for at least 16 weeks.

Both ISIS 388241 and its mixed backbone equivalent, ISIS 443139, have more than 3 mismatches with murine huntingtin mRNA (SEQ ID NO: 5) and therefore did not show significant inhibition of murine mRNA levels compared to the control.

TABLE 69

Effect of ISIS 388241 and ISIS 443139 administered ICV on human huntingtin mRNA expression at various time points

| Treatment | Weeks after dosage | anterior | posterior |
|---|---|---|---|
| ISIS 388241 | 0 | 63 | 64 |
|  | 4 | 79 | 56 |
|  | 8 | 67 | 51 |
|  | 12 | 76 | 68 |
|  | 16 | 35 | 34 |
| ISIS 443139 | 0 | 35 | 55 |
|  | 4 | 20 | 62 |
|  | 8 | 61 | 59 |
|  | 12 | 67 | 53 |
|  | 16 | 46 | 37 |
| PBS | 0 | 15 | 10 |
|  | 4 | 0 | 2 |
|  | 8 | 5 | 0 |
|  | 12 | 32 | 4 |
|  | 16 | 6 | 2 |

Figure 5:
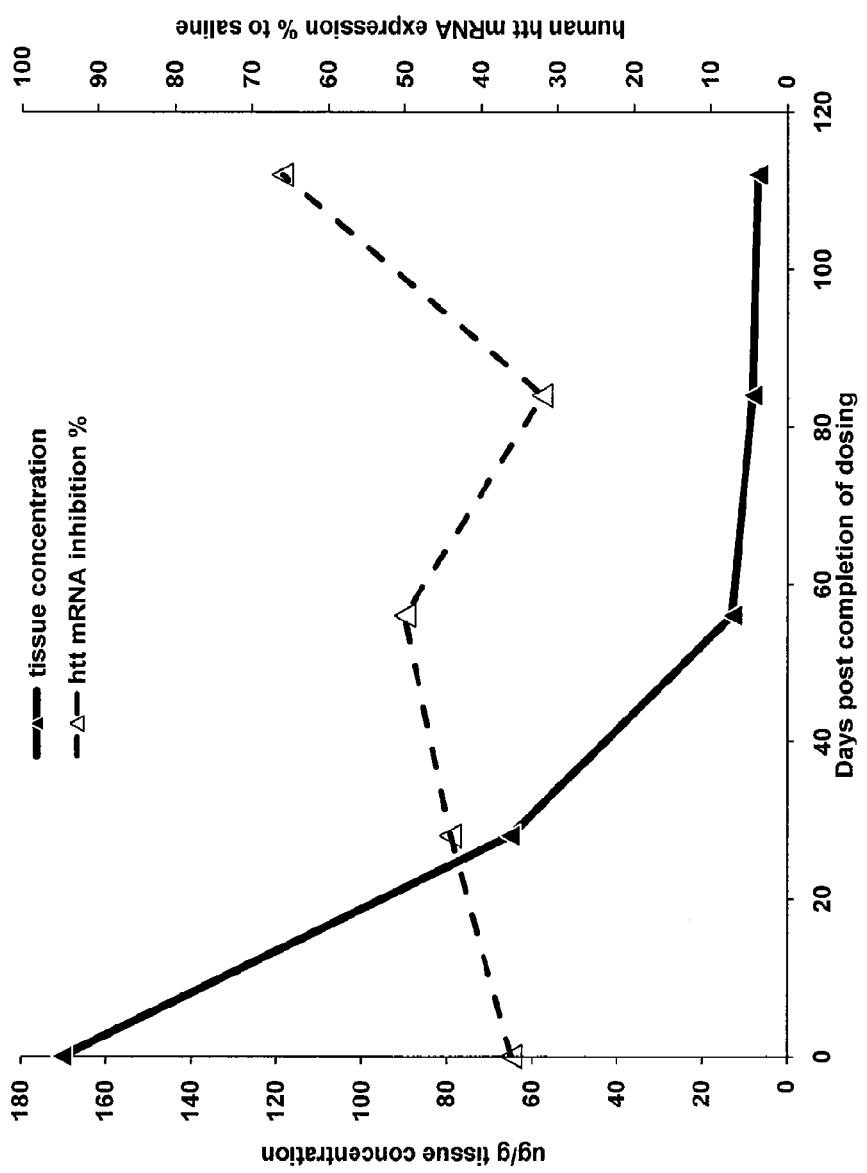
Figure 6:
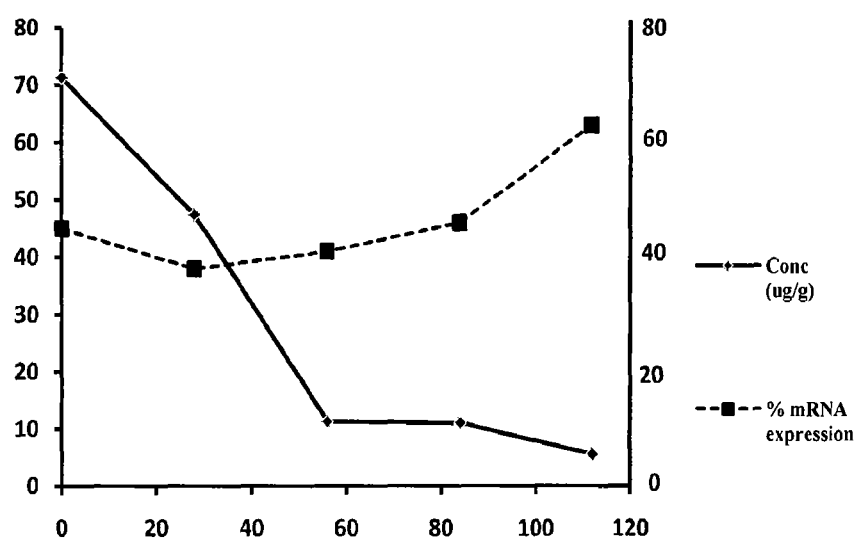

Analysis of Antisense Oligonucleotide Concentration in the Brain:

Brain tissue was processed in a procedure similar to that described in Example 9. The time-dependent concentration of ISIS 388241 in the posterior brain tissue was plotted (Table 70 and FIG. 5) and the half-life of the oligonucleotide was calculated as 20 days. The time-dependent concentration of ISIS 443139 in the posterior brain tissue was plotted (Table 71 and FIG. 6) and the half-life of the oligonucleotide was calculated as 20 days.

TABLE 70

Concentration of ISIS 384241 in brain tissue and its effect on htt mRNA expression as a percentage of the control

| Days after last dose | Conc (ug/g) | % mRNA expression |
|---|---|---|
| 0 | 170.3 | 36 |
| 28 | 65.2 | 43 |
| 56 | 13 | 49 |
| 84 | 8.2 | 32 |
| 112 | 6.9 | 66 |

TABLE 71

Concentration of ISIS 443139 in brain tissue and its effect on htt mRNA expression as a percentage of the control

| Days after last dose | Conc (ug/g) | % mRNA expression |
|---|---|---|
| 0 | 71.3 | 45 |
| 28 | 47.4 | 38 |
| 56 | 11.3 | 41 |
| 84 | 11.1 | 46 |
| 112 | 5.6 | 63 |

Example 12

Effect of Antisense Inhibition of Mutant Human Huntingtin on the Motor Performance of BACHD Mice BACHD mice were treated with ISIS oligonucleotides via intracerebroventricular (ICV) administration for the purpose of evaluating the effect of the oligonucleotides against huntingtin mRNA expression on their motor performance via the rotarod assay.

Treatment

The accelerating rotarod assay was performed on the Ugo Basile rotarod. Animals were placed on the rotarod at a speed of 2 RPM, the rotarod accelerated to 40 RPM over 5 minutes.

The duration to fall was recorded. Duration to fall is defined by the animal either falling from the rotarod, or stopping their run, hanging on to the rotarod and rotating on it. Six month old BACHD mice and their non-transgenic littermates were trained to run on the rotarod for one week prior to treatment. This consisted of three consecutive trials of 5 minutes each, with a 20 minute rest period between trials. A group of 15 BACHD mice were then treated with ISIS 388241 at 50 µg/day delivered ICV with Alzet 2002 pumps at the rate of 12 µL/day for 2 weeks. The mice were surgically implanted with the pumps in a similar procedure as that described in Example 6. A control group of 14 BACHD mice were treated with PBS in a similar manner. A control group of 9 non-transgenic littermates were treated with PBS in a similar manner.

Rotarod Performance Assay

Figure 7:
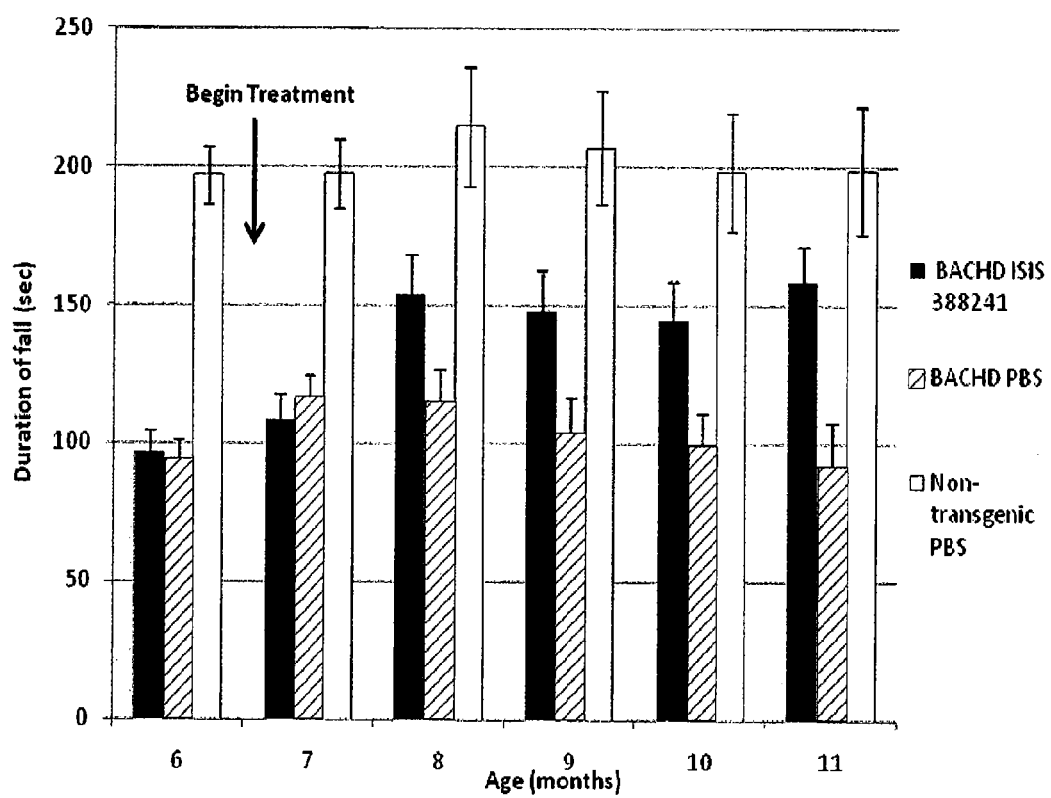

At the end of the treatment period, the pumps were removed and two weeks later, the first post-treatment rotarod assay was conducted. Rotarod behavior was analyzed monthly till the mice were 11 months of age. Each month, the animals were placed on the rotarod for three trial runs a day for 2 days. The results are presented in FIG. 7, as well as in Table 72 expressed as duration to fall in seconds. Baseline values at 6 months age were taken before the treatment and the time points given are the age of the mice at which the assay was conducted. The data indicates that treatment of BACHD mice with ISIS 388241 increased the duration to fall compared to that observed in untreated BACHD mice.

TABLE 72

Effect of antisense inhibition of mutant huntingtin mRNA on duration to fall (sec)

|  | 6 months | 7 month | 8 months | 9 months | 10 months | 11 months |
|---|---|---|---|---|---|---|
| ISIS 388241 | 97 | 108 | 154 | 148 | 144 | 159 |
| PBS control | 94 | 117 | 115 | 104 | 99 | 92 |
| Non-transgenic control | 197 | 198 | 215 | 207 | 198 | 199 |

Example 13

Effect of Antisense Inhibition of Mutant Human Huntingtin and Wild Type Murine Huntingtin mRNA on the Motor Performance of BACHD Mice BACHD mice were treated with ISIS oligonucleotides via intracerebroventricular (ICV) administration for the purpose of evaluating the effect of the oligonucleotides against huntingtin mRNA expression on their motor performance via the rotarod assay.

Treatment

The accelerating rotarod assay was performed on the Ugo Basile rotarod. Animals were placed on the rotarod at a speed of 2 RPM, the rotarod accelerated to 40 RPM over 5 minutes. The duration to fall was recorded. Duration to fall is defined by the animal either falling from the rotarod, or stopping their run, hanging on to the rotarod and rotating on it. Two month old BACHD mice and their non-transgenic littermates were trained to run on the rotarod for one week prior to treatment. This consisted of three consecutive trials of 5 minutes each, with a 20 minute rest period between trials. Groups of 17-21 BACHD mice each were then treated with ISIS 388241 at 50 µg/day, ISIS 408737 at 75 µg/day, or ISIS 387898 at 75 µg/day, delivered ICV with Alzet 2002 pumps at the rate of 0.5 µL/hour for 2 weeks. The mice were surgically implanted with the pumps in a similar procedure as that described in Example 6. A control group of 20 BACHD mice were treated with PBS in a similar manner. Groups of non-transgenic control mice were also similarly treated with ISIS oligonucleotides or PBS in a similar manner.

Rotarod Performance Assay

At the end of the treatment period, the pumps were removed and two weeks later, the first post-treatment rotarod assay was conducted. Rotarod behavior was analyzed monthly till the mice were 10 months of age. Each month, the animals were placed on the rotarod for 3-5 trial runs a day for 3 consecutive days. The results are presented in Table 73 expressed as duration to fall in seconds. Baseline values at 2 months age were taken before the treatment and the time points given are the age of the mice at which the assay was conducted. ISIS 387898 (designated in the table as Human-mouse ASO) is cross-reactive for both mouse and human huntingtin mRNA and therefore would inhibit both human mutant huntingtin mRNA and wild-type murine huntingtin mRNA in the mice. ISIS 388241 (designated in the table as Human ASO) specifically targets human huntingtin mRNA and is mismatched by 8 base pairs with murine huntingtin mRNA. Therefore, ISIS 388241 would specifically inhibit only human mutant huntingtin mRNA and not wild-type murine huntingtin mRNA in the mice. ISIS 408737 (designated in the table as Mouse ASO) specifically targets murine huntingtin mRNA and is mismatched by 7 base pairs with human huntingtin mRNA. Therefore, ISIS 408737 would specifically inhibit only wild-type murine huntingtin mRNA and not human mutant huntingtin mRNA in the mice. 'Tg' indicates the BACHD mice and 'Non-Tg' indicates the non-transgenic control mice.

The results of the study indicate that inhibition of human mutant huntingtin mRNA by ISIS 388241 (Tg-Human ASO) significantly improved the performance of the mice in the rotarod assay compared to the control (Tg-PBS). The results also indicate that treatment of mice with ISIS 387898 (Tg-Human-mouse ASO), which targets both mutant and wild-type huntingtin mRNA in the mice, did not cause any deleterious effects on the motor performance of the mice and, in fact, also significantly improved rotarod performance compared to the control (Tg-PBS). The mice treated with ISIS 408737 (Tg-Mouse ASO) did not show improved rotarod performance compared to the PBS control, as expected, since the oligonucleotide does not target the mutant huntingtin mRNA. The non-transgenic controls were utilized as positive controls in this assay.

TABLE 73

Effect of antisense inhibition of huntingtin mRNA on duration to fall (sec)

|  | 2 months | 3 months | 4 months | 5 months | 6 months | 7 months | 8 months | 9 months | 10 months |
|---|---|---|---|---|---|---|---|---|---|
| Tg-Human ASO | 146 | 167 | 190 | 192 | 190 | 188 | 181 | 191 | 191 |
| Tg-mouse ASO | 151 | 142 | 152 | 143 | 139 | 144 | 139 | 123 | 130 |

TABLE 73-continued

Effect of antisense inhibition of huntingtin mRNA on duration to fall (sec)

| | 2 months | 3 months | 4 months | 5 months | 6 months | 7 months | 8 months | 9 months | 10 months |
|---|---|---|---|---|---|---|---|---|---|
| Tg-Human-mouse ASO | 149 | 187 | 203 | 199 | 196 | 194 | 189 | 194 | 171 |
| Tg-PBS | 152 | 164 | 169 | 160 | 159 | 155 | 148 | 135 | 136 |
| Non-Tg-Human ASO | 212 | 223 | 234 | 236 | 247 | 248 | 245 | 247 | 235 |
| Non-Tg-Mouse ASO | 201 | 212 | 215 | 213 | 231 | 243 | 244 | 250 | 247 |
| Non-Tg-Human-mouse ASO | 220 | 240 | 239 | 224 | 243 | 244 | 246 | 229 | 235 |
| Non-Tg-PBS | 193 | 220 | 228 | 227 | 228 | 216 | 220 | 208 | 208 |

Example 14

Effect of Antisense Inhibition of Huntingtin mRNA on the Brain Mass of R6/2 Mice R6/2 mice were treated with ISIS oligonucleotides via intracerebroventricular (ICV) administration for the purpose of evaluating the effect of the oligonucleotides against huntingtin mRNA expression on brain weight and volume.

Treatment

R6/2 mice were housed in groups of up to 5 per cage (mixed genotypes, single sex), All mice were housed in shoe-box cages with sterile wood bedding covering the ground that were changed as frequently as needed to provide the animals with dry bedding. This basic environment was enriched with the addition of play tunnels, shredded nestlet, and plastic bones for all mice; i.e. an environmentally-enriched cage containing a Mouse Tunnel, (amber color, certified, transparent, BioSery Product#K3323), a Petite Green Gumabone (BioSery Product #K3214) and a nestlet (Hockley et al., Ann Neurol. 2002, 51: 235-242). Food and water were available ad libitum to the mice in their home cages.

A group of ten six month old R6/2 mice was administered 50 μg/day of ISIS 388817 delivered ICV with Alzet 1004 pumps at the rate of 0.12 μl/hr for 4 weeks. A group of two non-transgenic littermates was administered 50 μg/day of ISIS 388817 delivered in a similar manner. A control group of five R6/2 mice was administered 50 μg/day of ISIS 141923 delivered in a similar manner. A control group of nine R6/2 mice was administered PBS delivered in a similar manner. A group of eight non-transgenic littermates was administered PBS delivered in a similar manner. A group of four untreated eight-week old pre-symptomatic R6/2 were also included in the study.

Brain Weight Measurement

Figure 8:
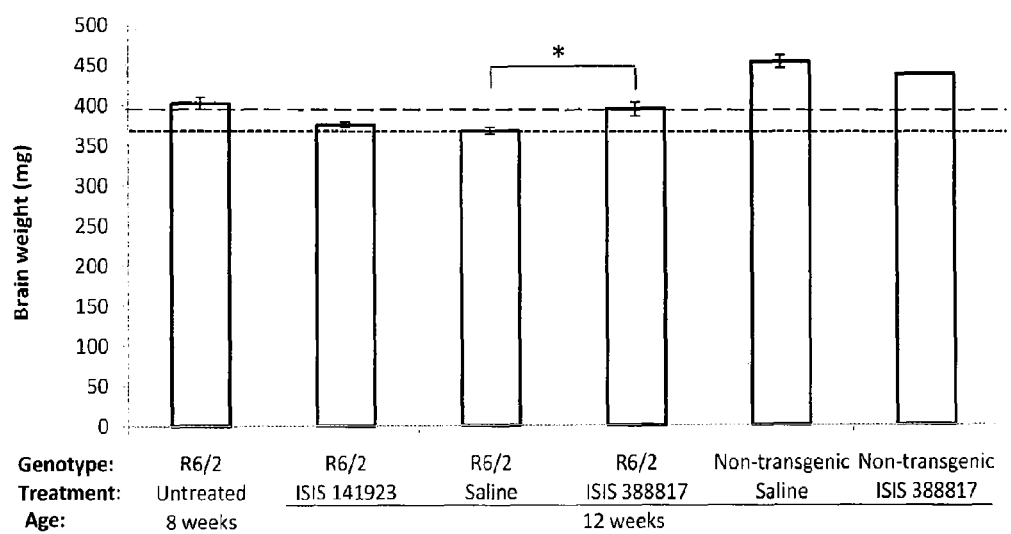

Animals were anaesthetized with isofluorane and then subjected to transcardial perfusion with ice-cold Sorenson's phosphate buffer (SPB), and fixed with 4% paraformaldyhyde in SPB. Brains were removed, and trimmed with coronal cuts immediately rostral to the forebrain (removing the olfactory bulbs) and immediately caudal to the cerebellum (removing the spinal cord). The remaining brain was weighed in mg. The results are presented in FIG. 8 and Table 74 and demonstrate the increase in brain weight in R6/2 mice treated with ISIS 388817 compared to the PBS control

TABLE 74

Effect of antisense inhibition of mutant huntingtin mRNA on brain weight (mg)

| Mouse model | Treatment | Brain weight |
|---|---|---|
| R6/2 | PBS | 367 |
| | ISIS 141923 | 375 |
| | ISIS 388817 | 394 |
| R6/2 (8 weeks old) | None | 402 |
| Non-transgenic | ISIS 141923 | 452 |
| | ISIS 388817 | 436 |

Example 15

Effect of Antisense Inhibition of Huntingtin mRNA on Anxiety Performance of YAC128 Mice YAC128 mice were treated with ISIS oligonucleotides via intracerebroventricular (ICV) administration for the purpose of evaluating the effect of the oligonucleotides against huntingtin mRNA expression on anxiety in these mice as measured by their performance in the open field and elevated plus maze assays.

Treatment

A group of seven five-month old YAC128 mice was administered 50 μg/day of ISIS 388241 delivered ICV with Alzet 1004 pumps at the rate of 0.5 μl/hr for 14 days. A control group of four YAC128 mice were similarly treated with PBS. A control group of eight non-transgenic FVB/NJ littermates were included in the study and did not receive any treatment. The mice were surgically implanted with the pumps in the following manner: Briefly, Alzet osmotic pumps (Model 2002) were assembled according to manufacturer's instructions. Pumps were filled with a solution containing the antisense oligonucleotide and incubated overnight at 37° C., 24 hours prior to implantation. Animals were anesthetized with 3% isofluorane and placed in a stereotactic frame. After sterilizing the surgical site, a midline incision was made over the skull, and a subcutaneous pocket was created over the back, in which a pre-filled osmotic pump was implanted. A small burr hole was made through the skull above the right lateral ventricle. A cannula, connected to the osmotic pump via a plastic catheter, was then placed in the ventricle and glued in place using Loctite adhesive. The incision was closed with sutures. Antisense oligonucleotide or PBS was infused for 14 days, after which the pumps were removed. The animals were allowed to recover for 2 weeks after which behavioral analysis was done and the mice were finally euthanized according to a humane protocol approved by the Institutional Animal Care and Use Committee. Brain and spinal cord tissue were harvested and snap frozen in liquid nitrogen. Prior to freezing, brain tissue was cut transversely into five sections (S1, S2, S3, S4, and S5) using a mouse brain matrix. Sections 1 to 5 were approximately 2 mm apart from each other with S1 being most rostral and S5 most caudal.

Open Field Assay

Figure 9:
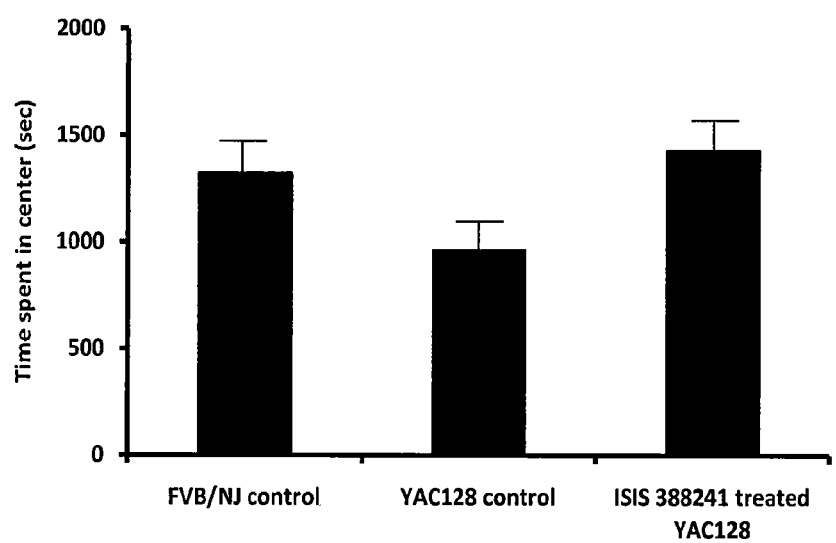

Mice were placed in an open field arena (Med Associates) that uses photobeam breaks to measure horizontal and vertical movement over a 30 min test session. Data was analyzed using Activity Monitor software to examine total ambulatory movement within the arena and movement within the center of the arena as a measure of anxiety. YAC128 control mice were expected to spend less time at the centre of the arena compared to their non-transgenic, less anxiety-prone FVB/NJ littermates. The results are presented in FIG. 9 and Table 75 and indicate that treatment of YAC128 mice with antisense oligonucleotide decreased anxiety in these mice, according to the parameters of the open field assay.

TABLE 75

Effect of antisense inhibition of mutant htt mRNA on open field performance of YAC128 mice

| Mice model | Time in center (sec) |
|---|---|
| FVB control | 1326 |
| YAC128 control | 964 |
| ISIS 388241 treated YAC128 | 1433 |

Elevated Plus Maze Assay

Figure 10:
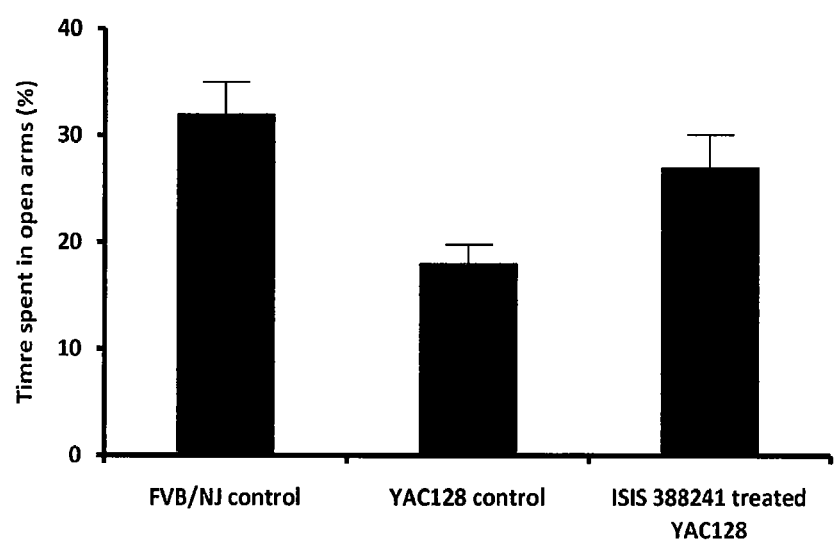

The apparatus consisted of two open arms and two closed arms each measuring 65×6.25 cm and elevated 50 cm above the ground. Mice were placed in the center of the apparatus and their location was recorded over a 5 minute test session. YAC128 control mice were expected to spend less time at the open arms of the apparatus compared to their non-transgenic, less anxiety-prone FVB/NJ littermates. The results are presented in FIG. 10 and Table 76 and indicate that treatment of YAC128 mice with antisense oligonucleotide decreased anxiety in these mice, according to the parameters of the elevated plus maze assay.

TABLE 76

Effect of antisense inhibition of mutant htt mRNA on elevated plus maze performance of YAC128 mice

| Mice model | % time in open arms |
|---|---|
| FVB control | 32 |
| YAC128 control | 18 |
| ISIS 388241 treated YAC128 | 27 |

RNA and Protein Analysis

Total RNA was extracted from mouse brain and spinal cord with RNeasy Protect Mini Kit (Qiagen, Mississauga, ON, Canada) for real-time PCR analysis of huntingtin mRNA levels using an RNeasy Mini prep kit (Qiagen). Q-PCR reactions were conducted and analyzed on an ABI Prism 7700 Sequence Detector (Applied Biosystems). Human huntingtin mRNA levels were measured using the human primer probe set RTS2686 and normalized to peptidylprolyl isomerase A mRNA levels.

Protein lysates were prepared from mouse brain slabs as described previously (Li S. H. and Li X. J., *Methods in Molecular Biology* (2008), 217:1940-6029). Lysates were run on 3-8% tris-acetate gel and transferred using the iBlot dry blotting system (Invitrogen). Blots were probed with anti-beta tubulin (Chemicon) and mouse monoclonal EM48 antibody that reacts specifically with human huntingtin protein (Millipore). Immunoblots were quantified using Odyssey V3.0 software.

The results are presented in Table 77 as percent reduction compared to the PBS control and demonstrate significant inhibition of huntingtin mRNA and protein levels by the antisense oligonucleotide.

TABLE 77

Percent inhibition of huntingtin mRNA in YAC128 mice

|  | % inhibition |
|---|---|
| mRNA | 85 |
| protein | 86 |

Example 16

Intracerebroventricular Administration of Antisense Oligonucleotides Against Huntingtin in C57/BL6 Mice C57/BL6 mice were treated with ISIS oligonucleotides via intracerebroventricular (ICV) administration to the right lateral ventricle, for the purpose of evaluating the tolerability of the oligonucleotides in these mice.

Treatment and Surgery

Groups of five C57/BL6 mice each were administered ISIS 387916, ISIS 437527, ISIS 444578, ISIS 444584, ISIS 444607, ISIS 444608, ISIS 444627, ISIS 444652, ISIS 444659, ISIS 444660, or ISIS 444661 at 150 µg/day delivered ICV with Alzet 2002 pumps at the rate of 0.5 µL/day for 2 weeks. A control group of six C57/BL6 mice were similarly treated with PBS. The procedure for implanting the pumps and oligonucleotide administration is described in Example 6.

The animals were allowed to recover for two weeks before being euthanized using isoflurane. Brain and spinal cord tissue were harvested and snap frozen in liquid nitrogen. Prior to freezing, brain tissue was cut transversely into five sections (51, S2, S3, S4, and S5) using a mouse brain matrix. Sections 1 to 5 were approximately 2 mm apart from each other with S1 being the most rostral and S5 the most caudal.

RNA Analysis

Total RNA was extracted from anterior and posterior cortices of the brain for real-time PCR analysis of huntingtin mRNA levels using an RNeasy Mini prep kit (Qiagen). RT-PCR reactions were conducted on an ABI Prism 7700 Sequence Detector (Applied Biosystems). Mouse huntingtin mRNA levels were measured using a murine primer probe set RTS2633 and normalized to cyclophilin mRNA levels. The results are presented in Table 78 as percent reduction compared to the PBS control. ISIS 387916, ISIS 437527, ISIS 444627, and ISIS 444652 all have one mismatch with the murine huntingtin mRNA (SEQ ID NO: 3) and therefore did not show significant inhibition of murine mRNA levels compared to the control.

The microglial marker, AIF1 was also measured by RT-PCR analysis using murine primer probe set mAIF1_LTS00328 (forward sequence TGGTCCCCCAGC- CAAGA, designated herein as SEQ ID NO: 54; reverse sequence CCCACCGTGTGACATCCA, designated herein as SEQ ID NO: 55; probe sequence AGCTATCTCCGAGCT-GCCCTGATTGG, designated herein as SEQ ID NO: 56). The results are presented in Table 79 and indicate that the tested ISIS oligonucleotides did not induce an inflammatory response.

TABLE 78

Percent inhibition of murine huntingtin mRNA compared to the control in C57/BL6 mice

| ISIS No | anterior | posterior |
|---|---|---|
| 387916 | 72 | 74 |
| 437527 | 59 | 62 |
| 444578 | 69 | 69 |
| 444584 | 0 | 9 |
| 444607 | 59 | 79 |
| 444608 | 41 | 66 |
| 444627 | 41 | 45 |
| 444652 | 61 | 64 |
| 444660 | 35 | 33 |
| 444661 | 72 | 69 |

TABLE 79

Percent increase in AIF1 mRNA expression compared to the control in C57/BL6 mice

| ISIS No | anterior | posterior |
|---|---|---|
| 387916 | 159 | 67 |
| 437527 | 102 | 77 |
| 444578 | 22 | 7 |
| 444584 | 33 | 37 |
| 444607 | 34 | 58 |
| 444608 | 29 | 1 |
| 444627 | 46 | 22 |
| 444652 | 59 | 50 |
| 444660 | -3 | 11 |
| 444661 | 67 | 62 |

Body Weight Measurements

Body weights were measured at regular intervals throughout the study period, and are presented in Table 80. These weights were utilized as an indicator of tolerability. Mice treated with ISIS 437527, ISIS 444584, and ISIS 444652 had consistent body weight throughout the study period and were deemed the most tolerable of all the ISIS oligonucleotides included in the study. 'n/a' indicates no data for that group of mice.

Example 17

Assay for Neurotoxic Effects of Bolus Administration of Antisense Oligonucleotides in the Striatal Tissue of Rats Sprague-Dawley rats were treated with ISIS oligonucleotides via bolus administration to the striatum, for the purpose of screening for the induction of the microglial marker AIF1 as a measure of CNS toxicity.

Treatment and Surgery

Groups of four Sprague-Dawley rats were administered ISIS 388241, ISIS 443139, ISIS 436671, ISIS 437527, ISIS 444584, ISIS 444591, or ISIS 444652 delivered as a single bolus at a concentration of 25 µg, 50 µg, 75 µg, or 100 µg.

A group of 4 rats were similarly treated with ISIS 387916, delivered as a single bolus at 10 µg, 25 µg, 50 µg, or 75 µg concentrations. A control group of 4 rats were similarly treated with PBS. Seven days after bolus administration, the rats were euthanized using isoflurane and the organs were removed. The animals were decapitated and the brain was removed for dissection of the striatal tissue. A pair of fine curved forceps was placed straight down into the brain just anterior to the hippocampus to make a transverse incision in the cortex and underlying tissues by blunt dissection. The tips of another pair of fine curved forceps were placed straight down along the midsaggital sinus midway between the hippocampus and the olfactory bulb to make a longitudinal incision, cutting the corpus callosum by blunt dissection. The first pair of forceps was then used to reflect back the resultant corner of cortex exposing the striatum and internal capsule, and then to dissect the internal capsule away from the striatum. The second set of forceps was placed such that the curved ends were on either side of the striatum and pressed down to isolate the tissue. The first set of forceps was used to pinch off the posterior end of the striatum and to remove the striatum from the brain.

RNA Analysis of AIF1 Expression Levels

RNA was extracted from striatal tissue for real-time PCR analysis of AIF1 mRNA levels. Rat AIF1 levels were measured using the rat primer probe set rAif1_LTS00219. Results were calculated as the percentage of AIF1 expression over that of the PBS control and are presented in Table 81. The results indicate that ISIS 388241, ISIS 443139, ISIS 436671, ISIS 444591, ISIS 437527, ISIS 444584, and ISIS 444652 were well tolerated in rat brain.

TABLE 80

Body weights of C57/BL6 mice after antisense oligonucleotide treatment

|  | Day 0 | Day 4 | Day 8 | Day 12 | Day 16 | Day 19 | Day 23 | Day 26 | Day 28 |
|---|---|---|---|---|---|---|---|---|---|
| PBS | 105 | 108 | 111 | 114 | 111 | 111 | 113 | 114 | 112 |
| ISIS 387916 | 107 | 108 | 106 | 111 | 106 | 104 | 101 | 101 | 97 |
| ISIS 437527 | 105 | 116 | 116 | 120 | 111 | 112 | 112 | 108 | 108 |
| ISIS 444578 | 105 | 116 | 112 | 115 | 103 | 98 | 83 | 81 | 87 |
| ISIS 444584 | 105 | 117 | 115 | 111 | 105 | 105 | 103 | 104 | 102 |
| ISIS 444607 | 105 | 115 | 112 | 110 | 101 | 98 | 106 | 109 | 106 |
| ISIS 444608 | 102 | 111 | 112 | 112 | 97 | 91 | 78 | 75 | 87 |
| ISIS 444627 | 105 | 116 | 124 | 126 | 105 | 104 | 93 | 94 | 91 |
| ISIS 444652 | 106 | 122 | 124 | 126 | 119 | 113 | 111 | 111 | 108 |
| ISIS 444659 | 105 | 118 | 123 | 116 | 92 | 89 | 68 | n/a | n/a |
| ISIS 444660 | 104 | 115 | 120 | 118 | 103 | 93 | 89 | 84 | 90 |
| ISIS 444661 | 107 | 125 | 120 | 106 | 76 | 86 | 89 | 86 | 91 |

TABLE 81

Percent expression of AIF1 mRNA levels in vivo as a measure of neurotoxicity

| ISIS No | Dose (µg) | % increase |
|---|---|---|
| 387916 | 10 | 145 |
|  | 25 | 157 |
|  | 50 | 247 |
|  | 75 | 316 |
| 388241 | 25 | 29 |
|  | 50 | 12 |
|  | 75 | 30 |
|  | 100 | 41 |
| 436671 | 25 | 37 |
|  | 50 | 2 |
|  | 75 | 13 |
|  | 100 | 50 |
| 443139 | 25 | 0 |
|  | 50 | 7 |
|  | 75 | 167 |
|  | 100 | 26 |
| 444591 | 25 | 18 |
|  | 50 | 80 |
|  | 75 | 50 |
|  | 100 | 207 |
| 437527 | 25 | 98 |
|  | 50 | 45 |
|  | 75 | 23 |
|  | 100 | 126 |
| 444584 | 25 | −1 |
|  | 50 | 10 |
|  | 75 | 35 |
|  | 100 | 31 |
| 444652 | 25 | 17 |
|  | 50 | 46 |
|  | 75 | 39 |
|  | 100 | 48 |

RNA Analysis of Huntingtin Expression Levels

RNA was extracted from striatal tissue for real-time PCR analysis of huntingtin mRNA levels. Rat huntingtin mRNA levels were measured using the rat primer probe set rHtt_LTS00343. Results were calculated as the percentage reduction of huntingtin expression over that of the PBS control and are presented in Table 82. ISIS 388241 and ISIS 443139 are each mismatched by 6 base pairs or more with the rat gene sequence (SEQ ID NO: 5) and therefore do not show significant inhibition of rat mRNA levels compared to the control. ISIS 444584 has 3 mismatches with the rat gene sequence (SEQ ID NO: 5) and therefore does not show significant inhibition of rat mRNA levels compared to the control.

TABLE 82

Percent reduction of rat huntingtin mRNA levels in rats

| ISIS No | Dose (µg) | % inhibition |
|---|---|---|
| 387916 | 10 | 6 |
|  | 25 | 39 |
|  | 50 | 55 |
|  | 75 | 60 |
| 388241 | 25 | 8 |
|  | 50 | 23 |
|  | 75 | 27 |
|  | 100 | 19 |
| 436671 | 25 | 52 |
|  | 50 | 57 |
|  | 75 | 57 |
|  | 100 | 70 |
| 443139 | 25 | 35 |
|  | 50 | 29 |
|  | 75 | 28 |
|  | 100 | 27 |
| 444591 | 25 | 26 |
|  | 50 | 57 |
|  | 75 | 68 |
|  | 100 | 69 |
| 437527 | 25 | 40 |
|  | 50 | 55 |
|  | 75 | 60 |
|  | 100 | 74 |
| 444584 | 25 | 43 |
|  | 50 | 38 |
|  | 75 | 38 |
|  | 100 | 41 |
| 444652 | 25 | 49 |
|  | 50 | 70 |
|  | 75 | 55 |
|  | 100 | 59 |

Example 18

Dose-Dependent Antisense Inhibition of Huntingtin mRNA in Cynomolgous Primary Hepatocytes ISIS 437527, ISIS 444584, and ISIS 444652 were tested in cynomolgous primary hepatocytes at various doses. The benchmark oligonucleotides, ISIS 387916 and ISIS 388241 were also included for comparison. Cells were plated at a density of 35,000 cells per well and transfected using electroporation with 39.0625 nM, 78.125 nM, 156.25 nM, 312.5 nM, 625 nM, 1,250 nM, 2,500 nM, 5,000 nM, 10,000 nM, and 20,000 nM concentrations of each antisense oligonucleotide. After approximately 16 hours, RNA was isolated from the cells and huntingtin mRNA transcript levels were measured by quantitative real-time PCR using primer probe set RTS2686. Huntingtin mRNA transcript levels were normalized to total RNA content, as measured by RIBOGREEN®. Results are presented in Table 83 as percent inhibition of huntingtin, relative to untreated control cells. Control oligonucleotide, ISIS 141923 was included in this assay and did not demonstrate inhibition of huntingtin mRNA, as expected.

ISIS 437527, ISIS 444584, and ISIS 444652 had lower $IC_{50}$ values than the benchmark oligonucleotide, ISIS 388241. ISIS 437527 and ISIS 444652 had as low or lower $IC_{50}$ values than the benchmark oligonucleotide, ISIS 387916.

TABLE 83

Dose-dependent antisense inhibition of huntingtin mRNA in cynomolgous primary hepatocytes

|  | ISIS 387916 | ISIS 388241 | ISIS 437527 | ISIS 444584 | ISIS 444652 | ISIS 141923 |
|---|---|---|---|---|---|---|
| 39.0625 nM | 0 | 6 | 0 | 0 | 0 | 0 |
| 78.125 nM | 17 | 4 | 19 | 0 | 16 | 0 |
| 156.25 nM | 6 | 0 | 27 | 11 | 12 | 3 |
| 312.5 nM | 19 | 0 | 23 | 16 | 35 | 0 |
| 625.0 nM | 31 | 0 | 37 | 30 | 50 | 0 |
| 1250.0 nM | 45 | 0 | 28 | 23 | 52 | 0 |
| 2500.0 nM | 62 | 4 | 33 | 47 | 74 | 0 |
| 5000.0 nM | 78 | 54 | 55 | 42 | 86 | 0 |
| 10000.0 nM | 82 | 80 | 68 | 77 | 91 | 0 |
| 20000.0 nM | 84 | 75 | 70 | 69 | 92 | 0 |
| $IC_{50}$ (µM) | 1.4 | 5.4 | 2.0 | 4.0 | 0.8 | >20 |

Example 19

Measurement of Half-Life of ISIS Oligonucleotides in BACHD Mice Via Single Intrastriatal Bolus Administration BACHD mice were administered ISIS oligonucleotides as a single bolus to the striatum for the purpose of measuring the duration of action of the antisense oligonucleotides against huntingtin mRNA expression, or its half-life, in that tissue.

Treatment and Surgery

Groups of 25 BACD mice each were treated with ISIS 388241, ISIS 436689, ISIS 436671, or ISIS 444591, delivered as a single bolus of 40 µg in a procedure similar to that described in Example 4. A control group of 25 BACHD mice were treated with PBS in a similar procedure. At various time points, 5 mice from each group were euthanized and striatal tissue was extracted. A pair of fine curved forceps was placed straight down into the brain just anterior to the hippocampus to make a transverse incision in the cortex and underlying tissues by blunt dissection. The tips of another pair of fine curved forceps were placed straight down along the midsaggital sinus midway between the hippocampus and the olfactory bulb to make a longitudinal incision, cutting the corpus callosum by blunt dissection. The first pair of forceps was then used to reflect back the resultant corner of cortex exposing the striatum and internal capsule, and then to dissect the internal capsule away from the striatum. The second set of forceps was placed such that the curved ends were on either side of the striatum and pressed down to isolate the tissue. The first set of forceps was used to pinch off the posterior end of the striatum and to remove the striatum from the brain.

RNA Analysis

RNA was extracted from anterior and posterior sections of the striatal tissue for real-time PCR analysis of huntingtin mRNA levels. Human mutant huntingtin mRNA levels were measured using RTS2617. Mouse normal huntingtin mRNA levels were measured using the murine primer probe set RTS2633. The results are presented in Tables 84 and 85 and are expressed as percent inhibition compared to the average of the PBS control group at week 1, week 10, and week 20. The half-life of the ISIS oligonucleotides in the anterior section of the brain was calculated from the inhibition data and is presented in Table 86.

TABLE 84

Percent inhibition of human huntingtin mRNA expression at various time points

| ISIS No | Time (weeks) | Posterior | Anterior |
|---|---|---|---|
| 388241 | 1 | 72 | 91 |
|  | 5 | 65 | 86 |
|  | 10 | 52 | 73 |
|  | 15 | 26 | 56 |
|  | 20 | 14 | 53 |
| 436671 | 1 | 82 | 92 |
|  | 5 | 78 | 89 |
|  | 10 | 68 | 82 |
|  | 15 | 61 | 77 |
|  | 20 | 30 | 77 |
| 444591 | 1 | 60 | 85 |
|  | 5 | 58 | 76 |
|  | 10 | 48 | 60 |
|  | 15 | 27 | 43 |
|  | 20 | 27 | 36 |
| 436689 | 1 | 72 | 83 |
|  | 5 | 72 | 87 |
|  | 10 | 60 | 74 |
|  | 15 | 50 | 74 |
|  | 20 | 44 | 59 |

TABLE 85

Percent inhibition of mouse huntingtin mRNA expression at various time points

| ISIS No | Time (weeks) | Posterior | Anterior |
|---|---|---|---|
| 388241 | 1 | 1 | 12 |
|  | 5 | 22 | 36 |
|  | 10 | 17 | 14 |
|  | 15 | 7 | 18 |
|  | 20 | 9 | 38 |
| 436671 | 1 | 84 | 96 |
|  | 5 | 77 | 80 |
|  | 10 | 64 | 86 |
|  | 15 | 51 | 78 |
|  | 20 | 19 | 75 |
| 444591 | 1 | 74 | 95 |
|  | 5 | 70 | 90 |
|  | 10 | 57 | 67 |
|  | 15 | 34 | 47 |
|  | 20 | 33 | 38 |
| 436689 | 1 | 40 | 32 |
|  | 5 | 47 | 40 |
|  | 10 | 35 | 18 |
|  | 15 | 34 | 22 |
|  | 20 | 36 | 5 |

TABLE 86

Half-life of ISIS oligonucleotides in the anterior section of the brain in BACHD mice after intrastriatal bolus injection

| ISIS No | Half-life (days) |
|---|---|
| 436671 | 46.6 |
| 436689 | 39.4 |
| 444591 | 24.3 |
| 388241 | 25.8 |

Body Weight Measurements

Body weights were measured at regular intervals, and are presented in Table 87 as a percent of the weight of the mice at the start of the study. These weights were utilized as an indicator of tolerability. There were no adverse changes in body weight in any of the mice treated with ISIS oligonucleotides.

TABLE 87

Percent change in body weight of BACHD mice after antisense oligonucleotide treatment

|  | Week 5 | Week 10 | Week 15 | Week 20 |
|---|---|---|---|---|
| PBS | 8 | 19 | 26 | 28 |
| ISIS 388241 | 9 | 22 | 29 | 26 |
| ISIS 436671 | 5 | 19 | 35 | 38 |
| ISIS 444591 | 7 | 21 | 30 | 43 |
| ISIS 436689 | 3 | 18 | 31 | 38 |

Example 20

Effect of Intrathecal Administration of ISIS 437527 in Sprague Dawley Rats

Sprague Dawley rats were dosed with ISIS 437527 by intrathecal (IT) administration either as a single dose, repeated doses, or continuous infusion.

Treatment and Surgery

Rats were anesthetized with isoflurane and a 28-gauge polyurethane catheter was placed into the IT lumbar space of each rat. The proximal end of the catheter was attached to a dosing pedestal that was extended through the skin for animals in groups receiving bolus injections. The catheter for animals in the group receiving continuous infusion was attached to an ALZET pump (Model 2ML1) which was placed in a subcutaneous pocket on the dorsal aspect of each animal. Post-surgically the animals received a single intramuscular dose of ceftiofur sodium (5 mg/kg) and butorphanol tartrate (0.05 mg/kg). The rats receiving continuous infusion began receiving the oligonucleotide dose immediately. The animals that would receive bolus injections were allowed a surgical recovery period of at least five days after which the patency of the catheter was evaluated.

A group of 5 Sprague Dawley rats was administered a single bolus injection of 350 µg of ISIS 437527 delivered intrathecally. Another group of 5 Sprague Dawley rats was administered bolus injections of 120 µg of ISIS 437527 delivered intrathecally three times over the course of 1 week. Another group of 5 Sprague Dawley rats was administered bolus injections of 350 µg of ISIS 437527 delivered intrathecally three times over the course of 1 week. Another group of 5 Sprague Dawley rats was administered 50 µg/day of ISIS 437527 delivered by continuous infusion at a rate of 0.01 mL/hr for 7 days. A control group of 5 Sprague Dawley rats was administered bolus injections of PBS delivered intrathecally three times over the course of 1 week. Each group was given a recovery period of 7 days, after which the rats were euthanized. The brain and spinal cord from all groups were harvested and analyzed.

RNA Analysis of Huntingtin Expression Levels

RNA was extracted from the frontal cortex, temporal cortex, and the cervical cord for real-time PCR analysis of huntingtin mRNA levels. Rat huntingtin mRNA levels were measured using the primer probe set rHtt_LTS00343 normalized to Cyclophilin levels. The results are presented in Table 88 and are expressed as percent inhibition compared to the average of the PBS control groups.

TABLE 88

Percent inhibition of huntingtin mRNA expression in Sprague Dawley rats

| Tissue | Dose schedule | Dose | % inhibition |
| --- | --- | --- | --- |
| Frontal Cortex | IT Infusion | 50 µg/day | 11 |
| | Single IT Bolus | 350 µg | 28 |
| | Repeated IT Bolus | 120 µg × 3 | 21 |
| | Repeated IT Bolus | 350 µg × 3 | 0 |
| Temporal Cortex | IT Infusion | 50 µg/day | 0 |
| | Single IT Bolus | 350 µg | 34 |
| | Repeated IT Bolus | 120 µg × 3 | 44 |
| | Repeated IT Bolus | 350 µg × 3 | 48 |
| Cervical Cord | IT Infusion | 50 µg/day | 22 |
| | Single IT Bolus | 350 µg | 45 |
| | Repeated IT Bolus | 120 µg × 3 | 58 |
| | Repeated IT Bolus | 350 µg × 3 | 46 |

RNA Analysis of AIF1 Expression Levels

RNA was extracted from frontal cortex, temporal cortex, and the cervical cord for real-time PCR analysis of AIF1 mRNA levels. Rat AIF1 levels were measured using the rat primer probe set rAif1_LTS00219. Results were calculated as the percentage of AIF1 expression over that of the PBS control and are presented in Table 89. The results indicate that repeated IT bolus administrations lead to inflammation at the cervical cord tissues. Continuous IT administration and single IT bolus administrations were well tolerated in the rats.

TABLE 89

Percent expression of AIF1 mRNA levels in Sprague Dawley rats as a measure of neurotoxicity

| Tissue | Dose schedule | Dose | % inhibition |
| --- | --- | --- | --- |
| Frontal Cortex | IT Infusion | 50 µg/day | −36 |
| | Single IT Bolus | 350 µg | −4 |
| | Repeated IT Bolus | 120 µg × 3 | 41 |
| | Repeated IT Bolus | 350 µg × 3 | −7 |
| Temporal Cortex | IT Infusion | 50 µg/day | 15 |
| | Single IT Bolus | 350 µg | 22 |
| | Repeated IT Bolus | 120 µg × 3 | 25 |
| | Repeated IT Bolus | 350 µg × 3 | 76 |
| Cervical Cord | IT Infusion | 50 µg/day | 108 |
| | Single IT Bolus | 350 µg | 72 |
| | Repeated IT Bolus | 120 µg × 3 | 473 |
| | Repeated IT Bolus | 350 µg × 3 | 268 |

Example 21

Measurement of Half-Life of ISIS 436689 in the CNS Tissues of Cynomolgus Monkeys Via Intrathecal Administration Cynomolgous monkeys were administered ISIS 436689 intrathecally (IT) for the purpose of measuring the half-life and duration of action of the antisense oligonucleotide against huntingtin mRNA expression in various CNS tissues.

Treatment

The study was conducted at Northern Biomedical Research, MI. Prior to the start of the treatment, the monkeys were kept in quarantine for a 4-week time period, during which standard panels of serum chemistry and hematology, examination of fecal samples for ova and parasites, and a tuberculosis test, were conducted to screen out abnormal or ailing monkeys. The monkeys were implanted with intrathecal lumbar catheters using polyurethane catheters connected to a subcutaneous titanium access port (P.A.S. PORT® Elite Plastic/Titanium portal with Ultra lock connector). For continuous infusion using an external pump, the animals were anesthetized to attach the dosing apparatus to the port. The animals were pretreated with atropine sulfate by subcutaneous injection at a dose of 0.04 mg/kg. Approximately 15 minutes later, an intramuscular dose of 8 mg/kg of ketamine HCl was administered to induce sedation. The animals were masked to a surgical plane of anesthesia, intubated and maintained on approximately 1 L/min of oxygen and 2% halothane or isoflurane. The animals received a single intramuscular dose of 5 mg/kg ceftiofur sodium antibiotic. An incision was made near the port for placement of the modified needle support. The modified needle was placed in the port and secured with sutures. Upon recovery from surgery, a jacket was placed on the animal.

Fifteen male cynomolgus monkeys were administered 4 mg/day of ISIS 436689 at a concentration of 1.67 mg/mL and at a flow rate of 2.4 mL/day for 21 days. A control group of 3 cynomolgus monkeys was administered with PBS in a similar manner for the same time period. Groups of 3 monkeys each were allowed recovery periods of 1 day, 2 weeks, 4 weeks, or 8 weeks, after which they were euthanized. During the study period, the monkeys were observed daily for signs of illness or distress.

All animals were sedated with an intramuscular injection of 8.0 mg/kg of ketamine HCl, maintained on a halothane or isoflurane/oxygen mixture, and provided with an intravenous bolus of heparin Na at 200 IU/kg. The animals were perfused via the left cardiac ventricle with 0.001% sodium nitrite in saline.

At the time of sacrifice, the brain was cut in a brain matrix at 3 mm coronal slice thickness. Several brain structures were sampled using a 4 mm biopsy punch. One 4 mm diameter sample from each structure was placed in 2 mL screw capped tubes containing 1.0 mL of RNAlater RNA stabilization solution (Qiagen, CA), incubated for 1 hour at ambient temperature and then frozen. Adjacent 6 mm diameter samples were placed in 2 mL screw capped tubes and frozen for pharmacokinetic analysis.

The spinal cord was sectioned into cervical, thoracic and lumbar sections, and approximately 3 mm thick sections of each area of the spinal cord were taken for RNA and pharmacokinetic analysis. These samples were processed in a manner similar to those of the brain samples.

Samples of the liver were harvested for RNA and pharmacokinetic analyses. These samples were processed in a manner similar to those of the brain and spinal cord described above.

RNA Analysis

RNA was extracted from the lumbar spinal cord, thoracic spinal cord, cervical spinal cord, frontal cortex, occipital cortex, cerebellar cortex, caudate tissue, hippocampus, middle brain, and pons for real-time PCR analysis of huntingtin mRNA levels with primer probe set RTS2617. The results measured in the various sections of the spinal cord are presented in Table 90 and are expressed as percent inhibition compared to that measured in the PBS control group at 8 weeks. The results measured in the various sections of the brain are presented in Table 91 and are expressed as percent inhibition compared to that measured in the PBS control group at 8 weeks.

TABLE 90

Effect of ISIS 436689 administered IT on huntingtin mRNA expression in the spinal cord at various time points

| Recovery period | Lumbar spinal cord | Thoracic spinal cord | Cervical spinal cord |
| --- | --- | --- | --- |
| 1 Day | 36 | 66 | 65 |
| 2 Weeks | 56 | 55 | 54 |
| 4 Weeks | 0 | 63 | 65 |
| 8 Weeks | 48 | 48 | 44 |

TABLE 91

Effect of ISIS 436689 administered IT on huntingtin mRNA expression in various brain tissues at various time points

| Recovery period | Frontal cortex | Occipital cortex | Cerebellar cortex | Caudate | Hippocampus | Middle brain | Pons |
| --- | --- | --- | --- | --- | --- | --- | --- |
| 1 Day | 53 | 37 | 8 | 21 | 19 | 24 | 22 |
| 2 Weeks | 42 | 28 | 16 | 3 | 28 | 0 | 32 |
| 4 Weeks | 47 | 32 | 25 | 7 | 22 | 2 | 43 |
| 8 Weeks | 33 | 34 | 11 | 17 | 27 | 5 | 22 |

Oligonucleotide Concentration Measurement by ELISA

Tissues (20 mg) were minced, weighed, and homogenized prior to liquid/liquid extraction using phenol/chloroform. The supernatant was removed, lyophilized, and reconstituted in human EDTA plasma (1 mL) before being analyzed using a hybridization ELISA procedure.

ISIS 436689 was detected in the tissues by hybridization to a labeled complementary cutting probe (digoxigenin at the 5' end and a C18 spacer and BioTEG at the 3' end). The complex was then captured on a neutravidin-coated plate and S1 nuclease was added to digest the unhybridized cutting probes. Since ISIS 436689 protected the cutting probe from digestion, the undigested cutting probe was used as a measure of the oligonucleotide concentration. The undigested cutting probe was detected using an anti-digoxigenin antibody conjugated to alkaline phosphatase followed by fluorogenic substrate readout. Oligonucleotide concentrations were measured in the cervical, thoracic, and lumbar sections of the spinal cord and in the liver on days 7, 20, 34, and 62 of the recovery period, and are presented in Table 92. The half-life of ISIS 436689 in these tissues was calculated from this data, and is presented in Table 93. The data indicates that the oligonucleotide was mainly concentrated in the CNS with negligible concentrations in the systemic tissues.

TABLE 92

Concentrations (μg/g tissue) of ISIS 436689 administered IT on huntingtin mRNA expression in various tissues at various time points

| Organ | Day 7 | Day 20 | Day 34 | Day 62 |
|---|---|---|---|---|
| Cervical cord | 118.9 | 78.7 | 79.8 | 42.8 |
| Thoracic cord | 503.5 | 215.8 | 101.6 | 61.4 |
| Lumbar cord | 557.1 | 409.5 | 143.3 | 49.5 |
| Liver | 33.6 | 10.3 | 2.0 | 0.2 |

TABLE 93

Half-life of ISIS 436689 administered IT on huntingtin mRNA expression in various tissues

| Organ | Half-life |
|---|---|
| Cervical cord | 4.0 |
| Thoracic cord | 15.1 |
| Lumbar cord | 18.7 |
| Liver | 7.6 |

What is claimed is:

1. A method for reducing the rate of progression of one or more symptoms of Huntington's disease in a subject in need thereof, comprising administering to the subject ISIS 443139 (SEQ ID NO.: 22) or ISIS 444652 (SEQ ID NO.: 32).

2. The method of claim 1, wherein said symptom is a physical symptom, a psychiatric symptom, or a peripheral symptom.

3. The method of claim 2, wherein the physical symptom is restlessness, lack of coordination, unintentionally initiated motions, unintentionally completed motions, unsteady gait, chorea, rigidity, writhing motions, abnormal posturing, instability, abnormal facial expressions, difficulty chewing, difficulty swallowing, difficulty speaking, or seizure.

4. The method of claim 2, wherein the psychiatric symptom is anxiety, depression, blunted affect, egocentrisms, aggression, compulsive behavior, irritability, or suicidal ideation.

5. The method of claim 2, wherein the peripheral symptom is reduced brain mass.

6. The method of claim 4, wherein the psychiatric symptom is anxiety.

7. The method of claim 1, comprising administering ISIS 443139 (SEQ ID NO.: 22) to the subject.

8. The method of claim 1, comprising administering ISIS 444652 (SEQ ID NO.: 32) to the subject.

* * * * *